US011890339B2

(12) United States Patent
Graham et al.

(10) Patent No.: US 11,890,339 B2
(45) Date of Patent: Feb. 6, 2024

(54) NIPAH VIRUS IMMUNOGENS AND THEIR USE

(71) Applicants: The United States of America, as represented by the Secretary, Department of Health and Human Services, Bethesda, MD (US); Trustees of Dartmouth College, Hanover, NH (US)

(72) Inventors: Barney Graham, Rockville, MD (US); Rebecca Loomis, Bethesda, MD (US); Guillaume Stewart-Jones, Cambridge, MA (US); John Mascola, Rockville, MD (US); Jason McLellan, Austin, TX (US)

(73) Assignees: The United States of Americam as represented by the Secretary, Department of Health and Human Services, Bethesda, MD (US); Trustees of Dartmouth College, Hanover, NH (US)

(*) Notice: Subject to any disclaimer, the term of this patent is extended or adjusted under 35 U.S.C. 154(b) by 445 days.

(21) Appl. No.: 17/261,828

(22) PCT Filed: Aug. 5, 2019

(86) PCT No.: PCT/US2019/045110

§ 371 (c)(1),
(2) Date: Jan. 20, 2021

(87) PCT Pub. No.: WO2020/028902

PCT Pub. Date: Feb. 6, 2020

(65) Prior Publication Data

US 2021/0299242 A1 Sep. 30, 2021

Related U.S. Application Data

(60) Provisional application No. 62/714,230, filed on Aug. 3, 2018.

(51) Int. Cl.

| | |
|---|---|
| ***A61K 39/155*** | (2006.01) |
| ***A61P 31/14*** | (2006.01) |
| ***C07K 14/005*** | (2006.01) |
| *A61K 39/00* | (2006.01) |

(52) U.S. Cl.

CPC ............ *A61K 39/155* (2013.01); *A61P 31/14* (2018.01); *C07K 14/005* (2013.01); *A61K 2039/70* (2013.01); *C07K 2319/03* (2013.01); *C12N 2760/18222* (2013.01); *C12N 2760/18223* (2013.01); *C12N 2760/18234* (2013.01)

(58) Field of Classification Search

None

See application file for complete search history.

(56) References Cited

U.S. PATENT DOCUMENTS

| | | | |
|---|---|---|---|
| 2009/0041772 A1 | 2/2009 | Broder et al. |
| 2011/0223172 A1 | 9/2011 | Chan et al. |
| 2016/0347827 A1 | 12/2016 | Yee-Peng et al. |

FOREIGN PATENT DOCUMENTS

| | | |
|---|---|---|
| WO | WO 2006/115843 A2 | 11/2006 |
| WO | WO 2009/117035 A1 | 9/2009 |
| WO | WO 2015/112836 A2 | 7/2015 |

OTHER PUBLICATIONS

Xu et al. (PLOS Pathogens 11(12), e1005322 (Year: 2015).*

Battles et al., "Structure and immunogenicity of pre-fusion-stabilized human metapneumovirus F glycoprotein," *Nat Commun.* 8.1: 1528, Nov. 2017 (11 pages).

Bose et al., "Mutations in the parainfluenza virus 5 fusion protein reveal domains important for fusion triggering and metastability," *J Virol.* 87.24: 13520-13531, Dec. 2013.

Chan et al., "Biochemical, conformational, and immunogenic analysis of soluble trimeric forms of henipavirus fusion glycoproteins," *J Virol.* 86.21: 11457-11471, Nov. 2012.

Ewer et al., "Chimpanzee adenoviral vectors as vaccines for outbreak pathogens," *Hum Vaccin Immunother.* 13.12: 3020-3032, Dec. 2017.

Feldman et al., "mRNA vaccines against H10N8 and H7N9 influenza viruses of pandemic potential are immunogenic and well tolerated in healthy adults in phase 1 randomized clinical trials," *Vaccine* 37: 3326-3334, May 2019.

Hassett et al., "Optimization of Lipid Nanoparticles for Intramuscular Administration of mRNA Vaccines," *Mol Ther Nucleic Acids* 15: 1-11, Apr. 2019.

Jagger et al., "Protective Efficacy of Nucleic Acid Vaccines Against Transmission of Zika Virus During Pregnancy in Mice," *J Infect Dis.* 220: 1577-1588, 2019.

Loomis et al., "Structure-Based Design of Nipah Virus Vaccines: A Generalizable Approach to Paramyxovirus Immunogen Development," *Front Immunol.* 11: 842, Jun. 2020 (21 pages).

(Continued)

*Primary Examiner* — Shanon A. Foley
*Assistant Examiner* — Myron G Hill
(74) *Attorney, Agent, or Firm* — Klarquist Sparkman, LLP

(57) ABSTRACT

Embodiments of immunogens comprising a recombinant Nipah virus (NiV) F ectodomain trimer stabilized in a prefusion conformation are provided. Also provided are embodiments of immunogens comprising chimeric proteins comprising the recombinant NiV F ectodomain trimer and one or more G ectodomains, a multimer of NiV G ectodomains, and protein nanoparticles comprising the recombinant NiV F ectodomain trimer or an NiV G ectodomain. Also disclosed are nucleic acids encoding the immunogens and methods of their production. Methods for inducing an immune response in a subject by administering a disclosed immunogen to the subject are also provided. In some embodiments, the immune response treats or inhibits NiV infection in a subject.

35 Claims, 38 Drawing Sheets

Specification includes a Sequence Listing.

(56) References Cited

OTHER PUBLICATIONS

Marcandalli et al., "Induction of Potent Neutralizing Antibody Responses by a Designed Protein Nanoparticle Vaccine for Respiratory Syncytial Virus," *Cell* 177: 1420-1431, Mar. 2019.
Pedrera et al., "Bovine Herpesvirus-4-Vectored Delivery of Nipah Virus Glycoproteins Enhances T Cell Immunogenicity in Pigs," *Vaccine* 8.115: 8010115, Mar. 2020 (26 pages).
Pickering et al., "Protection against henipaviruses in swine requires both, cell-mediated and humoral immune response," *Vaccine* 34.40: 4777-4786, Sep. 2016.
Roth et al., "A Modified mRNA Vaccine Targeting Immunodominant NS Epitopes Protects Against Dengue Virus Infection in HLA Class I Transgenic Mice," *Front Immunol.* 10: 1424, Jun. 2019 (14 pages).
Wong et al., "Structure and stabilization of the Hendra virus F glycoprotein in its prefusion form," *Proc Natl Acad Sci.* 113.4: 1056-1061, Jan. 2016.
Xu et al., "Crystal Structure of the Pre-fusion Nipah Virus Fusion Glycoprotein Reveals a Novel Hexamer-of-Trimers Assembly," *PLoS Path.* 11.12: e1005322, Dec. 2015 (20 pages).
Yin et al., "Structure of the parainfluenza virus 5 F protein in its metastable, prefusion conformation," *Nature* 439.7072: 38-44, Jan. 2006.
Loomis et al., "Chimeric Fusion (F) and Attachment (G) Glycoprotein Antigen Delivery by mRNA as a Candidate Nipah Vaccine," *Frontiers in Immunology* 12: 772864, Dec. 2021 (w/supplemental material; 23 pages).

* cited by examiner

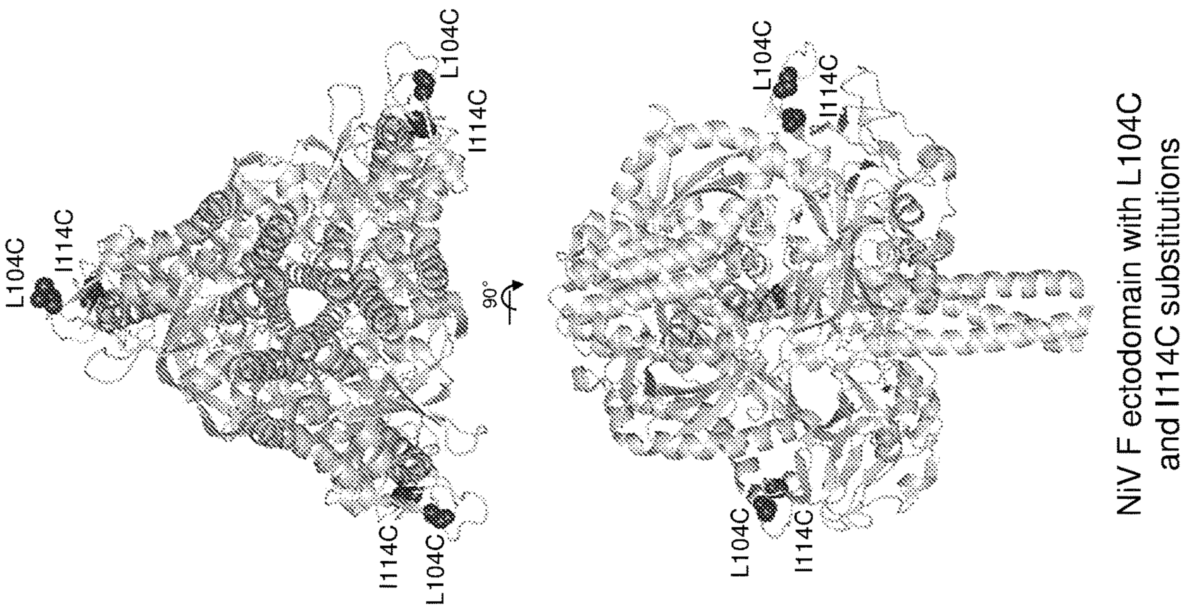
FIG. 1A
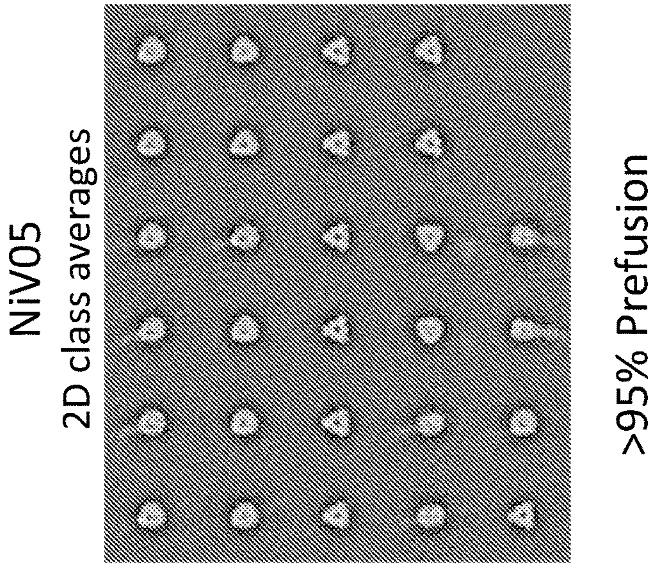

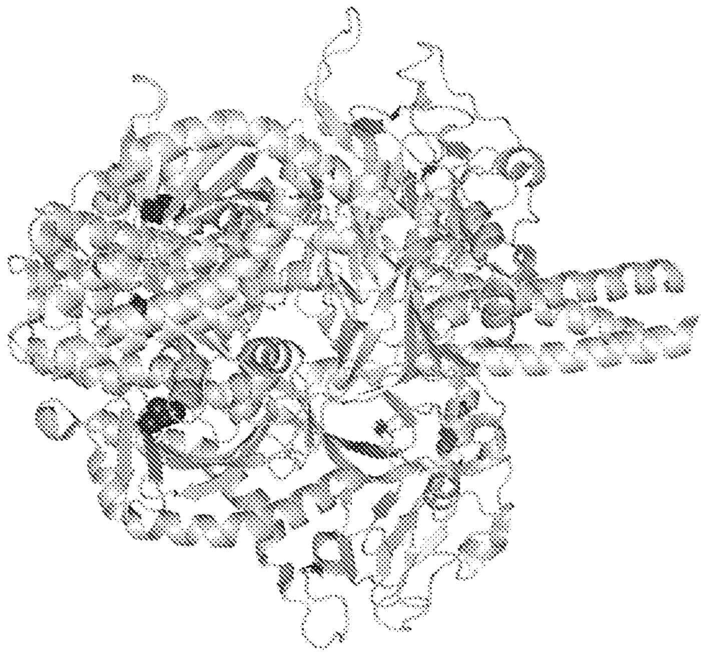
NiV F ectodomain with L172F substitutions
FIG. 1B
NiV08
2D class averages
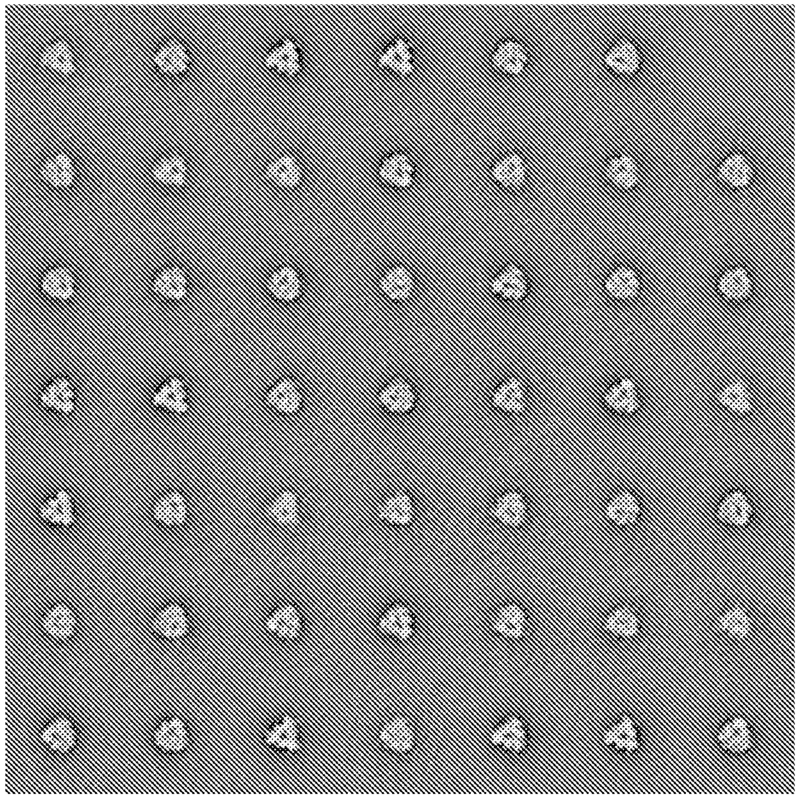
>95% Prefusion NiV09
2D class averages >95% Prefusion NiV F ectodomain with S191P substitutions NiV06
2D class averages >95% Postfusion

Mouse Immunization Schema and Immunogens

| Group | Name | Group | Name |
|---|---|---|---|
| 1 | NiVop02 | 8 | NiVop06-2 |
| 2 | NiV04 | 9 | NiVop08 |
| 3 | NiV05 | 10 | NiV09 |
| 4 | NiV07-1 | 11 | NiVop12 |
| 5 | NiV07-2 | 12 | NiVop14 |
| 6 | NiV06 | 13 | NiVop13 |
| 7 | NiVop05 | 14 | NiV08 |

Stabilized Prefusion NiV F Designs are Immunogenic

Stabilized Prefusion NiV F Designs Elicit Neutralizing Antibodies

NiV pseudovirus neutralization using immune sera

| Immunogen | IC80 |
|---|---|
| NiV06 (Post-F) | <25 |
| NiVop02 (Pre-F) | 1370 |
| NiVop05 (Pre-F) | 1374 |
| NiVop08 (Pre-F) | 1091 |
| NiVop12 (Pre-F) | 849 |

FIG. 5A

NiV G-5aa Linker-Ferritin

Representative Images at 50,000x

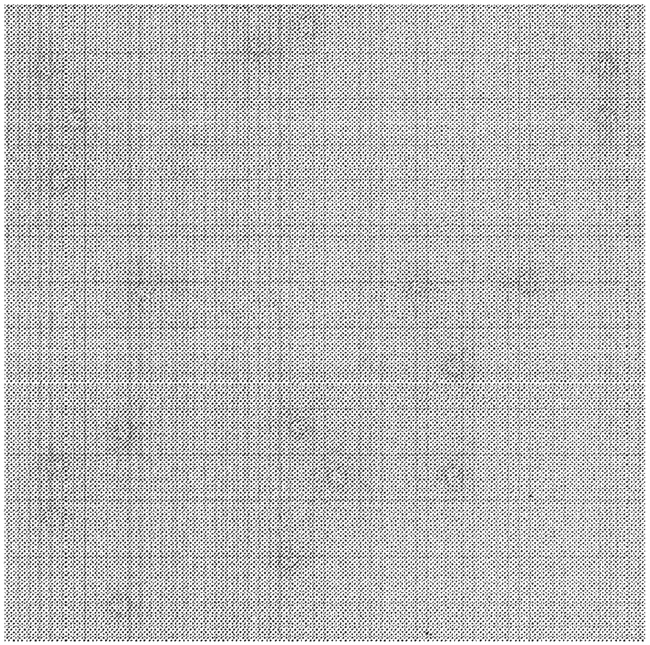

2D Class Averages

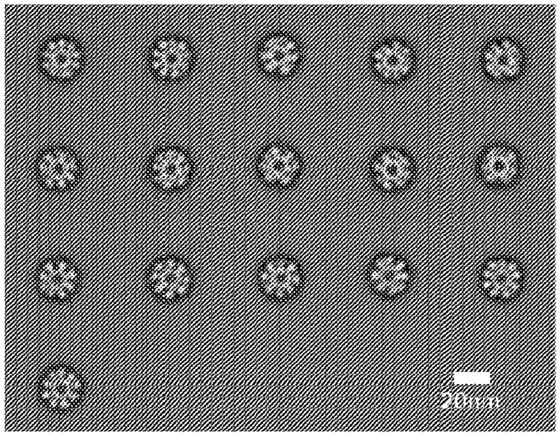

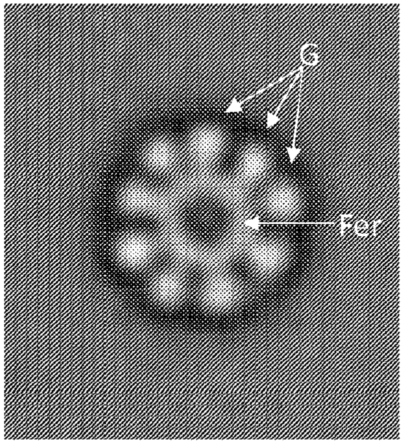

Protein expression: 1.6 mg/L

5aa G-Fer linker
(length 15 Å)

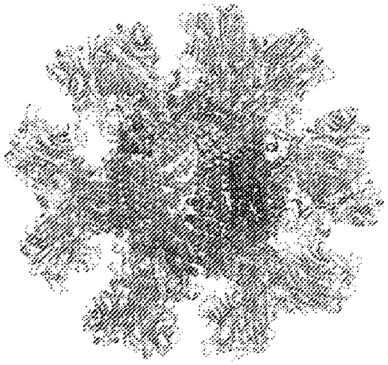

The sample is composed of well-formed, homogeneous particles. This was confirmed by the 2D class averages. The size of the core is 11.9 ± 0.4 nm. The length of the spike is 6.2 ± 0.7 nm (the spike is likely bigger because spike projections were measured in the plane of the micrograph).

NiV G-15aa Linker-Ferritin

The sample contains a mixture of objects. There are round nanoparticles, elongated nanoparticles, and some aggregates. 2D classification revealed the round cores, where present, as well as "spikes".

NiV G-25aa linker-Ferritin

Representative Image at 50,000x

2D Class Averages

The sample contains a mixture of objects. There are round nanoparticles, elongated nanoparticles, and some aggregates. Unassembled fragments are also present. 2D classification revealed the round cores, where present, as well as “spikes”.

Mouse Immunization Scheme

NiV G Immunogenic Readout of Monovalent vs Nanoparticle Immunogens

NiV G multimers Elicit Neutralizing Antibodies

NiV pseudovirus neutralization using immune sera

| Immunogen | IC80 |
| --- | --- |
| G monomer | 388 |
| G-Fd (3-mer) | 628 |
| G-Fd-G (6-mer) | 3426 |
| G-ferritin | 2103 |

NiV F/G Chimeras

NiV F/G ectodomain chimera multimers

Stabilized Prefusion NiV F-G Designs Elicit Neutralizing Antibodies

| Immunogen | IC80 |
|---|---|
| PreF (NiVop8) | 1091 |
| G-Fd (3-mer) | 628 |
| NiVop08-TD-G | 6763 |
| G-NiVop08-TD | 4535 |
| PreF (NiVop08) + G-Fd (3-mer) | 1406 |

FIG. 9A

- Immunization of ferrets with mRNA or protein
- 16 groups (4 immunogens x 4 doses)
  - pre-F
    - mRNA encoding full-length NiV F with NiVop08 ectodomain substitutions at a dose of 10 µg, 30 µg, or 100 µg
    - Soluble NiVop08 protein at a dose of 10 µg
  - post-F
    - mRNA encoding full-length NiV F with NiV06 ectodomain substitutions at a dose of 10 µg, 30 µg, or 100 µg
    - Soluble NiV06 protein at a dose of 10 µg
  - Soluble G hexamer
    - mRNA encoding G-Fd-G at a dose of 10 µg, 30 µg, or 100 µg
    - Soluble G-Fd-G protein at a dose of 10 µg
  - Soluble pre-F/G
    - mRNA encoding NiVop08-TD-G at a dose of 10 µg, 30 µg, or 100 µg
    - Soluble NiVop08-TD-G protein at a dose of 10 µg

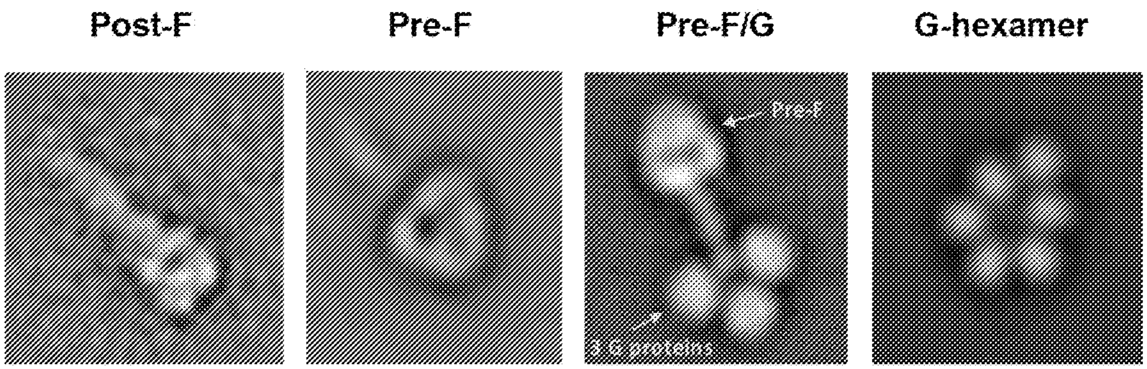

| Reciprocal IC80 | 100ug mRNA | 33ug mRNA | 10ug mRNA | 10ug protein |
|---|---|---|---|---|
| Pre-F | 870 | 668 | 527 | 1232 |
| Post-F | nn | nn | nn | nn |
| Hexameric G | 5389 | 3962 | 4999 | 10082 |
| Pre-F/G | 17004 | 5077 | 3292 | 13487 |

FIG. 12A

*Immunogen Comparison*

| Vaccine information | | | | | # of mice | Immunizations | |
|---|---|---|---|---|---|---|---|
| Group | Platform | Antigen | Signal Sequence | TM or S | Number | Week 0 | Week 3 |
| 1 | mRNA | Pre-F | Native | S | 10 | 1μg | 1μg |
| 2 | mRNA | Pre-F | Native | TM | 10 | 1μg | 1μg |
| 3 | mRNA | Pre-F | IL-2 | S | 10 | 1μg | 1μg |
| 4 | mRNA | Post-F | IL-2 | S | 10 | 1μg | 1μg |
| 5 | mRNA | WT-F | Native | TM | 10 | 1μg | 1μg |
| 6 | Protein | Pre-F | IL-2 | S | 10 | 1μg | 1μg |
| 7 | mRNA | G-hexamer | IL-2 | S | 10 | 1μg | 1μg |
| 8 | mRNA | G-hexamer | IL-2 | TM | 10 | 1μg | 1μg |
| 9 | Protein | G hexamer | IL-2 | S | 10 | 10μg | 10μg |
| 10 | Protein | G (+Stalk) | IL-2 | S | 10 | 10μg | 10μg |

FIG. 13B

| Group | Vaccine | Number | Week 0 | Week 3 |
|---|---|---|---|---|
| 1 | Pre-F Protein | 10 | 10μg | 10μg |
| 2 | Pre-F mRNA | 10 | 1μg | 1μg |
| 3 | Pre-F mRNA | 10 | 3μg | 3μg |
| 4 | Pre-F mRNA | 10 | 10μg | 10μg |
| 5 | Post-F Protein | 10 | 10μg | 10μg |
| 6 | Post-F mRNA | 10 | 1μg | 1μg |
| 7 | Post-F mRNA | 10 | 3μg | 3μg |
| 8 | Post-F mRNA | 10 | 10μg | 10μg |

| Group | Vaccine | Number | Week 0 | Week 3 |
|---|---|---|---|---|
| 1 | G-hexamer Protein | 10 | 10μg | 10μg |
| 2 | G-hexamer mRNA | 10 | 1μg | 1μg |
| 3 | G-hexamer mRNA | 10 | 3μg | 3μg |
| 4 | G-hexamer mRNA | 10 | 10μg | 10μg |
| 5 | Pre-F-G Protein | 10 | 10μg | 10μg |
| 6 | Pre-F-G mRNA | 10 | 1μg | 1μg |
| 7 | Pre-F-G mRNA | 10 | 3μg | 3μg |
| 8 | Pre-F-G mRNA | 10 | 10μg | 10μg |

SEQUENCE LISTING

<160> NUMBER OF SEQ ID NOS: 70

<210> SEQ ID NO 1
<211> LENGTH: 543
<212> TYPE: PRT
<213> ORGANISM: Artificial sequence
<220> FEATURE:
<223> OTHER INFORMATION: Recombinant Nipah virus F sequence

<400> SEQUENCE: 1

Met Tyr Ser Met Gln Leu Ala Ser Cys Val Thr Leu Thr Leu Val Leu
1 5 10 15

Leu Val Asn Ser Gln Gly Ile Leu His Tyr Glu Lys Leu Ser Lys Ile
20 25 30

Gly Leu Val Lys Gly Val Thr Arg Lys Tyr Lys Ile Lys Ser Asn Pro
35 40 45

Leu Thr Lys Asp Ile Val Ile Lys Met Ile Pro Asn Val Ser Asp Met
50 55 60

Ser Gln Cys Thr Gly Ser Val Met Glu Asn Tyr Lys Thr Arg Leu Asn
65 70 75 80

Gly Ile Leu Thr Pro Ile Lys Gly Ala Leu Glu Ile Tyr Lys Asn Asn
85 90 95

Thr His Asp Leu Val Gly Asp Val Arg Leu Ala Gly Val Ile Met Ala
100 105 110

Gly Val Ala Ile Gly Ile Ala Thr Ala Ala Gln Ile Thr Ala Gly Val
115 120 125

Ala Leu Tyr Glu Ala Met Lys Asn Ala Asp Asn Ile Asn Lys Leu Lys
130 135 140

Ser Ser Ile Glu Ser Thr Asn Glu Ala Val Val Lys Leu Gln Glu Thr
145 150 155 160

Ala Glu Lys Thr Val Tyr Val Leu Thr Ala Leu Gln Asp Tyr Ile Asn
165 170 175

Thr Asn Leu Val Pro Thr Ile Asp Lys Ile Ser Cys Lys Gln Thr Glu
180 185 190

Leu Ser Leu Asp Leu Ala Leu Ser Lys Tyr Leu Ser Asp Leu Leu Phe
195 200 205

Val Phe Gly Pro Asn Leu Gln Asp Pro Val Ser Asn Ser Met Thr Ile
210 215 220

Gln Ala Ile Ser Gln Ala Phe Gly Gly Asn Tyr Glu Thr Leu Leu Arg
225 230 235 240

Thr Leu Gly Tyr Ala Thr Glu Asp Phe Asp Asp Leu Leu Glu Ser Asp
245 250 255

Ser Ile Thr Gly Gln Ile Ile Tyr Val Asp Leu Ser Ser Tyr Tyr Ile
260 265 270

Ile Val Arg Val Tyr Phe Pro Ile Leu Thr Glu Ile Gln Gln Ala Tyr
275 280 285

Ile Gln Glu Leu Leu Pro Val Ser Phe Asn Asn Asp Asp Ser Glu Trp
290 295 300

Ile Ser Ile Val Pro Asn Phe Ile Leu Val Arg Asn Thr Leu Ile Ser
305 310 315 320

Asn Ile Glu Ile Gly Phe Cys Leu Ile Thr Lys Arg Ser Val Ile Cys
325 330 335

Asn Gln Asp Tyr Ala Thr Pro Met Thr Asn Asn Met Arg Glu Cys Leu
340 345 350

Thr Gly Ser Thr Glu Lys Cys Pro Arg Glu Leu Val Val Ser Ser His

-continued

```
        355                 360                 365

Val Pro Arg Phe Ala Leu Ser Asn Gly Val Leu Phe Ala Asn Cys Ile
    370                 375                 380

Ser Val Thr Cys Gln Cys Gln Thr Thr Gly Arg Ala Ile Ser Gln Ser
385                 390                 395                 400

Gly Glu Gln Thr Leu Leu Met Ile Asp Asn Thr Thr Cys Pro Thr Ala
                405                 410                 415

Val Leu Gly Asn Val Ile Ile Ser Leu Gly Lys Tyr Leu Gly Ser Val
            420                 425                 430

Asn Tyr Asn Ser Glu Gly Ile Ala Ile Gly Pro Pro Val Phe Thr Asp
        435                 440                 445

Lys Val Asp Ile Ser Ser Gln Ile Ser Ser Met Asn Gln Ser Leu Gln
    450                 455                 460

Gln Ser Lys Asp Tyr Ile Lys Glu Ala Gln Arg Leu Leu Asp Thr Val
465                 470                 475                 480

Asn Pro Ser Leu Lys Leu Met Lys Gln Ile Glu Asp Lys Ile Glu Glu
                485                 490                 495

Ile Leu Ser Lys Ile Tyr His Ile Glu Asn Glu Ile Ala Arg Ile Lys
            500                 505                 510

Lys Leu Ile Gly Glu Ala Pro Gly Gly Leu Val Pro Arg Gly Ser His
        515                 520                 525

His His His His His Ser Ala Trp Ser His Pro Gln Phe Glu Lys
    530                 535                 540


<210> SEQ ID NO 2
<211> LENGTH: 528
<212> TYPE: PRT
<213> ORGANISM: Artificial sequence
<220> FEATURE:
<223> OTHER INFORMATION: Recombinant Nipah virus F sequence

<400> SEQUENCE: 2

Met Tyr Ser Met Gln Leu Ala Ser Cys Val Thr Leu Thr Leu Val Leu
1               5                   10                  15

Leu Val Asn Ser Gln Gly Ile Leu His Tyr Glu Lys Leu Ser Lys Ile
            20                  25                  30

Gly Leu Val Lys Gly Val Thr Arg Lys Tyr Lys Ile Lys Ser Asn Pro
        35                  40                  45

Leu Thr Lys Asp Ile Val Ile Lys Met Ile Pro Asn Val Ser Asn Met
    50                  55                  60

Ser Gln Cys Thr Gly Ser Val Met Glu Asn Tyr Lys Thr Arg Leu Asn
65                  70                  75                  80

Gly Ile Leu Thr Pro Ile Lys Gly Ala Leu Glu Ile Tyr Lys Asn Asn
                85                  90                  95

Ser Gly Val Ala Ile Gly Ile Ala Thr Ala Ala Gln Ile Thr Ala Gly
            100                 105                 110

Val Ala Leu Tyr Glu Ala Met Lys Asn Ala Asp Asn Ile Asn Lys Leu
        115                 120                 125

Lys Ser Ser Ile Glu Ser Thr Asn Glu Ala Val Val Lys Leu Gln Glu
    130                 135                 140

Thr Ala Glu Lys Thr Val Tyr Val Leu Thr Ala Leu Gln Asp Tyr Ile
145                 150                 155                 160

Asn Thr Asn Leu Val Pro Thr Ile Asp Lys Ile Ser Cys Lys Gln Thr
                165                 170                 175

Glu Leu Ser Leu Asp Leu Ala Leu Ser Lys Tyr Leu Ser Asp Leu Leu
```

```
            180                 185                 190

Phe Val Phe Gly Pro Asn Leu Gln Asp Pro Val Ser Asn Ser Met Thr
        195                 200                 205

Ile Gln Ala Ile Ser Gln Ala Phe Gly Gly Asn Tyr Glu Thr Leu Leu
    210                 215                 220

Arg Thr Leu Gly Tyr Ala Thr Glu Asp Phe Asp Asp Leu Leu Glu Ser
225                 230                 235                 240

Asp Ser Ile Thr Gly Gln Ile Ile Tyr Val Asp Leu Ser Ser Tyr Tyr
                245                 250                 255

Ile Ile Val Arg Val Tyr Phe Pro Ile Leu Thr Glu Ile Gln Gln Ala
            260                 265                 270

Tyr Ile Gln Glu Leu Leu Pro Val Ser Phe Asn Asn Asp Asn Ser Glu
        275                 280                 285

Trp Ile Ser Ile Val Pro Asn Phe Ile Leu Val Arg Asn Thr Leu Ile
    290                 295                 300

Ser Asn Ile Glu Ile Gly Phe Cys Leu Ile Thr Lys Arg Ser Val Ile
305                 310                 315                 320

Cys Asn Gln Asp Tyr Ala Thr Pro Met Thr Asn Asn Met Arg Glu Cys
                325                 330                 335

Leu Thr Gly Ser Thr Glu Lys Cys Pro Arg Glu Leu Val Val Ser Ser
            340                 345                 350

His Val Pro Arg Phe Ala Leu Ser Asn Gly Val Leu Phe Ala Asn Cys
        355                 360                 365

Ile Ser Val Thr Cys Gln Cys Gln Thr Thr Gly Arg Ala Ile Ser Gln
    370                 375                 380

Ser Gly Glu Gln Thr Leu Leu Met Ile Asp Asn Thr Thr Cys Pro Thr
385                 390                 395                 400

Ala Val Leu Gly Asn Val Ile Ile Ser Leu Gly Lys Tyr Leu Gly Ser
                405                 410                 415

Val Asn Tyr Asn Ser Glu Gly Ile Ala Ile Gly Pro Pro Val Phe Thr
            420                 425                 430

Asp Lys Val Asp Ile Ser Ser Gln Ile Ser Ser Met Asn Gln Ser Leu
        435                 440                 445

Gln Gln Ser Lys Asp Tyr Ile Lys Glu Ala Gln Arg Leu Leu Asp Thr
    450                 455                 460

Val Asn Pro Ser Leu Lys Leu Met Lys Gln Ile Glu Asp Lys Ile Glu
465                 470                 475                 480

Glu Ile Leu Ser Lys Ile Tyr His Ile Glu Asn Glu Ile Ala Arg Ile
                485                 490                 495

Lys Lys Leu Ile Gly Glu Ala Pro Gly Gly Leu Val Pro Arg Gly Ser
            500                 505                 510

His His His His His His Ser Ala Trp Ser His Pro Gln Phe Glu Lys
        515                 520                 525


<210> SEQ ID NO 3
<211> LENGTH: 530
<212> TYPE: PRT
<213> ORGANISM: Artificial sequence
<220> FEATURE:
<223> OTHER INFORMATION: Recombinant Nipah virus F sequence

<400> SEQUENCE: 3

Met Tyr Ser Met Gln Leu Ala Ser Cys Val Thr Leu Thr Leu Val Leu
1               5                   10                  15

Leu Val Asn Ser Gln Gly Ile Leu His Tyr Glu Lys Leu Ser Lys Ile
```

-continued

```
            20                  25                  30

Gly Leu Val Lys Gly Val Thr Arg Lys Tyr Lys Ile Lys Ser Asn Pro
        35                  40                  45

Leu Thr Lys Asp Ile Val Ile Lys Met Ile Pro Asn Val Ser Asn Met
    50                  55                  60

Ser Gln Cys Thr Gly Ser Val Met Glu Asn Tyr Lys Thr Arg Leu Asn
65                  70                  75                  80

Gly Ile Leu Thr Pro Ile Lys Gly Ala Leu Glu Ile Tyr Lys Asn Gly
                85                  90                  95

Ser Gly Ala Gly Val Ala Ile Gly Ile Ala Thr Ala Ala Gln Ile Thr
            100                 105                 110

Ala Gly Val Ala Leu Tyr Glu Ala Met Lys Asn Ala Asp Asn Ile Asn
        115                 120                 125

Lys Leu Lys Ser Ser Ile Glu Ser Thr Asn Glu Ala Val Val Lys Leu
    130                 135                 140

Gln Glu Thr Ala Glu Lys Thr Val Tyr Val Leu Thr Ala Leu Gln Asp
145                 150                 155                 160

Tyr Ile Asn Thr Asn Leu Val Pro Thr Ile Asp Lys Ile Ser Cys Lys
                165                 170                 175

Gln Thr Glu Leu Ser Leu Asp Leu Ala Leu Ser Lys Tyr Leu Ser Asp
            180                 185                 190

Leu Leu Phe Val Phe Gly Pro Asn Leu Gln Asp Pro Val Ser Asn Ser
        195                 200                 205

Met Thr Ile Gln Ala Ile Ser Gln Ala Phe Gly Gly Asn Tyr Glu Thr
    210                 215                 220

Leu Leu Arg Thr Leu Gly Tyr Ala Thr Glu Asp Phe Asp Asp Leu Leu
225                 230                 235                 240

Glu Ser Asp Ser Ile Thr Gly Gln Ile Ile Tyr Val Asp Leu Ser Ser
                245                 250                 255

Tyr Tyr Ile Ile Val Arg Val Tyr Phe Pro Ile Leu Thr Glu Ile Gln
            260                 265                 270

Gln Ala Tyr Ile Gln Glu Leu Leu Pro Val Ser Phe Asn Asn Asp Asn
        275                 280                 285

Ser Glu Trp Ile Ser Ile Val Pro Asn Phe Ile Leu Val Arg Asn Thr
    290                 295                 300

Leu Ile Ser Asn Ile Glu Ile Gly Phe Cys Leu Ile Thr Lys Arg Ser
305                 310                 315                 320

Val Ile Cys Asn Gln Asp Tyr Ala Thr Pro Met Thr Asn Asn Met Arg
                325                 330                 335

Glu Cys Leu Thr Gly Ser Thr Glu Lys Cys Pro Arg Glu Leu Val Val
            340                 345                 350

Ser Ser His Val Pro Arg Phe Ala Leu Ser Asn Gly Val Leu Phe Ala
        355                 360                 365

Asn Cys Ile Ser Val Thr Cys Gln Cys Gln Thr Thr Gly Arg Ala Ile
    370                 375                 380

Ser Gln Ser Gly Glu Gln Thr Leu Leu Met Ile Asp Asn Thr Thr Cys
385                 390                 395                 400

Pro Thr Ala Val Leu Gly Asn Val Ile Ile Ser Leu Gly Lys Tyr Leu
                405                 410                 415

Gly Ser Val Asn Tyr Asn Ser Glu Gly Ile Ala Ile Gly Pro Pro Val
            420                 425                 430

Phe Thr Asp Lys Val Asp Ile Ser Ser Gln Ile Ser Ser Met Asn Gln
        435                 440                 445
```

Ser Leu Gln Gln Ser Lys Asp Tyr Ile Lys Glu Ala Gln Arg Leu Leu
    450                 455                 460

Asp Thr Val Asn Pro Ser Leu Lys Leu Met Lys Gln Ile Glu Asp Lys
465                 470                 475                 480

Ile Glu Glu Ile Leu Ser Lys Ile Tyr His Ile Glu Asn Glu Ile Ala
                485                 490                 495

Arg Ile Lys Lys Leu Ile Gly Glu Ala Pro Gly Gly Leu Val Pro Arg
            500                 505                 510

Gly Ser His His His His His His Ser Ala Trp Ser His Pro Gln Phe
        515                 520                 525

Glu Lys
    530

<210> SEQ ID NO 4
<211> LENGTH: 534
<212> TYPE: PRT
<213> ORGANISM: Artificial sequence
<220> FEATURE:
<223> OTHER INFORMATION: Recombinant Nipah virus F sequence

<400> SEQUENCE: 4

Met Tyr Ser Met Gln Leu Ala Ser Cys Val Thr Leu Thr Leu Val Leu
1               5                   10                  15

Leu Val Asn Ser Gln Gly Ile Leu His Tyr Glu Lys Leu Ser Lys Ile
            20                  25                  30

Gly Leu Val Lys Gly Val Thr Arg Lys Tyr Lys Ile Lys Ser Asn Pro
        35                  40                  45

Leu Thr Lys Asp Ile Val Ile Lys Met Ile Pro Asn Val Ser Asn Met
    50                  55                  60

Ser Gln Cys Thr Gly Ser Val Met Glu Asn Tyr Lys Thr Arg Leu Asn
65                  70                  75                  80

Gly Ile Leu Thr Pro Ile Lys Gly Ala Leu Glu Ile Tyr Lys Asn Asn
                85                  90                  95

Thr Gly Ser Gly Ile Met Ala Gly Val Ala Ile Gly Ile Ala Thr Ala
            100                 105                 110

Ala Gln Ile Thr Ala Gly Val Ala Leu Tyr Glu Ala Met Lys Asn Ala
        115                 120                 125

Asp Asn Ile Asn Lys Leu Lys Ser Ser Ile Glu Ser Thr Asn Glu Ala
    130                 135                 140

Val Val Lys Leu Gln Glu Thr Ala Glu Lys Thr Val Tyr Val Leu Thr
145                 150                 155                 160

Ala Leu Gln Asp Tyr Ile Asn Thr Asn Leu Val Pro Thr Ile Asp Lys
                165                 170                 175

Ile Ser Cys Lys Gln Thr Glu Leu Ser Leu Asp Leu Ala Leu Ser Lys
            180                 185                 190

Tyr Leu Ser Asp Leu Leu Phe Val Phe Gly Pro Asn Leu Gln Asp Pro
        195                 200                 205

Val Ser Asn Ser Met Thr Ile Gln Ala Ile Ser Gln Ala Phe Gly Gly
    210                 215                 220

Asn Tyr Glu Thr Leu Leu Arg Thr Leu Gly Tyr Ala Thr Glu Asp Phe
225                 230                 235                 240

Asp Asp Leu Leu Glu Ser Asp Ser Ile Thr Gly Gln Ile Ile Tyr Val
                245                 250                 255

Asp Leu Ser Ser Tyr Tyr Ile Ile Val Arg Val Tyr Phe Pro Ile Leu
            260                 265                 270

```
Thr Glu Ile Gln Gln Ala Tyr Ile Gln Glu Leu Leu Pro Val Ser Phe
        275                 280                 285

Asn Asn Asp Asn Ser Glu Trp Ile Ser Ile Val Pro Asn Phe Ile Leu
    290                 295                 300

Val Arg Asn Thr Leu Ile Ser Asn Ile Glu Ile Gly Phe Cys Leu Ile
305                 310                 315                 320

Thr Lys Arg Ser Val Ile Cys Asn Gln Asp Tyr Ala Thr Pro Met Thr
                325                 330                 335

Asn Asn Met Arg Glu Cys Leu Thr Gly Ser Thr Glu Lys Cys Pro Arg
            340                 345                 350

Glu Leu Val Val Ser Ser His Val Pro Arg Phe Ala Leu Ser Asn Gly
        355                 360                 365

Val Leu Phe Ala Asn Cys Ile Ser Val Thr Cys Gln Cys Gln Thr Thr
    370                 375                 380

Gly Arg Ala Ile Ser Gln Ser Gly Glu Gln Thr Leu Leu Met Ile Asp
385                 390                 395                 400

Asn Thr Thr Cys Pro Thr Ala Val Leu Gly Asn Val Ile Ile Ser Leu
                405                 410                 415

Gly Lys Tyr Leu Gly Ser Val Asn Tyr Asn Ser Glu Gly Ile Ala Ile
            420                 425                 430

Gly Pro Pro Val Phe Thr Asp Lys Val Asp Ile Ser Ser Gln Ile Ser
        435                 440                 445

Ser Met Asn Gln Ser Leu Gln Gln Ser Lys Asp Tyr Ile Lys Glu Ala
    450                 455                 460

Gln Arg Leu Leu Asp Thr Val Asn Pro Ser Leu Lys Leu Met Lys Gln
465                 470                 475                 480

Ile Glu Asp Lys Ile Glu Glu Ile Leu Ser Lys Ile Tyr His Ile Glu
                485                 490                 495

Asn Glu Ile Ala Arg Ile Lys Lys Leu Ile Gly Glu Ala Pro Gly Gly
            500                 505                 510

Leu Val Pro Arg Gly Ser His His His His His His Ser Ala Trp Ser
        515                 520                 525

His Pro Gln Phe Glu Lys
    530


<210> SEQ ID NO 5
<211> LENGTH: 543
<212> TYPE: PRT
<213> ORGANISM: Artificial sequence
<220> FEATURE:
<223> OTHER INFORMATION: Recombinant Nipah virus F sequence

<400> SEQUENCE: 5

Met Tyr Ser Met Gln Leu Ala Ser Cys Val Thr Leu Thr Leu Val Leu
1               5                   10                  15

Leu Val Asn Ser Gln Gly Ile Leu His Tyr Glu Lys Leu Ser Lys Ile
            20                  25                  30

Gly Leu Val Lys Gly Val Thr Arg Lys Tyr Lys Ile Lys Ser Asn Pro
        35                  40                  45

Leu Thr Lys Asp Ile Val Ile Lys Met Ile Pro Asn Val Ser Asn Met
    50                  55                  60

Ser Gln Cys Thr Gly Ser Val Met Glu Asn Tyr Lys Thr Arg Leu Asn
65                  70                  75                  80

Gly Ile Leu Thr Pro Ile Lys Gly Ala Leu Glu Ile Tyr Lys Asn Asn
                85                  90                  95
```

-continued

```
Thr His Asp Cys Val Gly Asp Val Arg Leu Ala Gly Val Cys Met Ala
            100                 105                 110

Gly Val Ala Ile Gly Ile Ala Thr Ala Ala Gln Ile Thr Ala Gly Val
        115                 120                 125

Ala Leu Tyr Glu Ala Met Lys Asn Ala Asp Asn Ile Asn Lys Leu Lys
    130                 135                 140

Ser Ser Ile Glu Ser Thr Asn Glu Ala Val Val Lys Leu Gln Glu Thr
145                 150                 155                 160

Ala Glu Lys Thr Val Tyr Val Leu Thr Ala Leu Gln Asp Tyr Ile Asn
                165                 170                 175

Thr Asn Leu Val Pro Thr Ile Asp Lys Ile Ser Cys Lys Gln Thr Glu
            180                 185                 190

Leu Ser Leu Asp Leu Ala Leu Ser Lys Tyr Leu Ser Asp Leu Leu Phe
        195                 200                 205

Val Phe Gly Pro Asn Leu Gln Asp Pro Val Ser Asn Ser Met Thr Ile
    210                 215                 220

Gln Ala Ile Ser Gln Ala Phe Gly Gly Asn Tyr Glu Thr Leu Leu Arg
225                 230                 235                 240

Thr Leu Gly Tyr Ala Thr Glu Asp Phe Asp Asp Leu Leu Glu Ser Asp
                245                 250                 255

Ser Ile Thr Gly Gln Ile Ile Tyr Val Asp Leu Ser Ser Tyr Tyr Ile
            260                 265                 270

Ile Val Arg Val Tyr Phe Pro Ile Leu Thr Glu Ile Gln Gln Ala Tyr
        275                 280                 285

Ile Gln Glu Leu Leu Pro Val Ser Phe Asn Asn Asp Asn Ser Glu Trp
    290                 295                 300

Ile Ser Ile Val Pro Asn Phe Ile Leu Val Arg Asn Thr Leu Ile Ser
305                 310                 315                 320

Asn Ile Glu Ile Gly Phe Cys Leu Ile Thr Lys Arg Ser Val Ile Cys
                325                 330                 335

Asn Gln Asp Tyr Ala Thr Pro Met Thr Asn Asn Met Arg Glu Cys Leu
            340                 345                 350

Thr Gly Ser Thr Glu Lys Cys Pro Arg Glu Leu Val Val Ser Ser His
        355                 360                 365

Val Pro Arg Phe Ala Leu Ser Asn Gly Val Leu Phe Ala Asn Cys Ile
    370                 375                 380

Ser Val Thr Cys Gln Cys Gln Thr Thr Gly Arg Ala Ile Ser Gln Ser
385                 390                 395                 400

Gly Glu Gln Thr Leu Leu Met Ile Asp Asn Thr Thr Cys Pro Thr Ala
                405                 410                 415

Val Leu Gly Asn Val Ile Ile Ser Leu Gly Lys Tyr Leu Gly Ser Val
            420                 425                 430

Asn Tyr Asn Ser Glu Gly Ile Ala Ile Gly Pro Pro Val Phe Thr Asp
        435                 440                 445

Lys Val Asp Ile Ser Ser Gln Ile Ser Ser Met Asn Gln Ser Leu Gln
    450                 455                 460

Gln Ser Lys Asp Tyr Ile Lys Glu Ala Gln Arg Leu Leu Asp Thr Val
465                 470                 475                 480

Asn Pro Ser Leu Lys Leu Met Lys Gln Ile Glu Asp Lys Ile Glu Glu
                485                 490                 495

Ile Leu Ser Lys Ile Tyr His Ile Glu Asn Glu Ile Ala Arg Ile Lys
            500                 505                 510
```

```
Lys Leu Ile Gly Glu Ala Pro Gly Gly Leu Val Pro Arg Gly Ser His
        515                 520                 525

His His His His His Ser Ala Trp Ser His Pro Gln Phe Glu Lys
    530                 535                 540


<210> SEQ ID NO 6
<211> LENGTH: 529
<212> TYPE: PRT
<213> ORGANISM: Artificial sequence
<220> FEATURE:
<223> OTHER INFORMATION: Recombinant Nipah virus F sequence

<400> SEQUENCE: 6

Met Tyr Ser Met Gln Leu Ala Ser Cys Val Thr Leu Thr Leu Val Leu
1               5                   10                  15

Leu Val Asn Ser Gln Gly Ile Leu His Tyr Glu Lys Leu Ser Lys Ile
            20                  25                  30

Gly Leu Val Lys Gly Val Thr Arg Lys Tyr Lys Ile Lys Ser Asn Pro
        35                  40                  45

Leu Thr Lys Asp Ile Val Ile Lys Met Ile Pro Asn Val Ser Asn Met
    50                  55                  60

Ser Gln Cys Thr Gly Ser Val Met Glu Asn Tyr Lys Thr Arg Leu Asn
65                  70                  75                  80

Gly Ile Leu Thr Pro Ile Lys Gly Ala Leu Glu Ile Tyr Lys Asn Gly
                85                  90                  95

Gly Ser Gly Val Ala Ile Gly Ile Ala Thr Ala Ala Gln Ile Thr Ala
            100                 105                 110

Gly Val Ala Leu Tyr Glu Ala Met Lys Asn Ala Asp Asn Ile Asn Lys
        115                 120                 125

Leu Lys Ser Ser Ile Glu Ser Thr Asn Glu Ala Val Val Lys Leu Gln
    130                 135                 140

Glu Thr Ala Glu Lys Thr Val Tyr Val Leu Thr Ala Leu Gln Asp Tyr
145                 150                 155                 160

Ile Asn Thr Asn Leu Val Pro Thr Ile Asp Lys Ile Ser Cys Lys Gln
                165                 170                 175

Thr Glu Leu Ser Leu Asp Leu Ala Leu Ser Lys Tyr Leu Ser Asp Leu
            180                 185                 190

Leu Phe Val Phe Gly Pro Asn Leu Gln Asp Pro Val Ser Asn Ser Met
        195                 200                 205

Thr Ile Gln Ala Ile Ser Gln Ala Phe Gly Gly Asn Tyr Glu Thr Leu
    210                 215                 220

Leu Arg Thr Leu Gly Tyr Ala Thr Glu Asp Phe Asp Asp Leu Leu Glu
225                 230                 235                 240

Ser Asp Ser Ile Thr Gly Gln Ile Ile Tyr Val Asp Leu Ser Ser Tyr
                245                 250                 255

Tyr Ile Ile Val Arg Val Tyr Phe Pro Ile Leu Thr Glu Ile Gln Gln
            260                 265                 270

Ala Tyr Ile Gln Glu Leu Leu Pro Val Ser Phe Asn Asn Asp Asn Ser
        275                 280                 285

Glu Trp Ile Ser Ile Val Pro Asn Phe Ile Leu Val Arg Asn Thr Leu
    290                 295                 300

Ile Ser Asn Ile Glu Ile Gly Phe Cys Leu Ile Thr Lys Arg Ser Val
305                 310                 315                 320

Ile Cys Asn Gln Asp Tyr Ala Thr Pro Met Thr Asn Asn Met Arg Glu
                325                 330                 335
```

-continued

```
Cys Leu Thr Gly Ser Thr Glu Lys Cys Pro Arg Glu Leu Val Val Ser
            340                 345                 350

Ser His Val Pro Arg Phe Ala Leu Ser Asn Gly Val Leu Phe Ala Asn
        355                 360                 365

Cys Ile Ser Val Thr Cys Gln Cys Gln Thr Thr Gly Arg Ala Ile Ser
    370                 375                 380

Gln Ser Gly Glu Gln Thr Leu Leu Met Ile Asp Asn Thr Thr Cys Pro
385                 390                 395                 400

Thr Ala Val Leu Gly Asn Val Ile Ile Ser Leu Gly Lys Tyr Leu Gly
                405                 410                 415

Ser Val Asn Tyr Asn Ser Glu Gly Ile Ala Ile Gly Pro Pro Val Phe
            420                 425                 430

Thr Asp Lys Val Asp Ile Ser Ser Gln Ile Ser Ser Met Asn Gln Ser
        435                 440                 445

Leu Gln Gln Ser Lys Asp Tyr Ile Lys Glu Ala Gln Arg Leu Leu Asp
    450                 455                 460

Thr Val Asn Pro Ser Leu Lys Leu Met Lys Gln Ile Glu Asp Lys Ile
465                 470                 475                 480

Glu Glu Ile Leu Ser Lys Ile Tyr His Ile Glu Asn Glu Ile Ala Arg
                485                 490                 495

Ile Lys Lys Leu Ile Gly Glu Ala Pro Gly Gly Leu Val Pro Arg Gly
            500                 505                 510

Ser His His His His His His Ser Ala Trp Ser His Pro Gln Phe Glu
        515                 520                 525

Lys


<210> SEQ ID NO 7
<211> LENGTH: 543
<212> TYPE: PRT
<213> ORGANISM: Artificial sequence
<220> FEATURE:
<223> OTHER INFORMATION: Recombinant Nipah virus F sequence

<400> SEQUENCE: 7

Met Tyr Ser Met Gln Leu Ala Ser Cys Val Thr Leu Thr Leu Val Leu
1               5                   10                  15

Leu Val Asn Ser Gln Gly Ile Leu His Tyr Glu Lys Leu Ser Lys Ile
            20                  25                  30

Gly Leu Val Lys Gly Val Thr Arg Lys Tyr Lys Ile Lys Ser Asn Pro
        35                  40                  45

Leu Thr Lys Asp Ile Val Ile Lys Met Ile Pro Asn Val Ser Asn Met
    50                  55                  60

Ser Gln Cys Thr Gly Ser Val Met Glu Asn Tyr Lys Thr Arg Leu Asn
65                  70                  75                  80

Gly Ile Leu Thr Pro Ile Lys Gly Ala Leu Glu Ile Tyr Lys Asn Asn
                85                  90                  95

Thr His Asp Leu Val Gly Asp Val Arg Leu Ala Gly Val Cys Met Ala
            100                 105                 110

Gly Val Ala Ile Gly Ile Ala Thr Ala Ala Gln Ile Thr Ala Gly Val
        115                 120                 125

Ala Leu Tyr Glu Ala Met Lys Asn Ala Asp Asn Ile Asn Lys Leu Lys
    130                 135                 140

Ser Ser Ile Glu Ser Thr Asn Glu Ala Val Val Lys Leu Gln Glu Thr
145                 150                 155                 160

Ala Glu Lys Thr Val Tyr Val Leu Thr Ala Leu Gln Asp Tyr Ile Asn
```

```
                165                 170                 175

Thr Asn Leu Val Pro Thr Ile Asp Lys Ile Ser Cys Lys Gln Thr Glu
            180                 185                 190

Leu Ser Leu Asp Leu Ala Leu Ser Lys Tyr Leu Ser Asp Leu Leu Phe
        195                 200                 205

Val Phe Gly Pro Asn Leu Gln Asp Pro Val Ser Asn Ser Met Thr Ile
    210                 215                 220

Gln Ala Ile Ser Gln Ala Phe Gly Gly Asn Tyr Glu Thr Leu Leu Arg
225                 230                 235                 240

Thr Leu Gly Tyr Ala Thr Glu Asp Phe Asp Asp Leu Leu Glu Ser Asp
                245                 250                 255

Ser Ile Thr Gly Gln Ile Ile Tyr Val Asp Leu Ser Ser Tyr Tyr Ile
            260                 265                 270

Ile Val Arg Val Tyr Phe Pro Ile Leu Thr Glu Ile Gln Gln Ala Tyr
        275                 280                 285

Ile Gln Glu Leu Leu Pro Val Ser Phe Asn Asn Asp Asn Ser Glu Trp
    290                 295                 300

Ile Ser Ile Val Pro Asn Phe Ile Leu Val Arg Asn Thr Leu Ile Ser
305                 310                 315                 320

Asn Ile Glu Ile Gly Phe Cys Leu Ile Thr Lys Arg Ser Val Ile Cys
                325                 330                 335

Asn Gln Asp Tyr Ala Thr Pro Met Thr Asn Asn Met Arg Glu Cys Leu
            340                 345                 350

Thr Gly Ser Thr Glu Lys Cys Pro Arg Glu Leu Val Val Ser Ser His
        355                 360                 365

Val Pro Arg Phe Ala Leu Ser Asn Gly Val Leu Phe Ala Asn Cys Ile
    370                 375                 380

Ser Val Thr Cys Gln Cys Gln Thr Thr Gly Arg Ala Ile Ser Gln Ser
385                 390                 395                 400

Gly Glu Gln Thr Leu Leu Met Ile Asp Asn Thr Thr Cys Pro Thr Ala
                405                 410                 415

Val Leu Gly Asn Val Cys Ile Ser Leu Gly Lys Tyr Leu Gly Ser Val
            420                 425                 430

Asn Tyr Asn Ser Glu Gly Ile Ala Ile Gly Pro Pro Val Phe Thr Asp
        435                 440                 445

Lys Val Asp Ile Ser Ser Gln Ile Ser Ser Met Asn Gln Ser Leu Gln
    450                 455                 460

Gln Ser Lys Asp Tyr Ile Lys Glu Ala Gln Arg Leu Leu Asp Thr Val
465                 470                 475                 480

Asn Pro Ser Leu Lys Leu Met Lys Gln Ile Glu Asp Lys Ile Glu Glu
                485                 490                 495

Ile Leu Ser Lys Ile Tyr His Ile Glu Asn Glu Ile Ala Arg Ile Lys
            500                 505                 510

Lys Leu Ile Gly Glu Ala Pro Gly Gly Leu Val Pro Arg Gly Ser His
        515                 520                 525

His His His His His Ser Ala Trp Ser His Pro Gln Phe Glu Lys
    530                 535                 540
```

<210> SEQ ID NO 8
<211> LENGTH: 543
<212> TYPE: PRT
<213> ORGANISM: Artificial sequence
<220> FEATURE:
<223> OTHER INFORMATION: Recombinant Nipah virus F sequence -continued

<400> SEQUENCE: 8

Met Tyr Ser Met Gln Leu Ala Ser Cys Val Thr Leu Thr Leu Val Leu
1 5 10 15

Leu Val Asn Ser Gln Gly Ile Leu His Tyr Glu Lys Leu Ser Lys Ile
20 25 30

Gly Leu Val Lys Gly Val Thr Arg Lys Tyr Lys Ile Lys Ser Asn Pro
35 40 45

Leu Thr Lys Asp Ile Val Ile Lys Met Ile Pro Asn Val Ser Asp Met
50 55 60

Ser Gln Cys Thr Gly Ser Val Met Glu Asn Tyr Lys Thr Arg Leu Asn
65 70 75 80

Gly Ile Leu Thr Pro Ile Lys Gly Ala Leu Glu Ile Tyr Lys Asn Asn
85 90 95

Thr His Asp Leu Val Gly Asp Val Arg Leu Ala Gly Val Ile Met Ala
100 105 110

Gly Val Ala Ile Gly Ile Ala Thr Ala Ala Gln Ile Thr Ala Gly Val
115 120 125

Ala Leu Tyr Glu Ala Met Lys Asn Ala Asp Asn Ile Asn Lys Leu Lys
130 135 140

Ser Ser Ile Glu Ser Thr Asn Glu Ala Val Val Lys Leu Gln Glu Thr
145 150 155 160

Ala Glu Lys Thr Val Tyr Val Phe Thr Ala Leu Gln Asp Tyr Ile Asn
165 170 175

Thr Asn Leu Val Pro Thr Ile Asp Lys Ile Ser Cys Lys Gln Thr Glu
180 185 190

Leu Ser Leu Asp Leu Ala Leu Ser Lys Tyr Leu Ser Asp Leu Leu Phe
195 200 205

Val Phe Gly Pro Asn Leu Gln Asp Pro Val Ser Asn Ser Met Thr Ile
210 215 220

Gln Ala Ile Ser Gln Ala Phe Gly Gly Asn Tyr Glu Thr Leu Leu Arg
225 230 235 240

Thr Leu Gly Tyr Ala Thr Glu Asp Phe Asp Asp Leu Leu Glu Ser Asp
245 250 255

Ser Ile Thr Gly Gln Ile Ile Tyr Val Asp Leu Ser Ser Tyr Tyr Ile
260 265 270

Ile Val Arg Val Tyr Phe Pro Ile Leu Thr Glu Ile Gln Gln Ala Tyr
275 280 285

Ile Gln Glu Leu Leu Pro Val Ser Phe Asn Asn Asp Asp Ser Glu Trp
290 295 300

Ile Ser Ile Val Pro Asn Phe Ile Leu Val Arg Asn Thr Leu Ile Ser
305 310 315 320

Asn Ile Glu Ile Gly Phe Cys Leu Ile Thr Lys Arg Ser Val Ile Cys
325 330 335

Asn Gln Asp Tyr Ala Thr Pro Met Thr Asn Asn Met Arg Glu Cys Leu
340 345 350

Thr Gly Ser Thr Glu Lys Cys Pro Arg Glu Leu Val Val Ser Ser His
355 360 365

Val Pro Arg Phe Ala Leu Ser Asn Gly Val Leu Phe Ala Asn Cys Ile
370 375 380

Ser Val Thr Cys Gln Cys Gln Thr Thr Gly Arg Ala Ile Ser Gln Ser
385 390 395 400

Gly Glu Gln Thr Leu Leu Met Ile Asp Asn Thr Thr Cys Pro Thr Ala
405 410 415

```
Val Leu Gly Asn Val Ile Ile Ser Leu Gly Lys Tyr Leu Gly Ser Val
            420                 425                 430

Asn Tyr Asn Ser Glu Gly Ile Ala Ile Gly Pro Pro Val Phe Thr Asp
        435                 440                 445

Lys Val Asp Ile Ser Ser Gln Ile Ser Ser Met Asn Gln Ser Leu Gln
    450                 455                 460

Gln Ser Lys Asp Tyr Ile Lys Glu Ala Gln Arg Leu Leu Asp Thr Val
465                 470                 475                 480

Asn Pro Ser Leu Lys Leu Met Lys Gln Ile Glu Asp Lys Ile Glu Glu
                485                 490                 495

Ile Leu Ser Lys Ile Tyr His Ile Glu Asn Glu Ile Ala Arg Ile Lys
            500                 505                 510

Lys Leu Ile Gly Glu Ala Pro Gly Gly Leu Val Pro Arg Gly Ser His
        515                 520                 525

His His His His His Ser Ala Trp Ser His Pro Gln Phe Glu Lys
    530                 535                 540


<210> SEQ ID NO 9
<211> LENGTH: 543
<212> TYPE: PRT
<213> ORGANISM: Artificial sequence
<220> FEATURE:
<223> OTHER INFORMATION: Recombinant Nipah virus F sequence

<400> SEQUENCE: 9

Met Tyr Ser Met Gln Leu Ala Ser Cys Val Thr Leu Thr Leu Val Leu
1               5                   10                  15

Leu Val Asn Ser Gln Gly Ile Leu His Tyr Glu Lys Leu Ser Lys Ile
            20                  25                  30

Gly Leu Val Lys Gly Val Thr Arg Lys Tyr Lys Ile Lys Ser Asn Pro
        35                  40                  45

Leu Thr Lys Asp Ile Val Ile Lys Met Ile Pro Asn Val Ser Asn Met
    50                  55                  60

Ser Gln Cys Thr Gly Ser Val Met Glu Asn Tyr Lys Thr Arg Leu Asn
65                  70                  75                  80

Gly Ile Leu Thr Pro Ile Lys Gly Ala Leu Glu Ile Tyr Lys Asn Asn
                85                  90                  95

Thr His Asp Leu Val Gly Asp Val Arg Leu Ala Gly Val Ile Met Ala
            100                 105                 110

Gly Val Ala Ile Gly Ile Ala Thr Ala Ala Gln Ile Thr Ala Gly Val
        115                 120                 125

Ala Leu Tyr Glu Ala Met Lys Asn Ala Asp Asn Ile Asn Lys Leu Lys
    130                 135                 140

Ser Ser Ile Glu Ser Thr Asn Glu Ala Val Val Lys Leu Gln Glu Thr
145                 150                 155                 160

Ala Glu Lys Thr Val Tyr Val Leu Thr Ala Leu Gln Asp Tyr Ile Asn
                165                 170                 175

Thr Asn Leu Val Pro Thr Ile Asp Lys Ile Pro Cys Lys Gln Thr Glu
            180                 185                 190

Leu Ser Leu Asp Leu Ala Leu Ser Lys Tyr Leu Ser Asp Leu Leu Phe
        195                 200                 205

Val Phe Gly Pro Asn Leu Gln Asp Pro Val Ser Asn Ser Met Thr Ile
    210                 215                 220

Gln Ala Ile Ser Gln Ala Phe Gly Gly Asn Tyr Glu Thr Leu Leu Arg
225                 230                 235                 240
```

```
Thr Leu Gly Tyr Ala Thr Glu Asp Phe Asp Asp Leu Leu Glu Ser Asp
                245                 250                 255

Ser Ile Thr Gly Gln Ile Ile Tyr Val Asp Leu Ser Ser Tyr Tyr Ile
            260                 265                 270

Ile Val Arg Val Tyr Phe Pro Ile Leu Thr Glu Ile Gln Gln Ala Tyr
        275                 280                 285

Ile Gln Glu Leu Leu Pro Val Ser Phe Asn Asn Asp Asn Ser Glu Trp
    290                 295                 300

Ile Ser Ile Val Pro Asn Phe Ile Leu Val Arg Asn Thr Leu Ile Ser
305                 310                 315                 320

Asn Ile Glu Ile Gly Phe Cys Leu Ile Thr Lys Arg Ser Val Ile Cys
                325                 330                 335

Asn Gln Asp Tyr Ala Thr Pro Met Thr Asn Asn Met Arg Glu Cys Leu
            340                 345                 350

Thr Gly Ser Thr Glu Lys Cys Pro Arg Glu Leu Val Val Ser Ser His
        355                 360                 365

Val Pro Arg Phe Ala Leu Ser Asn Gly Val Leu Phe Ala Asn Cys Ile
    370                 375                 380

Ser Val Thr Cys Gln Cys Gln Thr Thr Gly Arg Ala Ile Ser Gln Ser
385                 390                 395                 400

Gly Glu Gln Thr Leu Leu Met Ile Asp Asn Thr Thr Cys Pro Thr Ala
                405                 410                 415

Val Leu Gly Asn Val Ile Ile Ser Leu Gly Lys Tyr Leu Gly Ser Val
            420                 425                 430

Asn Tyr Asn Ser Glu Gly Ile Ala Ile Gly Pro Pro Val Phe Thr Asp
        435                 440                 445

Lys Val Asp Ile Ser Ser Gln Ile Ser Ser Met Asn Gln Ser Leu Gln
    450                 455                 460

Gln Ser Lys Asp Tyr Ile Lys Glu Ala Gln Arg Leu Leu Asp Thr Val
465                 470                 475                 480

Asn Pro Ser Leu Lys Leu Met Lys Gln Ile Glu Asp Lys Ile Glu Glu
                485                 490                 495

Ile Leu Ser Lys Ile Tyr His Ile Glu Asn Glu Ile Ala Arg Ile Lys
            500                 505                 510

Lys Leu Ile Gly Glu Ala Pro Gly Gly Leu Val Pro Arg Gly Ser His
        515                 520                 525

His His His His His Ser Ala Trp Ser His Pro Gln Phe Glu Lys
    530                 535                 540


<210> SEQ ID NO 10
<211> LENGTH: 526
<212> TYPE: PRT
<213> ORGANISM: Artificial sequence
<220> FEATURE:
<223> OTHER INFORMATION: Recombinant Nipah virus F sequence

<400> SEQUENCE: 10

Met Tyr Ser Met Gln Leu Ala Ser Cys Val Thr Leu Thr Leu Val Leu
1               5                   10                  15

Leu Val Asn Ser Gln Gly Ile Leu His Tyr Glu Lys Leu Ser Lys Ile
            20                  25                  30

Gly Leu Val Lys Gly Val Thr Arg Lys Tyr Lys Ile Lys Ser Asn Pro
        35                  40                  45

Leu Thr Lys Asp Ile Val Ile Lys Met Ile Pro Asn Val Ser Asn Met
    50                  55                  60
```

-continued

Ser Gln Cys Thr Gly Ser Val Met Glu Asn Tyr Lys Thr Arg Leu Asn
65 70 75 80

Gly Ile Leu Thr Pro Ile Lys Gly Ala Leu Glu Ile Tyr Lys Asn Gly
85 90 95

Val Ala Ile Gly Ile Ala Thr Ala Ala Gln Ile Thr Ala Gly Val Ala
100 105 110

Leu Tyr Glu Ala Met Lys Asn Ala Asp Asn Ile Asn Lys Leu Lys Ser
115 120 125

Ser Ile Glu Ser Thr Asn Glu Ala Val Val Lys Leu Gln Glu Thr Ala
130 135 140

Glu Lys Thr Val Tyr Val Leu Thr Ala Leu Gln Asp Tyr Ile Asn Thr
145 150 155 160

Asn Leu Val Pro Thr Ile Asp Lys Ile Ser Cys Lys Gln Thr Glu Leu
165 170 175

Ser Leu Asp Leu Ala Leu Ser Lys Tyr Leu Ser Asp Leu Leu Phe Val
180 185 190

Phe Gly Pro Asn Leu Gln Asp Pro Val Ser Asn Ser Met Thr Ile Gln
195 200 205

Ala Ile Ser Gln Ala Phe Gly Gly Asn Tyr Glu Thr Leu Leu Arg Thr
210 215 220

Leu Gly Tyr Ala Thr Glu Asp Phe Asp Asp Leu Leu Glu Ser Asp Ser
225 230 235 240

Ile Thr Gly Gln Ile Ile Tyr Val Asp Leu Ser Ser Tyr Tyr Ile Ile
245 250 255

Val Arg Val Tyr Phe Pro Ile Leu Thr Glu Ile Gln Gln Ala Tyr Ile
260 265 270

Gln Glu Leu Leu Pro Val Ser Phe Asn Asn Asp Asn Ser Glu Trp Ile
275 280 285

Ser Ile Val Pro Asn Phe Ile Leu Val Arg Asn Thr Leu Ile Ser Asn
290 295 300

Ile Glu Ile Gly Phe Cys Leu Ile Thr Lys Arg Ser Val Ile Cys Asn
305 310 315 320

Gln Asp Tyr Ala Thr Pro Met Thr Asn Asn Met Arg Glu Cys Leu Thr
325 330 335

Gly Ser Thr Glu Lys Cys Pro Arg Glu Leu Val Val Ser Ser His Val
340 345 350

Pro Arg Phe Ala Leu Ser Asn Gly Val Leu Phe Ala Asn Cys Ile Ser
355 360 365

Val Thr Cys Gln Cys Gln Thr Thr Gly Arg Ala Ile Ser Gln Ser Gly
370 375 380

Glu Gln Thr Leu Leu Met Ile Asp Asn Thr Thr Cys Pro Thr Ala Val
385 390 395 400

Leu Gly Asn Val Ile Ile Ser Leu Gly Lys Tyr Leu Gly Ser Val Asn
405 410 415

Tyr Asn Ser Glu Gly Ile Ala Ile Gly Pro Pro Val Phe Thr Asp Lys
420 425 430

Val Asp Ile Ser Ser Gln Ile Ser Ser Met Asn Gln Ser Leu Gln Gln
435 440 445

Ser Lys Asp Tyr Ile Lys Glu Ala Gln Arg Leu Leu Asp Thr Val Asn
450 455 460

Pro Ser Leu Lys Leu Met Lys Gln Ile Glu Asp Lys Ile Glu Glu Ile
465 470 475 480

-continued

```
Leu Ser Lys Ile Tyr His Ile Glu Asn Glu Ile Ala Arg Ile Lys Lys
                485                 490                 495

Leu Ile Gly Glu Ala Pro Gly Gly Leu Val Pro Arg Gly Ser His His
            500                 505                 510

His His His His Ser Ala Trp Ser His Pro Gln Phe Glu Lys
        515                 520                 525


<210> SEQ ID NO 11
<211> LENGTH: 543
<212> TYPE: PRT
<213> ORGANISM: Artificial sequence
<220> FEATURE:
<223> OTHER INFORMATION: Recombinant Nipah virus F sequence

<400> SEQUENCE: 11

Met Tyr Ser Met Gln Leu Ala Ser Cys Val Thr Leu Thr Leu Val Leu
1               5                   10                  15

Leu Val Asn Ser Gln Gly Ile Leu His Tyr Glu Lys Leu Ser Lys Ile
            20                  25                  30

Gly Leu Val Lys Gly Val Thr Arg Lys Tyr Lys Ile Lys Ser Asn Pro
        35                  40                  45

Leu Thr Lys Asp Ile Val Ile Lys Met Ile Pro Asn Val Ser Asn Met
    50                  55                  60

Ser Gln Cys Thr Gly Ser Val Met Glu Asn Tyr Lys Thr Arg Leu Asn
65                  70                  75                  80

Gly Ile Leu Thr Pro Ile Lys Gly Ala Leu Glu Ile Tyr Lys Asn Asn
                85                  90                  95

Thr His Asp Leu Val Gly Asp Val Arg Leu Ala Gly Val Ile Met Ala
            100                 105                 110

Gly Val Ala Ile Gly Ile Ala Thr Ala Ala Gln Ile Thr Ala Gly Val
        115                 120                 125

Ala Leu Tyr Glu Ala Met Lys Asn Ala Asp Asn Ile Asn Lys Leu Lys
    130                 135                 140

Ser Ser Ile Glu Ser Thr Asn Glu Ala Val Val Lys Leu Gln Glu Thr
145                 150                 155                 160

Ala Glu Lys Thr Val Tyr Val Leu Thr Ala Leu Gln Asp Trp Ile Asn
                165                 170                 175

Thr Asn Leu Val Pro Thr Ile Asp Lys Ile Ser Cys Lys Gln Thr Glu
            180                 185                 190

Leu Ser Leu Asp Leu Ala Leu Ser Lys Tyr Leu Ser Asp Leu Leu Phe
        195                 200                 205

Val Phe Gly Pro Asn Leu Gln Asp Pro Val Ser Asn Ser Met Thr Ile
    210                 215                 220

Gln Ala Ile Ser Gln Ala Phe Gly Gly Asn Tyr Glu Thr Leu Leu Arg
225                 230                 235                 240

Thr Leu Gly Tyr Ala Thr Glu Asp Phe Asp Asp Leu Leu Glu Ser Asp
                245                 250                 255

Ser Ile Thr Gly Gln Ile Ile Tyr Val Asp Leu Ser Ser Tyr Tyr Ile
            260                 265                 270

Ile Val Arg Val Tyr Phe Pro Ile Leu Thr Glu Ile Gln Gln Ala Tyr
        275                 280                 285

Ile Gln Glu Leu Leu Pro Val Ser Phe Asn Asn Asp Asn Ser Glu Trp
    290                 295                 300

Ile Ser Ile Val Pro Asn Phe Ile Leu Val Arg Asn Thr Leu Ile Ser
305                 310                 315                 320
```

```
Asn Ile Glu Ile Gly Phe Cys Leu Ile Thr Lys Arg Ser Val Ile Cys
                325                 330                 335

Asn Gln Asp Tyr Ala Thr Pro Met Thr Asn Asn Met Arg Glu Cys Leu
            340                 345                 350

Thr Gly Ser Thr Glu Lys Cys Pro Arg Glu Leu Val Val Ser Ser His
        355                 360                 365

Val Pro Arg Phe Ala Leu Ser Asn Gly Val Leu Phe Ala Asn Cys Ile
    370                 375                 380

Ser Val Thr Cys Gln Cys Gln Thr Thr Gly Arg Ala Ile Ser Gln Ser
385                 390                 395                 400

Gly Glu Gln Thr Leu Leu Met Ile Asp Asn Thr Thr Cys Pro Thr Ala
                405                 410                 415

Val Leu Gly Asn Val Ile Ile Ser Leu Gly Lys Tyr Leu Gly Ser Val
            420                 425                 430

Asn Tyr Asn Ser Glu Gly Ile Ala Ile Gly Pro Pro Val Phe Thr Asp
        435                 440                 445

Lys Val Asp Ile Ser Ser Gln Ile Ser Ser Met Asn Gln Ser Leu Gln
    450                 455                 460

Gln Ser Lys Asp Tyr Ile Lys Glu Ala Gln Arg Leu Leu Asp Thr Val
465                 470                 475                 480

Asn Pro Ser Leu Lys Leu Met Lys Gln Ile Glu Asp Lys Ile Glu Glu
                485                 490                 495

Ile Leu Ser Lys Ile Tyr His Ile Glu Asn Glu Ile Ala Arg Ile Lys
            500                 505                 510

Lys Leu Ile Gly Glu Ala Pro Gly Gly Leu Val Pro Arg Gly Ser His
        515                 520                 525

His His His His His Ser Ala Trp Ser His Pro Gln Phe Glu Lys
    530                 535                 540
```

<210> SEQ ID NO 12
<211> LENGTH: 543
<212> TYPE: PRT
<213> ORGANISM: Artificial sequence
<220> FEATURE:
<223> OTHER INFORMATION: Recombinant Nipah virus F sequence

<400> SEQUENCE: 12

```
Met Tyr Ser Met Gln Leu Ala Ser Cys Val Thr Leu Thr Leu Val Leu
1               5                   10                  15

Leu Val Asn Ser Gln Gly Ile Leu His Tyr Glu Lys Leu Ser Lys Ile
            20                  25                  30

Gly Leu Val Lys Gly Val Thr Arg Lys Tyr Lys Ile Lys Ser Asn Pro
        35                  40                  45

Leu Thr Lys Asp Ile Val Ile Lys Met Ile Pro Asn Val Ser Asn Met
    50                  55                  60

Ser Gln Cys Thr Gly Ser Val Met Glu Asn Tyr Lys Thr Arg Leu Asn
65                  70                  75                  80

Gly Ile Leu Thr Pro Ile Lys Gly Ala Leu Glu Ile Tyr Lys Asn Asn
                85                  90                  95

Thr His Asp Leu Val Gly Asp Val Arg Leu Ala Gly Val Ile Met Ala
            100                 105                 110

Gly Val Ala Ile Gly Ile Ala Thr Ala Ala Gln Ile Thr Cys Gly Val
        115                 120                 125

Ala Leu Tyr Glu Ala Met Lys Asn Ala Asp Asn Ile Asn Lys Leu Lys
    130                 135                 140
```

```
Ser Ser Ile Glu Ser Thr Asn Glu Ala Val Val Lys Leu Gln Glu Thr
145                 150                 155                 160

Ala Glu Lys Thr Val Tyr Val Leu Thr Ala Leu Gln Asp Tyr Ile Asn
                165                 170                 175

Thr Asn Leu Val Pro Thr Ile Asp Lys Ile Ser Cys Lys Gln Thr Glu
            180                 185                 190

Leu Ser Leu Asp Leu Ala Leu Ser Lys Tyr Leu Ser Asp Leu Leu Phe
        195                 200                 205

Val Phe Gly Pro Asn Leu Gln Asp Pro Cys Ser Asn Ser Met Thr Ile
    210                 215                 220

Gln Ala Ile Ser Gln Ala Phe Gly Gly Asn Tyr Glu Thr Leu Leu Arg
225                 230                 235                 240

Thr Leu Gly Tyr Ala Thr Glu Asp Phe Asp Asp Leu Leu Glu Ser Asp
                245                 250                 255

Ser Ile Thr Gly Gln Ile Ile Tyr Val Asp Leu Ser Ser Tyr Tyr Ile
            260                 265                 270

Ile Val Arg Val Tyr Phe Pro Ile Leu Thr Glu Ile Gln Gln Ala Tyr
        275                 280                 285

Ile Gln Glu Leu Leu Pro Val Ser Phe Asn Asn Asp Asn Ser Glu Trp
    290                 295                 300

Ile Ser Ile Val Pro Asn Phe Ile Leu Val Arg Asn Thr Leu Ile Ser
305                 310                 315                 320

Asn Ile Glu Ile Gly Phe Cys Leu Ile Thr Lys Arg Ser Val Ile Cys
                325                 330                 335

Asn Gln Asp Tyr Ala Thr Pro Met Thr Asn Asn Met Arg Glu Cys Leu
            340                 345                 350

Thr Gly Ser Thr Glu Lys Cys Pro Arg Glu Leu Val Val Ser Ser His
        355                 360                 365

Val Pro Arg Phe Ala Leu Ser Asn Gly Val Leu Phe Ala Asn Cys Ile
    370                 375                 380

Ser Val Thr Cys Gln Cys Gln Thr Thr Gly Arg Ala Ile Ser Gln Ser
385                 390                 395                 400

Gly Glu Gln Thr Leu Leu Met Ile Asp Asn Thr Thr Cys Pro Thr Ala
                405                 410                 415

Val Leu Gly Asn Val Ile Ile Ser Leu Gly Lys Tyr Leu Gly Ser Val
            420                 425                 430

Asn Tyr Asn Ser Glu Gly Ile Ala Ile Gly Pro Pro Val Phe Thr Asp
        435                 440                 445

Lys Val Asp Ile Ser Ser Gln Ile Ser Ser Met Asn Gln Ser Leu Gln
    450                 455                 460

Gln Ser Lys Asp Tyr Ile Lys Glu Ala Gln Arg Leu Leu Asp Thr Val
465                 470                 475                 480

Asn Pro Ser Leu Lys Leu Met Lys Gln Ile Glu Asp Lys Ile Glu Glu
                485                 490                 495

Ile Leu Ser Lys Ile Tyr His Ile Glu Asn Glu Ile Ala Arg Ile Lys
            500                 505                 510

Lys Leu Ile Gly Glu Ala Pro Gly Gly Leu Val Pro Arg Gly Ser His
        515                 520                 525

His His His His His Ser Ala Trp Ser His Pro Gln Phe Glu Lys
    530                 535                 540
```

<210> SEQ ID NO 13
<211> LENGTH: 543
<212> TYPE: PRT

<213> ORGANISM: Artificial sequence
<220> FEATURE:
<223> OTHER INFORMATION: Recombinant Nipah virus F sequence

<400> SEQUENCE: 13

Met Tyr Ser Met Gln Leu Ala Ser Cys Val Thr Leu Thr Leu Val Leu
1 5 10 15

Leu Val Asn Ser Gln Gly Ile Leu His Tyr Glu Lys Leu Ser Lys Ile
20 25 30

Gly Leu Val Lys Gly Val Thr Arg Lys Tyr Lys Ile Lys Ser Asn Pro
35 40 45

Leu Thr Lys Asp Ile Val Ile Lys Met Ile Pro Asn Val Ser Asn Met
50 55 60

Ser Gly Cys Thr Gly Ser Val Met Glu Asn Tyr Lys Thr Arg Leu Asn
65 70 75 80

Gly Ile Leu Thr Pro Ile Lys Gly Ala Leu Glu Ile Tyr Lys Asn Asn
85 90 95

Thr His Asp Leu Val Gly Asp Val Arg Leu Ala Gly Val Ile Met Ala
100 105 110

Gly Val Ala Ile Gly Ile Ala Thr Ala Ala Gln Ile Thr Ala Gly Val
115 120 125

Ala Leu Tyr Glu Ala Met Lys Asn Ala Asp Asn Ile Asn Lys Leu Lys
130 135 140

Ser Ser Ile Glu Ser Thr Asn Glu Ala Val Val Lys Leu Gln Glu Thr
145 150 155 160

Ala Glu Lys Thr Val Tyr Val Leu Thr Ala Leu Gln Asp Tyr Ile Asn
165 170 175

Thr Asn Leu Val Pro Thr Ile Asp Lys Ile Ser Cys Lys Gln Thr Glu
180 185 190

Leu Ser Leu Asp Leu Ala Leu Ser Lys Tyr Leu Ser Asp Leu Leu Phe
195 200 205

Val Phe Gly Pro Asn Leu Gln Asp Pro Val Ser Asn Ser Met Thr Ile
210 215 220

Gln Ala Ile Ser Gln Ala Phe Gly Gly Asn Tyr Glu Thr Leu Leu Arg
225 230 235 240

Thr Leu Gly Tyr Ala Thr Glu Asp Phe Asp Asp Leu Leu Glu Ser Asp
245 250 255

Ser Ile Thr Gly Gln Ile Ile Tyr Val Asp Leu Ser Ser Tyr Tyr Ile
260 265 270

Ile Val Arg Val Tyr Phe Pro Ile Leu Thr Glu Ile Gln Gln Ala Tyr
275 280 285

Ile Gln Glu Leu Leu Pro Val Ser Phe Asn Asn Asp Asn Ser Glu Trp
290 295 300

Ile Ser Ile Val Pro Asn Phe Ile Leu Val Arg Asn Thr Leu Ile Ser
305 310 315 320

Asn Ile Glu Ile Gly Phe Cys Leu Ile Thr Lys Arg Ser Val Ile Cys
325 330 335

Asn Gln Asp Tyr Ala Thr Pro Met Thr Asn Asn Met Arg Glu Cys Leu
340 345 350

Thr Gly Ser Thr Glu Lys Cys Pro Arg Glu Leu Val Val Ser Ser His
355 360 365

Val Pro Arg Phe Ala Leu Ser Asn Gly Val Leu Phe Ala Asn Cys Ile
370 375 380

Ser Val Thr Cys Gln Cys Gln Thr Thr Gly Arg Ala Ile Ser Gln Ser

-continued

```
385                 390                 395                 400

Gly Glu Gln Thr Leu Leu Met Ile Asp Asn Thr Thr Cys Pro Thr Ala
                405                 410                 415

Val Leu Gly Asn Val Ile Ile Ser Leu Gly Lys Tyr Leu Gly Ser Val
            420                 425                 430

Asn Tyr Asn Ser Glu Gly Ile Ala Ile Gly Pro Pro Val Phe Thr Asp
        435                 440                 445

Lys Val Asp Ile Ser Ser Gln Ile Ser Ser Met Asn Gln Ser Leu Gln
    450                 455                 460

Gln Ser Lys Asp Tyr Ile Lys Glu Ala Gln Arg Leu Leu Asp Thr Val
465                 470                 475                 480

Asn Pro Ser Leu Lys Leu Met Lys Gln Ile Glu Asp Lys Ile Glu Glu
                485                 490                 495

Ile Leu Ser Lys Ile Tyr His Ile Glu Asn Glu Ile Ala Arg Ile Lys
            500                 505                 510

Lys Leu Ile Gly Glu Ala Pro Gly Gly Leu Val Pro Arg Gly Ser His
        515                 520                 525

His His His His His Ser Ala Trp Ser His Pro Gln Phe Glu Lys
    530                 535                 540


<210> SEQ ID NO 14
<211> LENGTH: 543
<212> TYPE: PRT
<213> ORGANISM: Artificial sequence
<220> FEATURE:
<223> OTHER INFORMATION: Recombinant Nipah virus F sequence

<400> SEQUENCE: 14

Met Tyr Ser Met Gln Leu Ala Ser Cys Val Thr Leu Thr Leu Val Leu
1               5                   10                  15

Leu Val Asn Ser Gln Gly Ile Leu His Tyr Glu Lys Leu Ser Lys Ile
            20                  25                  30

Gly Leu Val Lys Gly Val Thr Arg Lys Tyr Lys Ile Lys Ser Asn Pro
        35                  40                  45

Leu Thr Lys Asp Ile Val Ile Lys Met Ile Pro Asn Val Ser Asn Met
    50                  55                  60

Ser Gln Cys Thr Gly Ser Val Met Glu Asn Tyr Lys Thr Arg Leu Asn
65                  70                  75                  80

Gly Ile Leu Thr Pro Ile Lys Gly Ala Leu Glu Ile Tyr Lys Asn Asn
                85                  90                  95

Thr His Asp Leu Val Gly Asp Val Arg Leu Ala Gly Val Ile Met Ala
            100                 105                 110

Gly Val Ala Ile Gly Ile Ala Thr Ala Ala Gln Ile Thr Ala Gly Val
        115                 120                 125

Ala Leu Tyr Glu Ala Met Lys Asn Ala Asp Asn Ile Asn Lys Leu Lys
    130                 135                 140

Ser Ser Ile Glu Ser Thr Asn Glu Ala Val Val Lys Leu Gln Glu Thr
145                 150                 155                 160

Ala Glu Lys Thr Val Tyr Val Leu Thr Ala Leu Gln Asp Tyr Ile Asn
                165                 170                 175

Thr Asn Leu Val Pro Thr Ile Gly Lys Ile Gly Cys Lys Gln Thr Glu
            180                 185                 190

Leu Ser Leu Asp Leu Ala Leu Ser Lys Tyr Leu Ser Asp Leu Leu Phe
        195                 200                 205

Val Phe Gly Pro Asn Leu Gln Asp Pro Val Ser Asn Ser Met Thr Ile
```

-continued

```
210                 215                 220

Gln Ala Ile Ser Gln Ala Phe Gly Gly Asn Tyr Glu Thr Leu Leu Arg
225                 230                 235                 240

Thr Leu Gly Tyr Ala Thr Glu Asp Phe Asp Asp Leu Leu Glu Ser Asp
                245                 250                 255

Ser Ile Thr Gly Gln Ile Ile Tyr Val Asp Leu Ser Ser Tyr Tyr Ile
            260                 265                 270

Ile Val Arg Val Tyr Phe Pro Ile Leu Thr Glu Ile Gln Gln Ala Tyr
        275                 280                 285

Ile Gln Glu Leu Leu Pro Val Ser Phe Asn Asn Asp Asn Ser Glu Trp
    290                 295                 300

Ile Ser Ile Val Pro Asn Phe Ile Leu Val Arg Asn Thr Leu Ile Ser
305                 310                 315                 320

Asn Ile Glu Ile Gly Phe Cys Leu Ile Thr Lys Arg Ser Val Ile Cys
                325                 330                 335

Asn Gln Asp Tyr Ala Thr Pro Met Thr Asn Asn Met Arg Glu Cys Leu
            340                 345                 350

Thr Gly Ser Thr Glu Lys Cys Pro Arg Glu Leu Val Val Ser Ser His
        355                 360                 365

Val Pro Arg Phe Ala Leu Ser Asn Gly Val Leu Phe Ala Asn Cys Ile
    370                 375                 380

Ser Val Thr Cys Gln Cys Gln Thr Thr Gly Arg Ala Ile Ser Gln Ser
385                 390                 395                 400

Gly Glu Gln Thr Leu Leu Met Ile Asp Asn Thr Thr Cys Pro Thr Ala
                405                 410                 415

Val Leu Gly Asn Val Ile Ile Ser Leu Gly Lys Tyr Leu Gly Ser Val
            420                 425                 430

Asn Tyr Asn Ser Glu Gly Ile Ala Ile Gly Pro Pro Val Phe Thr Asp
        435                 440                 445

Lys Val Asp Ile Ser Ser Gln Ile Ser Ser Met Asn Gln Ser Leu Gln
    450                 455                 460

Gln Ser Lys Asp Tyr Ile Lys Glu Ala Gln Arg Leu Leu Asp Thr Val
465                 470                 475                 480

Asn Pro Ser Leu Lys Leu Met Lys Gln Ile Glu Asp Lys Ile Glu Glu
                485                 490                 495

Ile Leu Ser Lys Ile Tyr His Ile Glu Asn Glu Ile Ala Arg Ile Lys
            500                 505                 510

Lys Leu Ile Gly Glu Ala Pro Gly Gly Leu Val Pro Arg Gly Ser His
        515                 520                 525

His His His His His Ser Ala Trp Ser His Pro Gln Phe Glu Lys
    530                 535                 540
```

<210> SEQ ID NO 15
<211> LENGTH: 543
<212> TYPE: PRT
<213> ORGANISM: Artificial sequence
<220> FEATURE:
<223> OTHER INFORMATION: Recombinant Nipah virus F sequence

<400> SEQUENCE: 15

```
Met Tyr Ser Met Gln Leu Ala Ser Cys Val Thr Leu Thr Leu Val Leu
1               5                   10                  15

Leu Val Asn Ser Gln Gly Ile Leu His Tyr Glu Lys Leu Ser Lys Ile
            20                  25                  30

Gly Leu Val Lys Gly Val Thr Arg Lys Tyr Lys Ile Lys Ser Asn Pro
```

-continued

```
        35                  40                  45

Leu Thr Lys Asp Ile Val Ile Lys Met Ile Pro Asn Val Ser Asp Met
    50                  55                  60

Ser Gln Cys Thr Gly Ser Val Met Glu Asn Tyr Lys Thr Arg Leu Asn
65                  70                  75                  80

Gly Ile Leu Thr Pro Ile Lys Gly Ala Leu Glu Ile Tyr Lys Asn Asn
                85                  90                  95

Thr His Asp Leu Val Gly Asp Val Arg Leu Ala Gly Val Ile Met Ala
            100                 105                 110

Gly Val Ala Ile Gly Ile Ala Thr Ala Ala Gln Ile Thr Ala Gly Val
        115                 120                 125

Ala Leu Tyr Glu Ala Met Lys Asn Ala Asp Asn Ile Asn Lys Leu Lys
    130                 135                 140

Ser Ser Ile Glu Ser Thr Asn Glu Ala Val Val Lys Leu Cys Glu Thr
145                 150                 155                 160

Ala Glu Lys Cys Val Tyr Val Leu Thr Ala Leu Gln Asp Tyr Ile Asn
                165                 170                 175

Thr Asn Leu Val Pro Thr Ile Asp Lys Ile Ser Cys Lys Gln Thr Glu
            180                 185                 190

Leu Ser Leu Asp Leu Ala Leu Ser Lys Tyr Leu Ser Asp Leu Leu Phe
        195                 200                 205

Val Phe Gly Pro Asn Leu Gln Asp Pro Val Ser Asn Ser Met Thr Ile
    210                 215                 220

Gln Ala Ile Ser Gln Ala Phe Gly Gly Asn Tyr Glu Thr Leu Leu Arg
225                 230                 235                 240

Thr Leu Gly Tyr Ala Thr Glu Asp Phe Asp Asp Leu Leu Glu Ser Asp
                245                 250                 255

Ser Ile Thr Gly Gln Ile Ile Tyr Val Asp Leu Ser Ser Tyr Tyr Ile
            260                 265                 270

Ile Val Arg Val Tyr Phe Pro Ile Leu Thr Glu Ile Gln Gln Ala Tyr
        275                 280                 285

Ile Gln Glu Leu Leu Pro Val Ser Phe Asn Asn Asp Asp Ser Glu Trp
    290                 295                 300

Ile Ser Ile Val Pro Asn Phe Ile Leu Val Arg Asn Thr Leu Ile Ser
305                 310                 315                 320

Asn Ile Glu Ile Gly Phe Cys Leu Ile Thr Lys Arg Ser Val Ile Cys
                325                 330                 335

Asn Gln Asp Tyr Ala Thr Pro Met Thr Asn Asn Met Arg Glu Cys Leu
            340                 345                 350

Thr Gly Ser Thr Glu Lys Cys Pro Arg Glu Leu Val Val Ser Ser His
        355                 360                 365

Val Pro Arg Phe Ala Leu Ser Asn Gly Val Leu Phe Ala Asn Cys Ile
    370                 375                 380

Ser Val Thr Cys Gln Cys Gln Thr Thr Gly Arg Ala Ile Ser Gln Ser
385                 390                 395                 400

Gly Glu Gln Thr Leu Leu Met Ile Asp Asn Thr Thr Cys Pro Thr Ala
                405                 410                 415

Val Leu Gly Asn Val Ile Ile Ser Leu Gly Lys Tyr Leu Gly Ser Val
            420                 425                 430

Asn Tyr Asn Ser Glu Gly Ile Ala Ile Gly Pro Pro Val Phe Thr Asp
        435                 440                 445

Lys Val Asp Ile Ser Ser Gln Ile Ser Ser Met Asn Gln Ser Leu Gln
    450                 455                 460
```

-continued

```
Gln Ser Lys Asp Tyr Ile Lys Glu Ala Gln Arg Leu Leu Asp Thr Val
465                 470                 475                 480

Asn Pro Ser Leu Lys Leu Met Lys Gln Ile Glu Asp Lys Ile Glu Glu
                485                 490                 495

Ile Leu Ser Lys Ile Tyr His Ile Glu Asn Glu Ile Ala Arg Ile Lys
            500                 505                 510

Lys Leu Ile Gly Glu Ala Pro Gly Gly Leu Val Pro Arg Gly Ser His
        515                 520                 525

His His His His His Ser Ala Trp Ser His Pro Gln Phe Glu Lys
    530                 535                 540


<210> SEQ ID NO 16
<211> LENGTH: 543
<212> TYPE: PRT
<213> ORGANISM: Artificial sequence
<220> FEATURE:
<223> OTHER INFORMATION: Recombinant Nipah virus F sequence

<400> SEQUENCE: 16

Met Tyr Ser Met Gln Leu Ala Ser Cys Val Thr Leu Thr Leu Val Leu
1               5                   10                  15

Leu Val Asn Ser Gln Gly Ile Leu His Tyr Glu Lys Leu Ser Lys Ile
            20                  25                  30

Gly Leu Val Lys Gly Val Thr Arg Lys Tyr Lys Ile Lys Ser Asn Pro
        35                  40                  45

Leu Thr Lys Asp Ile Val Ile Lys Met Ile Pro Asn Val Ser Asn Met
    50                  55                  60

Ser Gln Cys Thr Gly Ser Val Met Glu Asn Tyr Lys Thr Arg Leu Asn
65                  70                  75                  80

Gly Ile Leu Thr Pro Ile Lys Gly Ala Leu Glu Ile Tyr Lys Asn Asn
                85                  90                  95

Thr His Asp Leu Val Gly Asp Val Arg Leu Ala Gly Val Ile Met Ala
            100                 105                 110

Gly Val Ala Ile Gly Ile Ala Thr Ala Ala Gln Ile Thr Ala Gly Val
        115                 120                 125

Ala Leu Tyr Glu Ala Met Lys Asn Ala Asp Asn Ile Asn Lys Leu Lys
    130                 135                 140

Ser Ser Ile Glu Ser Thr Asn Glu Ala Val Val Lys Leu Gln Glu Thr
145                 150                 155                 160

Ala Glu Lys Thr Val Tyr Val Leu Thr Ala Leu Gln Asp Tyr Ile Asn
                165                 170                 175

Thr Asn Leu Val Pro Thr Ile Asp Lys Ile Ser Cys Lys Gln Thr Glu
            180                 185                 190

Leu Ser Leu Asp Leu Ala Leu Ser Lys Tyr Leu Ser Asp Leu Leu Phe
        195                 200                 205

Val Phe Gly Pro Asn Leu Gln Asp Pro Val Ser Asn Ser Met Thr Phe
    210                 215                 220

Gln Ala Ile Ser Gln Ala Phe Gly Gly Asn Tyr Glu Thr Leu Leu Arg
225                 230                 235                 240

Thr Leu Gly Tyr Ala Thr Glu Asp Phe Asp Asp Leu Leu Glu Ser Asp
                245                 250                 255

Ser Ile Thr Gly Gln Ile Ile Tyr Val Asp Leu Ser Ser Tyr Tyr Ile
            260                 265                 270

Ile Val Arg Val Tyr Phe Pro Ile Leu Thr Glu Ile Gln Gln Ala Tyr
        275                 280                 285
```

```
Ile Gln Glu Leu Leu Pro Val Ser Phe Asn Asn Asp Asn Ser Glu Trp
    290                 295                 300

Ile Ser Ile Val Pro Asn Phe Ile Leu Val Arg Asn Thr Leu Ile Ser
305                 310                 315                 320

Asn Ile Glu Ile Gly Phe Cys Leu Ile Thr Lys Arg Ser Val Ile Cys
                325                 330                 335

Asn Gln Asp Tyr Ala Thr Pro Met Thr Asn Asn Met Arg Glu Cys Leu
            340                 345                 350

Thr Gly Ser Thr Glu Lys Cys Pro Arg Glu Leu Val Val Ser Ser His
        355                 360                 365

Val Pro Arg Phe Ala Leu Ser Asn Gly Val Leu Phe Ala Asn Cys Ile
    370                 375                 380

Ser Val Thr Cys Gln Cys Gln Thr Thr Gly Arg Ala Ile Ser Gln Ser
385                 390                 395                 400

Gly Glu Gln Thr Leu Leu Met Ile Asp Asn Thr Thr Cys Pro Thr Ala
                405                 410                 415

Val Leu Gly Asn Val Ile Ile Ser Leu Gly Lys Tyr Leu Gly Ser Val
            420                 425                 430

Asn Tyr Asn Ser Glu Gly Ile Ala Ile Gly Pro Pro Val Phe Thr Asp
        435                 440                 445

Lys Val Asp Ile Ser Ser Gln Ile Ser Ser Met Asn Gln Ser Leu Gln
    450                 455                 460

Gln Ser Lys Asp Tyr Ile Lys Glu Ala Gln Arg Leu Leu Asp Thr Val
465                 470                 475                 480

Asn Pro Ser Leu Lys Leu Met Lys Gln Ile Glu Asp Lys Ile Glu Glu
                485                 490                 495

Ile Leu Ser Lys Ile Tyr His Ile Glu Asn Glu Ile Ala Arg Ile Lys
            500                 505                 510

Lys Leu Ile Gly Glu Ala Pro Gly Gly Leu Val Pro Arg Gly Ser His
        515                 520                 525

His His His His His Ser Ala Trp Ser His Pro Gln Phe Glu Lys
    530                 535                 540


<210> SEQ ID NO 17
<211> LENGTH: 543
<212> TYPE: PRT
<213> ORGANISM: Artificial sequence
<220> FEATURE:
<223> OTHER INFORMATION: Recombinant Nipah virus F sequence

<400> SEQUENCE: 17

Met Tyr Ser Met Gln Leu Ala Ser Cys Val Thr Leu Thr Leu Val Leu
1               5                   10                  15

Leu Val Asn Ser Gln Gly Ile Leu His Tyr Glu Lys Leu Ser Lys Ile
            20                  25                  30

Gly Leu Val Lys Gly Val Thr Arg Lys Tyr Lys Ile Lys Ser Asn Pro
        35                  40                  45

Leu Thr Lys Asp Ile Val Ile Lys Met Ile Pro Asn Val Ser Asn Met
    50                  55                  60

Ser Gln Cys Thr Gly Ser Val Met Glu Asn Tyr Lys Thr Arg Leu Asn
65                  70                  75                  80

Gly Ile Leu Thr Pro Ile Lys Gly Ala Leu Glu Ile Tyr Lys Asn Asn
                85                  90                  95

Thr His Asp Leu Val Gly Asp Val Arg Leu Ala Gly Val Cys Met Ala
            100                 105                 110
```

-continued

```
Gly Val Ala Ile Gly Ile Ala Thr Ala Ala Gln Ile Thr Ala Gly Val
        115                 120                 125

Ala Leu Tyr Glu Ala Met Lys Asn Ala Asp Asn Ile Asn Lys Leu Lys
    130                 135                 140

Ser Ser Ile Glu Ser Thr Asn Glu Ala Val Val Lys Leu Gln Glu Thr
145                 150                 155                 160

Ala Glu Lys Thr Val Tyr Val Phe Thr Ala Leu Gln Asp Tyr Ile Asn
                165                 170                 175

Thr Asn Leu Val Pro Thr Ile Asp Lys Ile Ser Cys Lys Gln Thr Glu
            180                 185                 190

Leu Ser Leu Asp Leu Ala Leu Ser Lys Tyr Leu Ser Asp Leu Leu Phe
        195                 200                 205

Val Phe Gly Pro Asn Leu Gln Asp Pro Val Ser Asn Ser Met Thr Ile
    210                 215                 220

Gln Ala Ile Ser Gln Ala Phe Gly Gly Asn Tyr Glu Thr Leu Leu Arg
225                 230                 235                 240

Thr Leu Gly Tyr Ala Thr Glu Asp Phe Asp Asp Leu Leu Glu Ser Asp
                245                 250                 255

Ser Ile Thr Gly Gln Ile Ile Tyr Val Asp Leu Ser Ser Tyr Tyr Ile
            260                 265                 270

Ile Val Arg Val Tyr Phe Pro Ile Leu Thr Glu Ile Gln Gln Ala Tyr
        275                 280                 285

Ile Gln Glu Leu Leu Pro Val Ser Phe Asn Asn Asp Asn Ser Glu Trp
    290                 295                 300

Ile Ser Ile Val Pro Asn Phe Ile Leu Val Arg Asn Thr Leu Ile Ser
305                 310                 315                 320

Asn Ile Glu Ile Gly Phe Cys Leu Ile Thr Lys Arg Ser Val Ile Cys
                325                 330                 335

Asn Gln Asp Tyr Ala Thr Pro Met Thr Asn Asn Met Arg Glu Cys Leu
            340                 345                 350

Thr Gly Ser Thr Glu Lys Cys Pro Arg Glu Leu Val Val Ser Ser His
        355                 360                 365

Val Pro Arg Phe Ala Leu Ser Asn Gly Val Leu Phe Ala Asn Cys Ile
    370                 375                 380

Ser Val Thr Cys Gln Cys Gln Thr Thr Gly Arg Ala Ile Ser Gln Ser
385                 390                 395                 400

Gly Glu Gln Thr Leu Leu Met Ile Asp Asn Thr Thr Cys Pro Thr Ala
                405                 410                 415

Val Leu Gly Asn Val Cys Ile Ser Leu Gly Lys Tyr Leu Gly Ser Val
            420                 425                 430

Asn Tyr Asn Ser Glu Gly Ile Ala Ile Gly Pro Pro Val Phe Thr Asp
        435                 440                 445

Lys Val Asp Ile Ser Ser Gln Ile Ser Ser Met Asn Gln Ser Leu Gln
    450                 455                 460

Gln Ser Lys Asp Tyr Ile Lys Glu Ala Gln Arg Leu Leu Asp Thr Val
465                 470                 475                 480

Asn Pro Ser Leu Lys Leu Met Lys Gln Ile Glu Asp Lys Ile Glu Glu
                485                 490                 495

Ile Leu Ser Lys Ile Tyr His Ile Glu Asn Glu Ile Ala Arg Ile Lys
            500                 505                 510

Lys Leu Ile Gly Glu Ala Pro Gly Gly Leu Val Pro Arg Gly Ser His
        515                 520                 525
```

His His His His His Ser Ala Trp Ser His Pro Gln Phe Glu Lys
530 535 540

<210> SEQ ID NO 18
<211> LENGTH: 543
<212> TYPE: PRT
<213> ORGANISM: Artificial sequence
<220> FEATURE:
<223> OTHER INFORMATION: Recombinant Nipah virus F sequence

<400> SEQUENCE: 18

Met Tyr Ser Met Gln Leu Ala Ser Cys Val Thr Leu Thr Leu Val Leu
1 5 10 15

Leu Val Asn Ser Gln Gly Ile Leu His Tyr Glu Lys Leu Ser Lys Ile
20 25 30

Gly Leu Val Lys Gly Val Thr Arg Lys Tyr Lys Ile Lys Ser Asn Pro
35 40 45

Leu Thr Lys Asp Ile Val Ile Lys Met Ile Pro Asn Val Ser Asn Met
50 55 60

Ser Gln Cys Thr Gly Ser Val Met Glu Asn Tyr Lys Thr Arg Leu Asn
65 70 75 80

Gly Ile Leu Thr Pro Ile Lys Gly Ala Leu Glu Ile Tyr Lys Asn Asn
85 90 95

Thr His Asp Cys Val Gly Asp Val Arg Leu Ala Gly Val Cys Met Ala
100 105 110

Gly Val Ala Ile Gly Ile Ala Thr Ala Ala Gln Ile Thr Ala Gly Val
115 120 125

Ala Leu Tyr Glu Ala Met Lys Asn Ala Asp Asn Ile Asn Lys Leu Lys
130 135 140

Ser Ser Ile Glu Ser Thr Asn Glu Ala Val Val Lys Leu Gln Glu Thr
145 150 155 160

Ala Glu Lys Thr Val Tyr Val Phe Thr Ala Leu Gln Asp Tyr Ile Asn
165 170 175

Thr Asn Leu Val Pro Thr Ile Asp Lys Ile Ser Cys Lys Gln Thr Glu
180 185 190

Leu Ser Leu Asp Leu Ala Leu Ser Lys Tyr Leu Ser Asp Leu Leu Phe
195 200 205

Val Phe Gly Pro Asn Leu Gln Asp Pro Val Ser Asn Ser Met Thr Ile
210 215 220

Gln Ala Ile Ser Gln Ala Phe Gly Gly Asn Tyr Glu Thr Leu Leu Arg
225 230 235 240

Thr Leu Gly Tyr Ala Thr Glu Asp Phe Asp Asp Leu Leu Glu Ser Asp
245 250 255

Ser Ile Thr Gly Gln Ile Ile Tyr Val Asp Leu Ser Ser Tyr Tyr Ile
260 265 270

Ile Val Arg Val Tyr Phe Pro Ile Leu Thr Glu Ile Gln Gln Ala Tyr
275 280 285

Ile Gln Glu Leu Leu Pro Val Ser Phe Asn Asn Asp Asn Ser Glu Trp
290 295 300

Ile Ser Ile Val Pro Asn Phe Ile Leu Val Arg Asn Thr Leu Ile Ser
305 310 315 320

Asn Ile Glu Ile Gly Phe Cys Leu Ile Thr Lys Arg Ser Val Ile Cys
325 330 335

Asn Gln Asp Tyr Ala Thr Pro Met Thr Asn Asn Met Arg Glu Cys Leu
340 345 350

Thr Gly Ser Thr Glu Lys Cys Pro Arg Glu Leu Val Val Ser Ser His
355 360 365

Val Pro Arg Phe Ala Leu Ser Asn Gly Val Leu Phe Ala Asn Cys Ile
370 375 380

Ser Val Thr Cys Gln Cys Gln Thr Thr Gly Arg Ala Ile Ser Gln Ser
385 390 395 400

Gly Glu Gln Thr Leu Leu Met Ile Asp Asn Thr Thr Cys Pro Thr Ala
405 410 415

Val Leu Gly Asn Val Ile Ile Ser Leu Gly Lys Tyr Leu Gly Ser Val
420 425 430

Asn Tyr Asn Ser Glu Gly Ile Ala Ile Gly Pro Pro Val Phe Thr Asp
435 440 445

Lys Val Asp Ile Ser Ser Gln Ile Ser Ser Met Asn Gln Ser Leu Gln
450 455 460

Gln Ser Lys Asp Tyr Ile Lys Glu Ala Gln Arg Leu Leu Asp Thr Val
465 470 475 480

Asn Pro Ser Leu Lys Leu Met Lys Gln Ile Glu Asp Lys Ile Glu Glu
485 490 495

Ile Leu Ser Lys Ile Tyr His Ile Glu Asn Glu Ile Ala Arg Ile Lys
500 505 510

Lys Leu Ile Gly Glu Ala Pro Gly Gly Leu Val Pro Arg Gly Ser His
515 520 525

His His His His His Ser Ala Trp Ser His Pro Gln Phe Glu Lys
530 535 540

<210> SEQ ID NO 19
<211> LENGTH: 534
<212> TYPE: PRT
<213> ORGANISM: Artificial sequence
<220> FEATURE:
<223> OTHER INFORMATION: Recombinant Nipah virus F sequence

<400> SEQUENCE: 19

Met Tyr Ser Met Gln Leu Ala Ser Cys Val Thr Leu Thr Leu Val Leu
1 5 10 15

Leu Val Asn Ser Gln Gly Ile Leu His Tyr Glu Lys Leu Ser Lys Ile
20 25 30

Gly Leu Val Lys Gly Val Thr Arg Lys Tyr Lys Ile Lys Ser Asn Pro
35 40 45

Leu Thr Lys Asp Ile Val Ile Lys Met Ile Pro Asn Val Ser Asn Met
50 55 60

Ser Gln Cys Thr Gly Ser Val Met Glu Asn Tyr Lys Thr Arg Leu Asn
65 70 75 80

Gly Ile Leu Thr Pro Ile Lys Gly Ala Leu Glu Ile Tyr Lys Asn Asn
85 90 95

Thr Gly Ser Gly Ile Met Ala Gly Val Ala Ile Gly Ile Ala Thr Ala
100 105 110

Ala Gln Ile Thr Ala Gly Val Ala Leu Tyr Glu Ala Met Lys Asn Ala
115 120 125

Asp Asn Ile Asn Lys Leu Lys Ser Ser Ile Glu Ser Thr Asn Glu Ala
130 135 140

Val Val Lys Leu Gln Glu Thr Ala Glu Lys Thr Val Tyr Val Phe Thr
145 150 155 160

Ala Leu Gln Asp Tyr Ile Asn Thr Asn Leu Val Pro Thr Ile Asp Lys
165 170 175

```
Ile Ser Cys Lys Gln Thr Glu Leu Ser Leu Asp Leu Ala Leu Ser Lys
            180                 185                 190

Tyr Leu Ser Asp Leu Leu Phe Val Phe Gly Pro Asn Leu Gln Asp Pro
        195                 200                 205

Val Ser Asn Ser Met Thr Ile Gln Ala Ile Ser Gln Ala Phe Gly Gly
    210                 215                 220

Asn Tyr Glu Thr Leu Leu Arg Thr Leu Gly Tyr Ala Thr Glu Asp Phe
225                 230                 235                 240

Asp Asp Leu Leu Glu Ser Asp Ser Ile Thr Gly Gln Ile Ile Tyr Val
                245                 250                 255

Asp Leu Ser Ser Tyr Tyr Ile Ile Val Arg Val Tyr Phe Pro Ile Leu
            260                 265                 270

Thr Glu Ile Gln Gln Ala Tyr Ile Gln Glu Leu Leu Pro Val Ser Phe
        275                 280                 285

Asn Asn Asp Asn Ser Glu Trp Ile Ser Ile Val Pro Asn Phe Ile Leu
    290                 295                 300

Val Arg Asn Thr Leu Ile Ser Asn Ile Glu Ile Gly Phe Cys Leu Ile
305                 310                 315                 320

Thr Lys Arg Ser Val Ile Cys Asn Gln Asp Tyr Ala Thr Pro Met Thr
                325                 330                 335

Asn Asn Met Arg Glu Cys Leu Thr Gly Ser Thr Glu Lys Cys Pro Arg
            340                 345                 350

Glu Leu Val Val Ser Ser His Val Pro Arg Phe Ala Leu Ser Asn Gly
        355                 360                 365

Val Leu Phe Ala Asn Cys Ile Ser Val Thr Cys Gln Cys Gln Thr Thr
    370                 375                 380

Gly Arg Ala Ile Ser Gln Ser Gly Glu Gln Thr Leu Leu Met Ile Asp
385                 390                 395                 400

Asn Thr Thr Cys Pro Thr Ala Val Leu Gly Asn Val Ile Ile Ser Leu
                405                 410                 415

Gly Lys Tyr Leu Gly Ser Val Asn Tyr Asn Ser Glu Gly Ile Ala Ile
            420                 425                 430

Gly Pro Pro Val Phe Thr Asp Lys Val Asp Ile Ser Ser Gln Ile Ser
        435                 440                 445

Ser Met Asn Gln Ser Leu Gln Gln Ser Lys Asp Tyr Ile Lys Glu Ala
    450                 455                 460

Gln Arg Leu Leu Asp Thr Val Asn Pro Ser Leu Lys Leu Met Lys Gln
465                 470                 475                 480

Ile Glu Asp Lys Ile Glu Glu Ile Leu Ser Lys Ile Tyr His Ile Glu
                485                 490                 495

Asn Glu Ile Ala Arg Ile Lys Lys Leu Ile Gly Glu Ala Pro Gly Gly
            500                 505                 510

Leu Val Pro Arg Gly Ser His His His His His His Ser Ala Trp Ser
        515                 520                 525

His Pro Gln Phe Glu Lys
    530
```

<210> SEQ ID NO 20
<211> LENGTH: 543
<212> TYPE: PRT
<213> ORGANISM: Artificial sequence
<220> FEATURE:
<223> OTHER INFORMATION: Recombinant Nipah virus F sequence

<400> SEQUENCE: 20

-continued

```
Met Tyr Ser Met Gln Leu Ala Ser Cys Val Thr Leu Thr Leu Val Leu
1               5                   10                  15

Leu Val Asn Ser Gln Gly Ile Leu His Tyr Glu Lys Leu Ser Lys Ile
            20                  25                  30

Gly Leu Val Lys Gly Val Thr Arg Lys Tyr Lys Ile Lys Ser Asn Pro
        35                  40                  45

Leu Thr Lys Asp Ile Val Ile Lys Met Ile Pro Asn Val Ser Asn Met
    50                  55                  60

Ser Gln Cys Thr Gly Ser Val Met Glu Asn Tyr Lys Thr Arg Leu Asn
65                  70                  75                  80

Gly Ile Leu Thr Pro Ile Lys Gly Ala Leu Glu Ile Tyr Lys Asn Asn
                85                  90                  95

Thr His Asp Leu Val Gly Asp Val Arg Leu Ala Gly Val Cys Met Ala
            100                 105                 110

Gly Val Ala Ile Gly Ile Ala Thr Ala Ala Gln Ile Thr Ala Gly Val
        115                 120                 125

Ala Leu Tyr Glu Ala Met Lys Asn Ala Asp Asn Ile Asn Lys Leu Lys
    130                 135                 140

Ser Ser Ile Glu Ser Thr Asn Glu Ala Val Val Lys Leu Gln Glu Thr
145                 150                 155                 160

Ala Glu Lys Thr Val Tyr Val Leu Thr Ala Leu Gln Asp Tyr Ile Asn
                165                 170                 175

Thr Asn Leu Val Pro Thr Ile Asp Lys Ile Pro Cys Lys Gln Thr Glu
            180                 185                 190

Leu Ser Leu Asp Leu Ala Leu Ser Lys Tyr Leu Ser Asp Leu Leu Phe
        195                 200                 205

Val Phe Gly Pro Asn Leu Gln Asp Pro Val Ser Asn Ser Met Thr Ile
    210                 215                 220

Gln Ala Ile Ser Gln Ala Phe Gly Gly Asn Tyr Glu Thr Leu Leu Arg
225                 230                 235                 240

Thr Leu Gly Tyr Ala Thr Glu Asp Phe Asp Asp Leu Leu Glu Ser Asp
                245                 250                 255

Ser Ile Thr Gly Gln Ile Ile Tyr Val Asp Leu Ser Ser Tyr Tyr Ile
            260                 265                 270

Ile Val Arg Val Tyr Phe Pro Ile Leu Thr Glu Ile Gln Gln Ala Tyr
        275                 280                 285

Ile Gln Glu Leu Leu Pro Val Ser Phe Asn Asn Asp Asn Ser Glu Trp
    290                 295                 300

Ile Ser Ile Val Pro Asn Phe Ile Leu Val Arg Asn Thr Leu Ile Ser
305                 310                 315                 320

Asn Ile Glu Ile Gly Phe Cys Leu Ile Thr Lys Arg Ser Val Ile Cys
                325                 330                 335

Asn Gln Asp Tyr Ala Thr Pro Met Thr Asn Asn Met Arg Glu Cys Leu
            340                 345                 350

Thr Gly Ser Thr Glu Lys Cys Pro Arg Glu Leu Val Val Ser Ser His
        355                 360                 365

Val Pro Arg Phe Ala Leu Ser Asn Gly Val Leu Phe Ala Asn Cys Ile
    370                 375                 380

Ser Val Thr Cys Gln Cys Gln Thr Thr Gly Arg Ala Ile Ser Gln Ser
385                 390                 395                 400

Gly Glu Gln Thr Leu Leu Met Ile Asp Asn Thr Thr Cys Pro Thr Ala
                405                 410                 415

Val Leu Gly Asn Val Cys Ile Ser Leu Gly Lys Tyr Leu Gly Ser Val
```

```
            420                 425                 430

Asn Tyr Asn Ser Glu Gly Ile Ala Ile Gly Pro Pro Val Phe Thr Asp
        435                 440                 445

Lys Val Asp Ile Ser Ser Gln Ile Ser Ser Met Asn Gln Ser Leu Gln
    450                 455                 460

Gln Ser Lys Asp Tyr Ile Lys Glu Ala Gln Arg Leu Leu Asp Thr Val
465                 470                 475                 480

Asn Pro Ser Leu Lys Leu Met Lys Gln Ile Glu Asp Lys Ile Glu Glu
                485                 490                 495

Ile Leu Ser Lys Ile Tyr His Ile Glu Asn Glu Ile Ala Arg Ile Lys
            500                 505                 510

Lys Leu Ile Gly Glu Ala Pro Gly Gly Leu Val Pro Arg Gly Ser His
        515                 520                 525

His His His His His Ser Ala Trp Ser His Pro Gln Phe Glu Lys
    530                 535                 540


<210> SEQ ID NO 21
<211> LENGTH: 543
<212> TYPE: PRT
<213> ORGANISM: Artificial sequence
<220> FEATURE:
<223> OTHER INFORMATION: Recombinant Nipah virus F sequence

<400> SEQUENCE: 21

Met Tyr Ser Met Gln Leu Ala Ser Cys Val Thr Leu Thr Leu Val Leu
1               5                   10                  15

Leu Val Asn Ser Gln Gly Ile Leu His Tyr Glu Lys Leu Ser Lys Ile
            20                  25                  30

Gly Leu Val Lys Gly Val Thr Arg Lys Tyr Lys Ile Lys Ser Asn Pro
        35                  40                  45

Leu Thr Lys Asp Ile Val Ile Lys Met Ile Pro Asn Val Ser Asn Met
    50                  55                  60

Ser Gln Cys Thr Gly Ser Val Met Glu Asn Tyr Lys Thr Arg Leu Asn
65                  70                  75                  80

Gly Ile Leu Thr Pro Ile Lys Gly Ala Leu Glu Ile Tyr Lys Asn Asn
                85                  90                  95

Thr His Asp Cys Val Gly Asp Val Arg Leu Ala Gly Val Cys Met Ala
            100                 105                 110

Gly Val Ala Ile Gly Ile Ala Thr Ala Ala Gln Ile Thr Ala Gly Val
        115                 120                 125

Ala Leu Tyr Glu Ala Met Lys Asn Ala Asp Asn Ile Asn Lys Leu Lys
    130                 135                 140

Ser Ser Ile Glu Ser Thr Asn Glu Ala Val Val Lys Leu Gln Glu Thr
145                 150                 155                 160

Ala Glu Lys Thr Val Tyr Val Leu Thr Ala Leu Gln Asp Tyr Ile Asn
                165                 170                 175

Thr Asn Leu Val Pro Thr Ile Asp Lys Ile Pro Cys Lys Gln Thr Glu
            180                 185                 190

Leu Ser Leu Asp Leu Ala Leu Ser Lys Tyr Leu Ser Asp Leu Leu Phe
        195                 200                 205

Val Phe Gly Pro Asn Leu Gln Asp Pro Val Ser Asn Ser Met Thr Ile
    210                 215                 220

Gln Ala Ile Ser Gln Ala Phe Gly Gly Asn Tyr Glu Thr Leu Leu Arg
225                 230                 235                 240

Thr Leu Gly Tyr Ala Thr Glu Asp Phe Asp Asp Leu Leu Glu Ser Asp
```

-continued

```
                245                 250                 255

Ser Ile Thr Gly Gln Ile Ile Tyr Val Asp Leu Ser Ser Tyr Tyr Ile
            260                 265                 270

Ile Val Arg Val Tyr Phe Pro Ile Leu Thr Glu Ile Gln Gln Ala Tyr
        275                 280                 285

Ile Gln Glu Leu Leu Pro Val Ser Phe Asn Asn Asp Asn Ser Glu Trp
    290                 295                 300

Ile Ser Ile Val Pro Asn Phe Ile Leu Val Arg Asn Thr Leu Ile Ser
305                 310                 315                 320

Asn Ile Glu Ile Gly Phe Cys Leu Ile Thr Lys Arg Ser Val Ile Cys
                325                 330                 335

Asn Gln Asp Tyr Ala Thr Pro Met Thr Asn Asn Met Arg Glu Cys Leu
            340                 345                 350

Thr Gly Ser Thr Glu Lys Cys Pro Arg Glu Leu Val Val Ser Ser His
        355                 360                 365

Val Pro Arg Phe Ala Leu Ser Asn Gly Val Leu Phe Ala Asn Cys Ile
    370                 375                 380

Ser Val Thr Cys Gln Cys Gln Thr Thr Gly Arg Ala Ile Ser Gln Ser
385                 390                 395                 400

Gly Glu Gln Thr Leu Leu Met Ile Asp Asn Thr Thr Cys Pro Thr Ala
                405                 410                 415

Val Leu Gly Asn Val Ile Ile Ser Leu Gly Lys Tyr Leu Gly Ser Val
            420                 425                 430

Asn Tyr Asn Ser Glu Gly Ile Ala Ile Gly Pro Pro Val Phe Thr Asp
        435                 440                 445

Lys Val Asp Ile Ser Ser Gln Ile Ser Ser Met Asn Gln Ser Leu Gln
    450                 455                 460

Gln Ser Lys Asp Tyr Ile Lys Glu Ala Gln Arg Leu Leu Asp Thr Val
465                 470                 475                 480

Asn Pro Ser Leu Lys Leu Met Lys Gln Ile Glu Asp Lys Ile Glu Glu
                485                 490                 495

Ile Leu Ser Lys Ile Tyr His Ile Glu Asn Glu Ile Ala Arg Ile Lys
            500                 505                 510

Lys Leu Ile Gly Glu Ala Pro Gly Gly Leu Val Pro Arg Gly Ser His
        515                 520                 525

His His His His His Ser Ala Trp Ser His Pro Gln Phe Glu Lys
    530                 535                 540


<210> SEQ ID NO 22
<211> LENGTH: 534
<212> TYPE: PRT
<213> ORGANISM: Artificial sequence
<220> FEATURE:
<223> OTHER INFORMATION: Recombinant Nipah virus F sequence

<400> SEQUENCE: 22

Met Tyr Ser Met Gln Leu Ala Ser Cys Val Thr Leu Thr Leu Val Leu
1               5                   10                  15

Leu Val Asn Ser Gln Gly Ile Leu His Tyr Glu Lys Leu Ser Lys Ile
            20                  25                  30

Gly Leu Val Lys Gly Val Thr Arg Lys Tyr Lys Ile Lys Ser Asn Pro
        35                  40                  45

Leu Thr Lys Asp Ile Val Ile Lys Met Ile Pro Asn Val Ser Asn Met
    50                  55                  60

Ser Gln Cys Thr Gly Ser Val Met Glu Asn Tyr Lys Thr Arg Leu Asn
```

-continued 65 70 75 80

Gly Ile Leu Thr Pro Ile Lys Gly Ala Leu Glu Ile Tyr Lys Asn Asn
85 90 95

Thr Gly Ser Gly Ile Met Ala Gly Val Ala Ile Gly Ile Ala Thr Ala
100 105 110

Ala Gln Ile Thr Ala Gly Val Ala Leu Tyr Glu Ala Met Lys Asn Ala
115 120 125

Asp Asn Ile Asn Lys Leu Lys Ser Ser Ile Glu Ser Thr Asn Glu Ala
130 135 140

Val Val Lys Leu Gln Glu Thr Ala Glu Lys Thr Val Tyr Val Leu Thr
145 150 155 160

Ala Leu Gln Asp Tyr Ile Asn Thr Asn Leu Val Pro Thr Ile Asp Lys
165 170 175

Ile Pro Cys Lys Gln Thr Glu Leu Ser Leu Asp Leu Ala Leu Ser Lys
180 185 190

Tyr Leu Ser Asp Leu Leu Phe Val Phe Gly Pro Asn Leu Gln Asp Pro
195 200 205

Val Ser Asn Ser Met Thr Ile Gln Ala Ile Ser Gln Ala Phe Gly Gly
210 215 220

Asn Tyr Glu Thr Leu Leu Arg Thr Leu Gly Tyr Ala Thr Glu Asp Phe
225 230 235 240

Asp Asp Leu Leu Glu Ser Asp Ser Ile Thr Gly Gln Ile Ile Tyr Val
245 250 255

Asp Leu Ser Ser Tyr Tyr Ile Ile Val Arg Val Tyr Phe Pro Ile Leu
260 265 270

Thr Glu Ile Gln Gln Ala Tyr Ile Gln Glu Leu Leu Pro Val Ser Phe
275 280 285

Asn Asn Asp Asn Ser Glu Trp Ile Ser Ile Val Pro Asn Phe Ile Leu
290 295 300

Val Arg Asn Thr Leu Ile Ser Asn Ile Glu Ile Gly Phe Cys Leu Ile
305 310 315 320

Thr Lys Arg Ser Val Ile Cys Asn Gln Asp Tyr Ala Thr Pro Met Thr
325 330 335

Asn Asn Met Arg Glu Cys Leu Thr Gly Ser Thr Glu Lys Cys Pro Arg
340 345 350

Glu Leu Val Val Ser Ser His Val Pro Arg Phe Ala Leu Ser Asn Gly
355 360 365

Val Leu Phe Ala Asn Cys Ile Ser Val Thr Cys Gln Cys Gln Thr Thr
370 375 380

Gly Arg Ala Ile Ser Gln Ser Gly Glu Gln Thr Leu Leu Met Ile Asp
385 390 395 400

Asn Thr Thr Cys Pro Thr Ala Val Leu Gly Asn Val Ile Ile Ser Leu
405 410 415

Gly Lys Tyr Leu Gly Ser Val Asn Tyr Asn Ser Glu Gly Ile Ala Ile
420 425 430

Gly Pro Pro Val Phe Thr Asp Lys Val Asp Ile Ser Ser Gln Ile Ser
435 440 445

Ser Met Asn Gln Ser Leu Gln Gln Ser Lys Asp Tyr Ile Lys Glu Ala
450 455 460

Gln Arg Leu Leu Asp Thr Val Asn Pro Ser Leu Lys Leu Met Lys Gln
465 470 475 480

Ile Glu Asp Lys Ile Glu Glu Ile Leu Ser Lys Ile Tyr His Ile Glu
485 490 495

```
Asn Glu Ile Ala Arg Ile Lys Lys Leu Ile Gly Glu Ala Pro Gly Gly
            500                 505                 510

Leu Val Pro Arg Gly Ser His His His His His His Ser Ala Trp Ser
        515                 520                 525

His Pro Gln Phe Glu Lys
    530


<210> SEQ ID NO 23
<211> LENGTH: 543
<212> TYPE: PRT
<213> ORGANISM: Artificial sequence
<220> FEATURE:
<223> OTHER INFORMATION: Recombinant Nipah virus F sequence

<400> SEQUENCE: 23

Met Tyr Ser Met Gln Leu Ala Ser Cys Val Thr Leu Thr Leu Val Leu
1               5                   10                  15

Leu Val Asn Ser Gln Gly Ile Leu His Tyr Glu Lys Leu Ser Lys Ile
            20                  25                  30

Gly Leu Val Lys Gly Val Thr Arg Lys Tyr Lys Ile Lys Ser Asn Pro
        35                  40                  45

Leu Thr Lys Asp Ile Val Ile Lys Met Ile Pro Asn Val Ser Asn Met
    50                  55                  60

Ser Gln Cys Thr Gly Ser Val Met Glu Asn Tyr Lys Thr Arg Leu Asn
65                  70                  75                  80

Gly Ile Leu Thr Pro Ile Lys Gly Ala Leu Glu Ile Tyr Lys Asn Asn
                85                  90                  95

Thr His Asp Leu Val Gly Asp Val Arg Leu Ala Gly Val Cys Met Ala
            100                 105                 110

Gly Val Ala Ile Gly Ile Ala Thr Ala Ala Gln Ile Thr Ala Gly Val
        115                 120                 125

Ala Leu Tyr Glu Ala Met Lys Asn Ala Asp Asn Ile Asn Lys Leu Lys
    130                 135                 140

Ser Ser Ile Glu Ser Thr Asn Glu Ala Val Val Lys Leu Gln Glu Thr
145                 150                 155                 160

Ala Glu Lys Thr Val Tyr Val Phe Thr Ala Leu Gln Asp Tyr Ile Asn
                165                 170                 175

Thr Asn Leu Val Pro Thr Ile Asp Lys Ile Pro Cys Lys Gln Thr Glu
            180                 185                 190

Leu Ser Leu Asp Leu Ala Leu Ser Lys Tyr Leu Ser Asp Leu Leu Phe
        195                 200                 205

Val Phe Gly Pro Asn Leu Gln Asp Pro Val Ser Asn Ser Met Thr Ile
    210                 215                 220

Gln Ala Ile Ser Gln Ala Phe Gly Gly Asn Tyr Glu Thr Leu Leu Arg
225                 230                 235                 240

Thr Leu Gly Tyr Ala Thr Glu Asp Phe Asp Asp Leu Leu Glu Ser Asp
                245                 250                 255

Ser Ile Thr Gly Gln Ile Ile Tyr Val Asp Leu Ser Ser Tyr Tyr Ile
            260                 265                 270

Ile Val Arg Val Tyr Phe Pro Ile Leu Thr Glu Ile Gln Gln Ala Tyr
        275                 280                 285

Ile Gln Glu Leu Leu Pro Val Ser Phe Asn Asn Asp Asn Ser Glu Trp
    290                 295                 300

Ile Ser Ile Val Pro Asn Phe Ile Leu Val Arg Asn Thr Leu Ile Ser
305                 310                 315                 320
```

-continued

```
Asn Ile Glu Ile Gly Phe Cys Leu Ile Thr Lys Arg Ser Val Ile Cys
                325                 330                 335

Asn Gln Asp Tyr Ala Thr Pro Met Thr Asn Asn Met Arg Glu Cys Leu
            340                 345                 350

Thr Gly Ser Thr Glu Lys Cys Pro Arg Glu Leu Val Val Ser Ser His
        355                 360                 365

Val Pro Arg Phe Ala Leu Ser Asn Gly Val Leu Phe Ala Asn Cys Ile
    370                 375                 380

Ser Val Thr Cys Gln Cys Gln Thr Thr Gly Arg Ala Ile Ser Gln Ser
385                 390                 395                 400

Gly Glu Gln Thr Leu Leu Met Ile Asp Asn Thr Thr Cys Pro Thr Ala
                405                 410                 415

Val Leu Gly Asn Val Cys Ile Ser Leu Gly Lys Tyr Leu Gly Ser Val
            420                 425                 430

Asn Tyr Asn Ser Glu Gly Ile Ala Ile Gly Pro Pro Val Phe Thr Asp
        435                 440                 445

Lys Val Asp Ile Ser Ser Gln Ile Ser Ser Met Asn Gln Ser Leu Gln
    450                 455                 460

Gln Ser Lys Asp Tyr Ile Lys Glu Ala Gln Arg Leu Leu Asp Thr Val
465                 470                 475                 480

Asn Pro Ser Leu Lys Leu Met Lys Gln Ile Glu Asp Lys Ile Glu Glu
                485                 490                 495

Ile Leu Ser Lys Ile Tyr His Ile Glu Asn Glu Ile Ala Arg Ile Lys
            500                 505                 510

Lys Leu Ile Gly Glu Ala Pro Gly Gly Leu Val Pro Arg Gly Ser His
        515                 520                 525

His His His His His Ser Ala Trp Ser His Pro Gln Phe Glu Lys
    530                 535                 540


<210> SEQ ID NO 24
<211> LENGTH: 543
<212> TYPE: PRT
<213> ORGANISM: Artificial sequence
<220> FEATURE:
<223> OTHER INFORMATION: Recombinant Nipah virus F sequence

<400> SEQUENCE: 24

Met Tyr Ser Met Gln Leu Ala Ser Cys Val Thr Leu Thr Leu Val Leu
1               5                   10                  15

Leu Val Asn Ser Gln Gly Ile Leu His Tyr Glu Lys Leu Ser Lys Ile
            20                  25                  30

Gly Leu Val Lys Gly Val Thr Arg Lys Tyr Lys Ile Lys Ser Asn Pro
        35                  40                  45

Leu Thr Lys Asp Ile Val Ile Lys Met Ile Pro Asn Val Ser Asn Met
    50                  55                  60

Ser Gln Cys Thr Gly Ser Val Met Glu Asn Tyr Lys Thr Arg Leu Asn
65                  70                  75                  80

Gly Ile Leu Thr Pro Ile Lys Gly Ala Leu Glu Ile Tyr Lys Asn Asn
                85                  90                  95

Thr His Asp Cys Val Gly Asp Val Arg Leu Ala Gly Val Cys Met Ala
            100                 105                 110

Gly Val Ala Ile Gly Ile Ala Thr Ala Ala Gln Ile Thr Ala Gly Val
        115                 120                 125

Ala Leu Tyr Glu Ala Met Lys Asn Ala Asp Asn Ile Asn Lys Leu Lys
    130                 135                 140
```

-continued

```
Ser Ser Ile Glu Ser Thr Asn Glu Ala Val Val Lys Leu Gln Glu Thr
145                 150                 155                 160

Ala Glu Lys Thr Val Tyr Val Phe Thr Ala Leu Gln Asp Tyr Ile Asn
                165                 170                 175

Thr Asn Leu Val Pro Thr Ile Asp Lys Ile Pro Cys Lys Gln Thr Glu
            180                 185                 190

Leu Ser Leu Asp Leu Ala Leu Ser Lys Tyr Leu Ser Asp Leu Leu Phe
        195                 200                 205

Val Phe Gly Pro Asn Leu Gln Asp Pro Val Ser Asn Ser Met Thr Ile
    210                 215                 220

Gln Ala Ile Ser Gln Ala Phe Gly Gly Asn Tyr Glu Thr Leu Leu Arg
225                 230                 235                 240

Thr Leu Gly Tyr Ala Thr Glu Asp Phe Asp Asp Leu Leu Glu Ser Asp
                245                 250                 255

Ser Ile Thr Gly Gln Ile Ile Tyr Val Asp Leu Ser Ser Tyr Tyr Ile
            260                 265                 270

Ile Val Arg Val Tyr Phe Pro Ile Leu Thr Glu Ile Gln Gln Ala Tyr
        275                 280                 285

Ile Gln Glu Leu Leu Pro Val Ser Phe Asn Asn Asp Asn Ser Glu Trp
    290                 295                 300

Ile Ser Ile Val Pro Asn Phe Ile Leu Val Arg Asn Thr Leu Ile Ser
305                 310                 315                 320

Asn Ile Glu Ile Gly Phe Cys Leu Ile Thr Lys Arg Ser Val Ile Cys
                325                 330                 335

Asn Gln Asp Tyr Ala Thr Pro Met Thr Asn Asn Met Arg Glu Cys Leu
            340                 345                 350

Thr Gly Ser Thr Glu Lys Cys Pro Arg Glu Leu Val Val Ser Ser His
        355                 360                 365

Val Pro Arg Phe Ala Leu Ser Asn Gly Val Leu Phe Ala Asn Cys Ile
    370                 375                 380

Ser Val Thr Cys Gln Cys Gln Thr Thr Gly Arg Ala Ile Ser Gln Ser
385                 390                 395                 400

Gly Glu Gln Thr Leu Leu Met Ile Asp Asn Thr Thr Cys Pro Thr Ala
                405                 410                 415

Val Leu Gly Asn Val Ile Ile Ser Leu Gly Lys Tyr Leu Gly Ser Val
            420                 425                 430

Asn Tyr Asn Ser Glu Gly Ile Ala Ile Gly Pro Pro Val Phe Thr Asp
        435                 440                 445

Lys Val Asp Ile Ser Ser Gln Ile Ser Ser Met Asn Gln Ser Leu Gln
    450                 455                 460

Gln Ser Lys Asp Tyr Ile Lys Glu Ala Gln Arg Leu Leu Asp Thr Val
465                 470                 475                 480

Asn Pro Ser Leu Lys Leu Met Lys Gln Ile Glu Asp Lys Ile Glu Glu
                485                 490                 495

Ile Leu Ser Lys Ile Tyr His Ile Glu Asn Glu Ile Ala Arg Ile Lys
            500                 505                 510

Lys Leu Ile Gly Glu Ala Pro Gly Gly Leu Val Pro Arg Gly Ser His
        515                 520                 525

His His His His His Ser Ala Trp Ser His Pro Gln Phe Glu Lys
    530                 535                 540
```

<210> SEQ ID NO 25
<211> LENGTH: 534

-continued

<212> TYPE: PRT
<213> ORGANISM: Artificial sequence
<220> FEATURE:
<223> OTHER INFORMATION: Recombinant Nipah virus F sequence

<400> SEQUENCE: 25

```
Met Tyr Ser Met Gln Leu Ala Ser Cys Val Thr Leu Thr Leu Val Leu
1               5                   10                  15

Leu Val Asn Ser Gln Gly Ile Leu His Tyr Glu Lys Leu Ser Lys Ile
            20                  25                  30

Gly Leu Val Lys Gly Val Thr Arg Lys Tyr Lys Ile Lys Ser Asn Pro
        35                  40                  45

Leu Thr Lys Asp Ile Val Ile Lys Met Ile Pro Asn Val Ser Asn Met
    50                  55                  60

Ser Gln Cys Thr Gly Ser Val Met Glu Asn Tyr Lys Thr Arg Leu Asn
65                  70                  75                  80

Gly Ile Leu Thr Pro Ile Lys Gly Ala Leu Glu Ile Tyr Lys Asn Asn
                85                  90                  95

Thr Gly Ser Gly Ile Met Ala Gly Val Ala Ile Gly Ile Ala Thr Ala
            100                 105                 110

Ala Gln Ile Thr Ala Gly Val Ala Leu Tyr Glu Ala Met Lys Asn Ala
        115                 120                 125

Asp Asn Ile Asn Lys Leu Lys Ser Ser Ile Glu Ser Thr Asn Glu Ala
    130                 135                 140

Val Val Lys Leu Gln Glu Thr Ala Glu Lys Thr Val Tyr Val Phe Thr
145                 150                 155                 160

Ala Leu Gln Asp Tyr Ile Asn Thr Asn Leu Val Pro Thr Ile Asp Lys
                165                 170                 175

Ile Pro Cys Lys Gln Thr Glu Leu Ser Leu Asp Leu Ala Leu Ser Lys
            180                 185                 190

Tyr Leu Ser Asp Leu Leu Phe Val Phe Gly Pro Asn Leu Gln Asp Pro
        195                 200                 205

Val Ser Asn Ser Met Thr Ile Gln Ala Ile Ser Gln Ala Phe Gly Gly
    210                 215                 220

Asn Tyr Glu Thr Leu Leu Arg Thr Leu Gly Tyr Ala Thr Glu Asp Phe
225                 230                 235                 240

Asp Asp Leu Leu Glu Ser Asp Ser Ile Thr Gly Gln Ile Ile Tyr Val
                245                 250                 255

Asp Leu Ser Ser Tyr Tyr Ile Ile Val Arg Val Tyr Phe Pro Ile Leu
            260                 265                 270

Thr Glu Ile Gln Gln Ala Tyr Ile Gln Glu Leu Leu Pro Val Ser Phe
        275                 280                 285

Asn Asn Asp Asn Ser Glu Trp Ile Ser Ile Val Pro Asn Phe Ile Leu
    290                 295                 300

Val Arg Asn Thr Leu Ile Ser Asn Ile Glu Ile Gly Phe Cys Leu Ile
305                 310                 315                 320

Thr Lys Arg Ser Val Ile Cys Asn Gln Asp Tyr Ala Thr Pro Met Thr
                325                 330                 335

Asn Asn Met Arg Glu Cys Leu Thr Gly Ser Thr Glu Lys Cys Pro Arg
            340                 345                 350

Glu Leu Val Val Ser Ser His Val Pro Arg Phe Ala Leu Ser Asn Gly
        355                 360                 365

Val Leu Phe Ala Asn Cys Ile Ser Val Thr Cys Gln Cys Gln Thr Thr
    370                 375                 380
```

-continued

Gly Arg Ala Ile Ser Gln Ser Gly Glu Gln Thr Leu Leu Met Ile Asp
385 390 395 400

Asn Thr Thr Cys Pro Thr Ala Val Leu Gly Asn Val Ile Ile Ser Leu
405 410 415

Gly Lys Tyr Leu Gly Ser Val Asn Tyr Asn Ser Glu Gly Ile Ala Ile
420 425 430

Gly Pro Pro Val Phe Thr Asp Lys Val Asp Ile Ser Ser Gln Ile Ser
435 440 445

Ser Met Asn Gln Ser Leu Gln Gln Ser Lys Asp Tyr Ile Lys Glu Ala
450 455 460

Gln Arg Leu Leu Asp Thr Val Asn Pro Ser Leu Lys Leu Met Lys Gln
465 470 475 480

Ile Glu Asp Lys Ile Glu Glu Ile Leu Ser Lys Ile Tyr His Ile Glu
485 490 495

Asn Glu Ile Ala Arg Ile Lys Lys Leu Ile Gly Glu Ala Pro Gly Gly
500 505 510

Leu Val Pro Arg Gly Ser His His His His His His Ser Ala Trp Ser
515 520 525

His Pro Gln Phe Glu Lys
530

<210> SEQ ID NO 26
<211> LENGTH: 543
<212> TYPE: PRT
<213> ORGANISM: Artificial sequence
<220> FEATURE:
<223> OTHER INFORMATION: Recombinant Nipah virus F sequence

<400> SEQUENCE: 26

Met Tyr Ser Met Gln Leu Ala Ser Cys Val Thr Leu Thr Leu Val Leu
1 5 10 15

Leu Val Asn Ser Gln Gly Ile Leu His Tyr Glu Lys Leu Ser Lys Ile
20 25 30

Gly Leu Val Lys Gly Val Thr Arg Lys Tyr Lys Ile Lys Ser Asn Pro
35 40 45

Leu Thr Lys Asp Ile Val Ile Lys Met Ile Pro Asn Val Ser Asn Met
50 55 60

Ser Gln Cys Thr Gly Ser Val Met Glu Asn Tyr Lys Thr Arg Leu Asn
65 70 75 80

Gly Ile Leu Thr Pro Ile Lys Gly Ala Leu Glu Ile Tyr Lys Asn Asn
85 90 95

Thr His Asp Leu Val Gly Asp Val Arg Leu Ala Gly Val Ile Met Ala
100 105 110

Gly Val Ala Ile Gly Ile Ala Thr Ala Ala Gln Ile Thr Ala Gly Val
115 120 125

Ala Leu Tyr Glu Ala Met Lys Asn Ala Asp Asn Ile Asn Lys Leu Lys
130 135 140

Ser Ser Ile Glu Ser Thr Asn Glu Ala Val Val Lys Leu Gln Glu Thr
145 150 155 160

Ala Glu Lys Thr Val Tyr Val Phe Thr Ala Leu Gln Asp Tyr Ile Asn
165 170 175

Thr Asn Leu Val Pro Thr Ile Asp Lys Ile Pro Cys Lys Gln Thr Glu
180 185 190

Leu Ser Leu Asp Leu Ala Leu Ser Lys Tyr Leu Ser Asp Leu Leu Phe
195 200 205

```
Val Phe Gly Pro Asn Leu Gln Asp Pro Val Ser Asn Ser Met Thr Ile
    210                 215                 220

Gln Ala Ile Ser Gln Ala Phe Gly Gly Asn Tyr Glu Thr Leu Leu Arg
225                 230                 235                 240

Thr Leu Gly Tyr Ala Thr Glu Asp Phe Asp Asp Leu Leu Glu Ser Asp
                245                 250                 255

Ser Ile Thr Gly Gln Ile Ile Tyr Val Asp Leu Ser Ser Tyr Tyr Ile
            260                 265                 270

Ile Val Arg Val Tyr Phe Pro Ile Leu Thr Glu Ile Gln Gln Ala Tyr
        275                 280                 285

Ile Gln Glu Leu Leu Pro Val Ser Phe Asn Asn Asp Asn Ser Glu Trp
    290                 295                 300

Ile Ser Ile Val Pro Asn Phe Ile Leu Val Arg Asn Thr Leu Ile Ser
305                 310                 315                 320

Asn Ile Glu Ile Gly Phe Cys Leu Ile Thr Lys Arg Ser Val Ile Cys
                325                 330                 335

Asn Gln Asp Tyr Ala Thr Pro Met Thr Asn Asn Met Arg Glu Cys Leu
            340                 345                 350

Thr Gly Ser Thr Glu Lys Cys Pro Arg Glu Leu Val Val Ser Ser His
        355                 360                 365

Val Pro Arg Phe Ala Leu Ser Asn Gly Val Leu Phe Ala Asn Cys Ile
    370                 375                 380

Ser Val Thr Cys Gln Cys Gln Thr Thr Gly Arg Ala Ile Ser Gln Ser
385                 390                 395                 400

Gly Glu Gln Thr Leu Leu Met Ile Asp Asn Thr Thr Cys Pro Thr Ala
                405                 410                 415

Val Leu Gly Asn Val Ile Ile Ser Leu Gly Lys Tyr Leu Gly Ser Val
            420                 425                 430

Asn Tyr Asn Ser Glu Gly Ile Ala Ile Gly Pro Pro Val Phe Thr Asp
        435                 440                 445

Lys Val Asp Ile Ser Ser Gln Ile Ser Ser Met Asn Gln Ser Leu Gln
    450                 455                 460

Gln Ser Lys Asp Tyr Ile Lys Glu Ala Gln Arg Leu Leu Asp Thr Val
465                 470                 475                 480

Asn Pro Ser Leu Lys Leu Met Lys Gln Ile Glu Asp Lys Ile Glu Glu
                485                 490                 495

Ile Leu Ser Lys Ile Tyr His Ile Glu Asn Glu Ile Ala Arg Ile Lys
            500                 505                 510

Lys Leu Ile Gly Glu Ala Pro Gly Gly Leu Val Pro Arg Gly Ser His
        515                 520                 525

His His His His His Ser Ala Trp Ser His Pro Gln Phe Glu Lys
    530                 535                 540


<210> SEQ ID NO 27
<211> LENGTH: 543
<212> TYPE: PRT
<213> ORGANISM: Artificial sequence
<220> FEATURE:
<223> OTHER INFORMATION: Recombinant Nipah virus F sequence

<400> SEQUENCE: 27

Met Tyr Ser Met Gln Leu Ala Ser Cys Val Thr Leu Thr Leu Val Leu
1               5                   10                  15

Leu Val Asn Ser Gln Gly Ile Leu His Tyr Glu Lys Leu Ser Lys Ile
            20                  25                  30
```

```
Gly Leu Val Lys Gly Val Thr Arg Lys Tyr Lys Ile Lys Ser Asn Pro
        35                  40                  45

Leu Thr Lys Asp Ile Val Ile Lys Met Ile Pro Asn Val Ser Asn Met
    50                  55                  60

Ser Gly Cys Thr Gly Ser Val Met Glu Asn Tyr Lys Thr Arg Leu Asn
65                  70                  75                  80

Gly Ile Leu Thr Pro Ile Lys Gly Ala Leu Glu Ile Tyr Lys Asn Asn
                85                  90                  95

Thr His Asp Leu Val Gly Asp Val Arg Leu Ala Gly Val Ile Met Ala
            100                 105                 110

Gly Val Ala Ile Gly Ile Ala Thr Ala Ala Gln Ile Thr Ala Gly Val
        115                 120                 125

Ala Leu Tyr Glu Ala Met Lys Asn Ala Asp Asn Ile Asn Lys Leu Lys
    130                 135                 140

Ser Ser Ile Glu Ser Thr Asn Glu Ala Val Val Lys Leu Gln Glu Thr
145                 150                 155                 160

Ala Glu Lys Thr Val Tyr Val Phe Thr Ala Leu Gln Asp Tyr Ile Asn
                165                 170                 175

Thr Asn Leu Val Pro Thr Ile Asp Lys Ile Pro Cys Lys Gln Thr Glu
            180                 185                 190

Leu Ser Leu Asp Leu Ala Leu Ser Lys Tyr Leu Ser Asp Leu Leu Phe
        195                 200                 205

Val Phe Gly Pro Asn Leu Gln Asp Pro Val Ser Asn Ser Met Thr Ile
    210                 215                 220

Gln Ala Ile Ser Gln Ala Phe Gly Gly Asn Tyr Glu Thr Leu Leu Arg
225                 230                 235                 240

Thr Leu Gly Tyr Ala Thr Glu Asp Phe Asp Asp Leu Leu Glu Ser Asp
                245                 250                 255

Ser Ile Thr Gly Gln Ile Ile Tyr Val Asp Leu Ser Ser Tyr Tyr Ile
            260                 265                 270

Ile Val Arg Val Tyr Phe Pro Ile Leu Thr Glu Ile Gln Gln Ala Tyr
        275                 280                 285

Ile Gln Glu Leu Leu Pro Val Ser Phe Asn Asn Asp Asn Ser Glu Trp
    290                 295                 300

Ile Ser Ile Val Pro Asn Phe Ile Leu Val Arg Asn Thr Leu Ile Ser
305                 310                 315                 320

Asn Ile Glu Ile Gly Phe Cys Leu Ile Thr Lys Arg Ser Val Ile Cys
                325                 330                 335

Asn Gln Asp Tyr Ala Thr Pro Met Thr Asn Asn Met Arg Glu Cys Leu
            340                 345                 350

Thr Gly Ser Thr Glu Lys Cys Pro Arg Glu Leu Val Val Ser Ser His
        355                 360                 365

Val Pro Arg Phe Ala Leu Ser Asn Gly Val Leu Phe Ala Asn Cys Ile
    370                 375                 380

Ser Val Thr Cys Gln Cys Gln Thr Thr Gly Arg Ala Ile Ser Gln Ser
385                 390                 395                 400

Gly Glu Gln Thr Leu Leu Met Ile Asp Asn Thr Thr Cys Pro Thr Ala
                405                 410                 415

Val Leu Gly Asn Val Ile Ile Ser Leu Gly Lys Tyr Leu Gly Ser Val
            420                 425                 430

Asn Tyr Asn Ser Glu Gly Ile Ala Ile Gly Pro Pro Val Phe Thr Asp
        435                 440                 445

Lys Val Asp Ile Ser Ser Gln Ile Ser Ser Met Asn Gln Ser Leu Gln
```

```
    450                 455                 460

Gln Ser Lys Asp Tyr Ile Lys Glu Ala Gln Arg Leu Leu Asp Thr Val
465                 470                 475                 480

Asn Pro Ser Leu Lys Leu Met Lys Gln Ile Glu Asp Lys Ile Glu Glu
                485                 490                 495

Ile Leu Ser Lys Ile Tyr His Ile Glu Asn Glu Ile Ala Arg Ile Lys
            500                 505                 510

Lys Leu Ile Gly Glu Ala Pro Gly Gly Leu Val Pro Arg Gly Ser His
        515                 520                 525

His His His His His Ser Ala Trp Ser His Pro Gln Phe Glu Lys
    530                 535                 540


<210> SEQ ID NO 28
<211> LENGTH: 543
<212> TYPE: PRT
<213> ORGANISM: Artificial sequence
<220> FEATURE:
<223> OTHER INFORMATION: Recombinant Nipah virus F sequence

<400> SEQUENCE: 28

Met Tyr Ser Met Gln Leu Ala Ser Cys Val Thr Leu Thr Leu Val Leu
1               5                   10                  15

Leu Val Asn Ser Gln Gly Ile Leu His Tyr Glu Lys Leu Ser Lys Ile
            20                  25                  30

Gly Leu Val Lys Gly Val Thr Arg Lys Tyr Lys Ile Lys Ser Asn Pro
        35                  40                  45

Leu Thr Lys Asp Ile Val Ile Lys Met Ile Pro Asn Val Ser Asn Met
    50                  55                  60

Ser Gly Cys Thr Gly Ser Val Met Glu Asn Tyr Lys Thr Arg Leu Asn
65                  70                  75                  80

Gly Ile Leu Thr Pro Ile Lys Gly Ala Leu Glu Ile Tyr Lys Asn Asn
                85                  90                  95

Thr His Asp Cys Val Gly Asp Val Arg Leu Ala Gly Val Cys Met Ala
            100                 105                 110

Gly Val Ala Ile Gly Ile Ala Thr Ala Ala Gln Ile Thr Ala Gly Val
        115                 120                 125

Ala Leu Tyr Glu Ala Met Lys Asn Ala Asp Asn Ile Asn Lys Leu Lys
    130                 135                 140

Ser Ser Ile Glu Ser Thr Asn Glu Ala Val Val Lys Leu Gln Glu Thr
145                 150                 155                 160

Ala Glu Lys Thr Val Tyr Val Phe Thr Ala Leu Gln Asp Tyr Ile Asn
                165                 170                 175

Thr Asn Leu Val Pro Thr Ile Asp Lys Ile Pro Cys Lys Gln Thr Glu
            180                 185                 190

Leu Ser Leu Asp Leu Ala Leu Ser Lys Tyr Leu Ser Asp Leu Leu Phe
        195                 200                 205

Val Phe Gly Pro Asn Leu Gln Asp Pro Val Ser Asn Ser Met Thr Ile
    210                 215                 220

Gln Ala Ile Ser Gln Ala Phe Gly Gly Asn Tyr Glu Thr Leu Leu Arg
225                 230                 235                 240

Thr Leu Gly Tyr Ala Thr Glu Asp Phe Asp Asp Leu Leu Glu Ser Asp
                245                 250                 255

Ser Ile Thr Gly Gln Ile Ile Tyr Val Asp Leu Ser Ser Tyr Tyr Ile
            260                 265                 270

Ile Val Arg Val Tyr Phe Pro Ile Leu Thr Glu Ile Gln Gln Ala Tyr
```

275 280 285

Ile Gln Glu Leu Leu Pro Val Ser Phe Asn Asn Asp Asn Ser Glu Trp
290 295 300

Ile Ser Ile Val Pro Asn Phe Ile Leu Val Arg Asn Thr Leu Ile Ser
305 310 315 320

Asn Ile Glu Ile Gly Phe Cys Leu Ile Thr Lys Arg Ser Val Ile Cys
325 330 335

Asn Gln Asp Tyr Ala Thr Pro Met Thr Asn Asn Met Arg Glu Cys Leu
340 345 350

Thr Gly Ser Thr Glu Lys Cys Pro Arg Glu Leu Val Val Ser Ser His
355 360 365

Val Pro Arg Phe Ala Leu Ser Asn Gly Val Leu Phe Ala Asn Cys Ile
370 375 380

Ser Val Thr Cys Gln Cys Gln Thr Thr Gly Arg Ala Ile Ser Gln Ser
385 390 395 400

Gly Glu Gln Thr Leu Leu Met Ile Asp Asn Thr Thr Cys Pro Thr Ala
405 410 415

Val Leu Gly Asn Val Ile Ile Ser Leu Gly Lys Tyr Leu Gly Ser Val
420 425 430

Asn Tyr Asn Ser Glu Gly Ile Ala Ile Gly Pro Pro Val Phe Thr Asp
435 440 445

Lys Val Asp Ile Ser Ser Gln Ile Ser Ser Met Asn Gln Ser Leu Gln
450 455 460

Gln Ser Lys Asp Tyr Ile Lys Glu Ala Gln Arg Leu Leu Asp Thr Val
465 470 475 480

Asn Pro Ser Leu Lys Leu Met Lys Gln Ile Glu Asp Lys Ile Glu Glu
485 490 495

Ile Leu Ser Lys Ile Tyr His Ile Glu Asn Glu Ile Ala Arg Ile Lys
500 505 510

Lys Leu Ile Gly Glu Ala Pro Gly Gly Leu Val Pro Arg Gly Ser His
515 520 525

His His His His His Ser Ala Trp Ser His Pro Gln Phe Glu Lys
530 535 540

<210> SEQ ID NO 29
<211> LENGTH: 543
<212> TYPE: PRT
<213> ORGANISM: Artificial sequence
<220> FEATURE:
<223> OTHER INFORMATION: Recombinant Nipah virus F sequence

<400> SEQUENCE: 29

Met Tyr Ser Met Gln Leu Ala Ser Cys Val Thr Leu Thr Leu Val Leu
1 5 10 15

Leu Val Asn Ser Gln Gly Ile Leu His Tyr Glu Lys Leu Ser Lys Ile
20 25 30

Gly Leu Val Lys Gly Val Thr Arg Lys Tyr Lys Ile Lys Ser Asn Pro
35 40 45

Leu Thr Lys Asp Ile Val Ile Lys Met Ile Pro Asn Val Ser Asn Met
50 55 60

Ser Gly Cys Thr Gly Ser Val Met Glu Asn Tyr Lys Thr Arg Leu Asn
65 70 75 80

Gly Ile Leu Thr Pro Ile Lys Gly Ala Leu Glu Ile Tyr Lys Asn Asn
85 90 95

Thr His Asp Cys Val Gly Asp Val Arg Leu Ala Gly Val Cys Met Ala

-continued

```
            100                 105                 110

Gly Val Ala Ile Gly Ile Ala Thr Ala Ala Gln Ile Thr Ala Gly Val
        115                 120                 125

Ala Leu Tyr Glu Ala Met Lys Asn Ala Asp Asn Ile Asn Lys Leu Lys
    130                 135                 140

Ser Ser Ile Glu Ser Thr Asn Glu Ala Val Val Lys Leu Gln Glu Thr
145                 150                 155                 160

Ala Glu Lys Thr Val Tyr Val Phe Thr Ala Leu Gln Asp Tyr Ile Asn
                165                 170                 175

Thr Asn Leu Val Pro Thr Ile Asp Lys Ile Ser Cys Lys Gln Thr Glu
            180                 185                 190

Leu Ser Leu Asp Leu Ala Leu Ser Lys Tyr Leu Ser Asp Leu Leu Phe
        195                 200                 205

Val Phe Gly Pro Asn Leu Gln Asp Pro Val Ser Asn Ser Met Thr Ile
    210                 215                 220

Gln Ala Ile Ser Gln Ala Phe Gly Gly Asn Tyr Glu Thr Leu Leu Arg
225                 230                 235                 240

Thr Leu Gly Tyr Ala Thr Glu Asp Phe Asp Asp Leu Leu Glu Ser Asp
                245                 250                 255

Ser Ile Thr Gly Gln Ile Ile Tyr Val Asp Leu Ser Ser Tyr Tyr Ile
            260                 265                 270

Ile Val Arg Val Tyr Phe Pro Ile Leu Thr Glu Ile Gln Gln Ala Tyr
        275                 280                 285

Ile Gln Glu Leu Leu Pro Val Ser Phe Asn Asn Asp Asn Ser Glu Trp
    290                 295                 300

Ile Ser Ile Val Pro Asn Phe Ile Leu Val Arg Asn Thr Leu Ile Ser
305                 310                 315                 320

Asn Ile Glu Ile Gly Phe Cys Leu Ile Thr Lys Arg Ser Val Ile Cys
                325                 330                 335

Asn Gln Asp Tyr Ala Thr Pro Met Thr Asn Asn Met Arg Glu Cys Leu
            340                 345                 350

Thr Gly Ser Thr Glu Lys Cys Pro Arg Glu Leu Val Val Ser Ser His
        355                 360                 365

Val Pro Arg Phe Ala Leu Ser Asn Gly Val Leu Phe Ala Asn Cys Ile
    370                 375                 380

Ser Val Thr Cys Gln Cys Gln Thr Thr Gly Arg Ala Ile Ser Gln Ser
385                 390                 395                 400

Gly Glu Gln Thr Leu Leu Met Ile Asp Asn Thr Thr Cys Pro Thr Ala
                405                 410                 415

Val Leu Gly Asn Val Ile Ile Ser Leu Gly Lys Tyr Leu Gly Ser Val
            420                 425                 430

Asn Tyr Asn Ser Glu Gly Ile Ala Ile Gly Pro Pro Val Phe Thr Asp
        435                 440                 445

Lys Val Asp Ile Ser Ser Gln Ile Ser Ser Met Asn Gln Ser Leu Gln
    450                 455                 460

Gln Ser Lys Asp Tyr Ile Lys Glu Ala Gln Arg Leu Leu Asp Thr Val
465                 470                 475                 480

Asn Pro Ser Leu Lys Leu Met Lys Gln Ile Glu Asp Lys Ile Glu Glu
                485                 490                 495

Ile Leu Ser Lys Ile Tyr His Ile Glu Asn Glu Ile Ala Arg Ile Lys
            500                 505                 510

Lys Leu Ile Gly Glu Ala Pro Gly Gly Leu Val Pro Arg Gly Ser His
        515                 520                 525
```

His His His His His Ser Ala Trp Ser His Pro Gln Phe Glu Lys
530 535 540

<210> SEQ ID NO 30
<211> LENGTH: 543
<212> TYPE: PRT
<213> ORGANISM: Artificial sequence
<220> FEATURE:
<223> OTHER INFORMATION: Recombinant Nipah virus F sequence

<400> SEQUENCE: 30

Met Tyr Ser Met Gln Leu Ala Ser Cys Val Thr Leu Thr Leu Val Leu
1 5 10 15

Leu Val Asn Ser Gln Gly Ile Leu His Tyr Glu Lys Leu Ser Lys Ile
20 25 30

Gly Leu Val Lys Gly Val Thr Arg Lys Tyr Lys Ile Lys Ser Asn Pro
35 40 45

Leu Thr Lys Asp Ile Val Ile Lys Met Ile Pro Asn Val Ser Asn Met
50 55 60

Ser Gly Cys Thr Gly Ser Val Met Glu Asn Tyr Lys Thr Arg Leu Asn
65 70 75 80

Gly Ile Leu Thr Pro Ile Lys Gly Ala Leu Glu Ile Tyr Lys Asn Asn
85 90 95

Thr His Asp Cys Val Gly Asp Val Arg Leu Ala Gly Val Cys Met Ala
100 105 110

Gly Val Ala Ile Gly Ile Ala Thr Ala Ala Gln Ile Thr Ala Gly Val
115 120 125

Ala Leu Tyr Glu Ala Met Lys Asn Ala Asp Asn Ile Asn Lys Leu Lys
130 135 140

Ser Ser Ile Glu Ser Thr Asn Glu Ala Val Val Lys Leu Gln Glu Thr
145 150 155 160

Ala Glu Lys Thr Val Tyr Val Leu Thr Ala Leu Gln Asp Tyr Ile Asn
165 170 175

Thr Asn Leu Val Pro Thr Ile Asp Lys Ile Ser Cys Lys Gln Thr Glu
180 185 190

Leu Ser Leu Asp Leu Ala Leu Ser Lys Tyr Leu Ser Asp Leu Leu Phe
195 200 205

Val Phe Gly Pro Asn Leu Gln Asp Pro Val Ser Asn Ser Met Thr Ile
210 215 220

Gln Ala Ile Ser Gln Ala Phe Gly Gly Asn Tyr Glu Thr Leu Leu Arg
225 230 235 240

Thr Leu Gly Tyr Ala Thr Glu Asp Phe Asp Asp Leu Leu Glu Ser Asp
245 250 255

Ser Ile Thr Gly Gln Ile Ile Tyr Val Asp Leu Ser Ser Tyr Tyr Ile
260 265 270

Ile Val Arg Val Tyr Phe Pro Ile Leu Thr Glu Ile Gln Gln Ala Tyr
275 280 285

Ile Gln Glu Leu Leu Pro Val Ser Phe Asn Asn Asp Asn Ser Glu Trp
290 295 300

Ile Ser Ile Val Pro Asn Phe Ile Leu Val Arg Asn Thr Leu Ile Ser
305 310 315 320

Asn Ile Glu Ile Gly Phe Cys Leu Ile Thr Lys Arg Ser Val Ile Cys
325 330 335

Asn Gln Asp Tyr Ala Thr Pro Met Thr Asn Asn Met Arg Glu Cys Leu
340 345 350

Thr Gly Ser Thr Glu Lys Cys Pro Arg Glu Leu Val Val Ser Ser His
355 360 365

Val Pro Arg Phe Ala Leu Ser Asn Gly Val Leu Phe Ala Asn Cys Ile
370 375 380

Ser Val Thr Cys Gln Cys Gln Thr Thr Gly Arg Ala Ile Ser Gln Ser
385 390 395 400

Gly Glu Gln Thr Leu Leu Met Ile Asp Asn Thr Thr Cys Pro Thr Ala
405 410 415

Val Leu Gly Asn Val Ile Ile Ser Leu Gly Lys Tyr Leu Gly Ser Val
420 425 430

Asn Tyr Asn Ser Glu Gly Ile Ala Ile Gly Pro Pro Val Phe Thr Asp
435 440 445

Lys Val Asp Ile Ser Ser Gln Ile Ser Ser Met Asn Gln Ser Leu Gln
450 455 460

Gln Ser Lys Asp Tyr Ile Lys Glu Ala Gln Arg Leu Leu Asp Thr Val
465 470 475 480

Asn Pro Ser Leu Lys Leu Met Lys Gln Ile Glu Asp Lys Ile Glu Glu
485 490 495

Ile Leu Ser Lys Ile Tyr His Ile Glu Asn Glu Ile Ala Arg Ile Lys
500 505 510

Lys Leu Ile Gly Glu Ala Pro Gly Gly Leu Val Pro Arg Gly Ser His
515 520 525

His His His His His Ser Ala Trp Ser His Pro Gln Phe Glu Lys
530 535 540

<210> SEQ ID NO 31
<211> LENGTH: 543
<212> TYPE: PRT
<213> ORGANISM: Artificial sequence
<220> FEATURE:
<223> OTHER INFORMATION: Recombinant Nipah virus F sequence

<400> SEQUENCE: 31

Met Tyr Ser Met Gln Leu Ala Ser Cys Val Thr Leu Thr Leu Val Leu
1 5 10 15

Leu Val Asn Ser Gln Gly Ile Leu His Tyr Glu Lys Leu Ser Lys Ile
20 25 30

Gly Leu Val Lys Gly Val Thr Arg Lys Tyr Lys Ile Lys Ser Asn Pro
35 40 45

Leu Thr Lys Asp Ile Val Ile Lys Met Ile Pro Asn Val Ser Asn Met
50 55 60

Ser Gln Cys Thr Gly Ser Val Met Glu Asn Tyr Lys Thr Arg Leu Asn
65 70 75 80

Gly Ile Leu Thr Pro Ile Lys Gly Ala Leu Glu Ile Tyr Lys Asn Asn
85 90 95

Thr His Asp Cys Val Gly Asp Val Arg Leu Ala Gly Val Cys Met Ala
100 105 110

Gly Val Ala Ile Gly Ile Ala Thr Ala Ala Gln Ile Thr Ala Gly Val
115 120 125

Ala Leu Tyr Glu Ala Met Lys Asn Ala Asp Asn Ile Asn Lys Leu Lys
130 135 140

Ser Ser Ile Glu Ser Thr Asn Glu Ala Val Val Lys Leu Cys Glu Thr
145 150 155 160

Ala Glu Lys Cys Val Tyr Val Phe Thr Ala Leu Gln Asp Tyr Ile Asn
165 170 175

```
Thr Asn Leu Val Pro Thr Ile Asp Lys Ile Pro Cys Lys Gln Thr Glu
            180                 185                 190

Leu Ser Leu Asp Leu Ala Leu Ser Lys Tyr Leu Ser Asp Leu Leu Phe
        195                 200                 205

Val Phe Gly Pro Asn Leu Gln Asp Pro Val Ser Asn Ser Met Thr Ile
    210                 215                 220

Gln Ala Ile Ser Gln Ala Phe Gly Gly Asn Tyr Glu Thr Leu Leu Arg
225                 230                 235                 240

Thr Leu Gly Tyr Ala Thr Glu Asp Phe Asp Asp Leu Leu Glu Ser Asp
                245                 250                 255

Ser Ile Thr Gly Gln Ile Ile Tyr Val Asp Leu Ser Ser Tyr Tyr Ile
            260                 265                 270

Ile Val Arg Val Tyr Phe Pro Ile Leu Thr Glu Ile Gln Gln Ala Tyr
        275                 280                 285

Ile Gln Glu Leu Leu Pro Val Ser Phe Asn Asn Asp Asn Ser Glu Trp
    290                 295                 300

Ile Ser Ile Val Pro Asn Phe Ile Leu Val Arg Asn Thr Leu Ile Ser
305                 310                 315                 320

Asn Ile Glu Ile Gly Phe Cys Leu Ile Thr Lys Arg Ser Val Ile Cys
                325                 330                 335

Asn Gln Asp Tyr Ala Thr Pro Met Thr Asn Asn Met Arg Glu Cys Leu
            340                 345                 350

Thr Gly Ser Thr Glu Lys Cys Pro Arg Glu Leu Val Val Ser Ser His
        355                 360                 365

Val Pro Arg Phe Ala Leu Ser Asn Gly Val Leu Phe Ala Asn Cys Ile
    370                 375                 380

Ser Val Thr Cys Gln Cys Gln Thr Thr Gly Arg Ala Ile Ser Gln Ser
385                 390                 395                 400

Gly Glu Gln Thr Leu Leu Met Ile Asp Asn Thr Thr Cys Pro Thr Ala
                405                 410                 415

Val Leu Gly Asn Val Ile Ile Ser Leu Gly Lys Tyr Leu Gly Ser Val
            420                 425                 430

Asn Tyr Asn Ser Glu Gly Ile Ala Ile Gly Pro Pro Val Phe Thr Asp
        435                 440                 445

Lys Val Asp Ile Ser Ser Gln Ile Ser Ser Met Asn Gln Ser Leu Gln
    450                 455                 460

Gln Ser Lys Asp Tyr Ile Lys Glu Ala Gln Arg Leu Leu Asp Thr Val
465                 470                 475                 480

Asn Pro Ser Leu Lys Leu Met Lys Gln Ile Glu Asp Lys Ile Glu Glu
                485                 490                 495

Ile Leu Ser Lys Ile Tyr His Ile Glu Asn Glu Ile Ala Arg Ile Lys
            500                 505                 510

Lys Leu Ile Gly Glu Ala Pro Gly Gly Leu Val Pro Arg Gly Ser His
        515                 520                 525

His His His His His Ser Ala Trp Ser His Pro Gln Phe Glu Lys
    530                 535                 540
```

<210> SEQ ID NO 32
<211> LENGTH: 543
<212> TYPE: PRT
<213> ORGANISM: Artificial sequence
<220> FEATURE:
<223> OTHER INFORMATION: Recombinant Nipah virus F sequence

<400> SEQUENCE: 32

-continued

```
Met Tyr Ser Met Gln Leu Ala Ser Cys Val Thr Leu Thr Leu Val Leu
1               5                   10                  15

Leu Val Asn Ser Gln Gly Ile Leu His Tyr Glu Lys Leu Ser Lys Ile
            20                  25                  30

Gly Leu Val Lys Gly Val Thr Arg Lys Tyr Lys Ile Lys Ser Asn Pro
        35                  40                  45

Leu Thr Lys Asp Ile Val Ile Lys Met Ile Pro Asn Val Ser Asn Met
    50                  55                  60

Ser Gln Cys Thr Gly Ser Val Met Glu Asn Tyr Lys Thr Arg Leu Asn
65                  70                  75                  80

Gly Ile Leu Thr Pro Ile Lys Gly Ala Leu Glu Ile Tyr Lys Asn Asn
                85                  90                  95

Thr His Asp Cys Val Gly Asp Val Arg Leu Ala Gly Val Cys Met Ala
            100                 105                 110

Gly Val Ala Ile Gly Ile Ala Thr Ala Ala Gln Ile Thr Cys Gly Val
        115                 120                 125

Ala Leu Tyr Glu Ala Met Lys Asn Ala Asp Asn Ile Asn Lys Leu Lys
    130                 135                 140

Ser Ser Ile Glu Ser Thr Asn Glu Ala Val Val Lys Leu Gln Glu Thr
145                 150                 155                 160

Ala Glu Lys Thr Val Tyr Val Phe Thr Ala Leu Gln Asp Tyr Ile Asn
                165                 170                 175

Thr Asn Leu Val Pro Thr Ile Asp Lys Ile Pro Cys Lys Gln Thr Glu
            180                 185                 190

Leu Ser Leu Asp Leu Ala Leu Ser Lys Tyr Leu Ser Asp Leu Leu Phe
        195                 200                 205

Val Phe Gly Pro Asn Leu Gln Asp Pro Cys Ser Asn Ser Met Thr Ile
    210                 215                 220

Gln Ala Ile Ser Gln Ala Phe Gly Gly Asn Tyr Glu Thr Leu Leu Arg
225                 230                 235                 240

Thr Leu Gly Tyr Ala Thr Glu Asp Phe Asp Asp Leu Leu Glu Ser Asp
                245                 250                 255

Ser Ile Thr Gly Gln Ile Ile Tyr Val Asp Leu Ser Ser Tyr Tyr Ile
            260                 265                 270

Ile Val Arg Val Tyr Phe Pro Ile Leu Thr Glu Ile Gln Gln Ala Tyr
        275                 280                 285

Ile Gln Glu Leu Leu Pro Val Ser Phe Asn Asn Asp Asn Ser Glu Trp
    290                 295                 300

Ile Ser Ile Val Pro Asn Phe Ile Leu Val Arg Asn Thr Leu Ile Ser
305                 310                 315                 320

Asn Ile Glu Ile Gly Phe Cys Leu Ile Thr Lys Arg Ser Val Ile Cys
                325                 330                 335

Asn Gln Asp Tyr Ala Thr Pro Met Thr Asn Asn Met Arg Glu Cys Leu
            340                 345                 350

Thr Gly Ser Thr Glu Lys Cys Pro Arg Glu Leu Val Val Ser Ser His
        355                 360                 365

Val Pro Arg Phe Ala Leu Ser Asn Gly Val Leu Phe Ala Asn Cys Ile
    370                 375                 380

Ser Val Thr Cys Gln Cys Gln Thr Thr Gly Arg Ala Ile Ser Gln Ser
385                 390                 395                 400

Gly Glu Gln Thr Leu Leu Met Ile Asp Asn Thr Thr Cys Pro Thr Ala
                405                 410                 415
```

-continued

```
Val Leu Gly Asn Val Ile Ile Ser Leu Gly Lys Tyr Leu Gly Ser Val
            420                 425                 430

Asn Tyr Asn Ser Glu Gly Ile Ala Ile Gly Pro Pro Val Phe Thr Asp
        435                 440                 445

Lys Val Asp Ile Ser Ser Gln Ile Ser Ser Met Asn Gln Ser Leu Gln
    450                 455                 460

Gln Ser Lys Asp Tyr Ile Lys Glu Ala Gln Arg Leu Leu Asp Thr Val
465                 470                 475                 480

Asn Pro Ser Leu Lys Leu Met Lys Gln Ile Glu Asp Lys Ile Glu Glu
                485                 490                 495

Ile Leu Ser Lys Ile Tyr His Ile Glu Asn Glu Ile Ala Arg Ile Lys
            500                 505                 510

Lys Leu Ile Gly Glu Ala Pro Gly Gly Leu Val Pro Arg Gly Ser His
        515                 520                 525

His His His His His Ser Ala Trp Ser His Pro Gln Phe Glu Lys
    530                 535                 540


<210> SEQ ID NO 33
<211> LENGTH: 1662
<212> TYPE: DNA
<213> ORGANISM: Artificial sequence
<220> FEATURE:
<223> OTHER INFORMATION: recombinant nipah virus F sequence

<400> SEQUENCE: 33

tctagagcca ccatggtggt catcctggac aagagatgct actgtaacct gctgatcctg      60

atcctgatga tcagcgagtg ctccgtgggc atcctgcact acgagaagct gtccaagatc     120

ggcctggtga agggcgtgac caggaagtat aagatcaagt ctaatcccct gacaaaggat     180

atcgtgatca agatgatccc taacgtgtct aatatgagcc agtgtaccgg ctccgtgatg     240

gagaactaca agaccagact gaatggcatc ctgacaccca tcaagggcgc cctggagatc     300

tataagaaca atacacacga ctgcgtgggc gatgtgaggc tggcaggcgt gtgcatggca     360

ggagtggcaa tcggaatcgc aaccgcagca cagatcacag caggagtggc cctgtatgag     420

gccatgaaga acgccgacaa catcaataag ctgaagagct ccatcgagag caccaatgag     480

gccgtggtga agctgcagga gaccgccgag aagacagtgt acgtgttcac agccctgcag     540

gactatatca acaccaatct ggtgcctaca atcgataaga tcccttgcaa gcagaccgag     600

ctgagcctgg acctggccct gagcaagtac ctgtccgatc tgctgttcgt gtttggccca     660

aacctgcagg accccgtgag caattccatg acaatccagg ccatctccca ggccttcggc     720

ggcaactacg agaccctgct gcgcacactg ggctatgcca ccgaggactt tgacgatctg     780

ctggagtctg atagcatcac aggccagatc atctatgtgg acctgtctag ctactatatc     840

atcgtgcggg tgtacttccc aatcctgacc gagatccagc aggcctatat ccaggagctg     900

ctgcccgtgt ccttcaacaa tgataactct gagtggatca gcatcgtgcc taacttcatc     960

ctggtgcgga acaccctgat ctctaatatc gagatcggct tttgcctgat cacaaagcgc    1020

agcgtgatct gtaatcagga ctacgccacc cctatgacaa acaatatgcg ggagtgcctg    1080

accggcagca cagagaagtg tcctcgggag ctggtggtgt cctctcacgt gccaagattc    1140

gccctgtcca acggcgtgct gtttgccaat tgcatctctg tgacctgcca gtgtcagacc    1200

acaggcaggg ccatctccca gtctggcgag cagaccctgc tgatgatcga taacaccaca    1260

tgtccaacag ccgtgctggg caatgtgatc atcagcctgg gcaagtacct gggcagcgtg    1320

aactataatt ccgagggaat cgcaatcgga ccacccgtgt tcaccgacaa ggtggatatc    1380
```

-continued agctcccaga tctctagcat gaaccagtcc ctgcagcagt ctaaggacta catcaaggag 1440
gcccagcgcc tgctggatac cgtgaatcca tccctgatct ctatgctgag catgatcatc 1500
ctgtatgtgc tgtccatcgc ctctctgtgc atcggcctga tcaccttcat cagctttatc 1560
atcgtggaga agaagaggaa cacatactcc cgcctggagg acaggagagt gcggcccacc 1620
tcctctggcg atctgtacta tatcggcaca tgatgaggat cc 1662

<210> SEQ ID NO 34
<211> LENGTH: 507
<212> TYPE: PRT
<213> ORGANISM: Artificial sequence
<220> FEATURE:
<223> OTHER INFORMATION: Recombinant Nipah virus G sequence

<400> SEQUENCE: 34

Met Tyr Ser Met Gln Leu Ala Ser Cys Val Thr Leu Thr Leu Val Leu
1 5 10 15

Leu Val Asn Ser Gln Gly Ser Gly Tyr Ile Pro Glu Ala Pro Arg Asp
20 25 30

Gly Gln Ala Tyr Val Arg Lys Asp Gly Glu Trp Val Leu Leu Ser Thr
35 40 45

Phe Leu Gly Ser Gly Gly Gly Gly Gly Gly Val Ser Asn Leu Val Gly
50 55 60

Leu Pro Asn Asn Ile Cys Leu Gln Lys Thr Ser Asn Gln Ile Leu Lys
65 70 75 80

Pro Lys Leu Ile Ser Tyr Thr Leu Pro Val Val Gly Gln Ser Gly Thr
85 90 95

Cys Ile Thr Asp Pro Leu Leu Ala Met Asp Glu Gly Tyr Phe Ala Tyr
100 105 110

Ser His Leu Glu Arg Ile Gly Ser Cys Ser Arg Gly Val Ser Lys Gln
115 120 125

Arg Ile Ile Gly Val Gly Glu Val Leu Asp Arg Gly Asp Glu Val Pro
130 135 140

Ser Leu Phe Met Thr Asn Val Trp Thr Pro Pro Asn Pro Asn Thr Val
145 150 155 160

Tyr His Cys Ser Ala Val Tyr Asn Asn Glu Phe Tyr Tyr Val Leu Cys
165 170 175

Ala Val Ser Thr Val Gly Asp Pro Ile Leu Asn Ser Thr Tyr Trp Ser
180 185 190

Gly Ser Leu Met Met Thr Arg Leu Ala Val Lys Pro Lys Ser Asn Gly
195 200 205

Gly Gly Tyr Asn Gln His Gln Leu Ala Leu Arg Ser Ile Glu Lys Gly
210 215 220

Arg Tyr Asp Lys Val Met Pro Tyr Gly Pro Ser Gly Ile Lys Gln Gly
225 230 235 240

Asp Thr Leu Tyr Phe Pro Ala Val Gly Phe Leu Val Arg Thr Glu Phe
245 250 255

Lys Tyr Asn Asp Ser Asn Cys Pro Ile Thr Lys Cys Gln Tyr Ser Lys
260 265 270

Pro Glu Asn Cys Arg Leu Ser Met Gly Ile Arg Pro Asn Ser His Tyr
275 280 285

Ile Leu Arg Ser Gly Leu Leu Lys Tyr Asn Leu Ser Asp Gly Glu Asn
290 295 300

Pro Lys Val Val Phe Ile Glu Ile Ser Asp Gln Arg Leu Ser Ile Gly 305 310 315 320

Ser Pro Ser Lys Ile Tyr Asp Ser Leu Gly Gln Pro Val Phe Tyr Gln
325 330 335

Ala Ser Phe Ser Trp Asp Thr Met Ile Lys Phe Gly Asp Val Leu Thr
340 345 350

Val Asn Pro Leu Val Val Asn Trp Arg Asn Asn Thr Val Ile Ser Arg
355 360 365

Pro Gly Gln Ser Gln Cys Pro Arg Phe Asn Thr Cys Pro Glu Ile Cys
370 375 380

Trp Glu Gly Val Tyr Asn Asp Ala Phe Leu Ile Asp Arg Ile Asn Trp
385 390 395 400

Ile Ser Ala Gly Val Phe Leu Asp Ser Asn Gln Thr Ala Glu Asn Pro
405 410 415

Val Phe Thr Val Phe Lys Asp Asn Glu Ile Leu Tyr Arg Ala Gln Leu
420 425 430

Ala Ser Glu Asp Thr Asn Ala Gln Lys Thr Ile Thr Asn Cys Phe Leu
435 440 445

Leu Lys Asn Lys Ile Trp Cys Ile Ser Leu Val Glu Ile Tyr Asp Thr
450 455 460

Gly Asp Asn Val Ile Arg Pro Lys Leu Phe Ala Val Lys Ile Pro Glu
465 470 475 480

Gln Cys Thr Gly Gly Leu Val Pro Arg Gly Ser His His His His His
485 490 495

His Ser Ala Trp Ser His Pro Gln Phe Glu Lys
500 505

<210> SEQ ID NO 35
<211> LENGTH: 939
<212> TYPE: PRT
<213> ORGANISM: Artificial sequence
<220> FEATURE:
<223> OTHER INFORMATION: Recombinant Nipah virus G sequence

<400> SEQUENCE: 35

Met Tyr Ser Met Gln Leu Ala Ser Cys Val Thr Leu Thr Leu Val Leu
1 5 10 15

Leu Val Asn Ser Gln Gly Ser Gly Tyr Ile Pro Glu Ala Pro Arg Asp
20 25 30

Gly Gln Ala Tyr Val Arg Lys Asp Gly Glu Trp Val Leu Leu Ser Thr
35 40 45

Phe Leu Gly Ser Gly Gly Gly Gly Gly Gly Val Ser Asn Leu Val Gly
50 55 60

Leu Pro Asn Asn Ile Cys Leu Gln Lys Thr Ser Asn Gln Ile Leu Lys
65 70 75 80

Pro Lys Leu Ile Ser Tyr Thr Leu Pro Val Val Gly Gln Ser Gly Thr
85 90 95

Cys Ile Thr Asp Pro Leu Leu Ala Met Asp Glu Gly Tyr Phe Ala Tyr
100 105 110

Ser His Leu Glu Arg Ile Gly Ser Cys Ser Arg Gly Val Ser Lys Gln
115 120 125

Arg Ile Ile Gly Val Gly Glu Val Leu Asp Arg Gly Asp Glu Val Pro
130 135 140

Ser Leu Phe Met Thr Asn Val Trp Thr Pro Pro Asn Pro Asn Thr Val
145 150 155 160

Tyr His Cys Ser Ala Val Tyr Asn Asn Glu Phe Tyr Tyr Val Leu Cys

```
                165                 170                 175

Ala Val Ser Thr Val Gly Asp Pro Ile Leu Asn Ser Thr Tyr Trp Ser
            180                 185                 190

Gly Ser Leu Met Met Thr Arg Leu Ala Val Lys Pro Lys Ser Asn Gly
        195                 200                 205

Gly Gly Tyr Asn Gln His Gln Leu Ala Leu Arg Ser Ile Glu Lys Gly
    210                 215                 220

Arg Tyr Asp Lys Val Met Pro Tyr Gly Pro Ser Gly Ile Lys Gln Gly
225                 230                 235                 240

Asp Thr Leu Tyr Phe Pro Ala Val Gly Phe Leu Val Arg Thr Glu Phe
                245                 250                 255

Lys Tyr Asn Asp Ser Asn Cys Pro Ile Thr Lys Cys Gln Tyr Ser Lys
            260                 265                 270

Pro Glu Asn Cys Arg Leu Ser Met Gly Ile Arg Pro Asn Ser His Tyr
        275                 280                 285

Ile Leu Arg Ser Gly Leu Leu Lys Tyr Asn Leu Ser Asp Gly Glu Asn
    290                 295                 300

Pro Lys Val Val Phe Ile Glu Ile Ser Asp Gln Arg Leu Ser Ile Gly
305                 310                 315                 320

Ser Pro Ser Lys Ile Tyr Asp Ser Leu Gly Gln Pro Val Phe Tyr Gln
                325                 330                 335

Ala Ser Phe Ser Trp Asp Thr Met Ile Lys Phe Gly Asp Val Leu Thr
            340                 345                 350

Val Asn Pro Leu Val Val Asn Trp Arg Asn Asn Thr Val Ile Ser Arg
        355                 360                 365

Pro Gly Gln Ser Gln Cys Pro Arg Phe Asn Thr Cys Pro Glu Ile Cys
    370                 375                 380

Trp Glu Gly Val Tyr Asn Asp Ala Phe Leu Ile Asp Arg Ile Asn Trp
385                 390                 395                 400

Ile Ser Ala Gly Val Phe Leu Asp Ser Asn Gln Thr Ala Glu Asn Pro
                405                 410                 415

Val Phe Thr Val Phe Lys Asp Asn Glu Ile Leu Tyr Arg Ala Gln Leu
            420                 425                 430

Ala Ser Glu Asp Thr Asn Ala Gln Lys Thr Ile Thr Asn Cys Phe Leu
        435                 440                 445

Leu Lys Asn Lys Ile Trp Cys Ile Ser Leu Val Glu Ile Tyr Asp Thr
    450                 455                 460

Gly Asp Asn Val Ile Arg Pro Lys Leu Phe Ala Val Lys Ile Pro Glu
465                 470                 475                 480

Gln Cys Thr Gly Gly Gly Gly Gly Gly Gly Val Ser Asn Leu Val Gly
                485                 490                 495

Leu Pro Asn Asn Ile Cys Leu Gln Lys Thr Ser Asn Gln Ile Leu Lys
            500                 505                 510

Pro Lys Leu Ile Ser Tyr Thr Leu Pro Val Val Gly Gln Ser Gly Thr
        515                 520                 525

Cys Ile Thr Asp Pro Leu Leu Ala Met Asp Glu Gly Tyr Phe Ala Tyr
    530                 535                 540

Ser His Leu Glu Arg Ile Gly Ser Cys Ser Arg Gly Val Ser Lys Gln
545                 550                 555                 560

Arg Ile Ile Gly Val Gly Glu Val Leu Asp Arg Gly Asp Glu Val Pro
                565                 570                 575

Ser Leu Phe Met Thr Asn Val Trp Thr Pro Pro Asn Pro Asn Thr Val
            580                 585                 590
```

-continued

```
Tyr His Cys Ser Ala Val Tyr Asn Asn Glu Phe Tyr Tyr Val Leu Cys
        595                 600                 605

Ala Val Ser Thr Val Gly Asp Pro Ile Leu Asn Ser Thr Tyr Trp Ser
    610                 615                 620

Gly Ser Leu Met Met Thr Arg Leu Ala Val Lys Pro Lys Ser Asn Gly
625                 630                 635                 640

Gly Gly Tyr Asn Gln His Gln Leu Ala Leu Arg Ser Ile Glu Lys Gly
                645                 650                 655

Arg Tyr Asp Lys Val Met Pro Tyr Gly Pro Ser Gly Ile Lys Gln Gly
            660                 665                 670

Asp Thr Leu Tyr Phe Pro Ala Val Gly Phe Leu Val Arg Thr Glu Phe
        675                 680                 685

Lys Tyr Asn Asp Ser Asn Cys Pro Ile Thr Lys Cys Gln Tyr Ser Lys
    690                 695                 700

Pro Glu Asn Cys Arg Leu Ser Met Gly Ile Arg Pro Asn Ser His Tyr
705                 710                 715                 720

Ile Leu Arg Ser Gly Leu Leu Lys Tyr Asn Leu Ser Asp Gly Glu Asn
                725                 730                 735

Pro Lys Val Val Phe Ile Glu Ile Ser Asp Gln Arg Leu Ser Ile Gly
            740                 745                 750

Ser Pro Ser Lys Ile Tyr Asp Ser Leu Gly Gln Pro Val Phe Tyr Gln
        755                 760                 765

Ala Ser Phe Ser Trp Asp Thr Met Ile Lys Phe Gly Asp Val Leu Thr
    770                 775                 780

Val Asn Pro Leu Val Val Asn Trp Arg Asn Asn Thr Val Ile Ser Arg
785                 790                 795                 800

Pro Gly Gln Ser Gln Cys Pro Arg Phe Asn Thr Cys Pro Glu Ile Cys
                805                 810                 815

Trp Glu Gly Val Tyr Asn Asp Ala Phe Leu Ile Asp Arg Ile Asn Trp
            820                 825                 830

Ile Ser Ala Gly Val Phe Leu Asp Ser Asn Gln Thr Ala Glu Asn Pro
        835                 840                 845

Val Phe Thr Val Phe Lys Asp Asn Glu Ile Leu Tyr Arg Ala Gln Leu
    850                 855                 860

Ala Ser Glu Asp Thr Asn Ala Gln Lys Thr Ile Thr Asn Cys Phe Leu
865                 870                 875                 880

Leu Lys Asn Lys Ile Trp Cys Ile Ser Leu Val Glu Ile Tyr Asp Thr
                885                 890                 895

Gly Asp Asn Val Ile Arg Pro Lys Leu Phe Ala Val Lys Ile Pro Glu
            900                 905                 910

Gln Cys Thr Gly Gly Leu Val Pro Arg Gly Ser His His His His His
        915                 920                 925

His Ser Ala Trp Ser His Pro Gln Phe Glu Lys
    930                 935
```

<210> SEQ ID NO 36
<211> LENGTH: 1371
<212> TYPE: PRT
<213> ORGANISM: Artificial sequence
<220> FEATURE:
<223> OTHER INFORMATION: Recombinant Nipah virus G sequence

<400> SEQUENCE: 36

```
Met Tyr Ser Met Gln Leu Ala Ser Cys Val Thr Leu Thr Leu Val Leu
1               5                   10                  15
```

```
Leu Val Asn Ser Gln Gly Ser Gly Tyr Ile Pro Glu Ala Pro Arg Asp
            20                  25                  30

Gly Gln Ala Tyr Val Arg Lys Asp Gly Glu Trp Val Leu Leu Ser Thr
        35                  40                  45

Phe Leu Gly Ser Gly Gly Gly Gly Gly Gly Val Ser Asn Leu Val Gly
    50                  55                  60

Leu Pro Asn Asn Ile Cys Leu Gln Lys Thr Ser Asn Gln Ile Leu Lys
65                  70                  75                  80

Pro Lys Leu Ile Ser Tyr Thr Leu Pro Val Val Gly Gln Ser Gly Thr
                85                  90                  95

Cys Ile Thr Asp Pro Leu Leu Ala Met Asp Glu Gly Tyr Phe Ala Tyr
            100                 105                 110

Ser His Leu Glu Arg Ile Gly Ser Cys Ser Arg Gly Val Ser Lys Gln
        115                 120                 125

Arg Ile Ile Gly Val Gly Glu Val Leu Asp Arg Gly Asp Glu Val Pro
    130                 135                 140

Ser Leu Phe Met Thr Asn Val Trp Thr Pro Pro Asn Pro Asn Thr Val
145                 150                 155                 160

Tyr His Cys Ser Ala Val Tyr Asn Asn Glu Phe Tyr Tyr Val Leu Cys
                165                 170                 175

Ala Val Ser Thr Val Gly Asp Pro Ile Leu Asn Ser Thr Tyr Trp Ser
            180                 185                 190

Gly Ser Leu Met Met Thr Arg Leu Ala Val Lys Pro Lys Ser Asn Gly
        195                 200                 205

Gly Gly Tyr Asn Gln His Gln Leu Ala Leu Arg Ser Ile Glu Lys Gly
    210                 215                 220

Arg Tyr Asp Lys Val Met Pro Tyr Gly Pro Ser Gly Ile Lys Gln Gly
225                 230                 235                 240

Asp Thr Leu Tyr Phe Pro Ala Val Gly Phe Leu Val Arg Thr Glu Phe
                245                 250                 255

Lys Tyr Asn Asp Ser Asn Cys Pro Ile Thr Lys Cys Gln Tyr Ser Lys
            260                 265                 270

Pro Glu Asn Cys Arg Leu Ser Met Gly Ile Arg Pro Asn Ser His Tyr
        275                 280                 285

Ile Leu Arg Ser Gly Leu Leu Lys Tyr Asn Leu Ser Asp Gly Glu Asn
    290                 295                 300

Pro Lys Val Val Phe Ile Glu Ile Ser Asp Gln Arg Leu Ser Ile Gly
305                 310                 315                 320

Ser Pro Ser Lys Ile Tyr Asp Ser Leu Gly Gln Pro Val Phe Tyr Gln
                325                 330                 335

Ala Ser Phe Ser Trp Asp Thr Met Ile Lys Phe Gly Asp Val Leu Thr
            340                 345                 350

Val Asn Pro Leu Val Val Asn Trp Arg Asn Asn Thr Val Ile Ser Arg
        355                 360                 365

Pro Gly Gln Ser Gln Cys Pro Arg Phe Asn Thr Cys Pro Glu Ile Cys
    370                 375                 380

Trp Glu Gly Val Tyr Asn Asp Ala Phe Leu Ile Asp Arg Ile Asn Trp
385                 390                 395                 400

Ile Ser Ala Gly Val Phe Leu Asp Ser Asn Gln Thr Ala Glu Asn Pro
                405                 410                 415

Val Phe Thr Val Phe Lys Asp Asn Glu Ile Leu Tyr Arg Ala Gln Leu
            420                 425                 430
```

-continued

```
Ala Ser Glu Asp Thr Asn Ala Gln Lys Thr Ile Thr Asn Cys Phe Leu
        435                 440                 445

Leu Lys Asn Lys Ile Trp Cys Ile Ser Leu Val Glu Ile Tyr Asp Thr
    450                 455                 460

Gly Asp Asn Val Ile Arg Pro Lys Leu Phe Ala Val Lys Ile Pro Glu
465                 470                 475                 480

Gln Cys Thr Gly Gly Gly Gly Gly Gly Gly Val Ser Asn Leu Val Gly
                485                 490                 495

Leu Pro Asn Asn Ile Cys Leu Gln Lys Thr Ser Asn Gln Ile Leu Lys
            500                 505                 510

Pro Lys Leu Ile Ser Tyr Thr Leu Pro Val Val Gly Gln Ser Gly Thr
        515                 520                 525

Cys Ile Thr Asp Pro Leu Leu Ala Met Asp Glu Gly Tyr Phe Ala Tyr
    530                 535                 540

Ser His Leu Glu Arg Ile Gly Ser Cys Ser Arg Gly Val Ser Lys Gln
545                 550                 555                 560

Arg Ile Ile Gly Val Gly Glu Val Leu Asp Arg Gly Asp Glu Val Pro
                565                 570                 575

Ser Leu Phe Met Thr Asn Val Trp Thr Pro Pro Asn Pro Asn Thr Val
            580                 585                 590

Tyr His Cys Ser Ala Val Tyr Asn Asn Glu Phe Tyr Tyr Val Leu Cys
        595                 600                 605

Ala Val Ser Thr Val Gly Asp Pro Ile Leu Asn Ser Thr Tyr Trp Ser
    610                 615                 620

Gly Ser Leu Met Met Thr Arg Leu Ala Val Lys Pro Lys Ser Asn Gly
625                 630                 635                 640

Gly Gly Tyr Asn Gln His Gln Leu Ala Leu Arg Ser Ile Glu Lys Gly
                645                 650                 655

Arg Tyr Asp Lys Val Met Pro Tyr Gly Pro Ser Gly Ile Lys Gln Gly
            660                 665                 670

Asp Thr Leu Tyr Phe Pro Ala Val Gly Phe Leu Val Arg Thr Glu Phe
        675                 680                 685

Lys Tyr Asn Asp Ser Asn Cys Pro Ile Thr Lys Cys Gln Tyr Ser Lys
    690                 695                 700

Pro Glu Asn Cys Arg Leu Ser Met Gly Ile Arg Pro Asn Ser His Tyr
705                 710                 715                 720

Ile Leu Arg Ser Gly Leu Leu Lys Tyr Asn Leu Ser Asp Gly Glu Asn
                725                 730                 735

Pro Lys Val Val Phe Ile Glu Ile Ser Asp Gln Arg Leu Ser Ile Gly
            740                 745                 750

Ser Pro Ser Lys Ile Tyr Asp Ser Leu Gly Gln Pro Val Phe Tyr Gln
        755                 760                 765

Ala Ser Phe Ser Trp Asp Thr Met Ile Lys Phe Gly Asp Val Leu Thr
    770                 775                 780

Val Asn Pro Leu Val Val Asn Trp Arg Asn Asn Thr Val Ile Ser Arg
785                 790                 795                 800

Pro Gly Gln Ser Gln Cys Pro Arg Phe Asn Thr Cys Pro Glu Ile Cys
                805                 810                 815

Trp Glu Gly Val Tyr Asn Asp Ala Phe Leu Ile Asp Arg Ile Asn Trp
            820                 825                 830

Ile Ser Ala Gly Val Phe Leu Asp Ser Asn Gln Thr Ala Glu Asn Pro
        835                 840                 845

Val Phe Thr Val Phe Lys Asp Asn Glu Ile Leu Tyr Arg Ala Gln Leu
```

```
    850                 855                 860

Ala Ser Glu Asp Thr Asn Ala Gln Lys Thr Ile Thr Asn Cys Phe Leu
865                 870                 875                 880

Leu Lys Asn Lys Ile Trp Cys Ile Ser Leu Val Glu Ile Tyr Asp Thr
                885                 890                 895

Gly Asp Asn Val Ile Arg Pro Lys Leu Phe Ala Val Lys Ile Pro Glu
            900                 905                 910

Gln Cys Thr Gly Gly Gly Gly Gly Gly Gly Val Ser Asn Leu Val Gly
        915                 920                 925

Leu Pro Asn Asn Ile Cys Leu Gln Lys Thr Ser Asn Gln Ile Leu Lys
    930                 935                 940

Pro Lys Leu Ile Ser Tyr Thr Leu Pro Val Val Gly Gln Ser Gly Thr
945                 950                 955                 960

Cys Ile Thr Asp Pro Leu Leu Ala Met Asp Glu Gly Tyr Phe Ala Tyr
                965                 970                 975

Ser His Leu Glu Arg Ile Gly Ser Cys Ser Arg Gly Val Ser Lys Gln
            980                 985                 990

Arg Ile Ile Gly Val Gly Glu Val  Leu Asp Arg Gly Asp  Glu Val Pro
        995                 1000                1005

Ser Leu  Phe Met Thr Asn Val  Trp Thr Pro Pro Asn  Pro Asn Thr
    1010                1015                1020

Val Tyr  His Cys Ser Ala Val  Tyr Asn Asn Glu Phe  Tyr Tyr Val
    1025                1030                1035

Leu Cys  Ala Val Ser Thr Val  Gly Asp Pro Ile Leu  Asn Ser Thr
    1040                1045                1050

Tyr Trp  Ser Gly Ser Leu Met  Met Thr Arg Leu Ala  Val Lys Pro
    1055                1060                1065

Lys Ser  Asn Gly Gly Gly Tyr  Asn Gln His Gln Leu  Ala Leu Arg
    1070                1075                1080

Ser Ile  Glu Lys Gly Arg Tyr  Asp Lys Val Met Pro  Tyr Gly Pro
    1085                1090                1095

Ser Gly  Ile Lys Gln Gly Asp  Thr Leu Tyr Phe Pro  Ala Val Gly
    1100                1105                1110

Phe Leu  Val Arg Thr Glu Phe  Lys Tyr Asn Asp Ser  Asn Cys Pro
    1115                1120                1125

Ile Thr  Lys Cys Gln Tyr Ser  Lys Pro Glu Asn Cys  Arg Leu Ser
    1130                1135                1140

Met Gly  Ile Arg Pro Asn Ser  His Tyr Ile Leu Arg  Ser Gly Leu
    1145                1150                1155

Leu Lys  Tyr Asn Leu Ser Asp  Gly Glu Asn Pro Lys  Val Val Phe
    1160                1165                1170

Ile Glu  Ile Ser Asp Gln Arg  Leu Ser Ile Gly Ser  Pro Ser Lys
    1175                1180                1185

Ile Tyr  Asp Ser Leu Gly Gln  Pro Val Phe Tyr Gln  Ala Ser Phe
    1190                1195                1200

Ser Trp  Asp Thr Met Ile Lys  Phe Gly Asp Val Leu  Thr Val Asn
    1205                1210                1215

Pro Leu  Val Val Asn Trp Arg  Asn Asn Thr Val Ile  Ser Arg Pro
    1220                1225                1230

Gly Gln  Ser Gln Cys Pro Arg  Phe Asn Thr Cys Pro  Glu Ile Cys
    1235                1240                1245

Trp Glu  Gly Val Tyr Asn Asp  Ala Phe Leu Ile Asp  Arg Ile Asn
    1250                1255                1260
```

Trp Ile Ser Ala Gly Val Phe Leu Asp Ser Asn Gln Thr Ala Glu
1265 1270 1275

Asn Pro Val Phe Thr Val Phe Lys Asp Asn Glu Ile Leu Tyr Arg
1280 1285 1290

Ala Gln Leu Ala Ser Glu Asp Thr Asn Ala Gln Lys Thr Ile Thr
1295 1300 1305

Asn Cys Phe Leu Leu Lys Asn Lys Ile Trp Cys Ile Ser Leu Val
1310 1315 1320

Glu Ile Tyr Asp Thr Gly Asp Asn Val Ile Arg Pro Lys Leu Phe
1325 1330 1335

Ala Val Lys Ile Pro Glu Gln Cys Thr Gly Gly Leu Val Pro Arg
1340 1345 1350

Gly Ser His His His His His His Ser Ala Trp Ser His Pro Gln
1355 1360 1365

Phe Glu Lys
1370

<210> SEQ ID NO 37
<211> LENGTH: 936
<212> TYPE: PRT
<213> ORGANISM: Artificial sequence
<220> FEATURE:
<223> OTHER INFORMATION: Recombinant Nipah virus G sequence

<400> SEQUENCE: 37

Met Tyr Ser Met Gln Leu Ala Ser Cys Val Thr Leu Thr Leu Val Leu
1 5 10 15

Leu Val Asn Ser Gln Glu Gly Val Ser Asn Leu Val Gly Leu Pro Asn
20 25 30

Asn Ile Cys Leu Gln Lys Thr Ser Asn Gln Ile Leu Lys Pro Lys Leu
35 40 45

Ile Ser Tyr Thr Leu Pro Val Val Gly Gln Ser Gly Thr Cys Ile Thr
50 55 60

Asp Pro Leu Leu Ala Met Asp Glu Gly Tyr Phe Ala Tyr Ser His Leu
65 70 75 80

Glu Arg Ile Gly Ser Cys Ser Arg Gly Val Ser Lys Gln Arg Ile Ile
85 90 95

Gly Val Gly Glu Val Leu Asp Arg Gly Asp Glu Val Pro Ser Leu Phe
100 105 110

Met Thr Asn Val Trp Thr Pro Pro Asn Pro Asn Thr Val Tyr His Cys
115 120 125

Ser Ala Val Tyr Asn Asn Glu Phe Tyr Tyr Val Leu Cys Ala Val Ser
130 135 140

Thr Val Gly Asp Pro Ile Leu Asn Ser Thr Tyr Trp Ser Gly Ser Leu
145 150 155 160

Met Met Thr Arg Leu Ala Val Lys Pro Lys Ser Asn Gly Gly Gly Tyr
165 170 175

Asn Gln His Gln Leu Ala Leu Arg Ser Ile Glu Lys Gly Arg Tyr Asp
180 185 190

Lys Val Met Pro Tyr Gly Pro Ser Gly Ile Lys Gln Gly Asp Thr Leu
195 200 205

Tyr Phe Pro Ala Val Gly Phe Leu Val Arg Thr Glu Phe Lys Tyr Asn
210 215 220

Asp Ser Asn Cys Pro Ile Thr Lys Cys Gln Tyr Ser Lys Pro Glu Asn
225 230 235 240

Cys Arg Leu Ser Met Gly Ile Arg Pro Asn Ser His Tyr Ile Leu Arg
245 250 255

Ser Gly Leu Leu Lys Tyr Asn Leu Ser Asp Gly Glu Asn Pro Lys Val
260 265 270

Val Phe Ile Glu Ile Ser Asp Gln Arg Leu Ser Ile Gly Ser Pro Ser
275 280 285

Lys Ile Tyr Asp Ser Leu Gly Gln Pro Val Phe Tyr Gln Ala Ser Phe
290 295 300

Ser Trp Asp Thr Met Ile Lys Phe Gly Asp Val Leu Thr Val Asn Pro
305 310 315 320

Leu Val Val Asn Trp Arg Asn Asn Thr Val Ile Ser Arg Pro Gly Gln
325 330 335

Ser Gln Cys Pro Arg Phe Asn Thr Cys Pro Glu Ile Cys Trp Glu Gly
340 345 350

Val Tyr Asn Asp Ala Phe Leu Ile Asp Arg Ile Asn Trp Ile Ser Ala
355 360 365

Gly Val Phe Leu Asp Ser Asn Gln Thr Ala Glu Asn Pro Val Phe Thr
370 375 380

Val Phe Lys Asp Asn Glu Ile Leu Tyr Arg Ala Gln Leu Ala Ser Glu
385 390 395 400

Asp Thr Asn Ala Gln Lys Thr Ile Thr Asn Cys Phe Leu Leu Lys Asn
405 410 415

Lys Ile Trp Cys Ile Ser Leu Val Glu Ile Tyr Asp Thr Gly Asp Asn
420 425 430

Val Ile Arg Pro Lys Leu Phe Ala Val Lys Ile Pro Glu Gln Cys Thr
435 440 445

Gly Gly Gly Ser Gly Tyr Ile Pro Glu Ala Pro Arg Asp Gly Gln Ala
450 455 460

Tyr Val Arg Lys Asp Gly Glu Trp Val Leu Leu Ser Thr Phe Leu Gly
465 470 475 480

Ser Gly Gly Gly Gly Gly Gly Val Ser Asn Leu Val Gly Leu Pro Asn
485 490 495

Asn Ile Cys Leu Gln Lys Thr Ser Asn Gln Ile Leu Lys Pro Lys Leu
500 505 510

Ile Ser Tyr Thr Leu Pro Val Val Gly Gln Ser Gly Thr Cys Ile Thr
515 520 525

Asp Pro Leu Leu Ala Met Asp Glu Gly Tyr Phe Ala Tyr Ser His Leu
530 535 540

Glu Arg Ile Gly Ser Cys Ser Arg Gly Val Ser Lys Gln Arg Ile Ile
545 550 555 560

Gly Val Gly Glu Val Leu Asp Arg Gly Asp Glu Val Pro Ser Leu Phe
565 570 575

Met Thr Asn Val Trp Thr Pro Pro Asn Pro Asn Thr Val Tyr His Cys
580 585 590

Ser Ala Val Tyr Asn Asn Glu Phe Tyr Tyr Val Leu Cys Ala Val Ser
595 600 605

Thr Val Gly Asp Pro Ile Leu Asn Ser Thr Tyr Trp Ser Gly Ser Leu
610 615 620

Met Met Thr Arg Leu Ala Val Lys Pro Lys Ser Asn Gly Gly Gly Tyr
625 630 635 640

Asn Gln His Gln Leu Ala Leu Arg Ser Ile Glu Lys Gly Arg Tyr Asp
645 650 655

-continued

```
Lys Val Met Pro Tyr Gly Pro Ser Gly Ile Lys Gln Gly Asp Thr Leu
            660                 665                 670

Tyr Phe Pro Ala Val Gly Phe Leu Val Arg Thr Glu Phe Lys Tyr Asn
        675                 680                 685

Asp Ser Asn Cys Pro Ile Thr Lys Cys Gln Tyr Ser Lys Pro Glu Asn
    690                 695                 700

Cys Arg Leu Ser Met Gly Ile Arg Pro Asn Ser His Tyr Ile Leu Arg
705                 710                 715                 720

Ser Gly Leu Leu Lys Tyr Asn Leu Ser Asp Gly Glu Asn Pro Lys Val
                725                 730                 735

Val Phe Ile Glu Ile Ser Asp Gln Arg Leu Ser Ile Gly Ser Pro Ser
            740                 745                 750

Lys Ile Tyr Asp Ser Leu Gly Gln Pro Val Phe Tyr Gln Ala Ser Phe
        755                 760                 765

Ser Trp Asp Thr Met Ile Lys Phe Gly Asp Val Leu Thr Val Asn Pro
    770                 775                 780

Leu Val Val Asn Trp Arg Asn Asn Thr Val Ile Ser Arg Pro Gly Gln
785                 790                 795                 800

Ser Gln Cys Pro Arg Phe Asn Thr Cys Pro Glu Ile Cys Trp Glu Gly
                805                 810                 815

Val Tyr Asn Asp Ala Phe Leu Ile Asp Arg Ile Asn Trp Ile Ser Ala
            820                 825                 830

Gly Val Phe Leu Asp Ser Asn Gln Thr Ala Glu Asn Pro Val Phe Thr
        835                 840                 845

Val Phe Lys Asp Asn Glu Ile Leu Tyr Arg Ala Gln Leu Ala Ser Glu
    850                 855                 860

Asp Thr Asn Ala Gln Lys Thr Ile Thr Asn Cys Phe Leu Leu Lys Asn
865                 870                 875                 880

Lys Ile Trp Cys Ile Ser Leu Val Glu Ile Tyr Asp Thr Gly Asp Asn
                885                 890                 895

Val Ile Arg Pro Lys Leu Phe Ala Val Lys Ile Pro Glu Gln Cys Thr
            900                 905                 910

Gly Gly Leu Val Pro Arg Gly Ser His His His His His His Ser Ala
        915                 920                 925

Trp Ser His Pro Gln Phe Glu Lys
    930                 935


<210> SEQ ID NO 38
<211> LENGTH: 652
<212> TYPE: PRT
<213> ORGANISM: Artificial sequence
<220> FEATURE:
<223> OTHER INFORMATION: Recombinant Nipah virus G sequence

<400> SEQUENCE: 38

Met Tyr Ser Met Gln Leu Ala Ser Cys Val Thr Leu Thr Leu Val Leu
1               5                   10                  15

Leu Val Asn Ser Gln His His His His His His Gly Ser Ala Trp Ser
            20                  25                  30

His Pro Gln Phe Glu Lys Gly Gly Leu Val Pro Arg Gly Ser Gly Asn
        35                  40                  45

Ser Gln Arg Pro Gln Thr Glu Gly Val Ser Asn Leu Val Gly Leu Pro
    50                  55                  60

Asn Asn Ile Cys Leu Gln Lys Thr Ser Asn Gln Ile Leu Lys Pro Lys
65                  70                  75                  80
```

```
Leu Ile Ser Tyr Thr Leu Pro Val Val Gly Gln Ser Gly Thr Cys Ile
                85                  90                  95

Thr Asp Pro Leu Leu Ala Met Asp Glu Gly Tyr Phe Ala Tyr Ser His
            100                 105                 110

Leu Glu Arg Ile Gly Ser Cys Ser Arg Gly Val Ser Lys Gln Arg Ile
        115                 120                 125

Ile Gly Val Gly Glu Val Leu Asp Arg Gly Asp Glu Val Pro Ser Leu
    130                 135                 140

Phe Met Thr Asn Val Trp Thr Pro Pro Asn Pro Asn Thr Val Tyr His
145                 150                 155                 160

Cys Ser Ala Val Tyr Asn Asn Glu Phe Tyr Tyr Val Leu Cys Ala Val
                165                 170                 175

Ser Thr Val Gly Asp Pro Ile Leu Asn Ser Thr Tyr Trp Ser Gly Ser
            180                 185                 190

Leu Met Met Thr Arg Leu Ala Val Lys Pro Lys Ser Asn Gly Gly Gly
        195                 200                 205

Tyr Asn Gln His Gln Leu Ala Leu Arg Ser Ile Glu Lys Gly Arg Tyr
    210                 215                 220

Asp Lys Val Met Pro Tyr Gly Pro Ser Gly Ile Lys Gln Gly Asp Thr
225                 230                 235                 240

Leu Tyr Phe Pro Ala Val Gly Phe Leu Val Arg Thr Glu Phe Lys Tyr
                245                 250                 255

Asn Asp Ser Asn Cys Pro Ile Thr Lys Cys Gln Tyr Ser Lys Pro Glu
            260                 265                 270

Asn Cys Arg Leu Ser Met Gly Ile Arg Pro Asn Ser His Tyr Ile Leu
        275                 280                 285

Arg Ser Gly Leu Leu Lys Tyr Asn Leu Ser Asp Gly Glu Asn Pro Lys
    290                 295                 300

Val Val Phe Ile Glu Ile Ser Asp Gln Arg Leu Ser Ile Gly Ser Pro
305                 310                 315                 320

Ser Lys Ile Tyr Asp Ser Leu Gly Gln Pro Val Phe Tyr Gln Ala Ser
                325                 330                 335

Phe Ser Trp Asp Thr Met Ile Lys Phe Gly Asp Val Leu Thr Val Asn
            340                 345                 350

Pro Leu Val Val Asn Trp Arg Asn Asn Thr Val Ile Ser Arg Pro Gly
        355                 360                 365

Gln Ser Gln Cys Pro Arg Phe Asn Thr Cys Pro Glu Ile Cys Trp Glu
    370                 375                 380

Gly Val Tyr Asn Asp Ala Phe Leu Ile Asp Arg Ile Asn Trp Ile Ser
385                 390                 395                 400

Ala Gly Val Phe Leu Asp Ser Asn Gln Thr Ala Glu Asn Pro Val Phe
                405                 410                 415

Thr Val Phe Lys Asp Asn Glu Ile Leu Tyr Arg Ala Gln Leu Ala Ser
            420                 425                 430

Glu Asp Thr Asn Ala Gln Lys Thr Ile Thr Asn Cys Phe Leu Leu Lys
        435                 440                 445

Asn Lys Ile Trp Cys Ile Ser Leu Val Glu Ile Tyr Asp Thr Gly Asp
    450                 455                 460

Asn Val Ile Arg Pro Lys Leu Phe Ala Val Lys Ile Pro Glu Gln Cys
465                 470                 475                 480

Thr Gly Gly Gly Ser Gly Gly Asp Ile Ile Lys Leu Leu Asn Glu Gln
                485                 490                 495

Val Asn Lys Glu Met Gln Ser Ser Asn Leu Tyr Met Ser Met Ser Ser
```

-continued 500 505 510

Trp Cys Tyr Thr His Ser Leu Asp Gly Ala Gly Leu Phe Leu Phe Asp
515 520 525

His Ala Ala Glu Glu Tyr Glu His Ala Lys Lys Leu Ile Ile Phe Leu
530 535 540

Asn Glu Asn Asn Val Pro Val Gln Leu Thr Ser Ile Ser Ala Pro Glu
545 550 555 560

His Lys Phe Glu Gly Leu Thr Gln Ile Phe Gln Lys Ala Tyr Glu His
565 570 575

Glu Gln His Ile Ser Glu Ser Ile Asn Asn Ile Val Asp His Ala Ile
580 585 590

Lys Ser Lys Asp His Ala Thr Phe Asn Phe Leu Gln Trp Tyr Val Ala
595 600 605

Glu Gln His Glu Glu Glu Val Leu Phe Lys Asp Ile Leu Asp Lys Ile
610 615 620

Glu Leu Ile Gly Asn Glu Asn His Gly Leu Tyr Leu Ala Asp Gln Tyr
625 630 635 640

Val Lys Gly Ile Ala Lys Ser Arg Lys Ser Gly Ser
645 650

<210> SEQ ID NO 39
<211> LENGTH: 661
<212> TYPE: PRT
<213> ORGANISM: Artificial sequence
<220> FEATURE:
<223> OTHER INFORMATION: Recombinant Nipah virus G sequence

<400> SEQUENCE: 39

Met Tyr Ser Met Gln Leu Ala Ser Cys Val Thr Leu Thr Leu Val Leu
1 5 10 15

Leu Val Asn Ser Gln His His His His His His Gly Ser Ala Trp Ser
20 25 30

His Pro Gln Phe Glu Lys Gly Gly Leu Val Pro Arg Gly Ser Gly Asn
35 40 45

Ser Gln Arg Pro Gln Thr Glu Gly Val Ser Asn Leu Val Gly Leu Pro
50 55 60

Asn Asn Ile Cys Leu Gln Lys Thr Ser Asn Gln Ile Leu Lys Pro Lys
65 70 75 80

Leu Ile Ser Tyr Thr Leu Pro Val Val Gly Gln Ser Gly Thr Cys Ile
85 90 95

Thr Asp Pro Leu Leu Ala Met Asp Glu Gly Tyr Phe Ala Tyr Ser His
100 105 110

Leu Glu Arg Ile Gly Ser Cys Ser Arg Gly Val Ser Lys Gln Arg Ile
115 120 125

Ile Gly Val Gly Glu Val Leu Asp Arg Gly Asp Glu Val Pro Ser Leu
130 135 140

Phe Met Thr Asn Val Trp Thr Pro Pro Asn Pro Asn Thr Val Tyr His
145 150 155 160

Cys Ser Ala Val Tyr Asn Asn Glu Phe Tyr Tyr Val Leu Cys Ala Val
165 170 175

Ser Thr Val Gly Asp Pro Ile Leu Asn Ser Thr Tyr Trp Ser Gly Ser
180 185 190

Leu Met Met Thr Arg Leu Ala Val Lys Pro Lys Ser Asn Gly Gly Gly
195 200 205

Tyr Asn Gln His Gln Leu Ala Leu Arg Ser Ile Glu Lys Gly Arg Tyr

-continued

```
    210                 215                 220

Asp Lys Val Met Pro Tyr Gly Pro Ser Gly Ile Lys Gln Gly Asp Thr
225                 230                 235                 240

Leu Tyr Phe Pro Ala Val Gly Phe Leu Val Arg Thr Glu Phe Lys Tyr
                245                 250                 255

Asn Asp Ser Asn Cys Pro Ile Thr Lys Cys Gln Tyr Ser Lys Pro Glu
            260                 265                 270

Asn Cys Arg Leu Ser Met Gly Ile Arg Pro Asn Ser His Tyr Ile Leu
        275                 280                 285

Arg Ser Gly Leu Leu Lys Tyr Asn Leu Ser Asp Gly Glu Asn Pro Lys
    290                 295                 300

Val Val Phe Ile Glu Ile Ser Asp Gln Arg Leu Ser Ile Gly Ser Pro
305                 310                 315                 320

Ser Lys Ile Tyr Asp Ser Leu Gly Gln Pro Val Phe Tyr Gln Ala Ser
                325                 330                 335

Phe Ser Trp Asp Thr Met Ile Lys Phe Gly Asp Val Leu Thr Val Asn
            340                 345                 350

Pro Leu Val Val Asn Trp Arg Asn Asn Thr Val Ile Ser Arg Pro Gly
        355                 360                 365

Gln Ser Gln Cys Pro Arg Phe Asn Thr Cys Pro Glu Ile Cys Trp Glu
    370                 375                 380

Gly Val Tyr Asn Asp Ala Phe Leu Ile Asp Arg Ile Asn Trp Ile Ser
385                 390                 395                 400

Ala Gly Val Phe Leu Asp Ser Asn Gln Thr Ala Glu Asn Pro Val Phe
                405                 410                 415

Thr Val Phe Lys Asp Asn Glu Ile Leu Tyr Arg Ala Gln Leu Ala Ser
            420                 425                 430

Glu Asp Thr Asn Ala Gln Lys Thr Ile Thr Asn Cys Phe Leu Leu Lys
        435                 440                 445

Asn Lys Ile Trp Cys Ile Ser Leu Val Glu Ile Tyr Asp Thr Gly Asp
    450                 455                 460

Asn Val Ile Arg Pro Lys Leu Phe Ala Val Lys Ile Pro Glu Gln Cys
465                 470                 475                 480

Thr Gly Gly Gly Ser Gly Gly Gly Gly Ser Gly Gly Ser Gly Gly Gly
                485                 490                 495

Asp Ile Ile Lys Leu Leu Asn Glu Gln Val Asn Lys Glu Met Gln Ser
            500                 505                 510

Ser Asn Leu Tyr Met Ser Met Ser Ser Trp Cys Tyr Thr His Ser Leu
        515                 520                 525

Asp Gly Ala Gly Leu Phe Leu Phe Asp His Ala Ala Glu Glu Tyr Glu
    530                 535                 540

His Ala Lys Lys Leu Ile Ile Phe Leu Asn Glu Asn Asn Val Pro Val
545                 550                 555                 560

Gln Leu Thr Ser Ile Ser Ala Pro Glu His Lys Phe Glu Gly Leu Thr
                565                 570                 575

Gln Ile Phe Gln Lys Ala Tyr Glu His Glu Gln His Ile Ser Glu Ser
            580                 585                 590

Ile Asn Asn Ile Val Asp His Ala Ile Lys Ser Lys Asp His Ala Thr
        595                 600                 605

Phe Asn Phe Leu Gln Trp Tyr Val Ala Glu Gln His Glu Glu Glu Val
    610                 615                 620

Leu Phe Lys Asp Ile Leu Asp Lys Ile Glu Leu Ile Gly Asn Glu Asn
625                 630                 635                 640
```

His Gly Leu Tyr Leu Ala Asp Gln Tyr Val Lys Gly Ile Ala Lys Ser
645 650 655

Arg Lys Ser Gly Ser
660

<210> SEQ ID NO 40
<211> LENGTH: 671
<212> TYPE: PRT
<213> ORGANISM: Artificial sequence
<220> FEATURE:
<223> OTHER INFORMATION: Recombinant Nipah virus G sequence

<400> SEQUENCE: 40

Met Tyr Ser Met Gln Leu Ala Ser Cys Val Thr Leu Thr Leu Val Leu
1 5 10 15

Leu Val Asn Ser Gln His His His His His His Gly Ser Ala Trp Ser
20 25 30

His Pro Gln Phe Glu Lys Gly Gly Leu Val Pro Arg Gly Ser Gly Asn
35 40 45

Ser Gln Arg Pro Gln Thr Glu Gly Val Ser Asn Leu Val Gly Leu Pro
50 55 60

Asn Asn Ile Cys Leu Gln Lys Thr Ser Asn Gln Ile Leu Lys Pro Lys
65 70 75 80

Leu Ile Ser Tyr Thr Leu Pro Val Val Gly Gln Ser Gly Thr Cys Ile
85 90 95

Thr Asp Pro Leu Leu Ala Met Asp Glu Gly Tyr Phe Ala Tyr Ser His
100 105 110

Leu Glu Arg Ile Gly Ser Cys Ser Arg Gly Val Ser Lys Gln Arg Ile
115 120 125

Ile Gly Val Gly Glu Val Leu Asp Arg Gly Asp Glu Val Pro Ser Leu
130 135 140

Phe Met Thr Asn Val Trp Thr Pro Pro Asn Pro Asn Thr Val Tyr His
145 150 155 160

Cys Ser Ala Val Tyr Asn Asn Glu Phe Tyr Tyr Val Leu Cys Ala Val
165 170 175

Ser Thr Val Gly Asp Pro Ile Leu Asn Ser Thr Tyr Trp Ser Gly Ser
180 185 190

Leu Met Met Thr Arg Leu Ala Val Lys Pro Lys Ser Asn Gly Gly Gly
195 200 205

Tyr Asn Gln His Gln Leu Ala Leu Arg Ser Ile Glu Lys Gly Arg Tyr
210 215 220

Asp Lys Val Met Pro Tyr Gly Pro Ser Gly Ile Lys Gln Gly Asp Thr
225 230 235 240

Leu Tyr Phe Pro Ala Val Gly Phe Leu Val Arg Thr Glu Phe Lys Tyr
245 250 255

Asn Asp Ser Asn Cys Pro Ile Thr Lys Cys Gln Tyr Ser Lys Pro Glu
260 265 270

Asn Cys Arg Leu Ser Met Gly Ile Arg Pro Asn Ser His Tyr Ile Leu
275 280 285

Arg Ser Gly Leu Leu Lys Tyr Asn Leu Ser Asp Gly Glu Asn Pro Lys
290 295 300

Val Val Phe Ile Glu Ile Ser Asp Gln Arg Leu Ser Ile Gly Ser Pro
305 310 315 320

Ser Lys Ile Tyr Asp Ser Leu Gly Gln Pro Val Phe Tyr Gln Ala Ser
325 330 335

```
Phe Ser Trp Asp Thr Met Ile Lys Phe Gly Asp Val Leu Thr Val Asn
            340                 345                 350

Pro Leu Val Val Asn Trp Arg Asn Asn Thr Val Ile Ser Arg Pro Gly
        355                 360                 365

Gln Ser Gln Cys Pro Arg Phe Asn Thr Cys Pro Glu Ile Cys Trp Glu
    370                 375                 380

Gly Val Tyr Asn Asp Ala Phe Leu Ile Asp Arg Ile Asn Trp Ile Ser
385                 390                 395                 400

Ala Gly Val Phe Leu Asp Ser Asn Gln Thr Ala Glu Asn Pro Val Phe
                405                 410                 415

Thr Val Phe Lys Asp Asn Glu Ile Leu Tyr Arg Ala Gln Leu Ala Ser
            420                 425                 430

Glu Asp Thr Asn Ala Gln Lys Thr Ile Thr Asn Cys Phe Leu Leu Lys
        435                 440                 445

Asn Lys Ile Trp Cys Ile Ser Leu Val Glu Ile Tyr Asp Thr Gly Asp
    450                 455                 460

Asn Val Ile Arg Pro Lys Leu Phe Ala Val Lys Ile Pro Glu Gln Cys
465                 470                 475                 480

Thr Gly Gly Gly Ser Gly Gly Gly Gly Ser Gly Gly Ser Gly Gly Gly
                485                 490                 495

Gly Ser Gly Gly Gly Gly Ser Gly Gly Gly Asp Ile Ile Lys Leu Leu
            500                 505                 510

Asn Glu Gln Val Asn Lys Glu Met Gln Ser Ser Asn Leu Tyr Met Ser
        515                 520                 525

Met Ser Ser Trp Cys Tyr Thr His Ser Leu Asp Gly Ala Gly Leu Phe
    530                 535                 540

Leu Phe Asp His Ala Ala Glu Glu Tyr Glu His Ala Lys Lys Leu Ile
545                 550                 555                 560

Ile Phe Leu Asn Glu Asn Asn Val Pro Val Gln Leu Thr Ser Ile Ser
                565                 570                 575

Ala Pro Glu His Lys Phe Glu Gly Leu Thr Gln Ile Phe Gln Lys Ala
            580                 585                 590

Tyr Glu His Glu Gln His Ile Ser Glu Ser Ile Asn Asn Ile Val Asp
        595                 600                 605

His Ala Ile Lys Ser Lys Asp His Ala Thr Phe Asn Phe Leu Gln Trp
    610                 615                 620

Tyr Val Ala Glu Gln His Glu Glu Glu Val Leu Phe Lys Asp Ile Leu
625                 630                 635                 640

Asp Lys Ile Glu Leu Ile Gly Asn Glu Asn His Gly Leu Tyr Leu Ala
                645                 650                 655

Asp Gln Tyr Val Lys Gly Ile Ala Lys Ser Arg Lys Ser Gly Ser
            660                 665                 670


<210> SEQ ID NO 41
<211> LENGTH: 681
<212> TYPE: PRT
<213> ORGANISM: Artificial sequence
<220> FEATURE:
<223> OTHER INFORMATION: Recombinant Nipah virus G sequence

<400> SEQUENCE: 41

Met Tyr Ser Met Gln Leu Ala Ser Cys Val Thr Leu Thr Leu Val Leu
1               5                   10                  15

Leu Val Asn Ser Gln His His His His His His Gly Ser Ala Trp Ser
            20                  25                  30
```

```
His Pro Gln Phe Glu Lys Gly Gly Leu Val Pro Arg Gly Ser Gly Asn
        35                  40                  45

Ser Gln Arg Pro Gln Thr Glu Gly Val Ser Asn Leu Val Gly Leu Pro
    50                  55                  60

Asn Asn Ile Cys Leu Gln Lys Thr Ser Asn Gln Ile Leu Lys Pro Lys
65                  70                  75                  80

Leu Ile Ser Tyr Thr Leu Pro Val Val Gly Gln Ser Gly Thr Cys Ile
                85                  90                  95

Thr Asp Pro Leu Leu Ala Met Asp Glu Gly Tyr Phe Ala Tyr Ser His
            100                 105                 110

Leu Glu Arg Ile Gly Ser Cys Ser Arg Gly Val Ser Lys Gln Arg Ile
        115                 120                 125

Ile Gly Val Gly Glu Val Leu Asp Arg Gly Asp Glu Val Pro Ser Leu
    130                 135                 140

Phe Met Thr Asn Val Trp Thr Pro Pro Asn Pro Asn Thr Val Tyr His
145                 150                 155                 160

Cys Ser Ala Val Tyr Asn Asn Glu Phe Tyr Tyr Val Leu Cys Ala Val
                165                 170                 175

Ser Thr Val Gly Asp Pro Ile Leu Asn Ser Thr Tyr Trp Ser Gly Ser
            180                 185                 190

Leu Met Met Thr Arg Leu Ala Val Lys Pro Lys Ser Asn Gly Gly Gly
        195                 200                 205

Tyr Asn Gln His Gln Leu Ala Leu Arg Ser Ile Glu Lys Gly Arg Tyr
    210                 215                 220

Asp Lys Val Met Pro Tyr Gly Pro Ser Gly Ile Lys Gln Gly Asp Thr
225                 230                 235                 240

Leu Tyr Phe Pro Ala Val Gly Phe Leu Val Arg Thr Glu Phe Lys Tyr
                245                 250                 255

Asn Asp Ser Asn Cys Pro Ile Thr Lys Cys Gln Tyr Ser Lys Pro Glu
            260                 265                 270

Asn Cys Arg Leu Ser Met Gly Ile Arg Pro Asn Ser His Tyr Ile Leu
        275                 280                 285

Arg Ser Gly Leu Leu Lys Tyr Asn Leu Ser Asp Gly Glu Asn Pro Lys
    290                 295                 300

Val Val Phe Ile Glu Ile Ser Asp Gln Arg Leu Ser Ile Gly Ser Pro
305                 310                 315                 320

Ser Lys Ile Tyr Asp Ser Leu Gly Gln Pro Val Phe Tyr Gln Ala Ser
                325                 330                 335

Phe Ser Trp Asp Thr Met Ile Lys Phe Gly Asp Val Leu Thr Val Asn
            340                 345                 350

Pro Leu Val Val Asn Trp Arg Asn Asn Thr Val Ile Ser Arg Pro Gly
        355                 360                 365

Gln Ser Gln Cys Pro Arg Phe Asn Thr Cys Pro Glu Ile Cys Trp Glu
    370                 375                 380

Gly Val Tyr Asn Asp Ala Phe Leu Ile Asp Arg Ile Asn Trp Ile Ser
385                 390                 395                 400

Ala Gly Val Phe Leu Asp Ser Asn Gln Thr Ala Glu Asn Pro Val Phe
                405                 410                 415

Thr Val Phe Lys Asp Asn Glu Ile Leu Tyr Arg Ala Gln Leu Ala Ser
            420                 425                 430

Glu Asp Thr Asn Ala Gln Lys Thr Ile Thr Asn Cys Phe Leu Leu Lys
        435                 440                 445
```

Asn Lys Ile Trp Cys Ile Ser Leu Val Glu Ile Tyr Asp Thr Gly Asp
    450                 455                 460

Asn Val Ile Arg Pro Lys Leu Phe Ala Val Lys Ile Pro Glu Gln Cys
465                 470                 475                 480

Thr Gly Gly Gly Ser Gly Gly Gly Gly Ser Gly Gly Ser Gly Gly Gly
                485                 490                 495

Gly Ser Gly Gly Gly Gly Ser Gly Gly Gly Gly Ser Gly Gly Gly Gly
            500                 505                 510

Ser Gly Gly Gly Asp Ile Ile Lys Leu Leu Asn Glu Gln Val Asn Lys
        515                 520                 525

Glu Met Gln Ser Ser Asn Leu Tyr Met Ser Met Ser Ser Trp Cys Tyr
    530                 535                 540

Thr His Ser Leu Asp Gly Ala Gly Leu Phe Leu Phe Asp His Ala Ala
545                 550                 555                 560

Glu Glu Tyr Glu His Ala Lys Lys Leu Ile Ile Phe Leu Asn Glu Asn
                565                 570                 575

Asn Val Pro Val Gln Leu Thr Ser Ile Ser Ala Pro Glu His Lys Phe
            580                 585                 590

Glu Gly Leu Thr Gln Ile Phe Gln Lys Ala Tyr Glu His Glu Gln His
        595                 600                 605

Ile Ser Glu Ser Ile Asn Asn Ile Val Asp His Ala Ile Lys Ser Lys
    610                 615                 620

Asp His Ala Thr Phe Asn Phe Leu Gln Trp Tyr Val Ala Glu Gln His
625                 630                 635                 640

Glu Glu Glu Val Leu Phe Lys Asp Ile Leu Asp Lys Ile Glu Leu Ile
                645                 650                 655

Gly Asn Glu Asn His Gly Leu Tyr Leu Ala Asp Gln Tyr Val Lys Gly
            660                 665                 670

Ile Ala Lys Ser Arg Lys Ser Gly Ser
        675                 680

<210> SEQ ID NO 42
<211> LENGTH: 647
<212> TYPE: PRT
<213> ORGANISM: Artificial sequence
<220> FEATURE:
<223> OTHER INFORMATION: Recombinant Nipah virus G sequence

<400> SEQUENCE: 42

Met Tyr Ser Met Gln Leu Ala Ser Cys Val Thr Leu Thr Leu Val Leu
1               5                   10                  15

Leu Val Asn Ser Gln His His His His His His Gly Ser Ala Trp Ser
            20                  25                  30

His Pro Gln Phe Glu Lys Gly Gly Leu Val Pro Arg Gly Ser Gly Asn
        35                  40                  45

Ser Gln Arg Pro Gln Thr Glu Gly Val Ser Asn Leu Val Gly Leu Pro
    50                  55                  60

Asn Asn Ile Cys Leu Gln Lys Thr Ser Asn Gln Ile Leu Lys Pro Lys
65                  70                  75                  80

Leu Ile Ser Tyr Thr Leu Pro Val Val Gly Gln Ser Gly Thr Cys Ile
                85                  90                  95

Thr Asp Pro Leu Leu Ala Met Asp Glu Gly Tyr Phe Ala Tyr Ser His
            100                 105                 110

Leu Glu Arg Ile Gly Ser Cys Ser Arg Gly Val Ser Lys Gln Arg Ile
        115                 120                 125

-continued

```
Ile Gly Val Gly Glu Val Leu Asp Arg Gly Asp Glu Val Pro Ser Leu
    130                 135                 140

Phe Met Thr Asn Val Trp Thr Pro Pro Asn Pro Asn Thr Val Tyr His
145                 150                 155                 160

Cys Ser Ala Val Tyr Asn Asn Glu Phe Tyr Tyr Val Leu Cys Ala Val
                165                 170                 175

Ser Thr Val Gly Asp Pro Ile Leu Asn Ser Thr Tyr Trp Ser Gly Ser
            180                 185                 190

Leu Met Met Thr Arg Leu Ala Val Lys Pro Lys Ser Asn Gly Gly Gly
        195                 200                 205

Tyr Asn Gln His Gln Leu Ala Leu Arg Ser Ile Glu Lys Gly Arg Tyr
    210                 215                 220

Asp Lys Val Met Pro Tyr Gly Pro Ser Gly Ile Lys Gln Gly Asp Thr
225                 230                 235                 240

Leu Tyr Phe Pro Ala Val Gly Phe Leu Val Arg Thr Glu Phe Lys Tyr
                245                 250                 255

Asn Asp Ser Asn Cys Pro Ile Thr Lys Cys Gln Tyr Ser Lys Pro Glu
            260                 265                 270

Asn Cys Arg Leu Ser Met Gly Ile Arg Pro Asn Ser His Tyr Ile Leu
        275                 280                 285

Arg Ser Gly Leu Leu Lys Tyr Asn Leu Ser Asp Gly Glu Asn Pro Lys
    290                 295                 300

Val Val Phe Ile Glu Ile Ser Asp Gln Arg Leu Ser Ile Gly Ser Pro
305                 310                 315                 320

Ser Lys Ile Tyr Asp Ser Leu Gly Gln Pro Val Phe Tyr Gln Ala Ser
                325                 330                 335

Phe Ser Trp Asp Thr Met Ile Lys Phe Gly Asp Val Leu Thr Val Asn
            340                 345                 350

Pro Leu Val Val Asn Trp Arg Asn Asn Thr Val Ile Ser Arg Pro Gly
        355                 360                 365

Gln Ser Gln Cys Pro Arg Phe Asn Thr Cys Pro Glu Ile Cys Trp Glu
    370                 375                 380

Gly Val Tyr Asn Asp Ala Phe Leu Ile Asp Arg Ile Asn Trp Ile Ser
385                 390                 395                 400

Ala Gly Val Phe Leu Asp Ser Asn Gln Thr Ala Glu Asn Pro Val Phe
                405                 410                 415

Thr Val Phe Lys Asp Asn Glu Ile Leu Tyr Arg Ala Gln Leu Ala Ser
            420                 425                 430

Glu Asp Thr Asn Ala Gln Lys Thr Ile Thr Asn Cys Phe Leu Leu Lys
        435                 440                 445

Asn Lys Ile Trp Cys Ile Ser Leu Val Glu Ile Tyr Asp Thr Gly Asp
    450                 455                 460

Asn Val Ile Arg Pro Lys Leu Phe Ala Val Lys Ile Pro Glu Gln Cys
465                 470                 475                 480

Thr Gly Gly Gly Ser Gly Gly Gly Ser Gly Gly Gly Ser Met Gln Ile
                485                 490                 495

Tyr Glu Gly Lys Leu Thr Ala Glu Gly Leu Arg Phe Gly Ile Val Ala
            500                 505                 510

Ser Arg Phe Asn His Ala Leu Val Asp Arg Leu Val Glu Gly Ala Ile
        515                 520                 525

Asp Cys Ile Val Arg His Gly Gly Arg Glu Glu Asp Ile Thr Leu Val
    530                 535                 540

Arg Val Pro Gly Ser Trp Glu Ile Pro Val Ala Ala Gly Glu Leu Ala
```

-continued

```
545                 550                 555                 560

Arg Lys Glu Asp Ile Asp Ala Val Ile Ala Ile Gly Val Leu Ile Arg
                565                 570                 575

Gly Ala Thr Pro His Phe Asp Tyr Ile Ala Ser Glu Val Ser Lys Gly
            580                 585                 590

Leu Ala Asp Leu Ser Leu Glu Leu Arg Lys Pro Ile Thr Phe Gly Val
        595                 600                 605

Ile Thr Ala Asp Thr Leu Glu Gln Ala Ile Glu Arg Ala Gly Thr Lys
    610                 615                 620

His Gly Asn Lys Gly Trp Glu Ala Ala Leu Ser Ala Ile Glu Met Ala
625                 630                 635                 640

Asn Leu Phe Lys Ser Leu Arg
                645


<210> SEQ ID NO 43
<211> LENGTH: 1005
<212> TYPE: PRT
<213> ORGANISM: Artificial sequence
<220> FEATURE:
<223> OTHER INFORMATION: Recombinant Nipah virus F sequence

<400> SEQUENCE: 43

Met Tyr Ser Met Gln Leu Ala Ser Cys Val Thr Leu Thr Leu Val Leu
1               5                   10                  15

Leu Val Asn Ser Gln Gly Ile Leu His Tyr Glu Lys Leu Ser Lys Ile
            20                  25                  30

Gly Leu Val Lys Gly Val Thr Arg Lys Tyr Lys Ile Lys Ser Asn Pro
        35                  40                  45

Leu Thr Lys Asp Ile Val Ile Lys Met Ile Pro Asn Val Ser Asn Met
    50                  55                  60

Ser Gln Cys Thr Gly Ser Val Met Glu Asn Tyr Lys Thr Arg Leu Asn
65                  70                  75                  80

Gly Ile Leu Thr Pro Ile Lys Gly Ala Leu Glu Ile Tyr Lys Asn Asn
                85                  90                  95

Thr His Asp Cys Val Gly Asp Val Arg Leu Ala Gly Val Cys Met Ala
            100                 105                 110

Gly Val Ala Ile Gly Ile Ala Thr Ala Ala Gln Ile Thr Ala Gly Val
        115                 120                 125

Ala Leu Tyr Glu Ala Met Lys Asn Ala Asp Asn Ile Asn Lys Leu Lys
    130                 135                 140

Ser Ser Ile Glu Ser Thr Asn Glu Ala Val Val Lys Leu Gln Glu Thr
145                 150                 155                 160

Ala Glu Lys Thr Val Tyr Val Phe Thr Ala Leu Gln Asp Tyr Ile Asn
                165                 170                 175

Thr Asn Leu Val Pro Thr Ile Asp Lys Ile Pro Cys Lys Gln Thr Glu
            180                 185                 190

Leu Ser Leu Asp Leu Ala Leu Ser Lys Tyr Leu Ser Asp Leu Leu Phe
        195                 200                 205

Val Phe Gly Pro Asn Leu Gln Asp Pro Val Ser Asn Ser Met Thr Ile
    210                 215                 220

Gln Ala Ile Ser Gln Ala Phe Gly Gly Asn Tyr Glu Thr Leu Leu Arg
225                 230                 235                 240

Thr Leu Gly Tyr Ala Thr Glu Asp Phe Asp Asp Leu Leu Glu Ser Asp
                245                 250                 255

Ser Ile Thr Gly Gln Ile Ile Tyr Val Asp Leu Ser Ser Tyr Tyr Ile
```

```
            260                 265                 270

Ile Val Arg Val Tyr Phe Pro Ile Leu Thr Glu Ile Gln Gln Ala Tyr
        275                 280                 285

Ile Gln Glu Leu Leu Pro Val Ser Phe Asn Asn Asp Asn Ser Glu Trp
    290                 295                 300

Ile Ser Ile Val Pro Asn Phe Ile Leu Val Arg Asn Thr Leu Ile Ser
305                 310                 315                 320

Asn Ile Glu Ile Gly Phe Cys Leu Ile Thr Lys Arg Ser Val Ile Cys
                325                 330                 335

Asn Gln Asp Tyr Ala Thr Pro Met Thr Asn Asn Met Arg Glu Cys Leu
            340                 345                 350

Thr Gly Ser Thr Glu Lys Cys Pro Arg Glu Leu Val Val Ser Ser His
        355                 360                 365

Val Pro Arg Phe Ala Leu Ser Asn Gly Val Leu Phe Ala Asn Cys Ile
    370                 375                 380

Ser Val Thr Cys Gln Cys Gln Thr Thr Gly Arg Ala Ile Ser Gln Ser
385                 390                 395                 400

Gly Glu Gln Thr Leu Leu Met Ile Asp Asn Thr Thr Cys Pro Thr Ala
                405                 410                 415

Val Leu Gly Asn Val Ile Ile Ser Leu Gly Lys Tyr Leu Gly Ser Val
            420                 425                 430

Asn Tyr Asn Ser Glu Gly Ile Ala Ile Gly Pro Pro Val Phe Thr Asp
        435                 440                 445

Lys Val Asp Ile Ser Ser Gln Ile Ser Ser Met Asn Gln Ser Leu Gln
    450                 455                 460

Gln Ser Lys Asp Tyr Ile Lys Glu Ala Gln Arg Leu Leu Asp Thr Val
465                 470                 475                 480

Asn Pro Ser Leu Lys Leu Met Lys Gln Ile Glu Asp Lys Ile Glu Glu
                485                 490                 495

Ile Leu Ser Lys Ile Tyr His Ile Glu Asn Glu Ile Ala Arg Ile Lys
            500                 505                 510

Lys Leu Ile Gly Glu Ala Pro Gly Ser Gly Tyr Ile Pro Glu Ala Pro
        515                 520                 525

Arg Asp Gly Gln Ala Tyr Val Arg Lys Asp Gly Glu Trp Val Leu Leu
    530                 535                 540

Ser Thr Phe Leu Gly Ser Gly Gly Gly Gly Gly Gly Val Ser Asn Leu
545                 550                 555                 560

Val Gly Leu Pro Asn Asn Ile Cys Leu Gln Lys Thr Ser Asn Gln Ile
                565                 570                 575

Leu Lys Pro Lys Leu Ile Ser Tyr Thr Leu Pro Val Val Gly Gln Ser
            580                 585                 590

Gly Thr Cys Ile Thr Asp Pro Leu Leu Ala Met Asp Glu Gly Tyr Phe
        595                 600                 605

Ala Tyr Ser His Leu Glu Arg Ile Gly Ser Cys Ser Arg Gly Val Ser
    610                 615                 620

Lys Gln Arg Ile Ile Gly Val Gly Glu Val Leu Asp Arg Gly Asp Glu
625                 630                 635                 640

Val Pro Ser Leu Phe Met Thr Asn Val Trp Thr Pro Pro Asn Pro Asn
                645                 650                 655

Thr Val Tyr His Cys Ser Ala Val Tyr Asn Asn Glu Phe Tyr Tyr Val
            660                 665                 670

Leu Cys Ala Val Ser Thr Val Gly Asp Pro Ile Leu Asn Ser Thr Tyr
        675                 680                 685
```

Trp Ser Gly Ser Leu Met Met Thr Arg Leu Ala Val Lys Pro Lys Ser
690 695 700

Asn Gly Gly Gly Tyr Asn Gln His Gln Leu Ala Leu Arg Ser Ile Glu
705 710 715 720

Lys Gly Arg Tyr Asp Lys Val Met Pro Tyr Gly Pro Ser Gly Ile Lys
725 730 735

Gln Gly Asp Thr Leu Tyr Phe Pro Ala Val Gly Phe Leu Val Arg Thr
740 745 750

Glu Phe Lys Tyr Asn Asp Ser Asn Cys Pro Ile Thr Lys Cys Gln Tyr
755 760 765

Ser Lys Pro Glu Asn Cys Arg Leu Ser Met Gly Ile Arg Pro Asn Ser
770 775 780

His Tyr Ile Leu Arg Ser Gly Leu Leu Lys Tyr Asn Leu Ser Asp Gly
785 790 795 800

Glu Asn Pro Lys Val Val Phe Ile Glu Ile Ser Asp Gln Arg Leu Ser
805 810 815

Ile Gly Ser Pro Ser Lys Ile Tyr Asp Ser Leu Gly Gln Pro Val Phe
820 825 830

Tyr Gln Ala Ser Phe Ser Trp Asp Thr Met Ile Lys Phe Gly Asp Val
835 840 845

Leu Thr Val Asn Pro Leu Val Val Asn Trp Arg Asn Asn Thr Val Ile
850 855 860

Ser Arg Pro Gly Gln Ser Gln Cys Pro Arg Phe Asn Thr Cys Pro Glu
865 870 875 880

Ile Cys Trp Glu Gly Val Tyr Asn Asp Ala Phe Leu Ile Asp Arg Ile
885 890 895

Asn Trp Ile Ser Ala Gly Val Phe Leu Asp Ser Asn Gln Thr Ala Glu
900 905 910

Asn Pro Val Phe Thr Val Phe Lys Asp Asn Glu Ile Leu Tyr Arg Ala
915 920 925

Gln Leu Ala Ser Glu Asp Thr Asn Ala Gln Lys Thr Ile Thr Asn Cys
930 935 940

Phe Leu Leu Lys Asn Lys Ile Trp Cys Ile Ser Leu Val Glu Ile Tyr
945 950 955 960

Asp Thr Gly Asp Asn Val Ile Arg Pro Lys Leu Phe Ala Val Lys Ile
965 970 975

Pro Glu Gln Cys Thr Gly Gly Leu Val Pro Arg Gly Ser His His His
980 985 990

His His His Ser Ala Trp Ser His Pro Gln Phe Glu Lys
995 1000 1005

<210> SEQ ID NO 44
<211> LENGTH: 1007
<212> TYPE: PRT
<213> ORGANISM: Artificial sequence
<220> FEATURE:
<223> OTHER INFORMATION: Recombinant Nipah virus F sequence

<400> SEQUENCE: 44

Met Tyr Ser Met Gln Leu Ala Ser Cys Val Thr Leu Thr Leu Val Leu
1 5 10 15

Leu Val Asn Ser Gln Arg Pro Gln Thr Glu Gly Val Ser Asn Leu Val
20 25 30

Gly Leu Pro Asn Asn Ile Cys Leu Gln Lys Thr Ser Asn Gln Ile Leu
35 40 45

```
Lys Pro Lys Leu Ile Ser Tyr Thr Leu Pro Val Val Gly Gln Ser Gly
    50                  55                  60

Thr Cys Ile Thr Asp Pro Leu Leu Ala Met Asp Glu Gly Tyr Phe Ala
65                  70                  75                  80

Tyr Ser His Leu Glu Arg Ile Gly Ser Cys Ser Arg Gly Val Ser Lys
                85                  90                  95

Gln Arg Ile Ile Gly Val Gly Glu Val Leu Asp Arg Gly Asp Glu Val
            100                 105                 110

Pro Ser Leu Phe Met Thr Asn Val Trp Thr Pro Pro Asn Pro Asn Thr
        115                 120                 125

Val Tyr His Cys Ser Ala Val Tyr Asn Asn Glu Phe Tyr Tyr Val Leu
    130                 135                 140

Cys Ala Val Ser Thr Val Gly Asp Pro Ile Leu Asn Ser Thr Tyr Trp
145                 150                 155                 160

Ser Gly Ser Leu Met Met Thr Arg Leu Ala Val Lys Pro Lys Ser Asn
                165                 170                 175

Gly Gly Gly Tyr Asn Gln His Gln Leu Ala Leu Arg Ser Ile Glu Lys
            180                 185                 190

Gly Arg Tyr Asp Lys Val Met Pro Tyr Gly Pro Ser Gly Ile Lys Gln
        195                 200                 205

Gly Asp Thr Leu Tyr Phe Pro Ala Val Gly Phe Leu Val Arg Thr Glu
    210                 215                 220

Phe Lys Tyr Asn Asp Ser Asn Cys Pro Ile Thr Lys Cys Gln Tyr Ser
225                 230                 235                 240

Lys Pro Glu Asn Cys Arg Leu Ser Met Gly Ile Arg Pro Asn Ser His
                245                 250                 255

Tyr Ile Leu Arg Ser Gly Leu Leu Lys Tyr Asn Leu Ser Asp Gly Glu
            260                 265                 270

Asn Pro Lys Val Val Phe Ile Glu Ile Ser Asp Gln Arg Leu Ser Ile
        275                 280                 285

Gly Ser Pro Ser Lys Ile Tyr Asp Ser Leu Gly Gln Pro Val Phe Tyr
    290                 295                 300

Gln Ala Ser Phe Ser Trp Asp Thr Met Ile Lys Phe Gly Asp Val Leu
305                 310                 315                 320

Thr Val Asn Pro Leu Val Val Asn Trp Arg Asn Asn Thr Val Ile Ser
                325                 330                 335

Arg Pro Gly Gln Ser Gln Cys Pro Arg Phe Asn Thr Cys Pro Glu Ile
            340                 345                 350

Cys Trp Glu Gly Val Tyr Asn Asp Ala Phe Leu Ile Asp Arg Ile Asn
        355                 360                 365

Trp Ile Ser Ala Gly Val Phe Leu Asp Ser Asn Gln Thr Ala Glu Asn
    370                 375                 380

Pro Val Phe Thr Val Phe Lys Asp Asn Glu Ile Leu Tyr Arg Ala Gln
385                 390                 395                 400

Leu Ala Ser Glu Asp Thr Asn Ala Gln Lys Thr Ile Thr Asn Cys Phe
                405                 410                 415

Leu Leu Lys Asn Lys Ile Trp Cys Ile Ser Leu Val Glu Ile Tyr Asp
            420                 425                 430

Thr Gly Asp Asn Val Ile Arg Pro Lys Leu Phe Ala Val Lys Ile Pro
        435                 440                 445

Glu Gln Cys Thr Gly Gly Gly Gln Gly Ile Leu His Tyr Glu Lys Leu
    450                 455                 460
```

-continued

```
Ser Lys Ile Gly Leu Val Lys Gly Val Thr Arg Lys Tyr Lys Ile Lys
465                 470                 475                 480

Ser Asn Pro Leu Thr Lys Asp Ile Val Ile Lys Met Ile Pro Asn Val
                485                 490                 495

Ser Asn Met Ser Gln Cys Thr Gly Ser Val Met Glu Asn Tyr Lys Thr
            500                 505                 510

Arg Leu Asn Gly Ile Leu Thr Pro Ile Lys Gly Ala Leu Glu Ile Tyr
        515                 520                 525

Lys Asn Asn Thr His Asp Cys Val Gly Asp Val Arg Leu Ala Gly Val
    530                 535                 540

Cys Met Ala Gly Val Ala Ile Gly Ile Ala Thr Ala Ala Gln Ile Thr
545                 550                 555                 560

Ala Gly Val Ala Leu Tyr Glu Ala Met Lys Asn Ala Asp Asn Ile Asn
                565                 570                 575

Lys Leu Lys Ser Ser Ile Glu Ser Thr Asn Glu Ala Val Val Lys Leu
            580                 585                 590

Gln Glu Thr Ala Glu Lys Thr Val Tyr Val Phe Thr Ala Leu Gln Asp
        595                 600                 605

Tyr Ile Asn Thr Asn Leu Val Pro Thr Ile Asp Lys Ile Pro Cys Lys
    610                 615                 620

Gln Thr Glu Leu Ser Leu Asp Leu Ala Leu Ser Lys Tyr Leu Ser Asp
625                 630                 635                 640

Leu Leu Phe Val Phe Gly Pro Asn Leu Gln Asp Pro Val Ser Asn Ser
                645                 650                 655

Met Thr Ile Gln Ala Ile Ser Gln Ala Phe Gly Gly Asn Tyr Glu Thr
            660                 665                 670

Leu Leu Arg Thr Leu Gly Tyr Ala Thr Glu Asp Phe Asp Asp Leu Leu
        675                 680                 685

Glu Ser Asp Ser Ile Thr Gly Gln Ile Ile Tyr Val Asp Leu Ser Ser
    690                 695                 700

Tyr Tyr Ile Ile Val Arg Val Tyr Phe Pro Ile Leu Thr Glu Ile Gln
705                 710                 715                 720

Gln Ala Tyr Ile Gln Glu Leu Leu Pro Val Ser Phe Asn Asn Asp Asn
                725                 730                 735

Ser Glu Trp Ile Ser Ile Val Pro Asn Phe Ile Leu Val Arg Asn Thr
            740                 745                 750

Leu Ile Ser Asn Ile Glu Ile Gly Phe Cys Leu Ile Thr Lys Arg Ser
        755                 760                 765

Val Ile Cys Asn Gln Asp Tyr Ala Thr Pro Met Thr Asn Asn Met Arg
    770                 775                 780

Glu Cys Leu Thr Gly Ser Thr Glu Lys Cys Pro Arg Glu Leu Val Val
785                 790                 795                 800

Ser Ser His Val Pro Arg Phe Ala Leu Ser Asn Gly Val Leu Phe Ala
                805                 810                 815

Asn Cys Ile Ser Val Thr Cys Gln Cys Gln Thr Thr Gly Arg Ala Ile
            820                 825                 830

Ser Gln Ser Gly Glu Gln Thr Leu Leu Met Ile Asp Asn Thr Thr Cys
        835                 840                 845

Pro Thr Ala Val Leu Gly Asn Val Ile Ile Ser Leu Gly Lys Tyr Leu
    850                 855                 860

Gly Ser Val Asn Tyr Asn Ser Glu Gly Ile Ala Ile Gly Pro Pro Val
865                 870                 875                 880

Phe Thr Asp Lys Val Asp Ile Ser Ser Gln Ile Ser Ser Met Asn Gln
```

-continued

```
                885                 890                 895

Ser Leu Gln Gln Ser Lys Asp Tyr Ile Lys Glu Ala Gln Arg Leu Leu
            900                 905                 910

Asp Thr Val Asn Pro Ser Leu Lys Leu Met Lys Gln Ile Glu Asp Lys
        915                 920                 925

Ile Glu Glu Ile Leu Ser Lys Ile Tyr His Ile Glu Asn Glu Ile Ala
    930                 935                 940

Arg Ile Lys Lys Leu Ile Gly Glu Ala Pro Gly Ser Gly Tyr Ile Pro
945                 950                 955                 960

Glu Ala Pro Arg Asp Gly Gln Ala Tyr Val Arg Lys Asp Gly Glu Trp
                965                 970                 975

Val Leu Leu Ser Thr Phe Leu Gly Ser Leu Val Pro Arg Gly Ser His
            980                 985                 990

His His His His His Ser Ala Trp  Ser His Pro Gln Phe  Glu Lys
        995                 1000                1005


<210> SEQ ID NO 45
<211> LENGTH: 991
<212> TYPE: PRT
<213> ORGANISM: Artificial sequence
<220> FEATURE:
<223> OTHER INFORMATION: Recombinant Nipah virus F sequence

<400> SEQUENCE: 45

Met Tyr Ser Met Gln Leu Ala Ser Cys Val Thr Leu Thr Leu Val Leu
1               5                   10                  15

Leu Val Asn Ser Gln Gly Ile Leu His Tyr Glu Lys Leu Ser Lys Ile
            20                  25                  30

Gly Leu Val Lys Gly Val Thr Arg Lys Tyr Lys Ile Lys Ser Asn Pro
        35                  40                  45

Leu Thr Lys Asp Ile Val Ile Lys Met Ile Pro Asn Val Ser Asn Met
    50                  55                  60

Ser Gln Cys Thr Gly Ser Val Met Glu Asn Tyr Lys Thr Arg Leu Asn
65                  70                  75                  80

Gly Ile Leu Thr Pro Ile Lys Gly Ala Leu Glu Ile Tyr Lys Asn Gly
                85                  90                  95

Gly Ser Gly Val Ala Ile Gly Ile Ala Thr Ala Ala Gln Ile Thr Ala
            100                 105                 110

Gly Val Ala Leu Tyr Glu Ala Met Lys Asn Ala Asp Asn Ile Asn Lys
        115                 120                 125

Leu Lys Ser Ser Ile Glu Ser Thr Asn Glu Ala Val Val Lys Leu Gln
    130                 135                 140

Glu Thr Ala Glu Lys Thr Val Tyr Val Leu Thr Ala Leu Gln Asp Tyr
145                 150                 155                 160

Ile Asn Thr Asn Leu Val Pro Thr Ile Asp Lys Ile Ser Cys Lys Gln
                165                 170                 175

Thr Glu Leu Ser Leu Asp Leu Ala Leu Ser Lys Tyr Leu Ser Asp Leu
            180                 185                 190

Leu Phe Val Phe Gly Pro Asn Leu Gln Asp Pro Val Ser Asn Ser Met
        195                 200                 205

Thr Ile Gln Ala Ile Ser Gln Ala Phe Gly Gly Asn Tyr Glu Thr Leu
    210                 215                 220

Leu Arg Thr Leu Gly Tyr Ala Thr Glu Asp Phe Asp Asp Leu Leu Glu
225                 230                 235                 240

Ser Asp Ser Ile Thr Gly Gln Ile Ile Tyr Val Asp Leu Ser Ser Tyr
```

-continued

```
                245                 250                 255

Tyr Ile Ile Val Arg Val Tyr Phe Pro Ile Leu Thr Glu Ile Gln Gln
            260                 265                 270

Ala Tyr Ile Gln Glu Leu Leu Pro Val Ser Phe Asn Asn Asp Asn Ser
        275                 280                 285

Glu Trp Ile Ser Ile Val Pro Asn Phe Ile Leu Val Arg Asn Thr Leu
    290                 295                 300

Ile Ser Asn Ile Glu Ile Gly Phe Cys Leu Ile Thr Lys Arg Ser Val
305                 310                 315                 320

Ile Cys Asn Gln Asp Tyr Ala Thr Pro Met Thr Asn Asn Met Arg Glu
                325                 330                 335

Cys Leu Thr Gly Ser Thr Glu Lys Cys Pro Arg Glu Leu Val Val Ser
            340                 345                 350

Ser His Val Pro Arg Phe Ala Leu Ser Asn Gly Val Leu Phe Ala Asn
        355                 360                 365

Cys Ile Ser Val Thr Cys Gln Cys Gln Thr Thr Gly Arg Ala Ile Ser
    370                 375                 380

Gln Ser Gly Glu Gln Thr Leu Leu Met Ile Asp Asn Thr Thr Cys Pro
385                 390                 395                 400

Thr Ala Val Leu Gly Asn Val Ile Ile Ser Leu Gly Lys Tyr Leu Gly
                405                 410                 415

Ser Val Asn Tyr Asn Ser Glu Gly Ile Ala Ile Gly Pro Pro Val Phe
            420                 425                 430

Thr Asp Lys Val Asp Ile Ser Ser Gln Ile Ser Ser Met Asn Gln Ser
        435                 440                 445

Leu Gln Gln Ser Lys Asp Tyr Ile Lys Glu Ala Gln Arg Leu Leu Asp
    450                 455                 460

Thr Val Asn Pro Ser Leu Lys Leu Met Lys Gln Ile Glu Asp Lys Ile
465                 470                 475                 480

Glu Glu Ile Leu Ser Lys Ile Tyr His Ile Glu Asn Glu Ile Ala Arg
                485                 490                 495

Ile Lys Lys Leu Ile Gly Glu Ala Pro Gly Ser Gly Tyr Ile Pro Glu
            500                 505                 510

Ala Pro Arg Asp Gly Gln Ala Tyr Val Arg Lys Asp Gly Glu Trp Val
        515                 520                 525

Leu Leu Ser Thr Phe Leu Gly Ser Gly Gly Gly Gly Gly Gly Val Ser
    530                 535                 540

Asn Leu Val Gly Leu Pro Asn Asn Ile Cys Leu Gln Lys Thr Ser Asn
545                 550                 555                 560

Gln Ile Leu Lys Pro Lys Leu Ile Ser Tyr Thr Leu Pro Val Val Gly
                565                 570                 575

Gln Ser Gly Thr Cys Ile Thr Asp Pro Leu Leu Ala Met Asp Glu Gly
            580                 585                 590

Tyr Phe Ala Tyr Ser His Leu Glu Arg Ile Gly Ser Cys Ser Arg Gly
        595                 600                 605

Val Ser Lys Gln Arg Ile Ile Gly Val Gly Glu Val Leu Asp Arg Gly
    610                 615                 620

Asp Glu Val Pro Ser Leu Phe Met Thr Asn Val Trp Thr Pro Pro Asn
625                 630                 635                 640

Pro Asn Thr Val Tyr His Cys Ser Ala Val Tyr Asn Asn Glu Phe Tyr
                645                 650                 655

Tyr Val Leu Cys Ala Val Ser Thr Val Gly Asp Pro Ile Leu Asn Ser
            660                 665                 670
```

Thr Tyr Trp Ser Gly Ser Leu Met Met Thr Arg Leu Ala Val Lys Pro
675 680 685

Lys Ser Asn Gly Gly Gly Tyr Asn Gln His Gln Leu Ala Leu Arg Ser
690 695 700

Ile Glu Lys Gly Arg Tyr Asp Lys Val Met Pro Tyr Gly Pro Ser Gly
705 710 715 720

Ile Lys Gln Gly Asp Thr Leu Tyr Phe Pro Ala Val Gly Phe Leu Val
725 730 735

Arg Thr Glu Phe Lys Tyr Asn Asp Ser Asn Cys Pro Ile Thr Lys Cys
740 745 750

Gln Tyr Ser Lys Pro Glu Asn Cys Arg Leu Ser Met Gly Ile Arg Pro
755 760 765

Asn Ser His Tyr Ile Leu Arg Ser Gly Leu Leu Lys Tyr Asn Leu Ser
770 775 780

Asp Gly Glu Asn Pro Lys Val Val Phe Ile Glu Ile Ser Asp Gln Arg
785 790 795 800

Leu Ser Ile Gly Ser Pro Ser Lys Ile Tyr Asp Ser Leu Gly Gln Pro
805 810 815

Val Phe Tyr Gln Ala Ser Phe Ser Trp Asp Thr Met Ile Lys Phe Gly
820 825 830

Asp Val Leu Thr Val Asn Pro Leu Val Val Asn Trp Arg Asn Asn Thr
835 840 845

Val Ile Ser Arg Pro Gly Gln Ser Gln Cys Pro Arg Phe Asn Thr Cys
850 855 860

Pro Glu Ile Cys Trp Glu Gly Val Tyr Asn Asp Ala Phe Leu Ile Asp
865 870 875 880

Arg Ile Asn Trp Ile Ser Ala Gly Val Phe Leu Asp Ser Asn Gln Thr
885 890 895

Ala Glu Asn Pro Val Phe Thr Val Phe Lys Asp Asn Glu Ile Leu Tyr
900 905 910

Arg Ala Gln Leu Ala Ser Glu Asp Thr Asn Ala Gln Lys Thr Ile Thr
915 920 925

Asn Cys Phe Leu Leu Lys Asn Lys Ile Trp Cys Ile Ser Leu Val Glu
930 935 940

Ile Tyr Asp Thr Gly Asp Asn Val Ile Arg Pro Lys Leu Phe Ala Val
945 950 955 960

Lys Ile Pro Glu Gln Cys Thr Gly Gly Leu Val Pro Arg Gly Ser His
965 970 975

His His His His His Ser Ala Trp Ser His Pro Gln Phe Glu Lys
980 985 990

<210> SEQ ID NO 46
<211> LENGTH: 1423
<212> TYPE: PRT
<213> ORGANISM: Artificial sequence
<220> FEATURE:
<223> OTHER INFORMATION: Recombinant Nipah virus F sequence

<400> SEQUENCE: 46

Met Tyr Ser Met Gln Leu Ala Ser Cys Val Thr Leu Thr Leu Val Leu
1 5 10 15

Leu Val Asn Ser Gln Gly Ile Leu His Tyr Glu Lys Leu Ser Lys Ile
20 25 30

Gly Leu Val Lys Gly Val Thr Arg Lys Tyr Lys Ile Lys Ser Asn Pro
35 40 45

-continued

```
Leu Thr Lys Asp Ile Val Ile Lys Met Ile Pro Asn Val Ser Asn Met
    50                  55                  60

Ser Gln Cys Thr Gly Ser Val Met Glu Asn Tyr Lys Thr Arg Leu Asn
65                  70                  75                  80

Gly Ile Leu Thr Pro Ile Lys Gly Ala Leu Glu Ile Tyr Lys Asn Gly
                85                  90                  95

Gly Ser Gly Val Ala Ile Gly Ile Ala Thr Ala Ala Gln Ile Thr Ala
            100                 105                 110

Gly Val Ala Leu Tyr Glu Ala Met Lys Asn Ala Asp Asn Ile Asn Lys
        115                 120                 125

Leu Lys Ser Ser Ile Glu Ser Thr Asn Glu Ala Val Val Lys Leu Gln
    130                 135                 140

Glu Thr Ala Glu Lys Thr Val Tyr Val Leu Thr Ala Leu Gln Asp Tyr
145                 150                 155                 160

Ile Asn Thr Asn Leu Val Pro Thr Ile Asp Lys Ile Ser Cys Lys Gln
                165                 170                 175

Thr Glu Leu Ser Leu Asp Leu Ala Leu Ser Lys Tyr Leu Ser Asp Leu
            180                 185                 190

Leu Phe Val Phe Gly Pro Asn Leu Gln Asp Pro Val Ser Asn Ser Met
        195                 200                 205

Thr Ile Gln Ala Ile Ser Gln Ala Phe Gly Gly Asn Tyr Glu Thr Leu
    210                 215                 220

Leu Arg Thr Leu Gly Tyr Ala Thr Glu Asp Phe Asp Asp Leu Leu Glu
225                 230                 235                 240

Ser Asp Ser Ile Thr Gly Gln Ile Ile Tyr Val Asp Leu Ser Ser Tyr
                245                 250                 255

Tyr Ile Ile Val Arg Val Tyr Phe Pro Ile Leu Thr Glu Ile Gln Gln
            260                 265                 270

Ala Tyr Ile Gln Glu Leu Leu Pro Val Ser Phe Asn Asn Asp Asn Ser
        275                 280                 285

Glu Trp Ile Ser Ile Val Pro Asn Phe Ile Leu Val Arg Asn Thr Leu
    290                 295                 300

Ile Ser Asn Ile Glu Ile Gly Phe Cys Leu Ile Thr Lys Arg Ser Val
305                 310                 315                 320

Ile Cys Asn Gln Asp Tyr Ala Thr Pro Met Thr Asn Asn Met Arg Glu
                325                 330                 335

Cys Leu Thr Gly Ser Thr Glu Lys Cys Pro Arg Glu Leu Val Val Ser
            340                 345                 350

Ser His Val Pro Arg Phe Ala Leu Ser Asn Gly Val Leu Phe Ala Asn
        355                 360                 365

Cys Ile Ser Val Thr Cys Gln Cys Gln Thr Thr Gly Arg Ala Ile Ser
    370                 375                 380

Gln Ser Gly Glu Gln Thr Leu Leu Met Ile Asp Asn Thr Thr Cys Pro
385                 390                 395                 400

Thr Ala Val Leu Gly Asn Val Ile Ile Ser Leu Gly Lys Tyr Leu Gly
                405                 410                 415

Ser Val Asn Tyr Asn Ser Glu Gly Ile Ala Ile Gly Pro Pro Val Phe
            420                 425                 430

Thr Asp Lys Val Asp Ile Ser Ser Gln Ile Ser Ser Met Asn Gln Ser
        435                 440                 445

Leu Gln Gln Ser Lys Asp Tyr Ile Lys Glu Ala Gln Arg Leu Leu Asp
    450                 455                 460
```

-continued

```
Thr Val Asn Pro Ser Leu Lys Leu Met Lys Gln Ile Glu Asp Lys Ile
465                 470                 475                 480

Glu Glu Ile Leu Ser Lys Ile Tyr His Ile Glu Asn Glu Ile Ala Arg
                485                 490                 495

Ile Lys Lys Leu Ile Gly Glu Ala Pro Gly Ser Gly Tyr Ile Pro Glu
            500                 505                 510

Ala Pro Arg Asp Gly Gln Ala Tyr Val Arg Lys Asp Gly Glu Trp Val
        515                 520                 525

Leu Leu Ser Thr Phe Leu Gly Ser Gly Gly Gly Gly Gly Gly Val Ser
    530                 535                 540

Asn Leu Val Gly Leu Pro Asn Asn Ile Cys Leu Gln Lys Thr Ser Asn
545                 550                 555                 560

Gln Ile Leu Lys Pro Lys Leu Ile Ser Tyr Thr Leu Pro Val Val Gly
                565                 570                 575

Gln Ser Gly Thr Cys Ile Thr Asp Pro Leu Leu Ala Met Asp Glu Gly
            580                 585                 590

Tyr Phe Ala Tyr Ser His Leu Glu Arg Ile Gly Ser Cys Ser Arg Gly
        595                 600                 605

Val Ser Lys Gln Arg Ile Ile Gly Val Gly Glu Val Leu Asp Arg Gly
    610                 615                 620

Asp Glu Val Pro Ser Leu Phe Met Thr Asn Val Trp Thr Pro Pro Asn
625                 630                 635                 640

Pro Asn Thr Val Tyr His Cys Ser Ala Val Tyr Asn Asn Glu Phe Tyr
                645                 650                 655

Tyr Val Leu Cys Ala Val Ser Thr Val Gly Asp Pro Ile Leu Asn Ser
            660                 665                 670

Thr Tyr Trp Ser Gly Ser Leu Met Met Thr Arg Leu Ala Val Lys Pro
        675                 680                 685

Lys Ser Asn Gly Gly Gly Tyr Asn Gln His Gln Leu Ala Leu Arg Ser
    690                 695                 700

Ile Glu Lys Gly Arg Tyr Asp Lys Val Met Pro Tyr Gly Pro Ser Gly
705                 710                 715                 720

Ile Lys Gln Gly Asp Thr Leu Tyr Phe Pro Ala Val Gly Phe Leu Val
                725                 730                 735

Arg Thr Glu Phe Lys Tyr Asn Asp Ser Asn Cys Pro Ile Thr Lys Cys
            740                 745                 750

Gln Tyr Ser Lys Pro Glu Asn Cys Arg Leu Ser Met Gly Ile Arg Pro
        755                 760                 765

Asn Ser His Tyr Ile Leu Arg Ser Gly Leu Leu Lys Tyr Asn Leu Ser
    770                 775                 780

Asp Gly Glu Asn Pro Lys Val Val Phe Ile Glu Ile Ser Asp Gln Arg
785                 790                 795                 800

Leu Ser Ile Gly Ser Pro Ser Lys Ile Tyr Asp Ser Leu Gly Gln Pro
                805                 810                 815

Val Phe Tyr Gln Ala Ser Phe Ser Trp Asp Thr Met Ile Lys Phe Gly
            820                 825                 830

Asp Val Leu Thr Val Asn Pro Leu Val Val Asn Trp Arg Asn Asn Thr
        835                 840                 845

Val Ile Ser Arg Pro Gly Gln Ser Gln Cys Pro Arg Phe Asn Thr Cys
    850                 855                 860

Pro Glu Ile Cys Trp Glu Gly Val Tyr Asn Asp Ala Phe Leu Ile Asp
865                 870                 875                 880

Arg Ile Asn Trp Ile Ser Ala Gly Val Phe Leu Asp Ser Asn Gln Thr
```

-continued

```
                885                 890                 895

Ala Glu Asn Pro Val Phe Thr Val Phe Lys Asp Asn Glu Ile Leu Tyr
            900                 905                 910

Arg Ala Gln Leu Ala Ser Glu Asp Thr Asn Ala Gln Lys Thr Ile Thr
        915                 920                 925

Asn Cys Phe Leu Leu Lys Asn Lys Ile Trp Cys Ile Ser Leu Val Glu
    930                 935                 940

Ile Tyr Asp Thr Gly Asp Asn Val Ile Arg Pro Lys Leu Phe Ala Val
945                 950                 955                 960

Lys Ile Pro Glu Gln Cys Thr Gly Gly Gly Gly Gly Gly Gly Val Ser
                965                 970                 975

Asn Leu Val Gly Leu Pro Asn Asn Ile Cys Leu Gln Lys Thr Ser Asn
            980                 985                 990

Gln Ile Leu Lys Pro Lys Leu Ile  Ser Tyr Thr Leu Pro  Val Val Gly
        995                 1000                1005

Gln Ser  Gly Thr Cys Ile Thr  Asp Pro Leu Leu Ala  Met Asp Glu
    1010                1015                1020

Gly Tyr  Phe Ala Tyr Ser His  Leu Glu Arg Ile Gly  Ser Cys Ser
    1025                1030                1035

Arg Gly  Val Ser Lys Gln Arg  Ile Ile Gly Val Gly  Glu Val Leu
    1040                1045                1050

Asp Arg  Gly Asp Glu Val Pro  Ser Leu Phe Met Thr  Asn Val Trp
    1055                1060                1065

Thr Pro  Pro Asn Pro Asn Thr  Val Tyr His Cys Ser  Ala Val Tyr
    1070                1075                1080

Asn Asn  Glu Phe Tyr Tyr Val  Leu Cys Ala Val Ser  Thr Val Gly
    1085                1090                1095

Asp Pro  Ile Leu Asn Ser Thr  Tyr Trp Ser Gly Ser  Leu Met Met
    1100                1105                1110

Thr Arg  Leu Ala Val Lys Pro  Lys Ser Asn Gly Gly  Gly Tyr Asn
    1115                1120                1125

Gln His  Gln Leu Ala Leu Arg  Ser Ile Glu Lys Gly  Arg Tyr Asp
    1130                1135                1140

Lys Val  Met Pro Tyr Gly Pro  Ser Gly Ile Lys Gln  Gly Asp Thr
    1145                1150                1155

Leu Tyr  Phe Pro Ala Val Gly  Phe Leu Val Arg Thr  Glu Phe Lys
    1160                1165                1170

Tyr Asn  Asp Ser Asn Cys Pro  Ile Thr Lys Cys Gln  Tyr Ser Lys
    1175                1180                1185

Pro Glu  Asn Cys Arg Leu Ser  Met Gly Ile Arg Pro  Asn Ser His
    1190                1195                1200

Tyr Ile  Leu Arg Ser Gly Leu  Leu Lys Tyr Asn Leu  Ser Asp Gly
    1205                1210                1215

Glu Asn  Pro Lys Val Val Phe  Ile Glu Ile Ser Asp  Gln Arg Leu
    1220                1225                1230

Ser Ile  Gly Ser Pro Ser Lys  Ile Tyr Asp Ser Leu  Gly Gln Pro
    1235                1240                1245

Val Phe  Tyr Gln Ala Ser Phe  Ser Trp Asp Thr Met  Ile Lys Phe
    1250                1255                1260

Gly Asp  Val Leu Thr Val Asn  Pro Leu Val Val Asn  Trp Arg Asn
    1265                1270                1275

Asn Thr  Val Ile Ser Arg Pro  Gly Gln Ser Gln Cys  Pro Arg Phe
    1280                1285                1290
```

-continued

Asn Thr Cys Pro Glu Ile Cys Trp Glu Gly Val Tyr Asn Asp Ala
1295 1300 1305

Phe Leu Ile Asp Arg Ile Asn Trp Ile Ser Ala Gly Val Phe Leu
1310 1315 1320

Asp Ser Asn Gln Thr Ala Glu Asn Pro Val Phe Thr Val Phe Lys
1325 1330 1335

Asp Asn Glu Ile Leu Tyr Arg Ala Gln Leu Ala Ser Glu Asp Thr
1340 1345 1350

Asn Ala Gln Lys Thr Ile Thr Asn Cys Phe Leu Leu Lys Asn Lys
1355 1360 1365

Ile Trp Cys Ile Ser Leu Val Glu Ile Tyr Asp Thr Gly Asp Asn
1370 1375 1380

Val Ile Arg Pro Lys Leu Phe Ala Val Lys Ile Pro Glu Gln Cys
1385 1390 1395

Thr Gly Gly Leu Val Pro Arg Gly Ser His His His His His His
1400 1405 1410

Ser Ala Trp Ser His Pro Gln Phe Glu Lys
1415 1420

<210> SEQ ID NO 47
<211> LENGTH: 1437
<212> TYPE: PRT
<213> ORGANISM: Artificial sequence
<220> FEATURE:
<223> OTHER INFORMATION: Recombinant Nipah virus F sequence

<400> SEQUENCE: 47

Met Tyr Ser Met Gln Leu Ala Ser Cys Val Thr Leu Thr Leu Val Leu
1 5 10 15

Leu Val Asn Ser Gln Gly Ile Leu His Tyr Glu Lys Leu Ser Lys Ile
20 25 30

Gly Leu Val Lys Gly Val Thr Arg Lys Tyr Lys Ile Lys Ser Asn Pro
35 40 45

Leu Thr Lys Asp Ile Val Ile Lys Met Ile Pro Asn Val Ser Asn Met
50 55 60

Ser Gln Cys Thr Gly Ser Val Met Glu Asn Tyr Lys Thr Arg Leu Asn
65 70 75 80

Gly Ile Leu Thr Pro Ile Lys Gly Ala Leu Glu Ile Tyr Lys Asn Asn
85 90 95

Thr His Asp Cys Val Gly Asp Val Arg Leu Ala Gly Val Cys Met Ala
100 105 110

Gly Val Ala Ile Gly Ile Ala Thr Ala Ala Gln Ile Thr Ala Gly Val
115 120 125

Ala Leu Tyr Glu Ala Met Lys Asn Ala Asp Asn Ile Asn Lys Leu Lys
130 135 140

Ser Ser Ile Glu Ser Thr Asn Glu Ala Val Val Lys Leu Gln Glu Thr
145 150 155 160

Ala Glu Lys Thr Val Tyr Val Phe Thr Ala Leu Gln Asp Tyr Ile Asn
165 170 175

Thr Asn Leu Val Pro Thr Ile Asp Lys Ile Pro Cys Lys Gln Thr Glu
180 185 190

Leu Ser Leu Asp Leu Ala Leu Ser Lys Tyr Leu Ser Asp Leu Leu Phe
195 200 205

Val Phe Gly Pro Asn Leu Gln Asp Pro Val Ser Asn Ser Met Thr Ile
210 215 220

-continued

```
Gln Ala Ile Ser Gln Ala Phe Gly Gly Asn Tyr Glu Thr Leu Leu Arg
225                 230                 235                 240

Thr Leu Gly Tyr Ala Thr Glu Asp Phe Asp Asp Leu Leu Glu Ser Asp
                245                 250                 255

Ser Ile Thr Gly Gln Ile Ile Tyr Val Asp Leu Ser Ser Tyr Tyr Ile
            260                 265                 270

Ile Val Arg Val Tyr Phe Pro Ile Leu Thr Glu Ile Gln Gln Ala Tyr
        275                 280                 285

Ile Gln Glu Leu Leu Pro Val Ser Phe Asn Asn Asp Asn Ser Glu Trp
    290                 295                 300

Ile Ser Ile Val Pro Asn Phe Ile Leu Val Arg Asn Thr Leu Ile Ser
305                 310                 315                 320

Asn Ile Glu Ile Gly Phe Cys Leu Ile Thr Lys Arg Ser Val Ile Cys
                325                 330                 335

Asn Gln Asp Tyr Ala Thr Pro Met Thr Asn Asn Met Arg Glu Cys Leu
            340                 345                 350

Thr Gly Ser Thr Glu Lys Cys Pro Arg Glu Leu Val Val Ser Ser His
        355                 360                 365

Val Pro Arg Phe Ala Leu Ser Asn Gly Val Leu Phe Ala Asn Cys Ile
    370                 375                 380

Ser Val Thr Cys Gln Cys Gln Thr Thr Gly Arg Ala Ile Ser Gln Ser
385                 390                 395                 400

Gly Glu Gln Thr Leu Leu Met Ile Asp Asn Thr Thr Cys Pro Thr Ala
                405                 410                 415

Val Leu Gly Asn Val Ile Ile Ser Leu Gly Lys Tyr Leu Gly Ser Val
            420                 425                 430

Asn Tyr Asn Ser Glu Gly Ile Ala Ile Gly Pro Pro Val Phe Thr Asp
        435                 440                 445

Lys Val Asp Ile Ser Ser Gln Ile Ser Ser Met Asn Gln Ser Leu Gln
    450                 455                 460

Gln Ser Lys Asp Tyr Ile Lys Glu Ala Gln Arg Leu Leu Asp Thr Val
465                 470                 475                 480

Asn Pro Ser Leu Lys Leu Met Lys Gln Ile Glu Asp Lys Ile Glu Glu
                485                 490                 495

Ile Leu Ser Lys Ile Tyr His Ile Glu Asn Glu Ile Ala Arg Ile Lys
            500                 505                 510

Lys Leu Ile Gly Glu Ala Pro Gly Ser Gly Tyr Ile Pro Glu Ala Pro
        515                 520                 525

Arg Asp Gly Gln Ala Tyr Val Arg Lys Asp Gly Glu Trp Val Leu Leu
    530                 535                 540

Ser Thr Phe Leu Gly Ser Gly Gly Gly Gly Gly Gly Val Ser Asn Leu
545                 550                 555                 560

Val Gly Leu Pro Asn Asn Ile Cys Leu Gln Lys Thr Ser Asn Gln Ile
                565                 570                 575

Leu Lys Pro Lys Leu Ile Ser Tyr Thr Leu Pro Val Val Gly Gln Ser
            580                 585                 590

Gly Thr Cys Ile Thr Asp Pro Leu Leu Ala Met Asp Glu Gly Tyr Phe
        595                 600                 605

Ala Tyr Ser His Leu Glu Arg Ile Gly Ser Cys Ser Arg Gly Val Ser
    610                 615                 620

Lys Gln Arg Ile Ile Gly Val Gly Glu Val Leu Asp Arg Gly Asp Glu
625                 630                 635                 640
```

-continued

```
Val Pro Ser Leu Phe Met Thr Asn Val Trp Thr Pro Pro Asn Pro Asn
                645                 650                 655

Thr Val Tyr His Cys Ser Ala Val Tyr Asn Asn Glu Phe Tyr Tyr Val
            660                 665                 670

Leu Cys Ala Val Ser Thr Val Gly Asp Pro Ile Leu Asn Ser Thr Tyr
        675                 680                 685

Trp Ser Gly Ser Leu Met Met Thr Arg Leu Ala Val Lys Pro Lys Ser
    690                 695                 700

Asn Gly Gly Gly Tyr Asn Gln His Gln Leu Ala Leu Arg Ser Ile Glu
705                 710                 715                 720

Lys Gly Arg Tyr Asp Lys Val Met Pro Tyr Gly Pro Ser Gly Ile Lys
                725                 730                 735

Gln Gly Asp Thr Leu Tyr Phe Pro Ala Val Gly Phe Leu Val Arg Thr
            740                 745                 750

Glu Phe Lys Tyr Asn Asp Ser Asn Cys Pro Ile Thr Lys Cys Gln Tyr
        755                 760                 765

Ser Lys Pro Glu Asn Cys Arg Leu Ser Met Gly Ile Arg Pro Asn Ser
    770                 775                 780

His Tyr Ile Leu Arg Ser Gly Leu Leu Lys Tyr Asn Leu Ser Asp Gly
785                 790                 795                 800

Glu Asn Pro Lys Val Val Phe Ile Glu Ile Ser Asp Gln Arg Leu Ser
                805                 810                 815

Ile Gly Ser Pro Ser Lys Ile Tyr Asp Ser Leu Gly Gln Pro Val Phe
            820                 825                 830

Tyr Gln Ala Ser Phe Ser Trp Asp Thr Met Ile Lys Phe Gly Asp Val
        835                 840                 845

Leu Thr Val Asn Pro Leu Val Val Asn Trp Arg Asn Asn Thr Val Ile
    850                 855                 860

Ser Arg Pro Gly Gln Ser Gln Cys Pro Arg Phe Asn Thr Cys Pro Glu
865                 870                 875                 880

Ile Cys Trp Glu Gly Val Tyr Asn Asp Ala Phe Leu Ile Asp Arg Ile
                885                 890                 895

Asn Trp Ile Ser Ala Gly Val Phe Leu Asp Ser Asn Gln Thr Ala Glu
            900                 905                 910

Asn Pro Val Phe Thr Val Phe Lys Asp Asn Glu Ile Leu Tyr Arg Ala
        915                 920                 925

Gln Leu Ala Ser Glu Asp Thr Asn Ala Gln Lys Thr Ile Thr Asn Cys
    930                 935                 940

Phe Leu Leu Lys Asn Lys Ile Trp Cys Ile Ser Leu Val Glu Ile Tyr
945                 950                 955                 960

Asp Thr Gly Asp Asn Val Ile Arg Pro Lys Leu Phe Ala Val Lys Ile
                965                 970                 975

Pro Glu Gln Cys Thr Gly Gly Gly Gly Gly Gly Gly Val Ser Asn Leu
            980                 985                 990

Val Gly Leu Pro Asn Asn Ile Cys  Leu Gln Lys Thr Ser  Asn Gln Ile
        995                 1000                1005

Leu Lys  Pro Lys Leu Ile Ser  Tyr Thr Leu Pro Val  Val Gly Gln
    1010                1015                1020

Ser Gly  Thr Cys Ile Thr Asp  Pro Leu Leu Ala Met  Asp Glu Gly
    1025                1030                1035

Tyr Phe  Ala Tyr Ser His Leu  Glu Arg Ile Gly Ser  Cys Ser Arg
    1040                1045                1050

Gly Val  Ser Lys Gln Arg Ile  Ile Gly Val Gly Glu  Val Leu Asp
```

```
    1055                1060                1065

Arg Gly  Asp Glu Val Pro Ser  Leu Phe Met Thr Asn  Val Trp Thr
    1070                1075                1080

Pro Pro  Asn Pro Asn Thr Val  Tyr His Cys Ser Ala  Val Tyr Asn
    1085                1090                1095

Asn Glu  Phe Tyr Tyr Val Leu  Cys Ala Val Ser Thr  Val Gly Asp
    1100                1105                1110

Pro Ile  Leu Asn Ser Thr Tyr  Trp Ser Gly Ser Leu  Met Met Thr
    1115                1120                1125

Arg Leu  Ala Val Lys Pro Lys  Ser Asn Gly Gly Gly  Tyr Asn Gln
    1130                1135                1140

His Gln  Leu Ala Leu Arg Ser  Ile Glu Lys Gly Arg  Tyr Asp Lys
    1145                1150                1155

Val Met  Pro Tyr Gly Pro Ser  Gly Ile Lys Gln Gly  Asp Thr Leu
    1160                1165                1170

Tyr Phe  Pro Ala Val Gly Phe  Leu Val Arg Thr Glu  Phe Lys Tyr
    1175                1180                1185

Asn Asp  Ser Asn Cys Pro Ile  Thr Lys Cys Gln Tyr  Ser Lys Pro
    1190                1195                1200

Glu Asn  Cys Arg Leu Ser Met  Gly Ile Arg Pro Asn  Ser His Tyr
    1205                1210                1215

Ile Leu  Arg Ser Gly Leu Leu  Lys Tyr Asn Leu Ser  Asp Gly Glu
    1220                1225                1230

Asn Pro  Lys Val Val Phe Ile  Glu Ile Ser Asp Gln  Arg Leu Ser
    1235                1240                1245

Ile Gly  Ser Pro Ser Lys Ile  Tyr Asp Ser Leu Gly  Gln Pro Val
    1250                1255                1260

Phe Tyr  Gln Ala Ser Phe Ser  Trp Asp Thr Met Ile  Lys Phe Gly
    1265                1270                1275

Asp Val  Leu Thr Val Asn Pro  Leu Val Val Asn Trp  Arg Asn Asn
    1280                1285                1290

Thr Val  Ile Ser Arg Pro Gly  Gln Ser Gln Cys Pro  Arg Phe Asn
    1295                1300                1305

Thr Cys  Pro Glu Ile Cys Trp  Glu Gly Val Tyr Asn  Asp Ala Phe
    1310                1315                1320

Leu Ile  Asp Arg Ile Asn Trp  Ile Ser Ala Gly Val  Phe Leu Asp
    1325                1330                1335

Ser Asn  Gln Thr Ala Glu Asn  Pro Val Phe Thr Val  Phe Lys Asp
    1340                1345                1350

Asn Glu  Ile Leu Tyr Arg Ala  Gln Leu Ala Ser Glu  Asp Thr Asn
    1355                1360                1365

Ala Gln  Lys Thr Ile Thr Asn  Cys Phe Leu Leu Lys  Asn Lys Ile
    1370                1375                1380

Trp Cys  Ile Ser Leu Val Glu  Ile Tyr Asp Thr Gly  Asp Asn Val
    1385                1390                1395

Ile Arg  Pro Lys Leu Phe Ala  Val Lys Ile Pro Glu  Gln Cys Thr
    1400                1405                1410

Gly Gly  Leu Val Pro Arg Gly  Ser His His His His  His His Ser
    1415                1420                1425

Ala Trp  Ser His Pro Gln Phe  Glu Lys
    1430                1435

<210> SEQ ID NO 48
```

-continued

<211> LENGTH: 1855
<212> TYPE: PRT
<213> ORGANISM: Artificial sequence
<220> FEATURE:
<223> OTHER INFORMATION: Recombinant Nipah virus F sequence

<400> SEQUENCE: 48

```
Met Tyr Ser Met Gln Leu Ala Ser Cys Val Thr Leu Thr Leu Val Leu
1               5                   10                  15

Leu Val Asn Ser Gln Gly Ile Leu His Tyr Glu Lys Leu Ser Lys Ile
            20                  25                  30

Gly Leu Val Lys Gly Val Thr Arg Lys Tyr Lys Ile Lys Ser Asn Pro
        35                  40                  45

Leu Thr Lys Asp Ile Val Ile Lys Met Ile Pro Asn Val Ser Asn Met
    50                  55                  60

Ser Gln Cys Thr Gly Ser Val Met Glu Asn Tyr Lys Thr Arg Leu Asn
65                  70                  75                  80

Gly Ile Leu Thr Pro Ile Lys Gly Ala Leu Glu Ile Tyr Lys Asn Gly
                85                  90                  95

Gly Ser Gly Val Ala Ile Gly Ile Ala Thr Ala Ala Gln Ile Thr Ala
            100                 105                 110

Gly Val Ala Leu Tyr Glu Ala Met Lys Asn Ala Asp Asn Ile Asn Lys
        115                 120                 125

Leu Lys Ser Ser Ile Glu Ser Thr Asn Glu Ala Val Val Lys Leu Gln
    130                 135                 140

Glu Thr Ala Glu Lys Thr Val Tyr Val Leu Thr Ala Leu Gln Asp Tyr
145                 150                 155                 160

Ile Asn Thr Asn Leu Val Pro Thr Ile Asp Lys Ile Ser Cys Lys Gln
                165                 170                 175

Thr Glu Leu Ser Leu Asp Leu Ala Leu Ser Lys Tyr Leu Ser Asp Leu
            180                 185                 190

Leu Phe Val Phe Gly Pro Asn Leu Gln Asp Pro Val Ser Asn Ser Met
        195                 200                 205

Thr Ile Gln Ala Ile Ser Gln Ala Phe Gly Gly Asn Tyr Glu Thr Leu
    210                 215                 220

Leu Arg Thr Leu Gly Tyr Ala Thr Glu Asp Phe Asp Asp Leu Leu Glu
225                 230                 235                 240

Ser Asp Ser Ile Thr Gly Gln Ile Ile Tyr Val Asp Leu Ser Ser Tyr
                245                 250                 255

Tyr Ile Ile Val Arg Val Tyr Phe Pro Ile Leu Thr Glu Ile Gln Gln
            260                 265                 270

Ala Tyr Ile Gln Glu Leu Leu Pro Val Ser Phe Asn Asn Asp Asn Ser
        275                 280                 285

Glu Trp Ile Ser Ile Val Pro Asn Phe Ile Leu Val Arg Asn Thr Leu
    290                 295                 300

Ile Ser Asn Ile Glu Ile Gly Phe Cys Leu Ile Thr Lys Arg Ser Val
305                 310                 315                 320

Ile Cys Asn Gln Asp Tyr Ala Thr Pro Met Thr Asn Asn Met Arg Glu
                325                 330                 335

Cys Leu Thr Gly Ser Thr Glu Lys Cys Pro Arg Glu Leu Val Val Ser
            340                 345                 350

Ser His Val Pro Arg Phe Ala Leu Ser Asn Gly Val Leu Phe Ala Asn
        355                 360                 365

Cys Ile Ser Val Thr Cys Gln Cys Gln Thr Thr Gly Arg Ala Ile Ser
    370                 375                 380
```

-continued

```
Gln Ser Gly Glu Gln Thr Leu Leu Met Ile Asp Asn Thr Thr Cys Pro
385                 390                 395                 400

Thr Ala Val Leu Gly Asn Val Ile Ile Ser Leu Gly Lys Tyr Leu Gly
                405                 410                 415

Ser Val Asn Tyr Asn Ser Glu Gly Ile Ala Ile Gly Pro Pro Val Phe
            420                 425                 430

Thr Asp Lys Val Asp Ile Ser Ser Gln Ile Ser Ser Met Asn Gln Ser
        435                 440                 445

Leu Gln Gln Ser Lys Asp Tyr Ile Lys Glu Ala Gln Arg Leu Leu Asp
    450                 455                 460

Thr Val Asn Pro Ser Leu Lys Leu Met Lys Gln Ile Glu Asp Lys Ile
465                 470                 475                 480

Glu Glu Ile Leu Ser Lys Ile Tyr His Ile Glu Asn Glu Ile Ala Arg
                485                 490                 495

Ile Lys Lys Leu Ile Gly Glu Ala Pro Gly Ser Gly Tyr Ile Pro Glu
            500                 505                 510

Ala Pro Arg Asp Gly Gln Ala Tyr Val Arg Lys Asp Gly Glu Trp Val
        515                 520                 525

Leu Leu Ser Thr Phe Leu Gly Ser Gly Gly Gly Gly Gly Gly Val Ser
    530                 535                 540

Asn Leu Val Gly Leu Pro Asn Asn Ile Cys Leu Gln Lys Thr Ser Asn
545                 550                 555                 560

Gln Ile Leu Lys Pro Lys Leu Ile Ser Tyr Thr Leu Pro Val Val Gly
                565                 570                 575

Gln Ser Gly Thr Cys Ile Thr Asp Pro Leu Leu Ala Met Asp Glu Gly
            580                 585                 590

Tyr Phe Ala Tyr Ser His Leu Glu Arg Ile Gly Ser Cys Ser Arg Gly
        595                 600                 605

Val Ser Lys Gln Arg Ile Ile Gly Val Gly Glu Val Leu Asp Arg Gly
    610                 615                 620

Asp Glu Val Pro Ser Leu Phe Met Thr Asn Val Trp Thr Pro Pro Asn
625                 630                 635                 640

Pro Asn Thr Val Tyr His Cys Ser Ala Val Tyr Asn Asn Glu Phe Tyr
                645                 650                 655

Tyr Val Leu Cys Ala Val Ser Thr Val Gly Asp Pro Ile Leu Asn Ser
            660                 665                 670

Thr Tyr Trp Ser Gly Ser Leu Met Met Thr Arg Leu Ala Val Lys Pro
        675                 680                 685

Lys Ser Asn Gly Gly Gly Tyr Asn Gln His Gln Leu Ala Leu Arg Ser
    690                 695                 700

Ile Glu Lys Gly Arg Tyr Asp Lys Val Met Pro Tyr Gly Pro Ser Gly
705                 710                 715                 720

Ile Lys Gln Gly Asp Thr Leu Tyr Phe Pro Ala Val Gly Phe Leu Val
                725                 730                 735

Arg Thr Glu Phe Lys Tyr Asn Asp Ser Asn Cys Pro Ile Thr Lys Cys
            740                 745                 750

Gln Tyr Ser Lys Pro Glu Asn Cys Arg Leu Ser Met Gly Ile Arg Pro
        755                 760                 765

Asn Ser His Tyr Ile Leu Arg Ser Gly Leu Leu Lys Tyr Asn Leu Ser
    770                 775                 780

Asp Gly Glu Asn Pro Lys Val Val Phe Ile Glu Ile Ser Asp Gln Arg
785                 790                 795                 800
```

-continued

```
Leu Ser Ile Gly Ser Pro Ser Lys Ile Tyr Asp Ser Leu Gly Gln Pro
                805                 810                 815

Val Phe Tyr Gln Ala Ser Phe Ser Trp Asp Thr Met Ile Lys Phe Gly
            820                 825                 830

Asp Val Leu Thr Val Asn Pro Leu Val Val Asn Trp Arg Asn Asn Thr
        835                 840                 845

Val Ile Ser Arg Pro Gly Gln Ser Gln Cys Pro Arg Phe Asn Thr Cys
    850                 855                 860

Pro Glu Ile Cys Trp Glu Gly Val Tyr Asn Asp Ala Phe Leu Ile Asp
865                 870                 875                 880

Arg Ile Asn Trp Ile Ser Ala Gly Val Phe Leu Asp Ser Asn Gln Thr
                885                 890                 895

Ala Glu Asn Pro Val Phe Thr Val Phe Lys Asp Asn Glu Ile Leu Tyr
            900                 905                 910

Arg Ala Gln Leu Ala Ser Glu Asp Thr Asn Ala Gln Lys Thr Ile Thr
        915                 920                 925

Asn Cys Phe Leu Leu Lys Asn Lys Ile Trp Cys Ile Ser Leu Val Glu
    930                 935                 940

Ile Tyr Asp Thr Gly Asp Asn Val Ile Arg Pro Lys Leu Phe Ala Val
945                 950                 955                 960

Lys Ile Pro Glu Gln Cys Thr Gly Gly Gly Gly Gly Gly Gly Val Ser
                965                 970                 975

Asn Leu Val Gly Leu Pro Asn Asn Ile Cys Leu Gln Lys Thr Ser Asn
            980                 985                 990

Gln Ile Leu Lys Pro Lys Leu Ile  Ser Tyr Thr Leu Pro  Val Val Gly
        995                 1000                1005

Gln Ser  Gly Thr Cys Ile Thr  Asp Pro Leu Leu Ala  Met Asp Glu
    1010                 1015                 1020

Gly Tyr  Phe Ala Tyr Ser His  Leu Glu Arg Ile Gly  Ser Cys Ser
    1025                 1030                 1035

Arg Gly  Val Ser Lys Gln Arg  Ile Ile Gly Val Gly  Glu Val Leu
    1040                 1045                 1050

Asp Arg  Gly Asp Glu Val Pro  Ser Leu Phe Met Thr  Asn Val Trp
    1055                 1060                 1065

Thr Pro  Pro Asn Pro Asn Thr  Val Tyr His Cys Ser  Ala Val Tyr
    1070                 1075                 1080

Asn Asn  Glu Phe Tyr Tyr Val  Leu Cys Ala Val Ser  Thr Val Gly
    1085                 1090                 1095

Asp Pro  Ile Leu Asn Ser Thr  Tyr Trp Ser Gly Ser  Leu Met Met
    1100                 1105                 1110

Thr Arg  Leu Ala Val Lys Pro  Lys Ser Asn Gly Gly  Gly Tyr Asn
    1115                 1120                 1125

Gln His  Gln Leu Ala Leu Arg  Ser Ile Glu Lys Gly  Arg Tyr Asp
    1130                 1135                 1140

Lys Val  Met Pro Tyr Gly Pro  Ser Gly Ile Lys Gln  Gly Asp Thr
    1145                 1150                 1155

Leu Tyr  Phe Pro Ala Val Gly  Phe Leu Val Arg Thr  Glu Phe Lys
    1160                 1165                 1170

Tyr Asn  Asp Ser Asn Cys Pro  Ile Thr Lys Cys Gln  Tyr Ser Lys
    1175                 1180                 1185

Pro Glu  Asn Cys Arg Leu Ser  Met Gly Ile Arg Pro  Asn Ser His
    1190                 1195                 1200

Tyr Ile  Leu Arg Ser Gly Leu  Leu Lys Tyr Asn Leu  Ser Asp Gly
```

```
    1205                1210                1215

Glu Asn  Pro Lys Val Val Phe  Ile Glu Ile Ser Asp  Gln Arg Leu
    1220                1225                1230

Ser Ile  Gly Ser Pro Ser Lys  Ile Tyr Asp Ser Leu  Gly Gln Pro
    1235                1240                1245

Val Phe  Tyr Gln Ala Ser Phe  Ser Trp Asp Thr Met  Ile Lys Phe
    1250                1255                1260

Gly Asp  Val Leu Thr Val Asn  Pro Leu Val Val Asn  Trp Arg Asn
    1265                1270                1275

Asn Thr  Val Ile Ser Arg Pro  Gly Gln Ser Gln Cys  Pro Arg Phe
    1280                1285                1290

Asn Thr  Cys Pro Glu Ile Cys  Trp Glu Gly Val Tyr  Asn Asp Ala
    1295                1300                1305

Phe Leu  Ile Asp Arg Ile Asn  Trp Ile Ser Ala Gly  Val Phe Leu
    1310                1315                1320

Asp Ser  Asn Gln Thr Ala Glu  Asn Pro Val Phe Thr  Val Phe Lys
    1325                1330                1335

Asp Asn  Glu Ile Leu Tyr Arg  Ala Gln Leu Ala Ser  Glu Asp Thr
    1340                1345                1350

Asn Ala  Gln Lys Thr Ile Thr  Asn Cys Phe Leu Leu  Lys Asn Lys
    1355                1360                1365

Ile Trp  Cys Ile Ser Leu Val  Glu Ile Tyr Asp Thr  Gly Asp Asn
    1370                1375                1380

Val Ile  Arg Pro Lys Leu Phe  Ala Val Lys Ile Pro  Glu Gln Cys
    1385                1390                1395

Thr Gly  Gly Gly Gly Gly Gly  Gly Val Ser Asn Leu  Val Gly Leu
    1400                1405                1410

Pro Asn  Asn Ile Cys Leu Gln  Lys Thr Ser Asn Gln  Ile Leu Lys
    1415                1420                1425

Pro Lys  Leu Ile Ser Tyr Thr  Leu Pro Val Val Gly  Gln Ser Gly
    1430                1435                1440

Thr Cys  Ile Thr Asp Pro Leu  Leu Ala Met Asp Glu  Gly Tyr Phe
    1445                1450                1455

Ala Tyr  Ser His Leu Glu Arg  Ile Gly Ser Cys Ser  Arg Gly Val
    1460                1465                1470

Ser Lys  Gln Arg Ile Ile Gly  Val Gly Glu Val Leu  Asp Arg Gly
    1475                1480                1485

Asp Glu  Val Pro Ser Leu Phe  Met Thr Asn Val Trp  Thr Pro Pro
    1490                1495                1500

Asn Pro  Asn Thr Val Tyr His  Cys Ser Ala Val Tyr  Asn Asn Glu
    1505                1510                1515

Phe Tyr  Tyr Val Leu Cys Ala  Val Ser Thr Val Gly  Asp Pro Ile
    1520                1525                1530

Leu Asn  Ser Thr Tyr Trp Ser  Gly Ser Leu Met Met  Thr Arg Leu
    1535                1540                1545

Ala Val  Lys Pro Lys Ser Asn  Gly Gly Gly Tyr Asn  Gln His Gln
    1550                1555                1560

Leu Ala  Leu Arg Ser Ile Glu  Lys Gly Arg Tyr Asp  Lys Val Met
    1565                1570                1575

Pro Tyr  Gly Pro Ser Gly Ile  Lys Gln Gly Asp Thr  Leu Tyr Phe
    1580                1585                1590

Pro Ala  Val Gly Phe Leu Val  Arg Thr Glu Phe Lys  Tyr Asn Asp
    1595                1600                1605
```

Ser Asn Cys Pro Ile Thr Lys Cys Gln Tyr Ser Lys Pro Glu Asn
    1610                1615                1620

Cys Arg Leu Ser Met Gly Ile Arg Pro Asn Ser His Tyr Ile Leu
    1625                1630                1635

Arg Ser Gly Leu Leu Lys Tyr Asn Leu Ser Asp Gly Glu Asn Pro
    1640                1645                1650

Lys Val Val Phe Ile Glu Ile Ser Asp Gln Arg Leu Ser Ile Gly
    1655                1660                1665

Ser Pro Ser Lys Ile Tyr Asp Ser Leu Gly Gln Pro Val Phe Tyr
    1670                1675                1680

Gln Ala Ser Phe Ser Trp Asp Thr Met Ile Lys Phe Gly Asp Val
    1685                1690                1695

Leu Thr Val Asn Pro Leu Val Val Asn Trp Arg Asn Asn Thr Val
    1700                1705                1710

Ile Ser Arg Pro Gly Gln Ser Gln Cys Pro Arg Phe Asn Thr Cys
    1715                1720                1725

Pro Glu Ile Cys Trp Glu Gly Val Tyr Asn Asp Ala Phe Leu Ile
    1730                1735                1740

Asp Arg Ile Asn Trp Ile Ser Ala Gly Val Phe Leu Asp Ser Asn
    1745                1750                1755

Gln Thr Ala Glu Asn Pro Val Phe Thr Val Phe Lys Asp Asn Glu
    1760                1765                1770

Ile Leu Tyr Arg Ala Gln Leu Ala Ser Glu Asp Thr Asn Ala Gln
    1775                1780                1785

Lys Thr Ile Thr Asn Cys Phe Leu Leu Lys Asn Lys Ile Trp Cys
    1790                1795                1800

Ile Ser Leu Val Glu Ile Tyr Asp Thr Gly Asp Asn Val Ile Arg
    1805                1810                1815

Pro Lys Leu Phe Ala Val Lys Ile Pro Glu Gln Cys Thr Gly Gly
    1820                1825                1830

Leu Val Pro Arg Gly Ser His His His His His His Ser Ala Trp
    1835                1840                1845

Ser His Pro Gln Phe Glu Lys
    1850                1855

<210> SEQ ID NO 49
<211> LENGTH: 1869
<212> TYPE: PRT
<213> ORGANISM: Artificial sequence
<220> FEATURE:
<223> OTHER INFORMATION: Recombinant Nipah virus F sequence

<400> SEQUENCE: 49

Met Tyr Ser Met Gln Leu Ala Ser Cys Val Thr Leu Thr Leu Val Leu
1               5                   10                  15

Leu Val Asn Ser Gln Gly Ile Leu His Tyr Glu Lys Leu Ser Lys Ile
            20                  25                  30

Gly Leu Val Lys Gly Val Thr Arg Lys Tyr Lys Ile Lys Ser Asn Pro
        35                  40                  45

Leu Thr Lys Asp Ile Val Ile Lys Met Ile Pro Asn Val Ser Asn Met
    50                  55                  60

Ser Gln Cys Thr Gly Ser Val Met Glu Asn Tyr Lys Thr Arg Leu Asn
65                  70                  75                  80

Gly Ile Leu Thr Pro Ile Lys Gly Ala Leu Glu Ile Tyr Lys Asn Asn
                85                  90                  95

```
Thr His Asp Cys Val Gly Asp Val Arg Leu Ala Gly Val Cys Met Ala
            100                 105                 110

Gly Val Ala Ile Gly Ile Ala Thr Ala Ala Gln Ile Thr Ala Gly Val
        115                 120                 125

Ala Leu Tyr Glu Ala Met Lys Asn Ala Asp Asn Ile Asn Lys Leu Lys
    130                 135                 140

Ser Ser Ile Glu Ser Thr Asn Glu Ala Val Val Lys Leu Gln Glu Thr
145                 150                 155                 160

Ala Glu Lys Thr Val Tyr Val Phe Thr Ala Leu Gln Asp Tyr Ile Asn
                165                 170                 175

Thr Asn Leu Val Pro Thr Ile Asp Lys Ile Pro Cys Lys Gln Thr Glu
            180                 185                 190

Leu Ser Leu Asp Leu Ala Leu Ser Lys Tyr Leu Ser Asp Leu Leu Phe
        195                 200                 205

Val Phe Gly Pro Asn Leu Gln Asp Pro Val Ser Asn Ser Met Thr Ile
    210                 215                 220

Gln Ala Ile Ser Gln Ala Phe Gly Gly Asn Tyr Glu Thr Leu Leu Arg
225                 230                 235                 240

Thr Leu Gly Tyr Ala Thr Glu Asp Phe Asp Asp Leu Leu Glu Ser Asp
                245                 250                 255

Ser Ile Thr Gly Gln Ile Ile Tyr Val Asp Leu Ser Ser Tyr Tyr Ile
            260                 265                 270

Ile Val Arg Val Tyr Phe Pro Ile Leu Thr Glu Ile Gln Gln Ala Tyr
        275                 280                 285

Ile Gln Glu Leu Leu Pro Val Ser Phe Asn Asn Asp Asn Ser Glu Trp
    290                 295                 300

Ile Ser Ile Val Pro Asn Phe Ile Leu Val Arg Asn Thr Leu Ile Ser
305                 310                 315                 320

Asn Ile Glu Ile Gly Phe Cys Leu Ile Thr Lys Arg Ser Val Ile Cys
                325                 330                 335

Asn Gln Asp Tyr Ala Thr Pro Met Thr Asn Asn Met Arg Glu Cys Leu
            340                 345                 350

Thr Gly Ser Thr Glu Lys Cys Pro Arg Glu Leu Val Val Ser Ser His
        355                 360                 365

Val Pro Arg Phe Ala Leu Ser Asn Gly Val Leu Phe Ala Asn Cys Ile
    370                 375                 380

Ser Val Thr Cys Gln Cys Gln Thr Thr Gly Arg Ala Ile Ser Gln Ser
385                 390                 395                 400

Gly Glu Gln Thr Leu Leu Met Ile Asp Asn Thr Thr Cys Pro Thr Ala
                405                 410                 415

Val Leu Gly Asn Val Ile Ile Ser Leu Gly Lys Tyr Leu Gly Ser Val
            420                 425                 430

Asn Tyr Asn Ser Glu Gly Ile Ala Ile Gly Pro Pro Val Phe Thr Asp
        435                 440                 445

Lys Val Asp Ile Ser Ser Gln Ile Ser Ser Met Asn Gln Ser Leu Gln
    450                 455                 460

Gln Ser Lys Asp Tyr Ile Lys Glu Ala Gln Arg Leu Leu Asp Thr Val
465                 470                 475                 480

Asn Pro Ser Leu Lys Leu Met Lys Gln Ile Glu Asp Lys Ile Glu Glu
                485                 490                 495

Ile Leu Ser Lys Ile Tyr His Ile Glu Asn Glu Ile Ala Arg Ile Lys
            500                 505                 510
```

```
Lys Leu Ile Gly Glu Ala Pro Gly Ser Gly Tyr Ile Pro Glu Ala Pro
        515                 520                 525

Arg Asp Gly Gln Ala Tyr Val Arg Lys Asp Gly Glu Trp Val Leu Leu
    530                 535                 540

Ser Thr Phe Leu Gly Ser Gly Gly Gly Gly Gly Gly Val Ser Asn Leu
545                 550                 555                 560

Val Gly Leu Pro Asn Asn Ile Cys Leu Gln Lys Thr Ser Asn Gln Ile
                565                 570                 575

Leu Lys Pro Lys Leu Ile Ser Tyr Thr Leu Pro Val Val Gly Gln Ser
            580                 585                 590

Gly Thr Cys Ile Thr Asp Pro Leu Leu Ala Met Asp Glu Gly Tyr Phe
        595                 600                 605

Ala Tyr Ser His Leu Glu Arg Ile Gly Ser Cys Ser Arg Gly Val Ser
    610                 615                 620

Lys Gln Arg Ile Ile Gly Val Gly Glu Val Leu Asp Arg Gly Asp Glu
625                 630                 635                 640

Val Pro Ser Leu Phe Met Thr Asn Val Trp Thr Pro Pro Asn Pro Asn
                645                 650                 655

Thr Val Tyr His Cys Ser Ala Val Tyr Asn Asn Glu Phe Tyr Tyr Val
            660                 665                 670

Leu Cys Ala Val Ser Thr Val Gly Asp Pro Ile Leu Asn Ser Thr Tyr
        675                 680                 685

Trp Ser Gly Ser Leu Met Met Thr Arg Leu Ala Val Lys Pro Lys Ser
    690                 695                 700

Asn Gly Gly Gly Tyr Asn Gln His Gln Leu Ala Leu Arg Ser Ile Glu
705                 710                 715                 720

Lys Gly Arg Tyr Asp Lys Val Met Pro Tyr Gly Pro Ser Gly Ile Lys
                725                 730                 735

Gln Gly Asp Thr Leu Tyr Phe Pro Ala Val Gly Phe Leu Val Arg Thr
            740                 745                 750

Glu Phe Lys Tyr Asn Asp Ser Asn Cys Pro Ile Thr Lys Cys Gln Tyr
        755                 760                 765

Ser Lys Pro Glu Asn Cys Arg Leu Ser Met Gly Ile Arg Pro Asn Ser
    770                 775                 780

His Tyr Ile Leu Arg Ser Gly Leu Leu Lys Tyr Asn Leu Ser Asp Gly
785                 790                 795                 800

Glu Asn Pro Lys Val Val Phe Ile Glu Ile Ser Asp Gln Arg Leu Ser
                805                 810                 815

Ile Gly Ser Pro Ser Lys Ile Tyr Asp Ser Leu Gly Gln Pro Val Phe
            820                 825                 830

Tyr Gln Ala Ser Phe Ser Trp Asp Thr Met Ile Lys Phe Gly Asp Val
        835                 840                 845

Leu Thr Val Asn Pro Leu Val Val Asn Trp Arg Asn Asn Thr Val Ile
    850                 855                 860

Ser Arg Pro Gly Gln Ser Gln Cys Pro Arg Phe Asn Thr Cys Pro Glu
865                 870                 875                 880

Ile Cys Trp Glu Gly Val Tyr Asn Asp Ala Phe Leu Ile Asp Arg Ile
                885                 890                 895

Asn Trp Ile Ser Ala Gly Val Phe Leu Asp Ser Asn Gln Thr Ala Glu
            900                 905                 910

Asn Pro Val Phe Thr Val Phe Lys Asp Asn Glu Ile Leu Tyr Arg Ala
        915                 920                 925

Gln Leu Ala Ser Glu Asp Thr Asn Ala Gln Lys Thr Ile Thr Asn Cys
```

-continued

```
    930                 935                 940

Phe Leu Leu Lys Asn Lys Ile Trp Cys Ile Ser Leu Val Glu Ile Tyr
945                 950                 955                 960

Asp Thr Gly Asp Asn Val Ile Arg Pro Lys Leu Phe Ala Val Lys Ile
                965                 970                 975

Pro Glu Gln Cys Thr Gly Gly Gly Gly Gly Gly Gly Val Ser Asn Leu
            980                 985                 990

Val Gly Leu Pro Asn Asn Ile Cys  Leu Gln Lys Thr Ser  Asn Gln Ile
        995                 1000                 1005

Leu Lys  Pro Lys Leu Ile Ser  Tyr Thr Leu Pro Val  Val Gly Gln
    1010                 1015                 1020

Ser Gly  Thr Cys Ile Thr Asp  Pro Leu Leu Ala Met  Asp Glu Gly
    1025                 1030                 1035

Tyr Phe  Ala Tyr Ser His Leu  Glu Arg Ile Gly Ser  Cys Ser Arg
    1040                 1045                 1050

Gly Val  Ser Lys Gln Arg Ile  Ile Gly Val Gly Glu  Val Leu Asp
    1055                 1060                 1065

Arg Gly  Asp Glu Val Pro Ser  Leu Phe Met Thr Asn  Val Trp Thr
    1070                 1075                 1080

Pro Pro  Asn Pro Asn Thr Val  Tyr His Cys Ser Ala  Val Tyr Asn
    1085                 1090                 1095

Asn Glu  Phe Tyr Tyr Val Leu  Cys Ala Val Ser Thr  Val Gly Asp
    1100                 1105                 1110

Pro Ile  Leu Asn Ser Thr Tyr  Trp Ser Gly Ser Leu  Met Met Thr
    1115                 1120                 1125

Arg Leu  Ala Val Lys Pro Lys  Ser Asn Gly Gly Gly  Tyr Asn Gln
    1130                 1135                 1140

His Gln  Leu Ala Leu Arg Ser  Ile Glu Lys Gly Arg  Tyr Asp Lys
    1145                 1150                 1155

Val Met  Pro Tyr Gly Pro Ser  Gly Ile Lys Gln Gly  Asp Thr Leu
    1160                 1165                 1170

Tyr Phe  Pro Ala Val Gly Phe  Leu Val Arg Thr Glu  Phe Lys Tyr
    1175                 1180                 1185

Asn Asp  Ser Asn Cys Pro Ile  Thr Lys Cys Gln Tyr  Ser Lys Pro
    1190                 1195                 1200

Glu Asn  Cys Arg Leu Ser Met  Gly Ile Arg Pro Asn  Ser His Tyr
    1205                 1210                 1215

Ile Leu  Arg Ser Gly Leu Leu  Lys Tyr Asn Leu Ser  Asp Gly Glu
    1220                 1225                 1230

Asn Pro  Lys Val Val Phe Ile  Glu Ile Ser Asp Gln  Arg Leu Ser
    1235                 1240                 1245

Ile Gly  Ser Pro Ser Lys Ile  Tyr Asp Ser Leu Gly  Gln Pro Val
    1250                 1255                 1260

Phe Tyr  Gln Ala Ser Phe Ser  Trp Asp Thr Met Ile  Lys Phe Gly
    1265                 1270                 1275

Asp Val  Leu Thr Val Asn Pro  Leu Val Val Asn Trp  Arg Asn Asn
    1280                 1285                 1290

Thr Val  Ile Ser Arg Pro Gly  Gln Ser Gln Cys Pro  Arg Phe Asn
    1295                 1300                 1305

Thr Cys  Pro Glu Ile Cys Trp  Glu Gly Val Tyr Asn  Asp Ala Phe
    1310                 1315                 1320

Leu Ile  Asp Arg Ile Asn Trp  Ile Ser Ala Gly Val  Phe Leu Asp
    1325                 1330                 1335
```

```
Ser Asn  Gln Thr Ala Glu Asn  Pro Val Phe Thr Val  Phe Lys Asp
    1340                 1345                 1350

Asn Glu  Ile Leu Tyr Arg Ala  Gln Leu Ala Ser Glu  Asp Thr Asn
    1355                 1360                 1365

Ala Gln  Lys Thr Ile Thr Asn  Cys Phe Leu Leu Lys  Asn Lys Ile
    1370                 1375                 1380

Trp Cys  Ile Ser Leu Val Glu  Ile Tyr Asp Thr Gly  Asp Asn Val
    1385                 1390                 1395

Ile Arg  Pro Lys Leu Phe Ala  Val Lys Ile Pro Glu  Gln Cys Thr
    1400                 1405                 1410

Gly Gly  Gly Gly Gly Gly Gly  Val Ser Asn Leu Val  Gly Leu Pro
    1415                 1420                 1425

Asn Asn  Ile Cys Leu Gln Lys  Thr Ser Asn Gln Ile  Leu Lys Pro
    1430                 1435                 1440

Lys Leu  Ile Ser Tyr Thr Leu  Pro Val Val Gly Gln  Ser Gly Thr
    1445                 1450                 1455

Cys Ile  Thr Asp Pro Leu Leu  Ala Met Asp Glu Gly  Tyr Phe Ala
    1460                 1465                 1470

Tyr Ser  His Leu Glu Arg Ile  Gly Ser Cys Ser Arg  Gly Val Ser
    1475                 1480                 1485

Lys Gln  Arg Ile Ile Gly Val  Gly Glu Val Leu Asp  Arg Gly Asp
    1490                 1495                 1500

Glu Val  Pro Ser Leu Phe Met  Thr Asn Val Trp Thr  Pro Pro Asn
    1505                 1510                 1515

Pro Asn  Thr Val Tyr His Cys  Ser Ala Val Tyr Asn  Asn Glu Phe
    1520                 1525                 1530

Tyr Tyr  Val Leu Cys Ala Val  Ser Thr Val Gly Asp  Pro Ile Leu
    1535                 1540                 1545

Asn Ser  Thr Tyr Trp Ser Gly  Ser Leu Met Met Thr  Arg Leu Ala
    1550                 1555                 1560

Val Lys  Pro Lys Ser Asn Gly  Gly Gly Tyr Asn Gln  His Gln Leu
    1565                 1570                 1575

Ala Leu  Arg Ser Ile Glu Lys  Gly Arg Tyr Asp Lys  Val Met Pro
    1580                 1585                 1590

Tyr Gly  Pro Ser Gly Ile Lys  Gln Gly Asp Thr Leu  Tyr Phe Pro
    1595                 1600                 1605

Ala Val  Gly Phe Leu Val Arg  Thr Glu Phe Lys Tyr  Asn Asp Ser
    1610                 1615                 1620

Asn Cys  Pro Ile Thr Lys Cys  Gln Tyr Ser Lys Pro  Glu Asn Cys
    1625                 1630                 1635

Arg Leu  Ser Met Gly Ile Arg  Pro Asn Ser His Tyr  Ile Leu Arg
    1640                 1645                 1650

Ser Gly  Leu Leu Lys Tyr Asn  Leu Ser Asp Gly Glu  Asn Pro Lys
    1655                 1660                 1665

Val Val  Phe Ile Glu Ile Ser  Asp Gln Arg Leu Ser  Ile Gly Ser
    1670                 1675                 1680

Pro Ser  Lys Ile Tyr Asp Ser  Leu Gly Gln Pro Val  Phe Tyr Gln
    1685                 1690                 1695

Ala Ser  Phe Ser Trp Asp Thr  Met Ile Lys Phe Gly  Asp Val Leu
    1700                 1705                 1710

Thr Val  Asn Pro Leu Val Val  Asn Trp Arg Asn Asn  Thr Val Ile
    1715                 1720                 1725
```

```
Ser Arg  Pro Gly Gln Ser Gln  Cys Pro Arg Phe Asn  Thr Cys Pro
    1730                 1735                 1740

Glu Ile  Cys Trp Glu Gly Val  Tyr Asn Asp Ala Phe  Leu Ile Asp
    1745                 1750                 1755

Arg Ile  Asn Trp Ile Ser Ala  Gly Val Phe Leu Asp  Ser Asn Gln
    1760                 1765                 1770

Thr Ala  Glu Asn Pro Val Phe  Thr Val Phe Lys Asp  Asn Glu Ile
    1775                 1780                 1785

Leu Tyr  Arg Ala Gln Leu Ala  Ser Glu Asp Thr Asn  Ala Gln Lys
    1790                 1795                 1800

Thr Ile  Thr Asn Cys Phe Leu  Leu Lys Asn Lys Ile  Trp Cys Ile
    1805                 1810                 1815

Ser Leu  Val Glu Ile Tyr Asp  Thr Gly Asp Asn Val  Ile Arg Pro
    1820                 1825                 1830

Lys Leu  Phe Ala Val Lys Ile  Pro Glu Gln Cys Thr  Gly Gly Leu
    1835                 1840                 1845

Val Pro  Arg Gly Ser His His  His His His His Ser  Ala Trp Ser
    1850                 1855                 1860

His Pro  Gln Phe Glu Lys
    1865


<210> SEQ ID NO 50
<211> LENGTH: 966
<212> TYPE: PRT
<213> ORGANISM: Artificial sequence
<220> FEATURE:
<223> OTHER INFORMATION: Recombinant Nipah virus F sequence

<400> SEQUENCE: 50

Met Tyr Ser Met Gln Leu Ala Ser Cys Val Thr Leu Thr Leu Val Leu
1               5                   10                  15

Leu Val Asn Ser Gln Arg Pro Gln Thr Glu Gly Val Ser Asn Leu Val
            20                  25                  30

Gly Leu Pro Asn Asn Ile Cys Leu Gln Lys Thr Ser Asn Gln Ile Leu
        35                  40                  45

Lys Pro Lys Leu Ile Ser Tyr Thr Leu Pro Val Val Gly Gln Ser Gly
    50                  55                  60

Thr Cys Ile Thr Asp Pro Leu Leu Ala Met Asp Glu Gly Tyr Phe Ala
65                  70                  75                  80

Tyr Ser His Leu Glu Arg Ile Gly Ser Cys Ser Arg Gly Val Ser Lys
                85                  90                  95

Gln Arg Ile Ile Gly Val Gly Glu Val Leu Asp Arg Gly Asp Glu Val
            100                 105                 110

Pro Ser Leu Phe Met Thr Asn Val Trp Thr Pro Pro Asn Pro Asn Thr
        115                 120                 125

Val Tyr His Cys Ser Ala Val Tyr Asn Asn Glu Phe Tyr Tyr Val Leu
    130                 135                 140

Cys Ala Val Ser Thr Val Gly Asp Pro Ile Leu Asn Ser Thr Tyr Trp
145                 150                 155                 160

Ser Gly Ser Leu Met Met Thr Arg Leu Ala Val Lys Pro Lys Ser Asn
                165                 170                 175

Gly Gly Gly Tyr Asn Gln His Gln Leu Ala Leu Arg Ser Ile Glu Lys
            180                 185                 190

Gly Arg Tyr Asp Lys Val Met Pro Tyr Gly Pro Ser Gly Ile Lys Gln
        195                 200                 205
```

-continued

```
Gly Asp Thr Leu Tyr Phe Pro Ala Val Gly Phe Leu Val Arg Thr Glu
    210                 215                 220

Phe Lys Tyr Asn Asp Ser Asn Cys Pro Ile Thr Lys Cys Gln Tyr Ser
225                 230                 235                 240

Lys Pro Glu Asn Cys Arg Leu Ser Met Gly Ile Arg Pro Asn Ser His
                245                 250                 255

Tyr Ile Leu Arg Ser Gly Leu Leu Lys Tyr Asn Leu Ser Asp Gly Glu
            260                 265                 270

Asn Pro Lys Val Val Phe Ile Glu Ile Ser Asp Gln Arg Leu Ser Ile
        275                 280                 285

Gly Ser Pro Ser Lys Ile Tyr Asp Ser Leu Gly Gln Pro Val Phe Tyr
    290                 295                 300

Gln Ala Ser Phe Ser Trp Asp Thr Met Ile Lys Phe Gly Asp Val Leu
305                 310                 315                 320

Thr Val Asn Pro Leu Val Val Asn Trp Arg Asn Asn Thr Val Ile Ser
                325                 330                 335

Arg Pro Gly Gln Ser Gln Cys Pro Arg Phe Asn Thr Cys Pro Glu Ile
            340                 345                 350

Cys Trp Glu Gly Val Tyr Asn Asp Ala Phe Leu Ile Asp Arg Ile Asn
        355                 360                 365

Trp Ile Ser Ala Gly Val Phe Leu Asp Ser Asn Gln Thr Ala Glu Asn
    370                 375                 380

Pro Val Phe Thr Val Phe Lys Asp Asn Glu Ile Leu Tyr Arg Ala Gln
385                 390                 395                 400

Leu Ala Ser Glu Asp Thr Asn Ala Gln Lys Thr Ile Thr Asn Cys Phe
                405                 410                 415

Leu Leu Lys Asn Lys Ile Trp Cys Ile Ser Leu Val Glu Ile Tyr Asp
            420                 425                 430

Thr Gly Asp Asn Val Ile Arg Pro Lys Leu Phe Ala Val Lys Ile Pro
        435                 440                 445

Glu Gln Cys Thr Gly Gly Gly Gly Gly Gln Gly Ile Leu His Tyr Glu
    450                 455                 460

Lys Leu Ser Lys Ile Gly Leu Val Lys Gly Val Thr Arg Lys Tyr Lys
465                 470                 475                 480

Ile Lys Ser Asn Pro Leu Thr Lys Asp Ile Val Ile Lys Met Ile Pro
                485                 490                 495

Asn Val Ser Asn Met Ser Gln Cys Thr Gly Ser Val Met Glu Asn Tyr
            500                 505                 510

Lys Thr Arg Leu Asn Gly Ile Leu Thr Pro Ile Lys Gly Ala Leu Glu
        515                 520                 525

Ile Tyr Lys Asn Gly Gly Ser Gly Val Ala Ile Gly Ile Ala Thr Ala
    530                 535                 540

Ala Gln Ile Thr Ala Gly Val Ala Leu Tyr Glu Ala Met Lys Asn Ala
545                 550                 555                 560

Asp Asn Ile Asn Lys Leu Lys Ser Ser Ile Glu Ser Thr Asn Glu Ala
                565                 570                 575

Val Val Lys Leu Gln Glu Thr Ala Glu Lys Thr Val Tyr Val Leu Thr
            580                 585                 590

Ala Leu Gln Asp Tyr Ile Asn Thr Asn Leu Val Pro Thr Ile Asp Lys
        595                 600                 605

Ile Ser Cys Lys Gln Thr Glu Leu Ser Leu Asp Leu Ala Leu Ser Lys
    610                 615                 620

Tyr Leu Ser Asp Leu Leu Phe Val Phe Gly Pro Asn Leu Gln Asp Pro
```

-continued 625 630 635 640

Val Ser Asn Ser Met Thr Ile Gln Ala Ile Ser Gln Ala Phe Gly Gly
645 650 655

Asn Tyr Glu Thr Leu Leu Arg Thr Leu Gly Tyr Ala Thr Glu Asp Phe
660 665 670

Asp Asp Leu Leu Glu Ser Asp Ser Ile Thr Gly Gln Ile Ile Tyr Val
675 680 685

Asp Leu Ser Ser Tyr Tyr Ile Ile Val Arg Val Tyr Phe Pro Ile Leu
690 695 700

Thr Glu Ile Gln Gln Ala Tyr Ile Gln Glu Leu Leu Pro Val Ser Phe
705 710 715 720

Asn Asn Asp Asn Ser Glu Trp Ile Ser Ile Val Pro Asn Phe Ile Leu
725 730 735

Val Arg Asn Thr Leu Ile Ser Asn Ile Glu Ile Gly Phe Cys Leu Ile
740 745 750

Thr Lys Arg Ser Val Ile Cys Asn Gln Asp Tyr Ala Thr Pro Met Thr
755 760 765

Asn Asn Met Arg Glu Cys Leu Thr Gly Ser Thr Glu Lys Cys Pro Arg
770 775 780

Glu Leu Val Val Ser Ser His Val Pro Arg Phe Ala Leu Ser Asn Gly
785 790 795 800

Val Leu Phe Ala Asn Cys Ile Ser Val Thr Cys Gln Cys Gln Thr Thr
805 810 815

Gly Arg Ala Ile Ser Gln Ser Gly Glu Gln Thr Leu Leu Met Ile Asp
820 825 830

Asn Thr Thr Cys Pro Thr Ala Val Leu Gly Asn Val Ile Ile Ser Leu
835 840 845

Gly Lys Tyr Leu Gly Ser Val Asn Tyr Asn Ser Glu Gly Ile Ala Ile
850 855 860

Gly Pro Pro Val Phe Thr Asp Lys Val Asp Ile Ser Ser Gln Ile Ser
865 870 875 880

Ser Met Asn Gln Ser Leu Gln Gln Ser Lys Asp Tyr Ile Lys Glu Ala
885 890 895

Gln Arg Leu Leu Asp Thr Val Asn Pro Ser Leu Lys Leu Met Lys Gln
900 905 910

Ile Glu Asp Lys Ile Glu Glu Ile Leu Ser Lys Ile Tyr His Ile Glu
915 920 925

Asn Glu Ile Ala Arg Ile Lys Lys Leu Ile Gly Glu Ala Pro Gly Gly
930 935 940

Leu Val Pro Arg Gly Ser His His His His His His Ser Ala Trp Ser
945 950 955 960

His Pro Gln Phe Glu Lys
965

<210> SEQ ID NO 51
<211> LENGTH: 1013
<212> TYPE: PRT
<213> ORGANISM: Artificial sequence
<220> FEATURE:
<223> OTHER INFORMATION: Recombinant Nipah virus F sequence

<400> SEQUENCE: 51

Met Tyr Ser Met Gln Leu Ala Ser Cys Val Thr Leu Thr Leu Val Leu
1 5 10 15

Leu Val Asn Ser Gln Arg Pro Gln Thr Glu Gly Val Ser Asn Leu Val

-continued

```
            20                  25                  30

Gly Leu Pro Asn Asn Ile Cys Leu Gln Lys Thr Ser Asn Gln Ile Leu
        35                  40                  45

Lys Pro Lys Leu Ile Ser Tyr Thr Leu Pro Val Val Gly Gln Ser Gly
    50                  55                  60

Thr Cys Ile Thr Asp Pro Leu Leu Ala Met Asp Glu Gly Tyr Phe Ala
65                  70                  75                  80

Tyr Ser His Leu Glu Arg Ile Gly Ser Cys Ser Arg Gly Val Ser Lys
                85                  90                  95

Gln Arg Ile Ile Gly Val Gly Glu Val Leu Asp Arg Gly Asp Glu Val
            100                 105                 110

Pro Ser Leu Phe Met Thr Asn Val Trp Thr Pro Pro Asn Pro Asn Thr
        115                 120                 125

Val Tyr His Cys Ser Ala Val Tyr Asn Asn Glu Phe Tyr Tyr Val Leu
    130                 135                 140

Cys Ala Val Ser Thr Val Gly Asp Pro Ile Leu Asn Ser Thr Tyr Trp
145                 150                 155                 160

Ser Gly Ser Leu Met Met Thr Arg Leu Ala Val Lys Pro Lys Ser Asn
                165                 170                 175

Gly Gly Gly Tyr Asn Gln His Gln Leu Ala Leu Arg Ser Ile Glu Lys
            180                 185                 190

Gly Arg Tyr Asp Lys Val Met Pro Tyr Gly Pro Ser Gly Ile Lys Gln
        195                 200                 205

Gly Asp Thr Leu Tyr Phe Pro Ala Val Gly Phe Leu Val Arg Thr Glu
    210                 215                 220

Phe Lys Tyr Asn Asp Ser Asn Cys Pro Ile Thr Lys Cys Gln Tyr Ser
225                 230                 235                 240

Lys Pro Glu Asn Cys Arg Leu Ser Met Gly Ile Arg Pro Asn Ser His
                245                 250                 255

Tyr Ile Leu Arg Ser Gly Leu Leu Lys Tyr Asn Leu Ser Asp Gly Glu
            260                 265                 270

Asn Pro Lys Val Val Phe Ile Glu Ile Ser Asp Gln Arg Leu Ser Ile
        275                 280                 285

Gly Ser Pro Ser Lys Ile Tyr Asp Ser Leu Gly Gln Pro Val Phe Tyr
    290                 295                 300

Gln Ala Ser Phe Ser Trp Asp Thr Met Ile Lys Phe Gly Asp Val Leu
305                 310                 315                 320

Thr Val Asn Pro Leu Val Val Asn Trp Arg Asn Asn Thr Val Ile Ser
                325                 330                 335

Arg Pro Gly Gln Ser Gln Cys Pro Arg Phe Asn Thr Cys Pro Glu Ile
            340                 345                 350

Cys Trp Glu Gly Val Tyr Asn Asp Ala Phe Leu Ile Asp Arg Ile Asn
        355                 360                 365

Trp Ile Ser Ala Gly Val Phe Leu Asp Ser Asn Gln Thr Ala Glu Asn
    370                 375                 380

Pro Val Phe Thr Val Phe Lys Asp Asn Glu Ile Leu Tyr Arg Ala Gln
385                 390                 395                 400

Leu Ala Ser Glu Asp Thr Asn Ala Gln Lys Thr Ile Thr Asn Cys Phe
                405                 410                 415

Leu Leu Lys Asn Lys Ile Trp Cys Ile Ser Leu Val Glu Ile Tyr Asp
            420                 425                 430

Thr Gly Asp Asn Val Ile Arg Pro Lys Leu Phe Ala Val Lys Ile Pro
        435                 440                 445
```

-continued

```
Glu Gln Cys Thr Gly Gly Gly Gly Ser Gly Gly Gly Gly Gln Gly Ile
    450                 455                 460

Leu His Tyr Glu Lys Leu Ser Lys Ile Gly Leu Val Lys Gly Val Thr
465                 470                 475                 480

Arg Lys Tyr Lys Ile Lys Ser Asn Pro Leu Thr Lys Asp Ile Val Ile
                485                 490                 495

Lys Met Ile Pro Asn Val Ser Asn Met Ser Gln Cys Thr Gly Ser Val
            500                 505                 510

Met Glu Asn Tyr Lys Thr Arg Leu Asn Gly Ile Leu Thr Pro Ile Lys
        515                 520                 525

Gly Ala Leu Glu Ile Tyr Lys Asn Asn Thr His Asp Cys Val Gly Asp
    530                 535                 540

Val Arg Leu Ala Gly Val Cys Met Ala Gly Val Ala Ile Gly Ile Ala
545                 550                 555                 560

Thr Ala Ala Gln Ile Thr Ala Gly Val Ala Leu Tyr Glu Ala Met Lys
                565                 570                 575

Asn Ala Asp Asn Ile Asn Lys Leu Lys Ser Ser Ile Glu Ser Thr Asn
            580                 585                 590

Glu Ala Val Val Lys Leu Gln Glu Thr Ala Glu Lys Thr Val Tyr Val
        595                 600                 605

Phe Thr Ala Leu Gln Asp Tyr Ile Asn Thr Asn Leu Val Pro Thr Ile
    610                 615                 620

Asp Lys Ile Pro Cys Lys Gln Thr Glu Leu Ser Leu Asp Leu Ala Leu
625                 630                 635                 640

Ser Lys Tyr Leu Ser Asp Leu Leu Phe Val Phe Gly Pro Asn Leu Gln
                645                 650                 655

Asp Pro Val Ser Asn Ser Met Thr Ile Gln Ala Ile Ser Gln Ala Phe
            660                 665                 670

Gly Gly Asn Tyr Glu Thr Leu Leu Arg Thr Leu Gly Tyr Ala Thr Glu
        675                 680                 685

Asp Phe Asp Asp Leu Leu Glu Ser Asp Ser Ile Thr Gly Gln Ile Ile
    690                 695                 700

Tyr Val Asp Leu Ser Ser Tyr Tyr Ile Ile Val Arg Val Tyr Phe Pro
705                 710                 715                 720

Ile Leu Thr Glu Ile Gln Gln Ala Tyr Ile Gln Glu Leu Leu Pro Val
                725                 730                 735

Ser Phe Asn Asn Asp Asn Ser Glu Trp Ile Ser Ile Val Pro Asn Phe
            740                 745                 750

Ile Leu Val Arg Asn Thr Leu Ile Ser Asn Ile Glu Ile Gly Phe Cys
        755                 760                 765

Leu Ile Thr Lys Arg Ser Val Ile Cys Asn Gln Asp Tyr Ala Thr Pro
    770                 775                 780

Met Thr Asn Asn Met Arg Glu Cys Leu Thr Gly Ser Thr Glu Lys Cys
785                 790                 795                 800

Pro Arg Glu Leu Val Val Ser Ser His Val Pro Arg Phe Ala Leu Ser
                805                 810                 815

Asn Gly Val Leu Phe Ala Asn Cys Ile Ser Val Thr Cys Gln Cys Gln
            820                 825                 830

Thr Thr Gly Arg Ala Ile Ser Gln Ser Gly Glu Gln Thr Leu Leu Met
        835                 840                 845

Ile Asp Asn Thr Thr Cys Pro Thr Ala Val Leu Gly Asn Val Ile Ile
    850                 855                 860
```

Ser Leu Gly Lys Tyr Leu Gly Ser Val Asn Tyr Asn Ser Glu Gly Ile
865 870 875 880

Ala Ile Gly Pro Pro Val Phe Thr Asp Lys Val Asp Ile Ser Ser Gln
885 890 895

Ile Ser Ser Met Asn Gln Ser Leu Gln Gln Ser Lys Asp Tyr Ile Lys
900 905 910

Glu Ala Gln Arg Leu Leu Asp Thr Val Asn Pro Ser Leu Lys Leu Met
915 920 925

Lys Gln Ile Glu Asp Lys Ile Glu Glu Ile Leu Ser Lys Ile Tyr His
930 935 940

Ile Glu Asn Glu Ile Ala Arg Ile Lys Lys Leu Ile Gly Glu Ala Pro
945 950 955 960

Gly Ser Gly Tyr Ile Pro Glu Ala Pro Arg Asp Gly Gln Ala Tyr Val
965 970 975

Arg Lys Asp Gly Glu Trp Val Leu Leu Ser Thr Phe Leu Gly Ser Leu
980 985 990

Val Pro Arg Gly Ser His His His His His His Ser Ala Trp Ser His
995 1000 1005

Pro Gln Phe Glu Lys
1010

<210> SEQ ID NO 52
<211> LENGTH: 546
<212> TYPE: PRT
<213> ORGANISM: Nipah virus

<400> SEQUENCE: 52

Met Val Val Ile Leu Asp Lys Arg Cys Tyr Cys Asn Leu Leu Ile Leu
1 5 10 15

Ile Leu Met Ile Ser Glu Cys Ser Val Gly Ile Leu His Tyr Glu Lys
20 25 30

Leu Ser Lys Ile Gly Leu Val Lys Gly Val Thr Arg Lys Tyr Lys Ile
35 40 45

Lys Ser Asn Pro Leu Thr Lys Asp Ile Val Ile Lys Met Ile Pro Asn
50 55 60

Val Ser Asn Met Ser Gln Cys Thr Gly Ser Val Met Glu Asn Tyr Lys
65 70 75 80

Thr Arg Leu Asn Gly Ile Leu Thr Pro Ile Lys Gly Ala Leu Glu Ile
85 90 95

Tyr Lys Asn Asn Thr His Asp Leu Val Gly Asp Val Arg Leu Ala Gly
100 105 110

Val Ile Met Ala Gly Val Ala Ile Gly Ile Ala Thr Ala Ala Gln Ile
115 120 125

Thr Ala Gly Val Ala Leu Tyr Glu Ala Met Lys Asn Ala Asp Asn Ile
130 135 140

Asn Lys Leu Lys Ser Ser Ile Glu Ser Thr Asn Glu Ala Val Val Lys
145 150 155 160

Leu Gln Glu Thr Ala Glu Lys Thr Val Tyr Val Leu Thr Ala Leu Gln
165 170 175

Asp Tyr Ile Asn Thr Asn Leu Val Pro Thr Ile Asp Lys Ile Ser Cys
180 185 190

Lys Gln Thr Glu Leu Ser Leu Asp Leu Ala Leu Ser Lys Tyr Leu Ser
195 200 205

Asp Leu Leu Phe Val Phe Gly Pro Asn Leu Gln Asp Pro Val Ser Asn
210 215 220

Ser Met Thr Ile Gln Ala Ile Ser Gln Ala Phe Gly Gly Asn Tyr Glu
225 230 235 240

Thr Leu Leu Arg Thr Leu Gly Tyr Ala Thr Glu Asp Phe Asp Asp Leu
245 250 255

Leu Glu Ser Asp Ser Ile Thr Gly Gln Ile Ile Tyr Val Asp Leu Ser
260 265 270

Ser Tyr Tyr Ile Ile Val Arg Val Tyr Phe Pro Ile Leu Thr Glu Ile
275 280 285

Gln Gln Ala Tyr Ile Gln Glu Leu Leu Pro Val Ser Phe Asn Asn Asp
290 295 300

Asn Ser Glu Trp Ile Ser Ile Val Pro Asn Phe Ile Leu Val Arg Asn
305 310 315 320

Thr Leu Ile Ser Asn Ile Glu Ile Gly Phe Cys Leu Ile Thr Lys Arg
325 330 335

Ser Val Ile Cys Asn Gln Asp Tyr Ala Thr Pro Met Thr Asn Asn Met
340 345 350

Arg Glu Cys Leu Thr Gly Ser Thr Glu Lys Cys Pro Arg Glu Leu Val
355 360 365

Val Ser Ser His Val Pro Arg Phe Ala Leu Ser Asn Gly Val Leu Phe
370 375 380

Ala Asn Cys Ile Ser Val Thr Cys Gln Cys Gln Thr Thr Gly Arg Ala
385 390 395 400

Ile Ser Gln Ser Gly Glu Gln Thr Leu Leu Met Ile Asp Asn Thr Thr
405 410 415

Cys Pro Thr Ala Val Leu Gly Asn Val Ile Ile Ser Leu Gly Lys Tyr
420 425 430

Leu Gly Ser Val Asn Tyr Asn Ser Glu Gly Ile Ala Ile Gly Pro Pro
435 440 445

Val Phe Thr Asp Lys Val Asp Ile Ser Ser Gln Ile Ser Ser Met Asn
450 455 460

Gln Ser Leu Gln Gln Ser Lys Asp Tyr Ile Lys Glu Ala Gln Arg Leu
465 470 475 480

Leu Asp Thr Val Asn Pro Ser Leu Ile Ser Met Leu Ser Met Ile Ile
485 490 495

Leu Tyr Val Leu Ser Ile Ala Ser Leu Cys Ile Gly Leu Ile Thr Phe
500 505 510

Ile Ser Phe Ile Ile Val Glu Lys Lys Arg Asn Thr Tyr Ser Arg Leu
515 520 525

Glu Asp Arg Arg Val Arg Pro Thr Ser Ser Gly Asp Leu Tyr Tyr Ile
530 535 540

Gly Thr
545

<210> SEQ ID NO 53
<211> LENGTH: 602
<212> TYPE: PRT
<213> ORGANISM: Nipah virus

<400> SEQUENCE: 53

Met Pro Ala Glu Asn Lys Lys Val Arg Phe Glu Asn Thr Thr Ser Asp
1 5 10 15

Lys Gly Lys Ile Pro Ser Lys Val Ile Lys Ser Tyr Tyr Gly Thr Met
20 25 30

Asp Ile Lys Lys Ile Asn Glu Gly Leu Leu Asp Ser Lys Ile Leu Ser

```
        35                  40                  45

Ala Phe Asn Thr Val Ile Ala Leu Leu Gly Ser Ile Val Ile Ile Val
    50                  55                  60

Met Asn Ile Met Ile Ile Gln Asn Tyr Thr Arg Ser Thr Asp Asn Gln
65                  70                  75                  80

Ala Val Ile Lys Asp Ala Leu Gln Gly Ile Gln Gln Gln Ile Lys Gly
                85                  90                  95

Leu Ala Asp Lys Ile Gly Thr Glu Ile Gly Pro Lys Val Ser Leu Ile
            100                 105                 110

Asp Thr Ser Ser Thr Ile Thr Ile Pro Ala Asn Ile Gly Leu Leu Gly
        115                 120                 125

Ser Lys Ile Ser Gln Ser Thr Ala Ser Ile Asn Glu Asn Val Asn Glu
    130                 135                 140

Lys Cys Lys Phe Thr Leu Pro Pro Leu Lys Ile His Glu Cys Asn Ile
145                 150                 155                 160

Ser Cys Pro Asn Pro Leu Pro Phe Arg Glu Tyr Arg Pro Gln Thr Glu
                165                 170                 175

Gly Val Ser Asn Leu Val Gly Leu Pro Asn Asn Ile Cys Leu Gln Lys
            180                 185                 190

Thr Ser Asn Gln Ile Leu Lys Pro Lys Leu Ile Ser Tyr Thr Leu Pro
        195                 200                 205

Val Val Gly Gln Ser Gly Thr Cys Ile Thr Asp Pro Leu Leu Ala Met
    210                 215                 220

Asp Glu Gly Tyr Phe Ala Tyr Ser His Leu Glu Arg Ile Gly Ser Cys
225                 230                 235                 240

Ser Arg Gly Val Ser Lys Gln Arg Ile Ile Gly Val Gly Glu Val Leu
                245                 250                 255

Asp Arg Gly Asp Glu Val Pro Ser Leu Phe Met Thr Asn Val Trp Thr
            260                 265                 270

Pro Pro Asn Pro Asn Thr Val Tyr His Cys Ser Ala Val Tyr Asn Asn
        275                 280                 285

Glu Phe Tyr Tyr Val Leu Cys Ala Val Ser Thr Val Gly Asp Pro Ile
    290                 295                 300

Leu Asn Ser Thr Tyr Trp Ser Gly Ser Leu Met Met Thr Arg Leu Ala
305                 310                 315                 320

Val Lys Pro Lys Ser Asn Gly Gly Gly Tyr Asn Gln His Gln Leu Ala
                325                 330                 335

Leu Arg Ser Ile Glu Lys Gly Arg Tyr Asp Lys Val Met Pro Tyr Gly
            340                 345                 350

Pro Ser Gly Ile Lys Gln Gly Asp Thr Leu Tyr Phe Pro Ala Val Gly
        355                 360                 365

Phe Leu Val Arg Thr Glu Phe Lys Tyr Asn Asp Ser Asn Cys Pro Ile
    370                 375                 380

Thr Lys Cys Gln Tyr Ser Lys Pro Glu Asn Cys Arg Leu Ser Met Gly
385                 390                 395                 400

Ile Arg Pro Asn Ser His Tyr Ile Leu Arg Ser Gly Leu Leu Lys Tyr
                405                 410                 415

Asn Leu Ser Asp Gly Glu Asn Pro Lys Val Val Phe Ile Glu Ile Ser
            420                 425                 430

Asp Gln Arg Leu Ser Ile Gly Ser Pro Ser Lys Ile Tyr Asp Ser Leu
        435                 440                 445

Gly Gln Pro Val Phe Tyr Gln Ala Ser Phe Ser Trp Asp Thr Met Ile
    450                 455                 460
```

Lys Phe Gly Asp Val Leu Thr Val Asn Pro Leu Val Val Asn Trp Arg
465 470 475 480

Asn Asn Thr Val Ile Ser Arg Pro Gly Gln Ser Gln Cys Pro Arg Phe
485 490 495

Asn Thr Cys Pro Glu Ile Cys Trp Glu Gly Val Tyr Asn Asp Ala Phe
500 505 510

Leu Ile Asp Arg Ile Asn Trp Ile Ser Ala Gly Val Phe Leu Asp Ser
515 520 525

Asn Gln Thr Ala Glu Asn Pro Val Phe Thr Val Phe Lys Asp Asn Glu
530 535 540

Ile Leu Tyr Arg Ala Gln Leu Ala Ser Glu Asp Thr Asn Ala Gln Lys
545 550 555 560

Thr Ile Thr Asn Cys Phe Leu Leu Lys Asn Lys Ile Trp Cys Ile Ser
565 570 575

Leu Val Glu Ile Tyr Asp Thr Gly Asp Asn Val Ile Arg Pro Lys Leu
580 585 590

Phe Ala Val Lys Ile Pro Glu Gln Cys Thr
595 600

<210> SEQ ID NO 54
<211> LENGTH: 602
<212> TYPE: PRT
<213> ORGANISM: Nipah virus

<400> SEQUENCE: 54

Met Pro Thr Glu Ser Lys Lys Val Arg Phe Glu Asn Thr Ala Ser Asp
1 5 10 15

Lys Gly Lys Asn Pro Ser Lys Val Ile Lys Ser Tyr Tyr Gly Thr Met
20 25 30

Asp Ile Lys Lys Ile Asn Glu Gly Leu Leu Asp Ser Lys Ile Leu Ser
35 40 45

Ala Phe Asn Thr Val Ile Ala Leu Leu Gly Ser Ile Val Ile Ile Val
50 55 60

Met Asn Ile Met Ile Ile Gln Asn Tyr Thr Arg Ser Thr Asp Asn Gln
65 70 75 80

Ala Met Ile Lys Asp Ala Leu Gln Ser Ile Gln Gln Gln Ile Lys Gly
85 90 95

Leu Ala Asp Lys Ile Gly Thr Glu Ile Gly Pro Lys Val Ser Leu Ile
100 105 110

Asp Thr Ser Ser Thr Ile Thr Ile Pro Ala Asn Ile Gly Leu Leu Gly
115 120 125

Ser Lys Ile Ser Gln Ser Thr Ala Ser Ile Asn Glu Asn Val Asn Glu
130 135 140

Lys Cys Lys Phe Thr Leu Pro Pro Leu Lys Ile His Glu Cys Asn Ile
145 150 155 160

Ser Cys Pro Asn Pro Leu Pro Phe Arg Glu Tyr Lys Pro Gln Thr Glu
165 170 175

Gly Val Ser Asn Leu Val Gly Leu Pro Asn Asn Ile Cys Leu Gln Lys
180 185 190

Thr Ser Asn Gln Ile Leu Lys Pro Lys Leu Ile Ser Tyr Thr Leu Pro
195 200 205

Val Val Gly Gln Ser Gly Thr Cys Ile Thr Asp Pro Leu Leu Ala Met
210 215 220

Asp Glu Gly Tyr Phe Ala Tyr Ser His Leu Glu Lys Ile Gly Ser Cys

-continued

```
225                 230                 235                 240

Ser Arg Gly Val Ser Lys Gln Arg Ile Ile Gly Val Gly Glu Val Leu
                245                 250                 255

Asp Arg Gly Asp Glu Val Pro Ser Leu Phe Met Thr Asn Val Trp Thr
            260                 265                 270

Pro Ser Asn Pro Asn Thr Val Tyr His Cys Ser Ala Val Tyr Asn Asn
        275                 280                 285

Glu Phe Tyr Tyr Val Leu Cys Ala Val Ser Val Val Gly Asp Pro Ile
    290                 295                 300

Leu Asn Ser Thr Tyr Trp Ser Gly Ser Leu Met Met Thr Arg Leu Ala
305                 310                 315                 320

Val Lys Pro Lys Asn Asn Gly Glu Ser Tyr Asn Gln His Gln Phe Ala
                325                 330                 335

Leu Arg Asn Ile Glu Lys Gly Lys Tyr Asp Lys Val Met Pro Tyr Gly
            340                 345                 350

Pro Ser Gly Ile Lys Gln Gly Asp Thr Leu Tyr Phe Pro Ala Val Gly
        355                 360                 365

Phe Leu Val Arg Thr Glu Phe Lys Tyr Asn Asp Ser Asn Cys Pro Ile
    370                 375                 380

Ala Glu Cys Gln Tyr Ser Lys Pro Glu Asn Cys Arg Leu Ser Met Gly
385                 390                 395                 400

Ile Arg Pro Asn Ser His Tyr Ile Leu Arg Ser Gly Leu Leu Lys Tyr
                405                 410                 415

Asn Leu Ser Asp Glu Glu Asn Ser Lys Ile Val Phe Ile Glu Ile Ser
            420                 425                 430

Asp Gln Arg Leu Ser Ile Gly Ser Pro Ser Lys Ile Tyr Asp Ser Leu
        435                 440                 445

Gly Gln Pro Val Phe Tyr Gln Ala Ser Phe Ser Trp Asp Thr Met Ile
    450                 455                 460

Lys Phe Gly Asp Val Gln Thr Val Asn Pro Leu Val Val Asn Trp Arg
465                 470                 475                 480

Asp Asn Thr Val Ile Ser Arg Pro Gly Gln Ser Gln Cys Pro Arg Phe
                485                 490                 495

Asn Lys Cys Pro Glu Val Cys Trp Glu Gly Val Tyr Asn Asp Ala Phe
            500                 505                 510

Leu Ile Asp Arg Ile Asn Trp Ile Ser Ala Gly Val Phe Leu Asp Ser
        515                 520                 525

Asn Gln Thr Ala Glu Asn Pro Val Phe Thr Val Phe Lys Asp Asn Glu
    530                 535                 540

Val Leu Tyr Arg Ala Gln Leu Ala Ser Glu Asp Thr Asn Ala Gln Lys
545                 550                 555                 560

Thr Ile Thr Asn Cys Phe Leu Leu Lys Asn Lys Ile Trp Cys Ile Ser
                565                 570                 575

Leu Val Glu Ile Tyr Asp Thr Gly Asp Asn Val Ile Arg Pro Lys Leu
            580                 585                 590

Phe Ala Val Lys Ile Pro Glu Gln Cys Thr
        595                 600


<210> SEQ ID NO 55
<211> LENGTH: 163
<212> TYPE: PRT
<213> ORGANISM: Artificial Sequence
<220> FEATURE:
<223> OTHER INFORMATION: Recombinant ferritin sequence
```

<400> SEQUENCE: 55

```
Asp Ile Ile Lys Leu Leu Asn Glu Gln Val Asn Lys Glu Met Gln Ser
1               5                   10                  15

Ser Asn Leu Tyr Met Ser Met Ser Ser Trp Cys Tyr Thr His Ser Leu
            20                  25                  30

Asp Gly Ala Gly Leu Phe Leu Phe Asp His Ala Ala Glu Glu Tyr Glu
        35                  40                  45

His Ala Lys Lys Leu Ile Ile Phe Leu Asn Glu Asn Asn Val Pro Val
    50                  55                  60

Gln Leu Thr Ser Ile Ser Ala Pro Glu His Lys Phe Glu Gly Leu Thr
65                  70                  75                  80

Gln Ile Phe Gln Lys Ala Tyr Glu His Glu Gln His Ile Ser Glu Ser
                85                  90                  95

Ile Asn Asn Ile Val Asp His Ala Ile Lys Ser Lys Asp His Ala Thr
            100                 105                 110

Phe Asn Phe Leu Gln Trp Tyr Val Ala Glu Gln His Glu Glu Glu Val
        115                 120                 125

Leu Phe Lys Asp Ile Leu Asp Lys Ile Glu Leu Ile Gly Asn Glu Asn
    130                 135                 140

His Gly Leu Tyr Leu Ala Asp Gln Tyr Val Lys Gly Ile Ala Lys Ser
145                 150                 155                 160

Arg Lys Ser
```

<210> SEQ ID NO 56
<211> LENGTH: 154
<212> TYPE: PRT
<213> ORGANISM: Artificial Sequence
<220> FEATURE:
<223> OTHER INFORMATION: Recombinant lumazine synthase sequence

<400> SEQUENCE: 56

```
Met Gln Ile Tyr Glu Gly Lys Leu Thr Ala Glu Gly Leu Arg Phe Gly
1               5                   10                  15

Ile Val Ala Ser Arg Phe Asn His Ala Leu Val Asp Arg Leu Val Glu
            20                  25                  30

Gly Ala Ile Asp Cys Ile Val Arg His Gly Gly Arg Glu Glu Asp Ile
        35                  40                  45

Thr Leu Val Arg Val Pro Gly Ser Trp Glu Ile Pro Val Ala Ala Gly
    50                  55                  60

Glu Leu Ala Arg Lys Glu Asp Ile Asp Ala Val Ile Ala Ile Gly Val
65                  70                  75                  80

Leu Ile Arg Gly Ala Thr Pro His Phe Asp Tyr Ile Ala Ser Glu Val
                85                  90                  95

Ser Lys Gly Leu Ala Asp Leu Ser Leu Glu Leu Arg Lys Pro Ile Thr
            100                 105                 110

Phe Gly Val Ile Thr Ala Asp Thr Leu Glu Gln Ala Ile Glu Arg Ala
        115                 120                 125

Gly Thr Lys His Gly Asn Lys Gly Trp Glu Ala Ala Leu Ser Ala Ile
    130                 135                 140

Glu Met Ala Asn Leu Phe Lys Ser Leu Arg
145                 150
```

<210> SEQ ID NO 57
<211> LENGTH: 265
<212> TYPE: PRT
<213> ORGANISM: Artificial Sequence
<220> FEATURE:
<223> OTHER INFORMATION: Recombinant encapsulin sequence

<400> SEQUENCE: 57

Met Glu Phe Leu Lys Arg Ser Phe Ala Pro Leu Thr Glu Lys Gln Trp
1               5                   10                  15

Gln Glu Ile Asp Asn Arg Ala Arg Glu Ile Phe Lys Thr Gln Leu Tyr
            20                  25                  30

Gly Arg Lys Phe Val Asp Val Glu Gly Pro Tyr Gly Trp Glu Tyr Ala
        35                  40                  45

Ala His Pro Leu Gly Glu Val Glu Val Leu Ser Asp Glu Asn Glu Val
    50                  55                  60

Val Lys Trp Gly Leu Arg Lys Ser Leu Pro Leu Ile Glu Leu Arg Ala
65                  70                  75                  80

Thr Phe Thr Leu Asp Leu Trp Glu Leu Asp Asn Leu Glu Arg Gly Lys
                85                  90                  95

Pro Asn Val Asp Leu Ser Ser Leu Glu Glu Thr Val Arg Lys Val Ala
            100                 105                 110

Glu Phe Glu Asp Glu Val Ile Phe Arg Gly Cys Glu Lys Ser Gly Val
        115                 120                 125

Lys Gly Leu Leu Ser Phe Glu Glu Arg Lys Ile Glu Cys Gly Ser Thr
    130                 135                 140

Pro Lys Asp Leu Leu Glu Ala Ile Val Arg Ala Leu Ser Ile Phe Ser
145                 150                 155                 160

Lys Asp Gly Ile Glu Gly Pro Tyr Thr Leu Val Ile Asn Thr Asp Arg
                165                 170                 175

Trp Ile Asn Phe Leu Lys Glu Glu Ala Gly His Tyr Pro Leu Glu Lys
            180                 185                 190

Arg Val Glu Glu Cys Leu Arg Gly Gly Lys Ile Ile Thr Thr Pro Arg
        195                 200                 205

Ile Glu Asp Ala Leu Val Val Ser Glu Arg Gly Gly Asp Phe Lys Leu
    210                 215                 220

Ile Leu Gly Gln Asp Leu Ser Ile Gly Tyr Glu Asp Arg Glu Lys Asp
225                 230                 235                 240

Ala Val Arg Leu Phe Ile Thr Glu Thr Phe Thr Phe Gln Val Val Asn
                245                 250                 255

Pro Glu Ala Leu Ile Leu Leu Lys Phe
            260                 265

<210> SEQ ID NO 58
<211> LENGTH: 265
<212> TYPE: PRT
<213> ORGANISM: Artificial Sequence
<220> FEATURE:
<223> OTHER INFORMATION: Recombinant sulfur oxygenase reductase sequence

<400> SEQUENCE: 58

Met Glu Phe Leu Lys Arg Ser Phe Ala Pro Leu Thr Glu Lys Gln Trp
1               5                   10                  15

Gln Glu Ile Asp Asn Arg Ala Arg Glu Ile Phe Lys Thr Gln Leu Tyr
            20                  25                  30

Gly Arg Lys Phe Val Asp Val Glu Gly Pro Tyr Gly Trp Glu Tyr Ala
        35                  40                  45

Ala His Pro Leu Gly Glu Val Glu Val Leu Ser Asp Glu Asn Glu Val
    50                  55                  60

Val Lys Trp Gly Leu Arg Lys Ser Leu Pro Leu Ile Glu Leu Arg Ala

```
65                  70                  75                  80

Thr Phe Thr Leu Asp Leu Trp Glu Leu Asp Asn Leu Glu Arg Gly Lys
                85                  90                  95

Pro Asn Val Asp Leu Ser Ser Leu Glu Glu Thr Val Arg Lys Val Ala
            100                 105                 110

Glu Phe Glu Asp Glu Val Ile Phe Arg Gly Cys Glu Lys Ser Gly Val
        115                 120                 125

Lys Gly Leu Leu Ser Phe Glu Glu Arg Lys Ile Glu Cys Gly Ser Thr
    130                 135                 140

Pro Lys Asp Leu Leu Glu Ala Ile Val Arg Ala Leu Ser Ile Phe Ser
145                 150                 155                 160

Lys Asp Gly Ile Glu Gly Pro Tyr Thr Leu Val Ile Asn Thr Asp Arg
                165                 170                 175

Trp Ile Asn Phe Leu Lys Glu Glu Ala Gly His Tyr Pro Leu Glu Lys
            180                 185                 190

Arg Val Glu Glu Cys Leu Arg Gly Gly Lys Ile Ile Thr Thr Pro Arg
        195                 200                 205

Ile Glu Asp Ala Leu Val Val Ser Glu Arg Gly Gly Asp Phe Lys Leu
    210                 215                 220

Ile Leu Gly Gln Asp Leu Ser Ile Gly Tyr Glu Asp Arg Glu Lys Asp
225                 230                 235                 240

Ala Val Arg Leu Phe Ile Thr Glu Thr Phe Thr Phe Gln Val Val Asn
                245                 250                 255

Pro Glu Ala Leu Ile Leu Leu Lys Phe
            260                 265


<210> SEQ ID NO 59
<211> LENGTH: 976
<212> TYPE: PRT
<213> ORGANISM: Artificial sequence
<220> FEATURE:
<223> OTHER INFORMATION: Recombinant Nipah virus F sequence

<400> SEQUENCE: 59

Met Tyr Ser Met Gln Leu Ala Ser Cys Val Thr Leu Thr Leu Val Leu
1               5                   10                  15

Leu Val Asn Ser Gln Gly Ile Leu His Tyr Glu Lys Leu Ser Lys Ile
            20                  25                  30

Gly Leu Val Lys Gly Val Thr Arg Lys Tyr Lys Ile Lys Ser Asn Pro
        35                  40                  45

Leu Thr Lys Asp Ile Val Ile Lys Met Ile Pro Asn Val Ser Asn Met
    50                  55                  60

Ser Gln Cys Thr Gly Ser Val Met Glu Asn Tyr Lys Thr Arg Leu Asn
65                  70                  75                  80

Gly Ile Leu Thr Pro Ile Lys Gly Ala Leu Glu Ile Tyr Lys Asn Asn
                85                  90                  95

Thr His Asp Cys Val Gly Asp Val Arg Leu Ala Gly Val Cys Met Ala
            100                 105                 110

Gly Val Ala Ile Gly Ile Ala Thr Ala Ala Gln Ile Thr Ala Gly Val
        115                 120                 125

Ala Leu Tyr Glu Ala Met Lys Asn Ala Asp Asn Ile Asn Lys Leu Lys
    130                 135                 140

Ser Ser Ile Glu Ser Thr Asn Glu Ala Val Val Lys Leu Gln Glu Thr
145                 150                 155                 160

Ala Glu Lys Thr Val Tyr Val Phe Thr Ala Leu Gln Asp Tyr Ile Asn
```

-continued

```
                165                 170                 175

Thr Asn Leu Val Pro Thr Ile Asp Lys Ile Pro Cys Lys Gln Thr Glu
            180                 185                 190

Leu Ser Leu Asp Leu Ala Leu Ser Lys Tyr Leu Ser Asp Leu Leu Phe
        195                 200                 205

Val Phe Gly Pro Asn Leu Gln Asp Pro Val Ser Asn Ser Met Thr Ile
    210                 215                 220

Gln Ala Ile Ser Gln Ala Phe Gly Gly Asn Tyr Glu Thr Leu Leu Arg
225                 230                 235                 240

Thr Leu Gly Tyr Ala Thr Glu Asp Phe Asp Asp Leu Leu Glu Ser Asp
                245                 250                 255

Ser Ile Thr Gly Gln Ile Ile Tyr Val Asp Leu Ser Ser Tyr Tyr Ile
            260                 265                 270

Ile Val Arg Val Tyr Phe Pro Ile Leu Thr Glu Ile Gln Gln Ala Tyr
        275                 280                 285

Ile Gln Glu Leu Leu Pro Val Ser Phe Asn Asn Asp Asn Ser Glu Trp
    290                 295                 300

Ile Ser Ile Val Pro Asn Phe Ile Leu Val Arg Asn Thr Leu Ile Ser
305                 310                 315                 320

Asn Ile Glu Ile Gly Phe Cys Leu Ile Thr Lys Arg Ser Val Ile Cys
                325                 330                 335

Asn Gln Asp Tyr Ala Thr Pro Met Thr Asn Asn Met Arg Glu Cys Leu
            340                 345                 350

Thr Gly Ser Thr Glu Lys Cys Pro Arg Glu Leu Val Val Ser Ser His
        355                 360                 365

Val Pro Arg Phe Ala Leu Ser Asn Gly Val Leu Phe Ala Asn Cys Ile
    370                 375                 380

Ser Val Thr Cys Gln Cys Gln Thr Thr Gly Arg Ala Ile Ser Gln Ser
385                 390                 395                 400

Gly Glu Gln Thr Leu Leu Met Ile Asp Asn Thr Thr Cys Pro Thr Ala
                405                 410                 415

Val Leu Gly Asn Val Ile Ile Ser Leu Gly Lys Tyr Leu Gly Ser Val
            420                 425                 430

Asn Tyr Asn Ser Glu Gly Ile Ala Ile Gly Pro Pro Val Phe Thr Asp
        435                 440                 445

Lys Val Asp Ile Ser Ser Gln Ile Ser Ser Met Asn Gln Ser Leu Gln
    450                 455                 460

Gln Ser Lys Asp Tyr Ile Lys Glu Ala Gln Arg Leu Leu Asp Thr Val
465                 470                 475                 480

Asn Pro Ser Leu Lys Leu Met Lys Gln Ile Glu Asp Lys Ile Glu Glu
                485                 490                 495

Ile Leu Ser Lys Ile Tyr His Ile Glu Asn Glu Ile Ala Arg Ile Lys
            500                 505                 510

Lys Leu Ile Gly Glu Ala Pro Gly Ser Gly Gly Gly Gly Gly Gly Val
        515                 520                 525

Ser Asn Leu Val Gly Leu Pro Asn Asn Ile Cys Leu Gln Lys Thr Ser
    530                 535                 540

Asn Gln Ile Leu Lys Pro Lys Leu Ile Ser Tyr Thr Leu Pro Val Val
545                 550                 555                 560

Gly Gln Ser Gly Thr Cys Ile Thr Asp Pro Leu Leu Ala Met Asp Glu
                565                 570                 575

Gly Tyr Phe Ala Tyr Ser His Leu Glu Arg Ile Gly Ser Cys Ser Arg
            580                 585                 590
```

```
Gly Val Ser Lys Gln Arg Ile Ile Gly Val Gly Glu Val Leu Asp Arg
        595                 600                 605

Gly Asp Glu Val Pro Ser Leu Phe Met Thr Asn Val Trp Thr Pro Pro
    610                 615                 620

Asn Pro Asn Thr Val Tyr His Cys Ser Ala Val Tyr Asn Asn Glu Phe
625                 630                 635                 640

Tyr Tyr Val Leu Cys Ala Val Ser Thr Val Gly Asp Pro Ile Leu Asn
                645                 650                 655

Ser Thr Tyr Trp Ser Gly Ser Leu Met Met Thr Arg Leu Ala Val Lys
            660                 665                 670

Pro Lys Ser Asn Gly Gly Gly Tyr Asn Gln His Gln Leu Ala Leu Arg
        675                 680                 685

Ser Ile Glu Lys Gly Arg Tyr Asp Lys Val Met Pro Tyr Gly Pro Ser
    690                 695                 700

Gly Ile Lys Gln Gly Asp Thr Leu Tyr Phe Pro Ala Val Gly Phe Leu
705                 710                 715                 720

Val Arg Thr Glu Phe Lys Tyr Asn Asp Ser Asn Cys Pro Ile Thr Lys
                725                 730                 735

Cys Gln Tyr Ser Lys Pro Glu Asn Cys Arg Leu Ser Met Gly Ile Arg
            740                 745                 750

Pro Asn Ser His Tyr Ile Leu Arg Ser Gly Leu Leu Lys Tyr Asn Leu
        755                 760                 765

Ser Asp Gly Glu Asn Pro Lys Val Val Phe Ile Glu Ile Ser Asp Gln
    770                 775                 780

Arg Leu Ser Ile Gly Ser Pro Ser Lys Ile Tyr Asp Ser Leu Gly Gln
785                 790                 795                 800

Pro Val Phe Tyr Gln Ala Ser Phe Ser Trp Asp Thr Met Ile Lys Phe
                805                 810                 815

Gly Asp Val Leu Thr Val Asn Pro Leu Val Val Asn Trp Arg Asn Asn
            820                 825                 830

Thr Val Ile Ser Arg Pro Gly Gln Ser Gln Cys Pro Arg Phe Asn Thr
        835                 840                 845

Cys Pro Glu Ile Cys Trp Glu Gly Val Tyr Asn Asp Ala Phe Leu Ile
    850                 855                 860

Asp Arg Ile Asn Trp Ile Ser Ala Gly Val Phe Leu Asp Ser Asn Gln
865                 870                 875                 880

Thr Ala Glu Asn Pro Val Phe Thr Val Phe Lys Asp Asn Glu Ile Leu
                885                 890                 895

Tyr Arg Ala Gln Leu Ala Ser Glu Asp Thr Asn Ala Gln Lys Thr Ile
            900                 905                 910

Thr Asn Cys Phe Leu Leu Lys Asn Lys Ile Trp Cys Ile Ser Leu Val
        915                 920                 925

Glu Ile Tyr Asp Thr Gly Asp Asn Val Ile Arg Pro Lys Leu Phe Ala
    930                 935                 940

Val Lys Ile Pro Glu Gln Cys Thr Gly Gly Leu Val Pro Arg Gly Ser
945                 950                 955                 960

His His His His His His Ser Ala Trp Ser His Pro Gln Phe Glu Lys
                965                 970                 975
```

<210> SEQ ID NO 60
<211> LENGTH: 970
<212> TYPE: PRT
<213> ORGANISM: Artificial sequence
<220> FEATURE:

<223> OTHER INFORMATION: Recombinant Nipah virus F sequence

<400> SEQUENCE: 60

```
Met Tyr Ser Met Gln Leu Ala Ser Cys Val Thr Leu Thr Leu Val Leu
1               5                   10                  15

Leu Val Asn Ser Gln Gly Ile Leu His Tyr Glu Lys Leu Ser Lys Ile
            20                  25                  30

Gly Leu Val Lys Gly Val Thr Arg Lys Tyr Lys Ile Lys Ser Asn Pro
        35                  40                  45

Leu Thr Lys Asp Ile Val Ile Lys Met Ile Pro Asn Val Ser Asn Met
    50                  55                  60

Ser Gln Cys Thr Gly Ser Val Met Glu Asn Tyr Lys Thr Arg Leu Asn
65                  70                  75                  80

Gly Ile Leu Thr Pro Ile Lys Gly Ala Leu Glu Ile Tyr Lys Asn Asn
                85                  90                  95

Thr His Asp Cys Val Gly Asp Val Arg Leu Ala Gly Val Cys Met Ala
            100                 105                 110

Gly Val Ala Ile Gly Ile Ala Thr Ala Ala Gln Ile Thr Ala Gly Val
        115                 120                 125

Ala Leu Tyr Glu Ala Met Lys Asn Ala Asp Asn Ile Asn Lys Leu Lys
    130                 135                 140

Ser Ser Ile Glu Ser Thr Asn Glu Ala Val Val Lys Leu Gln Glu Thr
145                 150                 155                 160

Ala Glu Lys Thr Val Tyr Val Phe Thr Ala Leu Gln Asp Tyr Ile Asn
                165                 170                 175

Thr Asn Leu Val Pro Thr Ile Asp Lys Ile Pro Cys Lys Gln Thr Glu
            180                 185                 190

Leu Ser Leu Asp Leu Ala Leu Ser Lys Tyr Leu Ser Asp Leu Leu Phe
        195                 200                 205

Val Phe Gly Pro Asn Leu Gln Asp Pro Val Ser Asn Ser Met Thr Ile
    210                 215                 220

Gln Ala Ile Ser Gln Ala Phe Gly Gly Asn Tyr Glu Thr Leu Leu Arg
225                 230                 235                 240

Thr Leu Gly Tyr Ala Thr Glu Asp Phe Asp Asp Leu Leu Glu Ser Asp
                245                 250                 255

Ser Ile Thr Gly Gln Ile Ile Tyr Val Asp Leu Ser Ser Tyr Tyr Ile
            260                 265                 270

Ile Val Arg Val Tyr Phe Pro Ile Leu Thr Glu Ile Gln Gln Ala Tyr
        275                 280                 285

Ile Gln Glu Leu Leu Pro Val Ser Phe Asn Asn Asp Asn Ser Glu Trp
    290                 295                 300

Ile Ser Ile Val Pro Asn Phe Ile Leu Val Arg Asn Thr Leu Ile Ser
305                 310                 315                 320

Asn Ile Glu Ile Gly Phe Cys Leu Ile Thr Lys Arg Ser Val Ile Cys
                325                 330                 335

Asn Gln Asp Tyr Ala Thr Pro Met Thr Asn Asn Met Arg Glu Cys Leu
            340                 345                 350

Thr Gly Ser Thr Glu Lys Cys Pro Arg Glu Leu Val Val Ser Ser His
        355                 360                 365

Val Pro Arg Phe Ala Leu Ser Asn Gly Val Leu Phe Ala Asn Cys Ile
    370                 375                 380

Ser Val Thr Cys Gln Cys Gln Thr Thr Gly Arg Ala Ile Ser Gln Ser
385                 390                 395                 400
```

Gly Glu Gln Thr Leu Leu Met Ile Asp Asn Thr Thr Cys Pro Thr Ala
405 410 415

Val Leu Gly Asn Val Ile Ile Ser Leu Gly Lys Tyr Leu Gly Ser Val
420 425 430

Asn Tyr Asn Ser Glu Gly Ile Ala Ile Gly Pro Pro Val Phe Thr Asp
435 440 445

Lys Val Asp Ile Ser Ser Gln Ile Ser Ser Met Asn Gln Ser Leu Gln
450 455 460

Gln Ser Lys Asp Tyr Ile Lys Glu Ala Gln Arg Leu Leu Asp Thr Val
465 470 475 480

Asn Pro Ser Leu Gly Ser Gly Tyr Ile Pro Glu Ala Pro Arg Asp Gly
485 490 495

Gln Ala Tyr Val Arg Lys Asp Gly Glu Trp Val Leu Leu Ser Thr Phe
500 505 510

Leu Gly Ser Gly Gly Gly Gly Gly Gly Val Ser Asn Leu Val Gly Leu
515 520 525

Pro Asn Asn Ile Cys Leu Gln Lys Thr Ser Asn Gln Ile Leu Lys Pro
530 535 540

Lys Leu Ile Ser Tyr Thr Leu Pro Val Val Gly Gln Ser Gly Thr Cys
545 550 555 560

Ile Thr Asp Pro Leu Leu Ala Met Asp Glu Gly Tyr Phe Ala Tyr Ser
565 570 575

His Leu Glu Arg Ile Gly Ser Cys Ser Arg Gly Val Ser Lys Gln Arg
580 585 590

Ile Ile Gly Val Gly Glu Val Leu Asp Arg Gly Asp Glu Val Pro Ser
595 600 605

Leu Phe Met Thr Asn Val Trp Thr Pro Pro Asn Pro Asn Thr Val Tyr
610 615 620

His Cys Ser Ala Val Tyr Asn Asn Glu Phe Tyr Tyr Val Leu Cys Ala
625 630 635 640

Val Ser Thr Val Gly Asp Pro Ile Leu Asn Ser Thr Tyr Trp Ser Gly
645 650 655

Ser Leu Met Met Thr Arg Leu Ala Val Lys Pro Lys Ser Asn Gly Gly
660 665 670

Gly Tyr Asn Gln His Gln Leu Ala Leu Arg Ser Ile Glu Lys Gly Arg
675 680 685

Tyr Asp Lys Val Met Pro Tyr Gly Pro Ser Gly Ile Lys Gln Gly Asp
690 695 700

Thr Leu Tyr Phe Pro Ala Val Gly Phe Leu Val Arg Thr Glu Phe Lys
705 710 715 720

Tyr Asn Asp Ser Asn Cys Pro Ile Thr Lys Cys Gln Tyr Ser Lys Pro
725 730 735

Glu Asn Cys Arg Leu Ser Met Gly Ile Arg Pro Asn Ser His Tyr Ile
740 745 750

Leu Arg Ser Gly Leu Leu Lys Tyr Asn Leu Ser Asp Gly Glu Asn Pro
755 760 765

Lys Val Val Phe Ile Glu Ile Ser Asp Gln Arg Leu Ser Ile Gly Ser
770 775 780

Pro Ser Lys Ile Tyr Asp Ser Leu Gly Gln Pro Val Phe Tyr Gln Ala
785 790 795 800

Ser Phe Ser Trp Asp Thr Met Ile Lys Phe Gly Asp Val Leu Thr Val
805 810 815

Asn Pro Leu Val Val Asn Trp Arg Asn Asn Thr Val Ile Ser Arg Pro

```
            820                 825                 830

Gly Gln Ser Gln Cys Pro Arg Phe Asn Thr Cys Pro Glu Ile Cys Trp
        835                 840                 845

Glu Gly Val Tyr Asn Asp Ala Phe Leu Ile Asp Arg Ile Asn Trp Ile
    850                 855                 860

Ser Ala Gly Val Phe Leu Asp Ser Asn Gln Thr Ala Glu Asn Pro Val
865                 870                 875                 880

Phe Thr Val Phe Lys Asp Asn Glu Ile Leu Tyr Arg Ala Gln Leu Ala
                885                 890                 895

Ser Glu Asp Thr Asn Ala Gln Lys Thr Ile Thr Asn Cys Phe Leu Leu
            900                 905                 910

Lys Asn Lys Ile Trp Cys Ile Ser Leu Val Glu Ile Tyr Asp Thr Gly
        915                 920                 925

Asp Asn Val Ile Arg Pro Lys Leu Phe Ala Val Lys Ile Pro Glu Gln
    930                 935                 940

Cys Thr Gly Gly Leu Val Pro Arg Gly Ser His His His His His His
945                 950                 955                 960

Ser Ala Trp Ser His Pro Gln Phe Glu Lys
                965                 970


<210> SEQ ID NO 61
<211> LENGTH: 3038
<212> TYPE: DNA
<213> ORGANISM: Artificial Sequence
<220> FEATURE:
<223> OTHER INFORMATION: recombinant Nipah virus F sequence

<400> SEQUENCE: 61

tctagagcca ccatgtactc tatgcagctg gccagctgcg tgaccctgac actggtgctg     60

ctggtgaact ctcagggcat cctgcactac gagaagctga gcaagatcgg cctggtgaag    120

ggcgtgacca gaaagtataa gatcaagtcc aacccactga caaaggacat cgtgatcaag    180

atgatcccca acgtgagcaa tatgtctcag tgtaccggct ctgtgatgga gaactacaag    240

acccgcctga atggcatcct gacaccaatc aagggcgccc tggagatcta taagaacaat    300

acacacgact gcgtgggcga tgtgcggctg gcaggcgtgt gcatggcagg agtggcaatc    360

ggaatcgcaa ccgcagcaca gatcacagca ggagtggccc tgtatgaggc catgaagaac    420

gccgacaaca tcaataagct gaagagctcc atcgagagca ccaatgaggc cgtggtgaag    480

ctgcaggaga cagccgagaa gacagtgtac gtgttcacag ccctgcagga ctatatcaac    540

accaatctgg tgcccacaat cgataagatc cccctgcaagc agaccgagct gtccctggac    600

ctggccctgt ctaagtacct gagcgatctg ctgttcgtgt ttggcccaaa cctgcaggac    660

cccgtgtcca attctatgac aatccaggcc atctcccagg ccttcggcgg caattacgag    720

acactgctga gaacactggg ctatgccacc gaggactttg acgatctgct ggagagcgat    780

tccatcacag gccagatcat ctatgtggat ctgtctagct actatatcat cgtgagggtg    840

tacttcccta tcctgaccga gatccagcag gcctatatcc aggagctgct gccagtgagc    900

ttcaacaatg acaattccga gtggatctct atcgtgccca actttatcct ggtgcggaac    960

accctgatca gcaatatcga gatcggcttt tgcctgatca caaagagatc cgtgatctgt   1020

aatcaggact acgccacccc catgacaaac aatatgaggg agtgcctgac cggctccaca   1080

gagaagtgtc cccgggagct ggtggtgtcc tctcacgtgc ctagattcgc cctgtccaac   1140

ggcgtgctgt ttgccaattg catctctgtg acctgccagt gtcagaccac aggaagggca   1200
```

atctctcaga gcggagagca gaccctgctg atgatcgata acaccacatg tcctacagcc 1260
gtgctgggca atgtgatcat cagcctgggc aagtacctgg gctccgtgaa ctataattct 1320
gagggaatcg caatcggacc acccgtgttc accgacaagg tggatatcag ctcccagatc 1380
tctagcatga accagagcct gcagcagtcc aaggactaca tcaaggaggc ccagcggctg 1440
ctggataccg tgaatccttc tctgaagctg atgaagcaga tcgaggataa gatcgaggag 1500
atcctgagca agatctatca catcgagaac gagatcgcca ggatcaagaa gctgatcgga 1560
gaggcacctg gatctggtta catcccagag gctccgcggg atggacaggc ctacgtgaga 1620
aaggacggcg agtgggtgct gctgagcacc ttcctgggaa gcggtggagg aggcggaggc 1680
gtgagcaatc tggtgggcct gcccaacaat atctgtctgc agaagacctc caaccagatc 1740
ctgaagccca agctgatctc ctatacactg cctgtggtgg gccagtctgg cacctgcatc 1800
acagaccctc tgctggccat ggatgagggc tacttcgcct attctcacct ggagaggatc 1860
ggctcctgtt ctcgcggcgt gagcaagcag cggatcatcg gagtgggaga ggtgctggac 1920
aggggcgatg aggtgccttc cctgttcatg accaacgtgt ggacaccacc caatccaaac 1980
accgtgtacc actgctctgc cgtgtataac aatgagtttt actacgtgct gtgcgccgtg 2040
agcaccgtgg gcgatcctat cctgaactcc acatactgga gcggctccct gatgatgacc 2100
agactggccg tgaagccaaa gtccaatggc ggcggctata accagcacca gctggccctg 2160
agatctatcg agaagggcag gtacgataaa gtgatgcctt atggcccatc tggcatcaag 2220
cagggcgaca cactgtactt ccccgccgtg ggctttctgg tgaggaccga gttcaagtac 2280
aatgactcca actgccctat cacaaagtgt cagtattcta agccagagaa ttgccgcctg 2340
agcatgggca tccggcccaa ctctcactac atcctgagaa gcggcctgct gaagtataat 2400
ctgagcgacg gcgagaaccc taaggtggtg tttatcgaga tctccgatca gaggctgtct 2460
atcggctctc ccagcaagat ctacgactcc ctgggccagc ccgtgttcta ccaggcctcc 2520
ttttcttggg acacaatgat caagttcggc gatgtgctga ccgtgaatcc actggtggtg 2580
aactggagaa acaataccgt gatcagcagg ccaggacagt cccagtgtcc tcgctttaac 2640
acatgcccag agatctgttg ggagggcgtg tacaatgacg ccttcctgat cgatcggatc 2700
aactggatct ccgccggcgt gtttctggac tctaatcaga ccgccgagaa ccccgtgttc 2760
acagtgttta aggataatga gatcctgtac agggcacagc tggcaagcga ggacaccaac 2820
gcccagaaga ccatcacaaa ttgcttcctg ctgaagaaca agatctggtg tatctccctg 2880
gtggagatct atgacaccgg cgataacgtg atccggccaa agctgtttgc cgtgaagatc 2940
cccgagcagt gcacaggcgg cctggtgcct agaggctctc accaccacca tcaccacagc 3000
gcctggtccc acccccagtt cgagaagtga taggatcc 3038

<210> SEQ ID NO 62
<211> LENGTH: 3044
<212> TYPE: DNA
<213> ORGANISM: Artificial sequence
<220> FEATURE:
<223> OTHER INFORMATION: recombinant Nipah virus F sequence

<400> SEQUENCE: 62
tctagaccac catgtactca atgcagctgg cctcttgcgt cacactgaca ctggtcctgc 60
tggtcaactc acagagacca cagaccgagg gcgtgagcaa tctggtgggc ctgcccaaca 120
atatctgtct gcagaagacc tccaaccaga tcctgaagcc caagctgatc tcctatacac 180
tgcctgtggt gggccagtct ggcacctgca tcacagaccc tctgctggcc atggatgagg 240

```
gctacttcgc ctattctcac ctggagagga tcggctcctg ttctcgcggc gtgagcaagc    300
agcggatcat cggagtggga gaggtgctgg acaggggcga tgaggtgcct tccctgttca    360
tgaccaacgt gtggacacca cccaatccaa acaccgtgta ccactgctct gccgtgtata    420
acaatgagtt ttactacgtg ctgtgcgccg tgagcaccgt gggcgatcct atcctgaact    480
ccacatactg gagcggctcc ctgatgatga ccagactggc cgtgaagcca aagtccaatg    540
gcggcggcta taaccagcac cagctggccc tgagatctat cgagaagggc aggtacgata    600
aagtgatgcc ttatggccca tctggcatca agcagggcga cacactgtac ttccccgccg    660
tgggctttct ggtgaggacc gagttcaagt acaatgactc caactgccct atcacaaagt    720
gtcagtattc taagccagag aattgccgcc tgagcatggg catccggccc aactctcact    780
acatcctgag aagcggcctg ctgaagtata atctgagcga cggcgagaac cctaaggtgg    840
tgtttatcga gatctccgat cagaggctgt ctatcggctc tcccagcaag atctacgact    900
ccctgggcca gcccgtgttc taccaggcct ccttttcttg ggacacaatg atcaagttcg    960
gcgatgtgct gaccgtgaat ccactggtgg tgaactggag aaacaatacc gtgatcagca   1020
ggccaggaca gtcccagtgt cctcgcttta acacatgccc agagatctgt tgggagggcg   1080
tgtacaatga cgccttcctg atcgatcgga tcaactggat ctccgccggc gtgtttctgg   1140
actctaatca gaccgccgag aaccccgtgt tcacagtgtt taaggataat gagatcctgt   1200
acagggcaca gctggcaagc gaggacacca acgcccagaa gaccatcaca aattgcttcc   1260
tgctgaagaa caagatctgg tgtatctccc tggtggagat ctatgacacc ggcgataacg   1320
tgatccggcc aaagctgttt gccgtgaaga tccccgagca gtgcacaggc ggcggtcagg   1380
gcatcctgca ctacgagaag ctgagcaaga tcggcctggt gaagggcgtg accagaaagt   1440
ataagatcaa gtccaaccca ctgacaaagg acatcgtgat caagatgatc cccaacgtga   1500
gcaatatgtc tcagtgtacc ggctctgtga tggagaacta caagacccgc ctgaatggca   1560
tcctgacacc aatcaagggc gccctggaga tctataagaa caatacacac gactgcgtgg   1620
gcgatgtgcg gctggcaggc gtgtgcatgg caggagtggc aatcggaatc gcaaccgcag   1680
cacagatcac agcaggagtg gccctgtatg aggccatgaa gaacgccgac aacatcaata   1740
agctgaagag ctccatcgag agcaccaatg aggccgtggt gaagctgcag gagacagccg   1800
agaagacagt gtacgtgttc acagccctgc aggactatat caacaccaat ctggtgccca   1860
caatcgataa gatcccctgc aagcagaccg agctgtccct ggacctggcc ctgtctaagt   1920
acctgagcga tctgctgttc gtgtttggcc caaacctgca ggaccccgtg tccaattcta   1980
tgacaatcca ggccatctcc caggccttcg gcggcaatta cgagacactg ctgagaacac   2040
tgggctatgc caccgaggac tttgacgatc tgctggagag cgattccatc acaggccaga   2100
tcatctatgt ggatctgtct agctactata tcatcgtgag ggtgtacttc cctatcctga   2160
ccgagatcca gcaggcctat atccaggagc tgctgccagt gagcttcaac aatgacaatt   2220
ccgagtggat ctctatcgtg cccaacttta tcctggtgcg gaacaccctg atcagcaata   2280
tcgagatcgg cttttgcctg atcacaaaga gatccgtgat ctgtaatcag gactacgcca   2340
cccccatgac aaacaatatg agggagtgcc tgaccggctc cacagagaag tgtccccggg   2400
agctggtggt gtcctctcac gtgcctagat tcgccctgtc caacggcgtg ctgtttgcca   2460
attgcatctc tgtgacctgc cagtgtcaga ccacaggaag ggcaatctct cagagcggag   2520
agcagaccct gctgatgatc gataacacca catgtcctac agccgtgctg ggcaatgtga   2580
```

-continued

```
tcatcagcct gggcaagtac ctgggctccg tgaactataa ttctgaggga atcgcaatcg   2640

gaccacccgt gttcaccgac aaggtggata tcagctccca gatctctagc atgaaccaga   2700

gcctgcagca gtccaaggac tacatcaagg aggcccagcg gctgctggat accgtgaatc   2760

cttctctgaa gctgatgaag cagatcgagg ataagatcga ggagatcctg agcaagatct   2820

atcacatcga gaacgagatc gccaggatca agaagctgat cggagaggca cctggatctg   2880

gttacatccc agaggctccg cgggatggac aggcctacgt gagaaaggac ggcgagtggg   2940

tgctgctgag caccttcctg ggaagcctgg tgcctagggg ctcccaccac caccaccacc   3000

acagcgcctg gtcccaccca cagtttgaga agtgatgagg atcc                    3044
```

<210> SEQ ID NO 63
<211> LENGTH: 1653
<212> TYPE: DNA
<213> ORGANISM: Artificial sequence
<220> FEATURE:
<223> OTHER INFORMATION: recombinant nipah virus sequence

<400> SEQUENCE: 63

```
tctagagcca ccatgtactc tatgcagctg gccagctgcg tgaccctgac actggtgctg     60

ctggtgaact ctcagggcat cctgcactac gagaagctga gcaagatcgg cctggtgaag    120

ggcgtgacca gaaagtataa gatcaagtcc aacccactga caaaggacat cgtgatcaag    180

atgatcccca acgtgagcaa tatgtctcag tgtaccggct ctgtgatgga gaactacaag    240

acccgcctga atggcatcct gacaccaatc aagggcgccc tggagatcta taagaacaat    300

acacacgact gcgtgggcga tgtgcggctg gcaggcgtgt gcatggcagg agtggcaatc    360

ggaatcgcaa ccgcagcaca gatcacagca ggagtggccc tgtatgaggc catgaagaac    420

gccgacaaca tcaataagct gaagagctcc atcgagagca ccaatgaggc cgtggtgaag    480

ctgcaggaga cagccgagaa gacagtgtac gtgttcacag ccctgcagga ctatatcaac    540

accaatctgg tgcccacaat cgataagatc ccctgcaagc agaccgagct gtccctggac    600

ctggccctgt ctaagtacct gagcgatctg ctgttcgtgt ttggcccaaa cctgcaggac    660

cccgtgtcca attctatgac aatccaggcc atctcccagg ccttcggcgg caattacgag    720

acactgctga gaacactggg ctatgccacc gaggactttg acgatctgct ggagagcgat    780

tccatcacag gccagatcat ctatgtggat ctgtctagct actatatcat cgtgagggtg    840

tacttcccta tcctgaccga gatccagcag gcctatatcc aggagctgct gccagtgagc    900

ttcaacaatg acgattccga gtggatctct atcgtgccca actttatcct ggtgcggaac    960

accctgatca gcaatatcga gatcggcttt tgcctgatca caaagagatc cgtgatctgt   1020

aatcaggact acgccacccc catgacaaac aatatgaggg agtgcctgac cggctccaca   1080

gagaagtgtc cccgggagct ggtggtgtcc tctcacgtgc ctagattcgc cctgtccaac   1140

ggcgtgctgt ttgccaattg catctctgtg acctgccagt gtcagaccac aggaagggca   1200

atctctcaga gcggagagca gaccctgctg atgatcgata acaccacatg tcctacagcc   1260

gtgctgggca atgtgatcat cagcctgggc aagtacctgg gctccgtgaa ctataattct   1320

gagggaatcg caatcggacc acccgtgttc accgacaagg tggatatcag ctcccagatc   1380

tctagcatga accagagcct gcagcagtcc aaggactaca tcaaggaggc ccagcggctg   1440

ctggataccg tgaatccttc tctgaagctg atgaagcaga tcgaggataa gatcgaggag   1500

atcctgagca agatctatca catcgagaac gagatcgcca ggatcaagaa gctgatcgga   1560

gaggcacctg gaggcctggt gccaaggggc tcccaccacc accaccacca cagcgcctgg   1620
```

tcccacccac agtttgagaa gtgatgagga tcc 1653

<210> SEQ ID NO 64
<211> LENGTH: 1979
<212> TYPE: DNA
<213> ORGANISM: Artificial sequence
<220> FEATURE:
<223> OTHER INFORMATION: recombinant nipah virus G sequence

<400> SEQUENCE: 64
tctagaccac catgtactca atgcagctgg cctcttgcgt cacactgaca ctggtcctgc 60
tggtcaactc acagcaccac caccatcatc acggaagcgc ctggtcccac cctcagttcg 120
agaagggagg actggtgccc agaggatccg gcaacagcca gcgccctcag accgagggcg 180
tgagcaatct ggtgggcctg cccaacaata tctgtctgca gaagacctcc aaccagatcc 240
tgaagcccaa gctgatctcc tatacactgc ctgtggtggg ccagtctggc acctgcatca 300
cagaccctct gctggccatg gatgagggct acttcgccta ttctcacctg gagaggatcg 360
gctcctgttc tcgcggcgtg agcaagcagc ggatcatcgg agtgggagag gtgctggaca 420
ggggcgatga ggtgccttcc ctgttcatga ccaacgtgtg gacaccaccc aatccaaaca 480
ccgtgtacca ctgctctgcc gtgtataaca atgagtttta ctacgtgctg tgcgccgtga 540
gcaccgtggg cgatcctatc ctgaactcca catactggag cggctccctg atgatgacca 600
gactggccgt gaagccaaag tccaatggcg gcggctataa ccagcaccag ctggccctga 660
gatctatcga gaagggcagg tacgataaag tgatgcctta tggcccatct ggcatcaagc 720
agggcgacac actgtacttc cccgccgtgg gctttctggt gaggaccgag ttcaagtaca 780
atgactccaa ctgccctatc acaaagtgtc agtattctaa gccagagaat tgccgcctga 840
gcatgggcat ccggcccaac tctcactaca tcctgagaag cggcctgctg aagtataatc 900
tgagcgacgg cgagaaccct aaggtggtgt ttatcgagat ctccgatcag aggctgtcta 960
tcggctctcc cagcaagatc tacgactccc tgggccagcc cgtgttctac caggcctcct 1020
tttcttggga cacaatgatc aagttcggcg atgtgctgac cgtgaatcca ctggtggtga 1080
actggagaaa caataccgtg atcagcaggc caggacagtc ccagtgtcct cgctttaaca 1140
catgcccaga gatctgttgg gagggcgtgt acaatgacgc cttcctgatc gatcggatca 1200
actggatctc cgccggcgtg tttctggact ctaatcagac cgccgagaac cccgtgttca 1260
cagtgtttaa ggataatgag atcctgtaca gggcacagct ggcaagcgag gacaccaacg 1320
cccagaagac catcacaaat tgcttcctgc tgaagaacaa gatctggtgt atctccctgg 1380
tggagatcta tgacaccggc gataacgtga tccggccaaa gctgtttgcc gtgaagatcc 1440
ccgagcagtg cacaggcggc ggcagcggcg gggatatcat taagctgctg aacgaacagg 1500
tgaacaagga gatgcagtca agcaacctgt acatgtctat gtcctcttgg tgctatacac 1560
atagtctgga cggagctggc ctgttcctgt ttgatcacgc agccgaggaa tacgaacatg 1620
caaagaaact gatcattttc ctgaatgaga acaatgtgcc agtccagctg acaagtatct 1680
cagcccccga acacaagttc gaggggctga ctcagatctt tcagaaagct tacgaacacg 1740
agcagcatat tagcgaatcc atcaacaata ttgtggacca cgctatcaag tccaaagatc 1800
atgcaacctt caactttctg cagtggtacg tggccgagca gcacgaggaa gaggtcctgt 1860
ttaaggacat cctggataaa atcgaactga ttggcaacga gaatcatggg ctgtacctgg 1920
ccgatcagta tgtgaagggc attgctaagt cacggaaaag cggaagctga tgaccgcgg 1979

<210> SEQ ID NO 65
<211> LENGTH: 2951
<212> TYPE: DNA
<213> ORGANISM: Artificial sequence
<220> FEATURE:
<223> OTHER INFORMATION: recombinant nipah virus F sequence

<400> SEQUENCE: 65
tctagagcca ccatgtactc tatgcagctg gccagctgcg tgaccctgac actggtgctg 60
ctggtgaact ctcagggcat cctgcactac gagaagctga gcaagatcgg cctggtgaag 120
ggcgtgacca gaaagtataa gatcaagtcc aacccactga caaaggacat cgtgatcaag 180
atgatcccca acgtgagcaa tatgtctcag tgtaccggct ctgtgatgga gaactacaag 240
acccgcctga atggcatcct gacaccaatc aagggcgccc tggagatcta taagaacaat 300
acacacgact gcgtgggcga tgtgcggctg gcaggcgtgt gcatggcagg agtggcaatc 360
ggaatcgcaa ccgcagcaca gatcacagca ggagtggccc tgtatgaggc catgaagaac 420
gccgacaaca tcaataagct gaagagctcc atcgagagca ccaatgaggc cgtggtgaag 480
ctgcaggaga cagccgagaa gacagtgtac gtgttcacag ccctgcagga ctatatcaac 540
accaatctgg tgcccacaat cgataagatc ccctgcaagc agaccgagct gtccctggac 600
ctggccctgt ctaagtacct gagcgatctg ctgttcgtgt ttggcccaaa cctgcaggac 660
cccgtgtcca attctatgac aatccaggcc atctcccagg ccttcggcgg caattacgag 720
acactgctga gaacactggg ctatgccacc gaggactttg acgatctgct ggagagcgat 780
tccatcacag gccagatcat ctatgtggat ctgtctagct actatatcat cgtgagggtg 840
tacttcccta tcctgaccga gatccagcag gcctatatcc aggagctgct gccagtgagc 900
ttcaacaatg acaattccga gtggatctct atcgtgccca actttatcct ggtgcggaac 960
accctgatca gcaatatcga gatcggcttt tgcctgatca caaagagatc cgtgatctgt 1020
aatcaggact acgccacccc catgacaaac aatatgaggg agtgcctgac cggctccaca 1080
gagaagtgtc cccgggagct ggtggtgtcc tctcacgtgc ctagattcgc cctgtccaac 1140
ggcgtgctgt ttgccaattg catctctgtg acctgccagt gtcagaccac aggaagggca 1200
atctctcaga gcggagagca gaccctgctg atgatcgata acaccacatg tcctacagcc 1260
gtgctgggca atgtgatcat cagcctgggc aagtacctgg gctccgtgaa ctataattct 1320
gagggaatcg caatcggacc acccgtgttc accgacaagg tggatatcag ctcccagatc 1380
tctagcatga accagagcct gcagcagtcc aaggactaca tcaaggaggc ccagcggctg 1440
ctggataccg tgaatccttc tctgaagctg atgaagcaga tcgaggataa gatcgaggag 1500
atcctgagca agatctatca catcgagaac gagatcgcca ggatcaagaa gctgatcgga 1560
gaggcacctg gatctggtgg aggaggcgga ggcgtgagca atctggtggg cctgcccaac 1620
aatatctgtc tgcagaagac ctccaaccag atcctgaagc ccaagctgat ctcctataca 1680
ctgcctgtgg tgggccagtc tggcacctgc atcacagacc ctctgctggc catggatgag 1740
ggctacttcg cctattctca cctggagagg atcggctcct gttctcgcgg cgtgagcaag 1800
cagcggatca tcggagtggg agaggtgctg gacaggggcg atgaggtgcc ttccctgttc 1860
atgaccaacg tgtggacacc acccaatcca aacaccgtgt accactgctc tgccgtgtat 1920
aacaatgagt tttactacgt gctgtgcgcc gtgagcaccg tgggcgatcc tatcctgaac 1980
tccacatact ggagcggctc cctgatgatg accagactgg ccgtgaagcc aaagtccaat 2040
ggcggcggct ataaccagca ccagctggcc ctgagatcta tcgagaaggg caggtacgat 2100
aaagtgatgc cttatggccc atctggcatc aagcagggcg acacactgta cttccccgcc 2160
gtgggctttc tggtgaggac cgagttcaag tacaatgact ccaactgccc tatcacaaag 2220
tgtcagtatt ctaagccaga gaattgccgc ctgagcatgg gcatccggcc caactctcac 2280
tacatcctga gaagcggcct gctgaagtat aatctgagcg acggcgagaa ccctaaggtg 2340
gtgtttatcg agatctccga tcagaggctg tctatcggct ctcccagcaa gatctacgac 2400
tccctgggcc agcccgtgtt ctaccaggcc tccttttctt gggacacaat gatcaagttc 2460
ggcgatgtgc tgaccgtgaa tccactggtg gtgaactgga gaaacaatac cgtgatcagc 2520
aggccaggac agtcccagtg tcctcgcttt aacacatgcc cagagatctg ttgggagggc 2580
gtgtacaatg acgccttcct gatcgatcgg atcaactgga tctccgccgg cgtgtttctg 2640
gactctaatc agaccgccga gaaccccgtg ttcacagtgt ttaaggataa tgagatcctg 2700
tacagggcac agctggcaag cgaggacacc aacgcccaga agaccatcac aaattgcttc 2760
ctgctgaaga acaagatctg gtgtatctcc ctggtggaga tctatgacac cggcgataac 2820
gtgatccggc caaagctgtt tgccgtgaag atccccgagc agtgcacagg cggcctggtg 2880
cctagaggct ctcaccacca ccatcaccac agcgcctggt cccacccccca gttcgagaag 2940 tgataggatc c 2951

<210> SEQ ID NO 66
<211> LENGTH: 2933
<212> TYPE: DNA
<213> ORGANISM: Artificial Sequence
<220> FEATURE:
<223> OTHER INFORMATION: recombinant nipah virus F sequence

<400> SEQUENCE: 66
tctagagcca ccatgtactc tatgcagctg gccagctgcg tgaccctgac actggtgctg 60
ctggtgaact ctcagggcat cctgcactac gagaagctga gcaagatcgg cctggtgaag 120
ggcgtgacca gaaagtataa gatcaagtcc aacccactga caaaggacat cgtgatcaag 180
atgatcccca acgtgagcaa tatgtctcag tgtaccggct ctgtgatgga gaactacaag 240
acccgcctga atggcatcct gacaccaatc aagggcgccc tggagatcta taagaacaat 300
acacacgact gcgtgggcga tgtgcggctg gcaggcgtgt gcatggcagg agtggcaatc 360
ggaatcgcaa ccgcagcaca gatcacagca ggagtggccc tgtatgaggc catgaagaac 420
gccgacaaca tcaataagct gaagagctcc atcgagagca ccaatgaggc cgtggtgaag 480
ctgcaggaga cagccgagaa gacagtgtac gtgttcacag ccctgcagga ctatatcaac 540
accaatctgg tgcccacaat cgataagatc ccctgcaagc agaccgagct gtccctggac 600
ctggccctgt ctaagtacct gagcgatctg ctgttcgtgt ttggcccaaa cctgcaggac 660
cccgtgtcca attctatgac aatccaggcc atctcccagg ccttcggcgg caattacgag 720
acactgctga gaacactggg ctatgccacc gaggactttg acgatctgct ggagagcgat 780
tccatcacag gccagatcat ctatgtggat ctgtctagct actatatcat cgtgagggtg 840
tacttcccta tcctgaccga gatccagcag gcctatatcc aggagctgct gccagtgagc 900
ttcaacaatg acaattccga gtggatctct atcgtgccca actttatcct ggtgcggaac 960
accctgatca gcaatatcga gatcggcttt tgcctgatca caaagagatc cgtgatctgt 1020
aatcaggact acgccacccc catgacaaac aatatgaggg agtgcctgac cggctccaca 1080
gagaagtgtc cccgggagct ggtggtgtcc tctcacgtgc ctagattcgc cctgtccaac 1140
ggcgtgctgt ttgccaattg catctctgtg acctgccagt gtcagaccac aggaagggca 1200
atctctcaga gcggagagca gaccctgctg atgatcgata acaccacatg tcctacagcc 1260
gtgctgggca atgtgatcat cagcctgggc aagtacctgg gctccgtgaa ctataattct 1320
gagggaatcg caatcggacc acccgtgttc accgacaagg tggatatcag ctcccagatc 1380
tctagcatga accagagcct gcagcagtcc aaggactaca tcaaggaggc ccagcggctg 1440
ctggataccg tgaatccttc tctgggatct ggttacatcc cagaggctcc gcgggatgga 1500
caggcctacg tgagaaagga cggcgagtgg gtgctgctga gcaccttcct gggaagcggt 1560
ggaggaggcg gaggcgtgag caatctggtg ggcctgccca acaatatctg tctgcagaag 1620
acctccaacc agatcctgaa gcccaagctg atctcctata cactgcctgt ggtgggccag 1680
tctggcacct gcatcacaga ccctctgctg gccatggatg agggctactt cgcctattct 1740
cacctggaga ggatcggctc ctgttctcgc ggcgtgagca agcagcggat catcggagtg 1800
ggagaggtgc tggacagggg cgatgaggtg ccttccctgt tcatgaccaa cgtgtggaca 1860
ccacccaatc caaacaccgt gtaccactgc tctgccgtgt ataacaatga gttttactac 1920
gtgctgtgcg ccgtgagcac cgtgggcgat cctatcctga actccacata ctggagcggc 1980
tccctgatga tgaccagact ggccgtgaag ccaaagtcca atggcggcgg ctataaccag 2040
caccagctgg ccctgagatc tatcgagaag ggcaggtacg ataaagtgat gccttatggc 2100
ccatctggca tcaagcaggg cgacacactg tacttccccg ccgtgggctt tctggtgagg 2160
accgagttca agtacaatga ctccaactgc cctatcacaa agtgtcagta ttctaagcca 2220
gagaattgcc gcctgagcat gggcatccgg cccaactctc actacatcct gagaagcggc 2280
ctgctgaagt ataatctgag cgacggcgag aaccctaagg tggtgtttat cgagatctcc 2340
gatcagaggc tgtctatcgg ctctcccagc aagatctacg actccctggg ccagcccgtg 2400
ttctaccagg cctccttttc ttgggacaca atgatcaagt tcggcgatgt gctgaccgtg 2460
aatccactgg tggtgaactg gagaaacaat accgtgatca gcaggccagg acagtcccag 2520
tgtcctcgct ttaacacatg cccagagatc tgttgggagg gcgtgtacaa tgacgccttc 2580
ctgatcgatc ggatcaactg gatctccgcc ggcgtgtttc tggactctaa tcagaccgcc 2640
gagaaccccg tgttcacagt gtttaaggat aatgagatcc tgtacagggc acagctggca 2700
agcgaggaca ccaacgccca gaagaccatc acaaattgct tcctgctgaa gaacaagatc 2760
tggtgtatct ccctggtgga gatctatgac accggcgata acgtgatccg gccaaagctg 2820
tttgccgtga agatccccga gcagtgcaca ggcggcctgg tgcctagagg ctctcaccac 2880
caccatcacc acagcgcctg gtcccacccc cagttcgaga agtgatagga tcc 2933

<210> SEQ ID NO 67
<211> LENGTH: 2831
<212> TYPE: DNA
<213> ORGANISM: Artificial sequence
<220> FEATURE:
<223> OTHER INFORMATION: recombinant nipah virus F sequence

<400> SEQUENCE: 67
tctagagcca ccatgtactc tatgcagctg gccagctgcg tgaccctgac actggtgctg 60
ctggtgaact ctcaggaggg cgtgagcaat ctggtgggcc tgcccaacaa tatctgtctg 120
cagaagacct ccaaccagat cctgaagccc aagctgatct cctatacact gcctgtggtg 180
ggccagtctg gcacctgcat cacagaccct ctgctggcca tggatgaggg ctacttcgcc 240
tattctcacc tggagaggat cggctcctgt tctcgcggcg tgagcaagca gcggatcatc 300

-continued

```
ggagtgggag aggtgctgga caggggcgat gaggtgcctt ccctgttcat gaccaacgtg    360
tggacaccac ccaatccaaa caccgtgtac cactgctctg ccgtgtataa caatgagttt    420
tactacgtgc tgtgcgccgt gagcaccgtg ggcgatccta tcctgaactc cacatactgg    480
agcggctccc tgatgatgac cagactggcc gtgaagccaa agtccaatgg cggcggctat    540
aaccagcacc agctggccct gagatctatc gagaagggca ggtacgataa agtgatgcct    600
tatggcccat ctggcatcaa gcagggcgac acactgtact tccccgccgt gggctttctg    660
gtgaggaccg agttcaagta caatgactcc aactgcccta tcacaaagtg tcagtattct    720
aagccagaga attgccgcct gagcatgggc atccggccca actctcacta catcctgaga    780
agcggcctgc tgaagtataa tctgagcgac ggcgagaacc ctaaggtggt gtttatcgag    840
atctccgatc agaggctgtc tatcggctct cccagcaaga tctacgactc cctgggccag    900
cccgtgttct accaggcctc cttttcttgg gacacaatga tcaagttcgg cgatgtgctg    960
accgtgaatc cactggtggt gaactggaga aacaataccg tgatcagcag gccaggacag   1020
tcccagtgtc ctcgctttaa cacatgccca gagatctgtt gggagggcgt gtacaatgac   1080
gccttcctga tcgatcggat caactggatc tccgccggcg tgtttctgga ctctaatcag   1140
accgccgaga accccgtgtt cacagtgttt aaggataatg agatcctgta cagggcacag   1200
ctggcaagcg aggacaccaa cgcccagaag accatcacaa attgcttcct gctgaagaac   1260
aagatctggt gtatctccct ggtggagatc tatgacaccg gcgataacgt gatccggcca   1320
aagctgtttg ccgtgaagat ccccgagcag tgcacaggcg gcggatctgg ttacatccca   1380
gaggctccgc gggatggaca ggcctacgtg agaaaggacg gcgagtgggt gctgctgagc   1440
accttcctgg gaagcggtgg aggaggcgga ggcgtgagca atctggtggg cctgcccaac   1500
aatatctgtc tgcagaagac ctccaaccag atcctgaagc ccaagctgat ctcctataca   1560
ctgcctgtgg tgggccagtc tggcacctgc atcacagacc ctctgctggc catggatgag   1620
ggctacttcg cctattctca cctggagagg atcggctcct gttctcgcgg cgtgagcaag   1680
cagcggatca tcggagtggg agaggtgctg gacaggggcg atgaggtgcc ttccctgttc   1740
atgaccaacg tgtggacacc acccaatcca aacaccgtgt accactgctc tgccgtgtat   1800
aacaatgagt tttactacgt gctgtgcgcc gtgagcaccg tgggcgatcc tatcctgaac   1860
tccacatact ggagcggctc cctgatgatg accagactgg ccgtgaagcc aaagtccaat   1920
ggcggcggct ataaccagca ccagctggcc ctgagatcta tcgagaaggg caggtacgat   1980
aaagtgatgc cttatggccc atctggcatc aagcagggcg acacactgta cttccccgcc   2040
gtgggctttc tggtgaggac cgagttcaag tacaatgact ccaactgccc tatcacaaag   2100
tgtcagtatt ctaagccaga gaattgccgc ctgagcatgg gcatccggcc caactctcac   2160
tacatcctga gaagcggcct gctgaagtat aatctgagcg acggcgagaa ccctaaggtg   2220
gtgtttatcg agatctccga tcagaggctg tctatcggct ctcccagcaa gatctacgac   2280
tccctgggcc agcccgtgtt ctaccaggcc tccttttctt gggacacaat gatcaagttc   2340
ggcgatgtgc tgaccgtgaa tccactggtg gtgaactgga gaaacaatac cgtgatcagc   2400
aggccaggac agtcccagtg tcctcgcttt aacacatgcc cagagatctg ttgggagggc   2460
gtgtacaatg acgccttcct gatcgatcgg atcaactgga tctccgccgg cgtgtttctg   2520
gactctaatc agaccgccga gaaccccgtg ttcacagtgt ttaaggataa tgagatcctg   2580
tacagggcac agctggcaag cgaggacacc aacgcccaga agaccatcac aaattgcttc   2640
```

-continued

```
ctgctgaaga acaagatctg gtgtatctcc ctggtggaga tctatgacac cggcgataac   2700

gtgatccggc caaagctgtt tgccgtgaag atccccgagc agtgcacagg cggcctggtg   2760

cctagaggct ctcaccacca ccatcaccac agcgcctggt cccacccccca gttcgagaag   2820

tgataggatc c                                                         2831
```

<210> SEQ ID NO 68
<211> LENGTH: 436
<212> TYPE: PRT
<213> ORGANISM: Hendra virus

<400> SEQUENCE: 68

```
Arg Glu Tyr Arg Pro Ile Ser Gln Gly Val Ser Asp Leu Val Gly Leu
1               5                   10                  15

Pro Asn Gln Ile Cys Leu Gln Lys Thr Thr Ser Thr Ile Leu Lys Pro
            20                  25                  30

Arg Leu Ile Ser Tyr Thr Leu Pro Ile Asn Thr Arg Glu Gly Val Cys
        35                  40                  45

Ile Thr Asp Pro Leu Leu Ala Val Asp Asn Gly Phe Phe Ala Tyr Ser
    50                  55                  60

His Leu Glu Lys Ile Gly Ser Cys Thr Arg Gly Ile Ala Lys Gln Arg
65                  70                  75                  80

Ile Ile Gly Val Gly Glu Val Leu Asp Arg Gly Asp Lys Val Pro Ser
                85                  90                  95

Met Phe Met Thr Asn Val Trp Thr Pro Pro Asn Pro Ser Thr Ile His
            100                 105                 110

His Cys Ser Ser Thr Tyr His Glu Asp Phe Tyr Tyr Thr Leu Cys Ala
        115                 120                 125

Val Ser His Val Gly Asp Pro Ile Leu Asn Ser Thr Ser Trp Thr Glu
    130                 135                 140

Ser Leu Ser Leu Ile Arg Leu Ala Val Arg Pro Lys Ser Asp Ser Gly
145                 150                 155                 160

Asp Tyr Asn Gln Lys Tyr Ile Ala Ile Thr Lys Val Glu Arg Gly Lys
                165                 170                 175

Tyr Asp Lys Val Met Pro Tyr Gly Pro Ser Gly Ile Lys Gln Gly Asp
            180                 185                 190

Thr Leu Tyr Phe Pro Ala Val Gly Phe Leu Pro Arg Thr Glu Phe Gln
        195                 200                 205

Tyr Asn Asp Ser Asn Cys Pro Ile Ile His Cys Lys Tyr Ser Lys Ala
    210                 215                 220

Glu Asn Cys Arg Leu Ser Met Gly Val Asn Ser Lys Ser His Tyr Ile
225                 230                 235                 240

Leu Arg Ser Gly Leu Leu Lys Tyr Asn Leu Ser Leu Gly Gly Asp Ile
                245                 250                 255

Thr Leu Gln Phe Ile Glu Ile Ala Asp Asn Arg Leu Thr Ile Gly Ser
            260                 265                 270

Pro Ser Lys Ile Tyr Asn Ser Leu Gly Gln Pro Val Phe Tyr Gln Ala
        275                 280                 285

Ser Tyr Ser Trp Asp Thr Met Ile Lys Leu Gly Asp Val Asp Thr Val
    290                 295                 300

Asp Pro Leu Arg Val Gln Trp Arg Asn Asn Ser Val Ile Ser Arg Pro
305                 310                 315                 320

Gly Gln Ser Gln Cys Pro Arg Phe Asn Val Cys Pro Glu Val Cys Trp
                325                 330                 335
```

```
Glu Gly Thr Tyr Asn Asp Ala Phe Leu Ile Asp Arg Leu Asn Trp Val
            340                 345                 350

Ser Ala Gly Val Tyr Leu Asn Ser Asn Gln Thr Ala Glu Asn Pro Val
        355                 360                 365

Phe Ala Val Phe Lys Asp Asn Glu Ile Leu Tyr Gln Val Pro Leu Ala
    370                 375                 380

Glu Asp Asp Thr Asn Ala Gln Lys Thr Ile Thr Asp Cys Phe Leu Leu
385                 390                 395                 400

Glu Asn Val Ile Trp Cys Ile Ser Leu Val Glu Ile Tyr Asp Thr Gly
                405                 410                 415

Asp Ser Val Ile Arg Pro Lys Leu Phe Ala Val Lys Ile Pro Ala Gln
            420                 425                 430

Cys Ser Glu Ser
        435
```

<210> SEQ ID NO 69
<211> LENGTH: 1007
<212> TYPE: PRT
<213> ORGANISM: Artificial Sequence
<220> FEATURE:
<223> OTHER INFORMATION: Recombinant Nipah virus F sequence

<400> SEQUENCE: 69

```
Met Tyr Ser Met Gln Leu Ala Ser Cys Val Thr Leu Thr Leu Val Leu
1               5                   10                  15

Leu Val Asn Ser Gln Gly Ile Leu His Tyr Glu Lys Leu Ser Lys Ile
            20                  25                  30

Gly Leu Val Lys Gly Val Thr Arg Lys Tyr Lys Ile Lys Ser Asn Pro
        35                  40                  45

Leu Thr Lys Asp Ile Val Ile Lys Met Ile Pro Asn Val Ser Asn Met
    50                  55                  60

Ser Gln Cys Thr Gly Ser Val Met Glu Asn Tyr Lys Thr Arg Leu Asn
65                  70                  75                  80

Gly Ile Leu Thr Pro Ile Lys Gly Ala Leu Glu Ile Tyr Lys Asn Asn
                85                  90                  95

Thr His Asp Cys Val Gly Asp Val Arg Leu Ala Gly Val Cys Met Ala
            100                 105                 110

Gly Val Ala Ile Gly Ile Ala Thr Ala Ala Gln Ile Thr Ala Gly Val
        115                 120                 125

Ala Leu Tyr Glu Ala Met Lys Asn Ala Asp Asn Ile Asn Lys Leu Lys
    130                 135                 140

Ser Ser Ile Glu Ser Thr Asn Glu Ala Val Val Lys Leu Gln Glu Thr
145                 150                 155                 160

Ala Glu Lys Thr Val Tyr Val Phe Thr Ala Leu Gln Asp Tyr Ile Asn
                165                 170                 175

Thr Asn Leu Val Pro Thr Ile Asp Lys Ile Pro Cys Lys Gln Thr Glu
            180                 185                 190

Leu Ser Leu Asp Leu Ala Leu Ser Lys Tyr Leu Ser Asp Leu Leu Phe
        195                 200                 205

Val Phe Gly Pro Asn Leu Gln Asp Pro Val Ser Asn Ser Met Thr Ile
    210                 215                 220

Gln Ala Ile Ser Gln Ala Phe Gly Gly Asn Tyr Glu Thr Leu Leu Arg
225                 230                 235                 240

Thr Leu Gly Tyr Ala Thr Glu Asp Phe Asp Asp Leu Leu Glu Ser Asp
                245                 250                 255
```

-continued

```
Ser Ile Thr Gly Gln Ile Ile Tyr Val Asp Leu Ser Ser Tyr Tyr Ile
            260                 265                 270

Ile Val Arg Val Tyr Phe Pro Ile Leu Thr Glu Ile Gln Gln Ala Tyr
        275                 280                 285

Ile Gln Glu Leu Leu Pro Val Ser Phe Asn Asn Asp Asn Ser Glu Trp
    290                 295                 300

Ile Ser Ile Val Pro Asn Phe Ile Leu Val Arg Asn Thr Leu Ile Ser
305                 310                 315                 320

Asn Ile Glu Ile Gly Phe Cys Leu Ile Thr Lys Arg Ser Val Ile Cys
                325                 330                 335

Asn Gln Asp Tyr Ala Thr Pro Met Thr Asn Asn Met Arg Glu Cys Leu
            340                 345                 350

Thr Gly Ser Thr Glu Lys Cys Pro Arg Glu Leu Val Val Ser Ser His
        355                 360                 365

Val Pro Arg Phe Ala Leu Ser Asn Gly Val Leu Phe Ala Asn Cys Ile
    370                 375                 380

Ser Val Thr Cys Gln Cys Gln Thr Thr Gly Arg Ala Ile Ser Gln Ser
385                 390                 395                 400

Gly Glu Gln Thr Leu Leu Met Ile Asp Asn Thr Thr Cys Pro Thr Ala
                405                 410                 415

Val Leu Gly Asn Val Ile Ile Ser Leu Gly Lys Tyr Leu Gly Ser Val
            420                 425                 430

Asn Tyr Asn Ser Glu Gly Ile Ala Ile Gly Pro Pro Val Phe Thr Asp
        435                 440                 445

Lys Val Asp Ile Ser Ser Gln Ile Ser Ser Met Asn Gln Ser Leu Gln
    450                 455                 460

Gln Ser Lys Asp Tyr Ile Lys Glu Ala Gln Arg Leu Leu Asp Thr Val
465                 470                 475                 480

Asn Pro Ser Leu Lys Leu Met Lys Gln Ile Glu Asp Lys Ile Glu Glu
                485                 490                 495

Ile Leu Ser Lys Ile Tyr His Ile Glu Asn Glu Ile Ala Arg Ile Lys
            500                 505                 510

Lys Leu Ile Gly Glu Ala Pro Gly Ser Gly Tyr Ile Pro Glu Ala Pro
        515                 520                 525

Arg Asp Gly Gln Ala Tyr Val Arg Lys Asp Gly Glu Trp Val Leu Leu
    530                 535                 540

Ser Thr Phe Leu Gly Ser Gly Gly Gly Gly Gly Gly Val Ser Asp Leu
545                 550                 555                 560

Val Gly Leu Pro Asn Gln Ile Cys Leu Gln Lys Thr Thr Ser Thr Ile
                565                 570                 575

Leu Lys Pro Arg Leu Ile Ser Tyr Thr Leu Pro Ile Asn Thr Arg Glu
            580                 585                 590

Gly Val Cys Ile Thr Asp Pro Leu Leu Ala Val Asp Asn Gly Phe Phe
        595                 600                 605

Ala Tyr Ser His Leu Glu Lys Ile Gly Ser Cys Thr Arg Gly Ile Ala
    610                 615                 620

Lys Gln Arg Ile Ile Gly Val Gly Glu Val Leu Asp Arg Gly Asp Lys
625                 630                 635                 640

Val Pro Ser Met Phe Met Thr Asn Val Trp Thr Pro Pro Asn Pro Ser
                645                 650                 655

Thr Ile His His Cys Ser Ser Thr Tyr His Glu Asp Phe Tyr Tyr Thr
            660                 665                 670

Leu Cys Ala Val Ser His Val Gly Asp Pro Ile Leu Asn Ser Thr Ser
```

-continued

```
        675                 680                 685

Trp Thr Glu Ser Leu Ser Leu Ile Arg Leu Ala Val Arg Pro Lys Ser
    690                 695                 700

Asp Ser Gly Asp Tyr Asn Gln Lys Tyr Ile Ala Ile Thr Lys Val Glu
705                 710                 715                 720

Arg Gly Lys Tyr Asp Lys Val Met Pro Tyr Gly Pro Ser Gly Ile Lys
                725                 730                 735

Gln Gly Asp Thr Leu Tyr Phe Pro Ala Val Gly Phe Leu Pro Arg Thr
            740                 745                 750

Glu Phe Gln Tyr Asn Asp Ser Asn Cys Pro Ile Ile His Cys Lys Tyr
        755                 760                 765

Ser Lys Ala Glu Asn Cys Arg Leu Ser Met Gly Val Asn Ser Lys Ser
    770                 775                 780

His Tyr Ile Leu Arg Ser Gly Leu Leu Lys Tyr Asn Leu Ser Leu Gly
785                 790                 795                 800

Gly Asp Ile Thr Leu Gln Phe Ile Glu Ile Ala Asp Asn Arg Leu Thr
                805                 810                 815

Ile Gly Ser Pro Ser Lys Ile Tyr Asn Ser Leu Gly Gln Pro Val Phe
            820                 825                 830

Tyr Gln Ala Ser Tyr Ser Trp Asp Thr Met Ile Lys Leu Gly Asp Val
        835                 840                 845

Asp Thr Val Asp Pro Leu Arg Val Gln Trp Arg Asn Asn Ser Val Ile
    850                 855                 860

Ser Arg Pro Gly Gln Ser Gln Cys Pro Arg Phe Asn Val Cys Pro Glu
865                 870                 875                 880

Val Cys Trp Glu Gly Thr Tyr Asn Asp Ala Phe Leu Ile Asp Arg Leu
                885                 890                 895

Asn Trp Val Ser Ala Gly Val Tyr Leu Asn Ser Asn Gln Thr Ala Glu
            900                 905                 910

Asn Pro Val Phe Ala Val Phe Lys Asp Asn Glu Ile Leu Tyr Gln Val
        915                 920                 925

Pro Leu Ala Glu Asp Asp Thr Asn Ala Gln Lys Thr Ile Thr Asp Cys
    930                 935                 940

Phe Leu Leu Glu Asn Val Ile Trp Cys Ile Ser Leu Val Glu Ile Tyr
945                 950                 955                 960

Asp Thr Gly Asp Ser Val Ile Arg Pro Lys Leu Phe Ala Val Lys Ile
                965                 970                 975

Pro Ala Gln Cys Ser Glu Ser Gly Gly Leu Val Pro Arg Gly Ser His
            980                 985                 990

His His His His His Ser Ala Trp  Ser His Pro Gln Phe  Glu Lys
        995                 1000                1005


<210> SEQ ID NO 70
<211> LENGTH: 1007
<212> TYPE: PRT
<213> ORGANISM: Artificial Sequence
<220> FEATURE:
<223> OTHER INFORMATION: Recombinant Nipah virus F sequence

<400> SEQUENCE: 70

Met Tyr Ser Met Gln Leu Ala Ser Cys Val Thr Leu Thr Leu Val Leu
1               5                   10                  15

Leu Val Asn Ser Gln Arg Pro Gln Thr Glu Gly Val Ser Asn Leu Val
            20                  25                  30

Gly Leu Pro Asn Asn Ile Cys Leu Gln Lys Thr Ser Asn Gln Ile Leu
```

-continued

```
        35                  40                  45

Lys Pro Lys Leu Ile Ser Tyr Thr Leu Pro Val Val Gly Gln Ser Gly
    50                  55                  60

Thr Cys Ile Thr Asp Pro Leu Leu Ala Met Asp Glu Gly Tyr Phe Ala
65                  70                  75                  80

Tyr Ser His Leu Glu Arg Ile Gly Ser Cys Ser Arg Gly Val Ser Lys
                85                  90                  95

Gln Arg Ile Ile Gly Val Gly Glu Val Leu Asp Arg Gly Asp Glu Val
            100                 105                 110

Pro Ser Leu Phe Met Thr Asn Val Trp Thr Pro Pro Asn Pro Asn Thr
        115                 120                 125

Val Tyr His Cys Ser Ala Val Tyr Asn Asn Glu Phe Tyr Tyr Val Leu
    130                 135                 140

Cys Ala Val Ser Thr Val Gly Asp Pro Ile Leu Asn Ser Thr Tyr Trp
145                 150                 155                 160

Ser Gly Ser Leu Met Met Thr Arg Leu Ala Val Lys Pro Lys Ser Asn
                165                 170                 175

Gly Gly Gly Tyr Asn Gln His Gln Leu Ala Leu Arg Ser Ile Glu Lys
            180                 185                 190

Gly Arg Tyr Asp Lys Val Met Pro Tyr Gly Pro Ser Gly Ile Lys Gln
        195                 200                 205

Gly Asp Thr Leu Tyr Phe Pro Ala Val Gly Phe Leu Val Arg Thr Glu
    210                 215                 220

Phe Lys Tyr Asn Asp Ser Asn Cys Pro Ile Thr Lys Cys Gln Tyr Ser
225                 230                 235                 240

Lys Pro Glu Asn Cys Arg Leu Ser Met Gly Ile Arg Pro Asn Ser His
                245                 250                 255

Tyr Ile Leu Arg Ser Gly Leu Leu Lys Tyr Asn Leu Ser Asp Gly Glu
            260                 265                 270

Asn Pro Lys Val Val Phe Ile Glu Ile Ser Asp Gln Arg Leu Ser Ile
        275                 280                 285

Gly Ser Pro Ser Lys Ile Tyr Asp Ser Leu Gly Gln Pro Val Phe Tyr
    290                 295                 300

Gln Ala Ser Phe Ser Trp Asp Thr Met Ile Lys Phe Gly Asp Val Leu
305                 310                 315                 320

Thr Val Asn Pro Leu Val Val Asn Trp Arg Asn Asn Thr Val Ile Ser
                325                 330                 335

Arg Pro Gly Gln Ser Gln Cys Pro Arg Phe Asn Thr Cys Pro Glu Ile
            340                 345                 350

Cys Trp Glu Gly Val Tyr Asn Asp Ala Phe Leu Ile Asp Arg Ile Asn
        355                 360                 365

Trp Ile Ser Ala Gly Val Phe Leu Asp Ser Asn Gln Thr Ala Glu Asn
    370                 375                 380

Pro Val Phe Thr Val Phe Lys Asp Asn Glu Ile Leu Tyr Arg Ala Gln
385                 390                 395                 400

Leu Ala Ser Glu Asp Thr Asn Ala Gln Lys Thr Ile Thr Asn Cys Phe
                405                 410                 415

Leu Leu Lys Asn Lys Ile Trp Cys Ile Ser Leu Val Glu Ile Tyr Asp
            420                 425                 430

Thr Gly Asp Asn Val Ile Arg Pro Lys Leu Phe Ala Val Lys Ile Pro
        435                 440                 445

Glu Gln Cys Thr Gly Gly Gly Gln Gly Ile Leu His Tyr Glu Lys Leu
    450                 455                 460
```

```
Ser Lys Ile Gly Leu Val Lys Gly Val Thr Arg Lys Tyr Lys Ile Lys
465                 470                 475                 480

Ser Asn Pro Leu Thr Lys Asp Ile Val Ile Lys Met Ile Pro Asn Val
                485                 490                 495

Ser Asn Met Ser Gln Cys Thr Gly Ser Val Met Glu Asn Tyr Lys Thr
            500                 505                 510

Arg Leu Asn Gly Ile Leu Thr Pro Ile Lys Gly Ala Leu Glu Ile Tyr
        515                 520                 525

Lys Asn Asn Thr His Asp Cys Val Gly Asp Val Arg Leu Ala Gly Val
    530                 535                 540

Cys Met Ala Gly Val Ala Ile Gly Ile Ala Thr Ala Ala Gln Ile Thr
545                 550                 555                 560

Ala Gly Val Ala Leu Tyr Glu Ala Met Lys Asn Ala Asp Asn Ile Asn
                565                 570                 575

Lys Leu Lys Ser Ser Ile Glu Ser Thr Asn Glu Ala Val Val Lys Leu
            580                 585                 590

Gln Glu Thr Ala Glu Lys Thr Val Tyr Val Phe Thr Ala Leu Gln Asp
        595                 600                 605

Tyr Ile Asn Thr Asn Leu Val Pro Thr Ile Asp Lys Ile Pro Cys Lys
    610                 615                 620

Gln Thr Glu Leu Ser Leu Asp Leu Ala Leu Ser Lys Tyr Leu Ser Asp
625                 630                 635                 640

Leu Leu Phe Val Phe Gly Pro Asn Leu Gln Asp Pro Val Ser Asn Ser
                645                 650                 655

Met Thr Ile Gln Ala Ile Ser Gln Ala Phe Gly Gly Asn Tyr Glu Thr
            660                 665                 670

Leu Leu Arg Thr Leu Gly Tyr Ala Thr Glu Asp Phe Asp Asp Leu Leu
        675                 680                 685

Glu Ser Asp Ser Ile Thr Gly Gln Ile Ile Tyr Val Asp Leu Ser Ser
    690                 695                 700

Tyr Tyr Ile Ile Val Arg Val Tyr Phe Pro Ile Leu Thr Glu Ile Gln
705                 710                 715                 720

Gln Ala Tyr Ile Gln Glu Leu Leu Pro Val Ser Phe Asn Asn Asp Asn
                725                 730                 735

Ser Glu Trp Ile Ser Ile Val Pro Asn Phe Ile Leu Val Arg Asn Thr
            740                 745                 750

Leu Ile Ser Asn Ile Glu Ile Gly Phe Cys Leu Ile Thr Lys Arg Ser
        755                 760                 765

Val Ile Cys Asn Gln Asp Tyr Ala Thr Pro Met Thr Asn Asn Met Arg
    770                 775                 780

Glu Cys Leu Thr Gly Ser Thr Glu Lys Cys Pro Arg Glu Leu Val Val
785                 790                 795                 800

Ser Ser His Val Pro Arg Phe Ala Leu Ser Asn Gly Val Leu Phe Ala
                805                 810                 815

Asn Cys Ile Ser Val Thr Cys Gln Cys Gln Thr Thr Gly Arg Ala Ile
            820                 825                 830

Ser Gln Ser Gly Glu Gln Thr Leu Leu Met Ile Asp Asn Thr Thr Cys
        835                 840                 845

Pro Thr Ala Val Leu Gly Asn Val Ile Ile Ser Leu Gly Lys Tyr Leu
    850                 855                 860

Gly Ser Val Asn Tyr Asn Ser Glu Gly Ile Ala Ile Gly Pro Pro Val
865                 870                 875                 880
```

-continued

```
Phe Thr Asp Lys Val Asp Ile Ser Ser Gln Ile Ser Ser Met Asn Gln
                885                 890                 895

Ser Leu Gln Gln Ser Lys Asp Tyr Ile Lys Glu Ala Gln Arg Leu Leu
            900                 905                 910

Asp Thr Val Asn Pro Ser Leu Lys Leu Met Lys Gln Ile Glu Asp Lys
        915                 920                 925

Ile Glu Glu Ile Leu Ser Lys Ile Tyr His Ile Glu Asn Glu Ile Ala
    930                 935                 940

Arg Ile Lys Lys Leu Ile Gly Glu Ala Pro Gly Ser Gly Tyr Ile Pro
945                 950                 955                 960

Glu Ala Pro Arg Asp Gly Gln Ala Tyr Val Arg Lys Asp Gly Glu Trp
                965                 970                 975

Val Leu Leu Ser Thr Phe Leu Gly Ser Leu Val Pro Arg Gly Ser His
            980                 985                 990

His His His His His Ser Ala Trp  Ser His Pro Gln Phe  Glu Lys
        995                 1000                1005
```

NIPAH VIRUS IMMUNOGENS AND THEIR USE

CROSS REFERENCE TO RELATED APPLICATIONS

This is the U.S. National Stage of International Application No. PCT/US2019/045110, filed Aug. 5, 2019, which was published in English under PCT Article 21(2), which in turn claims priority to U.S. Provisional Application No. 62/714,230, filed Aug. 3, 2018. The provisional application is incorporated herein by reference in its entirety.

FIELD

This disclosure relates to polypeptides, polynucleotides, compositions, and methods of their use, for elicitation and detection of an immune response to Nipah virus (NiV).

BACKGROUND

NiV is an enveloped non-segmented negative-strand RNA virus of the family Paramyxoviridae. The natural NiV host are fruit bats of the Pteropodidae Family NiV infection in humans has a range of clinical presentations, from asymptomatic infection to acute respiratory syndrome and fatal encephalitis. About a quarter of the human patients have seizures and about 60% become comatose and might need mechanical ventilation. NiV is also capable of causing disease in pigs and other domestic animals.

The NiV viral envelop contains several membrane proteins, including an envelope protein, F, and an attachment protein, G. The NiV G protein is a Type II membrane protein that facilitates attachment of NiV to host cell membranes. The NiV F protein is a Type I membrane protein that binds to a host cell receptor and facilitates fusion of host and viral membranes. NiV F is a class I fusion protein initially expressed as a single polypeptide precursor, designated $F_0$. $F_0$ trimerizes in the endoplasmic reticulum and is processed by a cellular protease at a conserved site generating, $F_1$ and $F_2$ polypeptides. The $F_2$ polypeptide originates from the N-terminal portion of the $F_0$ precursor and links to the $F_1$ polypeptide via disulfide bonds. The $F_1$ polypeptide anchors the mature F protein in the membrane via a transmembrane domain, which is linked to a cytoplasmic tail. Three protomers of the $F_2$-$F_1$ heterodimer assemble to form a mature F protein, which adopts a metastable "prefusion" conformation that is triggered to undergo a conformational change that fuses the viral and target-cell membranes.

Although NiV is known to contribute to human illness and disease burden, a vaccine for this virus is not available.

SUMMARY

Disclosed herein are recombinant NiV F ectodomain trimers comprising protomers comprising one or more modifications (such as amino acid substitutions) that stabilize the F ectodomain trimer in its prefusion conformation. Embodiments of such prefusion-stabilized NiV F ectodomain trimers are demonstrated to produce a superior immune response in animal models compared to corresponding NiV F ectodomain trimers that are not stabilized in the prefusion conformation.

In some embodiments, the recombinant NiV F ectodomain trimer comprises protomers comprising one or more amino acid substitutions that stabilize the NiV F ectodomain trimer in a prefusion conformation, wherein the one or more amino acid substitutions comprise one or more of the following: cysteine substitutions at NiV F positions 104 and 114 (such as L104C and I114C substitutions) that form a non-natural intra-protomer disulfide bond or cysteine substitutions at NiV F positions 114 and 426 (such as I114C and I426C substitutions) that form a non-natural intra-protomer disulfide bond, a proline substitution at NiV F position 191 (such as a S191P substitution), a phenylalanine substitution at NiV F position 172 (such as a L172F substitution), a glycine substitution at NiV F position 70 (such as a Q70G substitution), and a deletion of NiV F positions 102-113 with positions 101 and 114 linked by a glycine-serine linker (such as a (HDLVGDVRLAGV)102-113(GSG) substitution). In a non-limiting embodiment, the one or more amino acid substitutions comprising the cysteine substitutions at NiV F positions 104 and 114 that form a non-natural intra-protomer disulfide bond, the proline substitution at NiV F position 191, and the phenylalanine substitution at NiV F position 172.

In some embodiments, a C-terminal residue of the protomers of the recombinant NiV F ectodomain trimer (such as a residue of the stem region of the trimer) is linked to a trimerization domain (such as GCN4 trimerization domain or a T4 fibritin trimerization domain) to promote trimerization of the ectodomain. In some embodiments, immunogen is soluble. In other embodiments, a C-terminal residue of the protomers of the recombinant NiV F ectodomain trimer (such as a residue of the stem region of the trimer) is linked to a transmembrane domain for membrane anchored forms of the NiV F ectodomain trimer.

In some embodiments, the recombinant NiV F ectodomain trimer is fused to one or more heterologous proteins. For example, in some embodiments, the protomers of the recombinant NiV F ectodomain trimer are fused to a NiV G ectodomain to provide a NiV F-G chimera. In some embodiments, the NiV F ectodomain trimer is linked to at least three NiV G ectodomains, wherein the NiV G ectodomains are fused, directly or indirectly via peptide linker, to an N-terminus of protomers of the recombinant NiV F ectodomain trimer and/or to a C-terminus of a trimerization domain fused to the C-terminus of protomers of the recombinant NiV F ectodomain trimer. In some embodiments, the trimerization domain comprises, for example, a GCN4 trimerization domain, a T4 fibritin trimerization domain, or a GCN4 trimerization domain and a T4 fibritin trimerization domain.

In some embodiments, the protomers of the recombinant NiV F ectodomain trimer further comprise one or more additional mutations, such as amino acid substitutions that stabilize the recombinant NiV F ectodomain trimer in the prefusion conformation, or amino acid substitutions to inhibit or prevent protease cleavage at a $F_1/F_2$ protease cleavage site of the F ectodomain.

In some embodiments, the recombinant NiV F ectodomain trimer can be included on a protein nanoparticle, such as a ferritin protein nanoparticle.

In some embodiments, an immunogen is provided that comprises a trimer of fusion proteins, each fusion protein comprising, in an N- to C-terminal direction: one or more NiV G ectodomains and a trimerization domain; a trimerization domain and one or more NiV G ectodomains; or one or more NiV G ectodomains, a trimerization domain, and one or more NiV G ectodomains.

In some embodiments, a protein nanoparticle, such as a ferritin nanoparticle, is provided that comprises a monomeric NiV G ectodomain.

Nucleic acid molecules encoding the disclosed proteins are also provided. For example, a nucleic acid molecule encoding a protomer of a disclosed recombinant NiV F ectodomain trimer stabilized in a prefusion conformation, a chimera of recombinant NiV F ectodomain trimer stabilized in a prefusion conformation and one or more G ectodomains, a multimer of NiV G ectodomains, or a self-assembling protein nanoparticle containing recombinant NiV F ectodomain trimer stabilized in a prefusion conformation or a NiV G ectodomains are also provided, as are vectors including the nucleic acid molecules, and methods of their production.

Immunogenic compositions including a disclosed immunogen that are suitable for administration to a subject are also provided, and may also be contained in a unit dosage form. The immunogen may also contain a carrier to facilitate presentation to the immune system.

Methods of inducing an immune response in a subject are disclosed, as are methods of treating, inhibiting or preventing a NiV infection in a subject, by administering to the subject an effective amount of a disclosed immunogen, nucleic acid molecule, or vector.

The foregoing and other features and advantages of this disclosure will become more apparent from the following detailed description of several embodiments which proceeds with reference to the accompanying figures.

BRIEF DESCRIPTION OF THE FIGURES

FIGS. 1A-1F show negative stain electron microscopy (EM) images and ribbon diagrams for the NiV05 (FIG. 1A), NiV08 (FIG. 1B), NiV09 (FIG. 1C), NiV14 (FIG. 1D), NiV15 (FIG. 1E), and NiV06 (FIG. 1F) NiV F ectodomain trimers.

FIG. 3B, Sera from immunized mice was assessed for binding to prefusion NiV F probe (NiVop08 ectodomain trimer) and postfusion NiV F probe (NiV06 ectodomain trimer) by Octet binding assay. FIG. 3C, Sera from mice immunized with the indicated immunogens was assessed for NiV neutralization.

FIGS. 5A-5C show negative stain EM images and ribbon diagrams for self-assembled ferritin nanoparticles containing the NiV G ectodomain linked to ferritin by a 5 amino acid peptide linker (FIG. 5A), a 15 amino acid peptide linker (FIG. 5B), or a 25 amino acid peptide linker (FIG. 5C).

FIG. 3B, Sera from immunized mice was assessed for binding to monovalent NiV G probe by Octet binding assay. FIG. 3C, Sera from mice immunized with the indicated immunogens was assessed for NiV neutralization.

FIG. 8E, Sera from mice immunized with the indicated immunogens was assessed for NiV neutralization.

FIGS. 9A-9D show an immunization protocol and schematic diagram (FIGS. 9A and 9B) and results (FIGS. 9C-9D) for an in vivo immunization assay of the NiV F, G, and F-G chimeric immunogens in a ferret model. The animals were immunized with the preF, postF, G hexamer, or preF/G chimera immunogen in 16 different groups. Sera collected from immunized animals at week six (FIG. 9C) and nine (FIG. 9D) assessed for NiV neutralization using the pseudovirus neutralization assay described above.

FIGS. 12A-12C show an immunization protocol (FIG. 12A) and results (FIGS. 12B and 12C) for an in vivo immunization assay of NiV Pre-F, Post-F, WT-F, G-hexamer, and G-tetramer (+stalk) immunogens in a mouse model, with several variations, including mRNA or protein-based immunization, signal sequence, and soluble or membrane-anchored immunogen.

FIGS. 12A-12C show an immunization protocol (FIG. 12A) and results (FIGS. 12B and 12C) for an in vivo immunization assay of NiV Pre-F, Post-F, WT-F, G-hexamer, and G-tetramer (+stalk) immunogens in a mouse model, with several variations, including mRNA or protein-based immunization, signal sequence, and soluble or membrane-anchored immunogen.

FIGS. 13A-13D show an immunization protocol and schematic diagram (FIGS. 13A and 13B) and results (FIGS. 13C-13D) for an in vivo immunization assay of NiV F, G, and F/G chimeric immunogens in a mouse model. The animals were immunized with the preF, postF, G-hexamer, or preF/G chimera immunogen in different groups using protein or mRNA based immunization systems (FIG. 13B). Sera collected from immunized animals at week six was assessed for preF-binding IgG (FIG. 13C) and G-binding IgG (FIG. 13D).

SEQUENCES

Figure 1C:
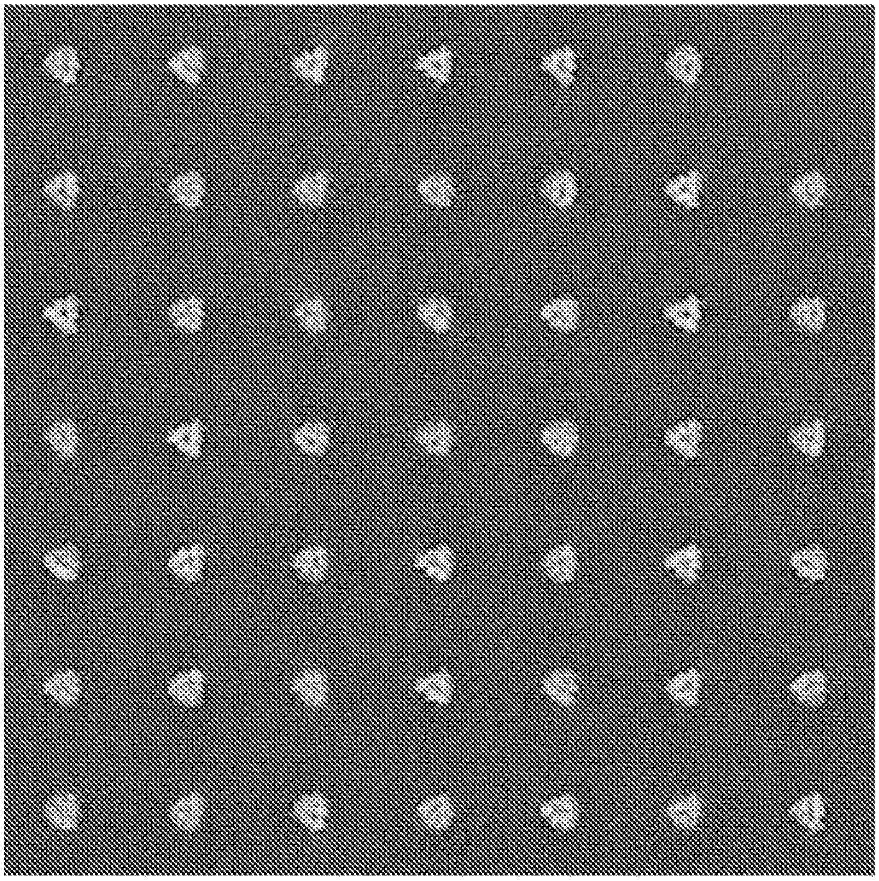
Figure 1C:
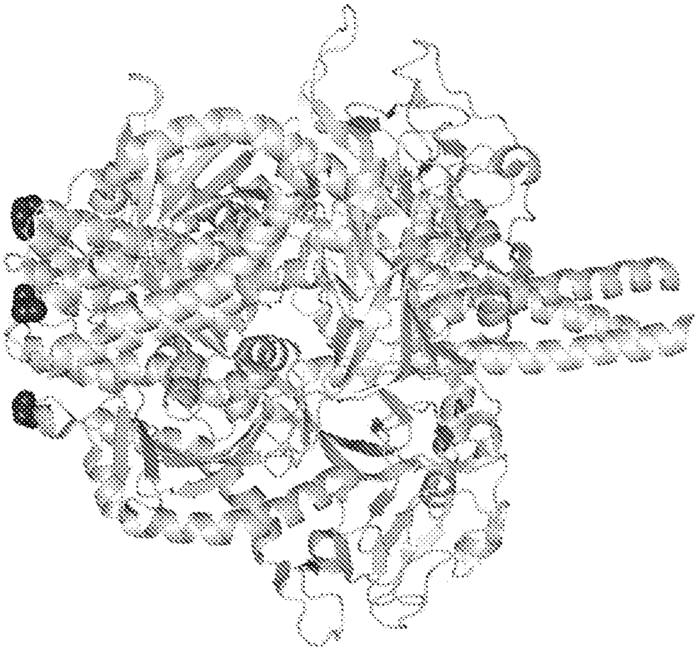
Figure 1D:
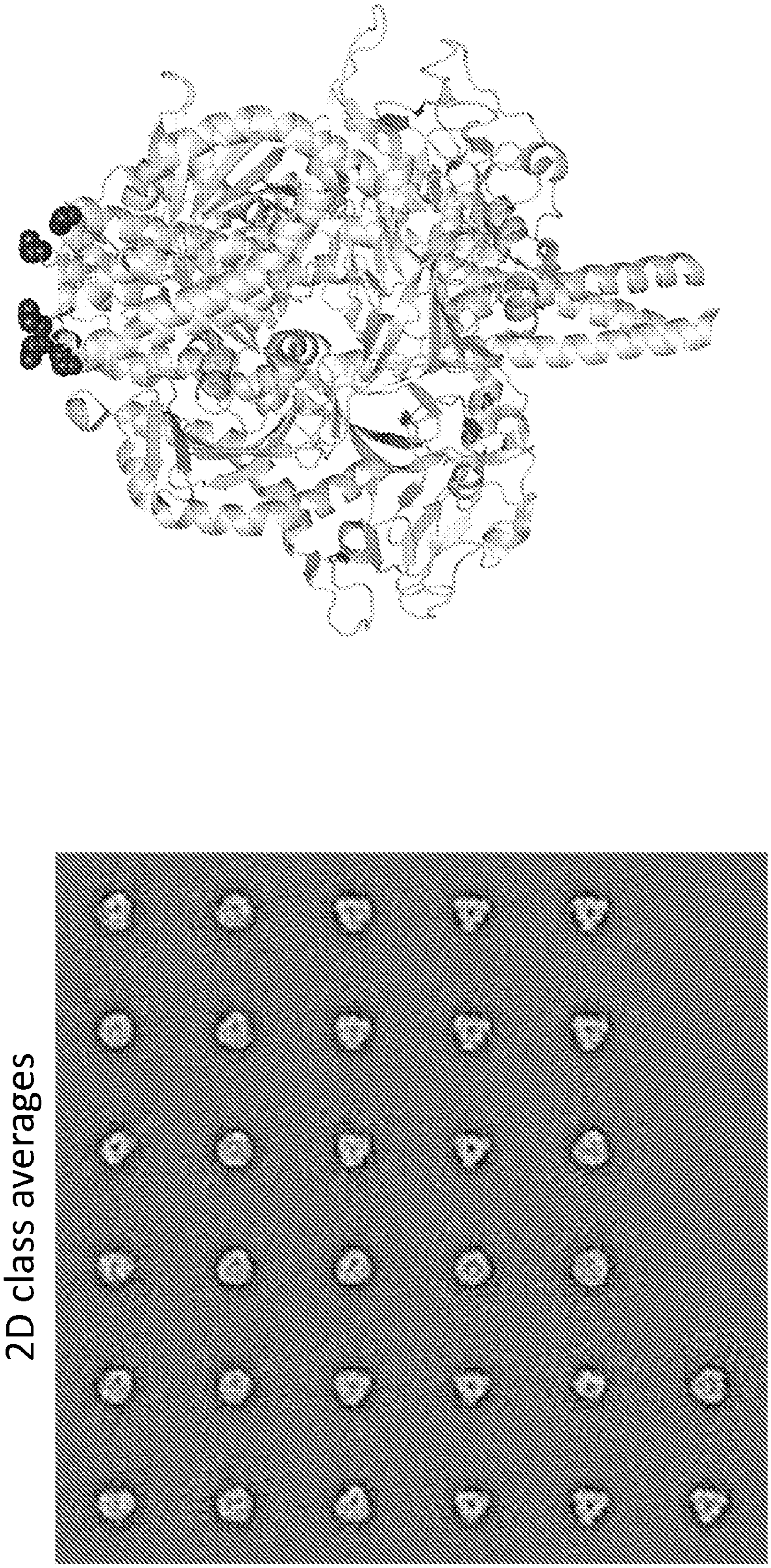
Figure 1E:
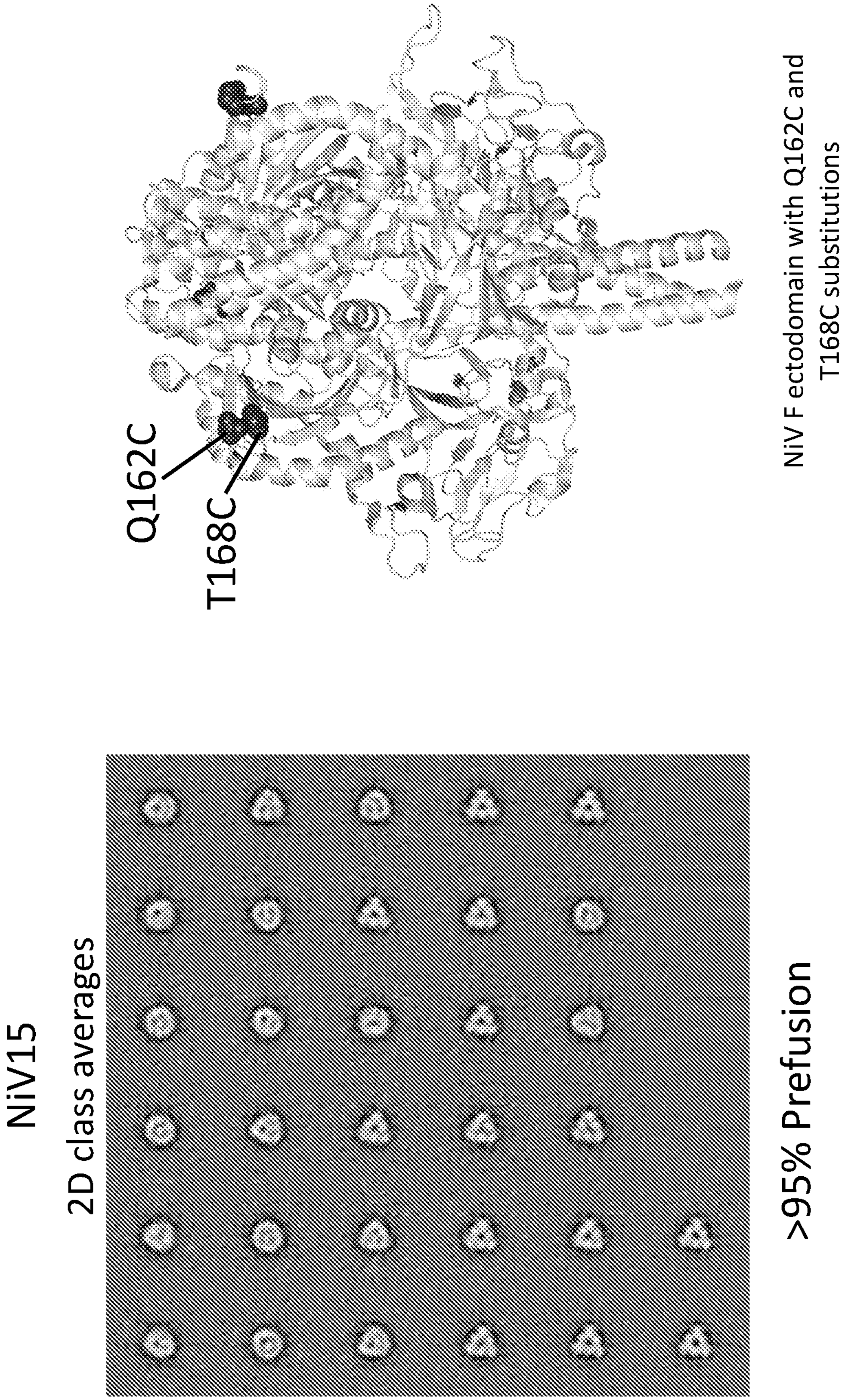

The nucleic and amino acid sequences listed herein are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file in the form of the file named "Sequence.txt" (~396 kb), which was created on Jan. 6, 2021, which is incorporated by reference herein. In the accompanying sequence listing:

SEQ ID NO: 1 is an amino acid sequence including NiV01 protein.

SEQ ID NO: 2 is an amino acid sequence including NiV02 protein.

SEQ ID NO: 3 is an amino acid sequence including NiV03 protein.

SEQ ID NO: 4 is an amino acid sequence including NiV04 protein.

SEQ ID NO: 5 is an amino acid sequence including NiV05 protein.

SEQ ID NO: 6 is an amino acid sequence including NiV06 protein.

SEQ ID NO: 7 is an amino acid sequence including NiV07 protein.

SEQ ID NO: 8 is an amino acid sequence including NiV08 protein.

SEQ ID NO: 9 is an amino acid sequence including NiV09 protein.

SEQ ID NO: 10 is an amino acid sequence including NiV10 protein.

SEQ ID NO: 11 is an amino acid sequence including NiV11 protein.

SEQ ID NO: 12 is an amino acid sequence including NiV12 protein.

SEQ ID NO: 13 is an amino acid sequence including NiV13 protein.

SEQ ID NO: 14 is an amino acid sequence including NiV14 protein.

SEQ ID NO: 15 is an amino acid sequence including NiV15 protein.

SEQ ID NO: 16 is an amino acid sequence including NiV16 protein.

SEQ ID NO: 17 is an amino acid sequence including NiVop01 protein.

SEQ ID NO: 18 is an amino acid sequence including NiVop02 protein.

SEQ ID NO: 19 is an amino acid sequence including NiVop03 protein.

SEQ ID NO: 20 is an amino acid sequence including NiVop04 protein.

SEQ ID NO: 21 is an amino acid sequence including NiVop05 protein.

SEQ ID NO: 22 is an amino acid sequence including NiVop06 protein.

SEQ ID NO: 23 is an amino acid sequence including NiVop07 protein.

SEQ ID NO: 24 is an amino acid sequence including NiVop08 protein.

SEQ ID NO: 25 is an amino acid sequence including NiVop09 protein.

SEQ ID NO: 26 is an amino acid sequence including NiVop12 protein.

SEQ ID NO: 27 is an amino acid sequence including NiVop13 protein.

SEQ ID NO: 28 is an amino acid sequence including NiVop14 protein.

SEQ ID NO: 29 is an amino acid sequence including NiVop15 protein.

SEQ ID NO: 30 is an amino acid sequence including NiVop16 protein.

SEQ ID NO: 31 is an amino acid sequence including NiVop17 protein.

SEQ ID NO: 32 is an amino acid sequence including NiVop18 protein.

SEQ ID NO: 33 is an exemplary nucleic acid sequence encoding full-length NiV F with NiVop08 substitutions.

SEQ ID NO: 34 is an amino acid sequence including Fd-G protein.

SEQ ID NO: 35 is an amino acid sequence including Fd-GG protein.

SEQ ID NO: 36 is an amino acid sequence including Fd-GGG protein.

SEQ ID NO: 37 is an amino acid sequence including G-Fd-G protein (soluble G-hexamer).

SEQ ID NO: 38 is an amino acid sequence including NiV G linked to a ferritin subunit by a five amino acid linker (G-1n5-Fer).

SEQ ID NO: 39 is an amino acid sequence including NiV G linked to a ferritin subunit by a 15 amino acid linker (G-1n15-Fer).

SEQ ID NO: 40 is an amino acid sequence including NiV G linked to a ferritin subunit by a 25 amino acid linker (G-1n25-Fer).

SEQ ID NO: 41 is an amino acid sequence including NiV G linked to a ferritin subunit by a 35 amino acid linker (G-1n35-Fer).

SEQ ID NO: 42 is an amino acid sequence including NiV G linked to a lumazine synthase subunit (G-LS).

SEQ ID NO: 43 is an amino acid sequence including NiVop08 linked to NiV G by GCN4 and Fd trimerization domains (NiVop08-TD-G).

SEQ ID NO: 44 is an amino acid sequence including NiV G linked to NiVop09 linked to GCN4 and Fd trimerization domains (G-NiVop08-TD).

SEQ ID NO: 45 is an amino acid sequence including NiVop06 linked to NiV G by GCN4 and Fd trimerization domains (NiV06-TD-G).

SEQ ID NO: 46 is an amino acid sequence including NiVop06 linked to two copies of NiV G by GCN4 and Fd trimerization domains (NiV06-TD-GG).

SEQ ID NO: 47 is an amino acid sequence including NiVop08 linked to two copies of NiV G by GCN4 and Fd trimerization domains (NiVop08-TD-GG).

SEQ ID NO: 48 is an amino acid sequence including NiVop06 linked to three copies of NiV G by GCN4 and Fd trimerization domains (NiV06-TD-GGG).

SEQ ID NO: 49 is an amino acid sequence including NiVop08 linked to three copies of NiV G by GCN4 and Fd trimerization domains (NiVop08-TD-GGG).

SEQ ID NO: 50 is an amino acid sequence including NiV G linked to NiV06 linked to GCN4 and Fd trimerization domains (G-NiV06-TD).

SEQ ID NO: 51 is an amino acid sequence including NIV G linked to NiVop08 linked to GCN4 and Fd trimerization domains (G-NiVop08-TD).

SEQ ID NO: 52 is an exemplary sequence of a wild-type NiV F protein.

SEQ ID NOs: 53 and 54 are exemplary sequences of wild-type NiV G proteins.

SEQ ID NOs: 55-58 are amino acid sequences of protein nanoparticle subunits.

SEQ ID NO: 59 is an amino acid sequence including NiVop08 linked to NiV G by a GCN4 trimerization domain (NiVop08-GCN4-G).

SEQ ID NO: 60 is an amino acid sequence including NiVop08 linked to NiV G by a Fd trimerization domains (NiVop08-Fd-G).

SEQ ID NO: 61 is an exemplary nucleic acid sequence encoding NiVop08-TD-G.

SEQ ID NO: 62 is an exemplary nucleic acid sequence encoding G-NiVop08-TD.

SEQ ID NO: 63 is an exemplary nucleic acid sequence encoding NiV08.

SEQ ID NO: 64 is an exemplary nucleic acid sequence encoding G-1n5-Ferritin.

SEQ ID NO: 65 is an exemplary nucleic acid sequence encoding NiVop08-GCN4-G.

SEQ ID NO: 66 is an exemplary nucleic acid sequence encoding NiVop08-Fd-G.

SEQ ID NO: 67 is an exemplary nucleic acid sequence encoding G-Fd-G.

SEQ ID NO: 68 is an exemplary sequence of a HeV G protein.

SEQ ID NOs: 69 and 70 are sequences of chimeric proteins containing NiVop8 and HeV G.

DETAILED DESCRIPTION

Disclosed herein are recombinant NiV F ectodomain trimers comprising protomers comprising one or more modifications (such as amino acid substitutions) that stabilize the F ectodomain trimer in its prefusion conformation. Additionally, provided are chimeras of the recombinant NiV F ectodomain trimer stabilized in the prefusion conformation and one or more G ectodomains, a multimer of NiV G ectodomains, and self-assembling protein nanoparticles containing the recombinant NiV F ectodomain trimer stabilized in the prefusion conformation or a NiV G ectodomain.

Embodiments of the prefusion-stabilized NiV F ectodomain trimer are demonstrated to produce a superior immune response in an animal model compared to corresponding NiV F ectodomain trimers that are not stabilized in the prefusion conformation. Several prefusion-stabilized NiV F ectodomain designs provide a surprisingly good combination of stability, homogeneity, yield, and immunogenicity.

Similarly, embodiments of the disclosed chimeras of the recombinant NiV F ectodomain trimer stabilized in the prefusion conformation and one or more G ectodomains provide an surprisingly good combination of stability, homogeneity, yield, and immunogenicity, particularly given the chimeric aspect of these constructs.

I. Summary of Terms

Unless otherwise noted, technical terms are used according to conventional usage. Definitions of common terms in molecular biology may be found in Benjamin Lewin, *Genes X*, published by Jones & Bartlett Publishers, 2009; and Meyers et al. (eds.), The Encyclopedia of Cell Biology and Molecular Medicine, published by Wiley-VCH in 16 volumes, 2008; and other similar references. As used herein, the singular forms "a," "an," and "the," refer to both the singular as well as plural, unless the context indicates otherwise. For example, the term "an antigen" includes single or plural antigens and can be considered equivalent to the phrase "at least one antigen." As used herein, the term "comprises" means "includes." It is further to be understood that any and all base sizes or amino acid sizes, and all molecular weight or molecular mass values, given for nucleic acids or polypeptides are approximate, and are provided for descriptive purposes, unless otherwise indicated. Although many methods and materials similar or equivalent to those described herein can be used, particular suitable methods and materials are described below. In case of conflict, the present specification, including explanations of terms, will control. In addition, the materials, methods, and examples are illustrative only and not intended to be limiting. To facilitate review of the various embodiments, the following explanations of terms are provided:

Adjuvant: A vehicle used to enhance antigenicity. In some embodiments, an adjuvant includes a suspension of minerals (alum, aluminum hydroxide, or phosphate) on which antigen is adsorbed; or water-in-oil emulsion, for example, in which antigen solution is emulsified in mineral oil (Freund incomplete adjuvant), sometimes with the inclusion of killed mycobacteria (Freund's complete adjuvant) to further enhance antigenicity (inhibits degradation of antigen and/or causes influx of macrophages). In some embodiments, the adjuvant used in a disclosed immunogenic composition is a combination of lecithin and carbomer homopolymer (such as the ADJUPLEX™ adjuvant available from Advanced BioAdjuvants, LLC, see also Wegmann, Clin Vaccine Immunol, 22(9): 1004-1012, 2015). Additional adjuvants for use in the disclosed immunogenic compositions include the QS21 purified plant extract, Matrix M, AS01, MF59, and ALFQ adjuvants. Immunostimulatory oligonucleotides (such as those including a CpG motif) can also be used as adjuvants. Adjuvants include biological molecules (a "biological adjuvant"), such as costimulatory molecules. Exemplary adjuvants include IL-2, RANTES, GM-CSF, TNF-α, IFN-γ, G-CSF, LFA-3, CD72, B7-1, B7-2, OX-40L, 4-1BBL, immune stimulating complex (ISCOM) matrix, and toll-like receptor (TLR) agonists, such as TLR-9 agonists, Poly I:C, or PolyICLC. (See, e.g., Singh (ed.) Vaccine Adjuvants and Delivery Systems. Wiley-Interscience, 2007).

Administration: The introduction of a composition into a subject by a chosen route. Administration can be local or systemic. For example, if the chosen route is intranasal, the composition (such as a composition including a disclosed recombinant NiV F ectodomain) is administered by introducing the composition into the nasal passages of the subject. Exemplary routes of administration include, but are not limited to, oral, injection (such as subcutaneous, intramuscular, intradermal, intraperitoneal, and intravenous), sublingual, rectal, transdermal (for example, topical), intranasal, vaginal, and inhalation routes.

Amino acid substitution: The replacement of an amino acid in a polypeptide with one or more different amino acids. In the context of a protein sequence, an amino acid substitution is also referred to as a mutation.

Antibody: An immunoglobulin, antigen-binding fragment, or derivative thereof, that specifically binds and recognizes an analyte (antigen) such as NiV F protein, an antigenic fragment thereof, or a dimer or multimer of the antigen. The term "antibody" is used herein in the broadest sense and encompasses various antibody structures, including but not limited to monoclonal antibodies, polyclonal antibodies, multispecific antibodies (e.g., bispecific antibodies), and antibody fragments, so long as they exhibit the desired antigen-binding activity. Non-limiting examples of antibodies include, for example, intact immunoglobulins and variants and fragments thereof that retain binding affinity for the antigen. Examples of antibody fragments include but are not limited to Fv, Fab, Fab', Fab'-SH, F(ab')2; diabodies; linear antibodies; single-chain antibody molecules (e.g. scFv); and multispecific antibodies formed from antibody fragments. Antibody fragments include antigen binding fragments either produced by the modification of whole antibodies or those synthesized de novo using recombinant DNA methodologies (see, e.g., Kontermann and Dubel (Ed), Antibody Engineering, Vols. 1-2, $2^{nd}$ Ed., Springer Press, 2010).

Carrier: An immunogenic molecule to which an antigen can be linked. When linked to a carrier, the antigen may become more immunogenic. Carriers are chosen to increase the immunogenicity of the antigen and/or to elicit antibodies against the carrier which are diagnostically, analytically, and/or therapeutically beneficial. Useful carriers include polymeric carriers, which can be natural (for example, proteins from bacteria or viruses), semi-synthetic or synthetic materials containing one or more functional groups to which a reactant moiety can be attached.

Cavity-filling amino acid substitution: An amino acid substitution that fills a cavity within the protein core of a protein, such as a NiV F ectodomain. Cavities are essentially voids within a folded protein where amino acids or amino acid side chains are not present. In several embodiments, a cavity filling amino acid substitution is introduced to fill a cavity present in the prefusion conformation of the NiV F ectodomain core that collapses (e.g., has reduced volume) after transition to the postfusion conformation.

Conservative variants: "Conservative" amino acid substitutions are those substitutions that do not substantially affect or decrease a function of a protein, such as the ability of the protein to induce an immune response when administered to a subject. The term conservative variation also includes the use of a substituted amino acid in place of an unsubstituted parent amino acid. Furthermore, individual substitutions, deletions or additions which alter, add or delete a single amino acid or a small percentage of amino acids (for instance less than 5%, in some embodiments less than 1%) in an encoded sequence are conservative variations where the alterations result in the substitution of an amino acid with a chemically similar amino acid.

The following six groups are examples of amino acids that are considered to be conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

Non-conservative substitutions are those that reduce an activity or function of the recombinant NiV F ectodomain trimer, such as the ability to induce an immune response when administered to a subject. For instance, if an amino acid residue is essential for a function of the protein, even an otherwise conservative substitution may disrupt that activity. Thus, a conservative substitution does not alter the basic function of a protein of interest.

Control: A reference standard. In some embodiments, the control is a negative control sample obtained from a healthy patient. In other embodiments, the control is a positive control sample obtained from a patient diagnosed with NiV infection. In still other embodiments, the control is a historical control or standard reference value or range of values (such as a previously tested control sample, such as a group of NiV patients with known prognosis or outcome, or group of samples that represent baseline or normal values).

A difference between a test sample and a control can be an increase or conversely a decrease. The difference can be a qualitative difference or a quantitative difference, for example a statistically significant difference. In some examples, a difference is an increase or decrease, relative to a control, of at least about 5%, such as at least about 10%, at least about 20%, at least about 30%, at least about 40%, at least about 50%, at least about 60%, at least about 70%, at least about 80%, at least about 90%, at least about 100%, at least about 150%, at least about 200%, at least about 250%, at least about 300%, at least about 350%, at least about 400%, at least about 500%, or greater than 500%.

Degenerate variant: In the context of the present disclosure, a "degenerate variant" refers to a polynucleotide encoding a polypeptide that includes a sequence that is degenerate as a result of the genetic code. There are 20 natural amino acids, most of which are specified by more than one codon. Therefore, all degenerate nucleotide sequences encoding a peptide are included as long as the amino acid sequence of the peptide encoded by the nucleotide sequence is unchanged.

Effective amount: An amount of agent, such as an immunogen, that is sufficient to elicit a desired response, such as an immune response in a subject. It is understood that to obtain a protective immune response against an antigen of interest can require multiple administrations of a disclosed immunogen, and/or administration of a disclosed immunogen as the "prime" in a prime boost protocol wherein the boost immunogen can be different from the prime immunogen. Accordingly, an effective amount of a disclosed immunogen can be the amount of the immunogen sufficient to elicit a priming immune response in a subject that can be subsequently boosted with the same or a different immunogen to elicit a protective immune response.

In one example, a desired response is to inhibit or reduce or prevent NiV infection. The NiV infection does not need to be completely eliminated or reduced or prevented for the method to be effective. For example, administration of an effective amount of the agent can decrease the NiV infection (for example, as measured by infection of cells, or by number or percentage of subjects infected by NiV) by a desired amount, for example by at least 50%, at least 60%, at least 70%, at least 80%, at least 90%, at least 95%, at least 98%, or even at least 100% (elimination or prevention of detectable NiV infection), as compared to a suitable control.

Expression: Transcription or translation of a nucleic acid sequence. For example, a gene is expressed when its DNA is transcribed into an RNA or RNA fragment, which in some examples is processed to become mRNA. A gene may also be expressed when its mRNA is translated into an amino acid sequence, such as a protein or a protein fragment. In a particular example, a heterologous gene is expressed when it is transcribed into an RNA. In another example, a heterologous gene is expressed when its RNA is translated into an amino acid sequence. The term "expression" is used herein to denote either transcription or translation. Regulation of expression can include controls on transcription, translation, RNA transport and processing, degradation of intermediary molecules such as mRNA, or through activation, inactivation, compartmentalization or degradation of specific protein molecules after they are produced.

Expression Control Sequences: Nucleic acid sequences that regulate the expression of a heterologous nucleic acid sequence to which it is operatively linked. Expression control sequences are operatively linked to a nucleic acid sequence when the expression control sequences control and regulate the transcription and, as appropriate, translation of the nucleic acid sequence. Thus expression control sequences can include appropriate promoters, enhancers, transcription terminators, a start codon (ATG) in front of a protein-encoding gene, splicing signal for introns, maintenance of the correct reading frame of that gene to permit proper translation of mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter.

A promoter is a minimal sequence sufficient to direct transcription. Also included are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters are included (see for example, Bitter et al., Methods in Enzymology 153:516-544, 1987). For example, when cloning in bacterial systems, inducible promoters such as pL of bacteriophage lambda, plac, ptrp, ptac (ptrp-lac hybrid promoter) and the like may be used. In one embodiment, when cloning in mammalian cell systems, promoters derived from the genome of mammalian cells (such as metallothionein promoter) or from mammalian viruses (such as the retrovirus long terminal repeat; the adenovirus late promoter; the vaccinia virus 7.5K promoter) can be used. Promoters produced by recombinant DNA or synthetic techniques may also be used to provide for transcription of the nucleic acid sequences.

Expression vector: A vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

GCN4 trimerization domain: A trimerization domain from the GCN4 protein that comprises a leucine zipper amino acid sequence that naturally forms a trimeric structure. Embodiments of the GCN4 trimerization domain is described, for example, Harbury et al. (1993 *Science* 262: 1401-1407). In some examples, a GCN4 trimerization domain can be included in the amino acid sequence of a disclosed recombinant protein so that the recombinant protein will trimerize. A non-limiting example of a GCN4 trimerization domain sequence for use with the disclosed embodiments is provided as KLMKQIEDKIEEILSKIYHIENEIARIKKLIGEAP (residues 485-519 of SEQ ID NO: 1).

Heterologous: Originating from a different genetic source.

Host cells: Cells in which a vector can be propagated and its nucleic acid expressed. The cell may be prokaryotic or eukaryotic. The term also includes any progeny of the subject host cell. It is understood that all progeny may not be identical to the parental cell since there may be mutations that occur during replication. However, such progeny are included when the term "host cell" is used.

Immune response: A response of a cell of the immune system, such as a B cell, T cell, or monocyte, to a stimulus. In one embodiment, the response is specific for a particular antigen (an "antigen-specific response"). In one embodiment, an immune response is a T cell response, such as a CD4+ response or a CD8+ response. In another embodiment, the response is a B cell response, and results in the production of specific antibodies.

Immunogen: A compound, composition, or substance (for example, a recombinant NiV F ectodomain trimer) that can elicit an immune response in an animal, including compositions that are injected or absorbed into an animal. Administration of an immunogen to a subject can lead to protective immunity against a pathogen of interest.

Immunogenic composition: A composition comprising a disclosed recombinant NiV F ectodomain trimer that induces a measurable CTL response against the NiV, or induces a measurable B cell response (such as production of antibodies) against the NiV, when administered to a subject. It further refers to isolated nucleic acid molecules and vectors encoding a protomer of a disclosed recombinant NiV F ectodomain trimer that can be used to express the protomer (and thus be used to elicit an immune response against recombinant NiV F ectodomain trimer). For in vivo use, the immunogenic composition will typically include the recombinant NiV F ectodomain trimer or a nucleic acid molecule encoding a protomer of the recombinant NiV F ectodomain trimer in a pharmaceutically acceptable carrier and may also include other agents, such as an adjuvant.

Inhibiting or treating a disease: Inhibiting the full development of a disease or condition, for example, in a subject who is at risk for a disease such as NiV infection. "Treatment" refers to a therapeutic intervention that ameliorates a sign or symptom of a disease or pathological condition after it has begun to develop. The term "ameliorating," with reference to a disease or pathological condition, refers to any observable beneficial effect of the treatment. Inhibiting a disease can include preventing or reducing the risk of the disease, such as preventing or reducing the risk of viral infection. The beneficial effect can be evidenced, for example, by a delayed onset of clinical symptoms of the disease in a susceptible subject, a reduction in severity of some or all clinical symptoms of the disease, a slower progression of the disease, a reduction in the viral load, an improvement in the overall health or well-being of the subject, or by other parameters that are specific to the particular disease. A "prophylactic" treatment is a treatment administered to a subject who does not exhibit signs of a disease or exhibits only early signs for the purpose of decreasing the risk of developing pathology.

Isolated: An "isolated" biological component has been substantially separated or purified away from other biological components, such as other biological components in which the component naturally occurs, such as other chromosomal and extrachromosomal DNA, RNA, and proteins. Proteins, peptides, nucleic acids, and viruses that have been "isolated" include those purified by standard purification methods. Isolated does not require absolute purity, and can include protein, peptide, nucleic acid, or virus molecules that are at least 50% isolated, such as at least 75%, 80%, 90%, 95%, 98%, 99%, or even 99.9% isolated.

Linker and Linked: A bi-functional molecule that can be used to link two molecules into one contiguous molecule. Non-limiting examples of peptide linkers include glycine-serine peptide linkers. Unless context indicates otherwise, reference to "linking" a first polypeptide and a second polypeptide, or to two polypeptides "linked" together, or to a first polypeptide having a "linkage" to a second polypeptide, refers to covalent linkage by peptide bond (for example via a peptide linker) such that the first and second polypeptides form a contiguous polypeptide chain. If a peptide linker is involved, the covalent linkage of the first and second polypeptides can be to the N- and C-termini of the peptide linker. Typically, such linkage is accomplished using molecular biology techniques to genetically manipulate DNA encoding the first polypeptide linked to the second polypeptide by the peptide linker.

Native protein, sequence, or disulfide bond: A polypeptide, sequence or disulfide bond that has not been modified, for example, by selective mutation. For example, selective mutation to focus the antigenicity of the antigen to a target epitope, or to introduce a disulfide bond into a protein that does not occur in the native protein. Native protein or native sequence are also referred to as wild-type protein or wild-type sequence. A non-native disulfide bond is a disulfide bond that is not present in a native protein, for example, a disulfide bond that forms in a protein due to introduction of one or more cysteine residues into the protein by genetic engineering.

Nipah Virus (NiV): Nipah henipavirus is an enveloped non-segmented negative-sense single-stranded RNA virus of the family Paramyxoviridae. The NiV genome is ~18,000 nucleotides in length and includes 6 genes encoding 9 proteins, including the glycoproteins G, and F. Exemplary native NiV strain sequences are known to the person of ordinary skill in the art. Several models of human NiV infection are available, including model organisms infected with NiV, such as ferrets, mice, golden hamsters, guinea pigs, and African Green Monkeys (see, e.g., Geisbert et al., Curr. Top. Microbiol. Immunol., 359:153-77, 2012, which is incorporated by reference herein in its entirety).

The natural NiV host are fruit bats of the Pteropodidae Family. NiV infection in humans has a range of clinical presentations, from asymptomatic infection to acute respiratory syndrome and fatal encephalitis. NiV is also capable of causing disease in pigs and other domestic animals. In humans, NiV infection typically presents as fever, headache and drowsiness. Cough, abdominal pain, nausea, vomiting, weakness, problems with swallowing and blurred vision are relatively common. About a quarter of the human patients have seizures and about 60% become comatose and might need mechanical ventilation. In patients with severe disease, their conscious state may deteriorate and they may develop severe hypertension, fast heart rate, and very high temperature.

NiV attachment glycoprotein (G): An NiV envelope glycoprotein that is a type II membrane protein and facilitates attachment of NiV to host cell membranes. The full-length G protein has an N-terminal cytoplasmic tail and transmembrane domain (CT and TM, approximately amino acids 1-176), and an ectodomain (approximately amino acids 177-602). An exemplary NiV G protein sequence from NiV G from a Malaysian stain is provided herein as SEQ ID NO: 53 (NCBI Reference Sequence NP_112027.1, which is incorporated by reference herein):

```
MPAENKKVRFENTTSDKGKIPSKVIKSYYGTMDIKKINEGLLDSKILSAF

NTVIALLGSIVIIVMNIMIIQNYTRSTDNQAVIKDALQGIQQQIKGLADK

IGTEIGPKVSLIDTSSTITIPANIGLLGSKISQSTASINENVNEKCKFTL

PPLKIHECNISCPNPLPFREYRPQTEGVSNLVGLPNNICLQKTSNQILKP

KLISYTLPVVGQSGTCITDPLLAMDEGYFAYSHLERIGSCSRGVSKQRII

GVGEVLDRGDEVPSLFMTNVWTPPNPNTVYHCSAVYNNEFYYVLCAVSTV

GDPILNSTYWSGSLMMTRLAVKPKSNGGGYNQHQLALRSIEKGRYDKVMP

YGPSGIKQGDTLYFPAVGFLVRTEFKYNDSNCPITKCQYSKPENCRLSMG

IRPNSHYILRSGLLKYNLSDGENPKVVFIEISDQRLSIGSPSKIYDSLGQ

PVFYQASFSWDTMIKFGDVLTVNPLVVNWRNNTVISRPGQSQCPRFNTCP

EICWEGVYNDAFLIDRINWISAGVFLDSNQTAENPVFTVFKDNEILYRAQ

LASEDTNAQKTITNCFLLKNKIWCISLVEIYDTGDNVIRPKLFAVKIPEQ

CT
```

An exemplary NiV G protein sequence from NiV G from a Bangladesh stain is provided herein as SEQ ID NO: 54 (GenBank Reference No. AAY43916.1, which is incorporated by reference herein):

```
MPTESKKVRFENTASDKGKNPSKVIKSYYGTMDIKKINEGLLDSKILSAF

NTVIALLGSIVIIVMNIMIIQNYTRSTDNQAMIKDALQSIQQQIKGLADK
```

-continued

```
IGTEIGPKVSLIDTSSTITIPANIGLLGSKISQSTASINENVNEKCKFTL

PPLKIHECNISCPNPLPFREYKPQTEGVSNLVGLPNNICLQKTSNQILKP

KLISYTLPVVGQSGTCITDPLLAMDEGYFAYSHLEKIGSCSRGVSKQRII

GVGEVLDRGDEVPSLFMTNVWTPSNPNTVYHCSAVYNNEFYYVLCAVSVV

GDPILNSTYWSGSLMMTRLAVKPKNNGESYNQHQFALRNIEKGKYDKVMP

YGPSGIKQGDTLYFPAVGFLVRTEFKYNDSNCPIAECQYSKPENCRLSMG

IRPNSHYILRSGLLKYNLSDEENSKIVFIEISDQRLSIGSPSKIYDSLGQ

PVFYQASFSWDTMIKFGDVQTVNPLVVNWRDNTVISRPGQSQCPRFNKCP

EVCWEGVYNDAFLIDRINWISAGVFLDSNQTAENPVFTVFKDNEVLYRAQ

LASEDTNAQKTITNCFLLKNKIWCISLVEIYDTGDNVIRPKLFAVKIPEQ

CT
```

As used herein, NiV G residue positioning is made with reference to the sequence of the set forth as SEQ ID NO: 53.

NiV fusion (F) protein: An envelope glycoprotein of NiV that facilitates fusion of viral and cellular membranes. In nature, the F protein from NiV is initially synthesized as a single polypeptide precursor approximately 550 amino acids in length, designated $F_0$. $F_0$ includes an N-terminal signal peptide that directs localization to the endoplasmic reticulum, where the signal peptide is proteolytically cleaved. The remaining $F_0$ residues oligomerize to form a trimer and may be proteolytically processed by a cellular protease to generate two disulfide-linked fragments, $F_1$ and $F_2$. In NiV F the cleavage site is located approximately between residues 109/110. The smaller of these fragments, $F_2$, originates from the N-terminal portion of the $F_0$ precursor (approximately residues 25-109). The larger of these fragments, $F_1$, includes the C-terminal portion of the $F_0$ precursor (approximately residues 110-550) including an extracellular/lumenal region (approximately residues 110-495), and a transmembrane and cytosolic regions (approximately residues 495-550). The extracellular portion of the NiV F protein is the NiV F ectodomain, which includes the $F_2$ protein and the $F_1$ ectodomain. The fusion peptide is located at the N-terminal segment of the $F_1$ ectodomain, at approximately residues 110-122.

The NiV F protein exhibits remarkable sequence conservation within NiV strain. In view of this conservation, the person of ordinary skill in the art can easily compare amino acid positions of different NiV F proteins. Unless context indicates otherwise, the numbering of NiV F amino acids is made with reference to SEQ ID NO: 52 (NCBI Reference Sequence NP_112026.1, which is incorporated by reference herein):

```
MVVILDKRCYCNLLILILMISECSVGILHYEKLSKIGLVKGVTRKYKIKS

NPLTKDIVIKMIPNVSNMSQCTGSVMENYKTRLNGILTPIKGALEIYKNN

THDLVGDVRLAGVIMAGVAIGIATAAQITAGVALYEAMKNADNINKLKSS

IESTNEAVVKLQETAEKTVYVLTALQDYINTNLVPTIDKISCKQTELSLD

LALSKYLSDLLFVFGPNLQDPVSNSMTIQAISQAFGGNYETLLRTLGYAT

EDFDDLLESDSITGQIIYVDLSSYYIIVRVYFPILTEIQQAYIQELLPVS
```

-continued

```
FNNDNSEWISIVPNFILVRNTLISNIEIGFCLITKRSVICNQDYATPMTN

NMRECLTGSTEKCPRELVVSSHVPRFALSNGVLFANCISVTCQCQTTGRA

ISQSGEQTLLMIDNTTCPTAVLGNVIISLGKYLGSVNYNSEGIAIGPPVF

TDKVDISSQISSMNQSLQQSKDYIKEAQRLLDTVNPSLISMLSMIILYVL

SIASLCIGLITFISFIIVEKKRNTYSRLEDRRVRPTSSGDLYYIGT
```

Three NiV F protomers oligomerize in the mature F protein, which adopts a metastable prefusion conformation that is triggered to undergo a conformational change to a postfusion conformation upon contact with a target cell membrane. This conformational change exposes a hydrophobic sequence, known as the fusion peptide, which is located at the N-terminus of the $F_1$ ectodomain, and which associates with the host cell membrane and promotes fusion of the membrane of the virus, or an infected cell, with the target cell membrane.

An NiV F ectodomain trimer "stabilized in a prefusion conformation" comprises one or more amino acid substitutions, deletions, or insertions compared to a corresponding native NiV F sequence that provide for increased retention of the prefusion conformation compared to NiV F ectodomain trimers formed from a corresponding native NiV F sequence. The "stabilization" of the prefusion conformation can be, for example, energetic stabilization (for example, reducing the energy of the prefusion conformation relative to the postfusion open conformation) and/or kinetic stabilization (for example, reducing the rate of transition from the prefusion conformation to the postfusion conformation). Additionally, stabilization of the NiV F ectodomain trimer in the prefusion conformation can include an increase in resistance to denaturation compared to a corresponding native NiV F sequence. Methods of determining if a NiV F ectodomain trimer is in the prefusion conformation are provided herein, and include (but are not limited to) negative stain electron microscopy and antibody binding assays using a prefusion conformation specific antibody, such as the 5B3 antibody.

NiV F prefusion specific antibody: An antibody that specifically binds to the NiV F protein in a prefusion conformation, but does not specifically bind to the NiV F protein in a postfusion conformation. For example, the 5B3 antibody disclosed in US 2016/0347827 (incorporated by reference herein in its entirety) is a NiV prefusion specific antibody.

Nucleic acid molecule: A polymeric form of nucleotides, which may include both sense and anti-sense strands of RNA, cDNA, genomic DNA, and synthetic forms and mixed polymers of the above. A nucleotide refers to a ribonucleotide, deoxynucleotide or a modified form of either type of nucleotide. The term "nucleic acid molecule" as used herein is synonymous with "nucleic acid" and "polynucleotide." A nucleic acid molecule is usually at least 10 bases in length, unless otherwise specified. The term includes single- and double-stranded forms of DNA. A polynucleotide may include either or both naturally occurring and modified nucleotides linked together by naturally occurring and/or non-naturally occurring nucleotide linkages. "cDNA" refers to a DNA that is complementary or identical to an mRNA, in either single stranded or double stranded form. "Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked nucleic acid sequences are contiguous and, where necessary to join two protein-coding regions, in the same reading frame.

Pharmaceutically acceptable carriers: The pharmaceutically acceptable carriers of use are conventional. *Remington's Pharmaceutical Sciences*, by E. W. Martin, Mack Publishing Co., Easton, Pa., 19th Edition, 1995, describes compositions and formulations suitable for pharmaceutical delivery of the disclosed immunogens.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions (such as immunogenic compositions) to be administered can contain minor amounts of non-toxic auxiliary substances, such as wetting or emulsifying agents, preservatives, and pH buffering agents and the like, for example sodium acetate or sorbitan monolaurate. In particular embodiments, suitable for administration to a subject the carrier may be sterile, and/or suspended or otherwise contained in a unit dosage form containing one or more measured doses of the composition suitable to induce the desired immune response. It may also be accompanied by medications for its use for treatment purposes. The unit dosage form may be, for example, in a sealed vial that contains sterile contents or a syringe for injection into a subject, or lyophilized for subsequent solubilization and administration or in a solid or controlled release dosage.

Polypeptide: Any chain of amino acids, regardless of length or post-translational modification (e.g., glycosylation or phosphorylation). "Polypeptide" applies to amino acid polymers including naturally occurring amino acid polymers and non-naturally occurring amino acid polymer as well as in which one or more amino acid residue is a non-natural amino acid, for example, an artificial chemical mimetic of a corresponding naturally occurring amino acid. A "residue" refers to an amino acid or amino acid mimetic incorporated in a polypeptide by an amide bond or amide bond mimetic. A polypeptide has an amino terminal (N-terminal) end and a carboxy terminal (C-terminal) end. "Polypeptide" is used interchangeably with peptide or protein, and is used herein to refer to a polymer of amino acid residues.

Prime-boost vaccination: An immunotherapy including administration of a first immunogenic composition (the primer vaccine) followed by administration of a second immunogenic composition (the booster vaccine) to a subject to induce an immune response. The primer vaccine and/or the booster vaccine include a vector (such as a viral vector, RNA, or DNA vector) expressing the antigen to which the immune response is directed. The booster vaccine is administered to the subject after the primer vaccine; a suitable time interval between administration of the primer vaccine and the booster vaccine, and examples of such timeframes are disclosed herein. In some embodiments, the primer vaccine, the booster vaccine, or both primer vaccine and the booster vaccine additionally include an adjuvant. In one non-limiting example, the primer vaccine is a DNA-based vaccine (or other vaccine based on gene delivery), and the booster vaccine is a protein subunit or protein nanoparticle based vaccine.

Protein nanoparticle: A self-assembling, multi-subunit, protein-based polyhedron shaped structure. The subunits are each composed of proteins or polypeptides (for example a glycosylated polypeptide), and, optionally of single or multiple features of the following: nucleic acids, prosthetic groups, organic and inorganic compounds. Non-limiting examples of protein nanoparticles include ferritin nanoparticles (see, e.g., Zhang, Y. *Int. J. Mol. Sci.,* 12:5406-5421, 2011, incorporated by reference herein), encapsulin nanoparticles (see, e.g., Sutter et al., Nature Struct. and Mol. Biol., 15:939-947, 2008, incorporated by reference herein), Sulfur Oxygenase Reductase (SOR) nanoparticles (see, e.g., Urich et al., Science, 311:996-1000, 2006, incorporated by reference herein), lumazine synthase nanoparticles (see, e.g., Zhang et al., *J. Mol. Biol.,* 306: 1099-1114, 2001) or pyruvate dehydrogenase nanoparticles (see, e.g., Izard et al., *PNAS* 96: 1240-1245, 1999, incorporated by reference herein). Ferritin, encapsulin, SOR, lumazine synthase, and pyruvate dehydrogenase are monomeric proteins that self-assemble into a globular protein complexes that in some cases consists of 24, 60, 24, 60, and 60 protein subunits, respectively. In some examples, ferritin, encapsulin, SOR, lumazine synthase, or pyruvate dehydrogenase monomers are linked to a recombinant NiV F ectodomain and self-assemble into a protein nanoparticle presenting the recombinant NiV F ectodomain trimer or a NiV G ectodomain on its surface, which can be administered to a subject to stimulate an immune response to the antigen.

Recombinant: A recombinant nucleic acid molecule is one that has a sequence that is not naturally occurring, for example, includes one or more nucleic acid substitutions, deletions or insertions, and/or has a sequence that is made by an artificial combination of two otherwise separated segments of sequence. This artificial combination can be accomplished by chemical synthesis or, more commonly, by the artificial manipulation of isolated segments of nucleic acids, for example, by genetic engineering techniques.

A recombinant virus is one that includes a genome that includes a recombinant nucleic acid molecule.

A recombinant protein is one that has a sequence that is not naturally occurring or has a sequence that is made by an artificial combination of two otherwise separated segments of sequence. In several embodiments, a recombinant protein is encoded by a heterologous (for example, recombinant) nucleic acid that has been introduced into a host cell, such as a bacterial or eukaryotic cell, or into the genome of a recombinant virus.

Sequence identity: The similarity between amino acid sequences is expressed in terms of the similarity between the sequences, otherwise referred to as sequence identity. Sequence identity is frequently measured in terms of percentage identity; the higher the percentage, the more similar the two sequences are. Homologs, orthologs, or variants of a polypeptide will possess a relatively high degree of sequence identity when aligned using standard methods.

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene,* 73:237-44, 1988; Higgins & Sharp, *CABIOS* 5:151-3, 1989; Corpet et al., *Nuc. Acids Res.* 16:10881-90, 1988; Huang et al. *Computer Appls. In the Biosciences* 8, 155-65, 1992; and Pearson et al., *Meth. Mol. Bio.* 24:307-31, 1994. Altschul et al., *J. Mol. Biol.* 215:403-10, 1990, presents a detailed consideration of sequence alignment methods and homology calculations.

Variants of a polypeptide are typically characterized by possession of at least about 75%, for example, at least about 80%, 85%, 90%, 91%, 92%, 93%, 94%, 95%, 96%, 97%, 98% or 99% sequence identity counted over the full length alignment with the amino acid sequence of interest. Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or 95% depending on their similarity to the reference sequence. Methods for determining sequence identity over such short windows are available at the NCBI website on the internet.

As used herein, reference to "at least 90% identity" (or similar language) refers to "at least 90%, at least 91%, at least 92%, at least 93%, at least 94%, at least 95%, at least 96%, at least 97%, at least 98%, at least 99%, or even 100% identity" to a specified reference sequence.

Signal Peptide: A short amino acid sequence (e.g., approximately 18-25 amino acids in length) that directs newly synthesized secretory or membrane proteins to and through membranes (for example, the endoplasmic reticulum membrane). Signal peptides are typically located at the N-terminus of a polypeptide and are removed by signal peptidases after the polypeptide has crossed the membrane. Signal peptide sequences typically contain three common structural features: an N-terminal polar basic region (n-region), a hydrophobic core, and a hydrophilic c-region). An exemplary signal peptide sequence is set forth as MYSMQLASCVTLTLVLLVNS (residues 1-20 of SEQ ID NO: 1 (NiV01)

Specifically bind: When referring to the formation of an antibody:antigen protein complex, or a protein:protein complex, refers to a binding reaction which determines the presence of a target protein, peptide, or polysaccharide (for example, a glycoprotein), in the presence of a heterogeneous population of proteins and other biologics. Thus, under designated conditions, a particular antibody or protein binds preferentially to a particular target protein, peptide or polysaccharide (such as an antigen present on the surface of a pathogen, for example, an antigenic site at the membrane distal apex of the NiV F ectodomain timer) and does not bind in a significant amount to other proteins or polysaccharides present in the sample or subject. Specific binding can be determined by methods known in the art. A first protein or antibody specifically binds to a target protein when the interaction has a $K_D$ of less than $10^{-6}$ Molar, such as less than $10^{-7}$ Molar, less than $10^{-8}$ Molar, less than $10^{-9}$, or even less than $10^{-10}$ Molar.

Soluble protein: A protein capable of dissolving in aqueous liquid at room temperature and remaining dissolved. The solubility of a protein may change depending on the concentration of the protein in the water-based liquid, the buffering condition of the liquid, the concentration of other solutes in the liquid, for example salt and protein concentrations, and the heat of the liquid. In several embodiments, a soluble protein is one that dissolves to a concentration of at least 0.5 mg/ml in phosphate buffered saline (pH 7.4) at room temperature and remains dissolved for at least 48 hours.

Subject: Living multi-cellular vertebrate organisms, a category that includes human and non-human mammals. In an example, a subject is a human. In a particular example, the subject is a newborn infant. In an additional example, a subject is selected that is in need of inhibiting of a NiV infection. For example, the subject is either uninfected and at risk of NiV infection or is infected in need of treatment.

T4 fibritin trimerization domain: Also referred to as a "foldon" domain, the T4 fibritin trimerization domain comprises an amino acid sequence that naturally forms a trimeric structure. In some examples, a T4 fibritin trimerization domain can be included in the amino acid sequence of a disclosed recombinant protein so that the antigen will form a trimer. In one example, a T4 fibritin trimerization domain comprises the amino acid sequence set forth as (GYIPEAPRDGQAYVRKDGEWVLLSTF (residues 24-49 of SEQ ID NO: 34). Several embodiments include a T4 fibritin trimerization domain that can be cleaved from a purified protein, for example by incorporation of a thrombin cleave site adjacent to the T4 fibritin trimerization domain that can be used for cleavage purposes.

Transmembrane domain: An amino acid sequence that inserts into a lipid bilayer, such as the lipid bilayer of a cell or virus or virus-like particle. A transmembrane domain can be used to anchor an antigen to a membrane. In some examples a transmembrane domain is a NiV F transmembrane domain.

Under conditions sufficient for: A phrase that is used to describe any environment that permits a desired activity.

Vaccine: A preparation of immunogenic material capable of stimulating an immune response, administered for the prevention, amelioration, or treatment of infectious or other types of disease. The immunogenic material may include attenuated or killed microorganisms (such as bacteria or viruses), or antigenic proteins, peptides, or DNA derived from them. A vaccine may include a disclosed immunogen (such as a recombinant NiV F ectodomain trimer or nucleic acid molecule encoding same), a virus, a cell or one or more cellular constituents. Vaccines may elicit both prophylactic (preventative or protective) and therapeutic responses. Methods of administration vary according to the vaccine, but may include inoculation, ingestion, inhalation or other forms of administration. Vaccines may be administered with an adjuvant to boost the immune response. In one specific, non-limiting example, a vaccine prevents and/or reduces the severity of the symptoms associated with NiV infection and/or decreases the viral load compared to a control.

Vector: An entity containing a DNA or RNA molecule bearing a promoter(s) that is operationally linked to the coding sequence of an antigen(s) of interest and can express the coding sequence. Non-limiting examples include a naked or packaged (lipid and/or protein) DNA, a naked or packaged RNA, a subcomponent of a virus or bacterium or other microorganism that may be replication-incompetent, or a virus or bacterium or other microorganism that may be replication-competent. A vector is sometimes referred to as a construct. Recombinant DNA vectors are vectors having recombinant DNA. A vector can include nucleic acid sequences that permit it to replicate in a host cell, such as an origin of replication. A vector can also include one or more selectable marker genes and other genetic elements known in the art. Viral vectors are recombinant nucleic acid vectors having at least some nucleic acid sequences derived from one or more viruses.

Virus-like particle (VLP): A non-replicating, viral shell, derived from any of several viruses. VLPs are generally composed of one or more viral proteins, such as, but not limited to, those proteins referred to as capsid, coat, shell, surface and/or envelope proteins, or particle-forming polypeptides derived from these proteins. VLPs can form spontaneously upon recombinant expression of the protein in an appropriate expression system. Methods for producing particular VLPs are known in the art. The presence of VLPs following recombinant expression of viral proteins can be detected using conventional techniques known in the art, such as by electron microscopy, biophysical characterization, and the like. Further, VLPs can be isolated by known techniques, e.g., density gradient centrifugation and identified by characteristic density banding. See, for example, Baker et al. (1991) *Biophys. J.* 60:1445-1456; and Hagensee et al. (1994) *J. Virol.* 68:4503-4505; Vincente, *J Invertebr Pathol.,* 2011; Schneider-Ohrum and Ross, *Curr. Top. Microbiol. Immunol.,* 354: 53073, 2012).

II. Immunogens

A. Recombinant NiV F Ectodomain Trimers

Recombinant NiV F ectodomain trimers are disclosed herein that are modified from a native form (e.g., by introduction of one or more amino acid substitutions) to be stabilized in a prefusion conformation. As described in the Examples, embodiments of the disclosed NiV F ectodomain trimers have been selected through multiple rounds of structure based design for optimized solubility, stability, expression, and immunogenicity. The recombinant NiV F ectodomain trimers are useful to induce an immune response in a vertebrate animal (such humans) to NiV. Exemplary embodiments are shown to produce a superior immune response in an animal model compared to corresponding NiV F ectodomain trimers that are not stabilized in the prefusion conformation.

In some embodiments, the immunogen comprises a recombinant NiV F ectodomain trimer comprising protomers comprising one or more amino acid substitutions or deletions that stabilize the NiV F ectodomain trimer in the prefusion conformation.

In some embodiments, the protomers of the recombinant NiV F ectodomain trimer comprise cysteine substitutions at NiV F positions 104 and 114 that form a non-natural intra-protomer disulfide bond for stabilization in the prefusion conformation.

In some embodiments, the protomers of the recombinant NiV F ectodomain trimer comprise cysteine substitutions at NiV F positions 104 and 114 that form a non-natural intra-protomer disulfide bond and a proline substitution at NiV F position 191 for stabilization in the prefusion conformation.

In some embodiments, the protomers of the recombinant NiV F ectodomain trimer comprise cysteine substitutions at NiV F positions 104 and 114 that form a non-natural intra-protomer disulfide bond and a phenylalanine substitution at NiV F position 172 for stabilization in the prefusion conformation.

In some embodiments, the protomers of the recombinant NiV F ectodomain trimer comprise cysteine substitutions at NiV F positions 104 and 114 that form a non-natural intra-protomer disulfide bond and a glycine substitution at NiV F position 70 for stabilization in the prefusion conformation.

In some embodiments, the protomers of the recombinant NiV F ectodomain trimer comprise cysteine substitutions at NiV F positions 104 and 114 that form a non-natural intra-protomer disulfide bond, a proline substitution at NiV F position 191, and a phenylalanine substitution at NiV F position 172, for stabilization in the prefusion conformation.

In some embodiments, the protomers of the recombinant NiV F ectodomain trimer comprise cysteine substitutions at NiV F positions 104 and 114 that form a non-natural intra-protomer disulfide bond, a phenylalanine substitution at NiV F position 172, and a glycine substitution at NiV F position 70, for stabilization in the prefusion conformation.

In some embodiments, the protomers of the recombinant NiV F ectodomain trimer comprise cysteine substitutions at NiV F positions 104 and 114 that form a non-natural intra-protomer disulfide bond, a proline substitution at NiV F position 191, and a glycine substitution at NiV F position 70 for stabilization in the prefusion conformation.

In some embodiments, the protomers of the recombinant NiV F ectodomain trimer comprise cysteine substitutions at NiV F positions 104 and 114 that form a non-natural intra-protomer disulfide bond, a proline substitution at NiV F position 191, a phenylalanine substitution at NiV F position 172, and a glycine substitution at NiV F position 70, for stabilization in the prefusion conformation.

In some embodiments, the protomers of the recombinant NiV F ectodomain trimer comprise cysteine substitutions at NiV F positions 114 and 426 that form a non-natural intra-protomer disulfide bond for stabilization in the prefusion conformation.

In some embodiments, the protomers of the recombinant NiV F ectodomain trimer comprise cysteine substitutions at NiV F positions 114 and 426 that form a non-natural intra-protomer disulfide bond and a proline substitution at NiV F position 191 for stabilization in the prefusion conformation.

In some embodiments, the protomers of the recombinant NiV F ectodomain trimer comprise cysteine substitutions at NiV F positions 114 and 426 that form a non-natural intra-protomer disulfide bond and a phenylalanine substitution at NiV F position 172 for stabilization in the prefusion conformation.

In some embodiments, the protomers of the recombinant NiV F ectodomain trimer comprise cysteine substitutions at NiV F positions 114 and 426 that form a non-natural intra-protomer disulfide bond and a glycine substitution at NiV F position 70 for stabilization in the prefusion conformation.

In some embodiments, the protomers of the recombinant NiV F ectodomain trimer comprise cysteine substitutions at NiV F positions 114 and 426 that form a non-natural intra-protomer disulfide bond, a proline substitution at NW F position 191, and a phenylalanine substitution at NiV F position 172, for stabilization in the prefusion conformation.

In some embodiments, the protomers of the recombinant NiV F ectodomain trimer comprise cysteine substitutions at NiV F positions 114 and 426 that form a non-natural intra-protomer disulfide bond, a phenylalanine substitution at NiV F position 172, and a glycine substitution at NiV F position 70, for stabilization in the prefusion conformation.

In some embodiments, the protomers of the recombinant NiV F ectodomain trimer comprise cysteine substitutions at NiV F positions 114 and 426 that form a non-natural intra-protomer disulfide bond, a proline substitution at NiV F position 191, and a glycine substitution at NiV F position 70 for stabilization in the prefusion conformation.

In some embodiments, the protomers of the recombinant NiV F ectodomain trimer comprise cysteine substitutions at NiV F positions 114 and 426 that form a non-natural intra-protomer disulfide bond, a proline substitution at NiV F position 191, a phenylalanine substitution at NiV F position 172, and a glycine substitution at NiV F position 70, for stabilization in the prefusion conformation.

In some embodiments, the protomers of the recombinant NiV F ectodomain trimer comprise a proline substitution at NiV F position 191 for stabilization in the prefusion conformation.

In some embodiments, the protomers of the recombinant NiV F ectodomain trimer comprise a phenylalanine substitution at NiV F position 172 for stabilization in the prefusion conformation. In some embodiments, the protomers of the recombinant NiV F ectodomain trimer comprise a glycine substitution at NiV F position 70 for stabilization in the prefusion conformation.

In some embodiments, the protomers of the recombinant NiV F ectodomain trimer comprise a proline substitution at NiV F position 191 and a phenylalanine substitution at NiV F position 172 for stabilization in the prefusion conformation.

In some embodiments, the protomers of the recombinant NiV F ectodomain trimer comprise a proline substitution at NiV F position 191 and a glycine substitution at NiV F position 70 for stabilization in the prefusion conformation.

In some embodiments, the protomers of the recombinant NiV F ectodomain trimer comprise a phenylalanine substitution at NiV F position 172 and a glycine substitution at NiV F position 70 for stabilization in the prefusion conformation.

In some embodiments, the protomers of the recombinant NiV F ectodomain trimer comprise a proline substitution at NiV F position 191, a phenylalanine substitution at NiV F position 172, and a glycine substitution at NiV F position 70, for stabilization in the prefusion conformation.

Any of the above recombinant NW F proteins can further comprise modification to eliminate the protease cleavage site between the F1 and F2 polypeptides to generate a "single chain" recombinant F protein. For example, except for variants listed above including modification within positions 102-113, any of the above recombinant NiV proteins can comprise deletion of NiV F positions 102-113 with positions 101 and 114 linked by a glycine-serine linker For the embodiments listed above, non-limiting examples of specific amino acid substitutions include: L104C and I114C substitutions for the cysteine substitutions at NiV F positions 104 and 114; I114C and I426C substitutions for the cysteine substitutions at NiV F positions 114 and 426; a S191P substitution for the proline substitution at NiV F position 191; a L172F substitution for the phenylalanine substitution at NiV F position 172; a Q70G substitution for the glycine substitution at NiV F position 70; and a (HDLVGDVRLAGV)102-113(GSG) substitution for the deletion of NiV F positions 102-113 with positions 101 and 114 linked by a glycine-serine linker.

In several embodiments, the protomers of the recombinant NiV F ectodomain can comprise one or more additional amino acid substitutions, for example, to increase stabilization of the prefusion conformation, or for other purposes, such as to increase solubility or to reduce and unwanted immune response.

The above-listed non-native disulfide bonds stabilize the membrane-distal portion of the NiV F ectodomain in its prefusion conformation. Any of these mutations can be combined with modifications to the membrane proximal portion (such as the stem) of the NiV F ectodomain, for example, to increase trimerization of the ectodomain.

In several embodiments, the N-terminal position of the recombinant $F_2$ polypeptide in the protomer can be one of NiV F positions 20-30 (such as position 25), and the C-terminal position of the $F_1$ ectodomain can be from the stem region of the ectodomain, such as one of NiV F positions 475-495 (such as positions 480-490, for example, position 488).

Non-limiting examples of protomers of a NiV F ectodomain trimer including amino acid substitutions for stabilization in the prefusion conformation as well as a C-terminal linkage to a trimerization domain are provided as residues 21-486 of any one of SEQ ID NOs: 5, 7-7, 11-18, 20-21, 23-24, and 26-32, and residues 21-477 of any one of SEQ ID NOs: 19, 22, and 25. In some embodiments, the protomers of the NiV F ectodomain trimer comprise an amino acid sequence at least 90% identical to residues 21-486 of any one of SEQ ID NOs: 5, 7-7, 11-18, 20-21, 23-24, and 26-32, or residues 21-477 of any one of SEQ ID NOs: 19, 22, and 25; wherein the protomers comprise the one or more amino acid substitutions that stabilize the NiV F ectodomain trimer in the prefusion conformation. In some embodiments, the protomers of the NiV F ectodomain trimer comprise residues 21-486 of any one of SEQ ID NOs: 5, 7-7, 11-18, 20-21, 23-24, and 26-32, or residues 21-477 of any one of SEQ ID NOs: 19, 22, and 25.

In several embodiments, the recombinant NiV F ectodomain trimer is a soluble protein complex, for example, for use as a recombinant subunit vaccine. In several such embodiments, the protomers of the recombinant NiV F ectodomain trimer can each comprise a C-terminal linkage to a trimerization domain, such as a GCN4 trimerization domain or a T4 fibritin trimerization domain. The trimerization domain promotes trimerization and stabilization of the membrane proximal aspect of the recombinant NiV F ectodomain trimer. For example, a C-terminal residue of the protomers of the recombinant NiV F ectodomain trimer (such as a residue of the stem region of the trimer) can be directly linked to the trimerization domain, or indirectly linked to the trimerization domain via a peptide linker. Exemplary linkers include glycine and glycine-serine linkers. Non-limiting examples of exogenous multimerization domains that promote stable trimers of soluble recombinant proteins include: the GCN4 leucine zipper, a T4 fibritin trimerization domain, the trimerization motif from the lung surfactant protein (Hoppe et al. 1994 *FEBS Lett* 344:191-195) or collagen (McAlinden et al. 2003 *J Biol Chem* 278:42200-42207), any of which can be linked to the C-terminus of the protomers of a recombinant NiV F ectodomain to promote trimerization, as long as the recombinant NiV F ectodomain trimer retains the prefusion conformation. In some examples, the protomers of the recombinant NiV F ectodomain trimer can be linked to a NiV trimerization domain, for example, each protomer in the trimer can include a C-terminal linkage to the GCN4 trimerization domain, such as a linkage to any one of NiV F positions 470-490, such as NiV F position 488. In specific examples, the GCN4 fibritin trimerization domain can comprise the amino acid sequence IEDKIEEILSKIYHIENEIARIKKLIGEAP (residues 490-519 of NiV01, SEQ ID NO: 1).

Non-limiting examples of protomers of a NiV F ectodomain trimer including amino acid substitutions for stabilization in the prefusion conformation as well as a C-terminal linkage to a trimerization domain are provided as residues 21-519 of any one of SEQ ID NOs: 5, 7-7, 11-18, 20-21, 23-24, and 26-32, and residues 21-510 of any one of SEQ ID NOs: 19, 22, and 25. In some embodiments, the protomers of the NiV F ectodomain trimer comprise an amino acid sequence at least 90% identical to residues 21-519 of any one of SEQ ID NOs: 5, 7-7, 11-18, 20-21, 23-24, and 26-32, or residues 21-510 of any one of SEQ ID NOs: 19, 22, and 25; wherein the protomers comprise the one or more amino acid substitutions that stabilize the NiV F ectodomain trimer in the prefusion conformation. In some embodiments, the protomers of the NiV F ectodomain trimer comprise residues 21-519 of any one of SEQ ID NOs: 5, 7-7, 11-18, 20-21, 23-24, and 26-32, or residues 21-510 of any one of SEQ ID NOs: 19, 22, and 25.

In some embodiments, the recombinant NW F ectodomain trimer can be a membrane anchored protein complex, for example, for use in an attenuated virus or virus like particle vaccine. Membrane anchoring can be accomplished, for example, by C-terminal linkage of the protomers of the recombinant NiV F ectodomain trimer to a transmembrane domain and optionally a cytoplasmic tail, such as an NiV F transmembrane domain and cytoplasmic tail. In some embodiments, one or more peptide linkers (such as a gly-ser linker, for example, a 10 amino acid glycine-serine peptide linker can be used to link the protomers of the recombinant NiV F ectodomain trimer to the transmembrane domain. A non-limiting example of a transmembrane domain for use with the disclosed embodiments includes an NiV F transmembrane domain, such as ILYVLSIASLCIGLITFISFIIV (residues 496-518 of SEQ ID NO: 52).

Native NiV F proteins from different NiV strains, as well as nucleic acid sequences encoding such proteins and methods, are known and can be altered using the description provided herein to generate a recombinant NiV F ectodomain trimer.

B. NiV F Ectodomain Trimers linked to a Heterologous Moiety

The recombinant NiV F ectodomain can be derivatized or linked to another molecule (such as another peptide or protein). In general, the recombinant NiV F ectodomain is derivatized such that the binding to broadly neutralizing antibodies to a trimer of the recombinant NiV F protein is not affected adversely by the derivatization or labeling. For example, the recombinant NiV F ectodomain can be functionally linked (by chemical coupling, genetic fusion, noncovalent association or otherwise) to one or more other molecular entities, such as an antibody or protein or detection tag.

In some embodiments, the recombinant NiV F ectodomain trimers are fused to a NiV G ectodomain (such as the ectodomain of the G sequence set forth as SEQ ID NO: 53 or 54). For example, the protomers of the recombinant NiV F ectodomain trimer are each fused to a NiV G protein ectodomain. The fusion can be direct or via a peptide linker. In some embodiments, the NiV G ectodomain can be fused, directly or indirectly via a peptide linker to the N-terminus of the protomers of the NiV F ectodomain trimer. In some embodiments, the NiV G ectodomain can be fused, directly or indirectly via a peptide linker, to the C-terminus of the protomers of the NiV F ectodomain trimer. In some such embodiments, the NiV G ectodomain can be fused, directly or indirectly via a peptide linker, to the C-terminus of a trimerization domain (such as a GCN4 or T4 fibritin trimerization domain) fused to the C-terminus of the protomers of the NiV F ectodomain trimer. In some such embodiments, the protomers of the NiV F ectodomain trimer linked to the trimerization domain and the NiV G ectodomain comprise an amino acid sequence set forth as residues 21-981 of SEQ ID NO: 43 (NiVop08-TD(GCN4-Fd)-G) or residues 27-981 of SEQ ID NO: 44 (G-NiVop08-TD(GCN4-Fd)), residues 21-952 of SEQ ID NO: 59 (NiVop08-GCN4-G), or residues 21-946 of SEQ ID NO: 60 (NiVop08-Fd-G), or an amino acid sequence at least 90% identical to residues 21-981 of SEQ ID NO: 43 (NiVop08-TD(GCN4-Fd)-G), residues 27-981 of SEQ ID NO: 44 (G-NiVop08-TD(GCN4-Fd)), residues 21-952 of SEQ ID NO: 59 (NiVop08-GCN4-G), or residues 21-946 of SEQ ID NO: 60 (NiVop08-Fd-G).

In some embodiments, more than one (such as 2, 3, or 4) NiV G ectodomain is fused to the protomers of the NiV F trimer. For example, a first NiV G ectodomain can be fused, directly or indirectly via a peptide linker, to the N-terminus of the protomers of the NiV F ectodomain trimer, and a second NiV G ectodomain can be fused, directly or indirectly via a peptide linker, to the C-terminus of the protomers of the NiV F ectodomain trimer (or to the C-terminus of a trimerization domain (such as a GCN4 or T4 fibritin trimerization domain) fused to the C-terminus of the protomers of the NiV F ectodomain trimer).

In some embodiments, the recombinant NiV F ectodomain trimers are fused to an ectodomain of a G protein from a heterologous henipavirus, such as Hendra virus (HeV), Cedar virus (CedV), Kumasi virus (KV), Hendra virus (HeV), or Mòjiāng virus (MojV). For example, the recombinant NiV F ectodomain trimers are fused to an HeV G ectodomain comprising the sequence set forth as:

```
REYRPISQGVSDLVGLPNQICLQKTTSTILKPRLISYTLPINTREGVCIT
DPLLAVDNGFFAYSHLEKIGSCTRGIAKQRIIGVGEVLDRGDKVPSMFMT
NVWTPPNPSTIHHCSSTYHEDFYYTLCAVSHVGDPILNSTSWTESLSLIR
LAVRPKSDSGDYNQKYIAITKVERGKYDKVMPYGPSGIKQGDTLYFPAVG
FLPRTEFQYNDSNCPIIHCKYSKAENCRLSMGVNSKSHYILRSGLLKYNL
SLGGDITLQFIEIADNRLTIGSPSKIYNSLGQPVFYQASYSWDTMIKLGD
VDTVDPLRVQWRNNSVISRPGQSQCPRFNVCPEVCWEGTYNDAFLIDRLN
WVSAGVYLNSNQTAENPVFAVFKDNEILYQVPLAEDDTNAQKTITDCFLL
ENVIWCISLVEIYDTGDSVIRPKLFAVKIPAQCSES
```

In some such embodiments, the protomers of the recombinant NiV F ectodomain trimer are each fused to the ectodomain of the G protein from the henipavirus, such as an HeV G ectodomain. The fusion can be direct or via a peptide linker. In some embodiments, the ectodomain of the G protein from the henipavirus (such as HeV G ectodomain) can be fused, directly or indirectly via a peptide linker to the N-terminus of the protomers of the NiV F ectodomain trimer. In some embodiments, the ectodomain of the G protein from the henipavirus (such as HeV G ectodomain) can be fused, directly or indirectly via a peptide linker, to the C-terminus of the protomers of the NiV F ectodomain trimer. In some such embodiments, the ectodomain of the G protein from the henipavirus (such as HeV G ectodomain) can be fused, directly or indirectly via a peptide linker, to the C-terminus of a trimerization domain (such as a GCN4 or T4 fibritin trimerization domain) fused to the C-terminus of the protomers of the NiV F ectodomain trimer. In some such embodiments, the protomers of the NW F ectodomain trimer linked to the trimerization domain and the ectodomain of the G protein from the henipavirus (such as HeV G ectodomain) comprise an amino acid sequence set forth as:

```
NiVop8-HeV G (SEQ ID NO: 69):
mysmqlascvtltlvl1vnsQGILHYEKLSKIGLVKGVTRKYKIKSNPLT
KDIVIKMIPNVSNMSQCTGSVMENYKTRLNGILTPIKGALEIYKNNTHDC
VGDVRLAGVCMAGVAIGIATAAQITAGVALYEAMKNADNINKLKSSIEST
NEAVVKLQETAEKTVYVFTALQDYINTNLVPTIDKIPCKQTELSLDLALS
KYLSDLLFVFGPNLQDPVSNSMTIQAISQAFGGNYETLLRTLGYATEDFD
DLLESDSITGQIIYVDLSSYYIIVRVYFPILTEIQQAYIQELLPVSFNND
NSEWISIVPNFILVRNTLISNIEIGFCLITKRSVICNQDYATPMTNNMRE
CLTGSTEKCPRELVVSSHVPRFALSNGVLFANCISVTCQCQTTGRAISQS
GEQTLLMIDNTTCPTAVLGNVIISLGKYLGSVNYNSEGIAIGPPVFTDKV
DISSQISSMNQSLQQSKDYIKEAQRLLDTVNPSLKLMKQIEDKIEEILSK
IYHIENEIARIKKLIGEAPGSGYIPEAPRDGQAYVRKDGEWVLLSTFLGS
GGGGGGVSDLVGLPNQICLQKTTSTILKPRLISYTLPINTREGVCITDPL
LAVDNGFFAYSHLEKIGSCTRGIAKQRIIGVGEVLDRGDKVPSMFMTNVW
TPPNPSTIHHCSSTYHEDFYYTLCAVSHVGDPILNSTSWTESLSLIRLAV
RPKSDSGDYNQKYIAITKVERGKYDKVMPYGPSGIKQGDTLYFPAVGFLP
RTEFQYNDSNCPIIHCKYSKAENCRLSMGVNSKSHYILRSGLLKYNLSLG
GDITLQFIEIADNRLTIGSPSKIYNSLGQPVFYQASYSWDTMIKLGDVDT
VDPLRVQWRNNSVISRPGQSQCPRFNVCPEVCWEGTYNDAFLIDRLNWVS
AGVYLNSNQTAENPVFAVFKDNEILYQVPLAEDDTNAQKTITDCFLLENV
IWCISLVEIYDTGDSVIRPKLFAVKIPAQCSESgglvprgshhhhhhsaw
shpqfek
```

```
HeV G-NiVop8 (SEQ ID NO: 70):
mysmqlascvtltlvllvnsqrpqtegvsnlvglpnniclqktsnqilkp
klisytlpvvgqsgtcitdpllamdegyfayshlerigscsrgvskqrii
gvgevldrgdevpslfmtnvwtppnpntvyhcsavynnefyyvlcavstv
gdpilnstywsgs1mmtrlavkpksngggynqhqlalrsiekgrydkvmp
ygpsgikqgdtlyfpavgflvrtefkyndsncpitkcqyskpencrlsmg
irpnshyilrsgllkynlsdgenpkvvfieisdqrlsigspskiydslgq
pvfyqasfswdtmikfgdvltvnplvvnwrnntvisrpgqsqcprfntcp
eicwegvyndaflidrinwisagvfldsnqtaenpvftvfkdneilyraq
lasedtnaqktitncfllknkiwcislveiydtgdnvirpklfavkipeq
ctgggQGILHYEKLSKIGLVKGVTRKYKIKSNPLTKDIVIKMIPNVSNMS
QCTGSVMENYKTRLNGILTPIKGALEIYKNNTHDCVGDVRLAGVCMAGVA
IGIATAAQITAGVALYEAMKNADNINKLKSSIESTNEAVVKLQETAEKTV
YVFTALQDYINTNLVPTIDKIPCKQTELSLDLALSKYLSDLLFVFGPNLQ
DPVSNSMTIQAISQAFGGNYETLLRTLGYATEDFDDLLESDSITGQIIYV
DLSSYYIIVRVYFPILTEIQQAYIQELLPVSFNNDNSEWISIVPNFILVR
NTLISNIEIGFCLITKRSVICNQDYATPMTNNMRECLTGSTEKCPRELVV
SSHVPRFALSNGVLFANCISVTCQCQTTGRAISQSGEQTLLMIDNTTCPT
```

-continued

AVLGNVIISLGKYLGSVNYNSEGIAIGPPVFTDKVDISSQISSMNQSLQQ

SKDYIKEAQRLLDTVNPSLKLMKQIEDKIEEILSKIYHIENEIARIKKLI

GEAPGSGYIPEAPRDGQAYVRKDGEWVLLSTFLGSLVPRGSHHHHHHSAW

SHPQFEK

The above sequences include an N-terminal signal peptide, a NiV F ectodomain (NiVop8), a HeV G ectodomain, a GCN4 trimerization domain, a T4-fibritin trimerization domain, a thrombin cleavage site, a HIS tag and a Strep tag, as well as various linker residues between segments. Purified forms of these proteins typically lack the N-terminal signal peptide and C-terminal residues removed by thrombin cleavage.

In some embodiments, more than one (such as 2, 3, or 4) ectodomain of the G protein from the henipavirus (such as HeV G ectodomain) is fused to the protomers of the NiV F trimer. For example, a first the ectodomain of the G protein from the henipavirus (such as HeV G ectodomain) can be fused, directly or indirectly via a peptide linker, to the N-terminus of the protomers of the NiV F ectodomain trimer, and a second the ectodomain of the G protein from the henipavirus (such as HeV G ectodomain) can be fused, directly or indirectly via a peptide linker, to the C-terminus of the protomers of the NiV F ectodomain trimer (or to the C-terminus of a trimerization domain (such as a GCN4 or T4 fibritin trimerization domain) fused to the C-terminus of the protomers of the NW F ectodomain trimer).

C. NiV G Multimers Including a Trimerization Domain

In some embodiments, an immunogen is provided that comprises a multimer of NiV G ectodomains. In some embodiments, the immunogen comprises a trimer of fusion proteins, each fusion protein comprising one or more NiV G ectodomains and a trimerization domain (such as a GCN4 trimerization domain, a T4 fibritin trimerization domain, or a GCN4 trimerization domain fused to a T4 fibritin trimerization domain). In some embodiments, the fusion protein comprises, in an N- to C-terminal direction, one or more (such as one, two, or three) NiV G ectodomains and a trimerization domain. In some embodiments, the fusion protein comprises, in an N- to C-terminal direction, a trimerization domain and one or more (such as one, two, or three) NiV G ectodomains. In some embodiments, the fusion protein comprises, in an N- to C-terminal direction, one or more (such as one, two, or three) NiV G ectodomains, a trimerization domain, and one or more (such as one, two, or three) NiV G ectodomains. The trimerization domains interact to form the trimer. In some embodiment, the fusion proteins in the trimer comprise or consist of an amino acid sequence set forth as residues 21-463 of SEQ ID NO: 34, residues 21-895 of SEQ ID NO: 35, residues 21-1327 of SEQ ID NO: 36, residues 23-912 of SEQ ID NO: 37, or an sequence at least 90% identical to any one of residues 21-463 of SEQ ID NO: 34, residues 21-895 of SEQ ID NO: 35, residues 21-1327 of SEQ ID NO: 36, or residues 23-912 of SEQ ID NO: 37.

D. Additional Description

The protomers in the recombinant NiV F ectodomain trimer can comprise modifications of the native NiV F sequence in addition to those noted above, such as amino acid substitutions, deletions or insertions, glycosylation and/or covalent linkage to unrelated proteins (e.g., a protein tag), as long as the recombinant NiV F ectodomain trimer remains stabilized in the prefusion conformation and retains immunogenicity. Further, the fusion proteins in the NiV G ectodomain multimer can comprise modifications of the native NiV G sequence, such as amino acid substitutions, deletions or insertions, glycosylation and/or covalent linkage to unrelated proteins (e.g., a protein tag), as long as the NiV G ectodomain retains immunogenicity. These variations in sequence can be naturally occurring variations or they can be engineered through the use of genetic engineering technique known to those skilled in the art. Examples of such techniques are found in see, e.g., Sambrook et al. (Molecular Cloning: A Laboratory Manual, 4th ed., Cold Spring Harbor, N.Y., 2012) and Ausubel et al. (In Current Protocols in Molecular Biology, John Wiley & Sons, New York, through supplement 104, 2013, both of which are incorporated herein by reference in their entirety.

In some embodiments, the protomers in the recombinant NiV F ectodomain trimer or the NiV G multimer can comprise one or more amino acid substitutions compared to a corresponding native NiV F or G sequence. For example, in some embodiments, the $F_2$ polypeptide, $F_1$ ectodomain, or both, can include up to 20 (such as up to 1, 2, 3, 4, 5, 6, 7, 8, 9, 10, 11, 12, 13, 14, 15, 16, 17, 18, or 19) amino acid substitutions (such as conservative amino acid substitutions) compared to a native NiV F or G sequence. The simplest modifications involve the substitution of one or more amino acids for amino acids having similar biochemical properties, such as conservative amino acid substitutions. Such substitutions are likely to have minimal impact on the activity of the resultant protein.

In some embodiments, protomers in the recombinant NiV F ectodomain trimer or the NiV G multimer can be joined at either end to other unrelated sequences (for example non-NiV F or G protein sequences, non-viral envelope, or non-viral protein sequences)

In several embodiments, the recombinant NiV F ectodomain trimer or NiV G multimer is soluble in aqueous solution. In some embodiments, the recombinant NiV F ectodomain trimer or NiV G multimer dissolves to a concentration of at least 0.5 mg/ml (such as at least 1.0 mg/ml, 1.5 mg/ml, 2.0 mg/ml, 3.0 mg/ml, 4.0 mg/ml or at least 5.0 mg/ml) in aqueous solution (such as phosphate buffered saline (pH 7.4) or 350 mM NaCl (pH 7.0)) at room temperature (e.g., 20-22 degrees Celsius) and remain dissolved for at least 12 hours (such as at least 24 hours, at least 48 hours, at least one week, at least two weeks, at least one month, or more time). In one embodiment, the phosphate buffered saline includes NaCl (137 mM), KCl (2.7 mM), $Na_2HPO_4$ (10 mM), $KH_2PO_4$ (1.8 mM) at pH 7.4. In some embodiments, the phosphate buffered saline further includes $CaCl_2$ (1 mM) and $MgCl_2$ (0.5 mM). The person of skill in the art is familiar with methods of determining if a protein remains in solution over time. For example, the concentration of the protein dissolved in an aqueous solution can be tested over time using standard methods.

In some embodiments, the recombinant NiV F ectodomain trimer can be provided as a homogenous population of soluble trimers that does not include detectable NiV F ectodomain trimer in a postfusion conformation. The conformation of the NiV F ectodomain trimer can be detected, for example, by negative stain electron microscopy and/or specific binding by appropriate pre- or post-fusion specific antibody. In some embodiments, at least about 95% of the recombinant NiV F ectodomain trimer (such as at least about 95%, 96%, 97%, 98%, 99% or 99.9% of the NiV F proteins) in the homogeneous population are stabilized in the prefusion conformation.

In some embodiments, the recombinant NW F ectodomain trimer retains specific binding for a prefusion specific antibody following incubation at 50° C. for one hour in phosphate buffered saline. In some embodiments, the recombinant NiV F ectodomain trimer retains specific binding for a prefusion specific antibody following incubation at 4° C. for six months in phosphate buffered saline.

In certain embodiments, an immunogen provided herein may be further modified to contain additional nonproteinaceous moieties that are known in the art and readily available. The moieties suitable for derivatization of the immunogen include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, prolypropylene oxide/ethylene oxide copolymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the immunogen to be improved or altered, whether the immunogen derivative will be used in a therapy under defined conditions, etc.

Some of the sequences including recombinant NiV F or G ectodomain provided herein include the sequence of protease cleavage sites (such as thrombin sites), protein tags (such as a His tag, a Strep Tag II, a Avi tag, etc.), and signal peptides; such sequences can be removed from an isolated immunogen including a recombinant NiV F or G ectodomain trimer for therapeutic use.

E. Protein Nanoparticles

In some embodiments, a protein nanoparticle is provided that includes one or more of the disclosed recombinant NiV F ectodomain trimers or a NiV G ectodomain. Non-limiting example of nanoparticles include ferritin nanoparticles, encapsulin nanoparticles, Sulfur Oxygenase Reductase (SOR) nanoparticles, and lumazine synthase nanoparticles, which are comprised of an assembly of monomeric subunits including ferritin proteins, encapsulin proteins, SOR proteins, and lumazine synthase, respectively. To construct such protein nanoparticles a protomer of the NiV F ectodomain trimer can be linked to a subunit of the protein nanoparticle (such as a ferritin protein, an encapsulin protein, a SOR protein, or a lumazine synthase protein) and expressed in cells under appropriate conditions. The fusion protein self-assembles into a nanoparticle any can be purified.

In some embodiments, a protomer of a disclosed recombinant NiV F ectodomain trimer, or a NiV G ectodomain, can be linked to a ferritin subunit to construct a ferritin nanoparticle. Ferritin nanoparticles and their use for immunization purposes (e.g., for immunization against influenza antigens) have been disclosed in the art (see, e.g., Kanekiyo et al., Nature, 499:102-106, 2013, incorporated by reference herein in its entirety). The globular form of the ferritin nanoparticle is made up of monomeric subunits, which are polypeptides having a molecule weight of approximately 17-20 kDa. Following production, these monomeric subunit proteins self-assemble into the globular ferritin protein. Thus, the globular form of ferritin comprises 24 monomeric, subunit proteins, and has a capsid-like structure having 432 symmetry. Methods of constructing ferritin nanoparticles are further described herein (see, e.g., Zhang, Int. J. Mol. Sci., 12:5406-5421, 2011, which is incorporated herein by reference in its entirety). An example of the amino acid sequence of one such monomeric ferritin subunit is represented by:

```
                                    (SEQ ID NO: 55)
DIIKLLNEQVNKEMQSSNLYMSMSSWCYTHSLDGAGLFLFDHAAEEYEH

AKKLIIFLNENNVPVQLTSISAPEHKFEGLTQIFQKAYEHEQHISESIN

NIVDHAIKSKDHATFNFLQWYVAEQHEEEVLFKDILDKIELIGNENHGL

YLADQYVKGIAKSRKS
```

In specific examples, the ferritin polypeptide is *E. coli* ferritin, *Helicobacter pylori* ferritin, human light chain ferritin, bullfrog ferritin or a hybrid thereof, such as *E. coli*-human hybrid ferritin, *E. coli*-bullfrog hybrid ferritin, or human-bullfrog hybrid ferritin. Exemplary amino acid sequences of ferritin polypeptides and nucleic acid sequences encoding ferritin polypeptides for use to make a ferritin nanoparticle including a recombinant NiV F ectodomain trimer can be found in GENBANK®, for example at accession numbers ZP_03085328, ZP_06990637, EJB64322.1, AAA35832, NP_000137 AAA49532, AAA49525, AAA49524 and AAA49523, which are specifically incorporated by reference herein in their entirety as available Apr. 10, 2015. In some embodiments, a protomer of a recombinant NiV F ectodomain trimer can be linked to a ferritin subunit including an amino acid sequence at least 80% (such as at least 85%, at least 90%, at least 95%, or at least 97%) identical to amino acid sequence set forth as SEQ ID NO: 55.

In some embodiments, the self-assembling fusion proteins that form the ferritin nanoparticle comprise or consist of an amino acid sequence set forth as any one of residues 57-652 of SEQ ID NO: 38, residues 57-661 of SEQ ID NO: 39, residues 57-671 of SEQ ID NO: 40, residues 57-681 of SEQ ID NO: 41, or a sequence at least 90% identical to any one of residues 57-652 of SEQ ID NO: 38, residues 57-661 of SEQ ID NO: 39, residues 57-671 of SEQ ID NO: 40, residues 57-681 of SEQ ID NO: 41.

In some embodiments, a protomer of a disclosed recombinant NiV F ectodomain trimer, or a NiV G ectodomain, can be linked to a lumazine synthase subunit to construct a lumazine synthase nanoparticle. The globular form of lumazine synthase nanoparticle is made up of monomeric subunits; an example of the sequence of one such lumazine synthase subunit is provides as the amino acid sequence set forth as:

```
                                    (SEQ ID NO: 56)
MQIYEGKLTAEGLRFGIVASRFNHALVDRLVEGAIDCIVRHGGREEDITL

VRVPGSWEIPVAAGELARKEDIDAVIAIGVLIRGATPHFDYIASEVSKGL

ADLSLELRKPITFGVITADTLEQAIERAGTKHGNKGWEAALSAIEMANLF

KSLR.
```

In some embodiments, a protomer of a disclosed recombinant NiV F ectodomain trimer, or a NiV G ectodomain, can be linked to a lumazine synthase subunit including an amino acid sequence at least 80% (such as at least 85%, at least 90%, at least 95%, or at least 97%) identical to amino acid sequence set forth as SEQ ID NO: 56.

In some embodiments, the self-assembling fusion proteins that form the lumazine synthase nanoparticle comprise or consist of an amino acid sequence set forth as any one of residues 57-647 of SEQ ID NO: 42, or a sequence at least 90% identical to any one of residues 57-647 of SEQ ID NO: 42.

In some embodiments, a protomer of a disclosed recombinant NiV F ectodomain trimer, or a NiV G ectodomain, can be linked to an encapsulin nanoparticle subunit to construct an encapsulin nanoparticle. The globular form of the encapsulin nanoparticle is made up of monomeric subunits; an example of the sequence of one such encapsulin subunit is provides as the amino acid sequence set forth as (SEQ ID NO: 57)
MEFLKRSFAPLTEKQWQEIDNRAREIFKTQLYGRKFVDVEGPYGWEYAAH

PLGEVEVLSDENEVVKWGLRKSLPLIELRATFTLDLWELDNLERGKPNVD

LSSLEETVRKVAEFEDEVIFRGCEKSGVKGLLSFEERKIECGSTPKDLLE

AIVRALSIFSKDGIEGPYTLVINTDRWINFLKEEAGHYPLEKRVEECLRG

GKIITTPRIEDALVVSERGGDFKLILGQDLSIGYEDREKDAVRLFITETF

TFQVVNPEALILLKF.

In some embodiments, a protomer of a disclosed recombinant NiV F ectodomain trimer, or a NiV G ectodomain, can be linked to an encapsulin subunit including an amino acid sequence at least 80% (such as at least 85%, at least 90%, at least 95%, or at least 97%) identical to amino acid sequence set forth as SEQ ID NO: 57.

Encapsulin proteins are a conserved family of bacterial proteins also known as linocin-like proteins that form large protein assemblies that function as a minimal compartment to package enzymes. The encapsulin assembly is made up of monomeric subunits, which are polypeptides having a molecule weight of approximately 30 kDa. Following production, the monomeric subunits self-assemble into the globular encapsulin assembly including 60, or in some cases, 180 monomeric subunits. Methods of constructing encapsulin nanoparticles are further described (see, for example, Sutter et al., Nature Struct. and Mol. Biol., 15:939-947, 2008, which is incorporated by reference herein in its entirety). In specific examples, the encapsulin polypeptide is bacterial encapsulin, such as *Thermotoga maritime* or *Pyrococcus furiosus* or *Rhodococcus erythropolis* or *Myxococcus xanthus* encapsulin.

In some embodiments, a protomer of a disclosed recombinant NiV F ectodomain trimer, or a NiV G ectodomain, can be linked to a Sulfur Oxygenase Reductase (SOR) subunit to construct a recombinant SOR nanoparticle. In some embodiments, the SOR subunit can include the amino acid sequence set forth as (SEQ ID NO: 58)
MEFLKRSFAPLTEKQWQEIDNRAREIFKTQLYGRKFVDVEGPYGWEYAAH

PLGEVEVLSDENEVVKWGLRKSLPLIELRATFTLDLWELDNLERGKPNVD

LSSLEETVRKVAEFEDEVIFRGCEKSGVKGLLSFEERKIECGSTPKDLLE

AIVRALSIFSKDGIEGPYTLVINTDRWINFLKEEAGHYPLEKRVEECLRG

GKIITTPRIEDALVVSERGGDFKLILGQDLSIGYEDREKDAVRLFITETF

TFQVVNPEALILLKF.

In some embodiments, a protomer of a disclosed recombinant NiV F ectodomain trimer, or a NiV G ectodomain, can be linked to a SOR subunit including an amino acid sequence at least 80% (such as at least 85%, at least 90%, at least 95%, or at least 97%) identical to amino acid sequence set forth as SEQ ID NO: 58.

SOR proteins are microbial proteins (for example from the thermoacidophilic archaeon *Acidianus ambivalens* that form 24 subunit protein assemblies. Methods of constructing SOR nanoparticlesare described in Urich et al., Science, 311:996-1000, 2006, which is incorporated by reference herein in its entirety. An example of an amino acid sequence of a SOR protein for use to make SOR nanoparticles is set forth in Urich et al., Science, 311:996-1000, 2006, which is incorporated by reference herein in its entirety.

For production purposes, the recombinant NiV F ectodomain, or the NiV G ectodomain, linked to the nanoparticle subunit can include an N-terminal signal peptide that is cleaved during cellular processing. For example, the recombinant NiV F ectodomain protomer, or the NiV G ectodomain, linked to the protein nanoparticle subunit can include a signal peptide at its N-terminus including, for example, a native NiV F or G signal peptide.

The protein nanoparticles can be expressed in appropriate cells (e.g., HEK 293 Freestyle cells) and fusion proteins are secreted from the cells self-assembled into nanoparticles. The nanoparticles can be purified using known techniques, for example by a few different chromatography procedures, e.g. Mono Q (anion exchange) followed by size exclusion (SUPEROSE® 6) chromatography.

Several embodiments include a monomeric subunit of a ferritin, encapsulin, SOR, or lumazine synthase protein, or any portion thereof which is capable of directing self-assembly of monomeric subunits into the globular form of the protein Amino acid sequences from monomeric subunits of any known ferritin, encapsulin, SOR, or lumazine synthase protein can be used to produce fusion proteins with the recombinant NiV F ectodomain, or the NiV G ectodomain, as long as the monomeric subunit is capable of self-assembling into a nanoparticle displaying the recombinant NiV F ectodomain trimer or the NiV G ectodomain on its surface.

The fusion proteins need not comprise the full-length sequence of a monomeric subunit polypeptide of a ferritin, encapsulin, SOR, or lumazine synthase protein. Portions, or regions, of the monomeric subunit polypeptide can be utilized so long as the portion comprises amino acid sequences that direct self-assembly of monomeric subunits into the globular form of the protein.

II. Polynucleotides and Expression

Also provided are polynucleotides encoding any of the disclosed immunogens. For example, a polynucleotide encoding a protomer of a NiV F ectodomain trimer stabilized in the prefusion conformation, a chimera of the recombinant NiV F ectodomain trimer and one or more G ectodomains, a multimer of NiV G ectodomains, or a subunit of a self-assembling protein nanoparticle containing a recombinant NiV F or G ectodomain. These polynucleotides include DNA, cDNA and RNA sequences which encode the protomer. The genetic code can be used to construct a variety of functionally equivalent nucleic acids, such as nucleic acids which differ in sequence but which encode the same protein sequence, or encode a conjugate or fusion protein including the nucleic acid sequence.

In several embodiments, the nucleic acid molecule encodes a precursor of a protomer of the NiV F ectodomain trimer, that, when expressed in an appropriate cell, is processed into a protomer of the F ectodomain trimer that can self-assemble into the corresponding trimer. For example, the nucleic acid molecule can encode a protomer of the NiV F ectodomain trimer including a N-terminal signal sequence for entry into the cellular secretory system that is proteolytically cleaved in the during processing of the recombinant F ectodomain in the cell.

In some embodiments, the nucleic acid molecule encodes a $F_0$ polypeptide that, when expressed in an appropriate cell, is processed into a protomer of the NiV F ectodomain trimer including an $F_2$ polypeptide linked to a $F_1$ ectodomain, wherein the recombinant $F_2$-$F_1$ ectodomain protomer includes any of the prefusion-stabilizing modifications described herein, and optionally can be linked to a trimerization domain, such as a GCN4 trimerization domain.

In some embodiments, the nucleic acid molecule encodes a full-length $F_0$ polypeptide that, when expressed in an appropriate cell, is processed into a protomer of NiV F trimer including an $F_2$ polypeptide linked to a $F_1$ polypeptide including the $F_1$ TM and CT, wherein the recombinant $F_2$-$F_1$ ectodomain protomer includes any of the prefusion-stabilizing modifications described herein.

Exemplary nucleic acid sequences include:

NiVop08-TD (GCN4-Fd)-G
(SEQ ID NO: 61, which encodes SEQ ID NO: 43)

tctagagccaccatgtactctatgcagctggccagctgcgtgaccctgac
actggtgctgctggtgaactctcagggcatcctgcactacgagaagctga
gcaagatcggcctggtgaagggcgtgaccagaaagtataagatcaagtcc
aacccactgacaaaggacatcgtgatcaagatgatccccaacgtgagcaa
tatgtctcagtgtaccggctctgtgatggagaactacaagacccgcctga
atggcatcctgacaccaatcaagggcgccctggagatctataagaacaat
acacacgactgcgtgggcgatgtatgaggccatgaagaacgccgacaaca
tcaataagctgaagagctccatcgagagcaccaatgaggccgtggtgaag
ctgcaggagacagccgagaagacagtgtacgtgttcacagccctgcagga
ctatatcaacaccaatctggtgcccacaatcgataagatcccctgcaagc
agaccgagctgtccctggacctggccctgtctaagtacctgagcgatctg
ctgttcgtgtttggcccaaacctgcaggaccccgtgtccaattctatgac
aatccaggccatctcccaggccttcggcggcaattacgagacactgctga
gaacactgggctatgccaccgaggactttgacgatctgctggagagcgat
tccatcacaggccagatcatctatgtggatctgtctagctactatatcat
cgtgagggtgtacttccctatcctgaccgagatccagcaggcctatatcc
aggagctgctgccagtgagcttcaacaatgacaattccgagtggatctct
atcgtgcccaactttatcctggtgcggaacaccctgatcagcaatatcga
gatcggcttttgcctgatcacaaagagatccgtgatctgtaatcaggact
acgccacccccatgacaaacaatatgagggagtgcctgaccggctccaca
gagaagtgtccccgggagctggtggtgtcctctcacgtgcctagattcgc
cctgtccaacggcgtgctgtttgccaattgcatctctgtgacctgccagt
gtcagaccacaggaagggcaatctctcagagcggagagcagaccctgctg
atgatcgataacaccacatgtcctacagccgtgctgggcaatgtgatcat -continued cagcctgggcaagtacctgggctccgtgaactataattctgagggaatcg
caatcggaccacccgtgttcaccgacaaggtggatatcagctcccagatc
tctagcatgaaccagagcctgcagcagtccaaggactacatcaaggaggc
ccagcggctgctggataccgtgaatccttctctgaagctgatgaagcaga
tcgaggataagatcgaggagatcctgagcaagatctatcacatcgagaac
gagatcgccaggatcaagaagctgatcggagaggcacctggatctggtta
catcccagaggctccgcgggatggacaggcctacgtgagaaaggacggcg
agtgggtgctgctgagcaccttcctgggaagcggtggaggaggcggaggc
gtgagcaatctggtgggcctgcccaacaatatctgtctgcagaagacctc
caaccagatcctgaagcccaagctgatctcctatacactgcctgtggtgg
gccagtctggcacctgcatcacagaccctctgctggccatggatgagggc
tacttcgcctattctcacctggagaggatcggctcctgttctcgcggcgt
gagcaagcagcggatcatcggagtgggagaggtgctggacaggggcgatg
aggtgccttccctgttcatgaccaacgtgtggacaccacccaatccaaac
accgtgtaccactgctctgccgtgtataacaatgagttttactacgtgct
gtgcgccgtgagcaccgtgggcgatcctatcctgaactccacatactgga
gcggctccctgatgatgaccagactggccgtgaagccaaagtccaatggc
ggcggctataaccagcaccagctggccctgagatctatcgagaagggcag
gtacgataaagtgatgccttatggcccatctggcatcaagcagggcgaca
cactgtacttccccgccgtgggctttctggtgaggaccgagttcaagtac
aatgactccaactgccctatcacaaagtgtcagtattctaagccagagaa
ttgccgcctgagcatgggcatccggcccaactctcactacatcctgagaa
gcggcctgctgaagtataatctgagcgacggcgagaaccctaaggtggtg
tttatcgagatctccgatcagaggctgtctatcggctctcccagcaagat
ctacgactccctgggccagcccgtgttctaccaggcctcctttttcttggg
acacaatgatcaagttcggcgatgtgctgaccgtgaatccactggtggtg
aactggagaaacaataccgtgatcagcaggccaggacagtcccagtgtcc
tcgctttaacacatgcccagagatctgttgggagggcgtgtacaatgacg
ccttcctgatcgatcggatcaactggatctccgccggcgtgtttctggac
tctaatcagaccgccgagaaccccgtgttcacagtgtttaaggataatga
gatcctgtacagggcacagctggcaagcgaggacaccaacgcccagaaga
ccatcacaaattgcttcctgctgaagaacaagatctggtgtatctccctg
gtggagatctatgacaccggcgataacgtgatccggccaaagctgtttgc
cgtgaagatccccgagcagtgcacaggcggcctggtgcctagaggctctc
accaccaccatcaccacagcgcctggtcccacccccagttcgagaagtga
taggatcc G-NiVop08-TD (GCN4-Fd)
(SEQ ID NO: 62, which encodes SEQ ID NO: 44)

tctagaccaccatgtactcaatgcagctggcctcttgcgtcacactgaca
ctggtcctgctggtcaactcacagagaccacagaccgagggcgtgagcaa -continued tctggtgggcctgcccaacaatatctgtctgcagaagacctccaaccaga tcctgaagcccaagctgatctcctatacactgcctgtggtgggccagtct ggcacctgcatcacagaccctctgctggccatggatgagggctacttcgc ctattctcacctggagaggatcggctcctgttctcgcggcgtgagcaagc agcggatcatcggagtgggagaggtgctggacaggggcgatgaggtgcct tccctgttcatgaccaacgtgtggacaccacccaatccaaacaccgtgta ccactgctctgccgtgtataacaatgagttttactacgtgctgtgcgccg tgagcaccgtgggcgatcctatcctgaactccacatactggagcggctcc ctgatgatgaccagactggccgtgaagccaaagtccaatggcggcggcta taaccagcaccagctggccctgagatctatcgagaagggcaggtacgata aagtgatgccttatggcccatctggcatcaagcagggcgacacactgtac ttccccgccgtgggctttctggtgaggaccgagttcaagtacaatgactc caactgccctatcacaaagtgtcagtattctaagccagagaattgccgcc tgagcatgggcatccggcccaactctcactacatcctgagaagcggcctg ctgaagtataatctgagcgacggcgagaaccctaaggtggtgtttatcga gatctccgatcagaggctgtctatcggctctcccagcaagatctacgact ccctgggccagcccgtgttctaccaggcctccttttcttgggacacaatg atcaagttcggcgatgtgctgaccgtgaatccactggtggtgaactggag aaacaataccgtgatcagcaggccaggacagtcccagtgtcctcgcttta acacatgcccagagatctgttgggagggcgtgtacaatgacgccttcctg atcgatcggatcaactggatctccgccggcgtgtttctggactctaatca gaccgccgagaaccccgtgttcacagtgtttaaggataatgagatcctgt acagggcacagctggcaagcgaggacaccaacgcccagaagaccatcaca aattgcttcctgctgaagaacaagatctggtgtatctccctggtggagat ctatgacaccggcgataacgtgatccggccaaagctgtttgccgtgaaga tccccgagcagtgcacaggcggcggtcagggcatcctgcactacgagaag ctgagcaagatcggcctggtgaagggcgtgaccagaaagtataagatcaa gtccaacccactgacaaaggacatcgtgatcaagatgatccccaacgtga gcaatatgtctcagtgtaccggctctgtgatggagaactacaagacccgc ctgaatggcatcctgacaccaatcaagggcgccctggagatctataagaa caatacacacgactgcgtgggcgatgtgcggctggcaggcgtgtgcatgg caggagtggcaatcggaatcgcaaccgcagcacagatcacagcaggagtg gccctgtatgaggccatgaagaacgccgacaacatcaataagctgaagag ctccatcgagagcaccaatgaggccgtggtgaagctgcaggagacagccg agaagacagtgtacgtgttcacagccctgcaggactatatcaacaccaat ctggtgcccacaatcgataagatcccctgcaagcagaccgagctgtccct ggacctggccctgtctaagtacctgagcgatctgctgttcgtgtttggcc caaacctgcaggaccccgtgtccaattctatgacaatccaggccatctcc caggccttcggcggcaattacgagacactgctgagaacactgggctatgc caccgaggactttgacgatctgctggagagcgattccatcacaggccaga tcatctatgtggatctgtctagctactatatcatcgtgagggtgtacttc -continued cctatcctgaccgagatccagcaggcctatatccaggagctgctgccagt gagcttcaacaatgacaattccgagtggatctctatcgtgcccaacttta tcctggtgcggaacaccctgatcagcaatatcgagatcggcttttgcctg atcacaaagagatccgtgatctgtaatcaggactacgccacccccatgac aaacaatatgagggagtgcctgaccggctccacagagaagtgtccccggg agctggtggtgtcctctcacgtgcctagattcgccctgtccaacggcgtg ctgtttgccaattgcatctctgtgacctgccagtgtcagaccacaggaag ggcaatctctcagagcggagagcagaccctgctgatgatcgataacacca catgtcctacagccgtgctgggcaatgtgatcatcagcctgggcaagtac ctgggctccgtgaactataattctgagggaatcgcaatcggaccacccgt gttcaccgacaaggtggatatcagctcccagatctctagcatgaaccaga gcctgcagcagtccaaggactacatcaaggaggcccagcggctgctggat accgtgaatccttctctgaagctgatgaagcagatcgaggataagatcga ggagatcctgagcaagatctatcacatcgagaacgagatcgccaggatca agaagctgatcggagaggcacctggatctggttacatcccagaggctccg cgggatggacaggcctacgtgagaaaggacggcgagtgggtgctgctgag caccttcctgggaagcctggtgcctaggggctcccaccaccaccaccacc acagcgcctggtcccacccacagtttgagaagtgatgaggatcc NiV08

(SEQ ID NO: 63, which encodes SEQ ID NO: 24)

tctagagccaccatgtactctatgcagctggccagctgcgtgaccctgac actggtgctgctggtgaactctcagggcatcctgcactacgagaagctga gcaagatcggcctggtgaagggcgtgaccagaaagtataagatcaagtcc aacccactgacaaaggacatcgtgatcaagatgatccccaacgtgagcaa tatgtctcagtgtaccggctctgtgatggagaactacaagacccgcctga atggcatcctgacaccaatcaagggcgccctggagatctataagaacaat acacacgactgcgtgggcgatgtgcggctggcaggcgtgtgcatggcagg agtggcaatcggaatcgcaaccgcagcacagatcacagcaggagtggccc tgtatgaggccatgaagaacgccgacaacatcaataagctgaagagctcc atcgagagcaccaatgaggccgtggtgaagctgcaggagacagccgagaa gacagtgtacgtgttcacagccctgcaggactatatcaacaccaatctgg tgcccacaatcgataagatcccctgcaagcagaccgagctgtccctggac ctggccctgtctaagtacctgagcgatctgctgttcgtgtttggcccaaa cctgcaggaccccgtgtccaattctatgacaatccaggccatctcccagg ccttcggcggcaattacgagacactgctgagaacactgggctatgccacc gaggactttgacgatctgctggagagcgattccatcacaggccagatcat ctatgtggatctgtctagctactatatcatcgtgagggtgtacttcccta tcctgaccgagatccagcaggcctatatccaggagctgctgccagtgagc ttcaacaatgacgattccgagtggatctctatcgtgcccaactttatcct ggtgcggaacaccctgatcagcaatatcgagatcggcttttgcctgatca -continued caaagagatccgtgatctgtaatcaggactacgccacccccatgacaaac aatatgagggagtgcctgaccggctccacagagaagtgtccccgggagct ggtggtgtcctctcacgtgcctagattcgccctgtccaacggcgtgctgt ttgccaattgcatctctgtgacctgccagtgtcagaccacaggaagggca atctctcagagcggagagcagaccctgctgatgatcgataacaccacatg tcctacagccgtgctgggcaatgtgatcatcagcctgggcaagtacctgg gctccgtgaactataattctgagggaatcgcaatcggaccacccgtgttc accgacaaggtggatatcagctcccagatctctagcatgaaccagagcct gcagcagtccaaggactacatcaaggaggcccagcggctgctggataccg tgaatccttctctgaagctgatgaagcagatcgaggataagatcgaggag atcctgagcaagatctatcacatcgagaacgagatcgccaggatcaagaa gctgatcggagaggcacctggaggcctggtgccaaggggctcccaccacc accaccaccacagcgcctggtcccacccacagtttgagaagtgatgagga tcc G-ln5-Fer
(SEQ ID NO: 64, which encodes SEQ ID NO: 38)

tctagaccaccatgtactcaatgcagctggcctcttgcgtcacactgaca ctggtcctgctggtcaactcacagcaccaccaccatcatcacggaagcgc ctggtcccaccctcagttcgagaagggaggactggtgcccagaggatccg gcaacagccagcgccctcagaccgagggcgtgagcaatctggtgggcctg cccaacaatatctgtctgcagaagacctccaaccagatcctgaagcccaa gctgatctcctatacactgcctgtggtgggccagtctggcacctgcatca cagaccctctgctggccatggatgagggctacttcgcctattctcacctg gagaggatcggctcctgttctcgcggcgtgagcaagcagcggatcatcgg agtgggagaggtgctggacaggggcgatgaggtgccttccctgttcatga ccaacgtgtggacaccacccaatccaaacaccgtgtaccactgctctgcc gtgtataacaatgagttttactacgtgctgtgcgccgtgagcaccgtggg cgatcctatcctgaactccacatactggagcggctccctgatgatgacca gactggccgtgaagccaaagtccaatggcggcggctataaccagcaccag ctggccctgagatctatcgagaagggcaggtacgataaagtgatgcctta tggcccatctggcatcaagcagggcgacacactgtacttccccgccgtgg gctttctggtgaggaccgagttcaagtacaatgactccaactgccctatc acaaagtgtcagtattctaagccagagaattgccgcctgagcatgggcat ccggcccaactctcactacatcctgagaagcggcctgctgaagtataatc tgagcgacggcgagaaccctaaggtggtgtttatcgagatctccgatcag aggctgtctatcggctctcccagcaagatctacgactccctgggccagcc cgtgttctaccaggcctccttttcttgggacacaatgatcaagttcggcg atgtgctgaccgtgaatccactggtggtgaactggagaaacaataccgtg atcagcaggccaggacagtcccagtgtcctcgctttaacacatgcccaga gatctgttgggagggcgtgtacaatgacgccttcctgatcgatcggatca -continued actggatctccgccggcgtgtttctggactctaatcagaccgccgagaac cccgtgttcacagtgtttaaggataatgagatcctgtacagggcacagct ggcaagcgaggacaccaacgcccagaagaccatcacaaattgcttcctgc tgaagaacaagatctggtgtatctccctggtggagatctatgacaccggc gataacgtgatccggccaaagctgtttgccgtgaagatccccgagcagtg cacaggcggcggcagcggcggggatatcattaagctgctgaacgaacagg tgaacaaggagatgcagtcaagcaacctgtacatgtctatgtcctcttgg tgctatacacatagtctggacggagctggcctgttcctgtttgatcacgc agccgaggaatacgaacatgcaaagaaactgatcattttcctgaatgaga acaatgtgccagtccagctgacaagtatctcagccccgaacacaagttc gaggggctgactcagatctttcagaaagcttacgaacacgagcagcatat tagcgaatccatcaacaatattgtggaccacgctatcaagtccaaagatc atgcaaccttcaactttctgcagtggtacgtggccgagcagcacgaggaa gaggtcctgtttaaggacatcctggataaaatcgaactgattggcaacga gaatcatgggctgtacctggccgatcagtatgtgaagggcattgctaagt cacggaaaagcggaagctgatgaccgcgg NiVop08-GCN4-G
(SEQ ID NO: 65, which encodes SEQ ID NO: 59)

tctagagccaccatgtactctatgcagctggccagctgcgtgaccctgac actggtgctgctggtgaactctcagggcatcctgcactacgagaagctga gcaagatcggcctggtgaagggcgtgaccagaaagtataagatcaagtcc aacccactgacaaaggacatcgtgatcaagatgatccccaacgtgagcaa tatgtctcagtgtaccggctctgtgatggagaactacaagacccgcctga atggcatcctgacaccaatcaagggcgccctggagatctataagaacaat acacacgactgcgtgggcgatgtgcggctggcaggcgtgtgcatggcagg agtggcaatcggaatcgcaaccgcagcacagatcacagcaggagtggccc tgtatgaggccatgaagaacgccgacaacatcaataagctgaagagctcc atcgagagcaccaatgaggccgtggtgaagctgcaggagacagccgagaa gacagtgtacgtgttcacagccctgcaggactatatcaacaccaatctgg tgcccacaatcgataagatcccctgcaagcagaccgagctgtccctggac ctggccctgtctaagtacctgagcgatctgctgttcgtgtttggcccaaa cctgcaggaccccgtgtccaattctatgacaatccaggccatctcccagg ccttcggcggcaattacgagacactgctgagaacactgggctatgccacc gaggactttgacgatctgctggagagcgattccatcacaggccagatcat ctatgtggatctgtctagctactatatcatcgtgagggtgtacttcccta tcctgaccgagatccagcaggcctatatccaggagctgctgccagtgagc ttcaacaatgacaattccgagtggatctctatcgtgcccaactttatcct ggtgcggaacaccctgatcagcaatatcgagatcggcttttgcctgatca caaagagatccgtgatctgtaatcaggactacgccacccccatgacaaac aatatgagggagtgcctgaccggctccacagagaagtgtccccgggagct -continued ggtggtgtcctctcacgtgcctagattcgccctgtccaacggcgtgctgt
ttgccaattgcatctctgtgacctgccagtgtcagaccacaggaagggca
atctctcagagcggagagcagaccctgctgatgatcgataacaccacatg
tcctacagccgtgctgggcaatgtgatcatcagcctgggcaagtacctgg
gctccgtgaactataattctgagggaatcgcaatcggaccacccgtgttc
accgacaaggtggatatcagctcccagatctctagcatgaaccagagcct
gcagcagtccaaggactacatcaaggaggcccagcggctgctggataccg
tgaatccttctctgaagctgatgaagcagatcgaggataagatcgaggag
atcctgagcaagatctatcacatcgagaacgagatcgccaggatcaagaa
gctgatcggagaggcacctggatctggtggaggaggcggaggcgtgagca
atctggtgggcctgcccaacaatatctgtctgcagaagacctccaaccag
atcctgaagcccaagctgatctcctatacactgcctgtggtgggccagtc
tggcacctgcatcacagaccctctgctggccatggatgagggctacttcg
cctattctcacctggagaggatcggctcctgttctcgcggcgtgagcaag
cagcggatcatcggagtgggagaggtgctggacaggggcgatgaggtgcc
ttccctgttcatgaccaacgtgtggacaccacccaatccaaacaccgtgt
accactgctctgccgtgtataacaatgagttttactacgtgctgtgcgcc
gtgagcaccgtgggcgatcctatcctgaactccacatactggagcggctc
cctgatgatgaccagactggccgtgaagccaaagtccaatggcggcggct
ataaccagcaccagctggccctgagatctatcgagaagggcaggtacgat
aaagtgatgccttatggcccatctggcatcaagcagggcgacacactgta
cttccccgccgtgggctttctggtgaggaccgagttcaagtacaatgact
ccaactgccctatcacaaagtgtcagtattctaagccagagaattgccgc
ctgagcatgggcatccggcccaactctcactacatcctgagaagcggcct
gctgaagtataatctgagcgacggcgagaaccctaaggtggtgtttatcg
agatctccgatcagaggctgtctatcggctctcccagcaagatctacgac
tccctgggccagcccgtgttctaccaggcctccttttcttgggacacaat
gatcaagttcggcgatgtgctgaccgtgaatccactggtggtgaactgga
gaaacaataccgtgatcagcaggccaggacagtcccagtgtcctcgcttt
aacacatgcccagagatctgttgggagggcgtgtacaatgacgccttcct
gatcgatcggatcaactggatctccgccggcgtgtttctggactctaatc
agaccgccgagaaccccgtgttcacagtgtttaaggataatgagatcctg
tacagggcacagctggcaagcgaggacaccaacgcccagaagaccatcac
aaattgcttcctgctgaagaacaagatctggtgtatctccctggtggaga
tctatgacaccggcgataacgtgatccggccaaagctgtttgccgtgaag
atccccgagcagtgcacaggcggcctggtgcctagaggctctcaccacca
ccatcaccacagcgcctggtcccacccccagttcgagaagtgataggatc
c NiVop08-Fd-G
(SEQ ID NO: 66, which encodes SEQ ID NO: 60)
tctagagccaccatgtactctatgcagctggccagctgcgtgaccctgac
actggtgctgctggtgaactctcagggcatcctgcactacgagaagctga
gcaagatcggcctggtgaagggcgtgaccagaaagtataagatcaagtcc
aacccactgacaaaggacatcgtgatcaagatgatccccaacgtgagcaa
tatgtctcagtgtaccggctctgtgatggagaactacaagacccgcctga
atggcatcctgacaccaatcaagggcgccctggagatctataagaacaat
acacacgactgcgtgggcgatgtgcggctggcaggcgtgtgcatggcagg
agtggcaatcggaatcgcaaccgcagcacagatcacagcaggagtggccc
tgtatgaggccatgaagaacgccgacaacatcaataagctgaagagctcc
atcgagagcaccaatgaggccgtggtgaagctgcaggagacagccgagaa
gacagtgtacgtgttcacagccctgcaggactatatcaacaccaatctgg
tgcccacaatcgataagatcccctgcaagcagaccgagctgtccctggac
ctggccctgtctaagtacctgagcgatctgctgttcgtgtttggcccaaa
cctgcaggaccccgtgtccaattctatgacaatccaggccatctcccagg
ccttcggcggcaattacgagacactgctgagaacactgggctatgccacc
gaggactttgacgatctgctggagagcgattccatcacaggccagatcat
ctatgtggatctgtctagctactatatcatcgtgagggtgtacttcccta
tcctgaccgagatccagcaggcctatatccaggagctgctgccagtgagc
ttcaacaatgacaattccgagtggatctctatcgtgcccaactttatcct
ggtgcggaacaccctgatcagcaatatcgagatcggcttttgcctgatca
caaagagatccgtgatctgtaatcaggactacgccacccccatgacaaac
aatatgagggagtgcctgaccggctccacagagaagtgtccccgggagct
ggtggtgtcctctcacgtgcctagattcgccctgtccaacggcgtgctgt
ttgccaattgcatctctgtgacctgccagtgtcagaccacaggaagggca
atctctcagagcggagagcagaccctgctgatgatcgataacaccacatg
tcctacagccgtgctgggcaatgtgatcatcagcctgggcaagtacctgg
gctccgtgaactataattctgagggaatcgcaatcggaccacccgtgttc
accgacaaggtggatatcagctcccagatctctagcatgaaccagagcct
gcagcagtccaaggactacatcaaggaggcccagcggctgctggataccg
tgaatccttctctgggatctggttacatcccagaggctccgcgggatgga
caggcctacgtgagaaaggacggcgagtgggtgctgctgagcaccttcct
gggaagcggtggaggaggcggaggcgtgagcaatctggtgggcctgccca
acaatatctgtctgcagaagacctccaaccagatcctgaagcccaagctg
atctcctatacactgcctgtggtgggccagtctggcacctgcatcacaga
ccctctgctggccatggatgagggctacttcgcctattctcacctggaga
ggatcggctcctgttctcgcggcgtgagcaagcagcggatcatcggagtg
ggagaggtgctggacaggggcgatgaggtgccttccctgttcatgaccaa
cgtgtggacaccacccaatccaaacaccgtgtaccactgctctgccgtgt
ataacaatgagttttactacgtgctgtgcgccgtgagcaccgtgggcgat
cctatcctgaactccacatactggagcggctccctgatgatgaccagact -continued ggccgtgaagccaaagtccaatggcggcggctataaccagcaccagctgg
ccctgagatctatcgagaagggcaggtacgataaagtgatgccttatggc
ccatctggcatcaagcagggcgacacactgtacttccccgccgtgggctt
tctggtgaggaccgagttcaagtacaatgactccaactgccctatcacaa
agtgtcagtattctaagccagagaattgccgcctgagcatgggcatccgg
cccaactctcactacatcctgagaagcggcctgctgaagtataatctgag
cgacggcgagaaccctaaggtggtgtttatcgagatctccgatcagaggc
tgtctatcggctctcccagcaagatctacgactccctgggccagcccgtg
ttctaccaggcctccttttcttgggacacaatgatcaagttcggcgatgt
gctgaccgtgaatccactggtggtgaactggagaaacaataccgtgatca
gcaggccaggacagtcccagtgtcctcgctttaacacatgcccagagatc
tgttgggagggcgtgtacaatgacgccttcctgatcgatcggatcaactg
gatctccgccggcgtgtttctggactctaatcagaccgccgagaaccccg
tgttcacagtgtttaaggataatgagatcctgtacagggcacagctggca
agcgaggacaccaacgcccagaagaccatcacaaattgcttcctgctgaa
gaacaagatctggtgtatctccctggtggagatctatgacaccggcgata
acgtgatccggccaaagctgtttgccgtgaagatccccgagcagtgcaca
ggcggcctggtgcctagaggctctcaccaccaccatcaccacagcgcctg
gtcccacccccagttcgagaagtgataggatcc G-Fd-G
(SEQ ID NO: 67, which encodes SEQ ID NO: 37)

tctagagccaccatgtactctatgcagctggccagctgcgtgaccctgac
actggtgctgctggtgaactctcaggagggcgtgagcaatctggtgggcc
tgcccaacaatatctgtctgcagaagacctccaaccagatcctgaagccc
aagctgatctcctatacactgcctgtggtgggccagtctggcacctgcat
cacagaccctctgctggccatggatgagggctacttcgcctattctcacc
tggagaggatcggctcctgttctcgcggcgtgagcaagcagcggatcatc
ggagtgggagaggtgctggacaggggcgatgaggtgccttccctgttcat
gaccaacgtgtggacaccacccaatccaaacaccgtgtaccactgctctg
ccgtgtataacaatgagttttactacgtgctgtgcgccgtgagcaccgtg
ggcgatcctatcctgaactccacatactggagcggctccctgatgatgac
cagactggccgtgaagccaaagtccaatggcggcggctataaccagcacc
agctggccctgagatctatcgagaagggcaggtacgataaagtgatgcct
tatggcccatctggcatcaagcagggcgacacactgtacttccccgccgt
gggctttctggtgaggaccgagttcaagtacaatgactccaactgcccta
tcacaaagtgtcagtattctaagccagagaattgccgcctgagcatgggc
atccggcccaactctcactacatcctgagaagcggcctgctgaagtataa
tctgagcgacggcgagaaccctaaggtggtgtttatcgagatctccgatc
agaggctgtctatcggctctcccagcaagatctacgactccctgggccag
cccgtgttctaccaggcctccttttcttgggacacaatgatcaagttcgg -continued cgatgtgctgaccgtgaatccactggtggtgaactggagaaacaataccg
tgatcagcaggccaggacagtcccagtgtcctcgctttaacacatgccca
gagatctgttgggagggcgtgtacaatgacgccttcctgatcgatcggat
caactggatctccgccggcgtgtttctggactctaatcagaccgccgaga
accccgtgttcacagtgtttaaggataatgagatcctgtacagggcacag
ctggcaagcgaggacaccaacgcccagaagaccatcacaaattgcttcct
gctgaagaacaagatctggtgtatctccctggtggagatctatgacaccg
gcgataacgtgatccggccaaagctgtttgccgtgaagatccccgagcag
tgcacaggcggcggatctggttacatcccagaggctccgcgggatggaca
ggcctacgtgagaaaggacggcgagtgggtgctgctgagcaccttcctgg
gaagcggtggaggaggcggaggcgtgagcaatctggtgggcctgcccaac
aatatctgtctgcagaagacctccaaccagatcctgaagcccaagctgat
ctcctatacactgcctgtggtgggccagtctggcacctgcatcacagacc
ctctgctggccatggatgagggctacttcgcctattctcacctggagagg
atcggctcctgttctcgcggcgtgagcaagcagcggatcatcggagtggg
agaggtgctggacaggggcgatgaggtgccttccctgttcatgaccaacg
tgtggacaccacccaatccaaacaccgtgtaccactgctctgccgtgtat
aacaatgagttttactacgtgctgtgcgccgtgagcaccgtgggcgatcc
tatcctgaactccacatactggagcggctccctgatgatgaccagactgg
ccgtgaagccaaagtccaatggcggcggctataaccagcaccagctggcc
ctgagatctatcgagaagggcaggtacgataaagtgatgccttatggccc
atctggcatcaagcagggcgacacactgtacttccccgccgtgggctttc
tggtgaggaccgagttcaatacaatgactccaactgccctatcacaaagt
gtcagtattctaagccagagaattgccgcctgagcatgggcatccggccc
aactctcactacatcctgagaagcggcctgctgaagtataatctgagcga
cggcgagaaccctaaggtggtgtttatcgagatctccgatcagaggctgt
ctatcggctctcccagcaagatctacgactccctgggccagcccgtgttc
taccaggcctccttttcttgggacacaatgatcaagttcggcgatgtgct
gaccgtgaatccactggtggtgaactggagaaacaataccgtgatcagca
ggccaggacagtcccagtgtcctcgctttaacacatgcccagagatctgt
tgggagggcgtgtacaatgacgccttcctgatcgatcggatcaactggat
ctccgccggcgtgtttctggactctaatcagaccgccgagaaccccgtgt
tcacagtgtttaaggataatgagatcctgtacagggcacagctggcaagc
gaggacaccaacgcccagaagaccatcacaaattgcttcctgctgaagaa
caagatctggtgtatctccctggtggagatctatgacaccggcgataacg
tgatccggccaaagctgtttgccgtgaagatccccgagcagtgcacaggc
ggcctggtgcctagaggctctcaccaccaccatcaccacagcgcctggtc
ccacccccagttcgagaagtgataggatcc Full-length NiV F with NiVop08 substitutions (SEQ ID NO: 33)

```
tctagagccaccatggtggtcatcctggacaagagatgctactgtaacct
gctgatcctgatcctgatgatcagcgagtgctccgtgggcatcctgcact
acgagaagctgtccaagatcggcctggtgaagggcgtgaccaggaagtat
aagatcaagtctaatcccctgacaaaggatatcgtgatcaagatgatccc
taacgtgtctaatatgagccagtgtaccggctccgtgatggagaactaca
agaccagactgaatggcatcctgacacccatcaagggcgccctggagatc
tataagaacaatacacacgactgcgtgggcgatgtgaggctggcaggcgt
gtgcatggcaggagtggcaatcggaatccaaccgcagcacagatcacagc
aggagtggccctgtatgaggccatgaagaacgccgacaacatcaataagc
tgaagagctccatcgagagcaccaatgaggccgtggtgaagctgcaggag
accgccgagaagacagtgtacgtgttcacagccctgcaggactatatcaa
caccaatctggtgcctacaatcgataagatcccttgcaagcagaccgagc
tgagcctggacctggccctgagcaagtacctgtccgatctgctgttcgtg
tttggcccaaacctgcaggaccccgtgagcaattccatgacaatccaggc
catctcccaggccttcggcggcaactacgagaccctgctgcgcacactgg
gctatgccaccgaggactttgacgatctgctggagtctgatagcatcaca
ggccagatcatctatgtggacctgtctagctactatatcatcgtgcgggt
gtacttcccaatcctgaccgagatccagcaggcctatatccaggagctgc
tgcccgtgtccttcaacaatgataactctgagtggatcagcatcgtgcct
aacttcatcctggtgcggaacaccctgatctctaatatcgagatcggctt
ttgcctgatcacaaagcgcagcgtgatctgtaatcaggactacgccaccc
ctatgacaaacaatatgcgggagtgcctgaccggcagcacagagaagtgt
cctcgggagctggtggtgtcctctcacgtgccaagattcgccctgtccaa
cggcgtgctgtttgccaattgcatctctgtgacctgccagtgtcagacca
caggcagggccatctcccagtctggcgagcagaccctgctgatgatcgat
aacaccacatgtccaacagccgtgctgggcaatgtgatcatcagcctggg
caagtacctgggcagcgtgaactataattccgagggaatcgcaatcggac
cacccgtgttcaccgacaaggtggatatcagctcccagatctctagcatg
aaccagtccctgcagcagtctaaggactacatcaaggaggcccagcgcct
gctggataccgtgaatccatccctgatctctatgctgagcatgatcatcc
tgtatgtgctgtccatcgcctctctgtgcatcggcctgatcaccttcatc
agctttatcatcgtggagaagaagaggaacacatactcccgcctggagga
caggagagtgcggcccacctcctctggcgatctgtactatatcggcacat
gatgaggatcc
```

Exemplary nucleic acids can be prepared by cloning techniques. Examples of appropriate cloning and sequencing techniques, and instructions sufficient to direct persons of skill through many cloning exercises are known (see, e.g., Sambrook et al. (Molecular Cloning: A Laboratory Manual, $4^{th}$ ed, Cold Spring Harbor, N.Y., 2012) and Ausubel et al. (In Current Protocols in Molecular Biology, John Wiley & Sons, New York, through supplement 104, 2013).

Nucleic acids can also be prepared by amplification methods. Amplification methods include polymerase chain reaction (PCR), the ligase chain reaction (LCR), the transcription-based amplification system (TAS), the self-sustained sequence replication system (3SR). A wide variety of cloning methods, host cells, and in vitro amplification methodologies are well known to persons of skill.

The polynucleotides encoding a protomer of the NiV F ectodomain trimer can include a recombinant DNA which is incorporated into a vector (such as an expression vector) into an autonomously replicating plasmid or virus or into the genomic DNA of a prokaryote or eukaryote, or which exists as a separate molecule (such as a cDNA) independent of other sequences. The nucleotides can be ribonucleotides, deoxyribonucleotides, or modified forms of either nucleotide. The term includes single and double forms of DNA.

Polynucleotide sequences encoding a protomer of the NiV F ectodomain trimer can be operatively linked to expression control sequences. An expression control sequence operatively linked to a coding sequence is ligated such that expression of the coding sequence is achieved under conditions compatible with the expression control sequences. The expression control sequences include, but are not limited to, appropriate promoters, enhancers, transcription terminators, a start codon (i.e., ATG) in front of a protein-encoding gene, splicing signal for introns, maintenance of the correct reading frame of that gene to permit proper translation of mRNA, and stop codons.

DNA sequences encoding the protomer of the NiV F ectodomain trimer can be expressed in vitro by DNA transfer into a suitable host cell. The cell may be prokaryotic or eukaryotic. The term also includes any progeny of the subject host cell. It is understood that all progeny may not be identical to the parental cell since there may be mutations that occur during replication. Methods of stable transfer, meaning that the foreign DNA is continuously maintained in the host, are known in the art.

Hosts can include microbial, yeast, insect and mammalian organisms. Methods of expressing DNA sequences having eukaryotic or viral sequences in prokaryotes are well known in the art. Non-limiting examples of suitable host cells include bacteria, archea, insect, fungi (for example, yeast), plant, and animal cells (for example, mammalian cells, such as human) Exemplary cells of use include *Escherichia coli, Bacillus subtilis, Saccharomyces cerevisiae, Salmonella typhimurium*, SF9 cells, C129 cells, 293 cells, *Neurospora*, and immortalized mammalian myeloid and lymphoid cell lines. Techniques for the propagation of mammalian cells in culture are well-known (see, e.g., Helgason and Miller (Eds.), 2012, Basic Cell Culture Protocols (Methods in Molecular Biology), $4^{th}$ Ed., Humana Press). Examples of commonly used mammalian host cell lines are VERO and HeLa cells, CHO cells, and WI38, BHK, and COS cell lines, although cell lines may be used, such as cells designed to provide higher expression, desirable glycosylation patterns, or other features. In some embodiments, the host cells include HEK293 cells or derivatives thereof, such as $GnTI^{-/-}$ cells (ATCC® No. CRL-3022), or HEK-293F cells.

Transformation of a host cell with recombinant DNA can be carried out by conventional techniques. In some embodiments where the host is prokaryotic, such as, but not limited to, *E. coli*, competent cells which are capable of DNA uptake can be prepared from cells harvested after exponential growth phase and subsequently treated by the $CaCl_2$ method. Alternatively, $MgCl_2$ or RbCl can be used. Transformation can also be performed after forming a protoplast of the host cell if desired, or by electroporation.

When the host is a eukaryote, such methods of transfection of DNA as calcium phosphate coprecipitates, conventional mechanical procedures such as microinjection, electroporation, insertion of a plasmid encased in liposomes, or viral vectors can be used. Eukaryotic cells can also be co-transformed with polynucleotide sequences encoding a disclosed antigen, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein (see for example, Viral Expression Vectors, Springer press, Muzyczka ed., 2011). Appropriate expression systems such as plasmids and vectors of use in producing proteins in cells including higher eukaryotic cells such as the COS, CHO, HeLa and myeloma cell lines.

In one non-limiting example, a disclosed immunogen is expressed using the pVRC8400 vector (described in Barouch et al., *J. Virol.,* 79, 8828-8834, 2005, which is incorporated by reference herein).

Modifications can be made to a nucleic acid encoding a disclosed immunogen without diminishing its biological activity. Some modifications can be made to facilitate the cloning, expression, or incorporation of the targeting molecule into a fusion protein. Exemplary modifications include termination codons, a methionine added at the amino terminus to provide an initiation, site, additional amino acids placed on either terminus to create conveniently located restriction sites, or additional amino acids (such as poly His) to aid in purification steps.

In some embodiments, the nucleic acid encoding the protomer of a disclosed recombinant NiV F ectodomain protomer can be expressed in cells under conditions where the protomers self-assemble into trimers which are secreted from the cells into the cell media, for example as described for RSV F proteins (see, e.g., PCT Pub. WO2014160463, McLellan et al., *Science,* 340:1113-1117, 2013; McLellan et al., *Science,* 342:592-598, 2013, each of which is incorporated by reference herein in its entirety). In such embodiments, the protomer contains a leader sequence (signal peptide) that causes the protein to enter the secretory system, and the signal peptide is cleaved and the protomers form a trimer, before being secreted in the cell media. The medium can be centrifuged and recombinant NiV F ectodomain trimer purified from the supernatant.

III. Viral Vectors

A nucleic acid molecule encoding a disclosed immunogen can be included in a viral vector, for example, for expression of the immunogen in a host cell, or for immunization of a subject as disclosed herein. In some embodiments, the viral vectors are administered to a subject as part of a prime-boost vaccination. Typically such viral vectors include a nucleic acid molecule encoding an immunogen that contains a transmembrane domain. In several embodiments, the viral vectors are included in a vaccine, such as a primer vaccine or a booster vaccine for use in a prime-boost vaccination.

In some examples, the viral vector can be replication-competent. For example, the viral vector can have a mutation (e.g., insertion of nucleic acid encoding the protomer) in the viral genome that attenuates, but does not completely block viral replication in host cells.

In several embodiments, the viral vector can be delivered via the respiratory tract. For example, a hPIV vector, such as bovine parainfluenza virus (BPIV) vector (e.g., a BPIV1, BPIV2, or BPIV3 vector) or human hPIV vector (e.g., a hPIV3 vector), a metapneumovirus (MPV) vector, a Sendia virus vector, or a measles virus vector, is used to express a disclosed antigen.

Additional viral vectors are also available for expression of the disclosed antigens, including polyoma, i.e., SV40 (Madzak et al., 1992, *J. Gen. Virol.,* 73:15331536), adenovirus (Berkner, 1992, *Cur. Top. Microbiol. Immunol.,* 158: 39-6; Berliner et al., 1988, *Bio Techniques,* 6:616-629; Gorziglia et al., 1992, *J. Virol.,* 66:4407-4412; Quantin et al., 1992, *Proc. Natl. Acad. Sci. USA,* 89:2581-2584; Rosenfeld et al., 1992, *Cell,* 68:143-155; Wilkinson et al., 1992, *Nucl. Acids Res.,* 20:2233-2239; Stratford-Perricaudet et al., 1990, *Hum. Gene Ther.,* 1:241-256), vaccinia virus (Mackett et al., 1992, *Biotechnology,* 24:495-499), adeno-associated virus (Muzyczka, 1992, *Curr. Top. Microbiol. Immunol.,* 158:91-123; On et al., 1990, *Gene,* 89:279-282), herpes viruses including HSV and EBV and CMV (Margolskee, 1992, *Curr. Top. Microbiol. Immunol.,* 158:67-90; Johnson et al., 1992, *J. Virol.,* 66:29522965; Fink et al., 1992, *Hum. Gene Ther.* 3:11-19; Breakfield et al., 1987, *Mol. Neurobiol.,* 1:337-371; Fresse et al., 1990, *Biochem. Pharmacol.,* 40:2189-2199), Sindbis viruses (H. Herweijer et al., 1995, *Human Gene Therapy* 6:1161-1167; U.S. Pat. Nos. 5,091, 309 and 5,2217,879), alphaviruses (S. Schlesinger, 1993, *Trends Biotechnol.* 11:18-22; I. Frolov et al., 1996, *Proc. Natl. Acad. Sci. USA* 93:11371-11377) and retroviruses of avian (Brandyopadhyay et al., 1984, *Mol. Cell Biol.,* 4:749-754; Petropouplos et al., 1992, *J. Virol.,* 66:3391-3397), murine (Miller, 1992, *Curr. Top. Microbiol. Immunol.,* 158: 1-24; Miller et al., 1985, *Mol. Cell Biol.,* 5:431-437; Sorge et al., 1984, *Mol. Cell Biol.,* 4:1730-1737; Mann et al., 1985, *J. Virol.,* 54:401-407), and human origin (Page et al., 1990, *J. Virol.,* 64:5370-5276; Buchschalcher et al., 1992, *J. Virol.,* 66:2731-2739). Baculovirus (*Autographa californica* multinuclear polyhedrosis virus; AcMNPV) vectors are also known in the art, and may be obtained from commercial sources (such as PharMingen, San Diego, Calif.; Protein Sciences Corp., Meriden, Conn.; Stratagene, La Jolla, Calif.).

IV. Virus-Like Particles

In some embodiments, a virus-like particle (VLP) is provided that includes a disclosed immunogen. Typically such VLPs include an immunogen containing a transmembrane domain, for example, a recombinant NiV F ectodomain trimer with protomers containing a NiV F transmembrane domain and cytosolic tail. VLPs lack the viral components that are required for virus replication and thus represent a highly attenuated, replication-incompetent form of a virus. However, the VLP can display a polypeptide (e.g., a recombinant NiV F ectodomain trimer) that is analogous to that expressed on infectious virus particles and can eliciting an immune response to NiV when administered to a subject. Exemplary virus like particles and methods of their production, as well as viral proteins from several viruses that are known to form VLPs, including human papillomavirus, HIV (Kang et al., Biol. Chem. 380: 353-64 (1999)), Semliki-Forest virus (Notka et al., Biol. Chem. 380: 341-52 (1999)), human polyomavirus (Goldmann et al., J. Virol. 73: 4465-9 (1999)), rotavirus (Jiang et al., Vaccine 17: 1005-13 (1999)), parvovirus (Casal, Biotechnology and Applied Biochemistry, Vol 29, Part 2, pp 141-150 (1999)), canine parvovirus (Hurtado et al., J. Virol. 70: 5422-9 (1996)), hepatitis E virus (Li et al., J. Virol. 71: 7207-13 (1997)), and Newcastle disease virus. The formation of such VLPs can be detected by any suitable technique. Examples of suitable techniques for detection of VLPs in a medium include, e.g., electron microscopy techniques, dynamic light scattering (DLS), selective chromatographic separation (e.g., ion exchange, hydrophobic interaction, and/or size exclusion chromatographic separation of the VLPs) and density gradient centrifugation.

V. Immunogenic Compositions

Immunogenic compositions comprising a disclosed immunogen (e.g., recombinant NiV F ectodomain trimer, a nucleic acid molecule or vector encoding a protomer of the recombinant NiV F ectodomain trimer, or a protein nanoparticle or virus like particle comprising a disclosed recombinant NiV F ectodomain trimer) and a pharmaceutically acceptable carrier are also provided. Such compositions can be administered to subjects by a variety of administration modes, for example, intramuscular, subcutaneous, intravenous, intra-arterial, intra-articular, intraperitoneal, or parenteral routes. In several embodiments, a pharmaceutical composition including one or more of the disclosed immunogens are immunogenic compositions. Actual methods for preparing administrable compositions are described in more detail in such publications as *Remingtons Pharmaceutical Sciences,* $19^{th}$ Ed., Mack Publishing Company, Easton, Pa., 1995.

Thus, an immunogen described herein can be formulated with pharmaceutically acceptable carriers to help retain biological activity while also promoting increased stability during storage within an acceptable temperature range. Potential carriers include, but are not limited to, physiologically balanced culture medium, phosphate buffer saline solution, water, emulsions (e.g., oil/water or water/oil emulsions), various types of wetting agents, cryoprotective additives or stabilizers such as proteins, peptides or hydrolysates (e.g., albumin, gelatin), sugars (e.g., sucrose, lactose, sorbitol), amino acids (e.g., sodium glutamate), or other protective agents. The resulting aqueous solutions may be packaged for use as is or lyophilized Lyophilized preparations are combined with a sterile solution prior to administration for either single or multiple dosing.

Formulated compositions, especially liquid formulations, may contain a bacteriostat to prevent or minimize degradation during storage, including but not limited to effective concentrations (usually 1% w/v) of benzyl alcohol, phenol, m-cresol, chlorobutanol, methylparaben, and/or propylparaben. A bacteriostat may be contraindicated for some patients; therefore, a lyophilized formulation may be reconstituted in a solution either containing or not containing such a component.

The immunogenic compositions of the disclosure can contain as pharmaceutically acceptable vehicles substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, and triethanolamine oleate.

The immunogenic composition may optionally include an adjuvant to enhance an immune response of the host. Adjuvants, such as aluminum hydroxide (ALHYDROGEL®, available from Brenntag Biosector, Copenhagen, Denmark and Amphogel®, Wyeth Laboratories, Madison, N.J.), Freund's adjuvant, MPL™ (3-O-deacylated monophosphoryl lipid A; Corixa, Hamilton, Ind.) and IL-12 (Genetics Institute, Cambridge, Mass.), TLR agonists (such as TLR-9 agonists), among many other suitable adjuvants well known in the art, can be included in the compositions. Suitable adjuvants are, for example, toll-like receptor agonists, alum, AIPO4, alhydrogel, Lipid-A and derivatives or variants thereof, oil-emulsions, saponins, neutral liposomes, liposomes containing the vaccine and cytokines, non-ionic block copolymers, and chemokines. Non-ionic block polymers containing polyoxyethylene (POE) and polyxylpropylene (POP), such as POE-POP-POE block copolymers, MPL™ (3-O-deacylated monophosphoryl lipid A; Corixa, Hamilton, Ind.) and IL-12 (Genetics Institute, Cambridge, Mass.), may be used as an adjuvant (Newman et al., 1998, *Critical Reviews in Therapeutic Drug Carrier Systems* 15:89-142). These adjuvants have the advantage in that they help to stimulate the immune system in a non-specific way, thus enhancing the immune response to a pharmaceutical product.

In some instances, the adjuvant formulation is a mineral salt, such as a calcium or aluminum (alum) salt, for example calcium phosphate, aluminum phosphate or aluminum hydroxide. In some embodiments, the adjuvant includes an oil and water emulsion, e.g., an oil-in-water emulsion (such as MF59 (Novartis) or AS03 (GlaxoSmithKline). One example of an oil-in-water emulsion comprises a metabolisable oil, such as squalene, a tocol such as a tocopherol, e.g., alpha-tocopherol, and a surfactant, such as sorbitan trioleate (Span 85) or polyoxyethylene sorbitan monooleate (Tween 80), in an aqueous carrier.

In some instances it may be desirable to combine a disclosed immunogen with other pharmaceutical products (e.g., vaccines) which induce protective responses to other agents. For example, a composition including a recombinant NiV F ectodomain trimer as described herein can be can be administered simultaneously (typically separately) or sequentially with other vaccines recommended by the Advisory Committee on Immunization Practices (ACIP; cdc.gov/vaccines/acip/index.html) for the targeted age group (e.g., infants from approximately one to six months of age). As such, a disclosed immunogen described herein may be administered simultaneously or sequentially with vaccines against, for example, hepatitis B (HepB), diphtheria, tetanus and pertussis (DTaP), pneumococcal bacteria (PCV), *Haemophilus influenzae* type b (Hib), polio, influenza and rotavirus.

In some embodiments, the composition can be provided as a sterile composition. The immunogenic composition typically contains an effective amount of a disclosed immunogen and can be prepared by conventional techniques. Typically, the amount of immunogen in each dose of the immunogenic composition is selected as an amount which induces an immune response without significant, adverse side effects. In some embodiments, the composition can be provided in unit dosage form for use to induce an immune response in a subject, for example, to inhibit NiV infection in the subject. A unit dosage form contains a suitable single preselected dosage for administration to a subject, or suitable marked or measured multiples of two or more preselected unit dosages, and/or a metering mechanism for administering the unit dose or multiples thereof.

VI. Methods of Inducing an Immune Response

The disclosed immunogens (e.g., recombinant prefusion-stabilized NiV F ectodomain trimer, a nucleic acid molecule (such as an RNA molecule) or vector encoding a protomer of the prefusion-stabilized NiV F ectodomain trimer, or a protein nanoparticle or virus like particle comprising the prefusion-stabilized NiV F ectodomain trimer) can be administered to a subject to induce an immune response to NiV in the subject. In a particular example, the subject is a human. The immune response can be a protective immune response, for example a response that inhibits subsequent infection with NiV. Elicitation of the immune response can also be used to treat or inhibit NiV infection and illnesses associated therewith.

A subject can be selected for treatment that has, or is at risk for developing NiV infection, for example because of exposure or the possibility of exposure to NiV. Following administration of a disclosed immunogen, the subject can be monitored for the NW infection or symptoms associated therewith, or both.

Typical subjects intended for treatment with the therapeutics and methods of the present disclosure include humans and domestic animals such as pigs. In several embodiments, the subject is a human subject that is seronegative for NiV specific antibodies. To identify subjects for prophylaxis or treatment according to the methods of the disclosure, accepted screening methods are employed to determine risk factors associated with a targeted or suspected disease or condition, or to determine the status of an existing disease or condition in a subject. These screening methods include, for example, conventional work-ups to determine environmental, familial, occupational, and other such risk factors that may be associated with the targeted or suspected disease or condition, as well as diagnostic methods, such as various ELISA and other immunoassay methods to detect and/or characterize NiV infection. These and other routine methods allow the clinician to select patients in need of therapy using the methods and immunogenic compositions of the disclosure. In accordance with these methods and principles, a composition can be administered according to the teachings herein, or other conventional methods, as an independent prophylaxis or treatment program, or as a follow-up, adjunct or coordinate treatment regimen to other treatments.

The administration of a disclosed immunogen can be for prophylactic or therapeutic purpose. When provided prophylactically, the immunogen can be provided in advance of any symptom, for example in advance of infection. The prophylactic administration serves to prevent or ameliorate any subsequent infection. In some embodiments, the methods can involve selecting a subject at risk for contracting NiV infection, and administering a therapeutically effective amount of a disclosed immunogen to the subject. The immunogen can be provided prior to the anticipated exposure to NiV so as to attenuate the anticipated severity, duration or extent of an infection and/or associated disease symptoms, after exposure or suspected exposure to the virus, or after the actual initiation of an infection. When provided therapeutically, the disclosed immunogens are provided at or after the onset of a symptom of NiV infection, or after diagnosis of NiV infection. Treatment of NiV by inhibiting NiV replication or infection can include delaying and/or reducing signs or symptoms of NiV infection in a subject. In some examples, treatment using the methods disclosed herein prolongs the time of survival of the subject.

In some embodiments, administration of a disclosed immunogen to a subject can elicit the production of an immune response that is protective against serious lower respiratory tract disease, such as pneumonia and bronchiolitis, or croup, when the subject is subsequently infected or re-infected with a wild-type NiV. While the naturally circulating virus may still be capable of causing infection, particularly in the upper respiratory tract, there can be a reduced possibility of rhinitis as a result of the vaccination and a possible boosting of resistance by subsequent infection by wild-type virus. Following vaccination, there are detectable levels of host engendered serum and secretory antibodies which are capable of neutralizing homologous (of the same subgroup) wild-type virus in vitro and in vivo. In many instances the host antibodies will also neutralize wild-type virus of a different, non-vaccine subgroup.

The immunogens described herein, and immunogenic compositions thereof, are provided to a subject in an amount effective to induce or enhance an immune response against NiV in the subject, preferably a human. The actual dosage of disclosed immunogen will vary according to factors such as the disease indication and particular status of the subject (for example, the subject's age, size, fitness, extent of symptoms, susceptibility factors, and the like), time and route of administration, other drugs or treatments being administered concurrently, as well as the specific pharmacology of the composition for eliciting the desired activity or biological response in the subject. Dosage regimens can be adjusted to provide an optimum prophylactic or therapeutic response.

An immunogenic composition including one or more of the disclosed immunogens can be used in coordinate (or prime-boost) vaccination protocols or combinatorial formulations. In certain embodiments, novel combinatorial immunogenic compositions and coordinate immunization protocols employ separate immunogens or formulations, each directed toward eliciting an anti-viral immune response, such as an immune response to NiV F protein. Separate immunogenic compositions that elicit the anti-viral immune response can be combined in a polyvalent immunogenic composition administered to a subject in a single immunization step, or they can be administered separately (in monovalent immunogenic compositions) in a coordinate (or prime-boost) immunization protocol.

There can be several boosts, and each boost can be a different disclosed immunogen. In some examples that the boost may be the same immunogen as another boost, or the prime. The prime and boost can be administered as a single dose or multiple doses, for example two doses, three doses, four doses, five doses, six doses or more can be administered to a subject over days, weeks or months. Multiple boosts can also be given, such one to five (e.g., 1, 2, 3, 4 or 5 boosts), or more. Different dosages can be used in a series of sequential immunizations. For example a relatively large dose in a primary immunization and then a boost with relatively smaller doses.

In some embodiments, the boost can be administered about two, about three to eight, or about four, weeks following the prime, or about several months after the prime. In some embodiments, the boost can be administered about 5, about 6, about 7, about 8, about 10, about 12, about 18, about 24, months after the prime, or more or less time after the prime. Periodic additional boosts can also be used at appropriate time points to enhance the subject's "immune memory." The adequacy of the vaccination parameters chosen, e.g., formulation, dose, regimen and the like, can be determined by taking aliquots of serum from the subject and assaying antibody titers during the course of the immunization program. In addition, the clinical condition of the subject can be monitored for the desired effect, e.g., inhibition of NiV infection or improvement in disease state (e.g., reduction in viral load). If such monitoring indicates that vaccination is sub-optimal, the subject can be boosted with an additional dose of immunogenic composition, and the vaccination parameters can be modified in a fashion expected to potentiate the immune response.

In some embodiments, the prime-boost method can include DNA-primer and protein-boost vaccination protocol to a subject. The method can include two or more administrations of the nucleic acid molecule or the protein.

For protein therapeutics, typically, each human dose will comprise 1-1000 μg of protein, such as from about 1 μg to about 100 μg, for example, from about 1 μg to about 50 μg, such as about 1 μg, about 2 μg, about 5 μg, about 10 μg, about 15 μg, about 20 μg, about 25 μg, about 30 μg, about 40 μg, or about 50 μg. The amount utilized in an immunogenic composition is selected based on the subject population (e.g., infant or elderly). An optimal amount for a particular composition can be ascertained by standard studies involving observation of antibody titers and other responses in subjects. It is understood that a therapeutically effective amount of a disclosed immunogen, such as a recombinant NiV F ectodomain or immunogenic fragment thereof, viral vector, or nucleic acid molecule in a immunogenic composition, can include an amount that is ineffective at eliciting an immune response by administration of a single dose, but that is effective upon administration of multiple dosages, for example in a prime-boost administration protocol.

Upon administration of a disclosed immunogen the immune system of the subject typically responds to the immunogenic composition by producing antibodies specific for viral protein. Such a response signifies that an immunologically effective dose was delivered to the subject.

For each particular subject, specific dosage regimens can be evaluated and adjusted over time according to the individual need and professional judgment of the person administering or supervising the administration of the immunogenic composition. The dosage and number of doses will depend on the setting, for example, in an adult or anyone primed by prior NiV infection or immunization, a single dose may be a sufficient booster. In naïve subjects, in some examples, at least two doses would be given, for example, at least three doses. In some embodiments, an annual boost is given, for example, along with an annual influenza vaccination.

In some embodiments, the antibody response of a subject will be determined in the context of evaluating effective dosages/immunization protocols. In most instances it will be sufficient to assess the antibody titer in serum or plasma obtained from the subject. Decisions as to whether to administer booster inoculations and/or to change the amount of the therapeutic agent administered to the individual can be at least partially based on the antibody titer level. The antibody titer level can be based on, for example, an immunobinding assay which measures the concentration of antibodies in the serum which bind to an antigen including, for example, an NiV F protein.

Determination of effective dosages is typically based on animal model studies followed up by human clinical trials and is guided by administration protocols that significantly reduce the occurrence or severity of targeted disease symptoms or conditions in the subject, or that induce a desired response in the subject (such as a neutralizing immune response). Suitable models in this regard include, for example, murine, rat, porcine, feline, ferret, non-human primate, and other accepted animal model subjects known in the art. Alternatively, effective dosages can be determined using in vitro models (for example, immunologic and histopathologic assays). Using such models, only ordinary calculations and adjustments are required to determine an appropriate concentration and dose to administer a therapeutically effective amount of the composition (for example, amounts that are effective to elicit a desired immune response or alleviate one or more symptoms of a targeted disease). In alternative embodiments, an effective amount or effective dose of the composition may simply inhibit or enhance one or more selected biological activities correlated with a disease or condition, as set forth herein, for either therapeutic or diagnostic purposes.

Administration of an immunogenic composition that elicits an immune response to reduce or prevent an infection, can, but does not necessarily completely, eliminate such an infection, so long as the infection is measurably diminished. For example, administration of an effective amount of the agent can decrease the NiV infection (for example, as measured by infection of cells, or by number or percentage of subjects infected by NiV by a desired amount, for example by at least 10%, at least 20%, at least 50%, at least 60%, at least 70%, at least 80%, at least 90%, at least 95%, at least 98%, or even at least 100% (elimination or prevention of detectable NiV infection, as compared to a suitable control.

In some embodiments, administration of a therapeutically effective amount of one or more of the disclosed immunogens to a subject induces a neutralizing immune response in the subject. To assess neutralization activity, following immunization of a subject, serum can be collected from the subject at appropriate time points, frozen, and stored for neutralization testing. Methods to assay for neutralization activity include, but are not limited to, plaque reduction neutralization (PRNT) assays, microneutralization assays, flow cytometry based assays, single-cycle infection assays. In some embodiments, the serum neutralization activity can be assayed using a panel of NiV pseudoviruses.

One approach to administration of nucleic acids is direct immunization with plasmid DNA, such as with a mammalian expression plasmid Immunization by nucleic acid constructs is well known in the art and taught, for example, in U.S. Pat. No. 5,643,578 (which describes methods of immunizing vertebrates by introducing DNA encoding a desired antigen to elicit a cell-mediated or a humoral response), and U.S. Pat. Nos. 5,593,972 and 5,817,637 (which describe operably linking a nucleic acid sequence encoding an antigen to regulatory sequences enabling expression). U.S. Pat. No. 5,880,103 describes several methods of delivery of nucleic acids encoding immunogenic peptides or other antigens to an organism. The methods include liposomal delivery of the nucleic acids (or of the synthetic peptides themselves), and immune-stimulating constructs, or ISCOMS™, negatively charged cage-like structures of 30-40 nm in size formed spontaneously on mixing cholesterol and Quil A™ (saponin). Protective immunity has been generated in a variety of experimental models of infection, including toxoplasmosis and Epstein-Barr virus-induced tumors, using ISCOMS™ as the delivery vehicle for antigens (Mowat and Donachie, *Immunol. Today* 12:383, 1991). Doses of antigen as low as 1 μg encapsulated in ISCOMS™ have been found to produce Class I mediated CTL responses (Takahashi et al., *Nature* 344:873, 1990).

In some embodiments, a plasmid DNA vaccine is used to express a disclosed immunogen in a subject. For example, a nucleic acid molecule encoding a disclosed immunogen can be administered to a subject to elicit an immune response to the F protein of NiV. In some embodiments, the nucleic acid molecule can be included on a plasmid vector for DNA immunization, such as the pVRC8400 vector (described in Barouch et al., J. Virol, 79, 8828-8834, 2005, which is incorporated by reference herein).

In another approach to using nucleic acids for immunization, a disclosed immunogen can be expressed by attenuated viral hosts (such as an attenuated NiV vector) or vectors or bacterial vectors. Recombinant vaccinia virus, adeno-associated virus (AAV), herpes virus, retrovirus, cytogmeglovirus or other viral vectors can be used to express the peptide or protein, thereby eliciting a CTL response. For example, vaccinia vectors and methods useful in immunization protocols are described in U.S. Pat. No. 4,722,848. BCG (Bacillus Calmette Guerin) provides another vector for expression of the peptides (see Stover, *Nature* 351:456-460, 1991).

In another example, a disclosed immunogen can be administered to a subject using RNA immunization, such as with a lipid-encapsulated mRNA immunization platform (see, e.g., Roth et al., "A Modified mRNA Vaccine Targeting Immunodominant NS Epitopes Protects Against Dengue Virus Infection in HLA Class I Transgenic Mice," Frot Immunol., Jun. 21, 2019, Vol. 10, Article 1424; Jagger et al., J Infect Dis, "Protective Efficacy of Nucleic Acid Vaccines Against Transmission of Zika Virus During Pregnancy in Mice," jiz338, Jul. 1, 2019; Feldman et al., "mRNA vaccines against H10N8 and H7N9 influenza viruses of pandemic potential are immunogenic and well tolerated in healthy adults in phase 1 randomized clinical trials," Vaccine, 37(25), 3326-3334, 2019; and Hasset et al., "Optimization of Lipid Nanoparticles for Intramuscular Administration of mRNA Vaccines," Mol Ther Nucleic Acids, 15: 1-11, 2019.

In one embodiment, a nucleic acid encoding a protomer of a disclosed NiV F ectodomain trimer is introduced directly into cells. For example, the nucleic acid can be loaded onto gold microspheres by standard methods and introduced into the skin by a device such as Bio-Rad's HELIOS™ Gene Gun. The nucleic acids can be "naked," consisting of plasmids under control of a strong promoter. Typically, the DNA is injected into muscle, although it can also be injected directly into other sites. Dosages for injection are usually around 0.5 μg/kg to about 50 mg/kg, and typically are about 0.005 mg/kg to about 5 mg/kg (see, e.g., U.S. Pat. No. 5,589,466).

EXAMPLES

The following examples are provided to illustrate particular features of certain embodiments, but the scope of the claims should not be limited to those features exemplified.

Example 1

NiV F Proteins Stabilized in a Prefusion Conformation

The example illustrates embodiments of a NiV F ectodomain trimer stabilized in a prefusion conformation by one or more amino acid substitutions. The prefusion-stabilized NiV F ectodomain trimers are useful, for example, for inducing a neutralizing immune response to NiV in a subject.

When initially produced in cells, the NiV F ectodomain linked to a C-terminal GCN4 trimerization domain forms trimers that are mostly in the prefusion conformation. However, when stored at 4° C., the metastable trimers undergo a progressive structural transformation to the NiV F postfusion conformation.

Accordingly, structure-based vaccine design was used to identify mutations for the stabilization of the NiV F ectodomain in a prefusion conformation (based on prefusion NiV F structure PDB ID 2B9B), and also to eliminate the F1/F2 cleavage site to produce a "single chain NiV F protein with increased expression. Several different stabilization strategies were employed to "lock" the NiV F ectodomain in the prefusion conformation, including introduction of disulfide bonds, cavity-filling amino acid substitutions, and proline substitutions. In total, approximately 150 different mutants were designed, expressed, purified, and assessed for expression level and binding to antibody 5B3, which is specific for the prefusion conformation of NiV F. Of over 150 constructs tested, the following showed the best combination of prefusion stabilization and protein expression: NiV05, NiV07, NiV08, NiV09, NiV11, NiV12, NiV13, NiV14, NiV15, and NiV16.

The mutations were introduced into a NiV F ectodomain linked to a C-terminal GCN4 trimerization domain, and the resulting mutants were screened in a 96-well microculture high-throughput mini-expression and ELISA assay using prefusion NiV F antibody 5B3. Approximately 150 constructs were produced and expressed, including:

Wildtype ectodomain linked to GCN4 trimerization domain
- NiV01: NiV F (22-497) GCN4

Single chain ectodomain with fusion of F2/F1 and linkage to GCN4 trimerization domain
- NiV02: NiV F (22-497) GCN4, Δ101-116, residues N100-G117 linked by a serine
- NiV03: NiV F (22-497) GCN4, Δ100-115, residues N99-A116 linked by a GSG linker
- NiV04: NiV F (22-497) GCN4, Δ102-113, residues T1014114 linked by a GSG linker
- NiV06: NiV F (22-497) GCN4, Δ100-116, residues N99-G117 linked by a GGS linker
- NiV10: NiV F (22-497) GCN4, Δ100-116, residues N99-G117 directly linked Prefusion stabilized ectodomain linked to GCN4 trimerization domain
- NiV05: NiV F (22-497) GCN4, intraprotomer L104C4114C disulfide
- NiV07: NiV F (22-497) GCN4, intraprotomer I114C4426C disulfide
- NiV08: NiV F (22-497) GCN4, L172F cavity filling substitution
- NiV09: NiV F (22-497) GCN4, S191P
- NiV11: NiV F (22-497) GCN4, Y178W cavity filling substitution
- NiV12: NiV F (22-497) GCN4, intraprotomer A130C-V222C disulfide
- NiV13: NiV F (22-497) GCN4, Q70G
- NiV14: NiV F (22-497) GCN4, D188G, S191G
- NiV15: NiV F (22-497) GCN4, intraprotomer Q162C-T168C disulfide
- NiV16: NiV F (22-497) GCN4, I228F Expression and purification of the single chain and prefusion-stabilized NiV F proteins showed a substantial increase in expression level compared to corresponding the unmodified NiV F (NiV01):

| Construct | mg/L |
|---|---|
| NiV01 | 0.1 |
| NiV02 | 11.6 |
| NiV03 | 5.7 |
| NiV04 | 9.9 |
| NiV05 | 5.6 |
| NiV06 | 11.5 |
| NiV07 | 5.8 |
| NiV08 | 0.8 |
| NiV09 | 1.1 |

-continued

| Construct | mg/L |
|---|---|
| NiV10 | 4.9 |
| NiV11 | 1.2 |
| NiV12 | 0.4 |
| NiV13 | 0.6 |
| NiV14 | 1.0 |
| NiV15 | 1.0 |
| NiV16 | 1.1 |

Figure 1F:
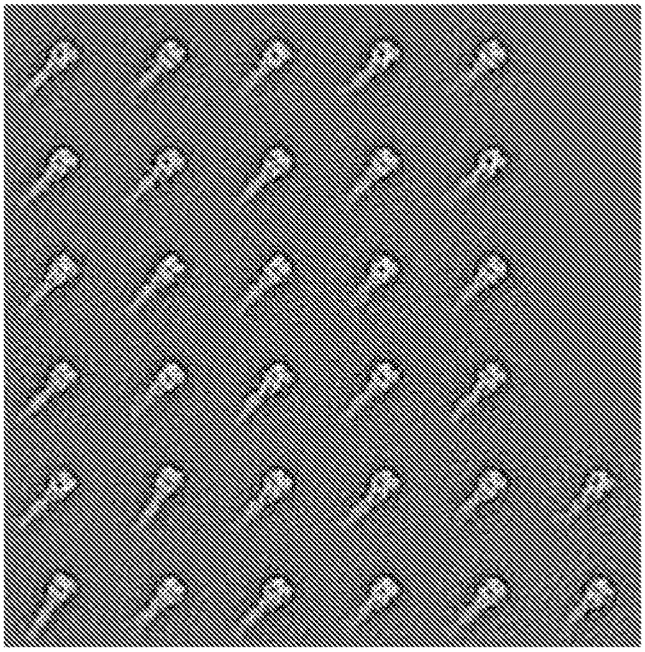

Negative stain EM was used to confirm the conformation of the NiV05, NiV07, NiV08, NiV09, NiV11, NiV12, NiV13, NiV14, NiV15, and NiV16 F variants. Exemplary images are provided in FIGS. 1A-1F. FIG. 1F shows that the NiV06 construct, which has a single-chain mutation, but no prefusion stabilization mutations is in the postfusion conformation.

Next, combinations of mutations for prefusion stabilization and protein production were also assessed. Of the many combinations tested, the following showed the best combination of prefusion stabilization and protein expression:

NiVop01: NiV F (22-497) GCN4, I114C-I426C, L172F
NiVop02: NiV F (22-497) GCN4, L104C-I114C, L172F
NiVop03: NiV F (22-497) GCN4, Δ102-113, T101-I114 linked by GSG, L172F
NiVop04: NiV F (22-497) GCN4, I114C-I426C, S191P
NiVop05: NiV F (22-497) GCN4, L104C-I114C, S191P
NiVop06: NiV F (22-497) GCN4, Δ102-113, T101-I114 linked by GSG, S191P
NiVop07: NiV F (22-497) GCN4, I114C-I426C, L172F, S191P
NiVop08: NiV F (22-497) GCN4, L104C-I114C, L172F, S191P
NiVop09: NiV F (22-497) GCN4, Δ102-113, T101-I114 linked by GSG, L172P, S191P
NiVop12: NiV F (22-497) GCN4, L172P, S191P
NiVop13: NiV F (22-497) GCN4, L172P, S191P, Q70G
NiVop14: NiV F (22-497) GCN4, L104C-I114C, L172F, S191P, Q70G
NiVop15: NiV F (22-497) GCN4, L104C-I114C, L172F, Q70G
NiVop16: NiV F (22-497) GCN4, L104C-I114C, Q70G
NiVop17: NiV F (22-497) GCN4, L104C-I114C, Q162C-T168C, L172F, S191P
NiVop18: NiV F (22-497) GCN4, L104C-I114C, A130C-V222C, L172F, S191P These constructs were expressed in cells, purified, and assessed for 5B3 binding. All of the purified proteins bound to 5B3, indicated that they were in the prefusion conformation. Further, all of these constructs showed a substantial increase in expression level compared to corresponding unmodified NiV F:

| Construct | mg/L |
|---|---|
| NiV01 | 0.1 |
| NiVop01 | 3.9 |
| NiVop02 | 4.0 |
| NiVop03 | 5.8 |
| NiVop04 | 2.8 |
| NiVop05 | 2.2 |
| NiVop06 | 5.6 |
| NiVop07 | 2.8 |
| NiVop08 | 5.6 |
| NiVop09 | 4.9 |
| NiVop12 | 0.6 |
| NiVop13 | 0.6 |

-continued

| Construct | mg/L |
|---|---|
| NiVop14 | 1.6 |
| NiVop15 | 2.9 |
| NiVop16 | 1.3 |

Negative stain EM showed that all of these constructs were in a prefusion-specific conformation. Exemplary negative stain EM images for NiVop08 alone and bound by 5B3 Fab are shown in FIG. 2.

Figure 2:
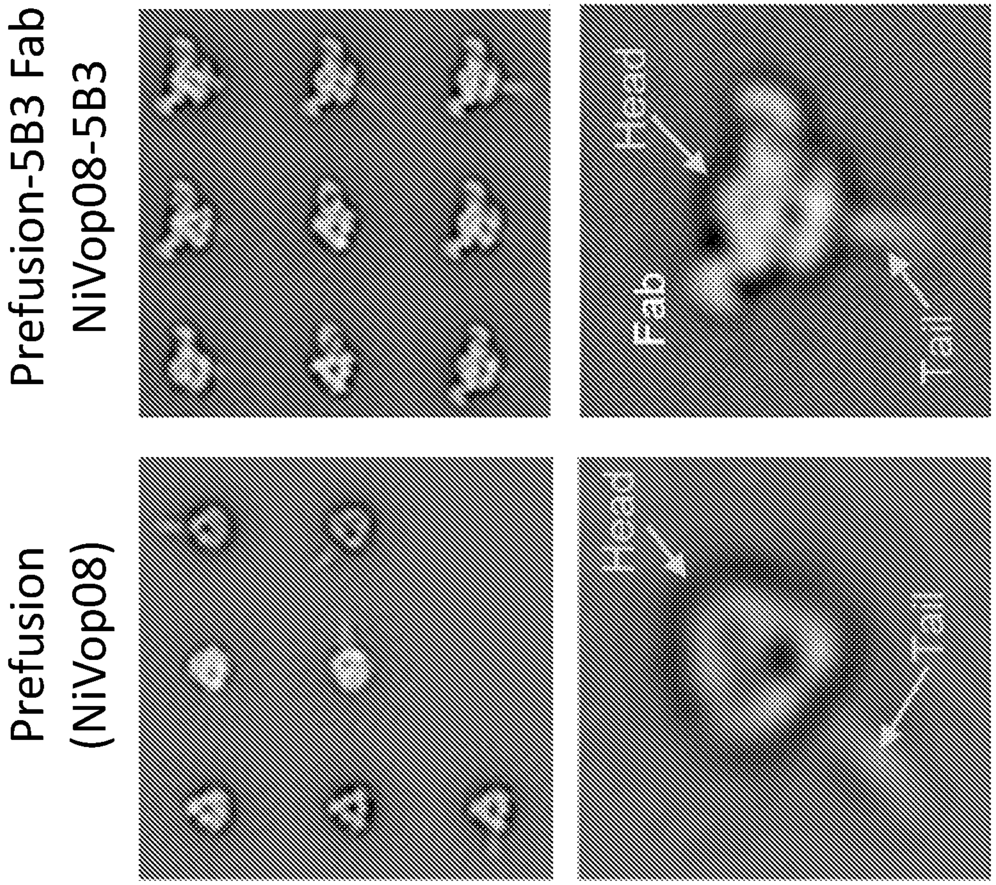
FIG. 2 shows negative stain EM images for the NiVop08 NiV F ectodomain trimer alone or in complex with the 5B3 Fab, which targets the prefusion conformation of NiV F.

As illustrated in FIGS. 1-2, negative EM can be used to distinguish NiV F ectodomain trimers that are in the prefusion conformation from those that are in the postfusion conformation.

Figure 3A:
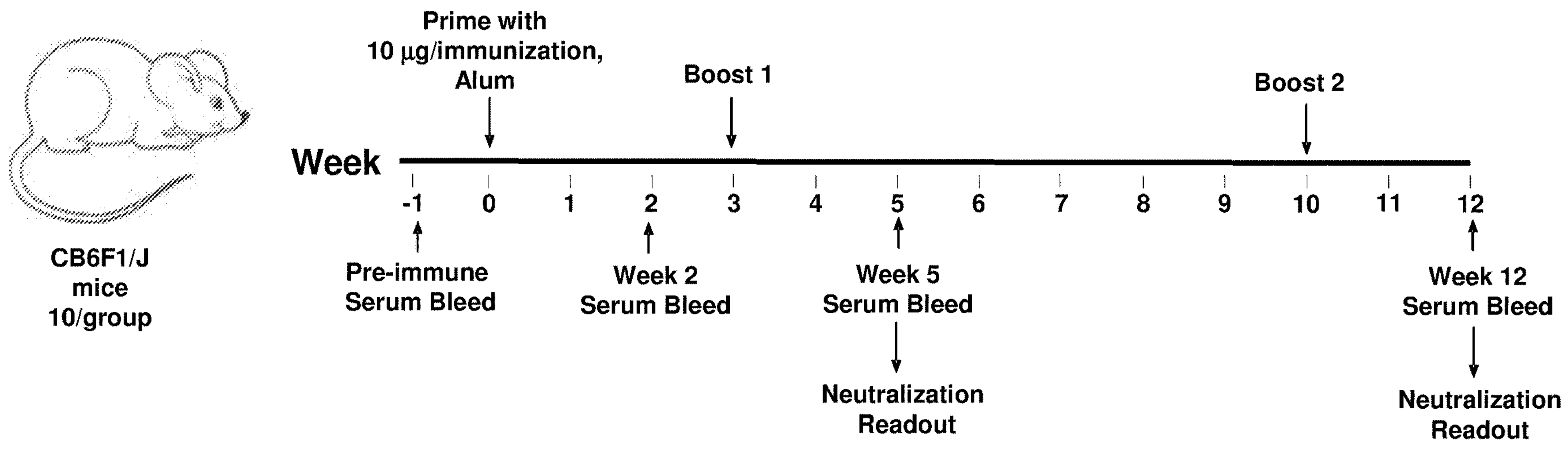
FIGS. 3A-3C show a schematic diagram (FIG. 3A) and results (FIGS. 3B-3D) for an in vivo immunization assay.
Figure 3B:
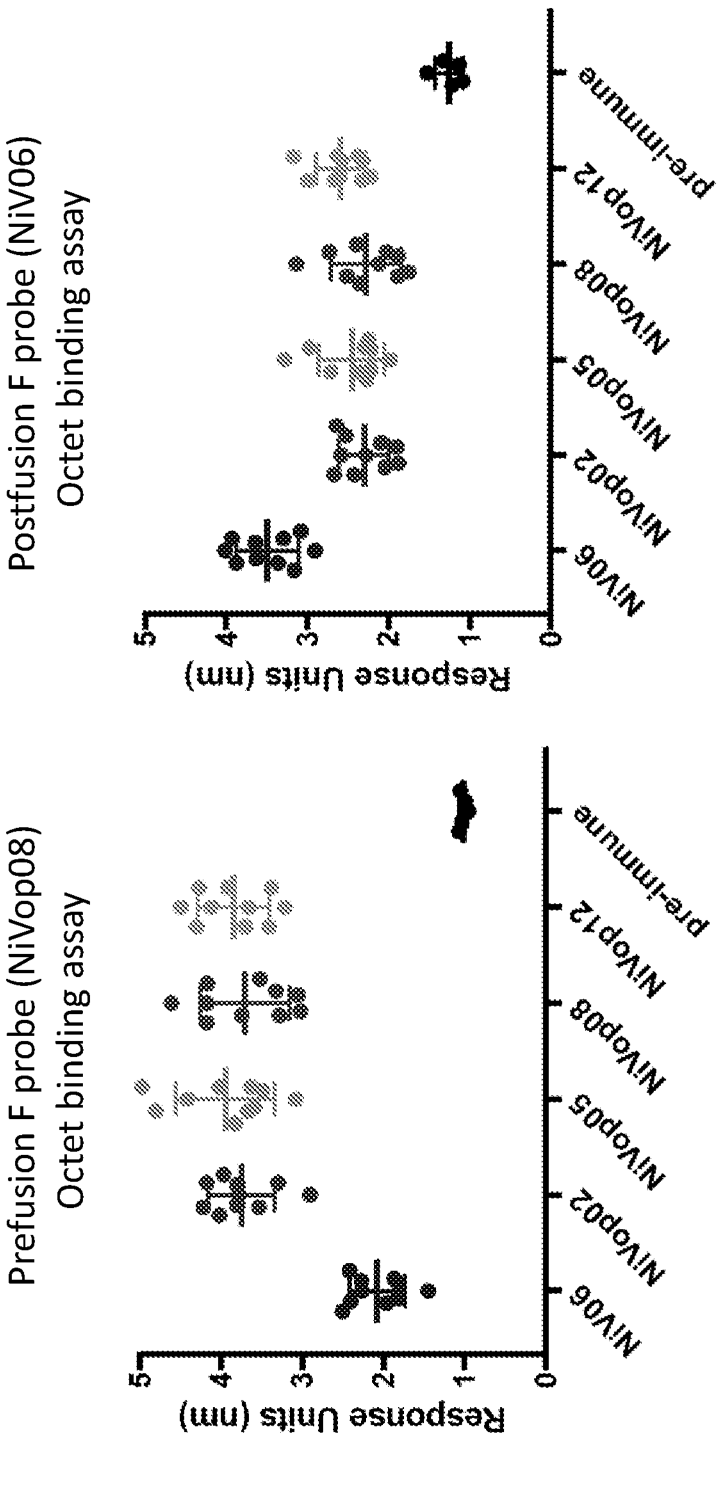

Immunization assays were conducted with several of the modified NiV F ectodomain trimers to determine if these trimers could produce a neutralizing immune response in an animal model. CB6F1/J mice were immunized with 10 μg of NiV F in Alum at weeks 0, 3, and 10, and the neutralization titer of sera from the immunized mice was assayed as weeks 5 and 12 (see FIG. 3A). Sera from immunized mice was tested for binding to prefusion-stabilized NiV F ectodomain trimer (NiVop08) and postfusion NiV F ectodomain trimer (NiV06) using an Octet binding assay (FIG. 3B). The NiVop08 or NiV06 trimer was linked to the sensor and sera from the indicated immunizations assayed for binding. Sera from NiVop02, NiVop05, NiVop08, and NiVop12 immunized animals bound preferentially to prefusion F (NiVop08) relative to postfusion F (NiV06). In contrast, sera from NiV06 immunized animals bound preferentially to postfusion F (NiV06) relative to prefusion F (NiVop08).

Figure 3C:
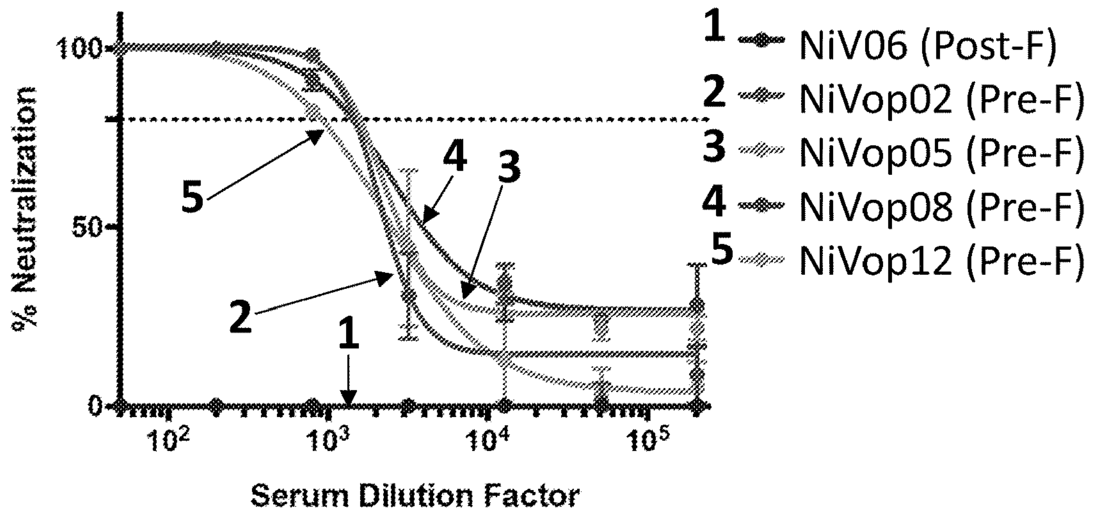

The immune sera was assessed in a NiV neutralization assay (FIG. 3C), which showed that immune sera from animals treated with the prefusion NiV F trimer neutralized NiV. Thus, immunization with soluble prefusion-stabilized NiV F ectodomain trimer elicited a neutralizing immune response in an animal model.

Summary of Methods

Protein expression and purification. NiV F mutations were made by site-directed mutagenesis using the Stratagene Quik-change procedure. NiV F variants were expressed by transient transfection of Expi293F cells with plasmid DNA encoding a precursor of the protomer of the variant NiV F trimer. Cell culture supernatants were harvested 5 days post transfection and centrifuged at 10,000 g to remove cell debris. The supernatants were sterile-filtered, and NiV F proteins were purified by nickel and streptactin-affinity chromatography followed by size-exclusion chromatography. The nickel and streptactin purification tags were removed for animal immunization.

Screening of prefusion-stabilized NiV F constructs. Prefusion NiV F variants were derived from the native NiV F sequences. A 96-well microplate-formatted transient gene expression approach was used to achieve high-throughput expression of various NiV F proteins using a previously described high-throughput assay developed for HIV (Pancera et al., PloS one, 8, e55701, 2013). Briefly, 24 h prior to transfection HEK 293T cells were seeded in each well of a 96-well microplate at a density of $2.5\times10^5$ cells/ml in expression medium (high glucose DMEM supplemented with 10% ultra-low IgG fetal bovine serum and 1×-non-essential amino acids), and incubated at 37° C., 5% CO2 for 20 h. Plasmid DNA encoding a precursor of the protomer of the variant NW F trimer and TrueFect-Max (United BioSystems, MD) were mixed and added to the growing cells, and the 96-well plate incubated at 37° C., 5% CO2. One day post transfection, enriched medium (high glucose DMEM plus 25% ultra-low IgG fetal bovine serum, 2× nonessential amino acids, 1× glutamine) was added to each well, and the 96-well plate was returned to the incubator for continuous culture. On day five, post transfection, supernatants with the expressed NiV F variants were harvested and tested by ELISA for binding to prefusion specific antibody 53B using Ni2+-NTA microplates.

Negative stain electron microscopy. Samples were adsorbed to freshly glow-discharged carbon-film grids, rinsed twice with buffer and stained with freshly made 0.75% uranyl formate. Images were recorded on an FEI T20 microscope with a 2k×2k Eagle CCD camera at a pixel size of 1.5 Å. Image analysis and 2D averaging was performed with Bsoft (Heymann and Belnap, J. Struct Biol., 157, 3, 2007) and EMAN (Ludtke, Baldwin, and Chiu, J. Struct. Biol., 128, 82, 1999).

Mouse immunizations. All animal experiments were reviewed and approved by the Animal Care and Use Committee of the Vaccine Research Center, NIAID, NIH, and all animals were housed and cared for in accordance with local, state, federal, and institute policies in an American Association for Accreditation of Laboratory Animal Care (AAALAC)-accredited facility at the NIH. Hybrid mice that were the first filial offspring of a cross between BALB/c females (C) and C57BL/6J males (B6) (The Jackson Laboratory) known as CB6F1/J at ages 6 weeks to 12 weeks were intramuscularly injected with NiV F ectodomain trimer immunogens at week 0, week 3, and week 10. The frozen NiV F ectodomain trimer variant immunogen proteins were thawed on ice and mixed with Alum adjuvant at 10 μg NiV F per animal per immunization, with injections taking place within 1 h of immunogen:adjuvant preparation. No adverse effect from immunization was observed. Blood was collected at least three days before immunization, and at week two, week five and week 12 post initial immunization.

Generation of NiV Pseudotypes. To obtain VSVΔG-luciferase pseudotyped with NiVF and G proteins, BHK21 cells were first cotransfected with VRC8400 $NiVF_{WT}$ and VRC8400 NiVG. Transfected cells showing extensive cell-to-cell fusion were infected with VSVG complemented VSVΔG-luciferase. At 1 hour post-infection, the input virus was removed and DMEM containing 10% FBS was added to the cells. Medium containing VSVΔG-luciferase pseudotyped with $NiVF_{WT}$ and G was collected between 24-36 hours and titered on Vero76 cells with anti-VSVG antibody measuring luciferase activity.

NiV neutralization assays. To measure NiV neutralizing antibodies in serum, VSVΔG-luciferase/NiVF-G pseudotypes were first incubated with anti-VSV G 8G5 antibody at 5 μg/mL for 30 minutes at room temperature to neutralize any trace infection due to residual VSV G that may have incorporated into the particles pseudotyped with $NiVF_{WT}$ and NiV G proteins. Pooled serum samples from each immunization group were serially diluted (1:100-1:12800) in DMEM/10% FBS and mixed 1:1 with appropriate amount of pseudotype particles. The mixture was incubated at room temperature for 30 minutes and 50 μL of each dilution was transferred to a monolayer of Vero 76 cells grown in a 96-well plate (in triplicate). Cells were incubated for 20-24 hours at 37° C. Cells were lysed in 20 μL of cell culture lysis buffer. Luciferase assay reagent was added to the cell lysate prior to measuring luciferase activity. The $IC_{50}$ for each sample was calculated by curve fitting and non-linear regression using GraphPad Prism (GraphPad Software Inc., CA)

Sera antigenic analysis. Mouse sera from the immunization groups were assessed for binding to pre- and post-fusion NiV F ectodomain trimers using a ForteBio Octet HTX instrument. Week 5 sera were diluted 1:400 in 1% BSA/PBS. Anti penta His, (HIS1K) sensor tips obtained from FortéBio were equilibrated in PBS prior to running an assay. NiV F trimeric protein at 20 μg/ml in 1% BSA/PBS was loaded onto HIS1K biosensors using the C-terminal His tag for 300s. HIS1K tips loaded with pre or postfusion NiV F trimers were equilibrated for 60s in 1% BSA/PBS followed by a serum association step for 300s and a subsequent dissociation step for an additional 300s. Data analysis was performed using Octet and GraphPad Prism 6 software.

Sequences:

NiV01

(SEQ ID NO: 1)

```
mysmqlascvtltlvllvnsQGILHYEKLSKIGLVKGVTRKYKIKSNPLT
KDIVIKMIPNVSDMSQCTGSVMENYKTRLNGILTPIKGALEIYKNNTHDL
VGDVRLAGVIMAGVAIGIATAAQITAGVALYEAMKNADNINKLKSSIEST
NEAVVKLQETAEKTVYVLTALQDYINTNLVPTIDKISCKQTELSLDLALS
KYLSDLLFVFGPNLQDPVSNSMTIQAISQAFGGNYETLLRTLGYATEDFD
DLLESDSITGQIIYVDLSSYYIIVRVYFPILTEIQQAYIQELLPVSFNND
DSEWISIVPNFILVRNTLISNIEIGFCLITKRSVICNQDYATPMTNNMRE
CLTGSTEKCPRELVVSSHVPRFALSNGVLFANCISVTCQCQTTGRAISQS
GEQTLLMIDNTTCPTAVLGNVIISLGKYLGSVNYNSEGIAIGPPVFTDKV
DISSQISSMNQSLQQSKDYIKEAQRLLDTVNPSLklmkqiedkieeilsk
iyhieneiarikkligeapgglvprgshhhhhhsawshpqfek
```

NiV02

(SEQ ID NO: 2)

```
mysmqlascvtltlvllvnsQGILHYEKLSKIGLVKGVTRKYKIKSNPLT
KDIVIKMIPNVSNMSQCTGSVMENYKTRLNGILTPIKGALEIYKNNSGVA
IGIATAAQITAGVALYEAMKNADNINKLKSSIESTNEAVVKLQETAEKTV
YVLTALQDYINTNLVPTIDKISCKQTELSLDLALSKYLSDLLFVFGPNLQ
DPVSNSMTIQAISQAFGGNYETLLRTLGYATEDFDDLLESDSITGQIIYV
DLSSYYIIVRVYFPILTEIQQAYIQELLPVSFNNDNSEWISIVPNFILVR
NTLISNIEIGFCLITKRSVICNQDYATPMTNNMRECLTGSTEKCPRELVV
SSHVPRFALSNGVLFANCISVTCQCQTTGRAISQSGEQTLLMIDNTTCPT
AVLGNVIISLGKYLGSVNYNSEGIAIGPPVFTDKVDISSQISSMNQSLQQ
SKDYIKEAQRLLDTVNPSLklmkqiedkieeilskiyhieneiarikkli
geapgglvprgshhhhhhsawshpqfek
```

NiV03

(SEQ ID NO: 3)

```
mysmqlascvtltlvllvnsQGILHYEKLSKIGLVKGVTRKYKIKSNPLT
KDIVIKMIPNVSNMSQCTGSVMENYKTRLNGILTPIKGALEIYKNGSGAG
VAIGIATAAQITAGVALYEAMKNADNINKLKSSIESTNEAVVKLQETAEK
```

-continued

TVYVLTALQDYINTNLVPTIDKISCKQTELSLDLALSKYLSDLLFVFGPN
LQDPVSNSMTIQAISQAFGGNYETLLRTLGYATEDFDDLLESDSITGQII
YVDLSSYYIIVRVYFPILTEIQQAYIQELLPVSFNNDNSEWISIVPNFIL
VRNTLISNIEIGFCLITKRSVICNQDYATPMTNNMRECLTGSTEKCPREL
VVSSHVPRFALSNGVLFANCISVTCQCQTTGRAISQSGEQTLLMIDNTTC
PTAVLGNVIISLGKYLGSVNYNSEGIAIGPPVFTDKVDISSQISSMNQSL
QQSKDYIKEAQRLLDTVNPSLklmkqiedkieeilskiyhieneiarikk
ligeapgglvprgshhhhhhsawshpqfek NiV04
(SEQ ID NO: 4)
mysmqlascvtltlvllvnsQGILHYEKLSKIGLVKGVTRKYKIKSNPLT
KDIVIKMIPNVSNMSQCTGSVMENYKTRLNGILTPIKGALEIYKNNTGSG
IMAGVAIGIATAAQITAGVALYEAMKNADNINKLKSSIESTNEAVVKLQE
TAEKTVYVLTALQDYINTNLVPTIDKISCKQTELSLDLALSKYLSDLLFV
FGPNLQDPVSNSMTIQAISQAFGGNYETLLRTLGYATEDFDDLLESDSIT
GQIIYVDLSSYYIIVRVYFPILTEIQQAYIQELLPVSFNNDNSEWISIVP
NFILVRNTLISNIEIGFCLITKRSVICNQDYATPMTNNMRECLTGSTEKC
PRELVVSSHVPRFALSNGVLFANCISVTCQCQTTGRAISQSGEQTLLMID
NTTCPTAVLGNVIISLGKYLGSVNYNSEGIAIGPPVFTDKVDISSQISSM
NQSLQQSKDYIKEAQRLLDTVNPSLklmkqiedkieeilskiyhieneia
rikkligeapgglvprgshhhhhhsawshpqfek NiV05
(SEQ ID NO: 5)
mysmqlascvtltlvllvnsQGILHYEKLSKIGLVKGVTRKYKIKSNPLT
KDIVIKMIPNVSNMSQCTGSVMENYKTRLNGILTPIKGALEIYKNNTHDC
VGDVRLAGVCMAGVAIGIATAAQITAGVALYEAMKNADNINKLKSSIEST
NEAVVKLQETAEKTVYVLTALQDYINTNLVPTIDKISCKQTELSLDLALS
KYLSDLLFVFGPNLQDPVSNSMTIQAISQAFGGNYETLLRTLGYATEDFD
DLLESDSITGQIIYVDLSSYYIIVRVYFPILTEIQQAYIQELLPVSFNND
NSEWISIVPNFILVRNTLISNIEIGFCLITKRSVICNQDYATPMTNNMRE
CLTGSTEKCPRELVVSSHVPRFALSNGVLFANCISVTCQCQTTGRAISQS
GEQTLLMIDNTTCPTAVLGNVIISLGKYLGSVNYNSEGIAIGPPVFTDKV
DISSQISSMNQSLQQSKDYIKEAQRLLDTVNPSLklmkqiedkieeilsk
iyhieneiarikkligeapgglvprgshhhhhhsawshpqfek NiV06
(SEQ ID NO: 6)
mysmqlascvtltlvllvnsQGILHYEKLSKIGLVKGVTRKYKIKSNPLT
KDIVIKMIPNVSNMSQCTGSVMENYKTRLNGILTPIKGALEIYKNGGSGV
AIGIATAAQITAGVALYEAMKNADNINKLKSSIESTNEAVVKLQETAEKT
VYVLTALQDYINTNLVPTIDKISCKQTELSLDLALSKYLSDLLFVFGPNL
QDPVSNSMTIQAISQAFGGNYETLLRTLGYATEDFDDLLESDSITGQIIY
VDLSSYYIIVRVYFPILTEIQQAYIQELLPVSFNNDNSEWISIVPNFILV
RNTLISNIEIGFCLITKRSVICNQDYATPMTNNMRECLTGSTEKCPRELV
VSSHVPRFALSNGVLFANCISVTCQCQTTGRAISQSGEQTLLMIDNTTCP
TAVLGNVIISLGKYLGSVNYNSEGIAIGPPVFTDKVDISSQISSMNQSLQ
QSKDYIKEAQRLLDTVNPSLklmkqiedkieeilskiyhieneiarikkl
igeapgglvprgshhhhhhsawshpqfek NiV07
(SEQ ID NO: 7)
mysmqlascvtltlvllvnsQGILHYEKLSKIGLVKGVTRKYKIKSNPLT
KDIVIKMIPNVSNMSQCTGSVMENYKTRLNGILTPIKGALEIYKNNTHDL
VGDVRLAGVCMAGVAIGIATAAQITAGVALYEAMKNADNINKLKSSIEST
NEAVVKLQETAEKTVYVLTALQDYINTNLVPTIDKISCKQTELSLDLALS
KYLSDLLFVFGPNLQDPVSNSMTIQAISQAFGGNYETLLRTLGYATEDFD
DLLESDSITGQIIYVDLSSYYIIVRVYFPILTEIQQAYIQELLPVSFNND
NSEWISIVPNFILVRNTLISNIEIGFCLITKRSVICNQDYATPMTNNMRE
CLTGSTEKCPRELVVSSHVPRFALSNGVLFANCISVTCQCQTTGRAISQS
GEQTLLMIDNTTCPTAVLGNVCISLGKYLGSVNYNSEGIAIGPPVFTDKV
DISSQISSMNQSLQQSKDYIKEAQRLLDTVNPSLklmkqiedkieeilsk
iyhieneiarikkligeapgglvprgshhhhhhsawshpqfek NiV08
(SEQ ID NO: 8)
mysmqlascvtltlvllvnsQGILHYEKLSKIGLVKGVTRKYKIKSNPLT
KDIVIKMIPNVSDMSQCTGSVMENYKTRLNGILTPIKGALEIYKNNTHDL
VGDVRLAGVIMAGVAIGIATAAQITAGVALYEAMKNADNINKLKSSIEST
NEAVVKLQETAEKTVYVFTALQDYINTNLVPTIDKISCKQTELSLDLALS
KYLSDLLFVFGPNLQDPVSNSMTIQAISQAFGGNYETLLRTLGYATEDFD
DLLESDSITGQIIYVDLSSYYIIVRVYFPILTEIQQAYIQELLPVSFNND
DSEWISIVPNFILVRNTLISNIEIGFCLITKRSVICNQDYATPMTNNMRE
CLTGSTEKCPRELVVSSHVPRFALSNGVLFANCISVTCQCQTTGRAISQS
GEQTLLMIDNTTCPTAVLGNVIISLGKYLGSVNYNSEGIAIGPPVFTDKV
DISSQISSMNQSLQQSKDYIKEAQRLLDTVNPSLklmkqiedkieeilsk
iyhieneiarikkligeapgglvprgshhhhhhsawshpqfek NiV09
(SEQ ID NO: 9)
mysmqlascvtltlvllvnsQGILHYEKLSKIGLVKGVTRKYKIKSNPLT
KDIVIKMIPNVSNMSQCTGSVMENYKTRLNGILTPIKGALEIYKNNTHDL
VGDVRLAGVIMAGVAIGIATAAQITAGVALYEAMKNADNINKLKSSIEST
NEAVVKLQETAEKTVYVLTALQDYINTNLVPTIDKIPCKQTELSLDLALS
KYLSDLLFVFGPNLQDPVSNSMTIQAISQAFGGNYETLLRTLGYATEDFD -continued DLLESDSITGQIIYVDLSSYYIIVRVYFPILTEIQQAYIQELLPVSFNND
NSEWISIVPNFILVRNTLISNIEIGFCLITKRSVICNQDYATPMTNNMRE
CLTGSTEKCPRELVVSSHVPRFALSNGVLFANCISVTCQCQTTGRAISQS
GEQTLLMIDNTTCPTAVLGNVIISLGKYLGSVNYNSEGIAIGPPVFTDKV
DISSQISSMNQSLQQSKDYIKEAQRLLDTVNPSLklmkqiedkieeilsk
iyhieneiarikkligeapgglvprgshhhhhhsawshpqfek NiV10

(SEQ ID NO: 10)

mysmqlascvtltlvllvnsQGILHYEKLSKIGLVKGVTRKYKIKSNPLT
KDIVIKMIPNVSNMSQCTGSVMENYKTRLNGILTPIKGALEIYKNGVAIG
IATAAQITAGVALYEAMKNADNINKLKSSIESTNEAVVKLQETAEKTVYV
LTALQDYINTNLVPTIDKISCKQTELSLDLALSKYLSDLLFVFGPNLQDP
VSNSMTIQAISQAFGGNYETLLRTLGYATEDFDDLLESDSITGQIIYVDL
SSYYIIVRVYFPILTEIQQAYIQELLPVSFNNDNSEWISIVPNFILVRNT
LISNIEIGFCLITKRSVICNQDYATPMTNNMRECLTGSTEKCPRELVVSS
HVPRFALSNGVLFANCISVTCQCQTTGRAISQSGEQTLLMIDNTTCPTAV
LGNVIISLGKYLGSVNYNSEGIAIGPPVFTDKVDISSQISSMNQSLQQSK
DYIKEAQRLLDTVNPSLklmkqiedkieeilskiyhieneiarikklige
apgglvprgshhhhhhsawshpqfek NiV11

(SEQ ID NO: 11)

mysmqlascvtltlvllvnsQGILHYEKLSKIGLVKGVTRKYKIKSNPLT
KDIVIKMIPNVSNMSQCTGSVMENYKTRLNGILTPIKGALEIYKNNTHDL
VGDVRLAGVIMAGVAIGIATAAQITAGVALYEAMKNADNINKLKSSIEST
NEAVVKLQETAEKTVYVLTALQDWINTNLVPTIDKISCKQTELSLDLALS
KYLSDLLFVFGPNLQDPVSNSMTIQAISQAFGGNYETLLRTLGYATEDFD
DLLESDSITGQIIYVDLSSYYIIVRVYFPILTEIQQAYIQELLPVSFNND
NSEWISIVPNFILVRNTLISNIEIGFCLITKRSVICNQDYATPMTNNMRE
CLTGSTEKCPRELVVSSHVPRFALSNGVLFANCISVTCQCQTTGRAISQS
GEQTLLMIDNTTCPTAVLGNVIISLGKYLGSVNYNSEGIAIGPPVFTDKV
DISSQISSMNQSLQQSKDYIKEAQRLLDTVNPSLklmkqiedkieeilsk
iyhieneiarikkligeapgglvprgshhhhhhsawshpqfek NiV12

(SEQ ID NO: 12)

mysmqlascvtltlvllvnsQGILHYEKLSKIGLVKGVTRKYKIKSNPLT
KDIVIKMIPNVSNMSQCTGSVMENYKTRLNGILTPIKGALEIYKNNTHDL
VGDVRLAGVIMAGVAIGIATAAQITCGVALYEAMKNADNINKLKSSIEST
NEAVVKLQETAEKTVYVLTALQDYINTNLVPTIDKISCKQTELSLDLALS
KYLSDLLFVFGPNLQDPCSNSMTIQAISQAFGGNYETLLRTLGYATEDFD
DLLESDSITGQIIYVDLSSYYIIVRVYFPILTEIQQAYIQELLPVSFNND -continued NSEWISIVPNFILVRNTLISNIEIGFCLITKRSVICNQDYATPMTNNMRE
CLTGSTEKCPRELVVSSHVPRFALSNGVLFANCISVTCQCQTTGRAISQS
GEQTLLMIDNTTCPTAVLGNVIISLGKYLGSVNYNSEGIAIGPPVFTDKV
DISSQISSMNQSLQQSKDYIKEAQRLLDTVNPSLklmkqiedkieeilsk
iyhieneiarikkligeapgglvprgshhhhhhsawshpqfek NiV13

(SEQ ID NO: 13)

mysmqlascvtltlvllvnsQGILHYEKLSKIGLVKGVTRKYKIKSNPLT
KDIVIKMIPNVSNMSGCTGSVMENYKTRLNGILTPIKGALEIYKNNTHDL
VGDVRLAGVIMAGVAIGIATAAQITAGVALYEAMKNADNINKLKSSIEST
NEAVVKLQETAEKTVYVLTALQDYINTNLVPTIDKISCKQTELSLDLALS
KYLSDLLFVFGPNLQDPVSNSMTIQAISQAFGGNYETLLRTLGYATEDFD
DLLESDSITGQIIYVDLSSYYIIVRVYFPILTEIQQAYIQELLPVSFNND
NSEWISIVPNFILVRNTLISNIEIGFCLITKRSVICNQDYATPMTNNMRE
CLTGSTEKCPRELVVSSHVPRFALSNGVLFANCISVTCQCQTTGRAISQS
GEQTLLMIDNTTCPTAVLGNVIISLGKYLGSVNYNSEGIAIGPPVFTDKV
DISSQISSMNQSLQQSKDYIKEAQRLLDTVNPSLklmkqiedkieeilsk
iyhieneiarikkligeapgglvprgshhhhhhsawshpqfek NiV14

(SEQ ID NO: 14)

mysmqlascvtltlvllvnsQGILHYEKLSKIGLVKGVTRKYKIKSNPLT
KDIVIKMIPNVSNMSQCTGSVMENYKTRLNGILTPIKGALEIYKNNTHDL
VGDVRLAGVIMAGVAIGIATAAQITAGVALYEAMKNADNINKLKSSIEST
NEAVVKLQETAEKTVYVLTALQDYINTNLVPTIGKIGCKQTELSLDLALS
KYLSDLLFVFGPNLQDPVSNSMTIQAISQAFGGNYETLLRTLGYATEDFD
DLLESDSITGQIIYVDLSSYYIIVRVYFPILTEIQQAYIQELLPVSFNND
NSEWISIVPNFILVRNTLISNIEIGFCLITKRSVICNQDYATPMTNNMRE
CLTGSTEKCPRELVVSSHVPRFALSNGVLFANCISVTCQCQTTGRAISQS
GEQTLLMIDNTTCPTAVLGNVIISLGKYLGSVNYNSEGIAIGPPVFTDKV
DISSQISSMNQSLQQSKDYIKEAQRLLDTVNPSLklmkqiedkieeilsk
iyhieneiarikkligeapgglvprgshhhhhhsawshpqfek NiV15

(SEQ ID NO: 15)

mysmqlascvtltlvllvnsQGILHYEKLSKIGLVKGVTRKYKIKSNPLT
KDIVIKMIPNVSDMSQCTGSVMENYKTRLNGILTPIKGALEIYKNNTHDL
VGDVRLAGVIMAGVAIGIATAAQITAGVALYEAMKNADNINKLKSSIEST
NEAVVKLCETAEKCVYVLTALQDYINTNLVPTIDKISCKQTELSLDLALS
KYLSDLLFVFGPNLQDPVSNSMTIQAISQAFGGNYETLLRTLGYATEDFD
DLLESDSITGQIIYVDLSSYYIIVRVYFPILTEIQQAYIQELLPVSFNND
DSEWISIVPNFILVRNTLISNIEIGFCLITKRSVICNQDYATPMTNNMRE -continued CLTGSTEKCPRELVVSSHVPRFALSNGVLFANCISVTCQCQTTGRAISQS
GEQTLLMIDNTTCPTAVLGNVIISLGKYLGSVNYNSEGIAIGPPVFTDKV
DISSQISSMNQSLQQSKDYIKEAQRLLDTVNPSLklmkqiedkieeilsk
iyhieneiarikkligeapgglvprgshhhhhhsawshpqfek NiV16

(SEQ ID NO: 16)
mysmqlascvtltlvllvnsQGILHYEKLSKIGLVKGVTRKYKIKSNPLT
KDIVIKMIPNVSNMSQCTGSVMENYKTRLNGILTPIKGALEIYKNNTHDL
VGDVRLAGVIMAGVAIGIATAAQITAGVALYEAMKNADNINKLKSSIEST
NEAVVKLQETAEKTVYVLTALQDYINTNLVPTIDKISCKQTELSLDLALS
KYLSDLLFVFGPNLQDPVSNSMTFQAISQAFGGNYETLLRTLGYATEDFD
DLLESDSITGQIIYVDLSSYYIIVRVYFPILTEIQQAYIQELLPVSFNND
NSEWISIVPNFILVRNTLISNIEIGFCLITKRSVICNQDYATPMTNNMRE
CLTGSTEKCPRELVVSSHVPRFALSNGVLFANCISVTCQCQTTGRAISQS
GEQTLLMIDNTTCPTAVLGNVIISLGKYLGSVNYNSEGIAIGPPVFTDKV
DISSQISSMNQSLQQSKDYIKEAQRLLDTVNPSLklmkqiedkieeilsk
iyhieneiarikkligeapgglvprgshhhhhhsawshpqfek NiVop1

(SEQ ID NO: 17)
mysmqlascvtltlvllvnsQGILHYEKLSKIGLVKGVTRKYKIKSNPLT
KDIVIKMIPNVSNMSQCTGSVMENYKTRLNGILTPIKGALEIYKNNTHDL
VGDVRLAGVCMAGVAIGIATAAQITAGVALYEAMKNADNINKLKSSIEST
NEAVVKLQETAEKTVYVFTALQDYINTNLVPTIDKISCKQTELSLDLALS
KYLSDLLFVFGPNLQDPVSNSMTIQAISQAFGGNYETLLRTLGYATEDFD
DLLESDSITGQIIYVDLSSYYIIVRVYFPILTEIQQAYIQELLPVSFNND
NSEWISIVPNFILVRNTLISNIEIGFCLITKRSVICNQDYATPMTNNMRE
CLTGSTEKCPRELVVSSHVPRFALSNGVLFANCISVTCQCQTTGRAISQS
GEQTLLMIDNTTCPTAVLGNVcISLGKYLGSVNYNSEGIAIGPPVFTDKV
DISSQISSMNQSLQQSKDYIKEAQRLLDTVNPSLKLMKQIEDKIEEILSK
IYHIENEIARIKKLIGEAPGGLVPRGSHHHHHHSAWSHPQFEK NiVop2

(SEQ ID NO: 18)
mysmqlascvtltlvllvnsQGILHYEKLSKIGLVKGVTRKYKIKSNPLT
KDIVIKMIPNVSNMSQCTGSVMENYKTRLNGILTPIKGALEIYKNNTHDC
VGDVRLAGVcMAGVAIGIATAAQITAGVALYEAMKNADNINKLKSSIEST
NEAVVKLQETAEKTVYVFTALQDYINTNLVPTIDKISCKQTELSLDLALS
KYLSDLLFVFGPNLQDPVSNSMTIQAISQAFGGNYETLLRTLGYATEDFD
DLLESDSITGQIIYVDLSSYYIIVRVYFPILTEIQQAYIQELLPVSFNND
NSEWISIVPNFILVRNTLISNIEIGFCLITKRSVICNQDYATPMTNNMRE
CLTGSTEKCPRELVVSSHVPRFALSNGVLFANCISVTCQCQTTGRAISQS -continued GEQTLLMIDNTTCPTAVLGNVIISLGKYLGSVNYNSEGIAIGPPVFTDKV
DISSQISSMNQSLQQSKDYIKEAQRLLDTVNPSLKLMKQIEDKIEEILSK
IYHIENEIARIKKLIGEAPGGLVPRGSHHHHHHSAWSHPQFEK NiVop3

(SEQ ID NO: 19)
mysmqlascvtltlvllvnsQGILHYEKLSKIGLVKGVTRKYKIKSNPLT
KDIVIKMIPNVSNMSQCTGSVMENYKTRLNGILTPIKGALETYKNNTgsg
IMAGVAIGIATAAQITAGVALYEAMKNADNINKLKSSIESTNEAVVKLQE
TAEKTVYVFTALQDYINTNLVPTIDKISCKQTELSLDLALSKYLSDLLFV
FGPNLQDPVSNSMTIQAISQAFGGNYETLLRTLGYATEDFDDLLESDSIT
GQIIYVDLSSYYIIVRVYFPILTEIQQAYIQELLPVSFNNDNSEWISIVP
NFILVRNTLISNIEIGFCLITKRSVICNQDYATPMTNNMRECLTGSTEKC
PRELVVSSHVPRFALSNGVLFANCISVTCQCQTTGRAISQSGEQTLLMID
NTTCPTAVLGNVIISLGKYLGSVNYNSEGIAIGPPVFTDKVDISSQISSM
NQSLQQSKDYIKEAQRLLDTVNPSLKLMKQIEDKIEEILSKIYHIENEIA
RIKKLIGEAPGGLVPRGSHHHHHHSAWSHPQFEK NiVop4

(SEQ ID NO: 20)
mysmqlascvtltlvllvnsQGILHYEKLSKIGLVKGVTRKYKIKSNPLT
KDIVIKMIPNVSNMSQCTGSVMENYKTRLNGILTPIKGALEIYKNNTHDL
VGDVRLAGVcMAGVAIGIATAAQITAGVALYEAMKNADNINKLKSSIEST
NEAVVKLQETAEKTVYVLTALQDYINTNLVPTIDKIPCKQTELSLDLALS
KYLSDLLFVFGPNLQDPVSNSMTIQAISQAFGGNYETLLRTLGYATEDFD
DLLESDSITGQIIYVDLSSYYIIVRVYFPILTEIQQAYIQELLPVSFNND
NSEWISIVPNFILVRNTLISNIEIGFCLITKRSVICNQDYATPMTNNMRE
CLTGSTEKCPRELVVSSHVPRFALSNGVLFANCISVTCQCQTTGRAISQS
GEQTLLMIDNTTCPTAVLGNVcISLGKYLGSVNYNSEGIAIGPPVFTDKV
DISSQISSMNQSLQQSKDYIKEAQRLLDTVNPSLKLMKQIEDKIEEILSK
IYHIENEIARIKKLIGEAPGGLVPRGSHHHHHHSAWSHPQFEK NiVop5

(SEQ ID NO: 21)
mysmqlascvtltlvllvnsQGILHYEKLSKIGLVKGVTRKYKIKSNPLT
KDIVIKMIPNVSNMSQCTGSVMENYKTRLNGILTPIKGALEIYKNNTHDC
VGDVRLAGVcMAGVAIGIATAAQITAGVALYEAMKNADNINKLKSSIEST
NEAVVKLQETAEKTVYVLTALQDYINTNLVPTIDKIPCKQTELSLDLALS
KYLSDLLFVFGPNLQDPVSNSMTIQAISQAFGGNYETLLRTLGYATEDFD
DLLESDSITGQIIYVDLSSYYIIVRVYFPILTEIQQAYIQELLPVSFNND
NSEWISIVPNFILVRNTLISNIEIGFCLITKRSVICNQDYATPMTNNMRE
CLTGSTEKCPRELVVSSHVPRFALSNGVLFANCISVTCQCQTTGRAISQS
GEQTLLMIDNTTCPTAVLGNVIISLGKYLGSVNYNSEGIAIGPPVFTDKV -continued

DISSQISSMNQSLQQSKDYIKEAQRLLDTVNPSLKLMKQIEDKIEEILSK

IYHIENEIARIKKLIGEAPGGLVPRGSHHHHHHSAWSHPQFEK

NiVop6

(SEQ ID NO: 22)

mysmqlascvtltlvllvnsQGILHYEKLSKIGLVKGVTRKYKIKSNPLT

KDIVIKMIPNVSNMSQCTGSVMENYKTRLNGILTPIKGALEIYKNNTgsg

IMAGVAIGIATAAQITAGVALYEAMKNADNINKLKSSIESTNEAVVKLQE

TAEKTVYVLTALQDYINTNLVPTIDKIPCKQTELSLDLALSKYLSDLLFV

FGPNLQDPVSNSMTIQAISQAFGGNYETLLRTLGYATEDFDDLLESDSIT

GQIIYVDLSSYYIIVRVYFPILTEIQQAYIQELLPVSFNNDNSEWISIVP

NFILVRNTLISNIEIGFCLITKRSVICNQDYATPMTNNMRECLTGSTEKC

PRELVVSSHVPRFALSNGVLFANCISVTCQCQTTGRAISQSGEQTLLMID

NTTCPTAVLGNVIISLGKYLGSVNYNSEGIAIGPPVFTDKVDISSQISSM

NQSLQQSKDYIKEAQRLLDTVNPSLKLMKQIEDKIEEILSKIYHIENEIA

RIKKLIGEAPGGLVPRGSHHHHHHSAWSHPQFEK

NiVop7

(SEQ ID NO: 23)

mysmqlascvtltlvllvnsQGILHYEKLSKIGLVKGVTRKYKIKSNPLT

KDIVIKMIPNVSNMSQCTGSVMENYKTRLNGILTPIKGALEIYKNNTHDL

VGDVRLAGVcMAGVAIGIATAAQITAGVALYEAMKNADNINKLKSSIEST

NEAVVKLQETAEKTVYVFTALQDYINTNLVPTIDKIPCKQTELSLDLALS

KYLSDLLFVFGPNLQDPVSNSMTIQAISQAFGGNYETLLRTLGYATEDFD

DLLESDSITGQIIYVDLSSYYIIVRVYFPILTEIQQAYIQELLPVSFNND

NSEWISIVPNFILVRNTLISNIEIGFCLITKRSVICNQDYATPMTNNMRE

CLTGSTEKCPRELVVSSHVPRFALSNGVLFANCISVTCQCQTTGRAISQS

GEQTLLMIDNTTCPTAVLGNVcISLGKYLGSVNYNSEGIAIGPPVFTDKV

DISSQISSMNQSLQQSKDYIKEAQRLLDTVNPSLKLMKQIEDKIEEILSK

IYHIENEIARIKKLIGEAPGGLVPRGSHHHHHHSAWSHPQFEK

NiVop8

(SEQ ID NO: 24)

mysmqlascvtltlvllvnsQGILHYEKLSKIGLVKGVTRKYKIKSNPLT

KDIVIKMIPNVSNMSQCTGSVMENYKTRLNGILTPIKGALEIYKNNTHDc

VGDVRLAGVcMAGVAIGIATAAQITAGVALYEAMKNADNINKLKSSIEST

NEAVVKLQETAEKTVYVFTALQDYINTNLVPTIDKIPCKQTELSLDLALS

KYLSDLLFVFGPNLQDPVSNSMTIQAISQAFGGNYETLLRTLGYATEDFD

DLLESDSITGQIIYVDLSSYYIIVRVYFPILTEIQQAYIQELLPVSFNND

NSEWISIVPNFILVRNTLISNIEIGFCLITKRSVICNQDYATPMTNNMRE

CLTGSTEKCPRELVVSSHVPRFALSNGVLFANCISVTCQCQTTGRAISQS

GEQTLLMIDNTTCPTAVLGNVIISLGKYLGSVNYNSEGIAIGPPVFTDKV

-continued

DISSQISSMNQSLQQSKDYIKEAQRLLDTVNPSLKLMKQIEDKIEEILSK

IYHIENEIARIKKLIGEAPGGLVPRGSHHHHHHSAWSHPQFEK

NiVop9

(SEQ ID NO: 25)

mysmqlascvtltlvllvnsQGILHYEKLSKIGLVKGVTRKYKIKSNPLT

KDIVIKMIPNVSNMSQCTGSVMENYKTRLNGILTPIKGALETYKNNTgsg

IMAGVAIGIATAAQITAGVALYEAMKNADNINKLKSSIESTNEAVVKLQE

TAEKTVYVFTALQDYINTNLVPTIDKIPCKQTELSLDLALSKYLSDLLFV

FGPNLQDPVSNSMTIQAISQAFGGNYETLLRTLGYATEDFDDLLESDSIT

GQIIYVDLSSYYIIVRVYFPILTEIQQAYIQELLPVSFNNDNSEWISIVP

NFILVRNTLISNIEIGFCLITKRSVICNQDYATPMTNNMRECLTGSTEKC

PRELVVSSHVPRFALSNGVLFANCISVTCQCQTTGRAISQSGEQTLLMID

NTTCPTAVLGNVIISLGKYLGSVNYNSEGIAIGPPVFTDKVDISSQISSM

NQSLQQSKDYIKEAQRLLDTVNPSLKLMKQIEDKIEEILSKIYHIENEIA

RIKKLIGEAPGGLVPRGSHHHHHHSAWSHPQFEK

NiVop12

(SEQ ID NO: 26)

mysmqlascvtltlvllvnsQGILHYEKLSKIGLVKGVTRKYKIKSNPLT

KDIVIKMIPNVSNMSQCTGSVMENYKTRLNGILTPIKGALEIYKNNTHDL

VGDVRLAGVIMAGVAIGIATAAQITAGVALYEAMKNADNINKLKSSIEST

NEAVVKLQETAEKTVYVFTALQDYINTNLVPTIDKIpCKQTELSLDLALS

KYLSDLLFVFGPNLQDPVSNSMTIQAISQAFGGNYETLLRTLGYATEDFD

DLLESDSITGQIIYVDLSSYYIIVRVYFPILTEIQQAYIQELLPVSFNND

NSEWISIVPNFILVRNTLISNIEIGFCLITKRSVICNQDYATPMTNNMRE

CLTGSTEKCPRELVVSSHVPRFALSNGVLFANCISVTCQCQTTGRAISQS

GEQTLLMIDNTTCPTAVLGNVIISLGKYLGSVNYNSEGIAIGPPVFTDKV

DISSQISSMNQSLQQSKDYIKEAQRLLDTVNPSLKLMKQIEDKIEEILSK

IYHIENEIARIKKLIGEAPGGLVPRGSHHHHHHSAWSHPQFEK

NiVop13

(SEQ ID NO: 27)

mysmqlascvtltlvllvnsQGILHYEKLSKIGLVKGVTRKYKIKSNPLT

KDIVIKMIPNVSNMSGCTGSVMENYKTRLNGILTPIKGALEIYKNNTHDL

VGDVRLAGVIMAGVAIGIATAAQITAGVALYEAMKNADNINKLKSSIEST

NEAVVKLQETAEKTVYVFTALQDYINTNLVPTIDKIpCKQTELSLDLALS

KYLSDLLFVFGPNLQDPVSNSMTIQAISQAFGGNYETLLRTLGYATEDFD

DLLESDSITGQIIYVDLSSYYIIVRVYFPILTEIQQAYIQELLPVSFNND

NSEWISIVPNFILVRNTLISNIEIGFCLITKRSVICNQDYATPMTNNMRE

CLTGSTEKCPRELVVSSHVPRFALSNGVLFANCISVTCQCQTTGRAISQS

GEQTLLMIDNTTCPTAVLGNVIISLGKYLGSVNYNSEGIAIGPPVFTDKV

-continued

DISSQISSMNQSLQQSKDYIKEAQRLLDTVNPSLKLMKQIEDKIEEILSK

IYHIENEIARIKKLIGEAPGGLVPRGSHHHHHHSAWSHPQFEK

NiVop14
(SEQ ID NO: 28)
mysmqlascvtltlvllvnsQGILHYEKLSKIGLVKGVTRKYKIKSNPLT

KDIVIKMIPNVSNMSGCTGSVMENYKTRLNGILTPIKGALEIYKNNTHDC

VGDVRLAGVcMAGVAIGIATAAQITAGVALYEAMKNADNINKLKSSIEST

NEAVVKLQETAEKTVYVFTALQDYINTNLVPTIDKIPCKQTELSLDLALS

KYLSDLLFVFGPNLQDPVSNSMTIQAISQAFGGNYETLLRTLGYATEDFD

DLLESDSITGQIIYVDLSSYYIIVRVYFPILTEIQQAYIQELLPVSFNND

NSEWISIVPNFILVRNTLISNIEIGFCLITKRSVICNQDYATPMTNNMRE

CLTGSTEKCPRELVVSSHVPRFALSNGVLFANCISVTCQCQTTGRAISQS

GEQTLLMIDNTTCPTAVLGNVIISLGKYLGSVNYNSEGIAIGPPVFTDKV

DISSQISSMNQSLQQSKDYIKEAQRLLDTVNPSLKLMKQIEDKIEEILSK

IYHIENEIARIKKLIGEAPGGLVPRGSHHHHHHSAWSHPQFEK

NiVop15
(SEQ ID NO: 29)
mysmqlascvtltlvllvnsQGILHYEKLSKIGLVKGVTRKYKIKSNPLT

KDIVIKMIPNVSNMSGCTGSVMENYKTRLNGILTPIKGALEIYKNNTHDc

VGDVRLAGVcMAGVAIGIATAAQITAGVALYEAMKNADNINKLKSSIEST

NEAVVKLQETAEKTVYVFTALQDYINTNLVPTIDKISCKQTELSLDLALS

KYLSDLLFVFGPNLQDPVSNSMTIQAISQAFGGNYETLLRTLGYATEDFD

DLLESDSITGQIIYVDLSSYYIIVRVYFPILTEIQQAYIQELLPVSFNND

NSEWISIVPNFILVRNTLISNIEIGFCLITKRSVICNQDYATPMTNNMRE

CLTGSTEKCPRELVVSSHVPRFALSNGVLFANCISVTCQCQTTGRAISQS

GEQTLLMIDNTTCPTAVLGNVIISLGKYLGSVNYNSEGIAIGPPVFTDKV

DISSQISSMNQSLQQSKDYIKEAQRLLDTVNPSLKLMKQIEDKIEEILSK

IYHIENEIARIKKLIGEAPGGLVPRGSHHHHHHSAWSHPQFEK

NiVop16
(SEQ ID NO: 30)
mysmqlascvtltlvllvnsQGILHYEKLSKIGLVKGVTRKYKIKSNPLT

KDIVIKMIPNVSNMSGCTGSVMENYKTRLNGILTPIKGALEIYKNNTHDc

VGDVRLAGVcMAGVAIGIATAAQITAGVALYEAMKNADNINKLKSSIEST

NEAVVKLQETAEKTVYVLTALQDYINTNLVPTIDKISCKQTELSLDLALS

KYLSDLLFVFGPNLQDPVSNSMTIQAISQAFGGNYETLLRTLGYATEDFD

DLLESDSITGQIIYVDLSSYYIIVRVYFPILTEIQQAYIQELLPVSFNND

NSEWISIVPNFILVRNTLISNIEIGFCLITKRSVICNQDYATPMTNNMRE

CLTGSTEKCPRELVVSSHVPRFALSNGVLFANCISVTCQCQTTGRAISQS

GEQTLLMIDNTTCPTAVLGNVIISLGKYLGSVNYNSEGIAIGPPVFTDKV

-continued

DISSQISSMNQSLQQSKDYIKEAQRLLDTVNPSLKLMKQIEDKIEEILSK

IYHIENEIARIKKLIGEAPGGLVPRGSHHHHHHSAWSHPQFEK

NiVop17
(SEQ ID NO: 31)
mysmqlascvtltlvllvnsQGILHYEKLSKIGLVKGVTRKYKIKSNPLT

KDIVIKMIPNVSNMSQCTGSVMENYKTRLNGILTPIKGALEIYKNNTHDc

VGDVRLAGVcMAGVAIGIATAAQITAGVALYEAMKNADNINKLKSSIEST

NEAVVKLCETAEKCVYVFTALQDYINTNLVPTIDKIPCKQTELSLDLALS

KYLSDLLFVFGPNLQDPVSNSMTIQAISQAFGGNYETLLRTLGYATEDFD

DLLESDSITGQIIYVDLSSYYIIVRVYFPILTEIQQAYIQELLPVSFNND

NSEWISIVPNFILVRNTLISNIEIGFCLITKRSVICNQDYATPMTNNMRE

CLTGSTEKCPRELVVSSHVPRFALSNGVLFANCISVTCQCQTTGRAISQS

GEQTLLMIDNTTCPTAVLGNVIISLGKYLGSVNYNSEGIAIGPPVFTDKV

DISSQISSMNQSLQQSKDYIKEAQRLLDTVNPSLKLMKQIEDKIEEILSK

IYHIENEIARIKKLIGEAPGGLVPRGSHHHHHHSAWSHPQFEK

NiVop18
(SEQ ID NO: 32)
mysmqlascvtltlvllvnsQGILHYEKLSKIGLVKGVTRKYKIKSNPLT

KDIVIKMIPNVSNMSQCTGSVMENYKTRLNGILTPIKGALEIYKNNTHDc

VGDVRLAGVcMAGVAIGIATAAQITCGVALYEAMKNADNINKLKSSIEST

NEAVVKLQETAEKTVYVFTALQDYINTNLVPTIDKIPCKQTELSLDLALS

KYLSDLLFVFGPNLQDPCSNSMTIQAISQAFGGNYETLLRTLGYATEDFD

DLLESDSITGQIIYVDLSSYYIIVRVYFPILTEIQQAYIQELLPVSFNND

NSEWISIVPNFILVRNTLISNIEIGFCLITKRSVICNQDYATPMTNNMRE

CLTGSTEKCPRELVVSSHVPRFALSNGVLFANCISVTCQCQTTGRAISQS

GEQTLLMIDNTTCPTAVLGNVIISLGKYLGSVNYNSEGIAIGPPVFTDKV

DISSQISSMNQSLQQSKDYIKEAQRLLDTVNPSLKLMKQIEDKIEEILSK

IYHIENEIARIKKLIGEAPGGLVPRGSHHHHHHSAWSHPQFEK

The above sequences include an N-terminal signal peptide, a NW F ectodomain, a GCN4 trimerization domain, a thrombin cleavage site, a HIS tag and a Strep tag, as well as various linker residues between segments.

Example 2

NiV G Multimers

The example illustrates embodiments of immunogens including multimers of the NiV G ectodomain.

The N-terminus of the NiV G ectodomain was linked to a T4 fibritin trimerization domain, and a C-terminal his tag. Different versions of the construct including one, two, or three G ectodomains in series were designed. A further multimer was designed that included two G ectodomains, one on either end (N- and C-termini) of the T4 fibritin trimerization domain (Fd). Sequences are as follows:

Fd-G (SEQ ID NO: 34)

mysmqlascvtltlvllvnsQGSGYIPEAPRDGQAYVRKDGEWVLLSTFL
GSGGGGGgvsnlvglpnniclqktsnqilkpklisytlpvvgqsgtcitd
pllamdegyfayshlerigscsrgvskqriigvgevldrgdevpslfmtn
vwtppnpntvyhcsavynnefyyvlcavstvgdpilnstywsgslmmtrl
avkpksngggynqhqlalrsiekgrydkvmpygpsgikqgdtlyfpavgf
lvrtefkyndsncpitkcqyskpencrlsmgirpnshyilrsgllkynls
dgenpkvvfieisdqrlsigspskiydslgqpvfyqasfswdtmikfgdv
ltvnplvvnwrnntvisrpgqsqcprfntcpeicwegvyndaflidrinw
isagvfldsnqtaenpvftvfkdneilyraqlasedtnaqktitncfllk
nkiwcislveiydtgdnvirpklfavkipeqctgglvprgshhhhhhsaw
shpqfek Fd-GG (SEQ ID NO: 35)

mysmqlascvtltlvllvnsQGSGYIPEAPRDGQAYVRKDGEWVLLSTFL
GSGGGGGgvsnlvglpnniclqktsnqilkpklisytlpvvgqsgtcitd
pllamdegyfayshlerigscsrgvskqriigvgevldrgdevpslfmtn
vwtppnpntvyhcsavynnefyyvlcavstvgdpilnstywsgslmmtrl
avkpksngggynqhqlalrsiekgrydkvmpygpsgikqgdtlyfpavgf
lvrtefkyndsncpitkcqyskpencrlsmgirpnshyilrsgllkynls
dgenpkvvfieisdqrlsigspskiydslgqpvfyqasfswdtmikfgdv
ltvnplvvnwrnntvisrpgqsqcprfntcpeicwegvyndaflidrinw
isagvfldsnqtaenpvftvfkdneilyraqlasedtnaqktitncfllk
nkiwcislveiydtgdnvirpklfavkipeqctggGGGGgvsnlvglpnn
iclqktsnqilkpklisytlpvvgqsgtcitdpllamdegyfayshleri
gscsrgvskqriigvgevldrgdevpslfmtnvwtppnpntvyhcsavyn
nefyyvlcavstvgdpilnstywsgslmmtrlavkpksngggynqhqlal
rsiekgrydkvmpygpsgikqgdtlyfpavgflvrtefkyndsncpitkc
qyskpencrlsmgirpnshyilrsgllkynlsdgenpkvvfieisdqrls
igspskiydslgqpvfyqasfswdtmikfgdvltvnplvvnwrnntvisr
pgqsqcprfntcpeicwegvyndaflidrinwisagvfldsnqtaenpvf
tvfkdneilyraqlasedtnaqktitncfllknkiwcislveiydtgdnv
irpklfavkipeqctgglvprgshhhhhhsawshpqfek Fd-GGG (SEQ ID NO: 36)

mysmqlascvtltlvllvnsQGSGYIPEAPRDGQAYVRKDGEWVLLSTFL
GSGGGGGgvsnlvglpnniclqktsnqilkpklisytlpvvgqsgtcitd
pllamdegyfayshlerigscsrgvskqriigvgevldrgdevpslfmtn
vwtppnpntvyhcsavynnefyyvlcavstvgdpilnstywsgslmmtrl
avkpksngggynqhqlalrsiekgrydkvmpygpsgikqgdtlyfpavgf -continued lvrtefkyndsncpitkcqyskpencrlsmgirpnshyilrsgllkynls
dgenpkvvfieisdqrlsigspskiydslgqpvfyqasfswdtmikfgdv
ltvnplvvnwrnntvisrpgqsqcprfntcpeicwegvyndaflidrinw
isagvfldsnqtaenpvftvfkdneilyraqlasedtnaqktitncfllk
nkiwcislveiydtgdnvirpklfavkipeqctggGGGGgvsnlvglpnn
iclqktsnqilkpklisytlpvvgqsgtcitdpllamdegyfayshleri
gscsrgvskqriigvgevldrgdevpslfmtnvwtppnpntvyhcsavyn
nefyyvlcavstvgdpilnstywsgslmmtrlavkpksngggynqhqlal
rsiekgrydkvmpygpsgikqgdtlyfpavgflvrtefkyndsncpitkc
qyskpencrlsmgirpnshyilrsgllkynlsdgenpkvvfieisdqrls
igspskiydslgqpvfyqasfswdtmikfgdvltvnplvvnwrnntvisr
pgqsqcprfntcpeicwegvyndaflidrinwisagvfldsnqtaenpvf
tvfkdneilyraqlasedtnaqktitncfllknkiwcislveiydtgdnv
irpklfavkipeqctggGGGGgvsnlvglpnniclqktsnqilkpklisy
tlpvvgqsgtcitdpllamdegyfayshlerigscsrgvskqriigvgev
ldrgdevpslfmtnvwtppnpntvyhcsavynnefyyvlcavstvgdpil
nstywsgslmmtrlavkpksngggynqhqlalrsiekgrydkvmpygpsg
ikqgdtlyfpavgflvrtefkyndsncpitkcqyskpencrlsmgirpns
hyilrsgllkynlsdgenpkvvfieisdqrlsigspskiydslgqpvfyq
asfswdtmikfgdvltvnplvvnwrnntvisrpgqsqcprfntcpeicwe
gvyndaflidrinwisagvfldsnqtaenpvftvfkdneilyraqlased
tnaqktitncfllknkiwcislveiydtgdnvirpklfavkipeqctggl
vprgshhhhhhsawshpafek G-Fd-G (SEQ ID NO: 37)

mysmqlascvtltlvllvnsQEgvsnlvglpnniclqktsnqilkpklis
ytlpvvgqsgtcitdpllamdegyfayshlerigscsrgvskqriigvge
vldrgdevpslfmtnvwtppnpntvyhcsavynnefyyvlcavstvgdpi
lnstywsgslmmtrlavkpksngggynqhqlalrsiekgrydkvmpygps
gikqgdtlyfpavgflvrtefkyndsncpitkcqyskpencrlsmgirpn
shyilrsgllkynlsdgenpkvvfieisdqrlsigspskiydslgqpvfy
qasfswdtmikfgdvltvnplvvnwrnntvisrpgqsqcprfntcpeicw
egvyndaflidrinwisagvfldsnqtaenpvftvfkdneilyraqlase
dtnaqktitncfllknkiwcislveiydtgdnvirpklfavkipeqctgg
GSGYIPEAPRDGQAYVRKDGEWVLLSTFLGSGGGGGgvsnlvglpnnicl
qktsnqilkpklisytlpvvgqsgtcitdpllamdegyfayshlerigsc
srgvskqriigvgevldrgdevpslfmtnvwtppnpntvyhcsavynnef
yyvlcavstvgdpilnstywsgslmmtrlavkpksngggynqhqlalrsi
ekgrydkvmpygpsgikqgdtlyfpavgflvrtefkyndsncpitkcqys
kpencrlsmgirpnshyilrsgllkynlsdgenpkvvfieisdqrlsigs -continued pskiydslgqpvfyqasfswdtmikfgdvltvnplvvnwrnntvisrpgq sqcprfntcpeicwegvyndaflidrinwisagvfldsnqtaenpvftvf kdneilyraqlasedtnaqktitncfllknkiwcislveiydtgdnvirp klfavkipeqctgglvprgshhhhhhsawshpqfek The above sequences include one or more G ectodomains, an N-terminal signal peptide, HIS tag, Strep tag, and a thrombin cleavage site to remove the two tags, a trimerization domain, and various linker residues between segments.

The Fd-G, Fd-GG, Fd-GGG, and G-Fd-G were expressed in cells and purified as discussed above for soluble NiV F ectodomain trimers in Example 1. Each of the constructs was successfully purified. The expression levels of the Fd-G and G-Fd-G constructs were 8 and 2.3 mg/mL.

Figure 4:
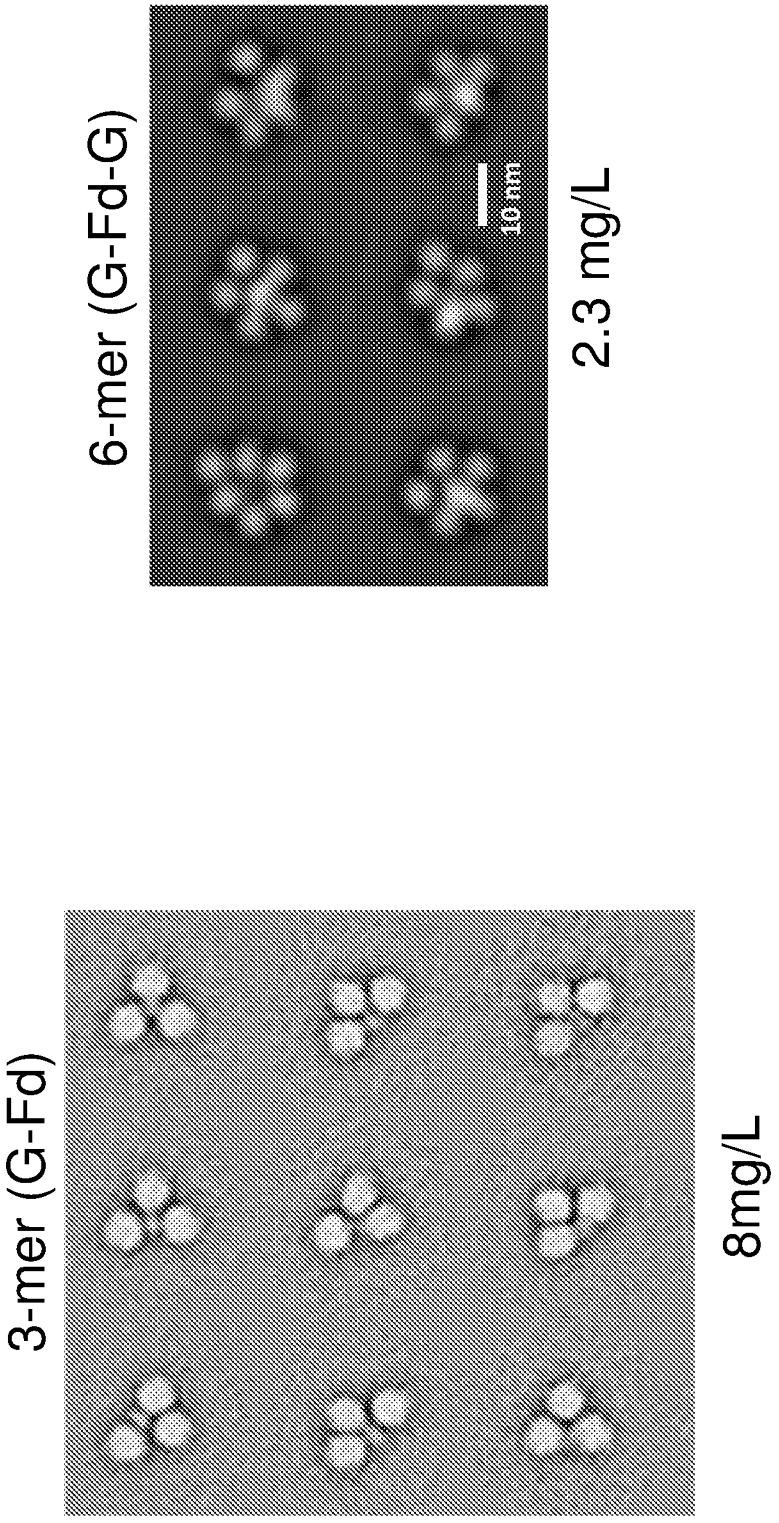
FIG. 4 shows negative stain EM for NiV G ectodomain multimers having a format of G-T4 fibritin trimerization domain (G-Fd) or G-T4 fibritin trimerization domain-G (G-Fd-G).

Negative stain EM showed that all of these constructs formed multimers. Exemplary negative stain EM images for G-Fd and G-Fd-G multimers are shown in FIG. 4.

Additional NiV G ectodomain multimers were constructed with the G ectodomain linked to the N-terminus of a subunit of a self-assembling ferritin nanoparticle. Different versions of the construct including a glycine-serine linker of 5, 15, 25, or 35 residues between the G ectodomain and the ferritin subunit. A further multimer was designed that included a NiV G ectodomain linked to the N-terminus of a subunit of a self-assembling lumazine synthase nanoparticle. Different versions of the constructs including a glycine-serine linker of 5, 15, 25, or 35 residues between the G ectodomain and the ferritin or lumazine synthase subunit were generated. Sequences are as follows:

G-ln5-Fer (SEQ ID NO: 38)

mysmqlascvtltlvllvnsqHHHHHHGSAWSHPQFEKGGLVPRGSGnsq rpqtegvsnlvglpnniclqktsnqilkpklisytlpvvgqsgtcitdpl lamdegyfayshlerigscsrgvskqriigvgevldrgdevpslfmtnvw tppnpntvyhcsavynnefyyvlcavstvqdpilnstywsqslmmtrlav kpksnqqqynqhqlalrsiekqrydkvmpyqpsqikqqdtlyfpavgflv rtefkyndsncpitkcqyskpencrlsmgirpnshyilrsgllkynlsdg enpkvvfieisdqrlsigspskiydslgqpvfyqasfswdtmikfgdvlt vnplvvnwrnntvisrpgqsqcprfntcpeicwegvyndaflidrinwis agvfldsnqtaenpvftvfkdneilyraqlasedtnaqktitncfllknk iwcislveiydtgdnvirpklfavkipeqctgggSGGDIIKLLNEQVNKE

MQSSNLYMSMSSWCYTHSLDGAGLFLFDHAAEEYEHAKKLIIFLNENNVP

VQLTSISAPEHKFEGLTQIFQKAYEHEQHISESINNIVDHAIKSKDHATF

NFLQWYVAEQHEEEVLFKDILDKIELIGNENHGLYLADQYVKGTAKSRKS

GS

G-ln15-Fer (SEQ ID NO: 39)

mysmqlascvtltlvllvnsqHHHHHHGSAWSHPQFEKGGLVPRGSGnsq rpqtegvsnlvglpnniclqktsnqilkpklisytlpvvgqsgtcitdpl lamdegyfayshlerigscsrgvskqriigvgevldrgdevpslfmtnvw -continued tppnpntvyhcsavynnefyyvlcavstvgdpilnstywsgslmmtrlav kpksngggynqhqlalrsiekgrydkvmpygpsgikqgdtlyfpavgflv rtefkyndsncpitkcqyskpencrlsmgirpnshyilrsgllkynlsdg enpkvvfieisdqrlsigspskiydslgqpvfyqasfswdtmikfgdvlt vnplvvnwrnntvisrpgqsqcprfntcpeicwegvyndaflidrinwis agvfldsnqtaenpvftvfkdneilyraqlasedtnaqktitncfllknk iwcislveiydtgdnvirpklfavkipeqctgggSGGggsggSGGgDIIK

LLNEQVNKEMQSSNLYMSMSSWCYTHSLDGAGLFLFDHAAEEYEHAKKLI

IFLNENNVPVQLTSISAPEHKFEGLTQIFQKAYEHEQHISESINNIVDHA

IKSKDHATFNFLQWYVAEQHEEEVLFKDILDKIELIGNENHGLYLADQYV

KGIAKSRKSGS

G-ln25-Fer (SEQ ID NO: 40)

mysmqlascvtltlvllvnsqHHHHHHGSAWSHPQFEKGGLVPRGSGns qrpqtegvsnlvglpnniclqktsnqilkpklisytlpvvgqsgtcitd pllamdegyfayshlerigscsrgvskqriigvgevldrgdevpslfmt nvwtppnpntvyhcsavynnefyyvlcavstvgdpilnstywsgslmmt rlavkpksngggynqhqlalrsiekgrydkvmpygpsgikqgdtlyfpa vgflvrtefkyndsncpitkcqyskpencrlsmgirpnshyilrsgllk ynlsdgenpkvvfieisdqrlsigspskiydslgqpvfyqasfswdtmi kfgdvltvnplvvnwrnntvisrpgqsqcprfntcpeicwegvyndafl idrinwisagvfldsnqtaenpvftvfkdneilyraqlasedtnaqkti tncfllknkiwcislveiydtgdnvirpklfavkipeqctgggSGGggs ggSGGggSGGggSGGgDIIKLLNEQVNKEMQSSNLYMSMSSWCYTHSLD

GAGLFLFDHAAEEYEHAKKLIDKIELIGNENHGLYLADQYVKGIAKSRK

SGS

G-ln35-Fer (SEQ ID NO: 41)

mysmqlascvtltlvllvnsqHHHHHHGSAWSHPQFEKGGLVPRGSGns qrpqtegvsnlvglpnniclqktsnqilkpklisytlpvvgqsgtcitd pllamdegyfayshlerigscsrgvskqriigvgevldrgdevpslfmt nvwtppnpntvyhcsavynnefyyvlcavstvgdpilnstywsgslmmt rlavkpksngggynqhqlalrsiekgrydkvmpygpsgikqgdtlyfpa vgflvrtefkyndsncpitkcqyskpencrlsmgirpnshyilrsgllk ynlsdgenpkvvfieisdqrlsigspskiydslgqpvfyqasfswdtmi kfgdvltvnplvvnwrnntvisrpgqsqcprfntcpeicwegvyndafl idrinwisagvfldsnqtaenpvftvfkdneilyraqlasedtnaqkti tncfllknkiwcislveiydtgdnvirpklfavkipeqctgggSGGggs ggSGGggSGGggSGGggSGGggSGGgDIIKLLNEQVNKEMQSSNLYMSM

SSWCYTHSLDGAGLFLFDHAAEEYEHAKKLIIFLNENNVPVQLTSISAP

-continued

EHKFEGLTQIFQKAYEHEQHISESINNIVDHAIKSKDHATFNFLQWYVA

EQHEEEVLFKDILDKIELIGNENHGLYLADQYVKGIAKSRKSGS

G-LS (SEQ ID NO: 42)

mysmqlascvtltlvllvnsqHHHHHHGSAWSHPQFEKGGLVPRGSGns qrpqtegvsnlvglpnniclqktsnqilkpklisytlpvvgqsgtcitd pllamdegyfayshlerigscsrgvskqriigvgevldrgdevpslfmt nvwtppnpntvyhcsavynnefyyvlcavstvgdpilnstywsgslmmt rlavkpksngggynqhqlalrsiekgrydkvmpygpsgikqgdtlyfpa vgflvrtefkyndsncpitkcqyskpencrlsmgirpnshyilrsgllk ynlsdgenpkvvfieisdqrlsigspskiydslgqpvfyqasfswdtmi kfgdvltvnplvvnwrnntvisrpgqsqcprfntcpeicwegvyndafl idrinwisagvfldsnqtaenpvftvfkdneilyraqlasedtnaqkti tncfllknkiwcislveiydtgdnvirpklfavkipeqctgggsgggsg ggsMQIYEGKLTAEGLRFGIVASRFNHALVDRLVEGAIDCIVRHGGREE

DITLVRVPGSWEIPVAAGELARKEDIDAVIAIGVLIRGATPHFDYIASE

VSKGLADLSLELRKPITFGVITADTLEQAIERAGTKHGNKGWEAALSAI

EMANLFKSLR

The above sequences include one or more G ectodomains, self-assembling nanoparticle subunit, an N-terminal signal peptide, HIS tag, Strep tag, a thrombin cleavage site to remove the two tags, and various linker residues between segments.

The G-1n5-Fer, G-1n15-Fer, G-1n25-Fer, G-1n35-Fer, and G-LS constructs were expressed in cells and purified as discussed above for soluble NiV F ectodomain trimers in Example 1. Each of the constructs was successfully purified as a multimerized nanoparticle.

Figure 5B:
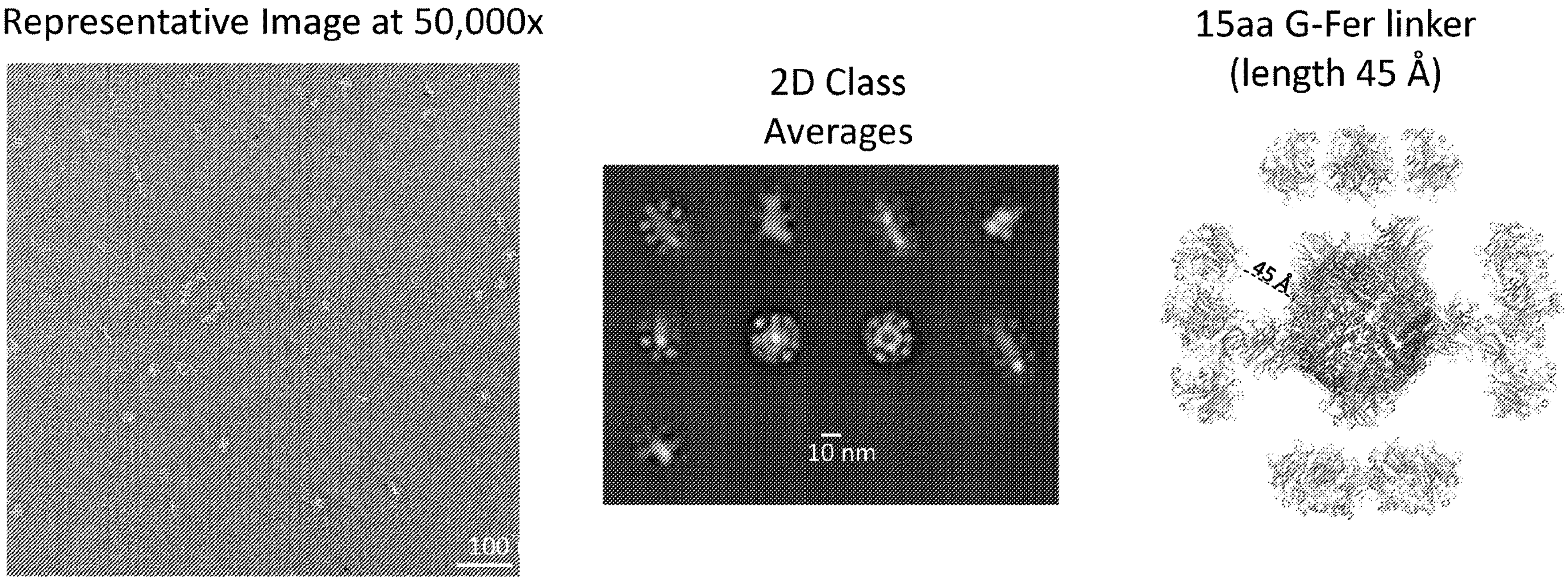
Figure 5C:
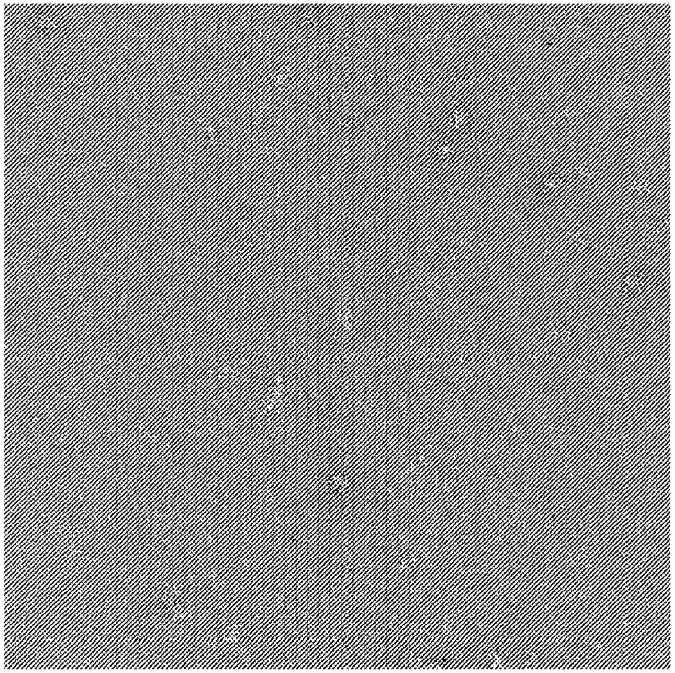
Figure 5C:
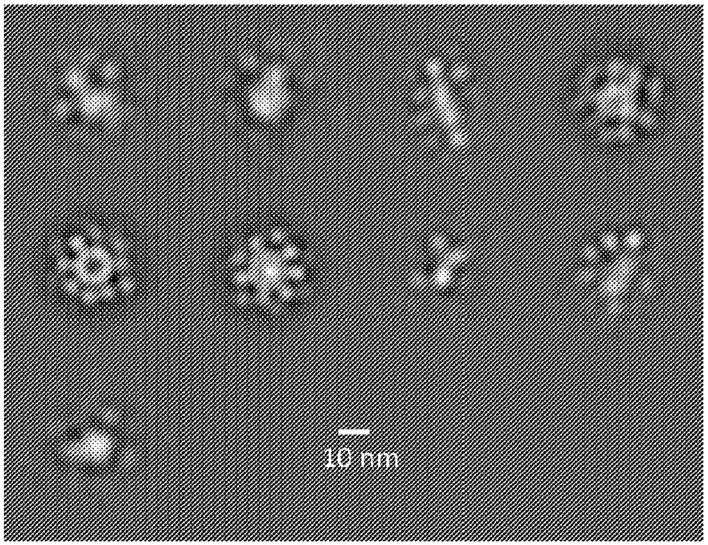

Negative stain EM showed that all of these constructs self-assembled into multimeric nanoparticles. Exemplary negative stain EM images for G-1n5-Fer, G-1n15-Fer, and G-1n25-Fer multimers are shown in FIGS. 5A-5C.

Figure 6A:
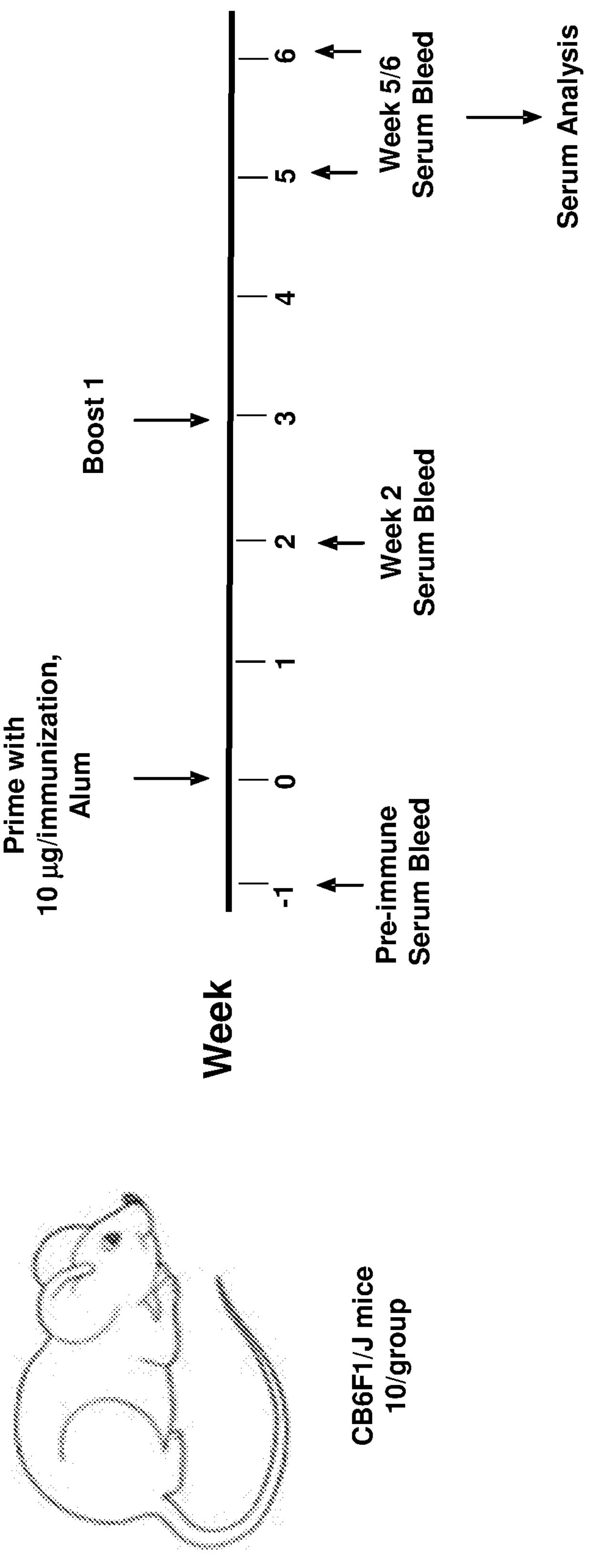
FIGS. 6A-6C show a schematic diagram (FIG. 6A) and results (FIGS. 6B-6C) for an in vivo immunization assay of the NiV G ectodomain multimers and NiV G ectodomain-containing ferritin nanoparticles.
Figure 6B:
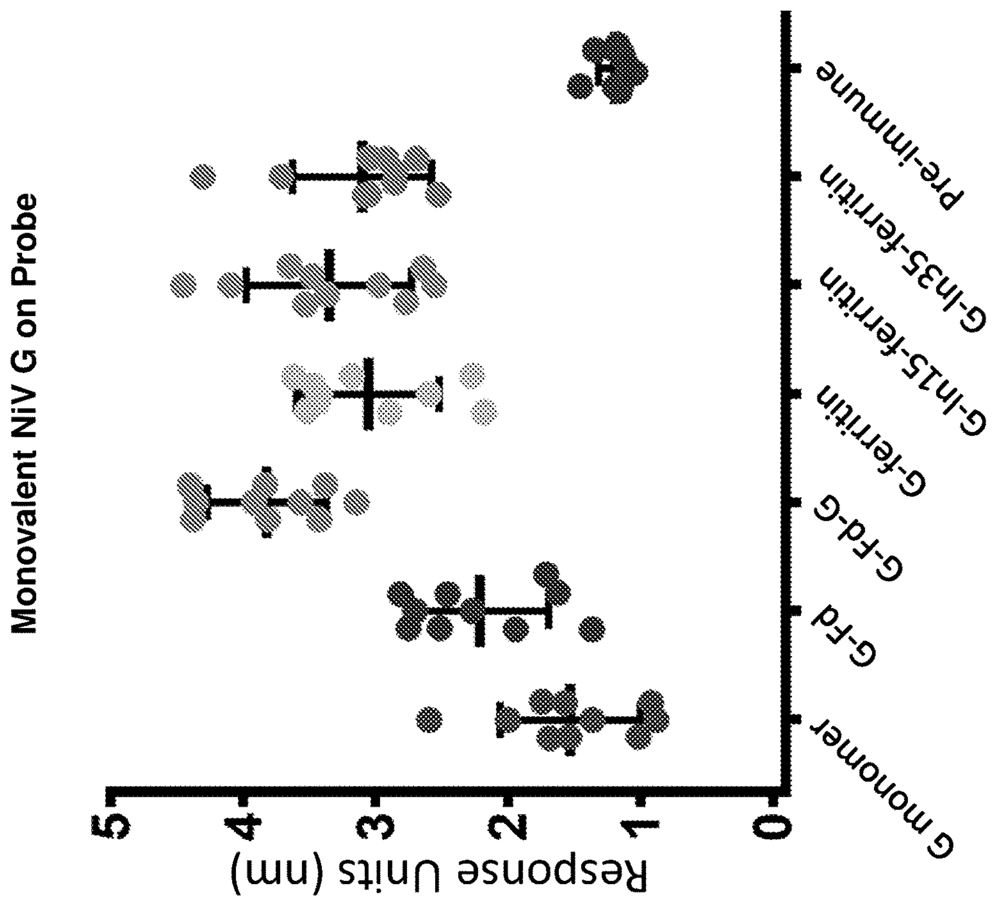
Figure 6C:
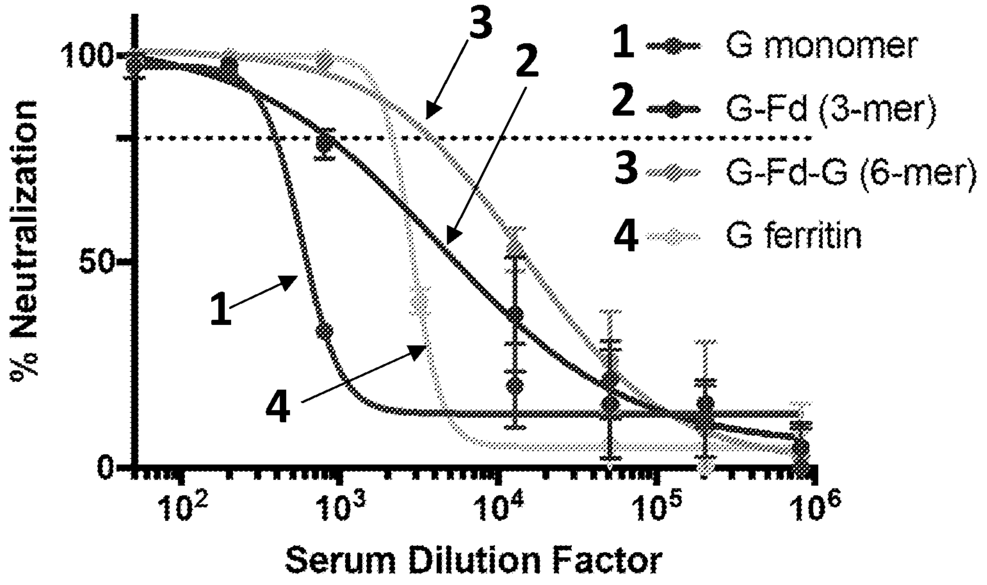

Immunization assays were conducted with the G-Fd, G-Fd-G, G-1n5-Fer, G-1n15-Fer, and G-1n35-Fer multimers. The assay was performed substantially as described in Example 1. CB6F1/J mice were immunized with 5 μg of multimer in Alum using the schedule shown in FIG. 6A. Sera from immunized mice was tested for binding to monomeric NiV G using an Octet binding assay (FIG. 6B). The NiV G was linked to the sensor and sera from the indicated immunizations assayed for binding. The immune sera was also assessed in a NiV pseudovirus neutralization assay (FIG. 6C), which showed that immune sera from animals treated with the multimeric NiV G constructs neutralized NiV. Thus, immunization with soluble multimeric NiV G constructs elicited a neutralizing immune response in an animal model.

Example 3

Multimers of NiV F-G Ectodomain Chimeras

The example illustrates embodiments of immunogens including multimers of the NiV F and G ectodomains.

Figure 7A:
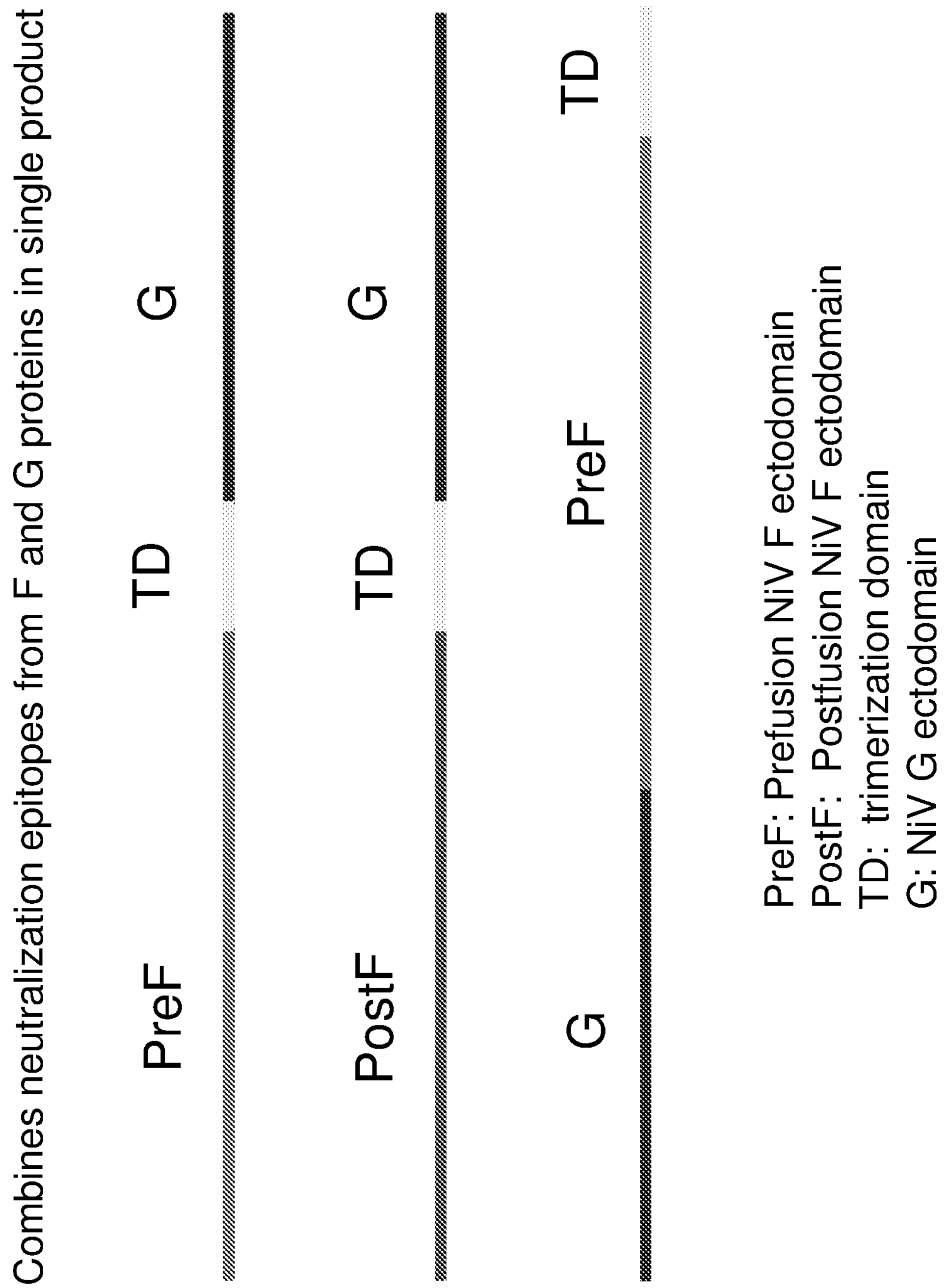
FIGS. 7A-7C show a schematic diagram (FIG. 7A) and negative stain EM images (FIGS. 7B and 7C) for chimeric NiV F-G constructs containing a NiV F ectodomain trimer and three monomeric NiV G ectodomains.

FIG. 7A illustrates the structure of the chimeric proteins included in the NiV F-G multimers. Multiple formats were assessed for the chimeric multimers, including:

- preF-TD-G: prefusion F ectodomain (e.g., NiVop08) fused to C-terminal trimerization domain (e.g., GCN4, Fd, or GCN4 and Fd) fused to G ectodomain
- G-preF-TD: G ectodomain fused to prefusion F ectodomain (e.g., NiVop08) fused to C-terminal trimerization domain (e.g., GCN4, Fd, or GCN4 and Fd)

As a control, a postfusion construct was also produced:

- postF-TD-G: postfusion F ectodomain (e.g., NiV06) fused to fused to C-terminal trimerization domain (e.g., GCN4, Fd, or GCN4 and Fd) fused to G ectodomain Sequences are as follows:

NiVop08-TD(GCN4-Fd)-G (SEQ ID NO: 43)

mysmqlascvtltlvllvnsQGILHYEKLSKIGLVKGVTRKYKIKSNPL

TKDIVIKMIPNVSNMSQCTGSVMENYKTRLNGILTPIKGALEIYKNNTH

DCVGDVRLAGVCMAGVAIGIATAAQITAGVALYEAMKNADNINKLKSSI

ESTNEAVVKLQETAEKTVYVFTALQDYINTNLVPTIDKIPCKQTELSLD

LALSKYLSDLLFVFGPNLQDPVSNSMTIQAISQAFGGNYETLLRTLGYA

TEDFDDLLESDSITGQIIYVDLSSYYIIVRVYFPILTEIQQAYIQELLP

VSFNNDNSEWISIVPNFILVRNTLISNIEIGFCLITKRSVICNQDYATP

MTNNMRECLTGSTEKCPRELVVSSHVPRFALSNGVLFANCISVTCQCQT

TGRAISQSGEQTLLMIDNTTCPTAVLGNVIISLGKYLGSVNYNSEGIAI

GPPVFTDKVDISSQISSMNQSLQQSKDYIKEAQRLLDTVNPSLKLMKQI

EDKIEEILSKIYHIENEIARIKKLIGEAPGSGYIPEAPRDGQAYVRKDG

EWVLLSTFLGSGGGGGgvsnlvglpnniclqktsnqilkpklisytlpv vgqsgtcitdpllamdegyfayshlerigscsrgvskqriigvgevldr gdevpslfmtnvwtppnpntvyhcsavynnefyyvlcavstvgdpilns tywsgslmmtrlavkpksngggynqhqlalrsiekgrydkvmpygpsgi kqgdtlyfpavgflvrtefkyndsncpitkcqyskpencrlsmgirpns hyilrsgllkynlsdgenpkvvfieisdqrlsigspskiydslgqpvfy qasfswdtmikfgdvltvnplvvnwrnntvisrpgqsqcprfntcpeic wegvyndaflidrinwisagvfldsnqtaenpvftvfkdneilyraqla sedtnaqktitncfllknkiwcislveiydtgdnvirpklfavkipeqc tgglvprgshhhhhhsawshpqfek G-NiVop08-TD (GCN4-Fd)

(SEQ ID NO: 44)

Mysmqlascvtltlvllvnsqrpqtegvsnlvglpnniclqktsnqilk pklisytlpvvgqsgtcitdpllamdegyfayshlerigscsrgvskqr iigvgevldrgdevpslfmtnvwtppnpntvyhcsavynnefyyvlcav stvgdpilnstywsgslmmtrlavkpksngggynqhqlalrsiekgryd kvmpygpsgikqgdtlyfpavgflvrtefkyndsncpitkcqyskpenc rlsmgirpnshyilrsgllkynlsdgenpkvvfieisdqrlsigspski ydslgqpvfyqasfswdtmikfgdvltvnplvvnwrnntvisrpgqsqc -continued prfntcpeicwegvyndaflidrinwisagvfldsnqtaenpvftvfkd
neilyraqlasedtnaqktitncfllknkiwcislveiydtgdnvirpk
lfavkipeqctgggQGILHYEKLSKIGLVKGVTRKYKIKSNPLTKDIVI
KMIPNVSNMSQCTGSVMENYKTRLNGILTPIKGALEIYKNNTHDCVGDV
RLAGVCMAGVAIGIATAAQITAGVALYEAMKNADNINKLKSSIESTNEA
VVKLQETAEKTVYVFTALQDYINTNLVPTIDKIPCKQTELSLDLALSKY
LSDLLFVFGPNLQDPVSNSMTIQAISQAFGGNYETLLRTLGYATEDFDD
LLESDSITGQIIYVDLSSYYIIVRVYFPILTEIQQAYIQELLPVSFNND
NSEWISIVPNFILVRNTLISNIEIGFCLITKRSVICNQDYATPMTNNMR
ECLTGSTEKCPRELVVSSHVPRFALSNGVLFANCISVTCQCQTTGRAIS
QSGEQTLLMIDNTTCPTAVLGNVIISLGKYLGSVNYNSEGIAIGPPVFT
DKVDISSQISSMNQSLQQSKDYIKEAQRLLDTVNPSLKLMKQIEDKIEE
ILSKIYHIENEIARIKKLIGEAPGSGYIPEAPRDGQAYVRKDGEWVLLS
TFLGSLVPRGSHHHHHHSAWSHPQFEK NiV06-TD(GCN4-Fd)-G
(SEQ ID NO: 45)

MysmqlascvtltlvllvnsQGILHYEKLSKIGLVKGVTRKYKIKSNPL
TKDIVIKMIPNVSNMSQCTGSVMENYKTRLNGILTPIKGALEIYKNGGS
GVAIGIATAAQITAGVALYEAMKNADNINKLKSSIESTNEAVVKLQETA
EKTVYVLTALQDYINTNLVPTIDKISCKQTELSLDLALSKYLSDLLFVF
GPNLQDPVSNSMTIQAISQAFGGNYETLLRTLGYATEDFDDLLESDSIT
GQIIYVDLSSYYIIVRVYFPILTEIQQAYIQELLPVSFNNDNSEWISIV
PNFILVRNTLISNIEIGFCLITKRSVTAVLGNVIISLGKYLGSVNYNSE
GIAIGPPVFTDKVDISSQISSMNQSLQQSKDYIKEAQRLLDTVNPSLKL
MKQIEDKIEEILSKIYHIENEIARIKKLIGEAPGSGYIPEAPRDGQAYV
RKDGEWVLLSTFLGSGGGGGgvsnlvglpnniclqktsnqilkpklisy
tlpvvgqsgtcitdpllamdegyfayshlerigscsrgvskqriigvge
vldrgdevpslfmtnvwtppnpntvyhcsavynnefyyvlcavstvgdp
ilnstywsgslmmtrlavkpksngggynqhqlalrsiekgrydkvmpyg
psgikqgdtlyfpavgflvrtefkyndsncpitkcqyskpencrlsmgi
rpnshyilrsgllkynlsdgenpkvvfieisdqrlsigspskiydslgq
pvfyqasfswdtmikfgdvltvnplvvnwrnntvisrpgqsqcprfntc
peicwegvyndaflidrinwisagvfldsnqtaenpvftvfkdneilyr
aqlasedtnaqktitncfllknkiwcislveiydtgdnvirpklfavki
peqctgglvprgshhhhhhsawshpqfek NiV06-TD(GCN4-Fd)-GG
(SEQ ID NO: 46)

MysmqlascvtltlvllvnsQGILHYEKLSKIGLVKGVTRKYKIKSNPL
TKDIVIKMIPNVSNMSQCTGSVMENYKTRLNGILTPIKGALEIYKNGGS
GVAIGIATAAQITAGVALYEAMKNADNINKLKSSIESTNEAVVKLQETA -continued EKTVYVLTALQDYINTNLVPTIDKISCKQTELSLDLALSKYLSDLLFVF
GPNLQDPVSNSMTIQAISQAFGGNYETLLRTLGYATEDFDDLLESDSIT
GQIIYVDLSSYYIIVRVYFPILTEIQQAYIQELLPVSFNNDNSEWISIV
PNFILVRNTLISNIEIGFCLITKRSVICNQDYATPMTNNMRECLTGSTE
KCPRELVVSSHVPRFALSNGVLFANCISVTCQCQTTGRAISQSGEQTLL
MIDNTTCPTAVLGNVIISLGKYLGSVNYNSEGIAIGPPVFTDKVDISSQ
ISSMNQSLQQSKDYIKEAQRLLDTVNPSLKLMKQIEDKIEEILSKIYHI
ENEIARIKKLIGEAPGSGYIPEAPRDGQAYVRKDGEWVLLSTFLGSGGG
GGgvsnlvglpnniclqktsnqilkpklisytlpvvgqsgtcitdplla
mdegyfayshlerigscsrgvskqriigvgevldrgdevpslfmtnvwt
ppnpntvyhcsavynnefyyvlcavstvgdpilnstywsgslmmtrlav
kpksngggynqhqlalrsiekgrydkvmpygpsgikqgdtlyfpavgfl
vrtefkyndsncpitkcqyskpencrlsmgirpnshyilrsgllkynls
dgenpkvvfieisdqrlsigspskiydslgqpvfyqasfswdtmikfgd
vltvnplvvnwrnntvisrpgqsqcprfntcpeicwegvyndaflidri
nwisagvfldsnqtaenpvftvfkdneilyraqlasedtnaqktitncf
llknkiwcislveiydtgdnvirpklfavkipeqctggGGGGgvsnlvg
lpnniclqktsnqilkpklisytlpvvgqsgtcitdpllamdegyfays
hlerigscsrgvskqriigvgevldrgdevpslfmtnvwtppnpntvyh
csavynnefyyvlcavstvgdpilnstywsgslmmtrlavkpksngggy
nqhqlalrsiekgrydkvmpygpsgikqgdtlyfpavgflvrtefkynd
sncpitkcqyskpencrlsmgirpnshyilrsgllkynlsdgenpkvvf
ieisdqrlsigspskiydslgqpvfyqasfswdtmikfgdvltvnplvv
nwrnntvisrpgqsqcprfntcpeicwegvyndaflidrinwisagvfl
dsnqtaenpvftvfkdneilyraqlasedtnaqktitncfllknkiwci
slveiydtgdnvirpklfavkipeqctgglvprgshhhhhhsawshpqf
ek NiVop08-TD (GCN4-Fd)-GG
(SEQ ID NO: 47)

MysmqlascvtltlvllvnsQGILHYEKLSKIGLVKGVTRKYKIKSNPL
TKDIVIKMIPNVSNMSQCTGSVMENYKTRLNGILTPIKGALEIYKNNTH
DCVGDVRLAGVCMAGVAIGIATAAQITAGVALYEAMKNADNINKLKSSI
ESTNEAVVKLQETAEKTVYVFTALQDYINTNLVPTIDKIPCKQTELSLD
LALSKYLSDLLFVFGPNLQDPVSNSMTIQAISQAFGGNYETLLRTLGYA
TEDFDDLLESDSITGQIIYVDLSSYYIIVRVYFPILTEIQQAYIQELLP
VSFNNDNSEWISIVPNFILVRNTLISNIEIGFCLITKRSVICNQDYATP
MTNNMRECLTGSTEKCPRELVVSSHVPRFALSNGVLFANCISVTCQCQT
TGRAISQSGEQTLLMIDNTTCPTAVLGNVIISLGKYLGSVNYNSEGIAI
GPPVFTDKVDISSQISSMNQSLQQSKDYIKEAQRLLDTVNPSLKLMKQI
EDKIEEILSKIYHIENEIARIKKLIGEAPGSGYIPEAPRDGQAYVRKDG -continued EWVLLSTFLGSGGGGGgvsnlvglpnniclqktsnqilkpklisytlpv
vgqsgtcitdpllamdegyfayshlerigscsrgvskqriigvgevldr
gdevpslfmtnvwtppnpntvyhcsavynnefyyvlcavstvgdpilns
tywsgslmmtrlavkpksngggynqhqlalrsiekgrydkvmpygpsgi
kqgdtlyfpavgflvrtefkyndsncpitkcqyskpencrlsmgirpns
hyilrsgllkynlsdgenpkvvfieisdqrlsigspskiydslgqpvfy
qasfswdtmikfgdvltvnplvvnwrnntvisrpgqsqcprfntcpeic
wegvyndaflidrinwisagvfldsnqtaenpvftvfkdneilyraqla
sedtnaqktitncfllknkiwcislveiydtgdnvirpklfavkipeqc
tggGGGGgvsnlvglpnniclqktsnqilkpklisytlpvvgqsgtcit
dpllamdegyfayshlerigscsrgvskqriigvgevldrgdevpslfm
tnvwtppnpntvyhcsavynnefyyvlcavstvgdpilnstywsgslmm
trlavkpksngggynqhqlalrsiekgrydkvmpygpsgikqgdtlyfp
avgflvrtefkyndsncpitkcqyskpencrlsmgirpnshyilrsgll
kynlsdgenpkvvfieisdqrlsigspskiydslgqpvfyqasfswdtm
ikfgdvltvnplvvnwrnntvisrpgqsqcprfntcpeicwegvyndaf
lidrinwisagvfldsnqtaenpvftvfkdneilyraqlasedtnaqkt
itncfllknkiwcislveiydtgdnvirpklfavkipeqctgglvprgs
hhhhhhsawshpqfek NiV06-TD (GCN4-Fd)-GGG
(SEQ ID NO: 48)

MysmqlascvtltlvllvnsQGILHYEKLSKIGLVKGVTRKYKIKSNPL
TKDIVIKMIPNVSNMSQCTGSVMENYKTRLNGILTPIKGALEIYKNGGS
GVAIGIATAAQITAGVALYEAMKNADNINKLKSSIESTNEAVVKLQETA
EKTVYVLTALQDYINTNLVPTIDKISCKQTELSLDLALSKYLSDLLFVF
GPNLQDPVSNSMTIQAISQAFGGNYETLLRTLGYATEDFDDLLESDSIT
GQIIYVDLSSYYIIVRVYFPILTEIQQAYIQELLPVSFNNDNSEWISIV
PNFILVRNTLISNIEIGFCLITKRSVICNQDYATPMTNNMRECLTGSTE
KCPRELVVSSHVPRFALSNGVLFANCISVTCQCQTTGRAISQSGEQTLL
MIDNTTCPTAVLGNVIISLGKYLGSVNYNSEGIAIGPPVFTDKVDISSQ
ISSMNQSLQQSKDYIKEAQRLLDTVNPSLKLMKQIEDKIEEILSKIYHI
ENEIARIKKLIGEAPGSGYIPEAPRDGQAYVRKDGEWVLLSTFLGSGGG
GGgvsnlvglpnniclqktsnqilkpklisytlpvvgqsgtcitdplla
mdegyfayshlerigscsrgvskqriigvgevldrgdevpslfmtnvwt
ppnpntvyhcsavynnefyyvlcavstvgdpilnstywsgslmmtrlav
kpksngggynqhqlalrsiekgrydkvmpygpsgikqgdtlyfpavgfl
vrtefkyndsncpitkcqyskpencrlsmgirpnshyilrsgllkynls
dgenpkvvfieisdqrlsigspskiydslgqpvfyqasfswdtmikfgd
vltvnplvvnwrnntvisrpgqsqcprfntcpeicwegvyndaflidri
nwisagvfldsnqtaenpvftvfkdneilyraqlasedtnaqktitncf -continued llknkiwcislveiydtgdnvirpklfavkipeqctggGGGGgvsnlvg
lpnniclqktsnqilkpklisytlpvvgqsgtcitdpllamdegyfays
hlerigscsrgvskqriigvgevldrgdevpslfmtnvwtppnpntvyh
csavynnefyyvlcavstvgdpilnstywsgslmmtrlavkpksngggy
nqhqlalrsiekgrydkvmpygpsgikqgdtlyfpavgflvrtefkynd
sncpitkcqyskpencrlsmgirpnshyilrsgllkynlsdgenpkvvf
ieisdqrlsigspskiydslgqpvfyqasfswdtmikfgdvltvnplvv
nwrnntvisrpgqsqcprfntcpeicwegvyndaflidrinwisagvfl
dsnqtaenpvftvfkdneilyraqlasedtnaqktitncfllknkiwci
slveiydtgdnvirpklfavkipeqctggGGGGgvsnlvglpnniclqk
tsnqilkpklisytlpvvgqsgtcitdpllamdegyfayshlerigscs
rgvskqriigvgevldrgdevpslfmtnvwtppnpntvyhcsavynnef
yyvlcavstvgdpilnstywsgslmmtrlavkpksngggynqhqlalrs
iekgrydkvmpygpsgikqgdtlyfpavgflvrtefkyndsncpitkcq
yskpencrlsmgirpnshyilrsgllkynlsdgenpkvvfieisdqrls
igspskiydslgqpvfyqasfswdtmikfgdvltvnplvvnwrnntvis
rpgqsqcprfntcpeicwegvyndaflidrinwisagvfldsnqtaenp
vftvfkdneilyraqlasedtnaqktitncfllknkiwcislveiydtg
dnvirpklfavkipeqctgglvprgshhhhhhsawshpqfek NiVop08-TD(GCN4-Fd)-GGG
(SEQ ID NO: 49)

MysmqlascvtltlvllvnsQGILHYEKLSKIGLVKGVTRKYKIKSNPL
TKDIVIKMIPNVSNMSQCTGSVMENYKTRLNGILTPIKGALEIYKNNTH
DCVGDVRLAGVCMAGVAIGIATAAQITAGVALYEAMKNADNINKLKSSI
ESTNEAVVKLQETAEKTVYVFTALQDYINTNLVPTIDKIPCKQTELSLD
LALSKYLSDLLFVFGPNLQDPVSNSMTIQAISQAFGGNYETLLRTLGYA
TEDFDDLLESDSITGQIIYVDLSSYYIIVRVYFPILTEIQQAYIQELLP
VSFNNDNSEWISIVPNFILVRNTLISNIEIGFCLITKRSVICNQDYATP
MTNNMRECLTGSTEKCPRELVVSSHVPRFALSNGVLFANCISVTCQCQT
TGRAISQSGEQTLLMIDNTTCPTAVLGNVIISLGKYLGSVNYNSEGIAI
GPPVFTDKVDISSQISSMNQSLQQSKDYIKEAQRLLDTVNPSLKLMKQI
EDKIEEILSKIYHIENEIARIKKLIGEAPGSGYIPEAPRDGQAYVRKDG
EWVLLSTFLGSGGGGGgvsnlvglpnniclqktsnqilkpklisytlpv
vgqsgtcitdpllamdegyfayshlerigscsrgvskqriigvgevldr
gdevpslfmtnvwtppnpntvyhcsavynnefyyvlcavstvgdpilns
tywsgslmmtrlavkpksngggynqhqlalrsiekgrydkvmpygpsgi
kqgdtlyfpavgflvrtefkyndsncpitkcqyskpencrlsmgirpns
hyilrsgllkynlsdgenpkvvfieisdqrlsigspskiydslgqpvfy
qasfswdtmikfgdvltvnplvvnwrnntvisrpgqsqcprfntcpeic
wegvyndaflidrinwisagvfldsnqtaenpvftvfkdneilyraqla -continued sedtnaqktitncfllknkiwcislveiydtgdnvirpklfavkipeqc tggGGGGgvsnlvglpnniclqktsnqilkpklisytlpvvgqsgtcit dpllamdegyfayshlerigscsrgvskqriigvgevldrgdevpslfm tnvwtppnpntvyhcsavynnefyyvlcavstvgdpilnstywsgslmm trlavkpksngggynqhqlalrsiekgrydkvmpygpsgikqgdtlyfp avgflvrtefkyndsncpitkcqyskpencrlsmgirpnshyilrsgll kynlsdgenpkvvfieisdqrlsigspskiydslgqpvfyqasfswdtm ikfgdvltvnplvvnwrnntvisrpgqsqcprfntcpeicwegvyndaf lidrinwisagvfldsnqtaenpvftvfkdneilyraqlasedtnaqkt itncfllknkiwcislveiydtgdnvirpklfavkipeqctggGGGGgv snlvglpnniclqktsnqilkpklisytlpvvgqsgtcitdpllamdeg yfayshlerigscsrgvskqriigvgevldrgdevpslfmtnvwtppnp ntvyhcsavynnefyyvlcavstvgdpilnstywsgslmmtrlavkpks ngggynqhqlalrsiekgrydkvmpygpsgikqgdtlyfpavgflvrte fkyndsncpitkcqyskpencrlsmgirpnshyilrsgllkynlsdgen pkvvfieisdqrlsigspskiydslgqpvfyqasfswdtmikfgdvltv nplvvnwrnntvisrpgqsqcprfntcpeicwegvyndaflidrinwis agvfldsnqtaenpvftvfkdneilyraqlasedtnaqktitncfllkn kiwcislveiydtgdnvirpklfavkipeqctgglvprgshhhhhhsaw shpqfek G-NiV06-TD(GCN4-Fd)

(SEQ ID NO: 50)

MysmqlascvtltlvllvnsQrpqtegvsnlvglpnniclqktsnqilk pklisytlpvvgqsgtcitdpllamdegyfayshlerigscsrgvskqr iigvgevldrgdevpslfmtnvwtppnpntvyhcsavynnefyyvlcav stvgdpilnstywsgslmmtrlavkpksngggynqhqlalrsiekgryd kvmpygpsgikqgdtlyfpavgflvrtefkyndsncpitkcqyskpenc rlsmgirpnshyilrsgllkynlsdgenpkvvfieisdqrlsigspski ydslgqpvfyqasfswdtmikfgdvltvnplvvnwrnntvisrpgqsqc prfntcpeicwegvyndaflidrinwisagvfldsnqtaenpvftvfkd neilyraqlasedtnaqktitncfllknkiwcislveiydtgdnvirpk lfavkipeqctgggGGQGILHYEKLSKIGLVKGVTRKYKIKSNPLTKDI

VIKMIPNVSNMSQCTGSVMENYKTRLNGILTPIKGALEIYKNGGSGVAI

GIATAAQITAGVALYEAMKNADNINKLKSSIESTNEAVVKLQETAEKTV

YVLTALQDYINTNLVPTIDKISCKQTELSLDLALSKYLSDLLFVFGPNL

QDPVSNSMTIQAISQAFGGNYETLLRTLGYATEDFDDLLESDSITGQII

YVDLSSYYIIVRVYFPILTEIQQAYIQELLPVSFNNDNSEWISIVPNFI

LVRNTLISNIEIGFCLITKRSVICNQDYATPMTNNMRECLTGSTEKCPR

ELVVSSHVPRFALSNGVLFANCISVTCQCQTTGRAISQSGEQTLLMIDN

TTCPTAVLGNVIISLGKYLGSVNYNSEGIAIGPPVFTDKVDISSQISSM

NQSLQQSKDYIKEAQRLLDTVNPSLklmkqiedkieeilskiyhienei arikkligeapgglvprgshhhhhhsawshpqfek G-NiVop08-TD(GCN4-Fd)

(SEQ ID NO: 51)

MysmqlascvtltlvllvnsQrpqtegvsnlvglpnniclqktsnqilk pklisytlpvvgqsgtcitdpllamdegyfayshlerigscsrgvskqr iigvgevldrgdevpslfmtnvwtppnpntvyhcsavynnefyyvlcav stvgdpilnstywsgslmmtrlavkpksngggynqhqlalrsiekgryd kvmpygpsgikqgdtlyfpavgflvrtefkyndsncpitkcqyskpenc rlsmgirpnshyilrsgllkynlsdgenpkvvfieisdqrlsigspski ydslgqpvfyqasfswdtmikfgdvltvnplvvnwrnntvisrpgqsqc prfntcpeicwegvyndaflidrinwisagvfldsnqtaenpvftvfkd neilyraqlasedtnaqktitncfllknkiwcislveiydtgdnvirpk lfavkipeqctggggsggggQGILHYEKLSKIGLVKGVTRKYKIKSNPL

TKDIVIKMIPNVSNMSQCTGSVMENYKTRLNGILTPIKGALEIYKNNTH

DCVGDVRLAGVCMAGVAIGIATAAQITAGVALYEAMKNADNINKLKSSI

ESTNEAVVKLQETAEKTVYVFTALQDYINTNLVPTIDKIPCKQTELSLD

LALSKYLSDLLFVFGPNLQDPVSNSMTIQAISQAFGGNYETLLRTLGYA

TEDFDDLLESDSITGQIIYVDLSSYYIIVRVYFPPRELVVSSHVPRFAL

SNGVLFANCISVTCQCQTTGRAISQSGEQTLLMIDNTTCPTAVLGNVII

SLGKYLGSVNYNSEGIAIGPPVFTDKVDISSQISSMNQSLQQSKDYIKE

AQRLLDTVNPSLKLMKQIEDKIEEILSKIYHIENEIARIKKLIGEAPGS

GYIPEAPRDGQAYVRKDGEWVLLSTFLGSLVPRGSHHHHHHSAWSHPQF

EK

NiVop08-GCN4-G (SEQ ID NO: 59)

MYSMQLASCVTLTLVLLVNSQGILHYEKLSKIGLVKGVTRKYKIKSNPL

TKDIVIKMIPNVSNMSQCTGSVMENYKTRLNGILTPIKGALEIYKNNTH

DCVGDVRLAGVCMAGVAIGIATAAQITAGVALYEAMKNADNINKLKSSI

ESTNEAVVKLQETAEKTVYVFTALQDYINTNLVPTIDKIPCKQTELSLD

LALSKYLSDLLFVFGPNLQDPVSNSMTIQAISQAFGGNYETLLRTLGYA

TEDFDDLLESDSITGQIIYVDLSSYYIIVRVYFPILTEIQQAYIQELLP

VSFNNDNSEWISIVPNFILVRNTLISNIEIGFCLITKRSVICNQDYATP

MTNNMRECLTGSTEKCPRELVVSSHVPRFALSNGVLFANCISVTCQCQT

TGRAISQSGEQTLLMIDNTTCPTAVLGNVIISLGKYLGSVNYNSEGIAI

GPPVFTDKVDISSQISSMNQSLQQSKDYIKEAQRLLDTVNPSLKLMKQI

EDKIEEILSKIYHIENEIARIKKLIGEAPGSGGGGGGVSNLVGLPNNIC

LQKTSNQILKPKLISYTLPVVGQSGTCITDPLLAMDEGYFAYSHLERIG

SCSRGVSKQRIIGVGEVLDRGDEVPSLFMTNVWTPPNPNTVYHCSAVYN

NEFYYVLCAVSTVGDPILNSTYWSGSLMMTRLAVKPKSNGGGYNQHQLA

-continued

```
LRSIEKGRYDKVMPYGPSGIKQGDTLYFPAVGFLVRTEFKYNDSNCPIT

KCQYSKPENCRLSMGIRPNSHYILRSGLLKYNLSDGENPKVVFIEISDQ

RLSIGSPSKIYDSLGQPVFYQASFSWDTMIKFGDVLTVNPLVVNWRNNT

VISRPGQSQCPRFNTCPEICWEGVYNDAFLIDRINWISAGVFLDSNQTA

ENPVFTVFKDNEILYRAQLASEDTNAQKTITNCFLLKNKIWCISLVEIY

DTGDNVIRPKLFAVKIPEQCTGGLVPRGSHHHHHHSAWSHPQFEK
```

NiVop08-Fd-G (SEQ ID NO: 60)

```
MYSMQLASCVTLTLVLLVNSQGILHYEKLSKIGLVKGVTRKYKIKSNPL

TKDIVIKMIPNVSNMSQCTGSVMENYKTRLNGILTPIKGALEIYKNNTH

DCVGDVRLAGVCMAGVAIGIATAAQITAGVALYEAMKNADNINKLKSSI

ESTNEAVVKLQETAEKTVYVFTALQDYINTNLVPTIDKIPCKQTELSLD

LALSKYLSDLLFVFGPNLQDPVSNSMTIQAISQAFGGNYETLLRTLGYA

TEDFDDLLESDSITGQIIYVDLSSYYIIVRVYFPILTEIQQAYIQELLP

VSFNNDNSEWISIVPNFILVRNTLISNIEIGFCLITKRSVICNQDYATP

MTNNMRECLTGSTEKCPRELVVSSHVPRFALSNGVLFANCISVTCQCQT

TGRAISQSGEQTLLMIDNTTCPTAVLGNVIISLGKYLGSVNYNSEGIAI

GPPVFTDKVDISSQISSMNQSLQQSKDYIKEAQRLLDTVNPSLGSGYIP

EAPRDGQAYVRKDGEWVLLSTFLGSGGGGGGVSNLVGLPNNICLQKTSN

QILKPKLISYTLPVVGQSGTCITDPLLAMDEGYFAYSHLERIGSCSRGV

SKQRIIGVGEVLDRGDEVPSLFMTNVWTPPNPNTVYHCSAVYNNEFYYV

LCAVSTVGDPILNSTYWSGSLMMTRLAVKPKSNGGGYNQHQLALRSIEK

GRYDKVMPYGPSGIKQGDTLYFPAVGFLVRTEFKYNDSNCPITKCQYSK

PENCRLSMGIRPNSHYILRSGLLKYNLSDGENPKVVFIEISDQRLSIGS

PSKIYDSLGQPVFYQASFSWDTMIKFGDVLTVNPLVVNWRNNTVISRPG

QSQCPRFNTCPEICWEGVYNDAFLIDRINWISAGVFLDSNQTAENPVFT

VFKDNEILYRAQLASEDTNAQKTITNCFLLKNKIWCISLVEIYDTGDNV

IRPKLFAVKIPEQCTGGLVPRGSHHHHHHSAWSHPQFEK
```

The above sequences include F and G ectodomains, an N-terminal signal peptide, a HIS tag, a Strep tag, and a thrombin cleavage site to remove the two tags, and various linker residues between segments.

Figure 7B:
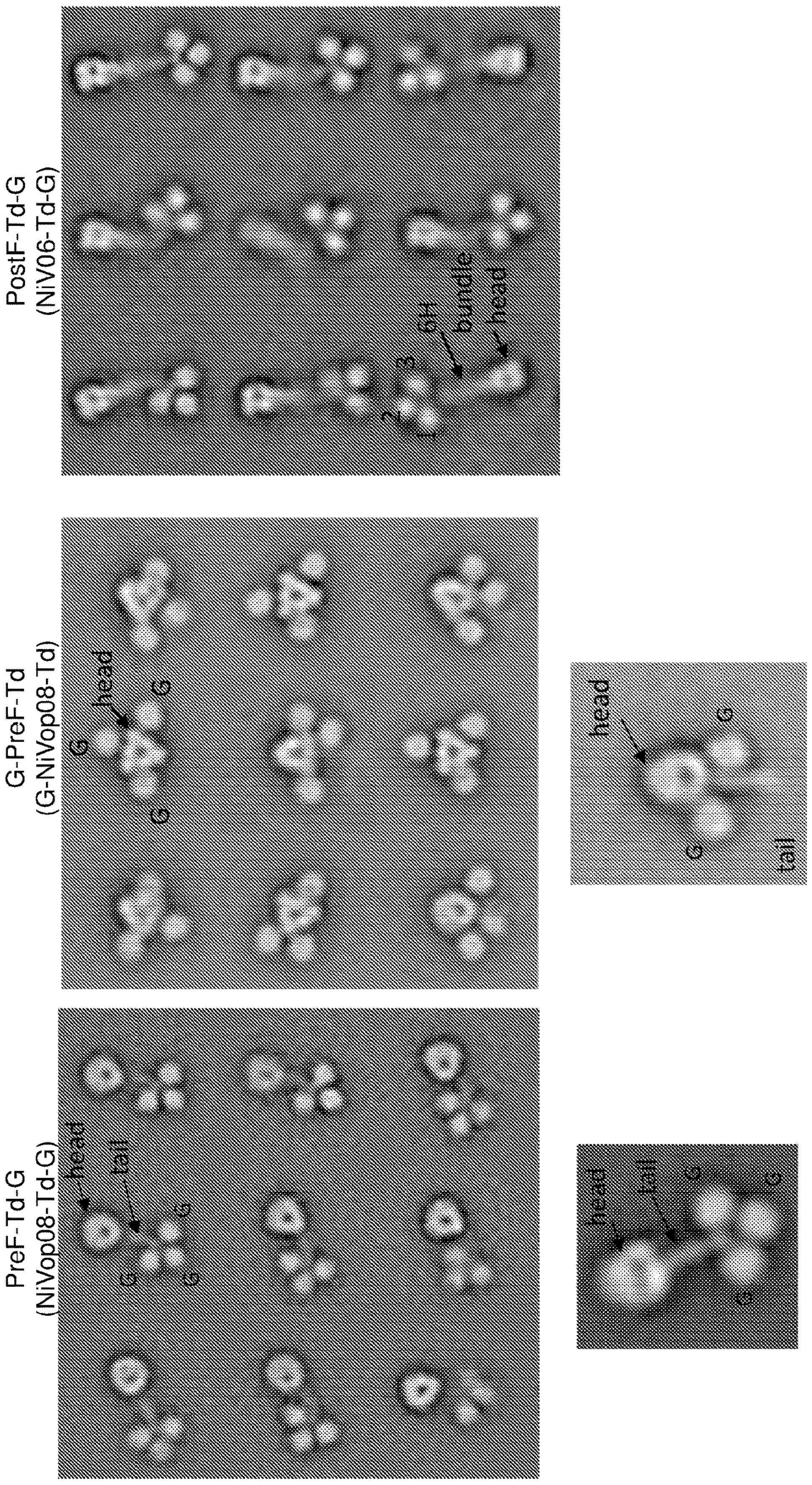
Figure 7C:
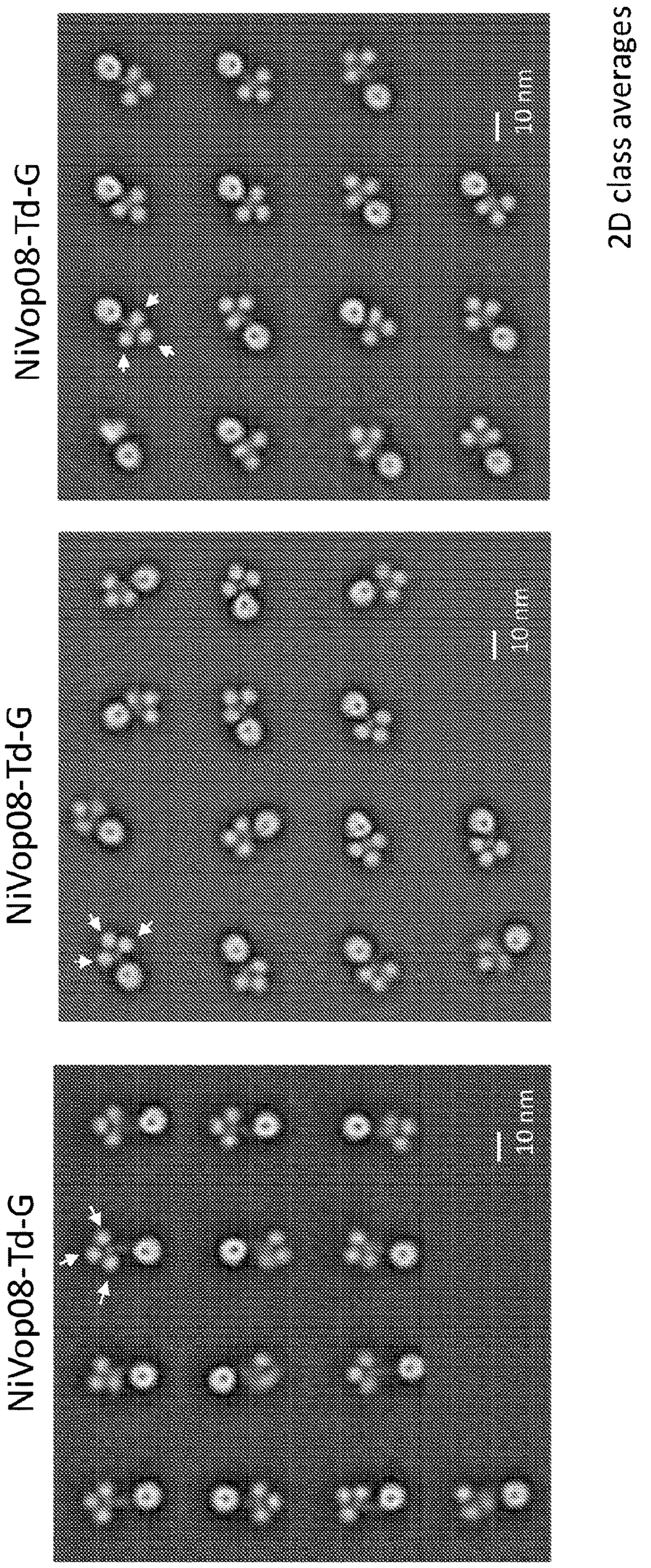

The NiVop08-TD-G (SEQ ID NO: 43), G-NiVop08-T (SEQ ID NO: 44), and NiV06-TD-G (SEQ ID NO: 45) constructs were expressed in cells and purified as discussed above for soluble NiV F ectodomain trimers in Example 1. Additional constructs based on NiVop08 that included a trimerization domain with GCN4 or Fd (but not both) were also expressed in cell and purified as discussed above for soluble NiV F ectodomain trimers in Example 1. Each of the constructs was successfully purified as a chimeric multimer. Further, negative stain EM showed that all of these constructs formed multimers. Exemplary negative stain EM images are shown in FIGS. 7B and 7C. These EM assessment shows that the pre-F-constructs contain viral fusion proteins in the prefusion form and that the molecules have three additional round G domains at the end of the tail for F-TD-G constructs and near the head for G-F-TD constructs (arrows show examples). There are some variations in the G positions since the tails are flexible.

Figure 8A:
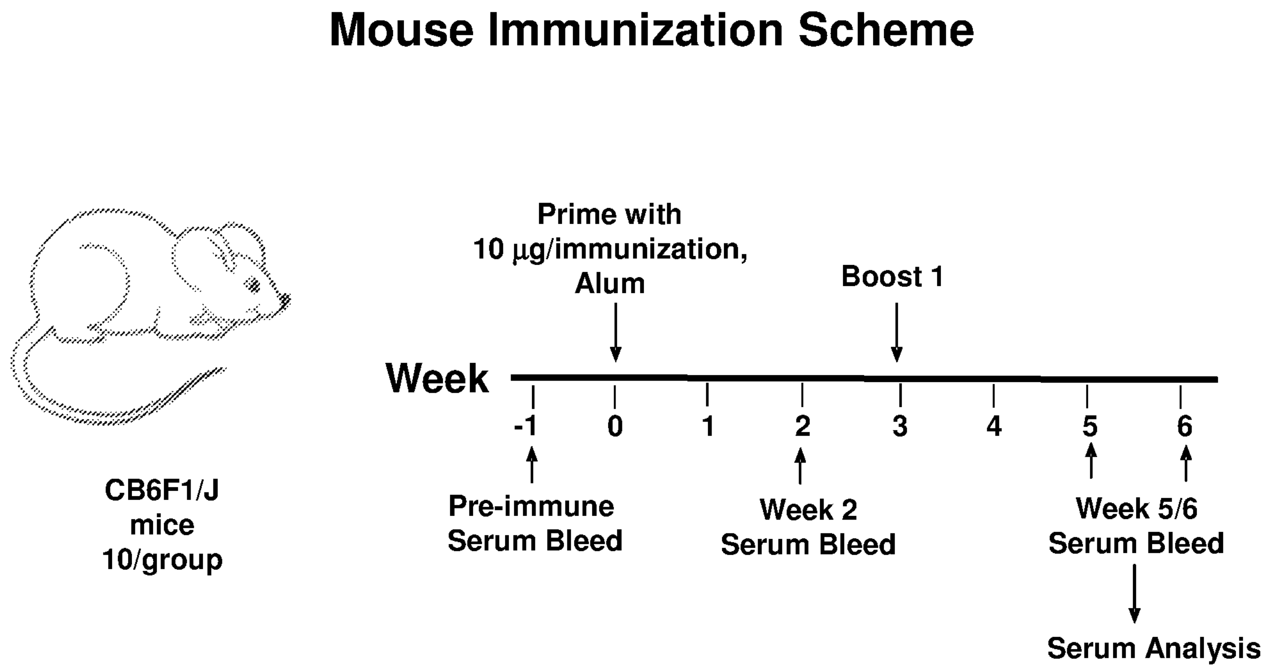
FIGS. 8A-8E show a schematic diagram (FIG. 8A) and results (FIGS. 8B-6E) for an in vivo immunization assay of the NiV F-G chimeras. Sera from immunized mice was assessed for binding to a prefusion NiV F ectodomain trimer (FIG. 8B), a postfusion NiV F ectodomain trimer (FIG. 8C), or a NiV G ectodomain monomer (FIG. 8D) by Octet binding assay.
Figure 8B:
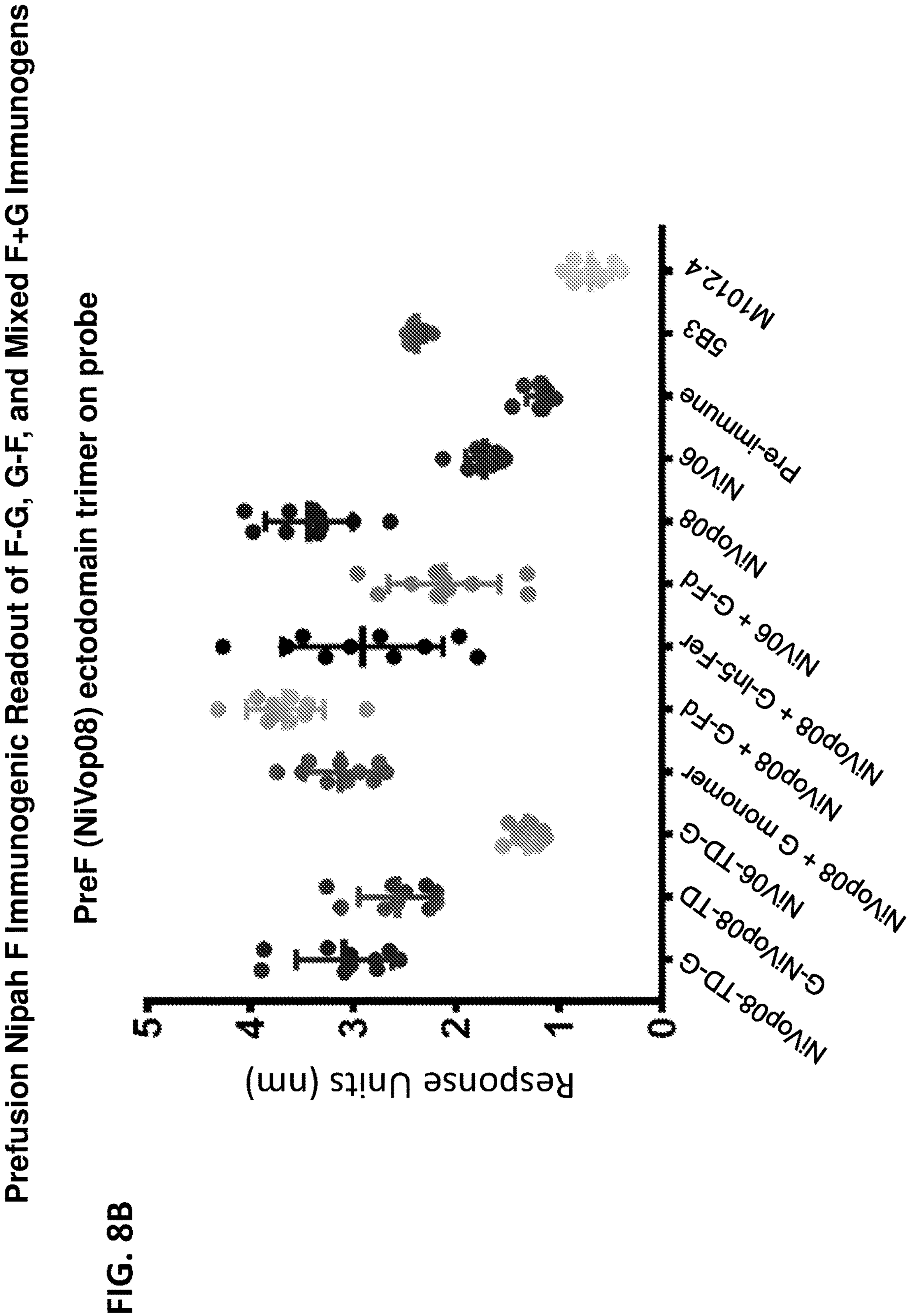
Figure 8C:
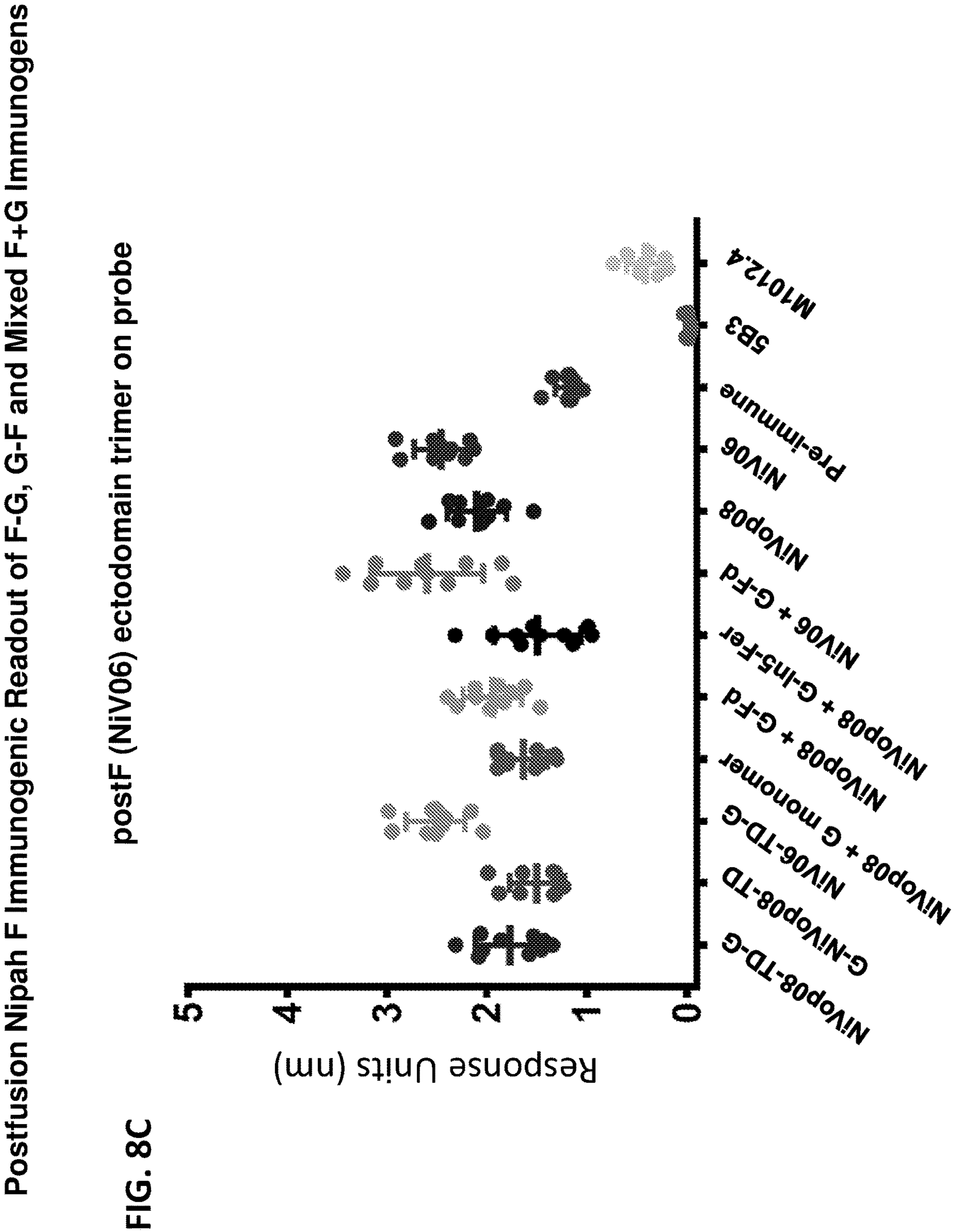
Figure 8D:
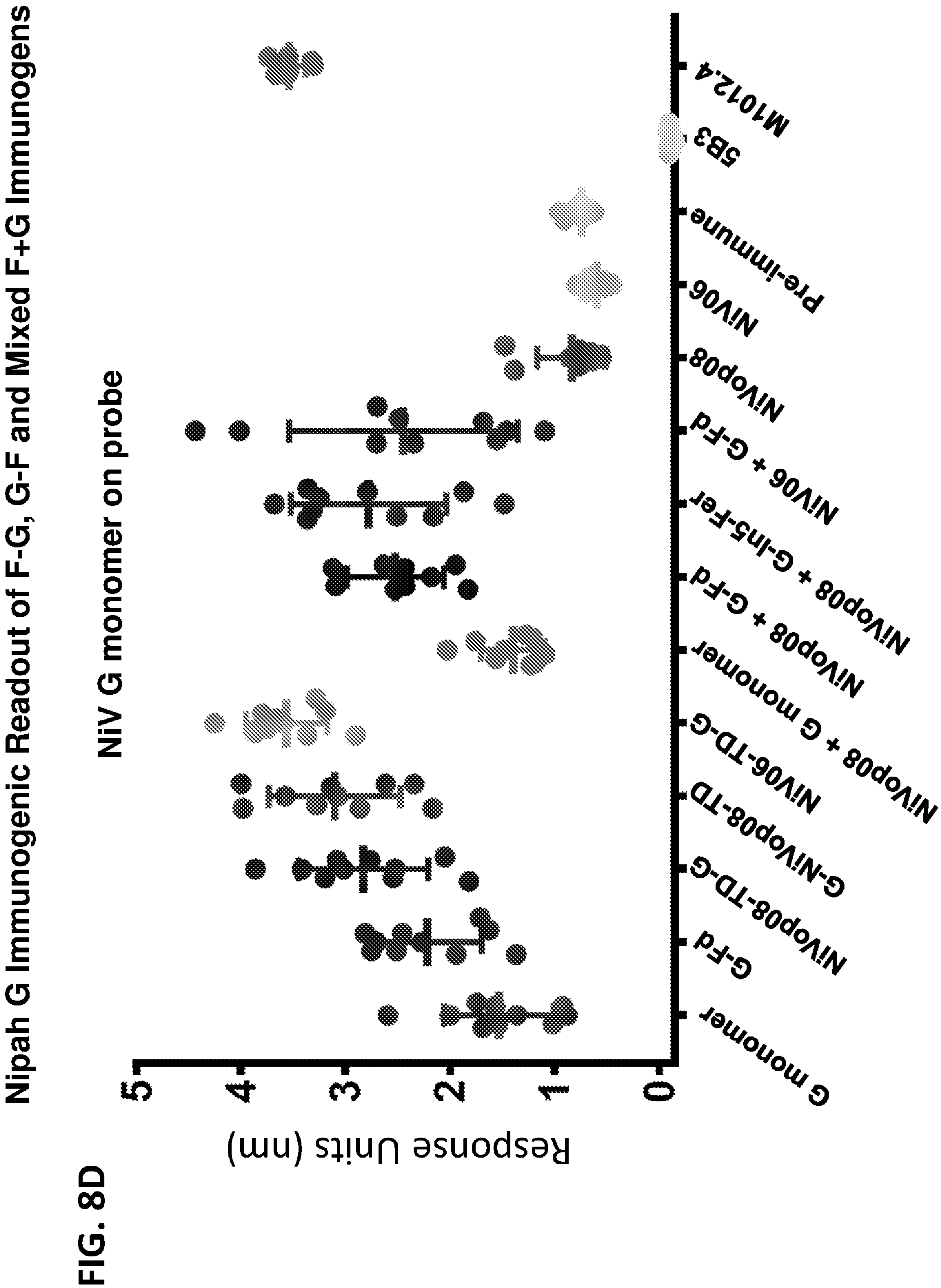
Figure 8E:
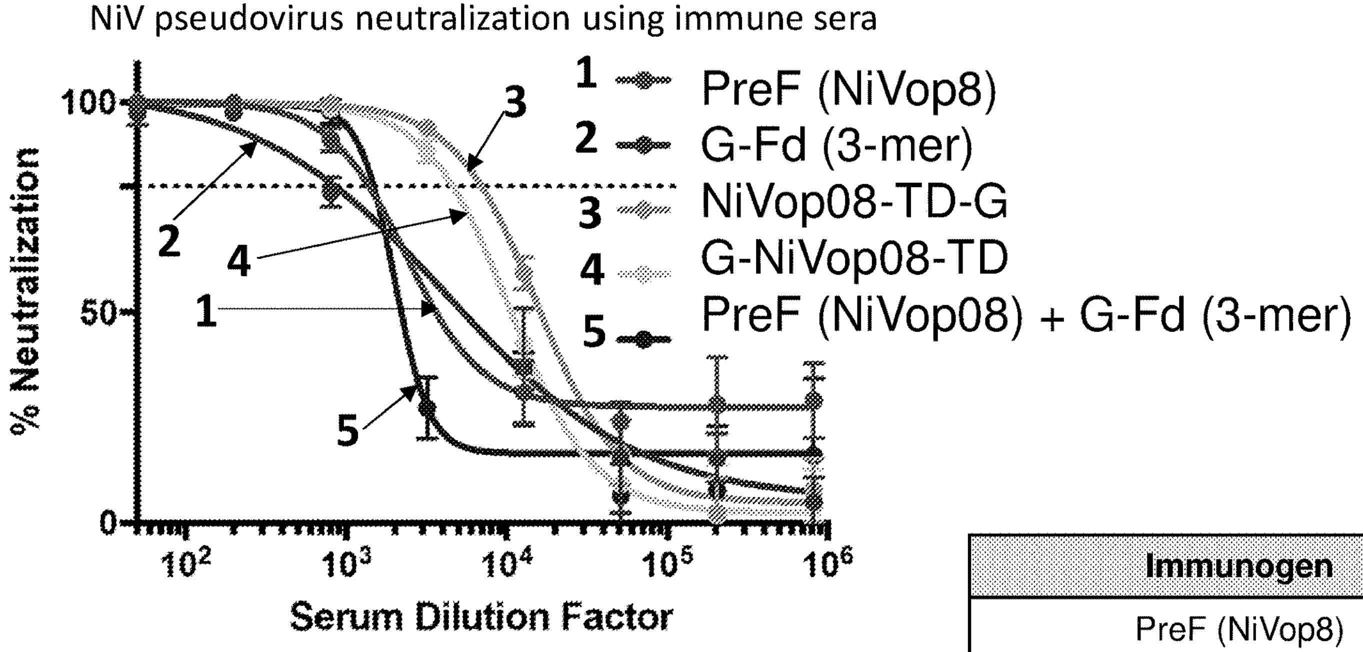

Immunization assays were conducted with the F-G chimeric multimers, and other constructs described herein. The immunization assays were performed substantially as described in Example 1. CB6F1/J mice were immunized with 10 μg of total protein in Alum (10 g for single immunogen assays, or 5 μg each for immunizations including two immunogens) using the schedule shown in FIG. 8A. Sera from immunized mice was tested for binding to prefusion F ectodomain trimer (NiVop08), postfusion F ectodomain trimer (NiV06), or monomeric NiV G using an Octet binding assay (see FIGS. 8A-8C). The immune sera was also assessed in a NiV pseudovirus neutralization assay (FIG. 8E), which showed that immune sera from animals treated with the multimeric NiV F-G constructs neutralized NiV.

Example 4

RNA and Protein Immunization in a Ferret Model

This example describes results from the immunization of ferrets with several of the disclosed NiV immunogens.

Figure 9B:
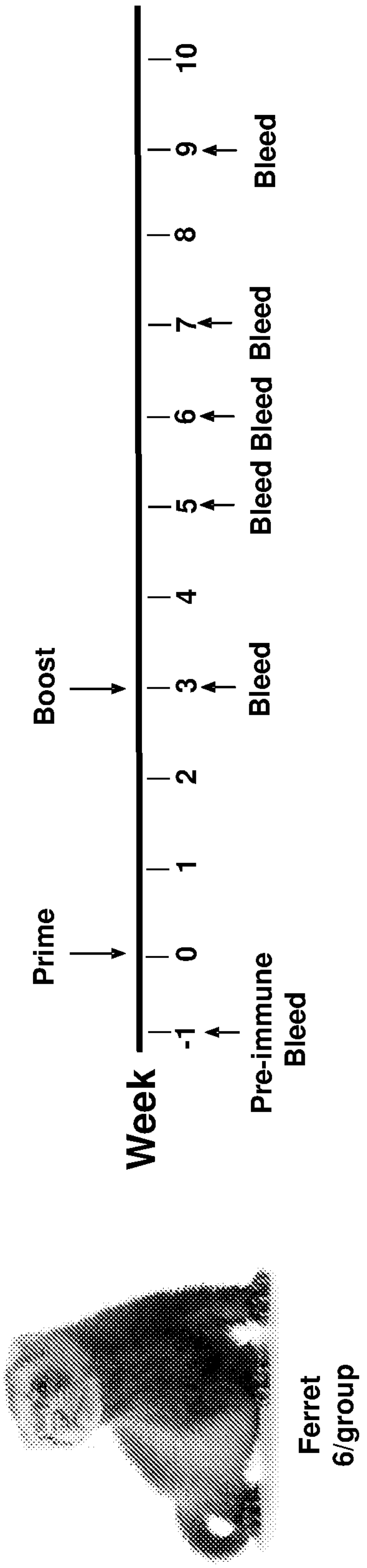

Ferrets were immunized with the preF, postF, G hexamer, or preF/G chimera immunogen based on a protein or RNA platform in 16 different groups according to the schedule shown in FIGS. 9A and 9B. The immunogens used were:

(1) preF: immunization with 10 μg mRNA encoding full-length NiV F with NiVop08 ectodomain substitutions (L104C-I114C, L172F, S191P).

(2) preF: immunization with 30 μg mRNA encoding full-length NiV F with NiVop08 ectodomain substitutions (L104C-I114C, L172F, S191P).

(3) preF: immunization with 100 μg mRNA encoding full-length NiV F with NiVop08 ectodomain substitutions (L104C-I114C, L172F, S191P).

(4) preF: immunization with 10 μg purified soluble NiVop08 protein.

(5) postF: immunization with 10 μg mRNA encoding full-length NiV F with NiV06 ectodomain substitutions (Δ100-116, residues N99-G117 linked by a GGS linker).

(6) postF: immunization with 30 μg mRNA encoding full-length NiV F with NiV06 ectodomain substitutions (Δ100-116, residues N99-G117 linked by a GGS linker).

(7) postF: immunization with 100 μg mRNA encoding full-length NiV F with NiV06 ectodomain substitutions (Δ100-116, residues N99-G117 linked by a GGS linker).

(8) postF: immunization with 10 μg purified soluble NiV06 protein.

(9) soluble G hexamer: immunization with 10 μg mRNA encoding G-Fd-G (SEQ ID NO: 37).

(10) soluble G hexamer: immunization with 30 μg mRNA encoding G-Fd-G (SEQ ID NO: 37).

(11) soluble G hexamer: immunization with 100 μg mRNA encoding G-Fd-G (SEQ ID NO: 37).

(12) soluble G hexamer: immunization with 10 μg purified soluble trimeric G-Fd-G (SEQ ID NO: 37) protein.

(13) soluble preF/G chimera: immunization with 10 μg mRNA encoding NiVop08-TD(GCN4-Fd)-G (SEQ ID NO: 43).

(14) soluble preF/G chimera: immunization with 30 μg mRNA encoding NiVop08-TD(GCN4-Fd)-G (SEQ ID NO: 43).

(15) soluble preF/G chimera: immunization with 100 μg mRNA encoding NiVop08-TD(GCN4-Fd)-G (SEQ ID NO: 43).

(16) soluble preF/G chimera: immunization with 10 μg purified soluble trimeric NiVop08-TD(GCN4-Fd)-G (SEQ ID NO: 43) protein.

Protein immunizations were performed as described above. RNA immunizations were performed with mRNA encoding the new immunogens using a lipid-encapsulated mRNA immunization platform substantially as previously described (see Roth et al., "A Modified mRNA Vaccine Targeting Immunodominant NS Epitopes Protects Against Dengue Virus Infection in HLA Class I Transgenic Mice," Frot Immunol., Jun. 21, 2019, Vol. 10, Article 1424; and Jagger et al., J Infect Dis, "Protective Efficacy of Nucleic Acid Vaccines Against Transmission of Zika Virus During Pregnancy in Mice," jiz338, Jul. 1, 2019).

Figure 9C:
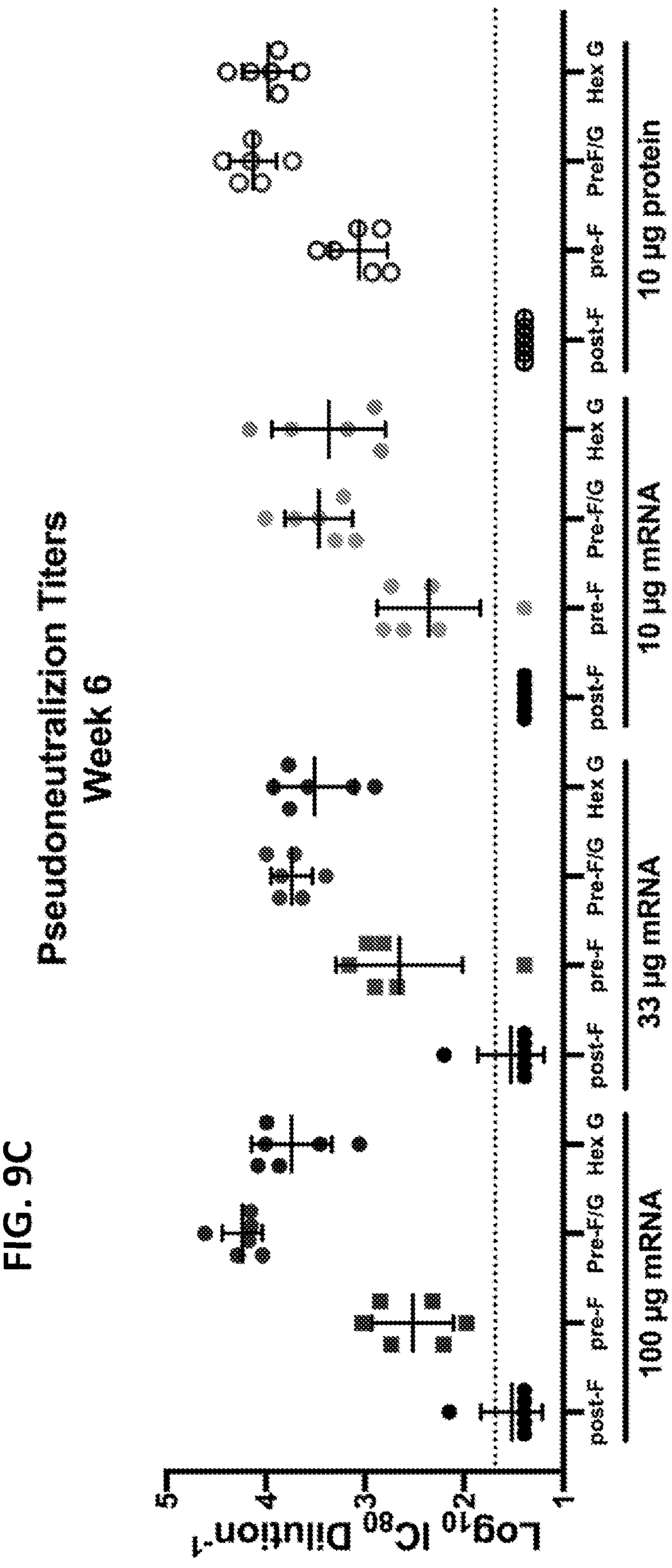
Figure 9D:
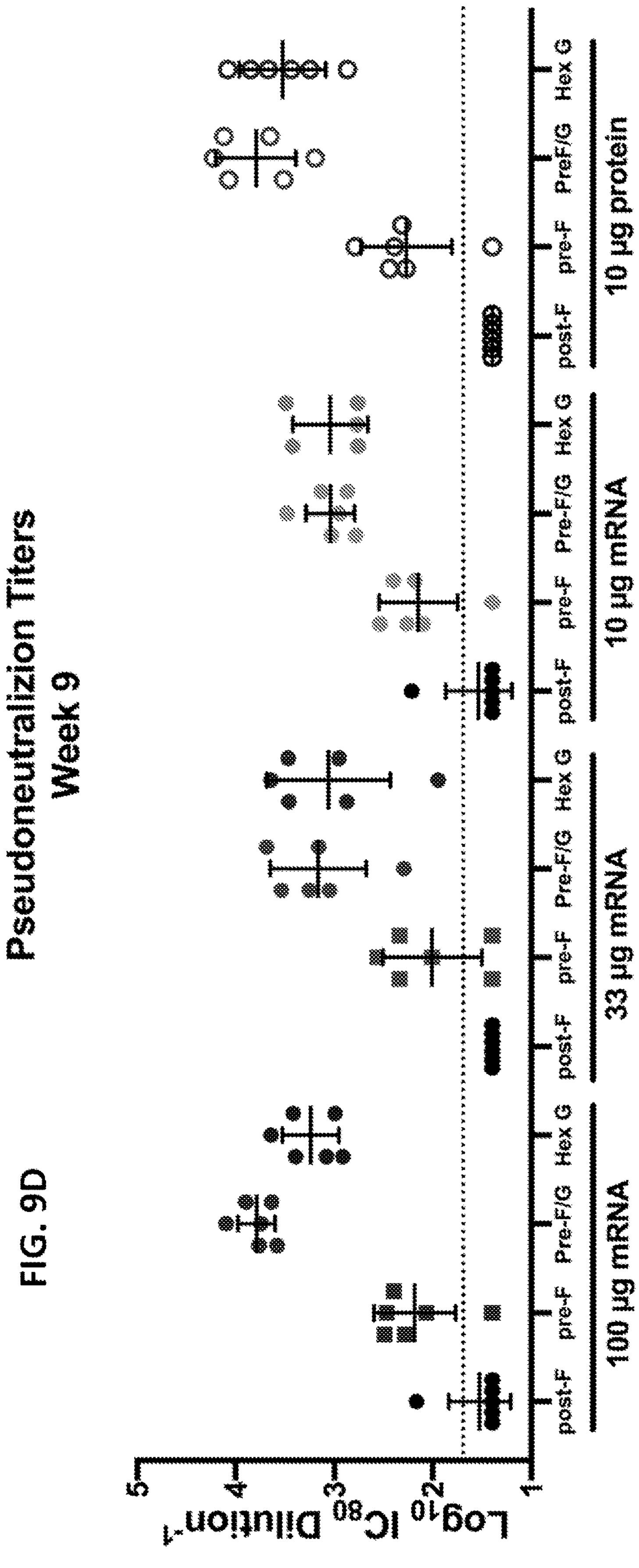

Sera was collected from the immunized animals at multiple time points. Sera from three and six weeks following the second dose was assessed for NiV neutralization using the pseudovirus neutralization assay described above (FIGS. 9C and 9D).

Figure 10:
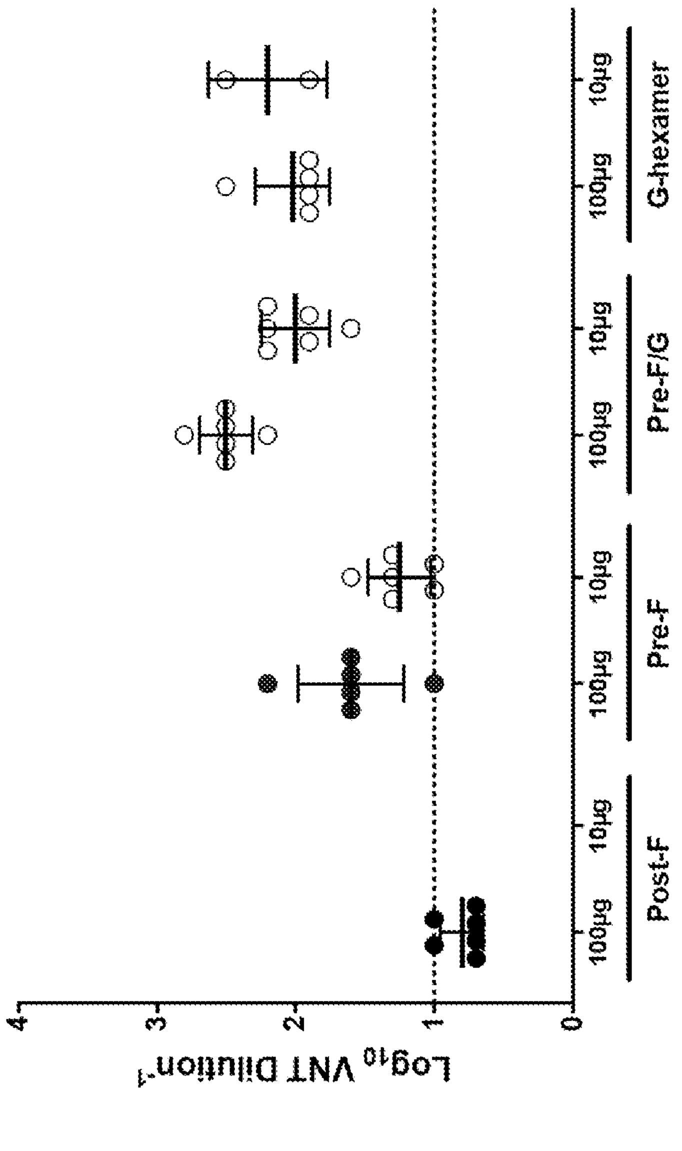
FIG. 10 shows results for a virus neutralization test (VNT) using live NiV infection of cells in vitro performed with sera from the 10 μg and 100 μg mRNA immunization conditions with the preF, preF/G chimera, and G-hexamer immunogens.

An in vitro virus neutralization test (VNT) using live NiV infection of cells was performed with sera from the 10 μg and 100 μg mRNA immunization conditions using the preF, preF/G chimera, and G-hexamer immunogens (FIG. 10). As shown, sera from each of the immunization conditions neutralized the live NiV infection of cells in vitro.

Figure 11:
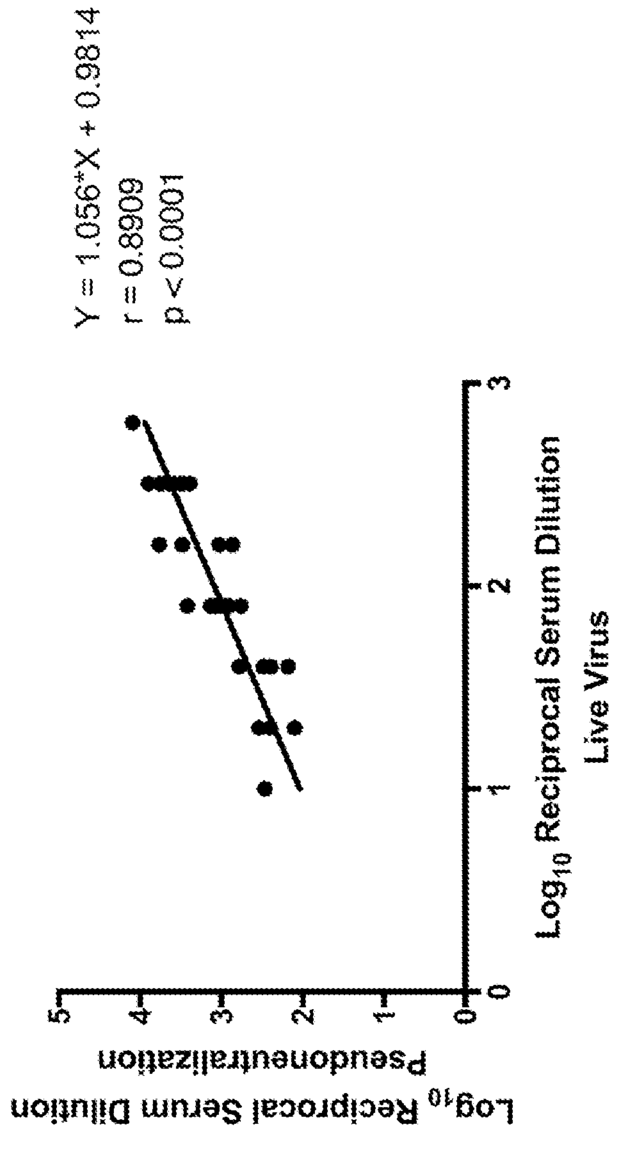
FIG. 11 is a graph illustrating the correlation of neutralization of NiV pseudovirus and live NiV.

The results of the pseudovirus neutralization assays were compared to the results of the VNT assays to determine if the immune sera neutralized live- and pseudo-NiV to a similar extent. The neutralization of NiV pseudovirus by sera from the preF, preF/G chimera, and G-hexamer immunization conditions correlated well with the neutralization of live NiV infection of cells in the VNT assay by the same sera. FIG. 11 shows an exemplary linear regression graph depicting the correlation of live and pseudovirus NiV neutralization.

Example 5

Immunogen Thermal Stability

This example provides the results of assays to ascertain the thermal stability of the preF, postF, preF/G chimera, and G-hexamer immunogens.

Three separate assays were used to interrogate the thermal stability of these immunogens: Differential Scanning calorimetry (DSC), Intrinsic Fluorescence spectral analysis, and Dynamic Light Scattering (DLS). DSC detects all thermally induced transitions, while other technique help interpret those transitions as conformational or colloidal changes in the molecule. For all proteins except PostF, the initial thermal event was linked to tertiary structure changes and/or aggregation. The following table provides the transition midpoint ($T_m$ in ° C.) for different thermal transitions identified using the DSC, Intrinsic Fluorescence, and DLS assays for the PreF (NiVop08), PostF (NiV06), HexG (G-Fd-G, SEQ ID NO: 37), and PreF-G (NiVop08-TD-G, SEQ ID NO: 43) immunogens. The results show that each of these immunogens is quite stable at temperatures below 35° C., which is comparable to other subunit vaccines that are suitable for clinical use.

| Technique | Reportable | Sample | Event A | Event B | Event C | Event D |
|---|---|---|---|---|---|---|
| Differential | Transition | PreF | 54.6 | 60.6 | ND | ND |
| Scanning | Midpoint | PostF | ND | ND | ND | 94.0 |
| Calorimetry | ($T_m$) | HexG | ND | 58.7 | 65.4 | ND |
| | | PreF-G | 52.0 | 60.8 | 65.7 | ND |
| Intrinsic | Transition | PreF | ND | 60.3 | ND | ND |
| Fluor. | Midpoint | PostF | ND | ND | ND | ND |
| | ($T_m$) | HexG | ND | 62.8 | ND | ND |
| | | PreF-G | ND | ND | 71.5 | ND |
| Dynamic | Transition | PreF | ND | 56.8 | ND | ND |
| Light | Onset | PostF | ND | ND | ND | ND |
| Scattering | ($T_{onset}$) | HexG | ND | 60.5 | ND | ND |
| (DLS) | | PreF-G | ND | 57.8 | ND | ND |

ND: No transition detected using standard analytical parameters.

Example 6

Immunogen Comparison: Signal Sequence and Transmembrane vs Soluble mRNA

Figure 12B:
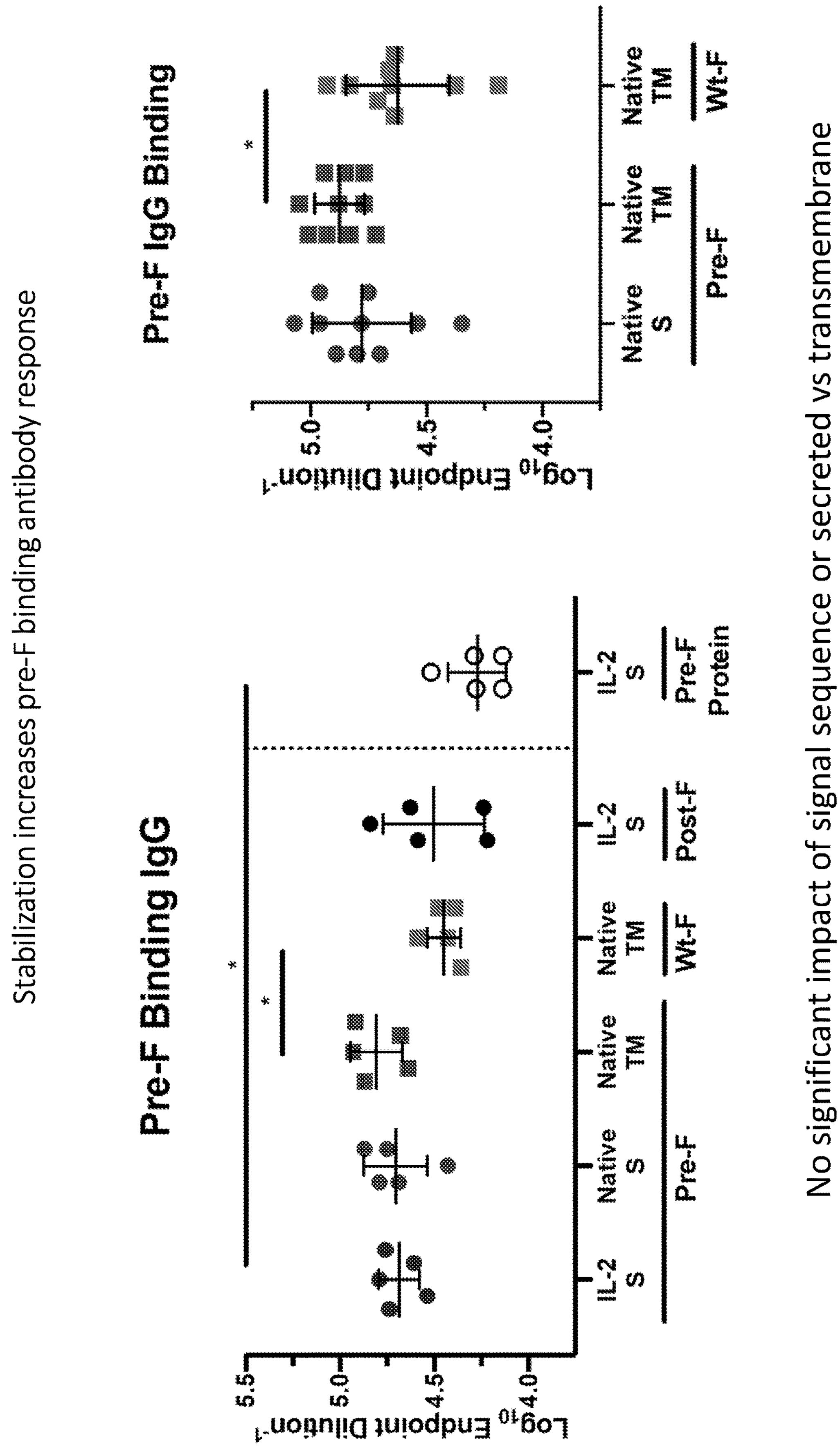

This example describes a comparison of different immunogen variations for eliciting an immune response to Nipah virus in an animal model. Variables assessed include prefusion stabilized vs. wild-type (WT) NiV F, NiV G as a trimer, hexamer, and tetramer (with stalk), transmembrane (TM) vs soluble/secreted NiV F and G, signal sequence (IL-2 signal sequence or native NiV signal sequence), and mRNA vs. protein immunization (See FIG. 12A). The native G ectodomain including both the stalk and head regions forms a tetramer (similar to the Hendra G vaccine approved for veterinary use).

Figure 12C:
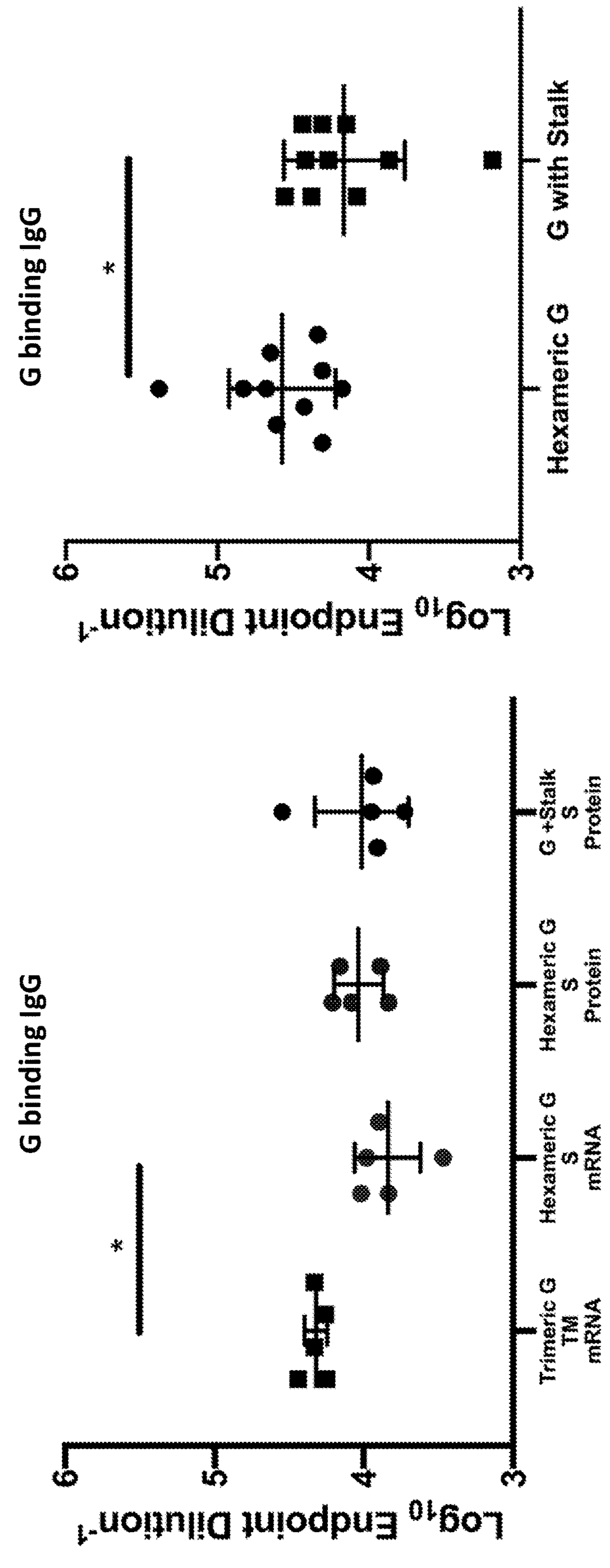

Protein and mRNA immunizations were performed as described above and sera collected from the immunized animals was assessed for NiV preF and G binding. The results (FIGS. 12B and 12C) show that immunization with a prefusion stabilized NiV F increases elicitation of pre-F binding antibody, that there was no significant impact of signal sequence or secreted vs transmembrane conditions, that trimeric G membrane-anchored is a little more immunogenic than hexameric G secreted, and that the G-hexamer immunogen is somewhat more immunogenic than the tetrameric G including stalk.

Example 7

RNA and Protein Immunization in a Mouse Model

Figure 13A:
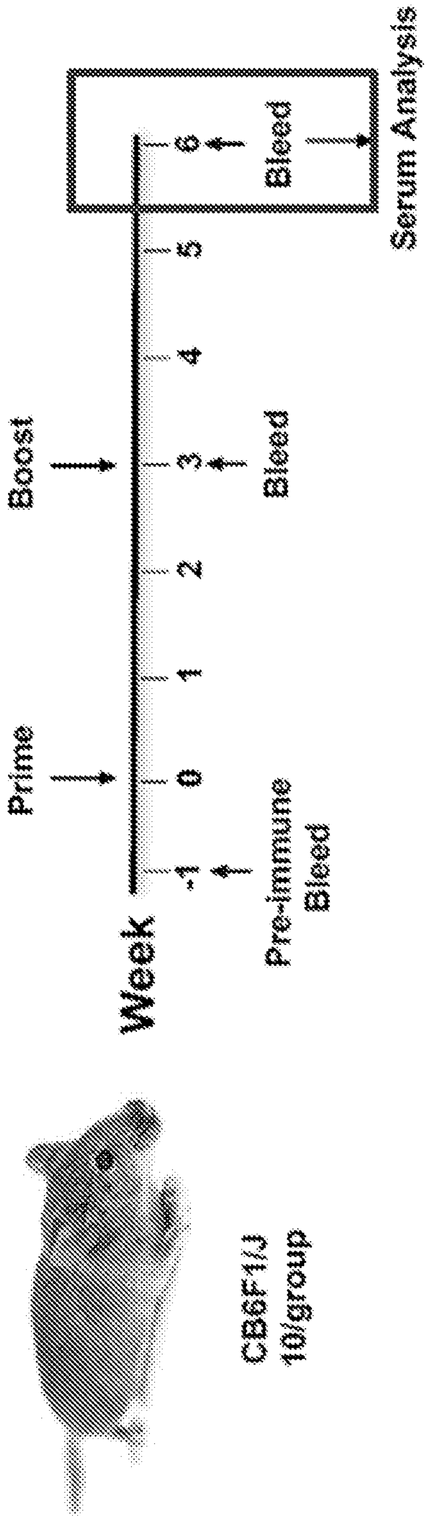
Figure 13C:
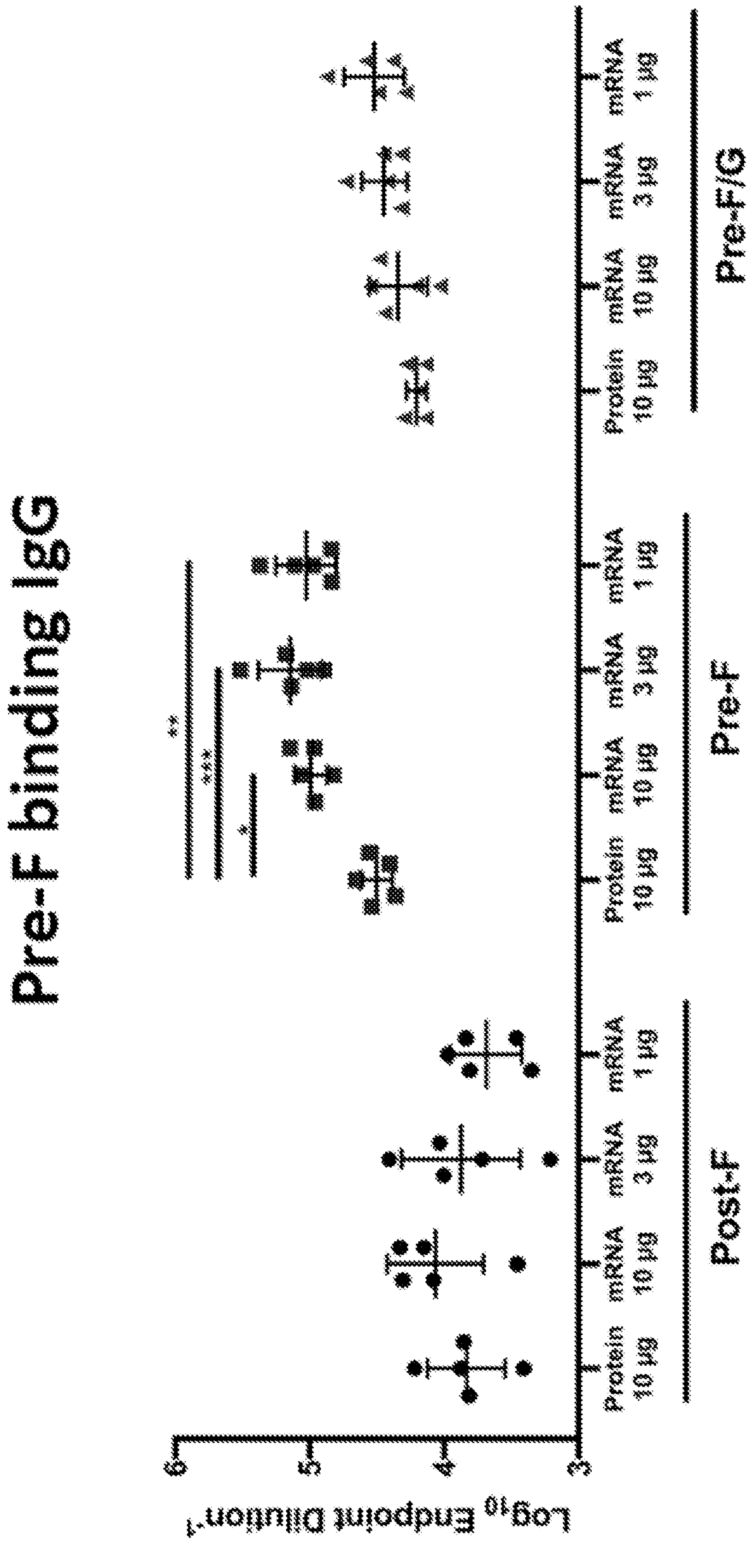
Figure 13D:
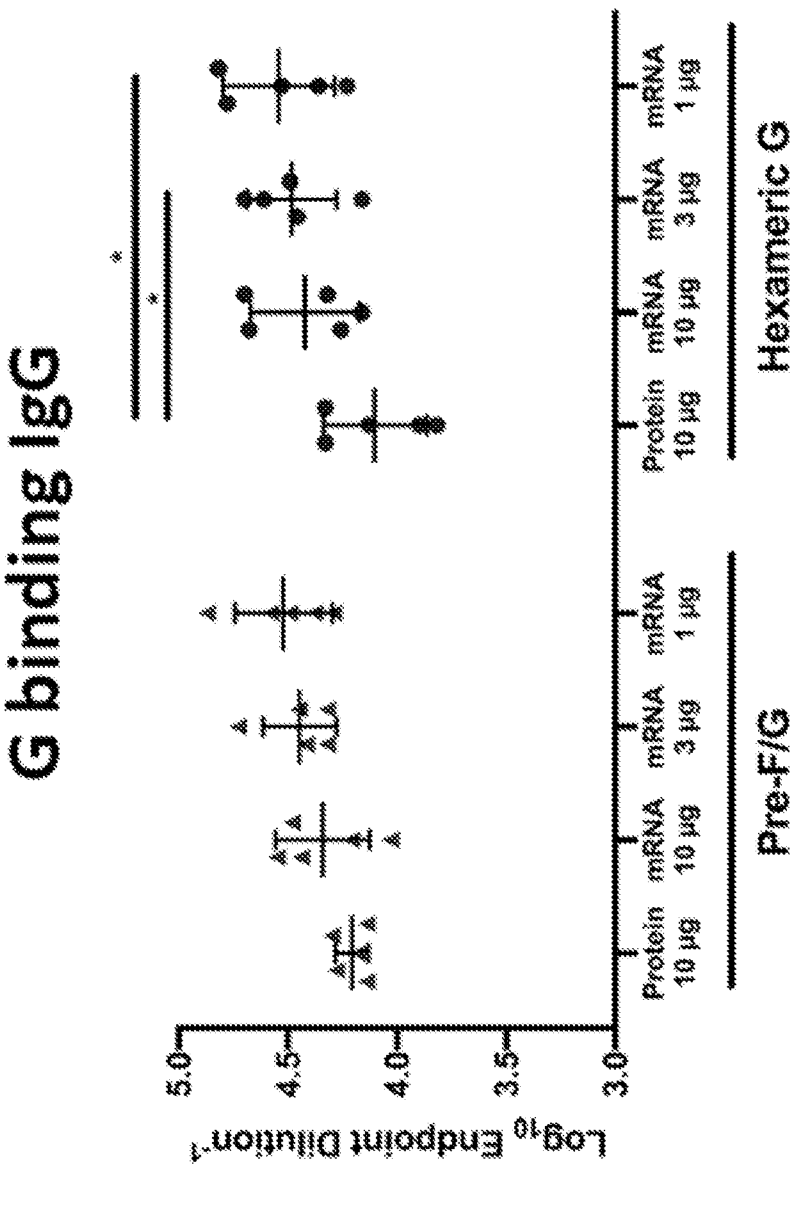

This example describes a comparison of different immunogens and dosages for eliciting an immune response to Nipah virus in a mouse model. The preF (NiVop08), postF (NiV06), G-hexamer (also referred to as hexG; G-Fd-G, SEQ ID NO: 37), and PreF-G (NiVop08-TD-G, SEQ ID NO: 43) immunogens were assessed using mRNA and protein-based immunization protocols as described above and sera collected from the immunized animals was assessed for NiV preF and G binding. The immunization scheme and summary is provided in FIGS. 13A and 13B. The results (FIGS. 13C and 13D) show that both mRNA and protein based immunizations elicited an immune response in mice.

It will be apparent that the precise details of the methods or compositions described may be varied or modified without departing from the spirit of the described embodiments. We claim all such modifications and variations that fall within the scope and spirit of the claims below.

The invention claimed is:

1. An immunogen, comprising:

a recombinant Nipah virus (NiV) F ectodomain trimer stabilized in a prefusion conformation by one or more amino acid substitutions in protomers of the trimer, the amino acid substitutions comprising one or more of the following:

cysteine substitutions at NiV F positions 104 and 114 that form a non-natural intra-protomer disulfide bond, or cysteine substitutions at NiV F positions 114 and 426 that form a non-natural intra-protomer disulfide bond;

a proline substitution at NiV F position 191;

a phenylalanine substitution at NiV F position 172;

a glycine substitution at NiV F position 70; and a deletion of NiV F positions 102-113 with positions 101 and 114 linked by a glycine-serine linker;

wherein the NiV F positions are according to the reference NiV F sequence set forth as SEQ ID NO: 52.

2. The immunogen of claim 1, wherein the recombinant NiV F ectodomain trimer is stabilized in the prefusion conformation by the cysteine substitutions at NiV F positions 104 and 114 that form a non-natural intra-protomer disulfide bond, the proline substitution at NiV F position 191, and the phenylalanine substitution at NiV F position 172.

3. The immunogen of claim 1, wherein the one or more amino acid substitutions comprise:

a) the cysteine substitutions at NiV F positions 104 and 114 that form a non-natural intra-protomer disulfide bond, and the proline substitution at NiV F position 191;

b) the cysteine substitutions at NiV F positions 104 and 114 that form a non-natural intra-protomer disulfide bond, and the phenylalanine substitution at NiV F position 172;

c) the cysteine substitutions at NiV F positions 104 and 114 that form a non-natural intra-protomer disulfide bond, the proline substitution at NiV F position 191, the phenylalanine substitution at NiV F position 172, and the glycine substitution at NiV F position 70;

d) the cysteine substitutions at NiV F positions 114 and 426 that form a non-natural intra-protomer disulfide bond, and the proline substitution at NiV F position 191;

e) the cysteine substitutions at NiV F positions 114 and 426 that form a non-natural intra-protomer disulfide bond, and the phenylalanine substitution at NiV F position 172;

f) the cysteine substitutions at NiV F positions 114 and 426 that form a non-natural intra-protomer disulfide bond, the proline substitution at NiV F position 191, and the phenylalanine substitution at NiV F position 172;

g) the cysteine substitutions at NiV F positions 114 and 426 that form a non-natural intra-protomer disulfide bond, the proline substitution at NiV F position 191, the phenylalanine substitution at NiV F position 172, and the glycine substitution at NiV F position 70;

h) the proline substitution at NiV F position 191, and the phenylalanine substitution at NiV F position 172;

i) the proline substitution at NiV F position 191, the phenylalanine substitution at NiV F position 172, and the glycine substitution at NiV F position 70;

j) the deletion of NiV F positions 102-113 with positions 101 and 114 linked by a glycine-serine linker, and the proline substitution at NiV F position 191, k) the deletion of NiV F positions 102-113 with positions 101 and 114 linked by a glycine-serine linker, and the phenylalanine substitution at NiV F position 172; or l) the deletion of NiV F positions 102-113 with positions 101 and 114 linked by a glycine-serine linker, the proline substitution at NiV F position 191, and the phenylalanine substitution at NiV F position 172.

4. The immunogen of claim 1, wherein:

the cysteine substitutions at NiV F positions 104 and 114 are L104C and 1114C substitutions;

the cysteine substitutions at NiV F positions 114 and 426 are 1114C and I426C substitutions;

the proline substitution at NiV F position 191 is a S191P substitution;

the phenylalanine substitution at NiV F position 172 is a L172F substitution;

the glycine substitution at NiV F position 70 is a Q70G substitution; and/or the deletion of NiV F positions 102-113 with positions 101 and 114 linked by a glycine-serine linker having the sequence GSG.

5. The immunogen of claim 1, wherein the protomers of the recombinant NiV F ectodomain trimer further comprise one or more additional amino acid substitutions.

6. The immunogen of claim 1, wherein the protomers of the recombinant NiV F ectodomain trimer comprise a F2 protein comprising or consisting of NiV F positions 25-109 and a $F_1$ ectodomain comprising or consisting of NiV F positions 110-488.

7. The immunogen of claim 1, wherein the protomers of the NiV F ectodomain trimer comprise an amino acid sequence at least 90% identical to residues 21-486 of any one of SEQ ID NOs: 5, 7-9, 11-18, 20-21, 23-24, and 26-32, or residues 21-477 of any one of SEQ ID NOs: 19, 22, and 25; and wherein the protomers comprise the one or more amino acid substitutions that stabilize the NiV F ectodomain trimer in the prefusion conformation.

8. The immunogen of claim 1, wherein the protomers of the NiV F ectodomain trimer comprise or consist of the amino acid sequence set forth as residues 21-486 of any one of SEQ ID NOs: 5, 7-9, 11-18, 20-21, 23-24, and 26-32, or residues 21-477 of any one of SEQ ID NOs: 19, 22, and 25.

9. The immunogen of claim 1, wherein the NiV F ectodomain protomer trimer is fused C-terminally to a trimerization domain.

10. The immunogen of claim 9, wherein the trimerization domain is a GCN4 trimerization domain or a T4 fibritin trimerization domain.

11. The immunogen of claim 10, wherein the GCN4 trimerization domain comprises an amino acid sequence set forth as KLMKQIEDKIEEILSKIYHIENEIARIKKLIGEAP (residues 485-519 of SEQ ID NO: 1).

12. The immunogen of claim 9, wherein the protomers of the NiV F ectodomain trimer fused to the trimerization domain comprise an amino acid sequence at least 90% identical to residues 21-519 of any one of SEQ ID NO: 5, 7-9, 11-18, 20-21, 23-24, and 26-32, residues 21-510 of any one of SEQ ID NOs: 19, 22, and 25; and wherein the protomers comprise the one or more amino acid substitutions that stabilize the NiV F ectodomain trimer in the prefusion conformation.

13. The immunogen of claim 9, wherein the protomers of the NiV F ectodomain trimer fused to the trimerization domain comprise or consist of the amino acid sequence set forth as residues 21-519 of any one of SEQ ID NO: 5, 7-9, 11-18, 20-21, 23-24, and 26-32, residues 21-510 of any one of SEQ ID NOs: 19, 22, and 25.

14. The immunogen of claim 1, conjugated to a heterologous carrier.

15. The immunogen of claim 1, wherein the recombinant NiV F ectodomain trimer is soluble.

16. The immunogen of claim 1, wherein the protomers of the recombinant NiV F ectodomain trimer are fused to a transmembrane domain by a peptide linker, or directly fused to the transmembrane domain.

17. The immunogen of claim 16, wherein the protomers of the recombinant NiV F ectodomain trimer comprise a full-length $F_1$ protein.

18. The immunogen of claim 1, wherein the protomers of the recombinant NiV F ectodomain trimer are fused to a heterologous protein.

19. The immunogen of claim 18, wherein the heterologous protein is an ectodomain of a henipavirus G protein.

20. The immunogen of claim 19, wherein the heterologous protein is a NiV G ectodomain.

21. The immunogen of claim 20, comprising:

the NiV F ectodomain trimer linked to at least three NiV G ectodomains, wherein the NiV G ectodomains are fused, directly or indirectly via peptide linker, to an N-terminus of protomers of the recombinant NiV F ectodomain trimer and/or to a C-terminus of a trimerization domain fused to the C-terminus of protomers of the recombinant NiV F ectodomain trimer.

22. The immunogen of claim 21, wherein the trimerization domain comprises a GCN4 trimerization domain, a T4 fibritin trimerization domain, or a GCN4 trimerization domain and a T4 fibritin trimerization domain.

23. The immunogen of claim 22, wherein the protomers of the NiV F ectodomain trimer linked to the trimerization domain and the NiV G ectodomain comprise an amino acid sequence set forth as residues 21-981 of SEQ ID NO: 43 (NiVop08-TD(GCN4-Fd)-G), residues 27-981 of SEQ ID NO: 44 (G-NiVop08-TD(GCN4-Fd)), residues 21-952 of SEQ ID NO: 59 (NiVop08-GCN4-G), or residues 21-946 of SEQ ID NO: 60 (NiVop08-Fd-G).

24. A virus-like particle comprising the recombinant NiV F ectodomain trimer of claim 1.

25. A nucleic acid molecule encoding the immunogen of claim 1.

26. The nucleic acid molecule of claim 25, operably linked to a promoter.

27. A vector comprising the nucleic acid molecule of claim 26.

28. The vector of claim 27, wherein the vector is an RNA vector.

29. A method of producing an immunogen, comprising:

expressing the nucleic acid molecule of claim 25 in a host cell; and purifying the immunogen.

30. The immunogen produced by the method of claim 29.

31. An immunogenic composition, comprising the immunogen of claim 1, and a pharmaceutically acceptable carrier.

32. A method of eliciting an immune response to NiV F in a subject, comprising administering to the subject an effective amount of the immunogenic composition of claim 31 to elicit the immune response.

33. The method of claim 32, wherein the immune response treats or inhibits NiV infection in the subject.

34. The immunogen of claim 1, wherein the protomers of the NiV F ectodomain trimer comprise the amino acid sequence set forth as residues 21-486 of SEQ ID NO: 24.

35. The immunogen of claim 9, wherein the protomers of the NiV F ectodomain trimer fused to the trimerization domain comprise or consist of the amino acid sequence set forth as residues 21-519 of SEQ ID NO: 24.

* * * * *